US011473151B2

(12) United States Patent
Guan et al.

(10) Patent No.: US 11,473,151 B2
(45) Date of Patent: Oct. 18, 2022

(54) DIAGNOSTIC AND THERAPEUTIC METHODS FOR CANCER

(71) Applicant: Genentech, Inc., South San Francisco, CA (US)

(72) Inventors: Yinghui Guan, South San Francisco, CA (US); Yasin Senbabaoglu, South San Francisco, CA (US); Shannon Turley, San Anselmo, CA (US); Yulei Wang, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 87 days.

(21) Appl. No.: 16/867,125

(22) Filed: May 5, 2020

(65) Prior Publication Data

US 2020/0263261 A1 Aug. 20, 2020

Related U.S. Application Data

(63) Continuation of application No. PCT/US2018/059271, filed on Nov. 5, 2018.

(60) Provisional application No. 62/657,468, filed on Apr. 13, 2018, provisional application No. 62/595,957, filed on Dec. 7, 2017, provisional application No. 62/582,207, filed on Nov. 6, 2017.

(51) Int. Cl.

*C12Q 1/6886* (2018.01)
*A61K 39/395* (2006.01)
*G01N 33/574* (2006.01)

(52) U.S. Cl.

CPC ...... *C12Q 1/6886* (2013.01); *A61K 39/39558* (2013.01); *G01N 33/57488* (2013.01); *C12Q 2600/106* (2013.01); *C12Q 2600/158* (2013.01)

(58) Field of Classification Search

CPC ............ C12Q 1/6886; C12Q 2600/106; C12Q 2600/158; A61K 39/39558; G01N 33/57488

See application file for complete search history.

(56) References Cited

U.S. PATENT DOCUMENTS

2019/0085087 A1 3/2019 Hegde et al.

FOREIGN PATENT DOCUMENTS

WO WO-2008/088854 A2 7/2008
WO WO-2016033555 A1 * 3/2016 .......... A61K 31/573
WO WO-2016/196298 A1 12/2016
WO WO-2017/201036 A1 11/2017

OTHER PUBLICATIONS

NCBI GEO Database Accession No. GPL96, Affymetrix GeneChip Human Genome U133 Array Set HG-U133A, submitted Feb. 19, 2002 (511 pages).

Affymetrix, "GeneChip Human Genome U133 Set," <www.helmholtz-hzi.de/fileadmin/user_upload/research/Research-Programme/Technological_Platforms/Gene_Expression_Analysis/Service/humangenomeu133.pdf>, retrieved Dec. 10, 2010 (2 pages).

Einstein et al., "Combined blockade of vascular endothelial growth factor and programmed death 1 pathways in advanced kidney cancer," Clin Adv Hematol Oncol. 15(6): 478-88 (2017).

GEO Accession No. GPL96, Affymetrix GeneChip Human Genome U133 Array Set HG-U133A (511 pages).

Mariathasan et al., "TGF-β attenuates tumour response to PD-L1 blockade by contributing to exclusion of T cells," Nature. 554(7693):1-28 (2018).

Rodriguez-Vida et al., "Predictive and prognostic biomarkers of targeted agents and modern immunotherapy in renal cell carcinoma," ESMO Open. 1(3):1-13 (2016) (14 pages).

EP Communication Pursuant to Rules 161 (1) and 162 EPC Patent Application No. 18812446.5, dated Jun. 18, 2020 (3 pages).

International Search Report and Written Opinion for International Patent Application No. PCT/US2018/059271, dated Apr. 10, 2019 (26 pages).

(Continued)

*Primary Examiner* — Misook Yu
*Assistant Examiner* — Dennis J Sullivan
(74) *Attorney, Agent, or Firm* — Clark & Elbing LLP; Thomas J. Takara

(57) ABSTRACT

The present invention provides diagnostic methods, therapeutic methods, and compositions for the treatment of cancer (e.g., a bladder cancer (e.g., UC, e.g., mUC), a kidney cancer, a lung cancer, a liver cancer, an ovarian cancer, a pancreatic cancer, a colorectal cancer, or a breast cancer). The invention is based, at least in part, on the discovery that expression levels of one or more biomarkers described herein in a sample from an individual having cancer can be used in methods of identifying an individual having a cancer who may benefit with an anti-cancer therapy that includes an immunotherapy (e.g., a PD-L1 axis binding antagonist such as an anti-PD-L1 antibody (e.g., atezolizumab)) and a suppressive stromal antagonist (e.g., a TGF-β antagonist), methods for selecting a therapy for an individual having cancer, methods of treating an individual having cancer, methods for assessing a response or monitoring the response of an individual to treatment with an anti-cancer therapy that includes an immunotherapy (e.g., a PD-L1 axis binding antagonist such as an anti-PD-L1 antibody (e.g., atezolizumab)) and a suppressive stromal antagonist (e.g., a TGF-β antagonist), and related kits, anti-cancer therapies, and uses.

21 Claims, 47 Drawing Sheets
(44 of 47 Drawing Sheet(s) Filed in Color)
Specification includes a Sequence Listing.

(56) References Cited

OTHER PUBLICATIONS

International Perliminary Report on Patentability for International Patent Application No. PCT/US2018/059271, dated May 12, 2020 (16 pages).
Invitation to Pay Additional Fees for International Patent Application No. PCT/US2018/059271, dated Feb. 4, 2019 (22 pages).

* cited by examiner

Immune excluded (CD8/Trichrome stain)

DIAGNOSTIC AND THERAPEUTIC METHODS FOR CANCER

SEQUENCE LISTING

The instant application contains a Sequence Listing which has been submitted electronically in ASCII format and is hereby incorporated by reference in its entirety. Said ASCII copy, created on May 1, 2020, is named 50474-172005_Sequence_Listing_05.01.20_ST25 and is 309,543 bytes in size.

FIELD OF THE INVENTION

The present invention is directed to diagnostic and therapeutic methods for the treatment of cancer. Also provided are related kits and assays.

BACKGROUND OF THE INVENTION

Cancer remains one of the most deadly threats to human health. In the U.S., cancer affects nearly 1.3 million new patients each year and is the second leading cause of death after heart disease, accounting for approximately 1 in 4 deaths. It is also predicted that cancer may surpass cardiovascular diseases as the number one cause of death within 5 years. Solid tumors are responsible for most of those deaths. Although there have been significant advances in the medical treatment of certain cancers, the overall 5-year survival rate for all cancers has improved only by about 10% in the past 20 years. Malignant solid tumors, in particular, metastasize and grow rapidly in an uncontrolled manner, making their timely detection and treatment extremely difficult.

Studies in humans with immune checkpoint inhibitors have demonstrated the promise of harnessing the immune system to control and eradicate tumor growth. The programmed death 1 (PD-1) receptor and its ligand programmed death-ligand 1 (PD-L1) are immune checkpoint proteins that have been implicated in the suppression of immune system responses during chronic infections, pregnancy, tissue allografts, autoimmune diseases, and cancer. PD-L1 regulates the immune response by binding to the inhibitory receptor PD-1, which is expressed on the surface of T-cells, B-cells, and monocytes. PD-L1 negatively regulates T-cell function also through interaction with another receptor, B7-1. Formation of the PD-L1/PD-1 and PD-L1/B7-1 complexes negatively regulates T-cell receptor signaling, resulting in the subsequent downregulation of T-cell activation and suppression of anti-tumor immune activity.

Despite the significant advancement in the treatment of cancer, improved diagnostic methods and cancer therapies and are still being sought.

SUMMARY OF THE INVENTION

The present invention provides diagnostic and therapeutic methods and compositions for treating an individual having a cancer, including, but not limited to, a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer.

In one aspect, the invention features a method of identifying an individual having a cancer who may benefit from treatment with an anti-cancer therapy comprising an immunotherapy and a suppressive stromal antagonist, the method comprising determining the expression level of three or more of the following genes in a sample from the individual: ACTA2, ADAM19, COMP, CTGF, TGFB1, or TGFBR2, wherein an expression level of three or more of ACTA2, ADAM19, COMP, CTGF, TGFB1, or TGFBR2 in the sample that is at or above a reference expression level of the three or more genes identifies the individual as one who may benefit from treatment with an anti-cancer therapy comprising an immunotherapy and a suppressive stromal antagonist.

In another aspect, the invention features a method for selecting a therapy for an individual having a cancer, the method comprising determining the expression level of three or more of the following genes in a sample from the individual: ACTA2, ADAM19, COMP, CTGF, TGFB1, or TGFBR2, wherein an expression level of three or more of ACTA2, ADAM19, COMP, CTGF, TGFB1, or TGFBR2 in the sample that is at or above a reference expression level of the three or more genes identifies the individual as one who may benefit from treatment with an anti-cancer therapy comprising an immunotherapy and a suppressive stromal antagonist.

In some embodiments of any of the preceding aspects, the expression level of three or more of ACTA2, ADAM19, COMP, CTGF, TGFB1, or TGFBR2 in the sample is at or above a reference expression level of the three or more genes, and the method further comprises administering to the individual an anti-cancer therapy comprising an immunotherapy and a suppressive stromal antagonist. In some embodiments, the expression level of at least four, at least five, or all six of ACTA2, ADAM19, COMP, CTGF, TGFB1, or TGFBR2 is at or above a reference expression level of the three or more genes. In some embodiments, the expression level of TGFB1 and/or TGFBR1 is at or above a reference level of TGFB1 and/or TGFBR1. In some embodiments, the expression level of ACTA2, ADAM19, COMP, CTGF, TGFB1, and TGFBR2 is at or above a reference expression level of ACTA2, ADAM19, COMP, CTGF, TGFB1, and TGFBR2.

In another aspect, the invention features a method of treating an individual having a cancer, the method comprising: (a) determining the expression level of three or more of the following genes in a sample from the individual: ACTA2, ADAM19, COMP, CTGF, TGFB1, or TGFBR2, wherein the expression level of three or more of ACTA2, ADAM19, COMP, CTGF, TGFB1, or TGFBR2 in the sample is determined to be at or above a reference expression level of the three or more genes; and (b) administering an anti-cancer therapy comprising an immunotherapy and a suppressive stromal antagonist to the individual based on the expression level of the three or more genes determined in step (a). In some embodiments, the expression level of at least four, at least five, or all six of ACTA2, ADAM19, COMP, CTGF, TGFB1, or TGFBR2 is determined to be at or above a reference expression level of the three or more genes. In some embodiments, the expression level of TGFB1 and/or TGFBR1 is determined to be at or above a reference level of TGFB1 and/or TGFBR1. In some embodiments, the expression level of ACTA2, ADAM19, COMP, CTGF, TGFB1, and TGFBR2 is determined to be at or above a reference expression level of ACTA2, ADAM19, COMP, CTGF, TGFB1, and TGFBR2.

In another aspect, the invention features a method of treating an individual having a cancer, the method comprising administering to the individual an anti-cancer therapy comprising an immunotherapy and a suppressive stromal antagonist, wherein prior to treatment the expression level of three or more of ACTA2, ADAM19, COMP, CTGF, TGFB1, or TGFBR2 in the sample has been determined to be at or above a reference expression level of the three or more genes. In some embodiments, the expression level of at least four, at least five, or all six of ACTA2, ADAM19, COMP, CTGF, TGFB1, or TGFBR2 has been determined to be at or above a reference expression level of the three or more genes. In some embodiments, the expression level of TGFB1 and/or TGFBR1 has been determined to be at or above a reference level of TGFB1 and/or TGFBR1. In some embodiments, the expression level of ACTA2, ADAM19, COMP, CTGF, TGFB1, and TGFBR2 in the sample has been determined to be at or above a reference expression level of ACTA2, ADAM19, COMP, CTGF, TGFB1, and TGFBR2.

In another aspect, the invention provides a method of treating cancer in an individual having been identified as having an expression level in a sample from the individual of three or more of ACTA2, ADAM19, COMP, CTGF, TGFB1, or TGFBR2 that is at or above a reference expression level of the three or more genes, the method comprising administering to the individual an anti-cancer therapy comprising an immunotherapy and a suppressive stromal antagonist. In some embodiments, the expression level of at least four, at least five, or all six of ACTA2, ADAM19, COMP, CTGF, TGFB1, or TGFBR2 has been identified to be at or above a reference expression level of the three or more genes. In some embodiments, the expression level of TGFB1 and/or TGFBR1 has been identified to be at or above a reference level of TGFB1 and/or TGFBR1. In some embodiments, the expression level of ACTA2, ADAM19, COMP, CTGF, TGFB1, and TGFBR2 in the sample has been identified to be at or above a reference expression level of ACTA2, ADAM19, COMP, CTGF, TGFB1, and TGFBR2.

In another aspect, the invention features a method of identifying an individual having a cancer who may benefit from treatment with an anti-cancer therapy comprising an immunotherapy and a suppressive stromal antagonist, the method comprising determining the expression level of one or more of the following genes in a sample from the individual: ACTA2, ADAM19, COMP, CTGF, TGFB1, or TGFBR2, wherein the one or more genes includes at least ADAM19 or COMP, and wherein an expression level of the one or more genes in the sample that is at or above a reference expression level of the one or more genes identifies the individual as one who may benefit from treatment with an anti-cancer therapy comprising an immunotherapy and a suppressive stromal antagonist.

In another aspect, the invention features a method for selecting a therapy for an individual having a cancer, the method comprising determining the expression level of one or more of the following genes in a sample from the individual: ACTA2, ADAM19, COMP, CTGF, TGFB1, or TGFBR2, wherein the one or more genes includes at least ADAM19 or COMP, and wherein an expression level of the one or more genes in the sample that is at or above a reference expression level of the one or more genes identifies the individual as one who may benefit from treatment with an anti-cancer therapy comprising an immunotherapy and a suppressive stromal antagonist.

In some embodiments of any of the preceding aspects, the expression level of the one or more genes in the sample is at or above a reference expression level of the one or more genes, and the method further comprises administering to the individual an anti-cancer therapy comprising an immunotherapy and a suppressive stromal antagonist. In some embodiments, the expression level of at least two, at least three, at least four, at least five, or all six of ACTA2, ADAM19, COMP, CTGF, TGFB1, or TGFBR2 is at or above a reference expression level of the one or more genes.

In some embodiments, the expression level of TGFB1 and/or TGFBR1 is at or above a reference level of TGFB1 and/or TGFBR1.

In another aspect, the invention features a method of treating an individual having a cancer, the method comprising: (a) determining the expression level of one or more of the following genes in a sample from the individual: ACTA2, ADAM19, COMP, CTGF, TGFB1, or TGFBR2, wherein the one or more genes includes at least ADAM19 or COMP, and wherein the expression level of the one or more genes in the sample is determined to be at or above a reference expression level of the one or more genes; and (b) administering an anti-cancer therapy comprising an immunotherapy and a suppressive stromal antagonist to the individual based on the expression level of the one or more genes determined in step (a). In some embodiments, the expression level of at least two, at least three, at least four, at least five, or all six of ACTA2, ADAM19, COMP, CTGF, TGFB1, or TGFBR2 is determined to be at or above a reference expression level of the one or more genes. In some embodiments, the expression level of TGFB1 and/or TGFBR1 is at or above a reference level of TGFB1 and/or TGFBR1.

In another aspect, the invention features a method of treating an individual having a cancer, the method comprising administering to the individual an anti-cancer therapy comprising an immunotherapy and a suppressive stromal antagonist, wherein prior to treatment the expression level of one or more of ACTA2, ADAM19, COMP, CTGF, TGFB1, or TGFBR2 in the sample has been determined to be at or above a reference expression level of the one or more genes, wherein the one or more genes includes at least ADAM19 or COMP. In some embodiments, the expression level of at least two, at least three, at least four, at least five, or all six of ACTA2, ADAM19, COMP, CTGF, TGFB1, or TGFBR2 has been determined to be at or above a reference expression level of the one or more genes. In some embodiments, the expression level of TGFB1 and/or TGFBR1 has been determined to be at or above a reference level of TGFB1 and/or TGFBR1.

In another aspect, the invention provides a method of treating cancer in an individual having been identified as having an expression level in a sample from the individual of one or more of ACTA2, ADAM19, COMP, CTGF, TGFB1, or TGFBR2 that is at or above a reference expression level of the one or more genes, the method comprising administering to the individual an anti-cancer therapy comprising an immunotherapy and a suppressive stromal antagonist, wherein the one or more genes includes at least ADAM19 or COMP. In some embodiments, the expression level of at least two, at least three, at least four, at least five, or all six of ACTA2, ADAM19, COMP, CTGF, TGFB1, or TGFBR2 has been identified to be at or above a reference expression level of the one or more genes. In some embodiments, the expression level of TGFB1 and/or TGFBR1 has been identified to be at or above a reference level of TGFB1 and/or TGFBR1.

In another aspect, the invention features a method for assessing a response of an individual having a cancer to treatment with an anti-cancer therapy comprising an immunotherapy and a suppressive stromal antagonist, the method comprising: (a) determining the expression level of five or more of the following genes in a sample from the individual at a time point during or after administration of an anti-cancer therapy comprising an immunotherapy and a suppressive stromal antagonist to the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1; and (b) maintaining, adjusting, or stopping the treatment based on a comparison of the expression level of the five or more genes in the sample with a reference expression level of the five or more genes, wherein a change in the expression level of the five or more genes in the sample from the individual compared to the reference expression level of the five or more genes is indicative of a response to treatment with the anti-cancer therapy. In some embodiments, the method comprises determining the expression level of at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1. In some embodiments, the method comprises determining the expression level of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, the expression level of at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1 is changed relative to a reference expression level of the five or more genes. In some embodiments, the expression level of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 is changed relative to a reference expression level of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, the change is an increase in the expression level of the five or more genes and the treatment is adjusted or stopped. In some embodiments, the change is a decrease in the expression level of the five or more genes and the treatment is maintained.

In another aspect, the invention features a method for monitoring the response of an individual having a cancer to treatment with an anti-cancer therapy comprising an immunotherapy and a suppressive stromal antagonist, the method comprising: (a) determining the expression level of five or more of the following genes in a sample from the individual at a time point during or after administration of an anti-cancer therapy comprising an immunotherapy and a suppressive stromal antagonist to the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1; and (b) comparing the expression level of the five or more genes in the sample from the individual with a reference expression level of the five or more genes, thereby monitoring the response of the individual undergoing treatment with the anti-cancer therapy. In some embodiments, the method comprises determining the expression level of at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1. In some embodiments, the method comprises determining the expression level of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, the expression level of at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1 is changed relative to a reference expression level of the five or more genes. In some embodiments, the expression level of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 is changed relative to a reference expression level of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, an increase in the expression level of the five or more genes is indicative of a lack of response of the individual to the treatment. In some embodiments, a decrease in the expression level of the five or more genes is indicative of a response of the individual to the treatment.

In another aspect, the invention features a method for assessing a response of an individual having a cancer to treatment with an anti-cancer therapy comprising an immunotherapy and a suppressive stromal antagonist, the method comprising: (a) determining the expression level of one or more of the following genes in a sample from the individual at a time point during or after administration of an anti-cancer therapy comprising an immunotherapy and a suppressive stromal antagonist to the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1, wherein the one or more genes includes at least ADAM19, ACTG2, CNN1, CTPS1, FAM101B, FSTL3, HSPB1, IGFBP3, PXDC1, SEMA7A, SH3PXD2A, TAGLN, TGFBI, TNS1, or TPM1; and (b) maintaining, adjusting, or stopping the treatment based on a comparison of the expression level of the one or more genes in the sample with a reference expression level of the one or more genes, wherein a change in the expression level of the one or more genes in the sample from the individual compared to the reference expression level of the one or more genes is indicative of a response to treatment with the anti-cancer therapy. In some embodiments, the method comprises determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1. In some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1 is changed relative to a reference expression level of the one or more genes. In some embodiments, the change is an increase in the expression level of the one or more genes and the treatment is adjusted or stopped. In some embodiments, the change is a decrease in the expression level of the one or more genes and the treatment is maintained.

In another aspect, the invention features a method for monitoring the response of an individual having a cancer to treatment with an anti-cancer therapy comprising an immunotherapy and a suppressive stromal antagonist, the method comprising: (a) determining the expression level of one or more of the following genes in a sample from the individual at a time point during or after administration of an anti-cancer therapy comprising an immunotherapy and a suppressive stromal antagonist to the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1, wherein the one or more genes includes at least ADAM19, ACTG2, CNN1, CTPS1, FAM101B, FSTL3, HSPB1, IGFBP3, PXDC1, SEMA7A, SH3PXD2A, TAGLN, TGFBI, TNS1, or TPM1; and (b) comparing the expression level of the one or more genes in the sample from the individual with a reference expression level of the one or more genes, thereby monitoring the response of the individual undergoing treatment with the anti-cancer therapy. In some embodiments, the method comprises determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1. In some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1 is changed relative to a reference expression level of the five or more genes. In some embodiments, an increase in the expression level of the one or more genes is indicative of a lack of response of the individual to the treatment. In some embodiments, a decrease in the expression level of the one or more genes is indicative of a response of the individual to the treatment.

In some embodiments of any of the preceding aspects, the method further comprises determining the expression level in the sample of one or more additional genes selected from the group consisting of PD-L1, CD8A, CXCL10, CXCL9, GZMA, GZMB, IFNG, PRF1, and TBX21. In some embodiments, the one or more additional genes is PD-L1. In some embodiments, the one or more additional genes is selected from the group consisting of CD8A, CXCL10, CXCL9, GZMA, GZMB, IFNG, PRF1, and TBX21. In some embodiments, the method further comprises determining the expression level of at least two, at least three, at least four, at least five, at least six, at least seven, or all eight of CD8A, CXCL10, CXCL9, GZMA, GZMB, IFNG, PRF1, and TBX21. In some embodiments, the method further comprises determining the expression level of CD8A, CXCL10, CXCL9, GZMA, GZMB, IFNG, PRF1, and TBX21.

In some embodiments of any of the preceding aspects, the method further comprises determining a tumor mutational burden (TMB) in a tumor sample from the individual.

In another aspect, the invention features a method of selecting a therapy for an individual having a cancer, the method comprising: determining (i) the expression level of one or more of the following genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1; and (ii) the expression level of one or more additional genes selected from the group consisting of CD8A, CXCL10, CXCL9, GZMA, GZMB, IFNG, PRF1, and TBX21 in the sample from the individual, or a TMB score in a tumor sample from the individual, wherein: an expression level of the one or more genes of (i) that is at or above a reference expression level of the one or more genes of (i) identifies the individual as one who may benefit from treatment with an anti-cancer therapy comprising an immunotherapy and a suppressive stromal antagonist, and an expression level of the one or more genes of (i) that is below a reference expression level of the one or more genes and an expression level of the one or more additional genes of (ii) that is at or above a reference expression level of the one or more additional genes of (ii), or a TMB score in the tumor sample that is at or above a reference TMB score, identifies the individual as one who may benefit from treatment with an anti-cancer therapy comprising an immunotherapy alone. In some embodiments, the method further comprises administering to the individual the anti-cancer therapy for which the individual may benefit from treatment.

In some embodiments of any of the preceding aspects, the cancer is selected from the group consisting of a bladder cancer, a kidney cancer, a lung cancer, a liver cancer, an ovarian cancer, a pancreatic cancer, a colorectal cancer, or a breast cancer. In some embodiments, the cancer is a bladder cancer. In some embodiments, the bladder cancer is a urothelial carcinoma (UC). In some embodiments, the UC is a metastatic UC. In some embodiments, the pancreatic cancer is pancreatic ductal adenocarcinoma (PDAC).

In some embodiments of any of the preceding aspects, a tumor from the individual has an immune excluded phenotype characterized by the localization of CD8+ T-cells in the peri-tumoral stromal compartment. In some embodiments, the CD8+ T-cells localize at or near collagen fibers.

In some embodiments of any of the preceding aspects, the reference expression level is determined from a population of individuals having a cancer. In some embodiments, the reference expression level is a median expression level and/or is determined by principle component analysis of Z-score-transformed expression levels.

In some embodiments of any of the preceding aspects, the expression level is a nucleic acid expression level. In some embodiments, the nucleic acid expression level is an mRNA expression level. In some embodiments, the mRNA expression level is determined by RNA-seq, RT-qPCR, qPCR, multiplex qPCR or RT-qPCR, microarray analysis, SAGE, MassARRAY technique, ISH, or a combination thereof.

In other embodiments of any of the preceding aspects, the expression level is a protein expression level. In some embodiments, the protein expression level is determined by immunohistochemistry (IHC), Western blot, enzyme-linked immunosorbent assay (ELISA), immunoprecipitation, immunofluorescence, radioimmunoassay, or mass spectrometry.

In some embodiments of any of the preceding aspects, the sample is a tissue sample, a cell sample, a whole blood sample, a plasma sample, a serum sample, or a combination thereof. In some embodiments, the tissue sample is a tumor tissue sample. In some embodiments, the tumor tissue sample comprises tumor cells, tumor-infiltrating immune cells, stromal cells, or a combination thereof. In some embodiments, the tumor tissue sample is a formalin-fixed and paraffin-embedded (FFPE) sample, an archival sample, a fresh sample, or a frozen sample.

In some embodiments of any of the preceding aspects, the suppressive stromal antagonist is a transforming growth factor beta (TGF-β), podoplanin (PDPN), leukocyte-associated immunoglobulin-like receptor 1 (LAIR1), SMAD, anaplastic lymphoma kinase (ALK), connective tissue growth factor (CTGF/CCN2), endothelial-1 (ET-1), AP-1, interleukin (IL)-13, lysyl oxidase homolog 2 (LOXL2), endoglin (CD105), fibroblast activation protein (FAP), vascular cell adhesion protein 1 (CD106), thymocyte antigen 1 (THY1), beta 1 integrin (CD29), platelet-derived growth factor (PDGF), PDGF receptor A (PDGFRα), PDGF receptor B (PDGFRβ), vimentin, smooth muscle actin alpha (ACTA2), desmin, endosialin (CD248), or S100 calcium-binding protein A4 (S100A4) antagonist. In some embodiments, the suppressive stromal antagonist is perfenidone, galunisertib, or nintedanib. In some embodiments, the suppressive stromal antagonist is a TGF-β antagonist. In some embodiments, the TGF-β antagonist is a TGF-β binding antagonist. In some embodiments, the TGF-β binding antagonist inhibits the binding of TGF-β to its ligand binding partners. In some embodiments, the TGF-β binding antagonist inhibits the binding of TGF-β to a cellular receptor for TGF-β. In some embodiments, the TGF-β binding antagonist inhibits activation of TGF-β. In some embodiments, the TGF-β antagonist inhibits TGF-β1, TGF-β2, and/or TGF-β3. In some embodiments, the TGF-β antagonist inhibits TGF-β1, TGF-β2, and TGF-β3. In some embodiments, the TGF-β antagonist inhibits TGF-β receptor-1 (TGFBR1), TGF-β receptor-2 (TGFBR2), and/or TGF-β receptor-3 (TGFBR3). In some embodiments, the TGF-β antagonist is a polypeptide, a small molecule, or a nucleic acid. In some embodiments, the TGF-β antagonist is a polypeptide. In some embodiments, the polypeptide is an anti-TGF-β antibody, a soluble TGF-β receptor, or a peptide. In some embodiments, the polypeptide is an anti-TGF-β antibody. In some embodiments, the anti-TGF-β antibody is a pan-specific anti-TGF-β antibody. In some embodiments, the anti-TGF-β antibody is fresolimumab, metelimumab, lerdelimumab, 1D11, 2G7, or derivatives thereof. In some embodiments, the peptide is disitertide (P144). In some embodiments, the TGF-β antagonist is a small molecule. In some embodiments, the small molecule is selected from the group consisting of galunisertib (LY2157299), LY2382770, LY3022859, SB-431542, SD208, SM16, tranilast, pirfenidone, TEW-7197, PF-03446962, and pyrrole-imidazole polyamide. In some embodiments, the TGF-β antagonist is a nucleic acid. In some embodiments, the nucleic acid is trabedersen (AP12009) or belagenpumatucel-L.

In some embodiments of any of the preceding aspects, the immunotherapy comprises a CD28, OX40, GITR, CD137, CD27, CD40, ICOS, HVEM, NKG2D, MICA, 2B4, IL-2, IL-12, IFNγ, IFNα, TNFα, IL-1, CDN, HMGB1, or TLR agonist.

In other embodiments of any of the preceding aspects, the immunotherapy comprises a PD-L1 axis, CTLA-4, TIM-3, BTLA, VISTA, LAG-3, B7H4, CD96, TIGIT, CD226, prostaglandin, VEGF, endothelin B, IDO, arginase, MICA/MICB, TIM-3, IL-10, IL-4, or IL-13 antagonist. In some embodiments, the immunotherapy is a PD-L1 axis antagonist. In some embodiments, the PD-L1 axis antagonist is a PD-L1 axis binding antagonist. In some embodiments, the PD-L1 axis binding antagonist is selected from the group consisting of a PD-L1 binding antagonist, a PD-1 binding antagonist, and a PD-L2 binding antagonist. In some embodiments, the PD-L1 axis binding antagonist is a PD-L1 binding antagonist. In some embodiments, the PD-L1 binding antagonist inhibits the binding of PD-L1 to one or more of its ligand binding partners. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an anti-PD-L1 antibody. In some embodiments, the anti-PD-L1 antibody is a monoclonal anti-PD-L1 antibody. In some embodiments, the anti-PD-L1 antibody is a human, humanized, or chimeric anti-PD-L1 antibody. In some embodiments, the anti-PD-L1 antibody is selected from the group consisting of: MPDL3280A (atezolizumab), YW243.55.S70, MDX-1105, MED14736 (durvalumab), and MSB0010718C (avelumab). In some embodiments, the anti-PD-L1 antibody comprises the following hypervariable regions (HVRs): (a) an HVR-H1 sequence of GFTFSDSWIH (SEQ ID NO: 63); (b) an HVR-H2 sequence of AWISPYGGSTYYADSVKG (SEQ ID NO: 64); (c) an HVR-H3 sequence of RHWPGGFDY (SEQ ID NO: 65); (d) an HVR-L1 sequence of RASQDVSTAVA (SEQ ID NO: 66); (e) an HVR-L2 sequence of SASFLYS (SEQ ID NO: 67); and (f) an HVR-L3 sequence of QQYLYHPAT (SEQ ID NO: 68). In some embodiments, the anti-PD-L1 antibody comprises: (a) a heavy chain variable (VH) domain comprising an amino acid sequence having at least 90% sequence identity to the amino acid sequence of EVQLVESGGGLVQPGGSLRLSCAASGFTFSDSWIHWVRQAPGKGLEWVAWISPYGGSTYYADSVKGRFTIS ADTSKNTAYLQMNSLRAEDTAVYYCARRHWPGGFDYWGQGTLVTVSS (SEQ ID NO: 69); (b) a light chain variable (VL) domain comprising an amino acid sequence having at least 90% sequence identity to the amino acid sequence of DIQMTQSPSSLSASVGDRVTITCRASQDVSTAVAWYQQKPGKAPKLLIYSASFLYSGVPSRFSGSGSGTDFT LTISSLQPEDFATYYCQQYLYHPATFGQGTKVEIKR (SEQ ID NO: 70); or (c) a VH domain as in (a) and a VL domain as in (b). In some embodiments, the anti-PD-L1 antibody comprises: (a) a VH domain comprising an amino acid sequence having at least 95% sequence identity to the amino acid sequence of SEQ ID NO: 69; (b) a VL domain comprising an amino acid sequence having at least 95% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 96% sequence identity to the amino acid sequence of SEQ ID NO: 69; (b) a VL domain comprising an amino acid sequence having at least 96% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 97% sequence identity to the amino acid sequence of SEQ ID NO: 69; (b) a VL domain comprising an amino acid sequence having at least 97% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 98% sequence identity to the amino acid sequence of SEQ ID NO: 69; (b) a VL domain comprising an amino acid sequence having at least 98% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 99% sequence identity to the amino acid sequence of SEQ ID NO: 69; (b) a VL domain comprising an amino acid sequence having at least 99% sequence identity to the amino acid sequence of SEQ ID NO: 70; or (c) a VH domain as in (a) and a VL domain as in (b). In some embodiments, the anti-PD-L1 antibody comprises: (a) a VH domain comprising the amino acid sequence of SEQ ID NO: 69; (b) a VL domain comprising the amino acid sequence of SEQ ID NO: 70; or (c) a VH domain as in (a) and a VL domain as in (b). In some embodiments, the anti-PD-L1 antibody comprises: (a) a VH domain comprising the amino acid sequence of SEQ ID NO: 69; and (b) a VL domain comprising the amino acid sequence of SEQ ID NO: 70. In some embodiments, the anti-PD-L1 antibody is atezolizumab. In some embodiments, the PD-L1 axis binding antagonist is a PD-1 binding antagonist. In some embodiments, the PD-1 binding antagonist inhibits the binding of PD-1 to its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2. In some embodiments, the PD-1 binding antagonist is an anti-PD-1 antibody. In some embodiments, the anti-PD-1 antibody is a monoclonal anti-PD-1 antibody. In some embodiments, the anti-PD-1 antibody is a human, humanized, or chimeric anti-PD-1 antibody.

In some embodiments, the method further comprises administering an additional therapeutic agent to the individual. In some embodiments, the additional therapeutic agent is selected from the group consisting of an immunotherapy agent, a cytotoxic agent, a growth inhibitory agent, a radiation therapy agent, an anti-angiogenic agent, and combinations thereof. In some embodiments, the individual is a human.

In another aspect, the invention features a kit for identifying an individual having a cancer who may benefit from treatment with an anti-cancer therapy comprising an immunotherapy and a suppressive stromal antagonist, the kit comprising: (a) reagents for determining the expression level of three or more of the following genes in a sample from the individual: ACTA2, ADAM19, COMP, CTGF, TGFB1, or TGFBR2; and, optionally, (b) instructions for using the reagents to identify an individual having a cancer who may benefit from a treatment with an anti-cancer therapy comprising an immunotherapy and a suppressive stromal antagonist.

In another aspect, the invention features a kit for identifying an individual having a cancer who may benefit from treatment with an anti-cancer therapy comprising an immunotherapy and a suppressive stromal antagonist, the kit comprising: (a) reagents for determining the expression level of one or more of the following genes in a sample from the individual: ACTA2, ADAM19, COMP, CTGF, TGFB1, or TGFBR2, wherein the one or more genes includes at least ADAM19 or COMP; and, optionally, (b) instructions for using the reagents to identify an individual having a cancer who may benefit from a treatment with an anti-cancer therapy comprising an immunotherapy and a suppressive stromal antagonist.

In another aspect, the invention features an anti-cancer therapy comprising an immunotherapy and a suppressive stromal antagonist for use in a method of treating an individual suffering from a cancer, wherein prior to treatment the expression level of three or more of ACTA2, ADAM19, COMP, CTGF, TGFB1, or TGFBR2 has been determined to be at or above a reference expression level of the one or more genes.

In another aspect, the invention features an anti-cancer therapy comprising an immunotherapy and a suppressive stromal antagonist for use in a method of treating an individual suffering from a cancer, wherein prior to treatment the expression level of one or more of ACTA2, ADAM19, COMP, CTGF, TGFB1, or TGFBR2 has been determined to be at or above a reference expression level of the one or more genes, wherein the one or more genes includes at least ADAM19 or COMP.

In another aspect, the invention provides for the use of an anti-cancer therapy comprising an immunotherapy and a suppressive stromal antagonist in the manufacture of a medicament for treating an individual suffering from a cancer, wherein prior to treatment the expression level of three or more of ACTA2, ADAM19, COMP, CTGF, TGFB1, or TGFBR2 has been determined to be at or above a reference expression level of the one or more genes.

In another aspect, the invention provides for the use of an anti-cancer therapy comprising an immunotherapy and a suppressive stromal antagonist in the manufacture of a medicament for treating an individual suffering from a cancer, wherein prior to treatment the expression level of one or more of ACTA2, ADAM19, COMP, CTGF, TGFB1, or TGFBR2 has been determined to be at or above a reference expression level of the one or more genes, wherein the one or more genes includes at least ADAM19 or COMP.

In another aspect, the invention features a kit for monitoring a response of an individual having a cancer, the kit comprising: (a) reagents for determining the expression level of five or more of the following genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1; and, optionally, (b) instructions for using the reagents to monitor the response of an individual having a cancer to treatment with an anti-cancer therapy comprising an immunotherapy and a suppressive stromal antagonist.

In another aspect, the invention features a kit for monitoring a response of an individual having a cancer, the kit comprising: (a) reagents for determining the expression level of one or more of the following genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1, wherein the one or more genes includes at least ADAM19, ACTG2, CNN1, CTPS1, FAM101B, FSTL3, HSPB1, IGFBP3, PXDC1, SEMA7A, SH3PXD2A, TAGLN, TGFBI, TNS1, or TPM1; and, optionally, (b) instructions for using the reagents to monitor the response of an individual having a cancer to treatment with an anti-cancer therapy comprising an immunotherapy and a suppressive stromal antagonist.

BRIEF DESCRIPTION OF THE DRAWINGS

The application file contains at least one drawing executed in color. Copies of this patent or patent application with color drawings will be provided by the Office upon request and payment of the necessary fee.

FIG. 2B is a graph showing TMB (y-axis) plotted against Lund (left panel) and TCGA subtypes (right panel) (x-axis). The Lund genomically-unstable (Wilcoxon test; p=0.0002) and TCGA luminal II subtypes ($p=5.94\times10^{-5}$) had a higher median TMB. UroA: Urothelial-like A, GU: Genomically-unstable, Inf: Infiltrated, UroB: Urothelial-like B, SCCL: SCC-like.

antigen processing machinery, D: immune checkpoint signature, E: MKI67 and cell cycle genes, F: DNA replication-dependent histones, G: DNA damage repair genes, H: ECM gene set, I: TGFB two-gene signature, J: angiogenesis signature, K: EMT markers, and L: Pan-F-TBRS genes (for details on these signatures see Example 1).

Figure 3B:
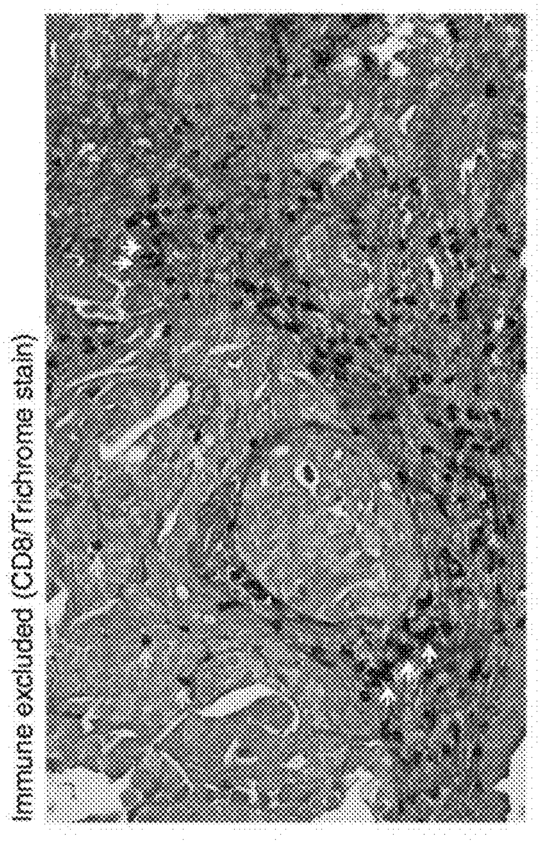
Figure 3A:
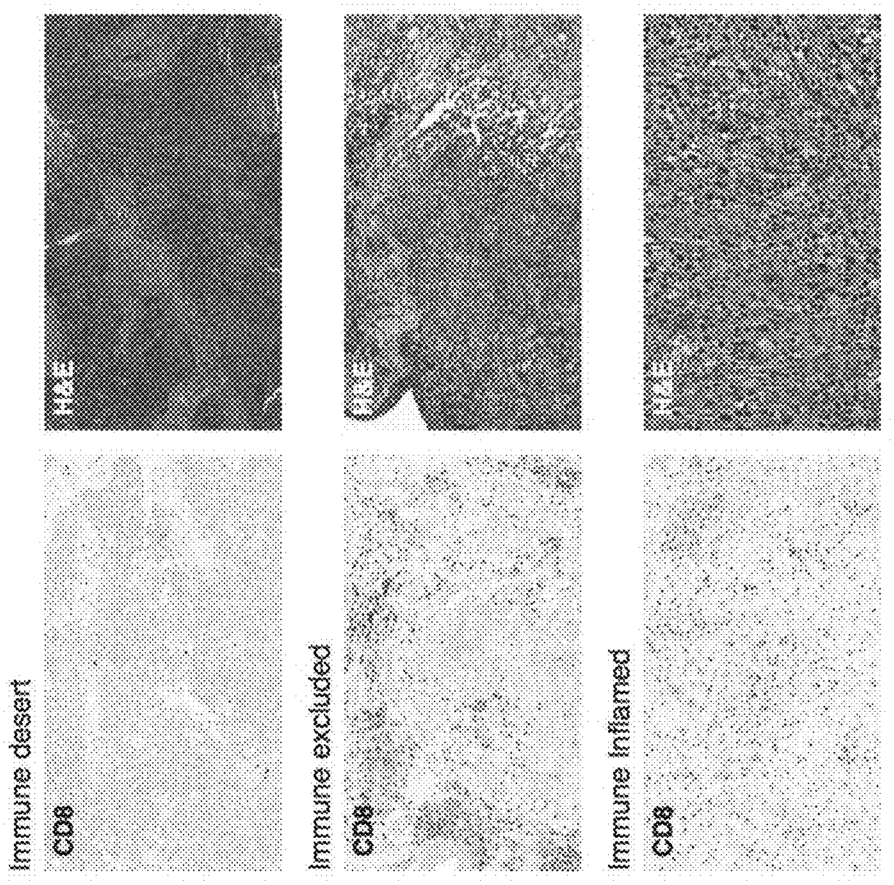

FIG. 3A is a series of images showing histology of the three tumor-immune phenotypes: immune "desert," immune "excluded," and immune "inflamed." Categorization of tumors into one of three immunophenotypic entities was performed on formalin-fixed, paraffin-embedded (FFPE) sections stained immunohistochemically for the presence of CD8+ T-cells. The categorization was based on prevalence of CD8+ cells as well as pattern of infiltration with respect to malignant epithelial cells. Tumors were categorized as "desert" when the prevalence of CD8+ cells was low (<10 CD8+ cells in an area of tumor and tumor-associated stroma at a magnification of 200×; in larger specimens, this was calculated as the average of 10 representative fields of view). Tumors were categorized as "excluded" if CD8+ cells were exclusively seen in stroma immediately adjacent to or within the main tumor mass. Tumors were categorized as "inflamed" if CD8+ cells were seen in direct contact with malignant epithelial cells either in the form of spillover of stromal infiltrates into tumor cell aggregates or of diffuse infiltration of CD8+ cells in aggregates or sheets of tumor cells. As these features were frequently observed in a focal manner, any such observation in a tumor lesion led to a categorization as "inflamed." H&E, hematoxylin and eosin stain.

FIG. 3B is an image showing combined CD8 IHC-trichrome stain performed on FFPE sections to visualize the spatial distribution of CD8+ T-cells and collagenous stroma. CD8+ T-cells outlined by 3,3'-diaminobenzidine (DAB) stain (brown) are primarily localized within collagenous (blue) stroma (white arrows). Rare CD8+ T-cells are interspersed between tumor cells (green arrows).

Figure 3C:
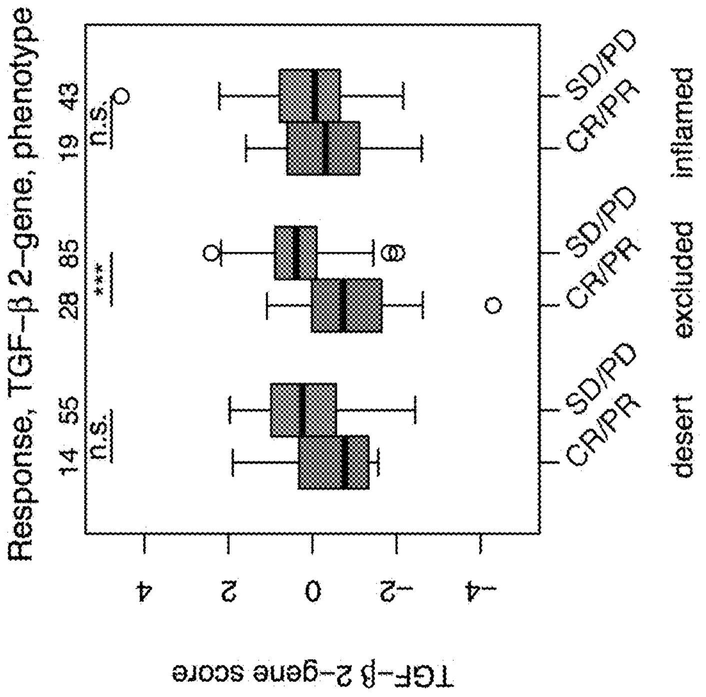
Figure 3D:
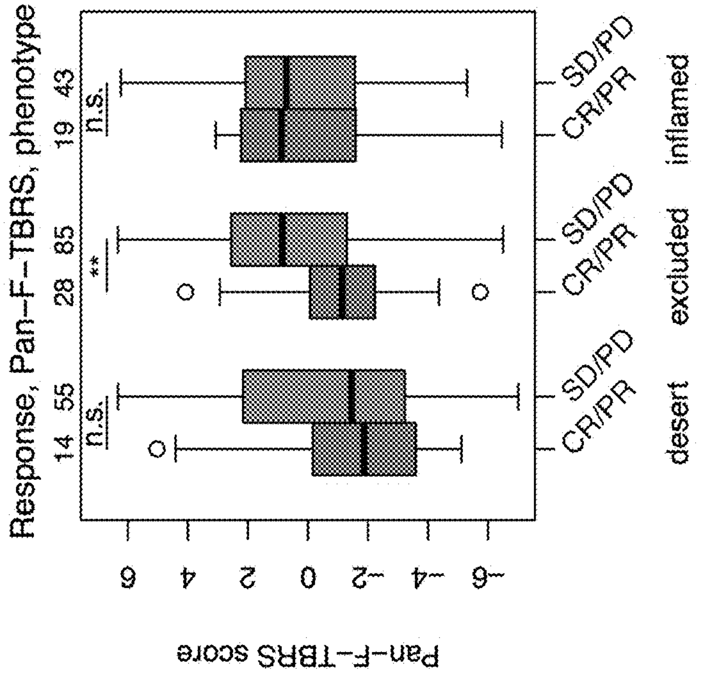

FIGS. 3C and 3D are a series of graphs showing the relationship between TGF-β 2-gene signature and pan-fibroblast TGF-β response signature (Pan-F-TBRS) scores and response status within each tumor-immune phenotype group. TGF-β 2-gene signature (FIG. 3C) or Pan-F-TBRS (FIG. 3D) scores (y-axis) are plotted by immune phenotype and response group. FIG. 3C shows that the TGF-β 2-gene signature was comparable across immune phenotypes but was significantly associated with response only in the excluded phenotype (adj. $p=5.7\times10^{-5}$; t test p-values Bonferroni corrected for three tests). A likelihood ratio test for interaction confirmed a phenotype-specific relationship between the TGF-β signature and response (p=0.02251). FIG. 3D shows that the Pan-F-TBRS was significantly associated with response only in the excluded phenotype (adj. p=0.0066; t test p-values Bonferroni corrected for three tests).

Figure 3E:
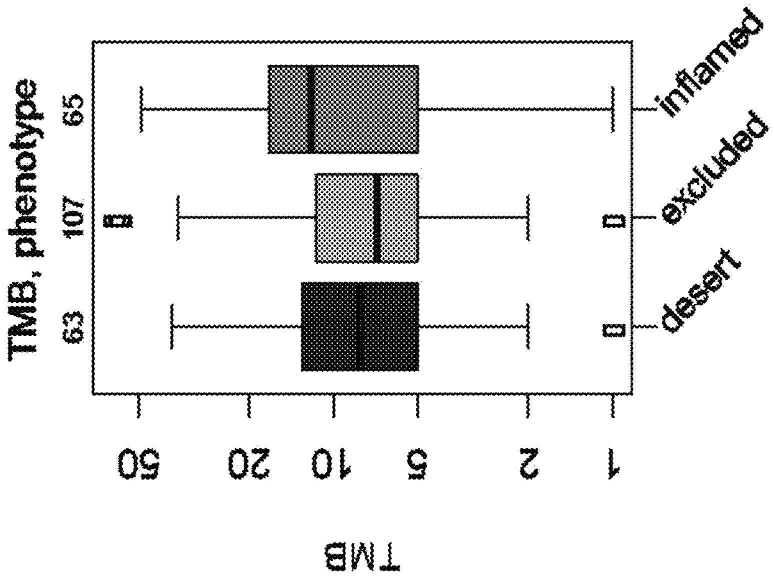

FIG. 3E is a graph showing TMB (y-axis) plotted against tumor-immune phenotype. There was no significant difference in TMB between cancer-immune phenotypes (Kruskal Wallis p=0.091).

Figure 4A:
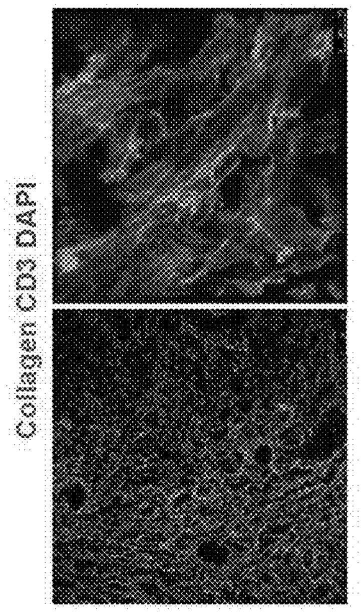

FIG. 4A is a series of images showing collagen (green) and T-cells (CD3, red) in EMT6 tumors stained by immunofluorescence.

Figure 4B:
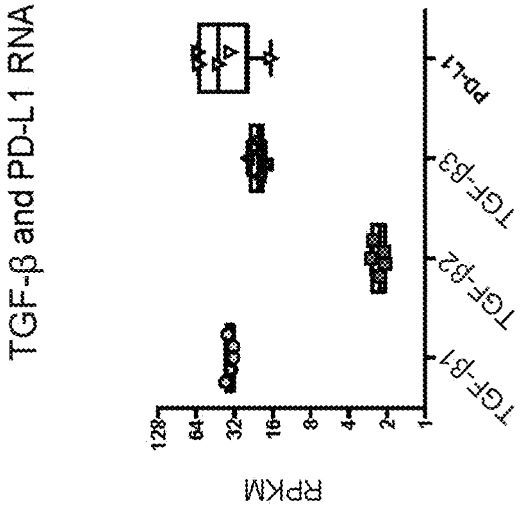

FIG. 4B is a graph showing quantification of TGF-β and PD-L1 RNA in whole EMT6 tumors by RNA sequencing (RNAseq). The tumors were inoculated orthotopically and collected when volume reached 300 $mm^3$ (N=5; data from one experiment).

Figure 4C:
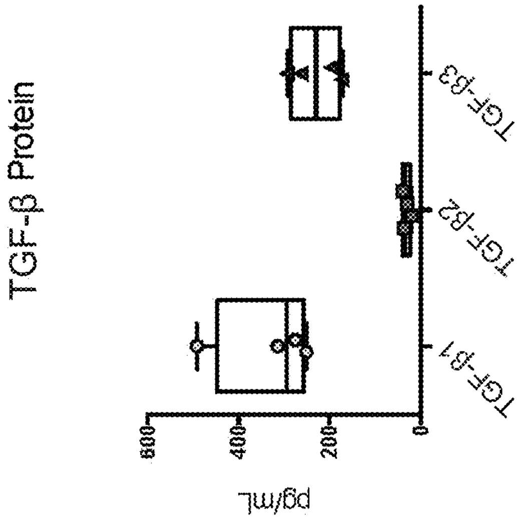

FIG. 4C is a graph showing quantification of TGF-β protein within whole EMT6 tumors by enzyme-linked immunosorbent assay (ELISA). Tumors were collected 14 days after inoculation, flash frozen, and lysed for protein quantification (N=4; data from one experiment).

Figure 4D:
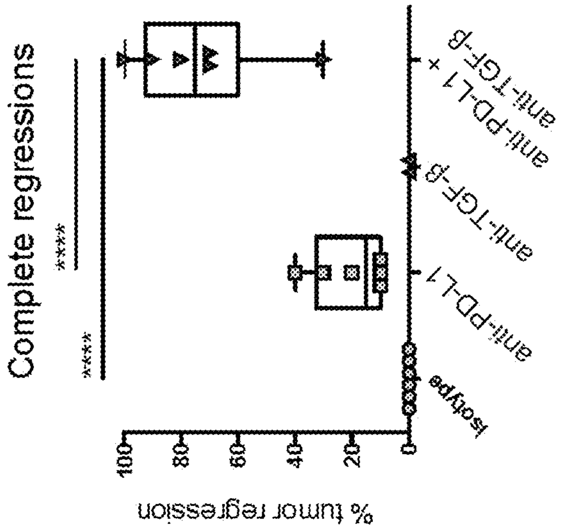
Figure 4E:
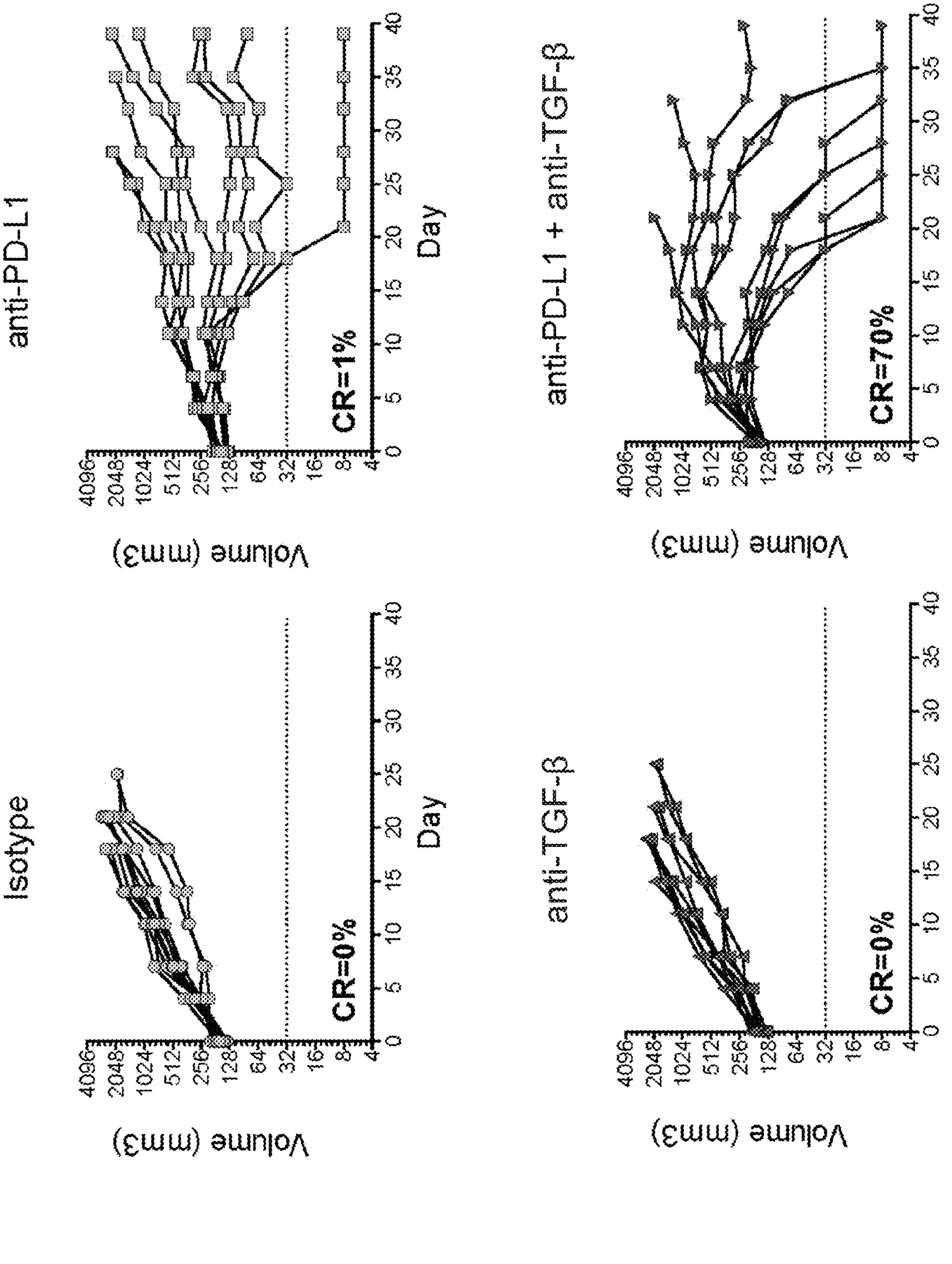
Figure 4F:
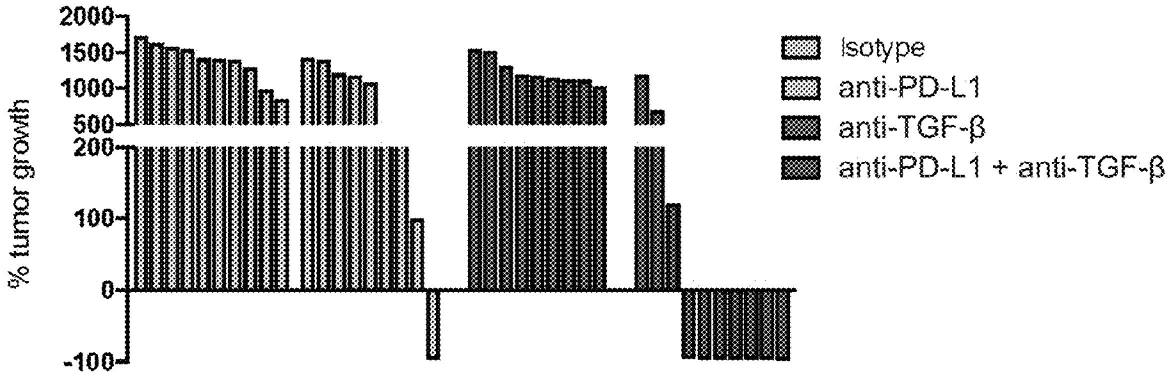

FIGS. 4D-4F is a series of graphs showing the results of studies in which BALB/c mice were inoculated with EMT6 tumor cells orthotopically in the mammary fat pad. When tumor volumes reached=160 $mm^3$ (mean±SD, 161.8±20.2 $mm^3$) approximately eight days after inoculation, mice were treated with isotype control, an anti-PD-L1 antibody, an anti-TGF-β antibody, or a combination of an anti-PD-L1 antibody with an anti-TGF-β antibody. Tumors were measured two times per week for approximately eight weeks by caliper. When tumor volumes fell below 32 $mm^3$ (lowest limit of detection), they were considered CR (100% tumor growth inhibition). FIG. 4D shows the percentage of CR across 2-6 independent studies. ****p<0.0001 by one-way ANOVA, Sidak multiple comparisons test. FIG. 4E shows tumor growth curves for each individual mouse. The data are from one representative of six independent experiments with 10 mice/group. FIG. 4F shows the change in tumor volume compared with baseline (onset of treatment). Data are from one representative of 6 independent experiments with 10 mice/group.

Figure 4G:
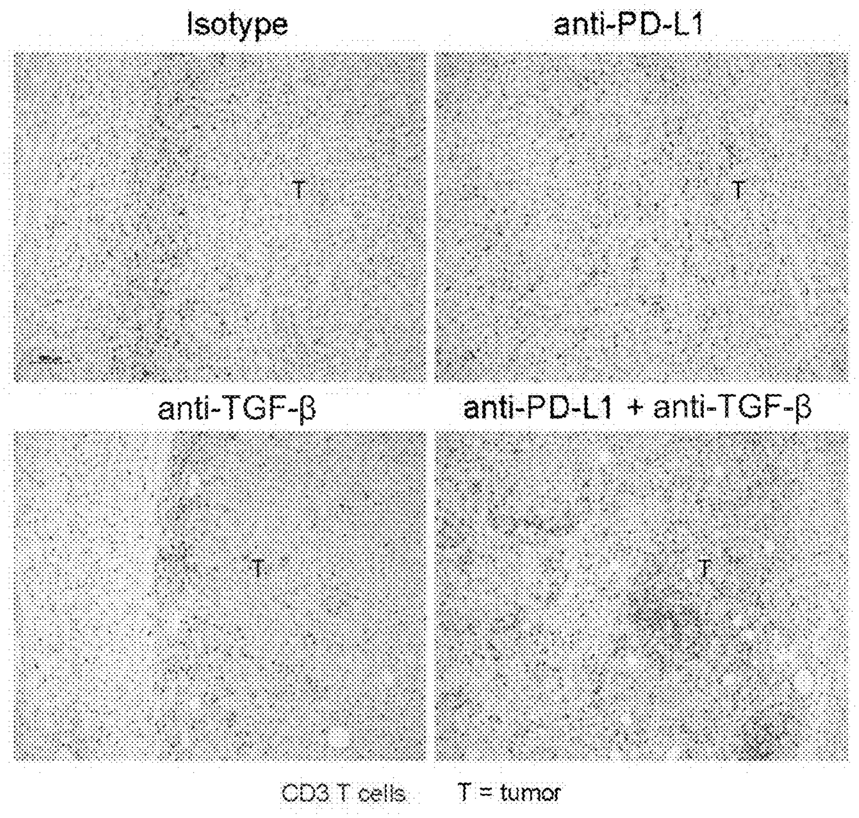

FIG. 4G is a series of images showing the distribution of tumor-infiltrating lymphocytes (TILs) assessed by IHC and digital imaging seven days after the initiation of treatment as described in FIGS. 4D-4F. Brown indicates representative CD3 staining. Scale bar, 100 microns.

Figure 4I:
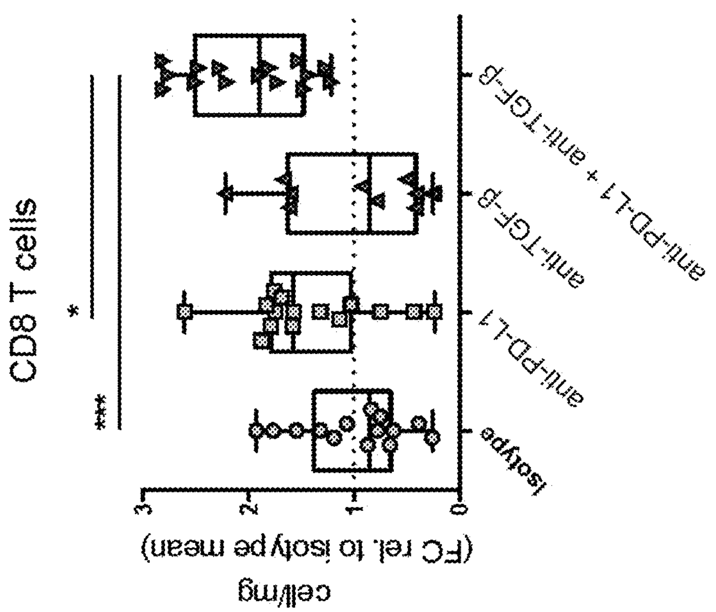
Figure 4H:
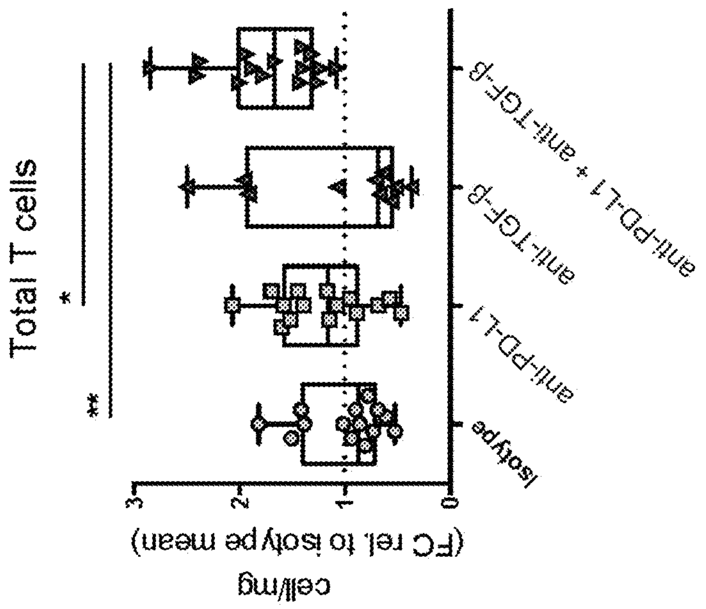
Figure 4K:
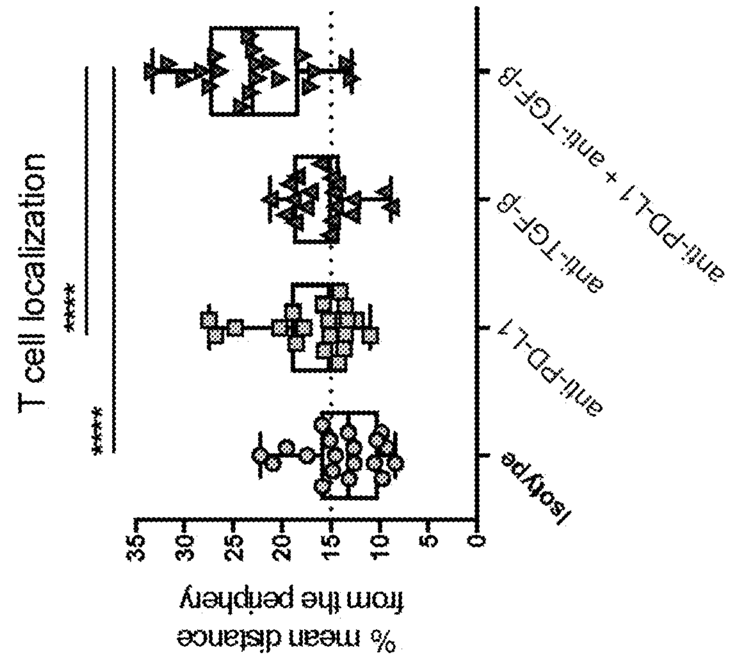
Figure 4J:
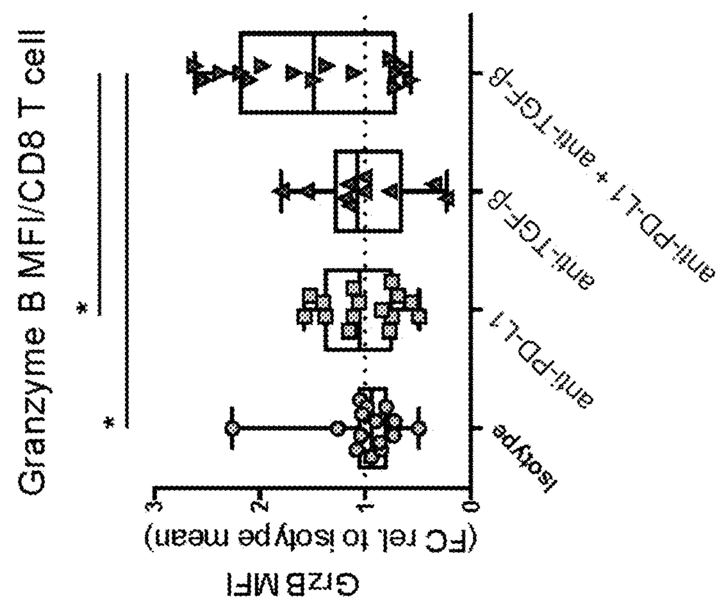

FIGS. 4H-4J are a series of graphs showing cytofluorimetric enumeration of TILs seven days after the initiation of treatment as described with respect to FIGS. 4D-4F. Abundance of total T-cells (FIG. 4H), CD8+ T-cells (FIG. 4I), and the mean fluorescence intensity (MFI) of granzyme B in CD8+ T-cells (FIG. 4J) are shown (N=15 for all groups, except anti-TGF-β antibody alone in which N=10; data from three combined experiments expressed as fold change relative to the isotype cell/mg average). *p<0.05; p<0.01; **p<0.0001 by one-way ANOVA, Sidak multiple comparisons test.

FIG. 4K is a graph showing TIL localization quantification at seven days after initiation of treatment as described in FIGS. 4D-4F. T-cells were stained by IHC (as in FIG. 4G) and their localization was digitally analyzed. Normalized mean distances of CD3 T-cells from the tumor periphery are shown as percentages (N=19-20; data from three combined experiments). ****p<0.0001 by Tukey HSD multiple comparison test.

Figure 4L:
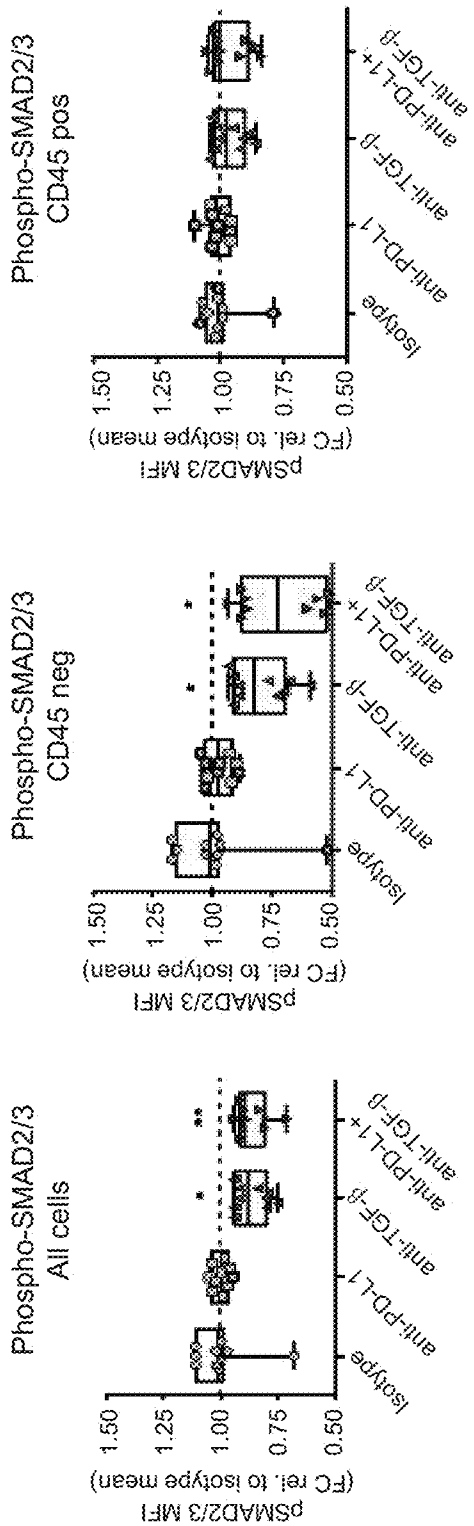

FIG. 4L is a graph showing phosphoflow analysis of SMAD2/3 in tumors seven days after the initiation of treatment as described in FIGS. 4D-4F. MFI of phospho-SMAD2/3 among total cells, CD45-, and CD45+ cells is shown. Data are expressed as fold change (FC) relative to the isotype MFI average. 10 mice/group from two combined experiments. *, p<0.05; **, p<0.01, one-way ANOVA, Dunnett's multiple comparisons test, compared to isotype.

Figure 4M:
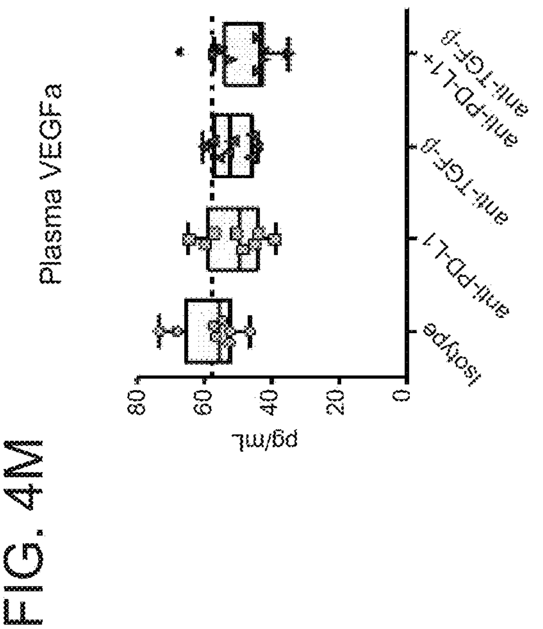

FIG. 4M is a graph showing quantification of VEGF-A protein in the plasma by ELISA seven days after the initiation of treatment as described in FIGS. 4D-4F. N=8 from one experiment. p=0.0194, one-way ANOVA, Dunnett's multiple comparisons test, compared to isotype.

Figure 4N:
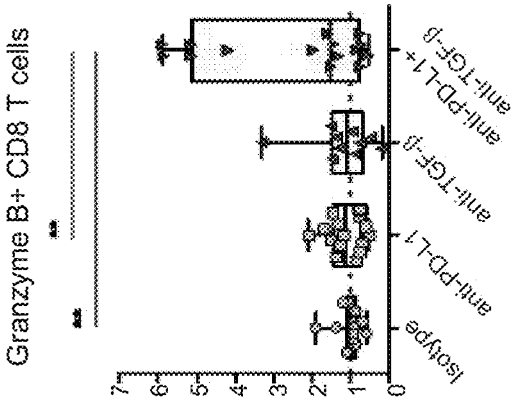

FIG. 4N is a graph showing cytofluorimetric analysis of T-cells seven days after initiation of the treatment as described in FIGS. 4D-4F. The percentage of GzmB+CD8 T-cells is shown. N=15 for all groups except for anti-TGF-β alone, in which N=10. These data are from three combined experiments expressed as fold change relative to the isotype cell/mg average. **, p<0.01 one-way ANOVA, Sidak's multiple comparisons test.

Figure 4O:
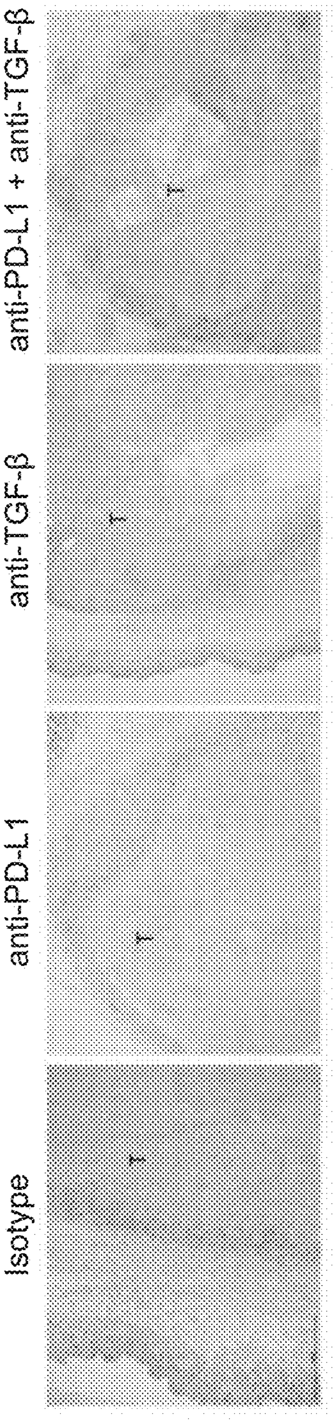

FIG. 4O is a graph showing distribution of TILs as assessed by immunohistochemistry and digital imaging seven days after the initiation of treatment as described in FIGS. 4D-4F. Brown indicates representative CD3 staining. Scale bar, 500 microns.

FIGS. 4P-4S are a series of graphs showing RNAseq analysis on whole tumors collected seven days after the initiation of treatment as described in FIGS. 4D-4F. Scores of Teff (FIG. 4P), Pan-F-TBRS (FIG. 4Q), T-cell and macrophage signatures (FIG. 4R), and the ratio of Teff to Pan-F-TBRS (FIG. 4S) in different treatment arms are shown. *p<0.05; p<0.01; *p<0.001.

Figure 4P:
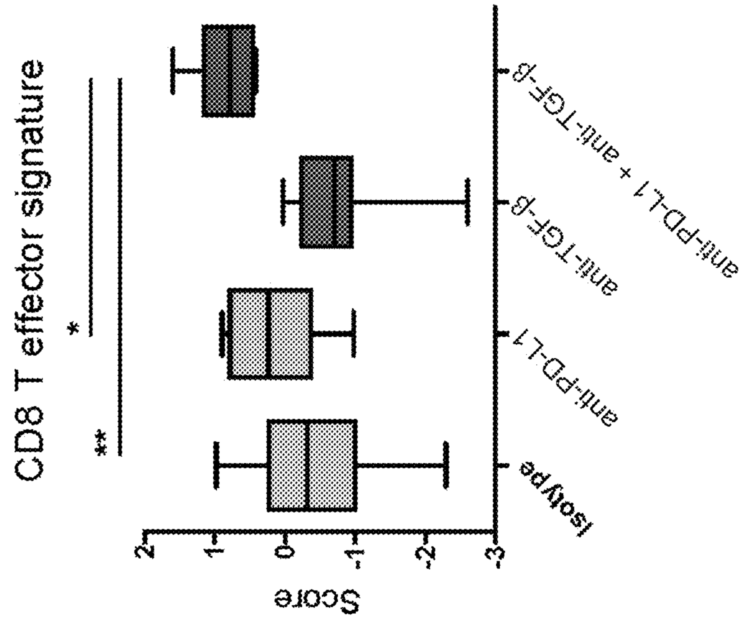
Figure 4Q:
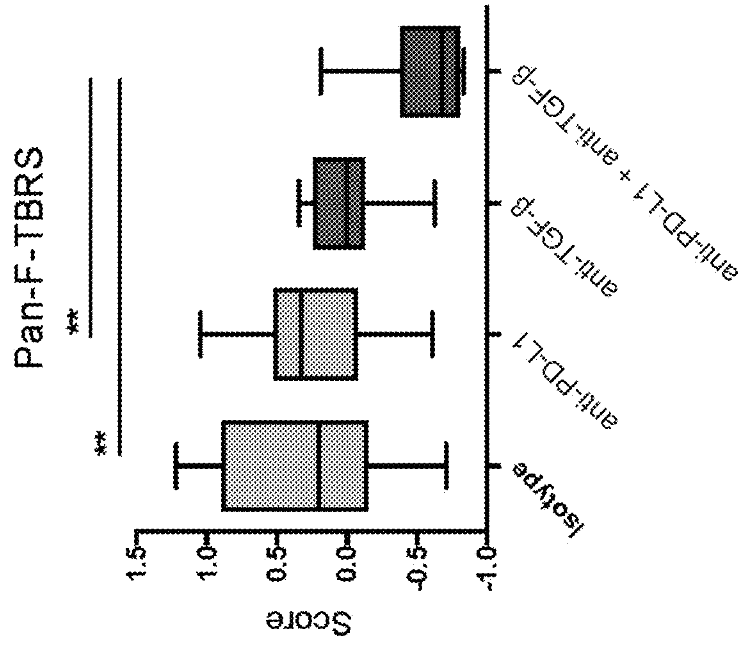
Figure 4R:
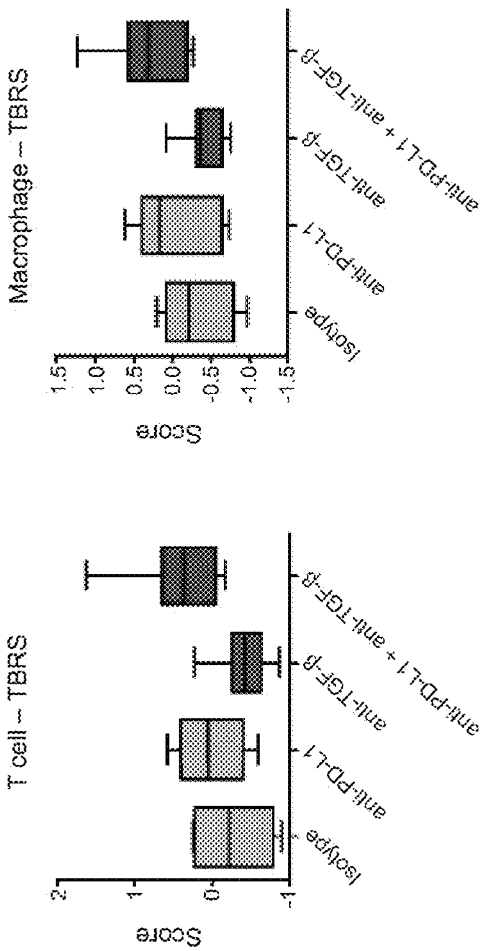
Figure 4S:
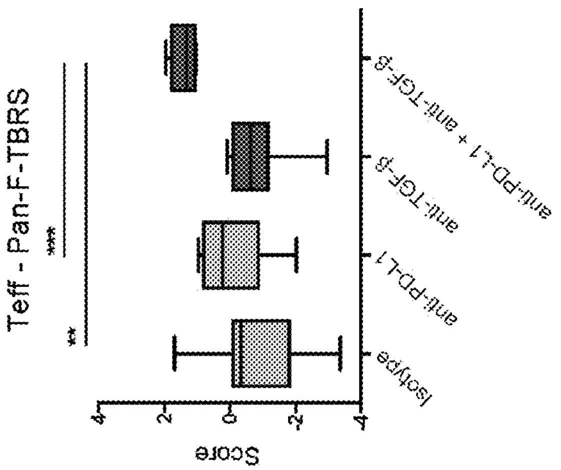
Figure 4T:
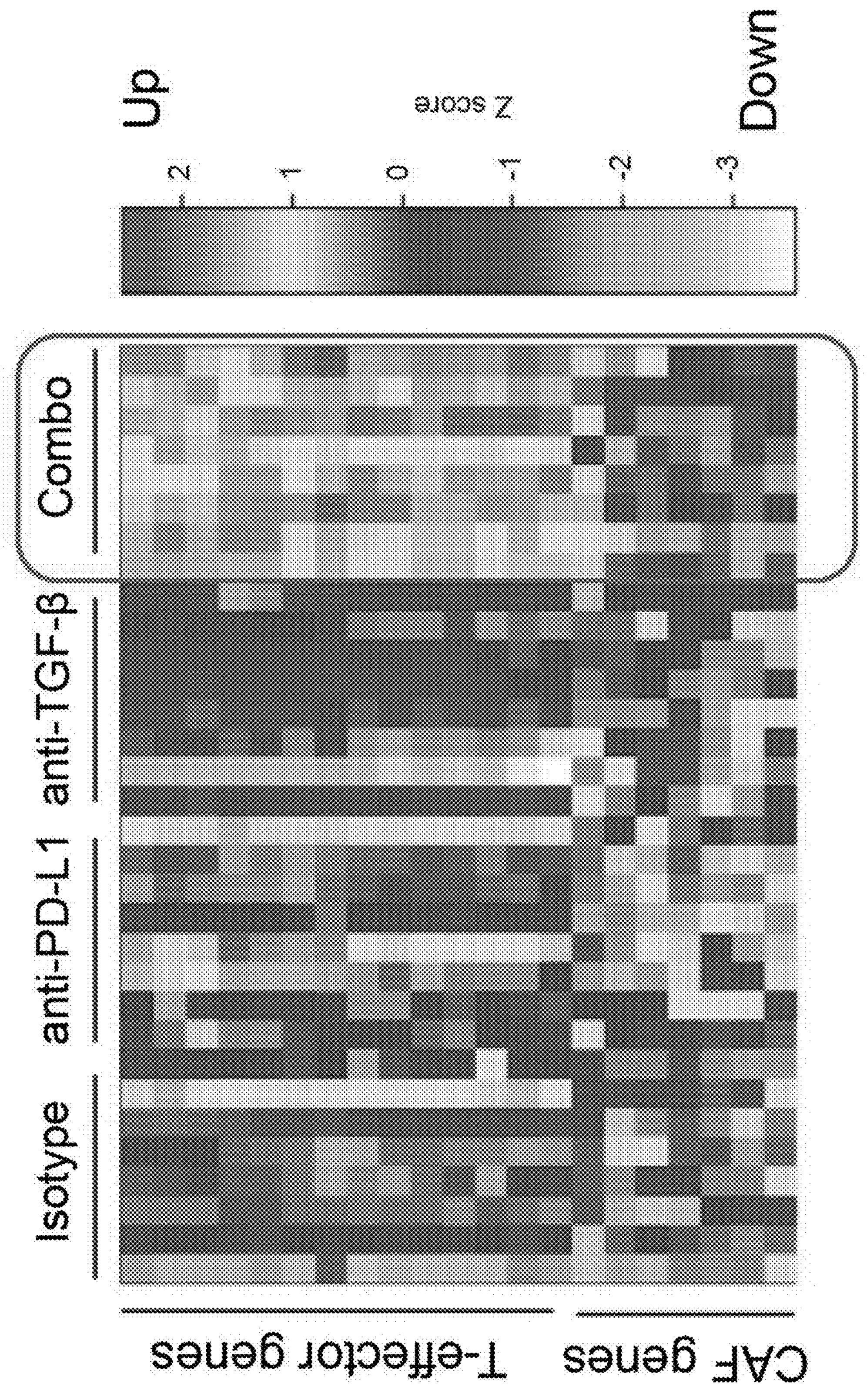

FIG. 4T is a heatmap showing expression of Teff and cancer-associated fibroblast remodeling (CAF) genes after the initiation of treatment as described with respect to FIGS. 4D-4F. Therapeutic administration of anti-TGF-β in combination with anti-PD-L1 promoted T-cell infiltration and CAF remodeling, resulting in complete responses.

Figure 4U:
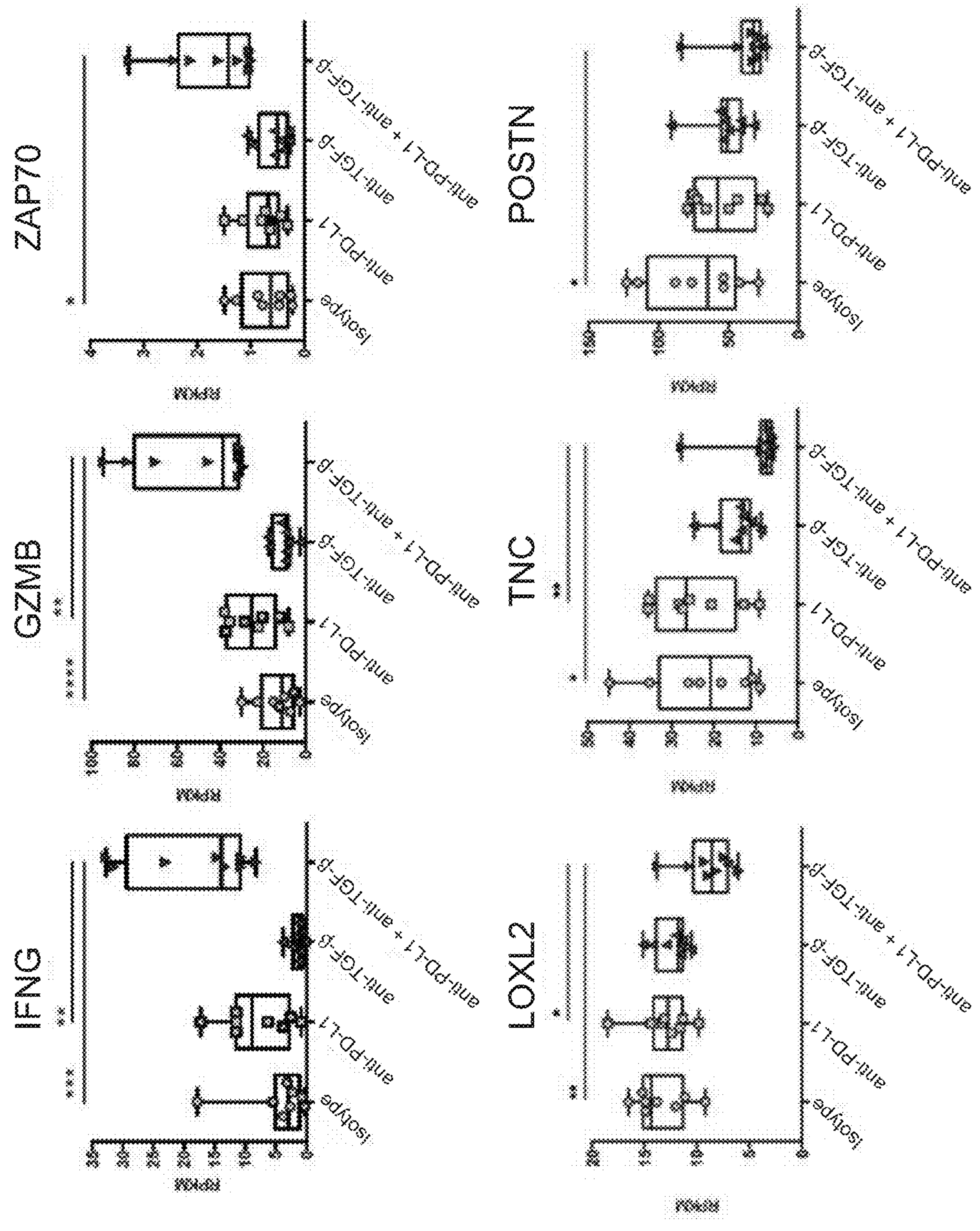

FIG. 4U is a series of graphs showing the expression of the indicated genes after the initiation of treatment as described with respect to FIGS. 4D-4F. Therapeutic administration of anti-TGF-β in combination with anti-PD-L1 resulted in increased expression of Teff genes including IFNG, GZMB, and ZAP70 (top) and decreased expression of CAF genes including LOXL2, TNC, and POSTN (bottom). RPKM, reads per kilobase per million mapped reads.

Figure 5:
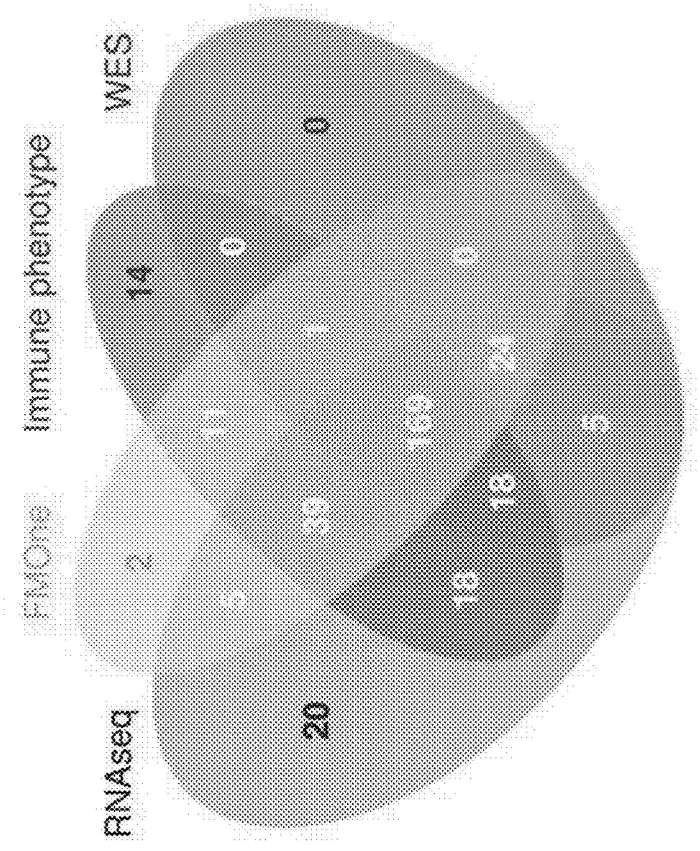

FIG. 5 is a Venn diagram showing overlap of the efficacy-evaluable patient populations with whole transcriptome (RNAseq), FMOne, cancer-immune phenotyping, and whole-exome sequencing (WES) data (n=326 for one or more of these assays). For gene expression analyses with respect to response, the complete RNAseq data set was used (n=298). For gene expression analyses in the context of TMB or immune phenotype, the intersect between RNAseq and FMOne (n=237) or immune phenotype (n=244) was used, respectively. For mutation analysis around immune phenotypes, the intersect between FMOne and immune phenotype was used (n=220). For associations between response or genes mutation status with TMB, the complete FMOne data set was used (n=251).

Figure 6A:
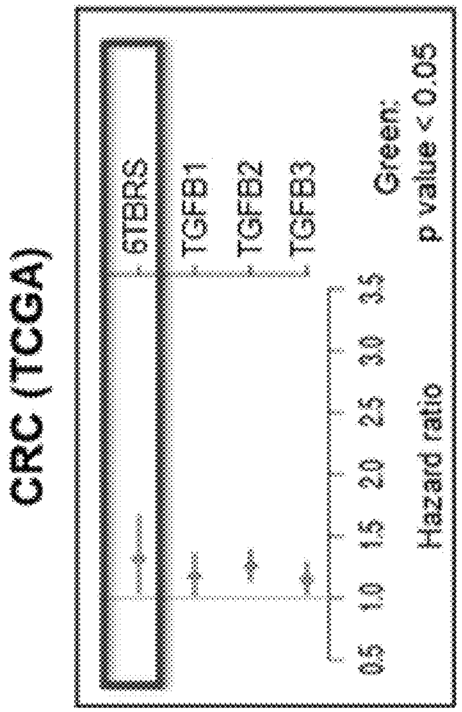
Figure 6B:
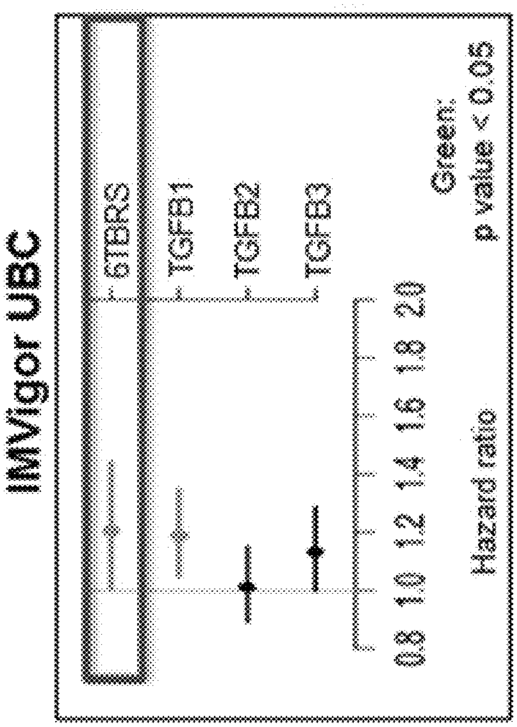
Figure 6C:
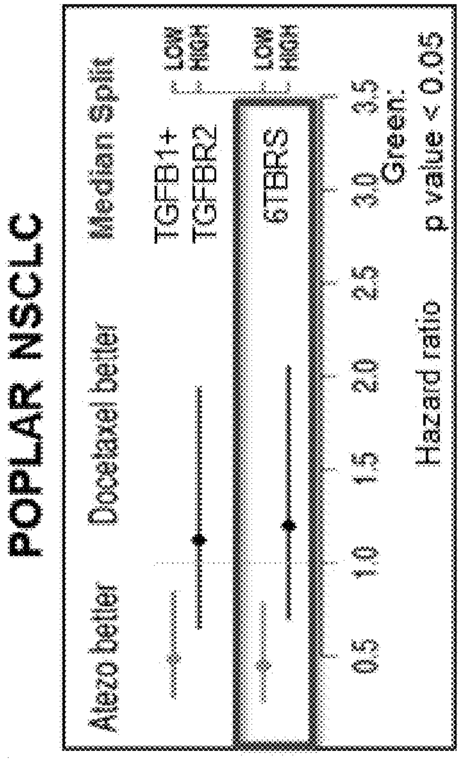

FIGS. 6A-6C are a series of graphs showing that high expression of the 6-gene signature ("6TBRS") is associated with poor prognosis (FIG. 6A) and with lack of benefit from atezolizumab monotherapy (FIGS. 6B and 6C). FIG. 6A shows data from the TCGA colorectal cancer dataset for the 6-gene signature, TGFB1, TGFB2, and TGFB3. FIG. 6B shows data from the IMvigor210 UC dataset for the 6-gene signature, TGFB1, TGFB2, and TGFB3. FIG. 6C shows data from the POPLAR NSCLC dataset for TGFB1+TGFBR2 and the 6-gene signature.

Figure 7B:
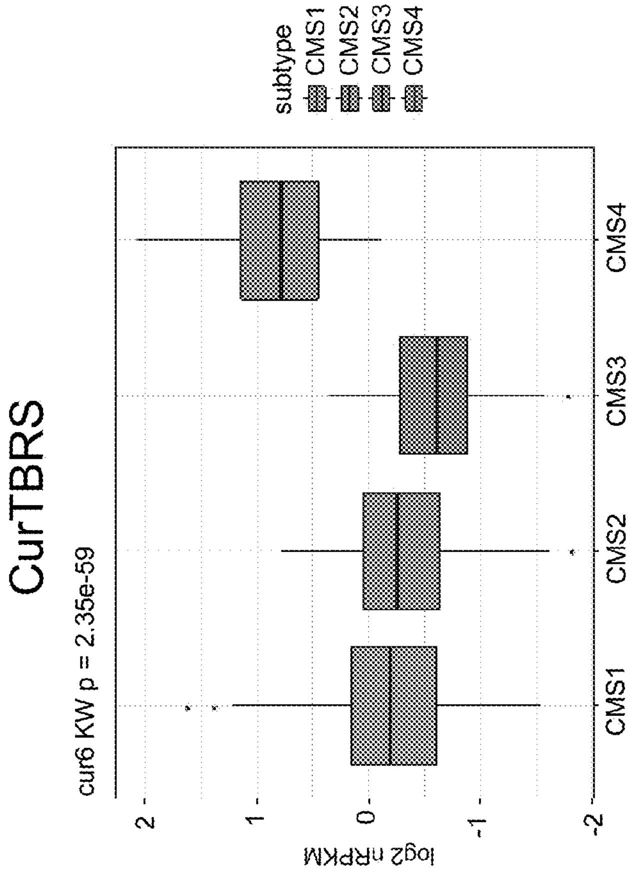
Figure 7A:
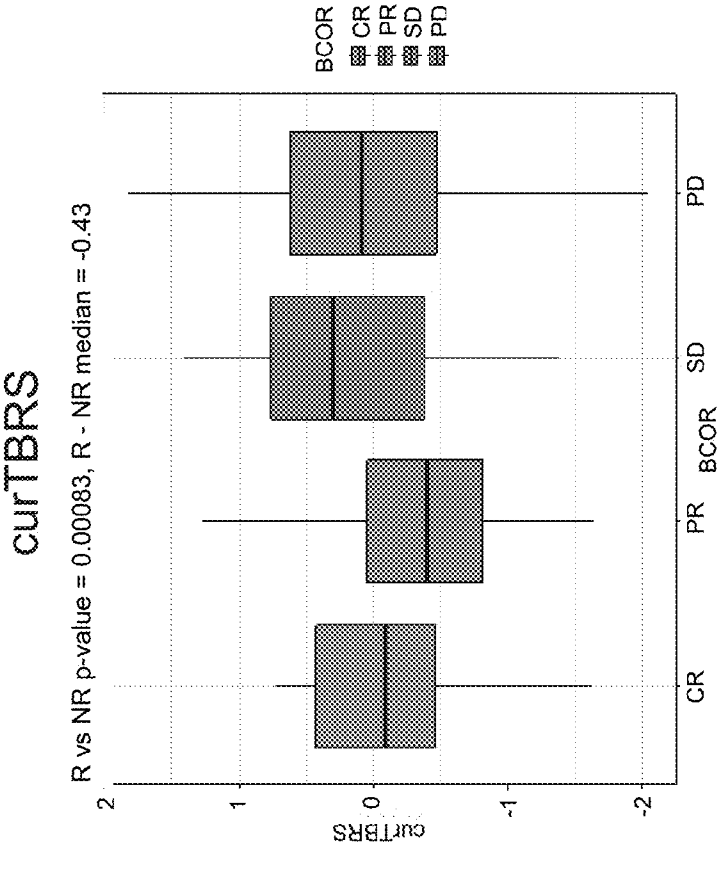

FIG. 7A is a graph showing that expression of the 6-gene signature (also referred to herein as "curTBRS") is associated with lack of response to atezolizumab.

FIG. 7B is a graph showing that high expression of the 6-gene signature is enriched in the CMS4 molecular subtype, a poor survival subgroup of CRC patients.

Figure 8A:
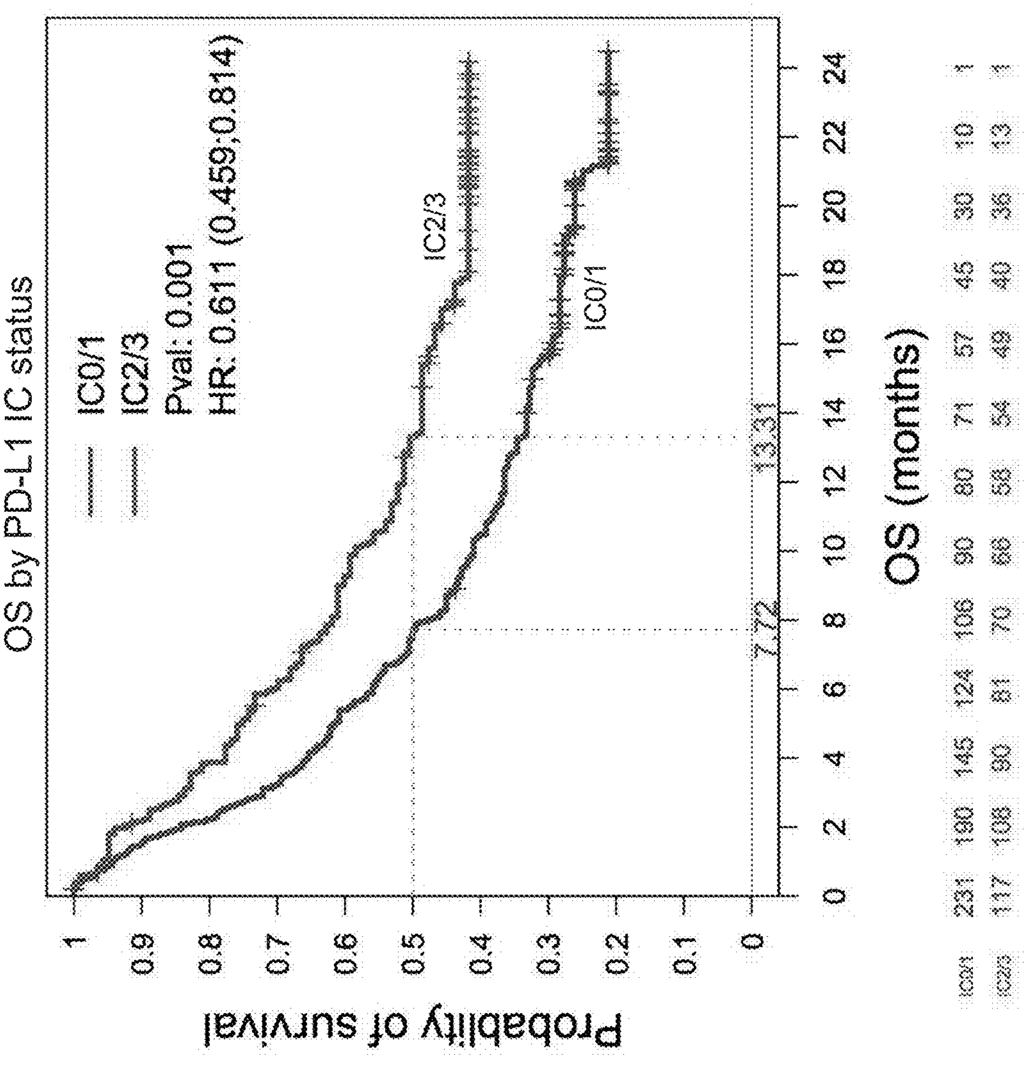
Figure 8B:
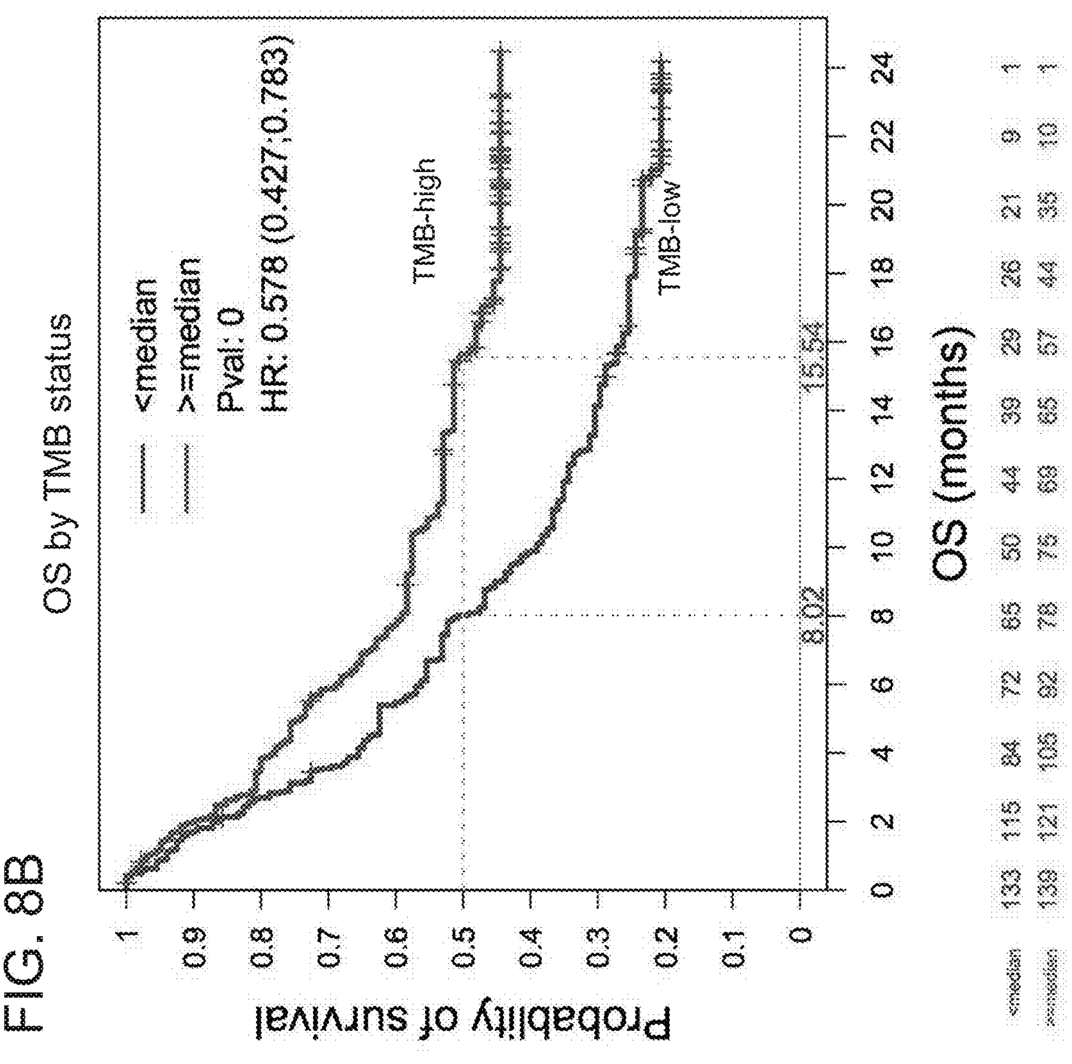
Figure 8C:
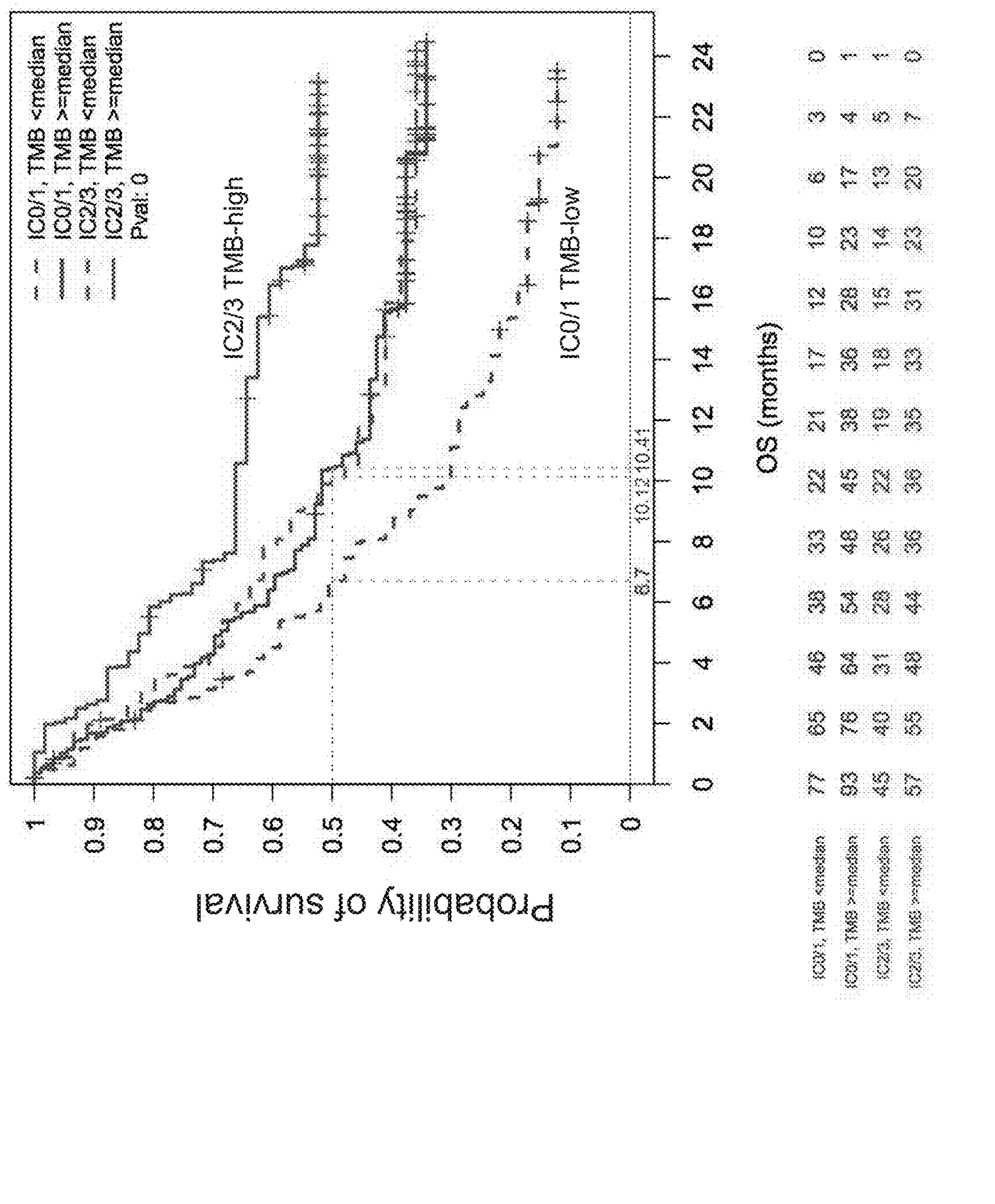

FIGS. 8A-8C are a series of graphs showing that high TMB and high PD-L1 IC scores are associated with improved OS benefit from atezolizumab therapy. FIG. 8A shows OS by PD-L1 status; FIG. 8B shows OS by TMB status; and FIG. 8C shows OS by combined PD-L1 IC and TMB status.

DETAILED DESCRIPTION OF THE INVENTION

The present invention provides diagnostic methods and uses, therapeutic methods and uses, and compositions for the treatment of cancer, including, but not limited to, a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer. The invention is based, at least in part, on the discovery that the expression level of one or more genes (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in a sample obtained from an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) can be used as a biomarker (including, but not limited to, a predictive biomarker and/or a pharmacodynamic biomarker) in methods of identifying whether the individual may benefit or is likely to respond to treatment with an anti-cancer therapy that includes an immunotherapy (including, but not limited to, a PD-L1 axis binding antagonist, e.g., an anti-PD-L1 antibody (e.g., atezolizumab)) and a suppressive stromal antagonist (including, but not limited to, a TGF-β antagonist, e.g., an anti-TGF-β antibody); selecting a therapy for treating the individual; optimizing therapeutic efficacy of a treatment that includes with an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody); and/or monitoring the response of the individual to a treatment that includes with an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody).

I. Definitions

It is to be understood that aspects and embodiments of the invention described herein include "comprising," "consisting," and "consisting essentially of" aspects and embodiments. As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se.

The term "biomarker" as used herein refers to an indicator, e.g., predictive, diagnostic, and/or prognostic, which can be detected in a sample. The biomarker may serve as an indicator of a particular subtype of a disease or disorder (e.g., cancer) characterized by certain, molecular, pathological, histological, and/or clinical features. In some embodiments, a biomarker is a gene. Biomarkers include, but are not limited to, polynucleotides (e.g., DNA, and/or RNA), polynucleotide copy number alterations (e.g., DNA copy numbers), polypeptides, polypeptide and polynucleotide modifications (e.g. posttranslational modifications), carbohydrates, and/or glycolipid-based molecular markers.

Such biomarkers include, but are not limited to, TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1. In some embodiments, the biomarker is one or more biomarkers selected from the group consisting of ACTA2, ADAM19, COMP, CTGF, TGFB1, and TGFBR2. In other embodiments, the biomarker is one or more biomarkers selected from the group consisting of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. Expression of such a biomarker may be determined to be higher or lower in a sample obtained from a patient sensitive or responsive to a treatment (e.g., treatment with an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody)) than a reference level (including, e.g., the median expression level of the biomarker in a sample from a group/population of patients, e.g., patients having cancer, and being tested for responsiveness to a treatment; the median expression level of the biomarker in a sample from a group/population of patients, e.g., patients having cancer, and identified as not responding to a treatment; the level in a sample previously obtained from the individual at a prior time; or the level in a sample from a patient who received prior treatment (e.g., treatment with an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody)) in a primary tumor setting, and who now may be experiencing metastasis).

The terms "biomarker signature," "signature," "biomarker expression signature," or "expression signature" are used interchangeably herein and refer to one or a combination of biomarkers whose expression is an indicator, e.g., predictive, diagnostic, and/or prognostic. The biomarker signature may serve as an indicator of a particular subtype of a disease or disorder (e.g., cancer) characterized by certain molecular, pathological, histological, and/or clinical features. In some embodiments, the biomarker signature is a "gene signature." The term "gene signature" is used interchangeably with "gene expression signature" and refers to one or a combination of polynucleotides whose expression is an indicator, e.g., predictive, diagnostic, and/or prognostic. In some embodiments, the biomarker signature is a "protein signature." The term "protein signature" is used interchangeably with "protein expression signature" and refers to one or a combination of polypeptides whose expression is an indicator, e.g., predictive, diagnostic, and/or prognostic. In some instances, the biomarker signature includes one or more biomarkers selected from the group consisting of TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1, which is also referred to herein as the "22-gene signature." In some instances, the biomarker signature includes one or more biomarkers selected from the group consisting of ACTA2, ADAM19, COMP, CTGF, TGFB1, and TGFBR2, which is also referred to herein as the "6-gene signature." In other instances, the biomarker signature includes one or more biomarkers selected from the group consisting of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 which is also referred to herein as is the "Pan-F-TBRS."

The term "TGFB1" as used herein, refers to any native TGFB1 (transforming growth factor beta 1) from any vertebrate source, including mammals such as primates (e.g., humans) and rodents (e.g., mice and rats), unless otherwise indicated. The term encompasses "full-length," unprocessed TGFB1 as well as any form of TGFB1 that results from processing in the cell. The term also encompasses naturally occurring variants of TGFB1, e.g., splice variants or allelic variants. The nucleic acid sequence of an exemplary human TGFB1 is shown under NCBI Reference Sequence: NM_000660.6 or in SEQ ID NO: 1. The amino acid sequence of an exemplary protein encoded by human TGFB1 is shown under UniProt Accession No. P01137 or in SEQ ID NO: 2.

The term "TGFBR2" as used herein, refers to any native TGFBR2 (transforming growth factor beta receptor 2; also known as TGFR-2 or TGFbeta-RII) from any vertebrate source, including mammals such as primates (e.g., humans) and rodents (e.g., mice and rats), unless otherwise indicated. The term encompasses "full-length," unprocessed TGFBR2 as well as any form of TGFBR2 that results from processing in the cell. The term also encompasses naturally occurring variants of TGFBR2, e.g., splice variants or allelic variants. The nucleic acid sequence of an exemplary human TGFBR2 is shown under NCBI Reference Sequence: NM_001024847 or in SEQ ID NO: 3. The amino acid sequence of an exemplary protein encoded by human TGFBR2 is shown under UniProt Accession No. P37173 or in SEQ ID NO: 4.

The term "ACTA2" as used herein, refers to any native ACTA2 (alpha-actin-2, also known as aortic smooth muscle actin or alpha smooth muscle actin) from any vertebrate source, including mammals such as primates (e.g., humans) and rodents (e.g., mice and rats), unless otherwise indicated. The term encompasses "full-length," unprocessed ACTA2 as well as any form of ACTA2 that results from processing in the cell. The term also encompasses naturally occurring variants of ACTA2, e.g., splice variants or allelic variants. The nucleic acid sequence of an exemplary human ACTA2 is shown under NCBI Reference Sequence: NM_001141945 or in SEQ ID NO: 5. The amino acid sequence of an exemplary protein encoded by human ACTA2 is shown under UniProt Accession No. P62736 or in SEQ ID NO: 6.

The term "ACTG2" as used herein, refers to any native ACTG2 (actin, gamma-enteric smooth muscle, also known as actin, gamma 2) from any vertebrate source, including mammals such as primates (e.g., humans) and rodents (e.g., mice and rats), unless otherwise indicated. The term encompasses "full-length," unprocessed ACTG2 as well as any form of ACTG2 that results from processing in the cell. The term also encompasses naturally occurring variants of ACTG2, e.g., splice variants or allelic variants. The nucleic acid sequence of an exemplary human ACTG2 is shown under NCBI Reference Sequence: NM_001615 or in SEQ ID NO: 7. The amino acid sequence of an exemplary protein encoded by human ACTG2 is shown under UniProt Accession No. P63267 or in SEQ ID NO: 8.

The term "ADAM12" as used herein, refers to any native ADAM12 (a disintegrin and metalloproteinase domain-containing protein 12, also known as ADAM metallopeptidase domain 12, MCMP, CAR10, and MLTN) from any vertebrate source, including mammals such as primates (e.g., humans) and rodents (e.g., mice and rats), unless otherwise indicated. The term encompasses "full-length," unprocessed ADAM12 as well as any form of ADAM12 that results from processing in the cell. The term also encompasses naturally occurring variants of ADAM12, e.g., splice variants or allelic variants. Splice variants include ADAM12-L, which has a transmembrane region and ADAM12-S, a shorter variant, which is soluble and lacks the transmembrane and cytoplasmic domains. The nucleic acid sequence of an exemplary human ADAM12 is shown under NCBI Reference Sequence: NM_003474 or in SEQ ID NO: 9. The amino acid sequence of an exemplary protein encoded by human ADAM12 is shown under UniProt Accession No. 043184 or in SEQ ID NO: 10.

The term "ADAM19" as used herein, refers to any native ADAM19 (a disintegrin and metalloproteinase domain-containing protein 19; also known as MADDAM or meltrin beta) from any vertebrate source, including mammals such as primates (e.g., humans) and rodents (e.g., mice and rats), unless otherwise indicated. The term encompasses "full-length," unprocessed ADAM19 as well as any form of ADAM19 that results from processing in the cell. The term also encompasses naturally occurring variants of ADAM19, e.g., splice variants or allelic variants. The nucleic acid sequence of an exemplary human ADAM19 is shown under NCBI Reference Sequence: NM_033274 or in SEQ ID NO: 11. The amino acid sequence of an exemplary protein encoded by human ADAM19 is shown under UniProt Accession No. Q9H013 or in SEQ ID NO: 12.

The term "COMP" as used herein, refers to any native COMP (cartilage oligomeric matrix protein; also known as thrombospondin-5) from any vertebrate source, including mammals such as primates (e.g., humans) and rodents (e.g., mice and rats), unless otherwise indicated. The term encompasses "full-length," unprocessed COMP as well as any form of COMP that results from processing in the cell. The term also encompasses naturally occurring variants of COMP, e.g., splice variants or allelic variants. The nucleic acid sequence of an exemplary human COMP is shown under NCBI Reference Sequence: NM_000095 or in SEQ ID NO: 81. The amino acid sequence of an exemplary protein encoded by human COMP is shown under UniProt Accession No. P49747 or in SEQ ID NO: 82.

The term "CNN1" as used herein, refers to any native CNN1 (calponin 1) from any vertebrate source, including mammals such as primates (e.g., humans) and rodents (e.g., mice and rats), unless otherwise indicated. The term encompasses "full-length," unprocessed CNN1 as well as any form of CNN1 that results from processing in the cell. The term also encompasses naturally occurring variants of CNN1, e.g., splice variants or allelic variants. The nucleic acid sequence of an exemplary human CNN1 is shown under NCBI Reference Sequence: NM_001299 or in SEQ ID NO: 13. The amino acid sequence of an exemplary protein encoded by human CNN1 is shown under UniProt Accession No. P51911 or in SEQ ID NO: 14.

The term "COL4A1" as used herein, refers to any native COL4A1 (collagen, type IV, alpha I, also known as collagen alpha-1(IV) chain) from any vertebrate source, including mammals such as primates (e.g., humans) and rodents (e.g., mice and rats), unless otherwise indicated. The term encompasses "full-length," unprocessed COL4A1 as well as any form of COL4A1 that results from processing in the cell. The term also encompasses naturally occurring variants of COL4A1, e.g., splice variants or allelic variants. The nucleic acid sequence of an exemplary human COL4A1 is shown under NCBI Reference Sequence: NM_001845 or in SEQ ID NO: 15. The amino acid sequence of an exemplary protein encoded by human COL4A1 is shown under UniProt Accession No. P02462 or in SEQ ID NO: 16.

The term "CTGF" as used herein, refers to any native CTGF (connective tissue growth factor, also known as CCN2 or IGFBP8) from any vertebrate source, including mammals such as primates (e.g., humans) and rodents (e.g., mice and rats), unless otherwise indicated. The term encompasses "full-length," unprocessed CTGF as well as any form of CTGF that results from processing in the cell. The term also encompasses naturally occurring variants of CTGF, e.g., splice variants or allelic variants. The nucleic acid sequence of an exemplary human CTGF is shown under NCBI Reference Sequence: NM_001901 or in SEQ ID NO: 17. The amino acid sequence of an exemplary protein encoded by human CTGF is shown under UniProt Accession No. P29279 or in SEQ ID NO: 18.

The term "CTPS1" as used herein, refers to any native CTPS1 (CTP synthase 1) from any vertebrate source, including mammals such as primates (e.g., humans) and rodents (e.g., mice and rats), unless otherwise indicated. The term encompasses "full-length," unprocessed CTPS1 as well as any form of CTPS1 that results from processing in the cell. The term also encompasses naturally occurring variants of CTPS1, e.g., splice variants or allelic variants. The nucleic acid sequence of an exemplary human CTPS1 is shown under NCBI Reference Sequence: NM_001905 or in SEQ ID NO: 19. The amino acid sequence of an exemplary protein encoded by human CTPS1 is shown under UniProt Accession No. P17812 or in SEQ ID NO: 20.

The term "FAM101B" as used herein, refers to any native FAM101B (family with sequence similarity 101, member B, also known as filamin-interacting protein FAM101B, refilin B, or RFLNB) from any vertebrate source, including mammals such as primates (e.g., humans) and rodents (e.g., mice and rats), unless otherwise indicated. The term encompasses "full-length," unprocessed FAM101B as well as any form of FAM101B that results from processing in the cell. The term also encompasses naturally occurring variants of FAM101B, e.g., splice variants or allelic variants. The nucleic acid sequence of an exemplary human FAM101B is shown under NCBI Reference Sequence: NM_182705 or in SEQ ID NO: 21. The amino acid sequence of an exemplary protein encoded by human FAM101B is shown under UniProt Accession No. Q8N5W9 or in SEQ ID NO: 22.

The term "FSTL3" as used herein, refers to any native FSTL3 (follistatin-related protein 3) from any vertebrate source, including mammals such as primates (e.g., humans) and rodents (e.g., mice and rats), unless otherwise indicated. The term encompasses "full-length," unprocessed FSTL3 as well as any form of FSTL3 that results from processing in the cell. The term also encompasses naturally occurring variants of FSTL3, e.g., splice variants or allelic variants. The nucleic acid sequence of an exemplary human FSTL3 is shown under NCBI Reference Sequence: NM_005860 or in SEQ ID NO: 23. The amino acid sequence of an exemplary protein encoded by human FSTL3 is shown under UniProt Accession No. 095633 or in SEQ ID NO: 24.

The term "HSPB1" as used herein, refers to any native HSPB1 (heat shock protein beta-1, also known as heat shock protein 27 or HSP27) from any vertebrate source, including mammals such as primates (e.g., humans) and rodents (e.g., mice and rats), unless otherwise indicated. The term encompasses "full-length," unprocessed HSPB1 as well as any form of HSPB1 that results from processing in the cell. The term also encompasses naturally occurring variants of HSPB1, e.g., splice variants or allelic variants. The nucleic acid sequence of an exemplary human HSPB1 is shown under NCBI Reference Sequence: NM_001540 or in SEQ ID NO: 25. The amino acid sequence of an exemplary protein encoded by human HSPB1 is shown under UniProt Accession No. P04792 or in SEQ ID NO: 26.

The term "IGFBP3" as used herein, refers to any native IGFBP3 (insulin-like growth factor-binding protein 3, also known as BP-53 or IBP3) from any vertebrate source, including mammals such as primates (e.g., humans) and rodents (e.g., mice and rats), unless otherwise indicated. The term encompasses "full-length," unprocessed IGFBP3 as well as any form of IGFBP3 that results from processing in the cell. The term also encompasses naturally occurring variants of IGFBP3, e.g., splice variants or allelic variants. The nucleic acid sequence of an exemplary human IGFBP3 is shown under NCBI Reference Sequence: NM_001013398 or in SEQ ID NO: 27. The amino acid sequence of an exemplary protein encoded by human IGFBP3 is shown under UniProt Accession No. P17936 or in SEQ ID NO: 28.

The term "PXDC1" as used herein, refers to any native PXDC1 (PX domain-containing protein 1) from any vertebrate source, including mammals such as primates (e.g., humans) and rodents (e.g., mice and rats), unless otherwise indicated. The term encompasses "full-length," unprocessed PXDC1 as well as any form of PXDC1 that results from processing in the cell. The term also encompasses naturally occurring variants of PXDC1, e.g., splice variants or allelic variants. The nucleic acid sequence of an exemplary human PXDC1 is shown under NCBI Reference Sequence: NM_183373 or in SEQ ID NO: 29. The amino acid sequence of an exemplary protein encoded by human PXDC1 is shown under UniProt Accession No. Q5TGL8 or in SEQ ID NO: 30.

The term "SEMA7A" as used herein, refers to any native SEMA7A (semaphorin 7A, also known as CD108 or John-Milton-Hagen blood group antigen) from any vertebrate source, including mammals such as primates (e.g., humans) and rodents (e.g., mice and rats), unless otherwise indicated. The term encompasses "full-length," unprocessed SEMA7A as well as any form of SEMA7A that results from processing in the cell. The term also encompasses naturally occurring variants of SEMA7A, e.g., splice variants or allelic variants. The nucleic acid sequence of an exemplary human SEMA7A is shown under NCBI Reference Sequence: NM_003612 or in SEQ ID NO: 31. The amino acid sequence of an exemplary protein encoded by human SEMA7A is shown under UniProt Accession No. 075326 or in SEQ ID NO: 32.

The term "SH3PXD2A" as used herein, refers to any native SH3PXD2A (SH3 and PX domain-containing protein 2A) from any vertebrate source, including mammals such as primates (e.g., humans) and rodents (e.g., mice and rats), unless otherwise indicated. The term encompasses "full-length," unprocessed SH3PXD2A as well as any form of SH3PXD2A that results from processing in the cell. The term also encompasses naturally occurring variants of SH3PXD2A, e.g., splice variants or allelic variants. The nucleic acid sequence of an exemplary human SH3PXD2A is shown under NCBI Reference Sequence: NM_014631 or in SEQ ID NO: 33. The amino acid sequence of an exemplary protein encoded by human SH3PXD2A is shown under UniProt Accession No. Q5TCZ1 or in SEQ ID NO: 34.

The term "TAGLN" as used herein, refers to any native TAGLN (transgelin) from any vertebrate source, including mammals such as primates (e.g., humans) and rodents (e.g., mice and rats), unless otherwise indicated. The term encompasses "full-length," unprocessed TAGLN as well as any form of TAGLN that results from processing in the cell. The term also encompasses naturally occurring variants of TAGLN, e.g., splice variants or allelic variants. The nucleic acid sequence of an exemplary human TAGLN is shown under NCBI Reference Sequence: NM_001001522 or in SEQ ID NO: 35. The amino acid sequence of an exemplary protein encoded by human TAGLN is shown under UniProt Accession No. Q01995 or in SEQ ID NO: 36.

The term "TGFBI" as used herein, refers to any native TGFBI (transforming growth factor, beta-induced) from any vertebrate source, including mammals such as primates (e.g., humans) and rodents (e.g., mice and rats), unless otherwise indicated. The term encompasses "full-length," unprocessed TGFBI as well as any form of TGFBI that results from processing in the cell. The term also encompasses naturally occurring variants of TGFBI, e.g., splice variants or allelic variants. The nucleic acid sequence of an exemplary human TGFBI is shown under NCBI Reference Sequence: NM_000358 or in SEQ ID NO: 37. The amino acid sequence of an exemplary protein encoded by human TGFBI is shown under UniProt Accession No. Q15582 or in SEQ ID NO: 38.

The term "TNS1" as used herein, refers to any native TNS1 (tensin-1) from any vertebrate source, including mammals such as primates (e.g., humans) and rodents (e.g., mice and rats), unless otherwise indicated. The term encompasses "full-length," unprocessed TNS1 as well as any form of TNS1 that results from processing in the cell. The term also encompasses naturally occurring variants of TNS1, e.g., splice variants or allelic variants. The nucleic acid sequence of an exemplary human TNS1 is shown under NCBI Reference Sequence: NM_022648 or in SEQ ID NO: 39. The amino acid sequence of an exemplary protein encoded by human TNS1 is shown under UniProt Accession No. Q9HBL0 or in SEQ ID NO: 40.

The term "TPM1" as used herein, refers to any native TPM1 (tropomyosin alpha-1 chain) from any vertebrate source, including mammals such as primates (e.g., humans) and rodents (e.g., mice and rats), unless otherwise indicated. The term encompasses "full-length," unprocessed TPM1 as well as any form of TPM1 that results from processing in the cell. The term also encompasses naturally occurring variants of TPM1, e.g., splice variants or allelic variants. The human TPM1 gene encodes at least 10 variants via alternative splicing and/or the use of two promoters. The nucleic acid sequence of an exemplary human TPM1 is shown under NCBI Reference Sequence: NM_001018005.1 or in SEQ ID NO: 41. The amino acid sequence of an exemplary protein encoded by human TPM1 is shown under UniProt Accession No. P09493 or in SEQ ID NO: 42. Sequences of human TPM1 protein isoforms are shown under UniProt Accession Nos. P09493-1, P09493-2, P09493-3, P09493-4, P09493-5, P09493-6, P09493-7, P09493-8, P09493-9, and P09493-10. In some embodiments, the human TPM1 protein has the amino acid sequence shown under UniProt Accession No. P09493-1.

The term "CD8A" as used herein, refers to any native CD8A from any vertebrate source, including mammals such as primates (e.g., humans) and rodents (e.g., mice and rats), unless otherwise indicated. The term encompasses "full-length," unprocessed CD8A as well as any form of CD8A that results from processing in the cell. The term also encompasses naturally occurring variants of CD8A, e.g., splice variants or allelic variants. The nucleic acid sequence of an exemplary human CD8A is shown under EMBL Accession No. M12824 or in SEQ ID NO: 43. The amino acid sequence of an exemplary protein encoded by human CD8A is shown under UniProt Accession No. P01732-1 or in SEQ ID NO: 44.

The term "CXCL9" as used herein, refers to any native CXCL9 (chemokine (C—X—C motif) ligand 9) from any vertebrate source, including mammals such as primates (e.g., humans) and rodents (e.g., mice and rats), unless otherwise indicated. The term encompasses "full-length," unprocessed CXCL9 as well as any form of CXCL9 that results from processing in the cell. The term also encompasses naturally occurring variants of CXCL9, e.g., splice variants or allelic variants. The nucleic acid sequence of an exemplary human CXCL9 is set forth in SEQ ID NO: 45. The amino acid sequence of an exemplary protein encoded by human CXCL9 is shown in SEQ ID NO: 46.

The term "CXCL10" as used herein, refers to any native CXCL10 (chemokine (C—X—C motif) ligand 10) from any vertebrate source, including mammals such as primates (e.g., humans) and rodents (e.g., mice and rats), unless otherwise indicated. The term encompasses "full-length," unprocessed CXCL10 as well as any form of CXCL10 that results from processing in the cell. The term also encompasses naturally occurring variants of CXCL10, e.g., splice variants or allelic variants. The nucleic acid sequence of an exemplary human CXCL10 is set forth in SEQ ID NO: 47. The amino acid sequence of an exemplary protein encoded by human CXCL10 is shown in SEQ ID NO: 48.

The term "GZMA" as used herein, refers to any native GZMA (granzyme A) from any vertebrate source, including mammals such as primates (e.g., humans) and rodents (e.g., mice and rats), unless otherwise indicated. The term encompasses "full-length," unprocessed GZMA as well as any form of GZMA that results from processing in the cell. The term also encompasses naturally occurring variants of GZMA, e.g., splice variants or allelic variants. The nucleic acid sequence of an exemplary human GZMA is set forth in SEQ ID NO: 49. The amino acid sequence of an exemplary protein encoded by human GZMA is shown in SEQ ID NO: 50.

The term "GZMB" as used herein, refers to any native GZMB (granzyme B) from any vertebrate source, including mammals such as primates (e.g., humans) and rodents (e.g., mice and rats), unless otherwise indicated. The term encompasses "full-length," unprocessed GZMB as well as any form of GZMB that results from processing in the cell. The term also encompasses naturally occurring variants of GZMB, e.g., splice variants or allelic variants. The nucleic acid sequence of an exemplary human GZMB is set forth in SEQ ID NO: 51. The amino acid sequence of an exemplary protein encoded by human GZMB is shown in SEQ ID NO: 52.

The term "PRF1" as used herein, refers to any native PRF1 (perforin 1; also known as pore forming protein) from any vertebrate source, including mammals such as primates (e.g., humans) and rodents (e.g., mice and rats), unless otherwise indicated. The term encompasses "full-length," unprocessed PRF1 as well as any form of PRF1 that results from processing in the cell. The term also encompasses naturally occurring variants of PRF1, e.g., splice variants or allelic variants. The nucleic acid sequence of an exemplary human PRF1 is set forth in SEQ ID NO: 53. The amino acid sequence of an exemplary protein encoded by human PRF1 is shown in SEQ ID NO: 54.

The term "IFNG" as used herein, refers to any native IFNG (interferon, gamma; also referred to herein as IFN-γ) from any vertebrate source, including mammals such as primates (e.g., humans) and rodents (e.g., mice and rats), unless otherwise indicated. The term encompasses "full-length," unprocessed IFNG as well as any form of IFNG that results from processing in the cell. The term also encompasses naturally occurring variants of IFNG, e.g., splice variants or allelic variants. The nucleic acid sequence of an exemplary human IFNG is set forth in SEQ ID NO: 55. The amino acid sequence of an exemplary protein encoded by human IFNG is shown in SEQ ID NO: 56.

The term "TBX21" as used herein, refers to any native TBX21 (T-box transcription factor 21) from any vertebrate source, including mammals such as primates (e.g., humans) and rodents (e.g., mice and rats), unless otherwise indicated. The term encompasses "full-length," unprocessed TBX21 as well as any form of TBX21 that results from processing in the cell. The term also encompasses naturally occurring variants of TBX21, e.g., splice variants or allelic variants. The nucleic acid sequence of an exemplary human TBX21 is shown under NCBI Reference Sequence: NM_013351.1 or in SEQ ID NO: 57. The amino acid sequence of an exemplary protein encoded by human TBX21 is shown under UniProt Accession No. Q9UL17 or in SEQ ID NO: 58.

The terms "Programmed Death Ligand 1" and "PD-L1" refer herein to a native sequence PD-L1 polypeptide, polypeptide variants, and fragments of a native sequence polypeptide and polypeptide variants (which are further defined herein). The PD-L1 polypeptide described herein may be that which is isolated from a variety of sources, such as from human tissue types or from another source, or prepared by recombinant or synthetic methods.

A "native sequence PD-L1 polypeptide" comprises a polypeptide having the same amino acid sequence as the corresponding PD-L1 polypeptide derived from nature. The term encompasses "full-length," unprocessed PD-L1 as well as any form of PD-L1 that results from processing in the cell. The term also encompasses naturally occurring variants of PD-L1, e.g., splice variants or allelic variants. For example, a native sequence PD-L1 polypeptide may be PD-L1 isoform 1 (also known as PD-L1I; see, e.g., UniProt Accession No. Q9NZQ7-1), PD-L1 isoform 2 (also known as PD-L1II; see, e.g., UniProt Accession No. Q9NZQ7-2), or PD-L1 isoform 3 (see, e.g., UniProt Accession No. Q9NZQ7-3). The nucleic acid sequence of an exemplary human PD-L1 is shown under NCBI Reference Sequence: NM_014143 or in SEQ ID NO: 59. The amino acid sequence of an exemplary protein encoded by human PD-L1 is shown under UniProt Accession No. Q9NZQ7 or in SEQ ID NO: 60.

A "PD-L1 polypeptide variant," or variations thereof, means a PD-L1 polypeptide, generally an active PD-L1 polypeptide, as defined herein having at least about 80% amino acid sequence identity with any of the native sequence PD-L1 polypeptide sequences as disclosed herein. Such PD-L1 polypeptide variants include, for instance, PD-L1 polypeptides wherein one or more amino acid residues are added, or deleted, at the N- or C-terminus of a native amino acid sequence. Ordinarily, a PD-L1 polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence PD-L1 polypeptide sequence as disclosed herein. Ordinarily, PD-L1 variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 281, 282, 283, 284, 285, 286, 287, 288, or 289 amino acids in length, or more. Optionally, PD-L1 variant polypeptides will have no more than one conservative amino acid substitution as compared to a native PD-L1 polypeptide sequence, alternatively no more than 2, 3, 4, 5, 6, 7, 8, 9, or 10 conservative amino acid substitutions as compared to the native PD-L1 polypeptide sequence.

The term "detecting" is used herein in the broadest sense to include both qualitative and quantitative measurements of a target molecule. Detecting includes identifying the mere presence of the target molecule in a sample as well as determining whether the target molecule is present in the sample at detectable levels. Detecting may be direct or indirect.

The terms "level of expression" or "expression level" in general are used interchangeably and generally refer to the amount of a biomarker in a biological sample. "Expression" generally refers to the process by which information (e.g., gene-encoded and/or epigenetic information) is converted into the structures present and operating in the cell. Therefore, as used herein, "expression" may refer to transcription into a polynucleotide, translation into a polypeptide, or even polynucleotide and/or polypeptide modifications (e.g., post-translational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs). An expression level for more than one gene of interest may be determined by aggregation methods known to one skilled in the art and also disclosed herein, including, for example, by calculating the median or mean of all the expression levels of the genes of interest. Before aggregation, the expression level of each gene of interest may be normalized by using statistical methods known to one skilled in the art and also disclosed herein, including, for example, normalized to the expression level of one or more housekeeping genes, or normalized to a total library size, or normalized to the median or mean expression level value across all genes measured. In some instances, before aggregation across multiple genes of interest, the normalized expression level of each gene of interest may be standardized by using statistical methods known to one skilled in the art and also disclosed herein, including, for example, by calculating the Z-score of the normalized expression level of each gene of interest.

The term "sample," as used herein, refers to a composition that is obtained or derived from a patient and/or individual of interest that contains a cellular and/or other molecular entity that is to be characterized and/or identified, for example, based on physical, biochemical, chemical, and/or physiological characteristics. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof.

A sample or cell that "expresses" a protein of interest is one in which mRNA encoding the protein, or the protein, including fragments thereof, is determined to be present in the sample or cell.

As used herein, the terms "reference expression level" and "reference level" are used interchangeably to refer to an expression level against which another expression level, e.g., the expression level of one or more genes described herein (e.g., any gene set forth in Table 1 or any combination thereof (e.g., any combination set forth in any one of Tables 2-5) in a sample from an individual is compared, e.g., to make a predictive, diagnostic, prognostic, and/or therapeutic determination. For example, the reference expression level may be derived from expression levels in a reference population (e.g., the median expression level in a reference population, e.g., a population of patients having a cancer), a reference sample, and/or a pre-assigned value (e.g., a cut-off value which was previously determined to significantly (e.g., statistically significantly) separate a first subset of individuals who have been treated with an anti-cancer therapy (e.g., an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody)) in a reference population and a second subset of individuals who have been treated with a different anti-cancer therapy (or who have not been treated with the anti-cancer therapy) in the same reference population based on a significant difference between an individual's responsiveness to treatment with the anti-cancer therapy and an individual's responsiveness to treatment with the different anti-cancer therapy above the cut-off value and/or below the cut-off value). In some embodiments, the cut-off value may be the median or mean expression level in the reference population. In other embodiments, the reference level may be the top 40%, the top 30%, the top 20%, the top 10%, the top 5%, or the top 1% of the expression level in the reference population. In particular embodiments, the cut-off value may be the median expression level in the reference population. It will be appreciated by one skilled in the art that the numerical value for the reference expression level may vary depending on the indication or disorder (e.g., a cancer (e.g., a bladder cancer, a kidney cancer, a lung cancer, a liver cancer, an ovarian cancer, a pancreatic cancer, a colorectal cancer, or a breast cancer)), the methodology used to detect expression levels (e.g., RNAseq or RT-qPCR), and/or the specific combinations of genes examined (e.g., any combination of the genes set forth in Table 1; or any one of the combinations of genes listed in Tables 2-6).

Expression "above" a level (e.g., above a reference level), "increased expression," "increased expression level," "increased levels," "elevated expression," "elevated expression levels," or "elevated levels" refers to an increased expression or increased levels of a biomarker in an individual relative to the expression level of the biomarker in a control (e.g., an individual or individuals who are not suffering from the disease or disorder (e.g., cancer), an internal control (e.g., a housekeeping biomarker), or the level of a biomarker in a sample obtained prior to administration of a therapy (e.g., an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody)), or relative to a reference level (e.g., the median expression level of the biomarker in samples from a group/population of patients, e.g., patients having cancer who are being tested for responsiveness to an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody); the median expression level of the biomarker in samples from a group/population of patients, e.g., patients having cancer who have been identified as not responding to an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody); or the level in a sample previously obtained from the individual at a prior time).

Expression "below" a level (e.g., below a reference level), "decreased expression," "decreased expression level," "decreased levels," "reduced expression," "reduced expression levels," or "reduced levels" refers to a decrease expression or decreased levels of a biomarker in an individual relative to the expression level of the biomarker in a control (e.g., an individual or individuals who are not suffering from the disease or disorder (e.g., cancer), an internal control (e.g., a housekeeping biomarker), or the level of a biomarker in a sample obtained prior to administration of a therapy (e.g., an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody)), or relative to a reference level (e.g., the median expression level of the biomarker in samples from a group/population of patients, e.g., patients having cancer who are being tested for responsiveness to an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody); the median expression level of the biomarker in samples from a group/population of patients, e.g., patients having cancer who have been identified as not responding to an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody); or the level in a sample previously obtained from the individual at a prior time). In some embodiments, reduced expression is little or no expression.

A "reference sample," "reference cell," "reference tissue," "control sample," "control cell," or "control tissue," as used herein, refers to a sample, cell, tissue, or standard that is used for comparison purposes. In one embodiment, a reference sample, reference cell, reference tissue, control sample, control cell, or control tissue is obtained from a healthy and/or non-diseased part of the body (e.g., tissue or cells) of the same patient or individual. For example, a reference sample, reference cell, reference tissue, control sample, control cell, or control tissue may be healthy and/or non-diseased cells or tissue adjacent to the diseased cells or tissue (e.g., cells or tissue adjacent to a tumor). In another embodiment, a reference sample is obtained from an untreated tissue and/or cell of the body of the same patient or individual. In yet another embodiment, a reference sample, reference cell, reference tissue, control sample, control cell, or control tissue is obtained from a healthy and/or non-diseased part of the body (e.g., tissues or cells) of an individual who is not the patient or individual. In even another embodiment, a reference sample, reference cell, reference tissue, control sample, control cell, or control tissue is obtained from an untreated tissue and/or cell of the body of an individual who is not the patient or individual. In another embodiment, a reference sample, reference cell, reference tissue, control sample, control cell, or control tissue is obtained from a patient prior to administration of a therapy (e.g., an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody)).

The phrase "based on" when used herein means that the information about one or more biomarkers is used to inform a treatment decision, information provided on a package insert, or marketing/promotional guidance, and the like.

The term "housekeeping biomarker" refers to a biomarker or group of biomarkers (e.g., polynucleotides and/or polypeptides) which are typically similarly present in all cell types. In some embodiments, the housekeeping biomarker is a "housekeeping gene." A "housekeeping gene" refers herein to a gene or group of genes which encode proteins whose activities are essential for the maintenance of cell function and which are typically similarly present in all cell types.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "multiplex-PCR" refers to a single PCR reaction carried out on nucleic acid obtained from a single source (e.g., an individual) using more than one primer set for the purpose of amplifying two or more DNA sequences in a single reaction.

The technique of "polymerase chain reaction" or "PCR" as used herein generally refers to a procedure wherein minute amounts of a specific piece of nucleic acid, RNA and/or DNA, are amplified as described, for example, in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.* 51:263 (1987) and Erlich, ed., *PCR Technology*, (Stockton Press, N Y, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Quantitative real-time polymerase chain reaction" or "qRT-PCR" refers to a form of PCR wherein the amount of PCR product is measured at each step in a PCR reaction. This technique has been described in various publications including, for example, Cronin et al., *Am. J. Pathol.* 164(1): 35-42 (2004) and Ma et al., *Cancer Cell* 5:607-616 (2004).

The term "microarray" refers to an ordered arrangement of hybridizable array elements, preferably polynucleotide probes, on a substrate.

The term "RNAseq," also called "RNA-seq," and "Whole Transcriptome Shotgun Sequencing (WTSS)," refers to the use of high-throughput sequencing technologies to sequence and/or quantify cDNA to obtain information about a sample's RNA content. Publications describing RNAseq include: Wang et al. *Nature Reviews Genetics* 10(1):57-63, 2009; Ryan et al. *BioTechniques* 45(1):81-94, 2008; and Maher et al. *Nature* 458(7234):97-101, 2009.

The term "diagnosis" is used herein to refer to the identification or classification of a molecular or pathological state, disease or condition (e.g., cancer (e.g., a bladder cancer (e.g., UC, e.g., mUC), a kidney cancer, a lung cancer, a liver cancer, an ovarian cancer, a pancreatic cancer, a colorectal cancer, or a breast cancer)). In some embodiments, the cancer is a bladder cancer (e.g., UC, e.g., mUC). For example, "diagnosis" may refer to identification of a particular type of cancer. "Diagnosis" may also refer to the classification of a particular subtype of cancer, for instance, by histopathological criteria, or by molecular features (e.g., a subtype characterized by expression of one or a combination of biomarkers (e.g., particular genes or proteins encoded by said genes)).

A "tumor-infiltrating immune cell," as used herein, refers to any immune cell present in a tumor or a sample thereof. Tumor-infiltrating immune cells include, but are not limited to, intratumoral immune cells, peritumoral immune cells, other tumor stroma cells (e.g., fibroblasts), or any combination thereof. Such tumor-infiltrating immune cells can be, for example, T lymphocytes (such as CD8+T lymphocytes and/or CD4+T lymphocytes), B lymphocytes, or other bone marrow-lineage cells, including granulocytes (e.g., neutrophils, eosinophils, and basophils), monocytes, macrophages (e.g., CD68+/CD163+ macrophages), dendritic cells (e.g., interdigitating dendritic cells), histiocytes, and natural killer (NK) cells.

A "tumor cell" as used herein, refers to any tumor cell present in a tumor or a sample thereof. Tumor cells may be distinguished from other cells that may be present in a tumor sample, for example, stromal cells and tumor-infiltrating immune cells, using methods known in the art and/or described herein.

As used herein, the terms "individual," "patient," or "subject" are used interchangeably and refer to any single animal, more preferably a mammal (including such non-human animals as, for example, cats, dogs, horses, rabbits, zoo animals, cows, pigs, sheep, and non-human primates) for which treatment is desired. In particular embodiments, the patient herein is a human. The patient may be a "cancer patient," i.e., one who is suffering from cancer (e.g., bladder cancer, kidney cancer, lung cancer, liver cancer, ovarian cancer, pancreatic cancer, colorectal cancer, or breast cancer), or at risk for suffering from cancer, or suffering from one or more symptoms of cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but are not limited to, bladder cancer (e.g., urothelial carcinoma (UC), including metastatic UC (mUC); muscle-invasive bladder cancer (MIBC), and non-muscle-invasive bladder cancer (NMIBC)); kidney or renal cancer (e.g., renal cell carcinoma (RCC)); lung cancer, including small-cell lung cancer, non-small cell lung cancer, adenocarcinoma of the lung, and squamous carcinoma of the lung; cancer of the urinary tract; breast cancer (e.g., HER2+ breast cancer and triple-negative breast cancer (TNBC), which are estrogen receptors (ER−), progesterone receptors (PR−), and HER2 (HER2−) negative); prostate cancer, such as castration-resistant prostate cancer (CRPC); cancer of the peritoneum; hepatocellular cancer; gastric or stomach cancer, including gastrointestinal cancer and gastrointestinal stromal cancer; pancreatic cancer (e.g., pancreatic ductal adenocarcinoma (PDAC)); glioblastoma; cervical cancer; ovarian cancer; liver cancer (e.g., hepatocellular carcinoma (HCC)); hepatoma; colon cancer; rectal cancer; colorectal cancer; endometrial or uterine carcinoma; salivary gland carcinoma; prostate cancer; vulval cancer; thyroid cancer; hepatic carcinoma; anal carcinoma; penile carcinoma; melanoma, including superficial spreading melanoma, lentigo maligna melanoma, acral lentiginous melanomas, and nodular melanomas; multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); acute myologenous leukemia (AML); hairy cell leukemia; chronic myeloblastic leukemia (CML); post-transplant lymphoproliferative disorder (PTLD); and myelodysplastic syndromes (MDS), as well as abnormal vascular proliferation associated with phakomatoses, edema (such as that associated with brain tumors), Meigs' syndrome, brain cancer, head and neck cancer, and associated metastases. In some embodiments, the cancer is bladder cancer (e.g., UC, e.g., mUC).

By "early stage cancer" or "early stage tumor" is meant a cancer that is not invasive or metastatic or is classified as a Stage 0, I, or II cancer.

An "advanced" cancer is one which has spread outside the site or organ of origin, either by local invasion or metastasis.

A "refractory" cancer is one which progresses even though an anti-tumor agent, such as a chemotherapeutic agent, is being administered to the cancer patient. An example of a refractory cancer is one which is platinum refractory.

A "recurrent" cancer is one which has regrown, either at the initial site or at a distant site, after a response to initial therapy.

The terms "cell proliferative disorder" and "proliferative disorder" refer to disorders that are associated with some degree of abnormal cell proliferation. In one embodiment, the cell proliferative disorder is cancer.

The term "tumor," as used herein, refers to all neoplastic cell growth and proliferation, whether malignant or benign, and all pre-cancerous and cancerous cells and tissues.

The terms "cancer," "cancerous," "cell proliferative disorder," "proliferative disorder," and "tumor" are not mutually exclusive as referred to herein.

The term "immune inflamed tumor," as used herein, refers to a tumor (e.g., a solid tumor) characterized by CD8+ T-cell infiltration and PD-L1 expression. See, e.g., Herbst et al. *Nature* 515:563-567, 2014 and Hegde et al. *Clin. Canc. Res.* 22: 1865-1874, 2016. In some embodiments, a tumor is categorized as an immune inflamed tumor if CD8+ cells are observed in direct contact with malignant epithelial cells, either in the form of spillover of stromal infiltrates into tumor cell aggregates or of diffuse infiltration of CD8+ cells in aggregates or sheets of tumor cells.

The term "immune excluded tumor," as used herein, refers to a tumor (e.g., a solid tumor) characterized by accumulation of T-cells in the extracellular matrix-rich stroma. See, e.g., Herbst et al. *Nature* 515:563-567, 2014 and Hegde et al. *Clin. Canc. Res.* 22: 1865-1874, 2016. In immune excluded tumors, the majority of T-cells migrate along aligned collagen and fibronectin fibers that run circumferentially around the tumor. See, e.g., Salmon et al. *J. Clin. Invest.* 122:899-910, 2012. In some embodiments, a tumor is categorized as an immune excluded tumor if CD8+ cells are observed substantially or exclusively in stroma immediately adjacent to or within a main tumor mass.

The term "immune desert tumor," as used herein, refers to a tumor (e.g., a solid tumor) with a paucity of infiltrating lymphocytes within the tumor or surrounding stroma. See, e.g., Herbst et al. *Nature* 515:563-567, 2014 and Hegde et al. *Clin. Canc. Res.* 22: 1865-1874, 2016. In some embodiments, a tumor is categorized as an immune desert tumor if the prevalence of CD8+ cells is low (e.g., less than about 10 CD8+ cells (e.g., about 10, 9, 8, 7, 6, 5, 4, 3, 2, 1, or 0 CD8+ cells) in an area of tumor and tumor-associated stroma at a magnification of about 200×, for example, as calculated as the average of 10 representative fields of view).

A "disorder" is any condition that would benefit from treatment including, but not limited to, chronic and acute disorders or diseases including those pathological conditions which predispose the mammal to the disorder in question.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, treatment is with an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody). In some embodiments, antibodies (e.g., anti-PD-L1 antibodies, anti-PD-1 antibodies, and/or anti-TGF-β antibodies) are used to delay development of a disease or to slow the progression of a disease or disorder (e.g., a cancer (e.g., a bladder cancer, a kidney cancer, a lung cancer, a liver cancer, an ovarian cancer, a pancreatic cancer, a colorectal cancer, or a breast cancer)).

As used herein, "administering" is meant a method of giving a dosage of a compound (e.g., an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody)) or a composition (e.g., a pharmaceutical composition, e.g., a pharmaceutical composition including an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody)) to a patient. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, intravitreally (e.g., by intravitreal injection), by eye drop, orally, topically, transdermally, parenterally, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated).

A "therapeutically effective amount" refers to an amount of a therapeutic agent to treat or prevent a disease or disorder (e.g., a cancer (e.g., a bladder cancer (e.g., UC, e.g., mUC), a kidney cancer, a lung cancer, a liver cancer, an ovarian cancer, a pancreatic cancer, a colorectal cancer, or a breast cancer)) in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival (e.g., overall survival or progression-free survival), time to disease progression (TTP), response rates (e.g., complete response (CR) and partial response (PR)), duration of response, and/or quality of life.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s). For example, in some embodiments, a VEGF antagonist and a PD-L1 axis binding antagonist may be administered concurrently.

By "reduce or inhibit" is meant the ability to cause an overall decrease of 20%, 30%, 40%, 50%, 60%, 70%, 75%, 80%, 85%, 90%, 95%, or greater. Reduce or inhibit can refer, for example, to the symptoms of the disorder being treated, the presence or size of metastases, or the size of the primary tumor.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose or "extended" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks.

"Response to a treatment," "responsiveness to treatment," or "benefit from a treatment" can be assessed using any endpoint indicating a benefit to the individual, including, without limitation, (1) inhibition, to some extent, of disease progression (e.g., cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metastasis; (5) relief, to some extent, of one or more symptoms associated with the disease or disorder (e.g., cancer); (6) increase or extend in the length of survival, including overall survival (OS HR<1) and progression free survival (PFS HR<1); and/or (9) decreased mortality at a given point of time following treatment (e.g., treatment with an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody)).

An "objective response" refers to a measurable response, including complete response (CR) or partial response (PR). In some embodiments, the "objective response rate (ORR)" refers to the sum of complete response (CR) rate and partial response (PR) rate.

By "complete response" or "CR" is intended the disappearance of all signs of cancer (e.g., disappearance of all target lesions) in response to treatment. This does not always mean the cancer has been cured.

As used herein, "partial response" or "PR" refers to a decrease in the size of one or more tumors or lesions, or in the extent of cancer in the body, in response to treatment. For example, in some embodiments, PR refers to at least a 30% decrease in the sum of the longest diameters (SLD) of target lesions, taking as reference the baseline SLD.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration, or longer.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

The term "survival" refers to the patient remaining alive, and includes overall survival as well as progression-free survival.

As used herein, "progression-free survival" or "PFS" refers to the length of time during and after treatment during which the disease being treated (e.g., cancer (e.g., a bladder cancer (e.g., UC, e.g., mUC), a kidney cancer, a lung cancer, a liver cancer, an ovarian cancer, a pancreatic cancer, a colorectal cancer, or a breast cancer)) does not progress or get worse. Progression-free survival may include the amount of time individuals have experienced a complete response or a partial response, as well as the amount of time individuals have experienced stable disease.

As used herein, "overall survival" or "OS" refers to the percentage of subjects in a group who are likely to be alive after a particular duration of time (e.g., 6 months, 1 year, 2 years, 3 years, 4 years, 5 years, 10 years, 15 years, 20 years, or more than 20 years from the time of diagnosis or treatment).

By "extending survival" is meant increasing overall or progression-free survival in a treated patient relative to an untreated patient (i.e. relative to a patient not treated with the medicament), or relative to a patient who does not express a biomarker at the designated level, and/or relative to a patient treated with an approved anti-tumor agent (e.g., an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody)).

As used herein, "hazard ratio" or "HR" is a statistical definition for rates of events. For the purpose of the invention, hazard ratio is defined as representing the probability of an event (e.g., PFS or OS) in the experimental (e.g., treatment) group/arm divided by the probability of an event in the control group/arm at any specific point in time. An HR with a value of 1 indicates that the relative risk of an endpoint (e.g., death) is equal in both the "treatment" and "control" groups; a value greater than 1 indicates that the risk is greater in the treatment group relative to the control group; and a value less than 1 indicates that the risk is greater in the control group relative to the treatment group. "Hazard ratio" in progression-free survival analysis (i.e., PFS HR) is a summary of the difference between two progression-free survival curves, representing the reduction in the risk of death on treatment compared to control, over a period of follow-up. "Hazard ratio" in overall survival analysis (i.e., OS HR) is a summary of the difference between two overall survival curves, representing the reduction in the risk of death on treatment compared to control, over a period of follow-up.

The term "anti-cancer therapy" refers to a therapy useful in treating cancer. Examples of anti-cancer therapeutic agents include, but are limited to, cytotoxic agents, chemotherapeutic agents, growth inhibitory agents, agents used in radiation therapy, anti-angiogenesis agents, apoptotic agents, anti-tubulin agents, and other agents to treat cancer, for example, anti-CD20 antibodies, platelet derived growth factor inhibitors (e.g., GLEEVEC™ (imatinib mesylate)), a COX-2 inhibitor (e.g., celecoxib), interferons, cytokines, antagonists (e.g., neutralizing antibodies) that bind to one or more of the following targets: PDGFR-β, BlyS, APRIL, BCMA receptor(s), TRAIL/Apo2, other bioactive and organic chemical agents, and the like. Combinations thereof are also included in the invention.

"Active" or "activity" for the purposes herein refer to form(s) of a polypeptide which retain a biological and/or an immunological activity of native or naturally-occurring polypeptide, wherein "biological" activity refers to a biological function (either inhibitory or stimulatory) caused by a native or naturally-occurring polypeptide other than the ability to induce the production of an antibody against an antigenic epitope possessed by a native or naturally-occurring polypeptide and an "immunological" activity refers to the ability to induce the production of an antibody against an antigenic epitope possessed by a native or naturally-occurring polypeptide.

The term "antagonist" is used in the broadest sense, and includes any molecule that partially or fully blocks, inhibits, or neutralizes a biological activity of a native polypeptide. In a similar manner, the term "agonist" is used in the broadest sense and includes any molecule that mimics a biological activity of a native polypeptide. Suitable agonist or antagonist molecules specifically include agonist or antagonist antibodies or antibody fragments, fragments or amino acid sequence variants of native polypeptides, and the like. Methods for identifying agonists or antagonists of a polypeptide may comprise contacting a polypeptide with a candidate agonist or antagonist molecule and measuring a detectable change in one or more biological activities normally associated with the polypeptide.

The term "immunotherapy" refers the use of a therapeutic agent that modulates an immune response. An immunotherapy may be an activating immunotherapy or a suppressing immunotherapy. The term "activating immunotherapy" refers to the use of a therapeutic agent that induces, enhances, or promotes an immune response, including, e.g., a T cell response. The term "suppressing immunotherapy" refers to the use of a therapeutic agent that interferes with, suppresses, or inhibits an immune response, including, e.g., a T cell response.

The term "PD-L1 axis binding antagonist" refers to a molecule that inhibits the interaction of a PD-L1 axis binding partner with one or more of its binding partners, so as to remove T cell dysfunction resulting from signaling on the PD-1 signaling axis, with a result being restored or enhanced T cell function. As used herein, a PD-L1 axis binding antagonist includes a PD-L1 binding antagonist and a PD-1 binding antagonist as well as molecules that interfere with the interaction between PD-L1 and PD-1 (e.g., a PD-L2-Fc fusion).

The term "PD-L1 binding antagonist" refers to a molecule that decreases, blocks, inhibits, abrogates, or interferes with signal transduction resulting from the interaction of PD-L1 with either one or more of its binding partners, such as PD-1 or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen-binding fragments thereof, immunoadhesins, fusion proteins, oligopeptides, and other molecules that decrease, block, inhibit, abrogate, or interfere with signal transduction resulting from the interaction of PD-L1 with one or more of its binding partners, such as PD-1 or B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific embodiment, the anti-PD-L1 antibody is atezolizumab (CAS Registry Number: 1422185-06-5), also known as MPDL3280A, and described herein. In another specific embodiment, the anti-PD-L1 antibody is YW243.55.S70, described herein. In another specific embodiment, the anti-PD-L1 antibody is MDX-1105, described herein. In still another specific aspect, the anti-PD-L1 antibody is MED14736 (durvalumab), described herein. In still another specific aspect, the anti-PD-L1 antibody is MSB0010718C (avelumab), described herein.

As used herein, a "PD-1 binding antagonist" is a molecule that decreases, blocks, inhibits, abrogates or interferes with signal transduction resulting from the interaction of PD-1 with one or more of its binding partners, such as PD-L1 and/or PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti PD-1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-1 with PD-L1 and/or PD-L2. In one embodiment, a PD-1 binding antagonist reduces the negative signal mediated by or through cell surface proteins expressed on T lymphocytes, and other cells, mediated signaling through PD-1 or PD-L1 so as render a dysfunctional T cell less dysfunctional. In some embodiments, the PD-1 binding antagonist is an anti-PD-1 antibody. In a specific aspect, a PD-1 binding antagonist is MDX-1106 (nivolumab). In another specific aspect, a PD-1 binding antagonist is MK-3475 (pembrolizumab). In another specific aspect, a PD-1 binding antagonist is CT-011 (pidilizumab). In another specific aspect, a PD-1 binding antagonist is MEDI-0680 (AMP-514). In another specific aspect, a PD-1 binding antagonist is PDR001. In another specific aspect, a PD-1 binding antagonist is REGN2810. In another specific aspect, a PD-1 binding antagonist is BGB-108. In another specific aspect, a PD-1 binding antagonist is AMP-224.

The terms "anti-PD-L1 antibody" and "an antibody that binds to PD-L1" refer to an antibody that is capable of binding PD-L1 with sufficient affinity such that the antibody is useful as a diagnostic and/or therapeutic agent in targeting PD-L1. In one embodiment, the extent of binding of an anti-PD-L1 antibody to an unrelated, non-PD-L1 protein is less than about 10% of the binding of the antibody to PD-L1 as measured, for example, by a RIA. In certain embodiments, an anti-PD-L1 antibody binds to an epitope of PD-L1 that is conserved among PD-L1 from different species.

The terms "anti-PD-1 antibody" and "an antibody that binds to PD-1" refer to an antibody that is capable of binding PD-1 with sufficient affinity such that the antibody is useful as a diagnostic and/or therapeutic agent in targeting PD-1. In one embodiment, the extent of binding of an anti-PD-1 antibody to an unrelated, non-PD-1 protein is less than about 10% of the binding of the antibody to PD-1 as measured, for example, by a RIA. In certain embodiments, an anti-PD-1 antibody binds to an epitope of PD-1 that is conserved among PD-1 from different species.

A "suppressive stromal antagonist" as defined herein is any molecule that partially or fully blocks, inhibits, or neutralizes a biological activity and/or function of a gene or gene product associated with stroma (e.g, tumor-associated stroma). In some embodiments, the suppressive stromal antagonist partially or fully blocks, inhibits, or neutralizes a biological activity and/or function of a gene or gene product associated with fibrotic tumors. In some embodiments, treatment with a suppressive stromal antagonist results in the reduction of stroma thereby resulting in an increase activity of an immunotherapy; for example, by increasing the ability of activating immune cells (e.g., proinflammatory cells) to infiltrate a fibrotic tissue (e.g., a fibrotic tumor). Targets for stromal gene antagonists are known in the art; for example, see Turley et al., *Nature Reviews Immunology* 15:669-682, 2015 and Rosenbloom et al., *Biochimica et Biophysica Acta* 1832:1088-1103, 2013. In some embodiments, the suppressive stromal antagonist is a transforming growth factor beta (TGF-β), podoplanin (PDPN), leukocyte-associated immunoglobulin-like receptor 1 (LAIR1), SMAD, anaplastic lymphoma kinase (ALK), connective tissue growth factor (CTGF/CCN2), endothelial-1 (ET-1), AP-1, interleukin (IL)-13, lysyl oxidase homolog 2 (LOXL2), endoglin (CD105), fibroblast activation protein (FAP), vascular cell adhesion protein 1 (CD106), thymocyte antigen 1 (THY1), beta 1 integrin (CD29), platelet-derived growth factor (PDGF), PDGF receptor A (PDGFRα), PDGF receptor B (PDGFRβ), vimentin, smooth muscle actin alpha (ACTA2), desmin, endosialin (CD248), or S100 calcium-binding protein A4 (S100A4) antagonist.

A "TGF-β antagonist" as defined herein is any molecule that decreases, blocks, inhibits, abrogates or interferes with signal transduction resulting from the interaction of TGF-β with one or more of its interaction partners, such as a TGF-β cellular receptor. In some embodiments, a "TGF-β binding antagonist" is a molecule that inhibits the binding of TGF-β to its binding partners. In some embodiments, the TGF-β antagonist inhibits the activation of TGF-β. In some embodiments, the TGF-β antagonist includes an anti-TGF-β antibody, antigen binding fragments thereof, an immunoadhesin, a fusion protein, an oligopeptide, and other molecules that decrease, block, inhibit, abrogate or interfere with signal transduction resulting from the interaction of TGF-β with one or more of its interaction partners. In some embodiments, the TGF-β antagonist is a polypeptide, a small molecule, or a nucleic acid. In some embodiments, the TGF-β antagonist (e.g., the TGF-β binding antagonist) inhibits TGF-β, TGF-β2, and/or TGF-β3. In some embodiments, the TGF-β antagonist (e.g., the TGF-β binding antagonist) inhibits TGF-β receptor-1 (TGFBR1), TGF-β receptor-2 (TGFBR2), and/or TGF-β receptor-3 (TGFBR3).

The terms "anti-TGF-β antibody" and "an antibody that binds to TGF-β" refer to an antibody that is capable of binding TGF-β with sufficient affinity such that the antibody is useful as a diagnostic and/or therapeutic agent in targeting TGF-β. In one embodiment, the extent of binding of an anti-TGF-β antibody to an unrelated, non-TGF-β protein is less than about 10% of the binding of the antibody to TGF-β as measured, for example, by a RIA. In certain embodiments, an anti-TGF-β antibody binds to an epitope of TGF-β that is conserved among TGF-β from different species. In some embodiments, the anti-TGF-β antibody inhibits TGF-β1, TGF-β2, and/or TGF-β3. In some embodiments, the anti-TGF-β antibody inhibits TGF-β1, TGF-β2, and TGF-β3. In some embodiments, the anti-TGF-β antibody is a pan-specific anti-TGF-β antibody. In some embodiments, the anti-TGF-β antibody may be any anti-TGF-β antibody disclosed in, for example, U.S. Pat. No. 5,571,714 or in International Patent Application Nos. WO 92/00330, WO 92/08480, WO 95/26203, WO 97/13844, WO 00/066631, WO 05/097832, WO 06/086469, WO 05/010049, WO 06/116002, WO 07/076391, WO 12/167143, WO 13/134365, WO 14/164709, or WO 16/201282, each of which is incorporated herein by reference in its entirety. In particular embodiments, the anti-TGF-β antibody is fresolimumab, metelimumab, lerdelimumab, 1D11, 2G7, or a derivative thereof.

An "angiogenesis inhibitor" or "anti-angiogenesis agent" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined above, e.g., antibodies to VEGF-A or the VEGF-A receptor (e.g., KDR receptor or Fit-1 receptor), anti-PDGFR inhibitors such as GLEEVEC™ (imatinib mesylate). Anti-angiogenesis agents also include native angiogenesis inhibitors, e.g., angiostatin, endostatin, etc. See, for example, Klagsbrun and D'Amore, *Annu. Rev. Physiol.,* 53:217-39 (1991); Streit and Detmar, *Oncogene,* 22:3172-3179 (2003) (e.g., Table 3 listing anti-angiogenic therapy in malignant melanoma); Ferrara & Alitalo, Nature Medicine 5(12):1359-1364 (1999); Tonini et al., *Oncogene,* 22:6549-6556 (2003) and, Sato *Int. J. Clin. Oncol.,* 8:200-206 (2003).

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof (e.g., nucleolytic enzymes), antibiotics, and toxins such as small molecule toxins or enzymatically active toxins of bacterial, fungal, plant or animal origin, including fragments and/or variants thereof, and the various antitumor or anticancer agents disclosed below. A tumoricidal agent causes destruction of tumor cells.

A "chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, rapamycin (Sirolimus, RAPAMUNE®, Pfizer), lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5a-reductases including finasteride and dutasteride; vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew. Chem. Intl. Ed. Engl.* 33:183-186, 1994); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agents also include anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); protein kinase inhibitors; lipid kinase inhibitors; antisense oligonucleotides, particularly those which inhibit expression of genes in signaling pathways implicated in aberrant cell proliferation, such as, for example, PKC-alpha, Ralf and H-Ras; ribozymes such as VEGF expression inhibitors (e.g., ANGIOZYME®) and HER2 expression inhibitors; vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and pharmaceutically acceptable salts, acids and derivatives of any of the above.

Chemotherapeutic agents also include antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories), which is a recombinant, exclusively human-sequence, full-length IgG1 A antibody genetically modified to recognize interleukin-12 p40 protein.

Chemotherapeutic agents also include "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396, WO 1999/09016, WO 1998/43960, WO 1997/38983, WO 1999/06378, WO 1999/06396, WO 1996/30347, WO 1996/33978, WO 1996/3397, and WO 1996/33980.

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, all-trans retinoic acid (ATRA), valrubicin, zoledronate, and zoledronic acid, and pharmaceutically acceptable salts thereof.

The term "prodrug" as used herein refers to a precursor or derivative form of a pharmaceutically active substance that is less cytotoxic to tumor cells compared to the parent drug and is capable of being enzymatically activated or converted into the more active parent form. See, for example, Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "growth inhibitory agent" when used herein refers to a compound or composition which inhibits growth and/or proliferation of a cell (e.g., a cell whose growth is dependent on PD-L1 expression) either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in "*The Molecular Basis of Cancer*," Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

The term "pharmaceutical formulation" refers to a preparation which is in such form as to permit the biological activity of an active ingredient contained therein to be effective, and which contains no additional components which are unacceptably toxic to a patient to which the formulation would be administered.

A "pharmaceutically acceptable carrier" refers to an ingredient in a pharmaceutical formulation, other than an active ingredient, which is nontoxic to a patient. A pharmaceutically acceptable carrier includes, but is not limited to, a buffer, excipient, stabilizer, or preservative.

The term "package insert" is used to refer to instructions customarily included in commercial packages of therapeutic products, that contain information about the indications, usage, dosage, administration, combination therapy, contraindications, and/or warnings concerning the use of such therapeutic products.

A "sterile" formulation is aseptic or free from all living microorganisms and their spores.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

The term "small molecule" refers to any molecule with a molecular weight of about 2000 daltons or less, preferably of about 500 daltons or less.

The word "label" when used herein refers to a compound or composition that is conjugated or fused directly or indirectly to a reagent such as a polynucleotide probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable. The term is intended to encompass direct labeling of a probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

The term "antibody" herein is used in the broadest sense and specifically covers monoclonal antibodies, polyclonal antibodies, half-antibodies, multispecific antibodies (e.g., bispecific antibodies) formed from at least two intact antibodies, and antibody fragments so long as they exhibit the desired biological activity. The term "immunoglobulin" (Ig) is used interchangeably with antibody herein.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody is one which has been identified and separated and/or recovered from a component of its natural environment. Contaminant components of its natural environment are materials which would interfere with research, diagnostic, and/or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. An isolated antibody includes the antibody in situ within recombinant cells since at least one component of the antibody's natural environment will not be present. Ordinarily, however, an isolated antibody will be prepared by at least one purification step.

A "blocking" antibody or an antibody "antagonist" is one which inhibits or reduces biological activity of the antigen it binds. For example, a PD-L1-specific antagonist antibody binds PD-L1 and decreases, blocks, inhibits, abrogates, or interferes with signal transduction resulting from the interaction of PD-1 with PD-L1 and/or PD-L2. Preferred blocking antibodies or antagonist antibodies completely inhibit the biological activity of the antigen.

Unless indicated otherwise, the expression "multivalent antibody" is used throughout this specification to denote an antibody comprising three or more antigen binding sites. The multivalent antibody is preferably engineered to have the three or more antigen binding sites and is generally not a native sequence IgM or IgA antibody.

The "light chains" of antibodies (immunoglobulins) from any mammalian species can be assigned to one of two clearly distinct types, called kappa ("κ") and lambda ("λ"), based on the amino acid sequences of their constant domains.

The term "constant domain" refers to the portion of an immunoglobulin molecule having a more conserved amino acid sequence relative to the other portion of the immunoglobulin, the variable domain, which contains the antigen binding site. The constant domain contains the CH1, CH2, and CH3 domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the span of the variable domains. Instead, the V regions consist of relatively invariant stretches called framework regions (FRs) of 15-30 amino acids separated by shorter regions of extreme variability called "hypervariable regions" that are each 9-12 amino acids long. The term "hypervariable region" or "HVR" when used herein refers to the amino acid residues of an antibody which are responsible for antigen-binding. The hypervariable region generally comprises amino acid residues from, for example, around about residues 24-34 (L1), 50-56 (L2) and 89-97 (L3) in the VL, and around about residues 26-35 (H1), 49-65 (H2) and 95-102 (H3) in the VH (in one embodiment, H1 is around about residues 31-35); Kabat et al., *Sequences of Proteins of Immunological Interest,* 5th Ed. Public Health Service, National Institutes of Health, Bethesda, Md. (1991)) and/or those residues from a "hypervariable loop" (e.g., residues 26-32 (L1), 50-52 (L2), and 91-96 (L3) in the VL, and 26-32 (H1), 53-55 (H2), and 96-101 (H3) in the VH; Chothia and Lesk, J. Mol. Biol. 196:901-917 (1987). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). Accordingly, the HVR and FR sequences generally appear in the following sequence in VH (or VL): FR1-H1(L1)-FR2-H2(L2)-FR3-H3(L3)-FR4. The constant domains are not involved directly in binding an antibody to an antigen, but exhibit various effector functions, such as participation of the antibody in antibody dependent cellular cytotoxicity (ADCC).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "hypervariable region," "HVR," or "HV," as used herein, refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, for example, Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, for example, Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35b | H26-H35b | H26-H32 | H30-H35b (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

Unless otherwise indicated, HVR residues and other residues in the variable domain (e.g., FR residues) are numbered herein according to Kabat et al., supra.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. In some embodiments, the antibody fragment described herein is an antigen-binding fragment. Examples of antibody fragments include Fab, Fab', F(ab')2, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md. (1991).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down-regulation of cell surface receptors (e.g. B cell receptor); and B cell activation.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "multispecific antibody" is used in the broadest sense and specifically covers an antibody comprising a heavy chain variable domain (VH) and a light chain variable domain (VL), where the VH-VL unit has polyepitopic specificity (i.e., is capable of binding to two different epitopes on one biological molecule or each epitope on a different biological molecule). Such multispecific antibodies include, but are not limited to, full-length antibodies, antibodies having two or more VL and VH domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 μM to 0.001 pM, 3 μM to 0.001 pM, 1 μM to 0.001 pM, 0.5 μM to 0.001 pM or 0.1 μM to 0.001 pM. "Monospecific" refers to the ability to bind only one epitope.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of antibodies are called α, δ, ε, γ, and μ, respectively.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature* 256:495-97 (1975); Hongo et al., *Hybridoma* 14 (3): 253-260 (1995), Harlow et al., *Antibodies: A Laboratory Manual* (Cold Spring Harbor Laboratory Press, 2nd ed. 1988); Hammerling et al., in: *Monoclonal Antibodies and T cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628, 1991; Marks et al., *J. Mol. Biol.* 222: 581-597, 1992; Sidhu et al., *J. Mol. Biol.* 338(2): 299-310, 2004; Lee et al., *J. Mol. Biol.* 340(5): 1073-1093, 2004; Fellouse, *Proc. Natl. Acad. Sci. USA* 101(34): 12467-12472, 2004; and Lee et al., *J. Immunol. Methods* 284(1-2): 119-132, 2004; and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551, 1993; Jakobovits et al., *Nature* 362: 255-258, 1993; Bruggemann et al., *Year in Immunol.* 7:33, 1993; U.S. Pat. Nos. 5,545,807; 5,545,806; 5,569,825; 5,625,126; 5,633,425; and 5,661,016; Marks et al., Bio/Technology 10: 779-783 (1992); Lonberg et al., *Nature* 368: 856-859, 1994; Morrison, *Nature* 368: 812-813, 1994; Fishwild et al., *Nature* Biotechnol. 14: 845-851, 1996; Neuberger, *Nature Biotechnol.* 14: 826, 1996; and Lonberg et al., *Intern. Rev. Immunol.* 13: 65-93, 1995.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, FR residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525, 1986; Riechmann et al., *Nature* 332:323-329, 1988; and Presta, *Curr. Op. Struct. Biol.* 2:593-596, 1992.

A "wild-type (WT)" or "reference" sequence or the sequence of a "wild-type" or "reference" protein/polypeptide, such as an HVR or a variable domain of a reference antibody, may be the reference sequence from which variant polypeptides are derived through the introduction of mutations. In general, the "wild-type" sequence for a given protein is the sequence that is most common in nature. Similarly, a "wild-type" gene sequence is the sequence for that gene which is most commonly found in nature. Mutations may be introduced into a "wild-type" gene (and thus the protein it encodes) either through natural processes or through man-induced means. The products of such processes are "variant" or "mutant" forms of the original "wild-type" protein or gene.

A "variant" or "mutant" of a starting or reference polypeptide (e.g., a reference antibody or its variable domain(s)/HVR(s)), is a polypeptide that (1) has an amino acid sequence different from that of the starting or reference polypeptide and (2) was derived from the starting or reference polypeptide through either natural or artificial (manmade) mutagenesis. Such variants include, for example, deletions from, and/or insertions into and/or substitutions of, residues within the amino acid sequence of the polypeptide of interest, referred to herein as "amino acid residue alterations." Thus, a variant HVR refers to a HVR comprising a variant sequence with respect to a starting or reference polypeptide sequence (such as that of a source antibody or antigen binding fragment). An amino acid residue alteration, in this context, refers to an amino acid different from the amino acid at the corresponding position in a starting or reference polypeptide sequence (such as that of a reference antibody or fragment thereof). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described herein.

With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a Kd in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and Kd values are inversely related. A high affinity for an antigen is measured by a low Kd value. In one embodiment, the term "specific binding" refers to binding where a molecule binds to a particular polypeptide or epitope on a particular polypeptide without substantially binding to any other polypeptide or polypeptide epitope.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

An "immunoconjugate" is an antibody conjugated to one or more heterologous molecule(s), including but not limited to a cytotoxic agent.

A "fusion protein" and a "fusion polypeptide" refer to a polypeptide having two portions covalently linked together, where each of the portions is a polypeptide having a different property. The property may be a biological property, such as activity in vitro or in vivo. The property may also be simple chemical or physical property, such as binding to a target molecule, catalysis of a reaction, and the like. The two portions may be linked directly by a single peptide bond or through a peptide linker but are in reading frame with each other.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG1, IgG2 (including IgG2A and IgG2B), IgG3, or IgG4 subtypes, IgA (including IgA1 and IgA2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130. For example, useful immunoadhesins as medicaments useful for therapy herein include polypeptides that comprise the extracellular domain (ECD) or PD-1-binding portions of PD-L1 or PD-L2, or the extracellular or PD-L1- or PD-L2-binding portions of PD-1, fused to a constant domain of an immunoglobulin sequence, such as a PD-L1 ECD-Fc, a PD-L2 ECD-Fc, and a PD-1 ECD-Fc, respectively. Immunoadhesin combinations of Ig Fc and ECD of cell surface receptors are sometimes termed soluble receptors.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally-occurring nucleotides with an analog, internucleotide modifications such as, for example, those with uncharged linkages (e.g., methyl phosphonates, phosphotriesters, phosphoamidates, carbamates, and the like) and with charged linkages (e.g., phosphorothioates, phosphorodithioates, and the like), those containing pendant moieties, such as, for example, proteins (e.g., nucleases, toxins, antibodies, signal peptides, poly-L-lysine, and the like), those with intercalators (e.g., acridine, psoralen, and the like), those containing chelators (e.g., metals, radioactive metals, boron, oxidative metals, and the like), those containing alkylators, those with modified linkages (e.g., alpha anomeric nucleic acids), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro-, or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, single stranded, polynucleotides that are, but not necessarily, less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single-stranded polynucleotide that is capable of hybridizing to a nucleic acid and allowing polymerization of a complementary nucleic acid, generally by providing a free 3'-OH group.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

As used herein, the terms "mutational load," "mutation load," "mutational burden," "tumor mutational burden score," "TMB score," "tissue tumor mutational burden score," and "tTMB score" each of which may be used interchangeably, refer to the level (e.g., number) of an alteration (e.g., one or more alterations, e.g., one or more somatic alterations) per a pre-selected unit (e.g., per megabase) in a pre-determined set of genes (e.g., in the coding regions of the pre-determined set of genes) detected in a tumor tissue sample (e.g., a FFPE tumor sample, an archival tumor sample, a fresh tumor sample, or a frozen tumor sample). The TMB score can be measured, for example, on a whole genome or exome basis, or on the basis of a subset of the genome or exome. In certain embodiments, the TMB score measured on the basis of a subset of the genome or exome can be extrapolated to determine a whole genome or exome mutation load. In some embodiments, a TMB score refers to the level of accumulated somatic mutations within an individual (e.g., an animal (e.g., a human)). The TMB score may refer to accumulated somatic mutations in a patient with cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer). In some embodiments, a TMB score refers to the accumulated mutations in the whole genome of an individual. In some embodiments, a TMB score refers to the accumulated mutations within a particular tissue sample (e.g., tumor tissue sample biopsy, e.g., a bladder cancer tumor sample, e.g., an UC tumor sample) collected from an individual.

The term "somatic mutation" or "somatic alteration" refers to a genetic alteration occurring in the somatic tissues (e.g., cells outside the germline). Examples of genetic alterations include, but are not limited to, point mutations (e.g., the exchange of a single nucleotide for another (e.g., silent mutations, missense mutations, and nonsense mutations)), insertions and deletions (e.g., the addition and/or removal of one or more nucleotides (e.g., indels)), amplifications, gene duplications, copy number alterations (CNAs), rearrangements, and splice variants. The presence of particular mutations can be associated with disease states (e.g., cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer)).

In certain embodiments, the somatic alteration is a silent mutation (e.g., a synonymous alteration). In other embodiments, the somatic alteration is a non-synonymous single nucleotide variant (SNV). In other embodiments, the somatic alteration is a passenger mutation (e.g., an alteration that has no detectable effect on the fitness of a clone). In certain embodiments, the somatic alteration is a variant of unknown significance (VUS), for example, an alteration, the pathogenicity of which can neither be confirmed nor ruled out. In certain embodiments, the somatic alteration has not been identified as being associated with a cancer phenotype.

In certain embodiments, the somatic alteration is not associated with, or is not known to be associated with, an effect on cell division, growth, or survival. In other embodiments, the somatic alteration is associated with an effect on cell division, growth, or survival.

In certain embodiments, the number of somatic alterations excludes a functional alteration in a sub-genomic interval.

In some embodiments, the functional alteration is an alteration that, compared with a reference sequence (e.g., a wild-type or unmutated sequence) has an effect on cell division, growth, or survival (e.g., promotes cell division, growth, or survival). In certain embodiments, the functional alteration is identified as such by inclusion in a database of functional alterations, e.g., the COSMIC database (see Forbes et al. *Nucl. Acids Res.* 43 (D1): D805-D811, 2015, which is herein incorporated by reference in its entirety). In other embodiments, the functional alteration is an alteration with known functional status (e.g., occurring as a known somatic alteration in the COSMIC database). In certain embodiments, the functional alteration is an alteration with a likely functional status (e.g., a truncation in a tumor suppressor gene). In certain embodiments, the functional alteration is a driver mutation (e.g., an alteration that gives a selective advantage to a clone in its microenvironment, e.g., by increasing cell survival or reproduction). In other embodiments, the functional alteration is an alteration capable of causing clonal expansions. In certain embodiments, the functional alteration is an alteration capable of causing one, two, three, four, five, or all six of the following: (a) self-sufficiency in a growth signal; (b) decreased, e.g., insensitivity, to an antigrowth signal; (c) decreased apoptosis; (d) increased replicative potential; (e) sustained angiogenesis; or (f) tissue invasion or metastasis.

In certain embodiments, the functional alteration is not a passenger mutation (e.g., is not an alteration that has no detectable effect on the fitness of a clone of cells). In certain embodiments, the functional alteration is not a variant of unknown significance (VUS) (e.g., is not an alteration, the pathogenicity of which can neither be confirmed nor ruled out).

In certain embodiments, a plurality (e.g., about 10%, 20%, 30%, 40%, 50%, 60%, 70%, 80%, 90%, or more) of functional alterations in a pre-selected tumor gene in the pre-determined set of genes are excluded. In certain embodiments, all functional alterations in a pre-selected gene (e.g., tumor gene) in the pre-determined set of genes are excluded. In certain embodiments, a plurality of functional alterations in a plurality of pre-selected genes (e.g., tumor genes) in the pre-determined set of genes are excluded. In certain embodiments, all functional alterations in all genes (e.g., tumor genes) in the pre-determined set of genes are excluded.

In certain embodiments, the number of somatic alterations excludes a germline mutation in a sub-genomic interval.

In certain embodiments, the germline alteration is an SNP, a base substitution, an insertion, a deletion, an indel, or a silent mutation (e.g., synonymous mutation).

In certain embodiments, the germline alteration is excluded by use of a method that does not use a comparison with a matched normal sequence. In other embodiments, the germline alteration is excluded by a method comprising the use of an algorithm. In certain embodiments, the germline alteration is identified as such by inclusion in a database of germline alterations, for example, the dbSNP database (see Sherry et al. *Nucleic Acids Res.* 29(1): 308-311, 2001, which is herein incorporated by reference in its entirety). In other embodiments, the germline alteration is identified as such by inclusion in two or more counts of the ExAC database (see Exome Aggregation Consortium et al. bioRxiv preprint, Oct. 30, 2015, which is herein incorporated by reference in its entirety). In some embodiments, the germline alteration is identified as such by inclusion in the 1000 Genome Project database (McVean et al. *Nature* 491, 56-65, 2012, which is herein incorporated by reference in its entirety). In some embodiments, the germline alteration is identified as such by inclusion in the ESP database (Exome Variant Server, NHLBI GO Exome Sequencing Project (ESP), Seattle, Wash.).

As used herein, the term "reference TMB score" refers to a TMB score against which another TMB score is compared, e.g., to make a diagnostic, predictive, prognostic, and/or therapeutic determination. For example, the reference TMB score may be a TMB score in a reference sample, a reference population, and/or a pre-determined value. In some instances, the reference TMB score is a cutoff value that significantly separates a first subset of individuals (e.g., patients) who have been treated with an immunotherapy, for example, a PD-L1 axis binding antagonist therapy, in a reference population and a second subset of individuals (e.g., patients) who have been treated with a non-PD-L1 axis binding antagonist therapy that does not comprise an immunotherapy, for example, a PD-L1 axis binding antagonist, in the same reference population based on a significant difference between an individual's responsiveness to treatment with the immunotherapy, for example, a PD-L1 axis binding antagonist therapy, and an individual's responsiveness to treatment with the non-PD-L1 axis binding antagonist therapy at or above the cutoff value and/or below the cutoff value. In some instances, the individual's responsiveness to treatment with the immunotherapy, for example, a PD-L1 axis binding antagonist therapy, is significantly improved relative to the individual's responsiveness to treatment with the non-PD-L1 axis binding antagonist therapy at or above the cutoff value. In some instances, the individual's responsiveness to treatment with the non-PD-L1 axis binding antagonist therapy is significantly improved relative to the individual's responsiveness to treatment with the immunotherapy, for example, a PD-L1 axis binding antagonist therapy, below the cutoff value.

It will be appreciated by one skilled in the art that the numerical value for the reference TMB score may vary depending on the type of, the methodology used to measure a TMB score, and/or the statistical methods used to generate a TMB score.

The term "equivalent TMB value" refers to a numerical value that corresponds to a TMB score that can be calculated by dividing the count of somatic variants (e.g., somatic mutations) by the number of bases sequenced (e.g., about 1.1 Mb (e.g., about 1.125 Mb), e.g., as assessed by the FOUNDATIONONE® panel). It is to be understood that, in general, the TMB score is linearly related to the size of the genomic region sequenced. Such equivalent TMB values indicate an equivalent degree of tumor mutational burden as compared to a TMB score and can be used interchangeably in the methods described herein, for example, to predict response of a cancer patient to an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody). As an example, in some embodiments, an equivalent TMB value is a normalized TMB value that can be calculated by dividing the count of somatic variants (e.g., somatic mutations) by the number of bases sequenced. For example, an equivalent TMB value can be represented as the number of somatic mutations counted over a defined number of sequenced bases (e.g., about 1.1 Mb (e.g., about 1.125 Mb), e.g., as assessed by the FOUNDATIONONE® panel). For example, a TMB score of about 25 (as determined as the number of somatic mutations counted over about 1.1 Mb) corresponds to an equivalent TMB value of about 23 mutations/Mb. It is to be understood that TMB scores as described herein (e.g., TMB scores represented as the number of somatic mutations counted over a defined number of sequenced bases (e.g., about 1.1 Mb (e.g., about 1.125 Mb), e.g., as assessed by the FOUNDATIONONE® panel)) encompass equivalent TMB values obtained using different methodologies (e.g., whole-exome sequencing or whole-genome sequencing). As an example, for a whole-exome panel, the target region may be approximately 50 Mb, and a sample with about 500 somatic mutations detected is an equivalent TMB value to a TMB score of about 10 mutations/Mb. In some embodiments, a TMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates by less than about 30% (e.g., less than about 30%, about 25%, about 20%, about 15%, about 10%, about 5%, about 4%, about 3%, about 2%, about 1%, or less) from a TMB score determined by whole-exome sequencing. See, e.g., Chalmers et al. Genome Medicine 9:34, 2017.

II. Diagnostic Methods and Assays

Provided herein are methods and uses for identifying an individual having a cancer (including, but not limited to, a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from a treatment with an anti-cancer therapy that includes an immunotherapy (including, but not limited to, a PD-L1 axis binding antagonist, e.g., an anti-PD-L1 antibody (e.g., atezolizumab)) and/or a suppressive stromal antagonist (including, but not limited to, a TGF-β antagonist, e.g., an anti-TGF-β antibody).

The methods and uses described herein are based, in part, on the finding that the expression level of one or more genes (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in a sample from the individual may be used to predict the therapeutic efficacy of an an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody).

Further provided herein are methods and assays for selecting a therapy for an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer); methods for determining whether an individual having a cancer is likely to respond to treatment with an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody); methods for predicting the responsiveness of an individual having a cancer to treatment with an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody); and methods for monitoring the response of an individual having a cancer to treatment with an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody. Any of the methods provided herein may further include administering to the individual an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) (e.g., as described below in Section IV) to the individual.

In any embodiment described herein in which the expression level of more than one biomarker is determined in a patient sample and compared to a reference expression level, it is to be understood that, in some embodiments, the expression level of each individual biomarker in the patient sample is compared to a reference expression level for each individual biomarker. For example, if the expression level of TGFB1 and TGFBR1 are determined in a sample from an individual and compared to reference expression levels for TGFB1 and TGFBR1, in some embodiments, the expression level of TGFB1 in the sample from the individual is compared to the reference expression level for TGFB1, and the expression level of TGFBR1 in the sample from the individual is compared to the reference expression level for TGFBR1. In other embodiments, an expression level for more than one gene of interest may be determined by aggregation methods known to one skilled in the art and also disclosed herein, including, for example, by calculating the median or mean of all the expression levels of the genes of interest. Before aggregation, the expression level of each gene of interest may be normalized by using statistical methods known to one skilled in the art and also disclosed herein, including, for example, normalized to the expression level of one or more housekeeping genes, or normalized to a total library size, or normalized to the median or mean expression level value across all genes measured. In some instances, before aggregation across multiple genes of interest, the normalized expression level of each gene of interest may be standardized by using statistical methods known to one skilled in the art and also disclosed herein, including, for example, by calculating the Z-score of the normalized expression level of each gene of interest.

A. Exemplary 22-Gene Signature

In some embodiments, the methods and uses herein involve determining the expression level of one or more (e.g., 1, 2, 3, 4, 5, 6, 7, 8, 9, 10, 11, 12, 13, 14, 15, 16, 17, 18, 19, 20, 21, or 22) genes selected from a 22-gene signature, which includes the genes set forth in Table 1.

For example, provided herein is a method of identifying an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from treatment with an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) that involves determining the expression level of one or more (e.g., 1, 2, 3, 4, 5, 6, 7, 8, 9, 10, 11, 12, 13, 14, 15, 16, 17, 18, 19, 20, 21, or 22) of the genes set forth in Table 1 in a sample from the individual, wherein a change in the expression level of one or more of the genes set forth in Table 1 identifies the individual as one who may benefit from treatment with an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody). In some instances, the change is an increase. In other instances, the change is a decrease.

TABLE 1

| Exemplary Biomarkers<br>Biomarkers |
|---|
| TGFB1 |
| TGFBR2 |
| ACTA2 |
| ACTG2 |
| ADAM12 |
| ADAM19 |
| COMP |

TABLE 1-continued

| Exemplary Biomarkers Biomarkers |
|---|
| CNN1 |
| COL4A1 |
| CTGF |
| CTPS1 |
| FAM101B |
| FSTL3 |
| HSPB1 |
| IGFBP3 |
| PXDC1 |
| SEMA7A |
| SH3PXD2A |
| TAGLN |
| TGFBI |
| TNS1 |
| TPM1 |

The invention also provides for selecting a therapy for an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) that includes determining the expression level of one or more (e.g., 1, 2, 3, 4, 5, 6, 7, 8, 9, 10, 11, 12, 13, 14, 15, 16, 17, 18, 19, 20, 21, or 22) of the genes set forth in Table 1 in a sample from the individual, wherein a change in the expression level of one or more of the genes set forth in Table 1 identifies the individual as one who may benefit from treatment with an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody). In some instances, the change is an increase. In other instances, the change is a decrease.

In another embodiment, provided herein is a method of diagnosing or prognosing a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) that includes determining the expression level of one or more (e.g., 1, 2, 3, 4, 5, 6, 7, 8, 9, 10, 11, 12, 13, 14, 15, 16, 17, 18, 19, 20, 21, or 22) biomarkers in a sample from an individual and comparing the expression level of the one or more biomarkers in the sample with a reference expression level, thereby diagnosing or prognosing the cancer. In some embodiments, a change in the expression level (e.g., an increase or a decrease) of the one or more biomarkers in the sample relative to the reference expression level diagnoses or prognoses the individual. In some embodiments, the biomarker is set forth in Table 1. In particular embodiments, the change is an increase.

In yet another embodiment, provided herein is a method of determining whether an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) is likely to respond to treatment with an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) that includes determining the expression level of one or more (e.g., 1, 2, 3, 4, 5, 6, 7, 8, 9, 10, 11, 12, 13, 14, 15, 16, 17, 18, 19, 20, 21, or 22) biomarkers in a sample from the individual and comparing the expression level of the one or more biomarkers in the sample with a reference expression level, thereby identifying the individual as one who is likely to respond to the anti-cancer therapy. In some embodiments, a change in the expression level (e.g., an increase or a decrease) of the one or more biomarkers in the biological sample relative to the reference expression level identifies the individual as likely to respond to treatment with the anti-cancer therapy. In some embodiments, the biomarker is set forth in Table 1. In particular embodiments, the change is an increase.

In other embodiments, provided herein is a method of optimizing therapeutic efficacy of an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) that includes determining the expression level of one or more (e.g., 1, 2, 3, 4, 5, 6, 7, 8, 9, 10, 11, 12, 13, 14, 15, 16, 17, 18, 19, 20, 21, or 22) biomarkers in a biological sample obtained from an individual and comparing the expression level of the one or more biomarkers in the sample with a reference expression level, wherein a change (e.g., an increase or decrease) in the expression level of the one or more biomarkers in the biological sample relative to the reference expression level identifies the individual as one who is likely to respond to the anti-cancer therapy. In some embodiments, the biomarker is set forth in Table 1. In particular embodiments, the change is an increase.

In some embodiments of any of the preceding methods involving the 22-gene signature, a reference expression level is the expression level of the one or more (e.g., 1, 2, 3, 4, 5, 6, 7, 8, 9, 10, 11, 12, 13, 14, 15, 16, 17, 18, 19, 20, 21, or 22) genes (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in a reference population, for example, a population of individuals having a cancer (e.g., a bladder cancer (e.g., UC, e.g., mUC), a kidney cancer, a lung cancer, a liver cancer, an ovarian cancer, a pancreatic cancer, a colorectal cancer, or a breast cancer). In particular embodiments, the cancer is a bladder cancer (e.g., UC, e.g., mUC). In certain embodiments, a reference expression level is the median expression level of the one or more genes in a reference population, for example, a population of individuals having a cancer. In other embodiments, the reference expression level may be the top 40%, the top 30%, the top 20%, the top 10%, the top 5%, or the top 1% of the expression level in the reference population. In some embodiments, the reference expression level is determined by principle component analysis of Z-score-transformed expression levels. In certain embodiments, the reference expression level is a pre-assigned expression level for the one or more genes. In some embodiments, the reference expression level is the expression level of the one or more genes in a biological sample obtained from the patient at a previous time point, wherein the previous time point is following administration of the anti-cancer therapy. In some embodiments of any of the preceding methods, a reference expression level is the expression level of the one or more genes (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in a biological sample from the patient obtained prior to (e.g., minutes, hours, days, weeks (e.g., 1, 2, 3, 4, 5, 6, or 7 weeks), months, or years prior to) administration of the anti-cancer therapy. In other embodiments, the reference expression level is the expression level of the one or more genes in a biological sample obtained from the patient at a subsequent time point (e.g., minutes, hours, days, weeks, months, or years after administration of an anti-cancer therapy).

In some embodiments of any of the preceding methods involving the 22-gene signature, an expression level above a reference expression level, or an elevated or increased expression or number, refers to an overall increase of about any of 10%, 20%, 30%, 40%, 50%, 60%, 70%, 80%, 90%, 95%, 96%, 97%, 98%, 99% or greater, in the level or number of a biomarker (e.g., protein, nucleic acid (e.g., gene or mRNA), or cell), detected by methods such as those described herein and/or known in the art, as compared to a reference expression level, reference sample, reference cell, reference tissue, control sample, control cell, or control tissue. In certain embodiments, the elevated expression or number refers to the increase in expression level/amount of a biomarker (e.g., one or more of TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in the sample wherein the increase is at least about any of 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× the expression level/amount of the respective biomarker in a reference expression level, reference sample, reference cell, reference tissue, control sample, control cell, or control tissue. In some embodiments, elevated expression or number refers to an overall increase in expression level/amount of a biomarker (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 22-gene signature, an expression level below a reference expression level, or a reduced (decreased) expression or number, refers to an overall reduction of about any of 10%, 20%, 30%, 40%, 50%, 60%, 70%, 80%, 90%, 95%, 96%, 97%, 98%, 99% or greater, in the level of biomarker (e.g., protein, nucleic acid (e.g., gene or mRNA), or cell), detected by standard art known methods such as those described herein, as compared to a reference expression level, reference sample, reference cell, reference tissue, control sample, control cell, or control tissue. In certain embodiments, reduced expression or number refers to the decrease in expression level/amount of a biomarker (e.g., one or more of TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference expression level, reference sample, reference cell, reference tissue, control sample, control cell, or control tissue. In some embodiments, reduced (decreased) expression or number refers to an overall decrease in expression level/amount of a biomarker (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 22-gene signature, a tumor from the individual has an immune excluded phenotype characterized by the localization of CD8+ T-cells in the peri-tumoral stromal compartment. In some embodiments, the CD8+ T-cells localize at or near collagen fibers.

B. Exemplary 6-Gene Signature

In some embodiments, the methods and uses herein involve determining the expression level of one or more (e.g., 1, 2, 3, 4, 5, or 6) genes selected from a 6-gene signature which includes ACTA2, ADAM19, COMP, CTGF, TGFB1, and TGFBR2.

For example, provided herein is a method of identifying an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from treatment with an anti-cancer therapy comprising an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method comprising determining the expression level of one or more (e.g., 1, 2, 3, 4, 5, or 6) of the following genes in a sample from the individual: ACTA2, ADAM19, COMP, CTGF, TGFB1, or TGFBR2, wherein an expression level of one or more of ACTA2, ADAM19, COMP, CTGF, TGFB1, or TGFBR2 in the sample that is at or above a reference expression level of the one or more genes identifies the individual as one who may benefit from treatment with an anti-cancer therapy comprising an immunotherapy and a suppressive stromal antagonist.

In yet another embodiment, provided herein is a method for selecting a therapy for an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method comprising determining the expression level of one or more (e.g., 1, 2, 3, 4, 5, or 6) of the following genes in a sample from the individual: ACTA2, ADAM19, COMP, CTGF, TGFB1, or TGFBR2, wherein an expression level of one or more of ACTA2, ADAM19, COMP, CTGF, TGFB1, or TGFBR2 in the sample that is at or above a reference expression level of the one or more genes identifies the individual as one who may benefit from treatment with an anti-cancer therapy comprising an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody).

In another embodiment, provided herein is a method of diagnosing or prognosing a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) that includes determining the expression level of one or more (e.g., 1, 2, 3, 4, 5, or 6) of the following genes in a sample from the individual: ACTA2, ADAM19, COMP, CTGF, TGFB1, or TGFBR2; and comparing the expression level of the one or more genes in the sample with a reference expression level, thereby diagnosing or prognosing the cancer. In some embodiments, a change in the expression level (e.g., an increase or a decrease) of the one or more biomarkers in the sample relative to the reference expression level diagnoses or prognoses the individual. In particular embodiments, the change is an increase.

In yet another embodiment, provided herein is a method of determining whether an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) is likely to respond to treatment with an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method comprising determining the expression level of one or more (e.g., 1, 2, 3, 4, 5, or 6) of the following genes in a sample from the individual: ACTA2, ADAM19, COMP, CTGF, TGFB1, or TGFBR2, wherein an expression level of one or more of ACTA2, ADAM19, COMP, CTGF, TGFB1, or TGFBR2 in the sample that is at or above a reference expression level of the one or more genes identifies the individual as one who is likely to respond to treatment with an anti-cancer therapy comprising an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody).

In other embodiments, provided herein is a method of optimizing therapeutic efficacy of an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody) that includes determining the expression level of one or more (e.g., 1, 2, 3, 4, 5, or 6) of the following genes in a sample from the individual: ACTA2, ADAM19, COMP, CTGF, TGFB1, or TGFBR2; and comparing the expression level of the one or more genes in the sample with a reference expression level, wherein an expression level of one or more of ACTA2, ADAM19, COMP, CTGF, TGFB1, or TGFBR2 in the sample that is at or above a reference expression level of the one or more genes identifies the individual as one who is likely to respond to treatment with an anti-cancer therapy comprising an immunotherapy and a suppressive stromal antagonist. In any of the preceding methods involving the 6-gene signature, the method may include determining the expression level of one or more (e.g., 1, 2, 3, 4, 5, or 6) of ACTA2, ADAM19, COMP, CTGF, TGFB1, or TGFBR2. In some embodiments, the method includes determining the expression level of at least two, at least three, at least four, at least five, or all six of ACTA2, ADAM19, COMP, CTGF, TGFB1, and TGFBR2. In some embodiments, the method includes determining the expression level of two of ACTA2, ADAM19, COMP, CTGF, TGFB1, and TGFBR2, for example, any of the exemplary combinations shown in Table 2. In some embodiments, the method includes determining the expression level of three of ACTA2, ADAM19, COMP, CTGF, TGFB1, and TGFBR2, for example, any of the exemplary combinations shown in Table 3. In some embodiments, the method includes determining the expression level of four of ACTA2, ADAM19, COMP, CTGF, TGFB1, and TGFBR2, for example, any of the exemplary combinations shown in Table 4. In some embodiments, the method includes determining the expression level of five of ACTA2, ADAM19, COMP, CTGF, TGFB1, and TGFBR2, for example, any of the exemplary combinations shown in Table 5. In some embodiments, the method involves determining the expression level of ACTA2, ADAM19, COMP, CTGF, TGFB1, and TGFBR2.

In any of the preceding methods involving the 6-gene signature, the method may include determining the expression level of TGFB1 and/or TGFBR2. In any of the preceding methods, the method may include determining the expression level of TGFB1 and TGFBR2.

In some embodiments of any of the preceding methods involving the 6-gene signature, the one or more genes includes at least ADAM19 or COMP. In some embodiments, the one or more genes includes ADAM19. In other embodiments, the one or more genes includes COMP. In still further embodiments, the one or more genes includes ADAM19 and COMP.

TABLE 2

| Two-Gene Combinations of ACTA2, ADAM19, COMP, CTGF, TGFB1, and TGFBR2 |
|---|
| ACTA2 and ADAM19 |
| ACTA2 and COMP |
| ACTA2 and CTGF |
| ACTA2 and TGFB1 |
| ACTA2 and TGFBR2 |
| ADAM19 and COMP |
| ADAM19 and CTGF |
| ADAM19 and TGFB1 |
| ADAM19 and TGFBR2 |
| COMP and CTGF |
| COMP and TGFB1 |
| COMP and TGFBR2 |
| CTGF and TGFB1 |
| CTGF and TGFBR2 |
| TGFB1 and TGFBR2 |

TABLE 3

| Three-Gene Combinations of ACTA2, ADAM19, COMP, CTGF, TGFB1, and TGFBR2 |
|---|
| ACTA2, ADAM19, and COMP |
| ACTA2, ADAM19, and CTGF |
| ACTA2, ADAM19, and TGFB1 |
| ACTA2, ADAM19, and TGFBR2 |
| ACTA2, COMP, and CTGF |
| ACTA2, COMP, and TGFB1 |
| ACTA2, COMP, and TGFBR2 |
| ACTA2, CTGF, and TGFB1 |
| ACTA2, CTGF, and TGFBR2 |
| ACTA2, TGFB1, and TGFBR2 |

TABLE 3-continued

| Three-Gene Combinations of ACTA2, ADAM19, COMP, CTGF, TGFB1, and TGFBR2 |
| --- |
| ADAM19, COMP, and CTGF |
| ADAM19, COMP, and TGFB1 |
| ADAM19, COMP, and TGFBR2 |
| ADAM19, CTGF, and TGFB1 |
| ADAM19, CTGF, and TGFBR2 |
| ADAM19, TGFB1, and TGFBR2 |
| COMP, CTGF, and TGFB1 |
| COMP, CTGF, and TGFBR2 |
| COMP, TGFB1, and TGFBR2 |
| CTGF, TGFB1, and TGFBR2 |

TABLE 4

| Four-Gene Combinations of ACTA2, ADAM19, COMP, CTGF, TGFB1, and TGFBR2 |
| --- |
| ACTA2, ADAM19, COMP, and CTGF |
| ACTA2, ADAM19, COMP, and TGFB1 |
| ACTA2, ADAM19, COMP, and TGFBR2 |
| ACTA2, ADAM19, CTGF, and TGFB1 |
| ACTA2, ADAM19, CTGF, and TGFBR2 |
| ACTA2, ADAM19, TGFB1, and TGFBR2 |
| ACTA2, COMP, CTGF, and TGFB1 |
| ACTA2, COMP, CTGF, and TGFBR2 |
| ACTA2, COMP, TGFB1, and TGFBR2 |
| ACTA2, CTGF, TGFB1, and TGFBR2 |
| ADAM19, COMP, CTGF, and TGFB1 |
| ADAM19, COMP, CTGF, and TGFBR2 |
| ADAM19, COMP, TGFB1, and TGFBR2 |
| ADAM19, CTGF, TGFB1, and TGFBR2 |
| COMP, CTGF, TGFB1, and TGFBR2 |

TABLE 5

| Five-Gene Combinations of ACTA2, ADAM19, COMP, CTGF, TGFB1, and TGFBR2 |
| --- |
| ACTA2, ADAM19, COMP, CTGF, and TGFB1 |
| ACTA2, ADAM19, COMP, CTGF, and TGFBR2 |
| ACTA2, ADAM19, COMP, TGFB1, and TGFBR2 |
| ACTA2, ADAM19, CTGF, TGFB1, and TGFBR2 |
| ACTA2, COMP, CTGF, TGFB1, and TGFBR2 |
| ADAM19, COMP, CTGF, TGFB1, and TGFBR2 |

In some embodiments of any of the preceding methods involving the 6-gene signature, the expression level of one or more (e.g., 1, 2, 3, 4, 5, or 6) of ACTA2, ADAM19, COMP, CTGF, TGFB1, and TGFBR2 in the sample is at or above a reference expression level of the one or more genes, and the method further includes administering to the individual an effective amount of the anti-cancer therapy. For example, in some embodiments, the expression level of at least two, at least three, at least four, at least five, or all six of ACTA2, ADAM19, COMP, CTGF, TGFB1, and TGFBR2 is at or above a reference expression level of the one or more genes. In some embodiments, the expression level of one or more of the exemplary combinations set forth in Tables 2-5 in the sample is at or above a reference expression level of the one or more genes. In some embodiments, the expression level of ACTA2, ADAM19, COMP, CTGF, TGFB1, and TGFBR2 is at or above a reference expression level of ACTA2, ADAM19, COMP, CTGF, TGFB1, and TGFBR2.

In some embodiments of any of the preceding methods involving the 6-gene signature, the expression level of TGFB1 and/or TGFBR1 is at or above a reference expression level of TGFB1 and/or TGFBR1. For example, in some embodiments, the expression level of TGFB1 is at or above a reference expression level of TGFB1. In some embodiments, the expression level of TGFBR1 is at or above a reference expression level of TGFBR1. In some embodiments, the expression level of TGFB1 and TGFBR1 is at or above a reference expression level of TGFB1 and TGFBR1.

In some embodiments of any of the preceding methods involving the 6-gene signature, the one or more genes includes at least ADAM19 or COMP. In some embodiments, the one or more genes includes ADAM19. In other embodiments, the one or more genes includes COMP. In still further embodiments, the one or more genes includes ADAM19 and COMP.

In other embodiments of any of the preceding methods involving the 6-gene signature, the expression level of one or more (e.g., 1, 2, 3, 4, 5, or 6) of ACTA2, ADAM19, COMP, CTGF, TGFB1, and TGFBR2 in the sample is below a reference expression level of the one or more genes, and the method further includes administering to the individual an effective amount of an anti-cancer therapy that includes an immunotherapy (e.g., a PD-L1 axis binding antagonist, e.g., an anti-PD-L1 antibody (e.g., atezolizumab)) alone. For example, in some embodiments, the expression level of at least two, at least three, at least four, at least five, or all six of ACTA2, ADAM19, COMP, CTGF, TGFB1, and TGFBR2 is below a reference expression level of the one or more genes. In some embodiments, the expression level of one or more of the exemplary combinations set forth in Tables 2-5 in the sample is below a reference expression level of the one or more genes. In some embodiments, the expression level of ACTA2, ADAM19, COMP, CTGF, TGFB1, and TGFBR2 is below a reference expression level of ACTA2, ADAM19, COMP, CTGF, TGFB1, and TGFBR2. In some embodiments, the one or more genes includes at least ADAM19 or COMP. In some embodiments, the one or more genes includes ADAM19. In other embodiments, the one or more genes includes COMP. In still further embodiments, the one or more genes includes ADAM19 and COMP.

For example, in certain embodiments of any of the preceding methods involving the 6-gene signature, a reference expression level is the expression level of the one or more (e.g., 1, 2, 3, 4, 5, or 6) genes (e.g., ACTA2, ADAM19, COMP, CTGF, TGFB1, and/or TGFBR2) in a reference population, for example, a population of individuals having a cancer (e.g., a bladder cancer (e.g., UC, e.g., mUC), a kidney cancer, a lung cancer, a liver cancer, an ovarian cancer, a pancreatic cancer, a colorectal cancer, or a breast cancer). In particular embodiments, the cancer is a bladder cancer (e.g., UC, e.g., mUC). In certain embodiments, a reference expression level is the median expression level of the one or more genes in a reference population, for example, a population of individuals having a cancer. In other embodiments, the reference expression level may be the top 40%, the top 30%, the top 20%, the top 10%, the top 5%, or the top 1% of the expression level in the reference population. In some embodiments, the reference expression level is determined by principle component analysis of Z-score-transformed expression levels. In certain embodiments, the reference expression level is a pre-assigned expression level for the one or more genes. In some embodiments, the reference expression level is the expression level of the one or more genes in a biological sample obtained from the patient at a previous time point, wherein the previous time point is following administration of the anti-cancer therapy. In some embodiments of any of the preceding methods, a reference expression level is the expression level of the one or more genes (e.g., ACTA2, ADAM19, COMP, CTGF, TGFB1, and/or TGFBR2) in a biological sample from the patient obtained prior to (e.g., minutes, hours, days, weeks (e.g., 1, 2, 3, 4, 5, 6, or 7 weeks), months, or years prior to) administration of the anti-cancer therapy. In other embodiments, the reference expression level is the expression level of the one or more genes in a biological sample obtained from the patient at a subsequent time point (e.g., minutes, hours, days, weeks, months, or years after administration of an anti-cancer therapy).

In some embodiments of any of the preceding methods involving the 6-gene signature, an expression level above a reference expression level, or an elevated or increased expression or number, refers to an overall increase of about any of 10%, 20%, 30%, 40%, 50%, 60%, 70%, 80%, 90%, 95%, 96%, 97%, 98%, 99% or greater, in the level or number of a biomarker (e.g., protein, nucleic acid (e.g., gene or mRNA), or cell), detected by methods such as those described herein and/or known in the art, as compared to a reference expression level, reference sample, reference cell, reference tissue, control sample, control cell, or control tissue. In certain embodiments, the elevated expression or number refers to the increase in expression level/amount of a biomarker (e.g., one or more of ACTA2, ADAM19, COMP, CTGF, TGFB1, and/or TGFBR2) in the sample wherein the increase is at least about any of 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× the expression level/amount of the respective biomarker in a reference expression level, reference sample, reference cell, reference tissue, control sample, control cell, or control tissue. In some embodiments, elevated expression or number refers to an overall increase in expression level/amount of a biomarker (e.g., ACTA2, ADAM19, COMP, CTGF, TGFB1, and/or TGFBR2) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 6-gene signature, an expression level below a reference expression level, or a reduced (decreased) expression or number, refers to an overall reduction of about any of 10%, 20%, 30%, 40%, 50%, 60%, 70%, 80%, 90%, 95%, 96%, 97%, 98%, 99% or greater, in the level of biomarker (e.g., protein, nucleic acid (e.g., gene or mRNA), or cell), detected by standard art known methods such as those described herein, as compared to a reference expression level, reference sample, reference cell, reference tissue, control sample, control cell, or control tissue. In certain embodiments, reduced expression or number refers to the decrease in expression level/amount of a biomarker (e.g., one or more of ACTA2, ADAM19, COMP, CTGF, TGFB1, and/or TGFBR2) in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference expression level, reference sample, reference cell, reference tissue, control sample, control cell, or control tissue. In some embodiments, reduced (decreased) expression or number refers to an overall decrease in expression level/amount of a biomarker (e.g., ACTA2, ADAM19, COMP, CTGF, TGFB1, and/or TGFBR2) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 6-gene signature, a tumor from the individual has an immune excluded phenotype characterized by the localization of CD8+ T-cells in the peri-tumoral stromal compartment. In some embodiments, the CD8+ T-cells localize at or near collagen fibers.

C. Exemplary 19-Gene Signature (Pan-F-TBRS)

In some embodiments, the methods and uses herein involve determining the expression level of one or more (e.g., 1, 2, 3, 4, 5, 6, 7, 8, 9, 10, 11, 12, 13, 14, 15, 16, 17, 18, or 19) genes selected from a 19-gene signature which includes ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1, which is also referred to herein as Pan-F-TBRS.

For example, provided herein is a method of identifying an individual having a cancer who may benefit from treatment with an anti-cancer therapy comprising an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method comprising determining the expression level of one or more (e.g., 1, 2, 3, 4, 5, 6, 7, 8, 9, 10, 11, 12, 13, 14, 15, 16, 17, 18, or 19) of the following genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1, wherein an expression level of one or more of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1 in the sample that is at or above a reference expression level of the one or more genes identifies the individual as one who may benefit from treatment with an anti-cancer therapy comprising an immunotherapy and a suppressive stromal antagonist.

In yet another embodiment, provided herein is a method for selecting a therapy for an individual having a cancer, the method comprising determining the expression level of one or more (e.g., 1, 2, 3, 4, 5, 6, 7, 8, 9, 10, 11, 12, 13, 14, 15, 16, 17, 18, or 19) of the following genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1, wherein an expression level of one or more of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1 in the sample that is at or above a reference expression level of the one or more genes identifies the individual as one who may benefit from treatment with an anti-cancer therapy comprising an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody).

In another embodiment, provided herein is a method of diagnosing or prognosing a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) that includes determining the expression level of one or more (e.g., 1, 2, 3, 4, 5, 6, 7, 8, 9, 10, 11, 12, 13, 14, 15, 16, 17, 18, or 19) of the following genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1; and comparing the expression level of the one or more genes in the sample with a reference expression level, thereby diagnosing or prognosing the cancer. In some embodiments, a change in the expression level (e.g., an increase or a decrease) of the one or more biomarkers in the sample relative to the reference expression level diagnoses or prognoses the individual. In particular embodiments, the change is an increase.

In yet another embodiment, provided herein is a method of determining whether an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) is likely to respond to treatment with an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method comprising determining the expression level of one or more (e.g., 1, 2, 3, 4, 5, 6, 7, 8, 9, 10, 11, 12, 13, 14, 15, 16, 17, 18, or 19) of the following genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1, wherein an expression level of one or more of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1 in the sample that is at or above a reference expression level of the one or more genes identifies the individual as one who is likely to respond to treatment with an anti-cancer therapy comprising an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody).

In other embodiments, provided herein is a method of optimizing therapeutic efficacy of an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody) that includes determining the expression level of one or more (e.g., 1, 2, 3, 4, 5, 6, 7, 8, 9, 10, 11, 12, 13, 14, 15, 16, 17, 18, or 19) of the following genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1; and comparing the expression level of the one or more genes in the sample with a reference expression level, wherein an expression level of one or more of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1 in the sample that is at or above a reference expression level of the one or more genes identifies the individual as one who is likely to respond to treatment with an anti-cancer therapy comprising an immunotherapy and a suppressive stromal antagonist.

In any of the preceding methods involving the 19-gene signature, the method may include determining the expression level of one or more (e.g., 1, 2, 3, 4, 5, 6, 7, 8, 9, 10, 11, 12, 13, 14, 15, 16, 17, 18, or 19) of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, the method includes determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, the method involves determining the expression level of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1.

In some embodiments of any of the preceding methods involving the 19-gene signature, the expression level of one or more (e.g., 1, 2, 3, 4, 5, 6, 7, 8, 9, 10, 11, 12, 13, 14, 15, 16, 17, 18, or 19) of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 in the sample is at or above a reference expression level of the one or more genes, and the method further includes administering to the individual an effective amount of the anti-cancer therapy. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 is at or above a reference expression level of the one or more genes. In some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 is at or above a reference expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1.

In some embodiments of any of the preceding methods involving the 19-gene signature, the one or more genes includes at least one or more (e.g., 1, 2, 3, 4, 5, 6, 7, 8, 9, 10, 11, 12, 13, 14, or 15) of ADAM19, ACTG2, CNN1, CTPS1, FAM101B, FSTL3, HSPB1, IGFBP3, PXDC1, SEMA7A, SH3PXD2A, TAGLN, TGFBI, TNS1, or TPM1.

In some embodiments of any of the preceding methods involving the 19-gene signature, a reference expression level is the expression level of the one or more (e.g., 1, 2, 3, 4, 5, 6, 7, 8, 9, 10, 11, 12, 13, 14, 15, 16, 17, 18, or 19) genes (e.g., ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in a reference population, for example, a population of individuals having a cancer (e.g., a bladder cancer (e.g., UC, e.g., mUC), a kidney cancer, a lung cancer, a liver cancer, an ovarian cancer, a pancreatic cancer, a colorectal cancer, or a breast cancer). In particular embodiments, the cancer is a bladder cancer (e.g., UC, e.g., mUC). In certain embodiments, a reference expression level is the median expression level of the one or more genes in a reference population, for example, a population of individuals having a cancer. In other embodiments, the reference level may be the top 40%, the top 30%, the top 20%, the top 10%, the top 5%, or the top 1% of the expression level in the reference population. In some embodiments, the reference expression level is determined by principle component analysis of Z-score-transformed expression levels. In certain embodiments, the reference expression level is a pre-assigned expression level for the one or more genes. In some embodiments, the reference expression level is the expression level of the one or more genes in a biological sample obtained from the patient at a previous time point, wherein the previous time point is following administration of the anti-cancer therapy. In some embodiments of any of the preceding methods, a reference expression level is the expression level of the one or more genes (e.g., ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in a biological sample from the patient obtained prior to (e.g., minutes, hours, days, weeks (e.g., 1, 2, 3, 4, 5, 6, or 7 weeks), months, or years prior to) administration of the anti-cancer therapy. In other embodiments, the reference expression level is the expression level of the one or more genes in a biological sample obtained from the patient at a subsequent time point (e.g., minutes, hours, days, weeks, months, or years after administration of an anti-cancer therapy).

In some embodiments of any of the preceding methods involving the 19-gene signature, an expression level above a reference expression level, or an elevated or increased expression or number, refers to an overall increase of about any of 10%, 20%, 30%, 40%, 50%, 60%, 70%, 80%, 90%, 95%, 96%, 97%, 98%, 99% or greater, in the level or number of a biomarker (e.g., protein, nucleic acid (e.g., gene or mRNA), or cell), detected by methods such as those described herein and/or known in the art, as compared to a reference expression level, reference sample, reference cell, reference tissue, control sample, control cell, or control tissue. In certain embodiments, the elevated expression or number refers to the increase in expression level/amount of a biomarker (e.g., one or more of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in the sample wherein the increase is at least about any of 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× the expression level/amount of the respective biomarker in a reference expression level, reference sample, reference cell, reference tissue, control sample, control cell, or control tissue. In some embodiments, elevated expression or number refers to an overall increase in expression level/amount of a biomarker (e.g., ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 19-gene signature, an expression level below a reference expression level, or a reduced (decreased) expression or number, refers to an overall reduction of about any of 10%, 20%, 30%, 40%, 50%, 60%, 70%, 80%, 90%, 95%, 96%, 97%, 98%, 99% or greater, in the level of biomarker (e.g., protein, nucleic acid (e.g., gene or mRNA), or cell), detected by standard art known methods such as those described herein, as compared to a reference expression level, reference sample, reference cell, reference tissue, control sample, control cell, or control tissue. In certain embodiments, reduced expression or number refers to the decrease in expression level/amount of a biomarker (e.g., one or more of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference expression level, reference sample, reference cell, reference tissue, control sample, control cell, or control tissue. In some embodiments, reduced (decreased) expression or number refers to an overall decrease in expression level/amount of a biomarker (e.g., ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 19-gene signature, a tumor from the individual has an immune excluded phenotype characterized by the localization of CD8+ T-cells in the peri-tumoral stromal compartment. In some embodiments, the CD8+ T-cells localize at or near collagen fibers.

D. Exemplary Additional Biomarkers (e.g., CD8+T-Effector Signature)

Any of the preceding methods (e.g., as described in Section II, Subsections A-C above, relating to the 22-, 6-, and 19-gene (Pan-F-TBRS) signatures, respectively) can further include determining the expression level in the sample of one or more (e.g., 1, 2, 3, 4, 5, 6, 7, 8 or 9) additional genes selected from the group consisting of PD-L1, CD8A, CXCL10, CXCL9, GZMA, GZMB, IFNG, PRF1, and TBX21. In some embodiments, the one or more additional gene is PD-L1. In other embodiments, the one or more (e.g., 1, 2, 3, 4, 5, 6, 7, or 8) additional genes is selected from the group consisting of CD8A, CXCL10, CXCL9, GZMA, GZMB, IFNG, PRF1, and TBX21, which is also referred to herein as a CD8+T-effector (Teff) signature. In some embodiments, the method further includes determining the expression level of at least two, at least three, at least four, at least five, at least six, at least seven, or all eight of CD8A, CXCL10, CXCL9, GZMA, GZMB, IFNG, PRF1, and TBX21. In some embodiments, the one or more additional genes are CD8A, CXCL10, CXCL9, GZMA, GZMB, IFNG, PRF1, and TBX21.

For example, provided herein is a method of identifying an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from treatment with an anti-cancer therapy comprising an immunotherapy (e.g., a PD-L1 axis binding antagonist, e.g., an anti-PD-L1 antibody (e.g., atezolizumab)), the method comprising determining the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21, and one or more (e.g., 1, 2, 3, 4, 5, 6, 7, 8, 9, 10, 11, 12, 13, 14, 15, 16, 17, 18, 19, 20, 21, or 22) of the following 22-gene signature genes in the sample: TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1, wherein an expression level of one or more of the Teff genes in the sample that is at or above a reference expression level of the one or more Teff genes and an expression level of one or more of the 22-gene signature genes that is below a reference expression level of the one or more 22-gene signature genes identifies the individual as one who may benefit from treatment with an anti-cancer therapy comprising an immunotherapy (e.g., a PD-L1 axis binding antagonist, e.g., an anti-PD-L1 antibody (e.g., atezolizumab)). In some embodiments, the immunotherapy is a monotherapy. In some embodiments, the method further includes administering the anti-cancer therapy to the patient.

In another embodiment, provided herein is a method of identifying an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from treatment with an anti-cancer therapy comprising an immunotherapy (e.g., a PD-L1 axis binding antagonist, e.g., an anti-PD-L1 antibody (e.g., atezolizumab)), the method comprising determining the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21, and one or more (e.g., 1, 2, 3, 4, 5, or 6) of the following 6-gene signature genes in the sample: ACTA2, ADAM19, COMP, CTGF, TGFB1, and TGFBR2, wherein an expression level of one or more of the Teff genes in the sample that is at or above a reference expression level of the one or more Teff genes and an expression level of one or more of the 6-gene signature genes that is below a reference expression level of the one or more 6-gene signature genes identifies the individual as one who may benefit from treatment with an anti-cancer therapy comprising an immunotherapy (e.g., a PD-L1 axis binding antagonist, e.g., an anti-PD-L1 antibody (e.g., atezolizumab)). In some embodiments, the immunotherapy is a monotherapy. In some embodiments, the method further includes administering the anti-cancer therapy to the patient.

In another embodiment, provided herein is a method of identifying an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from treatment with an anti-cancer therapy comprising an immunotherapy (e.g., a PD-L1 axis binding antagonist, e.g., an anti-PD-L1 antibody (e.g., atezolizumab)), the method comprising determining the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21, and one or more (e.g., 1, 2, 3, 4, 5, 6, 7, 8, 9, 10, 11, 12, 13, 14, 15, 16, 17, 18, or 19) of the following Pan-F-TBRS genes in the sample: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1, wherein an expression level of one or more of the Teff genes in the sample that is at or above a reference expression level of the one or more Teff genes and an expression level of one or more of the Pan-F-TBRS genes that is below a reference expression level of the one or more Pan-F-TBRS genes identifies the individual as one who may benefit from treatment with an anti-cancer therapy comprising an immunotherapy (e.g., a PD-L1 axis binding antagonist, e.g., an anti-PD-L1 antibody (e.g., atezolizumab)). In some embodiments, the immunotherapy is a monotherapy. In some embodiments, the method further includes administering the anti-cancer therapy to the patient.

For example, provided herein is a method for selecting a therapy for an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method comprising determining the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21, and one or more (e.g., 1, 2, 3, 4, 5, 6, 7, 8, 9, 10, 11, 12, 13, 14, 15, 16, 17, 18, 19, 20, 21, or 22) of the following 22-gene signature genes in the sample: TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1, wherein an expression level of one or more of the Teff genes in the sample that is at or above a reference expression level of the one or more Teff genes and an expression level of one or more of the 22-gene signature genes that is below a reference expression level of the one or more 22-gene signature genes identifies the individual as one who may benefit from treatment with an anti-cancer therapy comprising an immunotherapy (e.g., a PD-L1 axis binding antagonist, e.g., an anti-PD-L1 antibody (e.g., atezolizumab)). In some embodiments, the immunotherapy is a monotherapy. In some embodiments, the method further includes administering the anti-cancer therapy to the patient.

In another embodiment, provided herein is a method for selecting a therapy for an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method comprising determining the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21, and one or more (e.g., 1, 2, 3, 4, 5, or 6) of the following 6-gene signature genes in the sample: ACTA2, ADAM19, COMP, CTGF, TGFB1, and TGFBR2, wherein an expression level of one or more of the Teff genes in the sample that is at or above a reference expression level of the one or more Teff genes and an expression level of one or more of the 6-gene signature genes that is below a reference expression level of the one or more 6-gene signature genes identifies the individual as one who may benefit from treatment with an anti-cancer therapy comprising an immunotherapy (e.g., a PD-L1 axis binding antagonist, e.g., an anti-PD-L1 antibody (e.g., atezolizumab)). In some embodiments, the immunotherapy is a monotherapy. In some embodiments, the method further includes administering the anti-cancer therapy to the patient.

In yet another embodiment, provided herein is a method for selecting a therapy for an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method comprising determining the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21, and one or more (e.g., 1, 2, 3, 4, 5, 6, 7, 8, 9, 10, 11, 12, 13, 14, 15, 16, 17, 18, or 19) of the following Pan-F-TBRS genes in the sample: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1, wherein an expression level of one or more of the Teff genes in the sample that is at or above a reference expression level of the one or more Teff genes and an expression level of one or more of the Pan-F-TBRS genes that is below a reference level of the one or more Pan-F-TBRS genes identifies the individual as one who may benefit from treatment with an anti-cancer therapy comprising an immunotherapy (e.g., a PD-L1 axis binding antagonist, e.g., an anti-PD-L1 antibody (e.g., atezolizumab)). In some embodiments, the immunotherapy is a monotherapy. In some embodiments, the method further includes administering the anti-cancer therapy to the patient.

E. Tumor Mutational Burden (TMB)

Any of the preceding embodiments (e.g., as described in Section II, Subsections A-C above, relating to the 22-, 6-, and 19-gene (Pan-F-TBRS) signatures, respectively, or in Section II, Subsection D) may further include determining a TMB in a tumor sample from the individual. TMB may be determined using any suitable approach, for example, as described in Example 1 below or in International Patent Application No.: PCT/US2017/055669, which is incorporated herein by reference in its entirety. In some embodiments, the individual may have a TMB in a tumor sample that is at or above a reference TMB. In other embodiments, the individual may have a TMB that is below a reference TMB.

For example, the invention provides a method of identifying an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from a treatment with an immunotherapy (e.g., a PD-L1 axis binding antagonist, e.g., an anti-PD-L1 antibody (e.g., atezolizumab)), the method comprising determining (i) the expression level of one or more (e.g., 1, 2, 3, 4, 5, 6, 7, 8, 9, 10, 11, 12, 13, 14, 15, 16, 17, 18, 19, 20, 21, or 22) of the following 22-gene signature genes: TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 in a sample from the patient; and (ii) a TMB score from a tumor sample from the individual, wherein an expression level of the one or more 22-gene signature genes in the sample that is below a reference level and a TMB score from the tumor sample that is at or above a reference TMB score identifies the individual as one who may benefit from a treatment comprising an immunotherapy (e.g., a PD-L1 axis binding antagonist (e.g., an anti-PD-L1 antibody)). In some embodiments, the immunotherapy is a monotherapy.

The invention provides a method of identifying an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from a treatment with an immunotherapy (e.g., a PD-L1 axis binding antagonist, e.g., an anti-PD-L1 antibody (e.g., atezolizumab)), the method comprising determining (i) the expression level of one or more (e.g., 1, 2, 3, 4, 5, or 6) of the following 6-gene signature genes: ACTA2, ADAM19, COMP, CTGF, TGFB1, and TGFBR2 in a sample from the patient; and (ii) a TMB score from a tumor sample from the individual, wherein an expression level of the one or more 6-gene signature genes in the sample that is below a reference expression level and a TMB score from the tumor sample that is at or above a reference TMB score identifies the individual as one who may benefit from a treatment comprising an immunotherapy (e.g., a PD-L1 axis binding antagonist (e.g., an anti-PD-L1 antibody)). In some embodiments, the immunotherapy is a monotherapy.

The invention provides a method of identifying an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from a treatment with an immunotherapy (e.g., a PD-L1 axis binding antagonist, e.g., an anti-PD-L1 antibody (e.g., atezolizumab)), the method comprising determining (i) the expression level of one or more (e.g., 1, 2, 3, 4, 5, 6, 7, 8, 9, 10, 11, 12, 13, 14, 15, 16, 17, 18, or 19) of the following Pan-F-TBRS genes: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 in a sample from the patient; and (ii) a TMB score from a tumor sample from the individual, wherein an expression level of the one or more Pan-F-TBRS genes in the sample that is below a reference expression level and a TMB score from the tumor sample that is at or above a reference TMB score identifies the individual as one who may benefit from a treatment comprising an immunotherapy (e.g., a PD-L1 axis binding antagonist (e.g., an anti-PD-L1 antibody (e.g., atezolizumab))). In some embodiments, the immunotherapy is a monotherapy.

Any of the preceding methods involving TMB can further include determining the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21.

F. Exemplary Approaches for Determination of Biomarker Expression Levels

The presence and/or expression level of any of the biomarkers described above (e.g., as described in Section II, Subsections A-C above, relating to the 22-, 6-, and 19-gene (Pan-F-TBRS) signatures, respectively, or in Section II, Subsections D and E) may be assessed qualitatively and/or quantitatively based on any suitable criterion known in the art, including but not limited to DNA, mRNA, cDNA, proteins, protein fragments, and/or gene copy number. Methodologies for measuring such biomarkers are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (e.g., Serum ELISA), biochemical enzymatic activity assays, in situ hybridization (ISH), fluorescence in situ hybridization (FISH), Southern analysis, Northern analysis, whole genome sequencing, polymerase chain reaction (PCR) including quantitative real time PCR (qRT-PCR) and other amplification type detection methods, such as, for example, branched DNA, SISBA, TMA and the like, RNASeq, microarray analysis, gene expression profiling, whole-genome sequencing (WGS), and/or serial analysis of gene expression ("SAGE"), as well as any one of the wide variety of assays that can be performed by protein, gene, and/or tissue array analysis. Typical protocols for evaluating the status of genes and gene products are found, for example, in Ausubel et al. eds. (*Current Protocols In Molecular Biology,* 1995), Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In some embodiments of any of the preceding methods, the expression level of a biomarker may be a nucleic acid expression level (e.g., a DNA expression level or an RNA expression level (e.g., an mRNA expression level)). Any suitable method of determining a nucleic acid expression level may be used. In some embodiments, the nucleic acid expression level is determined using RNAseq, RT-qPCR, qPCR, multiplex qPCR or RT-qPCR, microarray analysis, SAGE, MassARRAY technique, ISH, or a combination thereof.

Methods for the evaluation of mRNAs in cells are well known and include, for example, serial analysis of gene expression (SAGE), whole genome sequencing (WGS), hybridization assays using complementary DNA probes (such as in situ hybridization using labeled riboprobes specific for the one or more genes, Northern blot and related techniques) and various nucleic acid amplification assays (such as RT-PCR (e.g., qRT-PCR) using complementary primers specific for one or more of the genes, and other amplification type detection methods, such as, for example, branched DNA, SISBA, TMA and the like). In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined. Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with increased or reduced clinical benefit of treatment comprising an immunotherapy and a suppressive stromal antagonist may be arrayed on a solid support. Hybridization of a labeled probe with a particular array member indicates that the sample from which the probe was derived expresses that gene.

In other embodiments of any of the preceding methods, the expression level of a biomarker may be a protein expression level. In certain embodiments, the method comprises contacting the sample with antibodies that specifically bind to a biomarker described herein under conditions permissive for binding of the biomarker, and detecting whether a complex is formed between the antibodies and biomarker. Such method may be an in vitro or in vivo method. In some instances, an antibody is used to select patients eligible for treatment with an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody), e.g., a biomarker for selection of individuals.

Any method of measuring protein expression levels known in the art or provided herein may be used. For example, in some embodiments, a protein expression level of a biomarker is determined using a method selected from the group consisting of flow cytometry (e.g., fluorescence-activated cell sorting (FACS™)), Western blot, enzyme-linked immunosorbent assay (ELISA), immunoprecipitation, immunohistochemistry (IHC), immunofluorescence, radioimmunoassay, dot blotting, immunodetection methods, HPLC, surface plasmon resonance, optical spectroscopy, mass spectrometry, and HPLC. In some embodiments, the protein expression level of the biomarker is determined in tumor-infiltrating immune cells. In some embodiments, the protein expression level of the biomarker is determined in tumor cells. In some embodiments, the protein expression level of the biomarker is determined in tumor-infiltrating immune cells and/or in tumor cells. In some embodiments, the protein expression level of the biomarker is determined in peripheral blood mononuclear cells (PBMCs).

In certain embodiments, the presence and/or expression level/amount of a biomarker protein in a sample is examined using IHC and staining protocols. IHC staining of tissue sections has been shown to be a reliable method of determining or detecting the presence of proteins in a sample. In some embodiments of any of the methods, assays and/or kits, the biomarker is one or more of the protein expression products of the following genes: TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1. In one embodiment, an expression level of biomarker is determined using a method comprising: (a) performing IHC analysis of a sample (such as a tumor sample obtained from a patient) with an antibody; and (b) determining expression level of a biomarker in the sample. In some embodiments, IHC staining intensity is determined relative to a reference. In some embodiments, the reference is a reference value. In some embodiments, the reference is a reference sample (e.g., a control cell line staining sample, a tissue sample from non-cancerous patient, or a tumor sample that is determined to be negative for the biomarker of interest).

IHC may be performed in combination with additional techniques such as morphological staining and/or in situ hybridization (e.g., ISH). Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for IHC typically will be labeled with a detectable moiety. Numerous labels are available which can be generally grouped into the following categories: (a) radioisotopes, such as $^{35}S$, $^{14}C$, $^{125}I$, $^{3}H$, and $^{131}I$; (b) colloidal gold particles; (c) fluorescent labels including, but are not limited to, rare earth chelates (europium chelates), Texas Red, rhodamine, fluorescein, dansyl, lissamine, umbelliferone, phycocrytherin, phycocyanin, or commercially-available fluorophores such as SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; see, e.g., U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). For a general review of these, see, for example, U.S. Pat. Nos. 4,275,149 and 4,318,980.

Specimens may be prepared, for example, manually, or using an automated staining instrument (e.g., a Ventana BenchMark XT or Benchmark ULTRA instrument). Specimens thus prepared may be mounted and coverslipped. Slide evaluation is then determined, for example, using a microscope, and staining intensity criteria, routinely used in the art, may be employed. In one embodiment, it is to be understood that when cells and/or tissue from a tumor is examined using IHC, staining is generally determined or assessed in tumor cell(s) and/or tissue (as opposed to stromal or surrounding tissue that may be present in the sample). In some embodiments, it is understood that when cells and/or tissue from a tumor is examined using IHC, staining includes determining or assessing in tumor-infiltrating immune cells, including intratumoral or peritumoral immune cells. In some embodiments, the presence of a biomarker is detected by IHC in >0% of the sample, in at least 1% of the sample, in at least 5% of the sample, in at least 10% of the sample, in at least 15% of the sample, in at least 15% of the sample, in at least 20% of the sample, in at least 25% of the sample, in at least 30% of the sample, in at least 35% of the sample, in at least 40% of the sample, in at least 45% of the sample, in at least 50% of the sample, in at least 55% of the sample, in at least 60% of the sample, in at least 65% of the sample, in at least 70% of the sample, in at least 75% of the sample, in at least 80% of the sample, in at least 85% of the sample, in at least 90% of the sample, in at least 95% of the sample, or more. Samples may be scored using any method known in the art, for example, by a pathologist or automated image analysis.

In some embodiments of any of the methods, the biomarker is detected by immunohistochemistry using a diagnostic antibody (i.e., primary antibody). In some embodiments, the diagnostic antibody specifically binds human antigen. In some embodiments, the diagnostic antibody is a non-human antibody. In some embodiments, the diagnostic antibody is a rat, mouse, or rabbit antibody. In some embodiments, the diagnostic antibody is a rabbit antibody. In some embodiments, the diagnostic antibody is a monoclonal antibody. In some embodiments, the diagnostic antibody is directly labeled. In other embodiments, the diagnostic antibody is indirectly labeled (e.g., by a secondary antibody).

In some embodiments of any of the preceding embodiments, the sample is obtained from the individual prior to (e.g., minutes, hours, days, weeks (e.g., 1, 2, 3, 4, 5, 6, or 7 weeks), months, or years prior to) administration of the anti-cancer therapy. In some embodiments of any of the preceding methods, the sample from the individual is obtained about 2 to about 10 weeks (e.g., 2, 3, 4, 5, 6, 7, 8, 9, or 10 weeks) following administration of the anti-cancer therapy. In some embodiments, the sample from the individual is obtained about 4 to about 6 weeks following administration of the anti-cancer therapy.

In some embodiments of any of the preceding methods, the expression level or number of a biomarker is detected in a tissue sample, a primary or cultured cells or cell line, a cell supernatant, a cell lysate, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, or any combination thereof. In some embodiments, the sample is a tissue sample (e.g., a tumor tissue sample), a cell sample, a whole blood sample, a plasma sample, a serum sample, or a combination thereof. In some embodiments, the tumor tissue sample wherein the tumor tissue sample includes tumor cells, tumor-infiltrating immune cells, stromal cells, or a combination thereof. In some embodiments, the tumor tissue sample is a formalin-fixed and paraffin-embedded (FFPE) sample, an archival sample, a fresh sample, or a frozen sample.

For example, in some embodiments of any of the preceding methods, the expression level of a biomarker is detected in tumor-infiltrating immune cells, tumor cells, PBMCs, or combinations thereof using known techniques (e.g., flow cytometry or IHC). Tumor-infiltrating immune cells include, but are not limited to, intratumoral immune cells, peritumoral immune cells or any combinations thereof, and other tumor stroma cells (e.g., fibroblasts). Such tumor infiltrating immune cells may be T lymphocytes (such as CD8+T lymphocytes (e.g., CD8+T effector (Teff) cells) and/or CD4+T lymphocytes (e.g., CD4+ Teff cells), B lymphocytes, or other bone marrow-lineage cells including granulocytes (neutrophils, eosinophils, basophils), monocytes, macrophages, dendritic cells (e.g., interdigitating dendritic cells), histiocytes, and natural killer (NK) cells. In some embodiments, the staining for a biomarker is detected as membrane staining, cytoplasmic staining, or combinations thereof. In other embodiments, the absence of a biomarker is detected as absent or no staining in the sample, relative to a reference sample.

In particular embodiments of any of the preceding methods, the expression level of a biomarker is assessed in a sample that contains or is suspected to contain cancer cells. The sample may be, for example, a tissue biopsy or a metastatic lesion obtained from a patient suffering from, suspected to suffer from, or diagnosed with cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer). In some embodiments, the sample is a sample of bladder tissue, a biopsy of a bladder tumor, a known or suspected metastatic bladder cancer lesion or section, or a blood sample, e.g., a peripheral blood sample, known or suspected to comprise circulating cancer cells, e.g., bladder cancer cells. The sample may comprise both cancer cells, i.e., tumor cells, and non-cancerous cells (e.g., lymphocytes, such as T cells or NK cells), and, in certain embodiments, comprises both cancerous and non-cancerous cells. Methods of obtaining biological samples including tissue resections, biopsies, and body fluids, e.g., blood samples comprising cancer/tumor cells, are well known in the art.

In some embodiments of any of the preceding methods, the patient has carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. In some embodiments, the cancer is bladder cancer (e.g., UC, e.g., mUC), kidney cancer (e.g., renal cell carcinoma (RCC), e.g., advanced RCC or metastatic RCC (mRCC)), squamous cell cancer (e.g., epithelial squamous cell cancer), lung cancer (including small-cell lung cancer (SCLC), non-small cell lung cancer (NSCLC), adenocarcinoma of the lung, and squamous carcinoma of the lung), cancer of the peritoneum, hepatocellular cancer, gastric or stomach cancer including gastrointestinal cancer, pancreatic cancer (e.g., PDAC), glioblastoma, cervical cancer, ovarian cancer, liver cancer (e.g., HCC), hepatoma, breast cancer (including metastatic breast cancer), colon cancer, rectal cancer, colorectal cancer, endometrial or uterine carcinoma, salivary gland carcinoma, prostate cancer, vulval cancer, thyroid cancer, hepatic carcinoma, anal carcinoma, penile carcinoma, Merkel cell cancer, mycoses fungoids, testicular cancer, esophageal cancer, tumors of the biliary tract, head and neck cancer, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), abnormal vascular proliferation associated with phakomatoses, edema (such as that associated with brain tumors), or Meigs' syndrome. In some embodiments, the cancer is a bladder cancer (e.g., UC, e.g., mUC), a kidney cancer (e.g., RCC), a lung cancer (e.g., NSCLC), a liver cancer (e.g., HCC), an ovarian cancer, or a breast cancer (e.g., TNBC). In preferred embodiments, the patient has a bladder cancer (e.g., UC, e.g., mUC). The patient may optionally have an advanced, refractory, recurrent, chemotherapy-resistant, and/or platinum-resistant form of the cancer.

In certain embodiments, the presence and/or expression levels/amount of a biomarker in a first sample is increased or elevated as compared to presence/absence and/or expression levels/amount in a second sample. In certain embodiments, the presence/absence and/or expression levels/amount of a biomarker in a first sample is decreased or reduced as compared to presence and/or expression levels/amount in a second sample. In certain embodiments, the second sample is a reference sample, reference cell, reference tissue, control sample, control cell, or control tissue.

In certain embodiments, a reference sample, reference cell, reference tissue, control sample, control cell, or control tissue is a single sample or combined multiple samples from the same patient or individual that are obtained at one or more different time points than when the test sample is obtained. For example, a reference sample, reference cell, reference tissue, control sample, control cell, or control tissue is obtained at an earlier time point from the same patient or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combined multiple samples from one or more healthy individuals who are not the patient. In certain embodiments, a reference sample, reference cell, reference tissue, control sample, control cell, or control tissue is a combined multiple samples from one or more individuals with a disease or disorder (e.g., cancer) who are not the patient or individual. In certain embodiments, a reference sample, reference cell, reference tissue, control sample, control cell, or control tissue is pooled RNA samples from normal tissues or pooled plasma or serum samples from one or more individuals who are not the patient. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the patient.

III. Therapeutic Methods and Uses

Provided herein are methods and uses for treating an individual having a cancer (including, but not limited to, a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer). In particular embodiments, the cancer is a bladder cancer, such as UC, e.g., metastatic UC. In some instances, the methods of the invention include administering to the individual an anti-cancer therapy that includes an immunotherapy (including, but not limited to, a PD-L1 axis binding antagonist, e.g., an anti-PD-L1 antibody (e.g., atezolizumab)) and/or a suppressive stromal antagonist (including, but not limited to, a TGF-β antagonist, e.g., an anti-TGF-β antibody) based on the expression level of a biomarker of the invention. Any of the immunotherapies (e.g., PD-L1 axis binding antagonists (e.g., anti-PD-L1 antibodies)), suppressive stromal antagonists (e.g., TGF-β antagonists (e.g., anti-TGF-β antibodies)), or other anti-cancer agents described herein (e.g., as described below in Section IV and/or the Examples) or known in the art may be used in the methods and uses. The invention further relates to methods for improving PFS and/or OS of a patient suffering from a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) by administration of an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody). The invention further relates to methods for improving response (e.g., ORR) of a patient suffering from a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) by administration of an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody). The expression level or number of any of the biomarkers described herein may be determined using any method known in the art and/or described herein, for example, in Section II above and/or in the working Examples.

In some embodiments, therapy with an immunotherapy (e.g., a PD-L1 axis binding antagonist, e.g., an anti-PD-L1 antibody (e.g., atezolizumab)) in combination with a suppressive stromal antagonist (e.g., a TGF-β antagonist, e.g., an anti-TGF-β antibody) preferably extends and/or improves survival, including PFS and/or OS. In one embodiment, therapy with an immunotherapy (e.g., a PD-L1 axis binding antagonist, e.g., an anti-PD-L1 antibody (e.g., atezolizumab)) in combination with a suppressive stromal antagonist (e.g., a TGF-β antagonist, e.g., an anti-TGF-β antibody) extends survival by at least about 10%, 20%, 30%, 40%, 50%, 60%, 70%, 80%, 90%, 100%, 200%, or more, relative to the survival achieved by administering an approved anti-tumor agent, or standard of care, for the cancer being treated. In another embodiment, therapy with an immunotherapy (e.g., a PD-L1 axis binding antagonist, e.g., an anti-PD-L1 antibody (e.g., atezolizumab)) in combination with a suppressive stromal antagonist (e.g., a TGF-β antagonist, e.g., an anti-TGF-β antibody) improves a response rate (e.g., an ORR, a CR rate, or a PR rate) by at least about 10%, 20%, 30%, 40%, 50%, 60%, 70%, 80%, 90%, 100%, 200%, or more, relative to the response rate achieved by administering an approved anti-tumor agent, or standard of care, for the cancer being treated.

A. Exemplary 22-Gene Signature

In some embodiments, the methods and uses herein involve determining the expression level of one or more (e.g., 1, 2, 3, 4, 5, 6, 7, 8, 9, 10, 11, 12, 13, 14, 15, 16, 17, 18, 19, 20, 21, or 22) genes selected from a 22-gene signature, which includes the genes set forth in Table 1. For example, provided herein is a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) that includes (a) determining the expression level of one or more (e.g., 1, 2, 3, 4, 5, 6, 7, 8, 9, 10, 11, 12, 13, 14, 15, 16, 17, 18, 19, 20, 21, or 22) of the genes set forth in Table 1 in a sample from the individual, wherein the expression level of one or more of the genes set forth in Table 1 is determined to be changed relative to a reference expression level; and (b) administering an effective amount of an anti-cancer therapy (e.g., an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody)) to the individual based on the expression level of the one or more genes determined in step (a). In some instances, the change is an increase. In other instances, the change is a decrease.

Also provided herein is a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) that includes administering an effective amount of an anti-cancer therapy (e.g., an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody)) to the individual, wherein the expression level of one or more (e.g., 1, 2, 3, 4, 5, 6, 7, 8, 9, 10, 11, 12, 13, 14, 15, 16, 17, 18, 19, 20, 21, or 22) of the genes set forth in Table 1 in a sample from the individual has been determined to be changed relative to a reference level, wherein a change in the expression level of one or more of the genes set forth in Table 1 identifies the individual as one who may benefit from treatment with an anti-cancer therapy. In some instances, the change is an increase. In other instances, the change is a decrease.

In another aspect, the invention provides a method of treating cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) in an individual having been identified as having an expression level in a sample from the individual of one or more (e.g., 1, 2, 3, 4, 5, 6, 7, 8, 9, 10, 11, 12, 13, 14, 15, 16, 17, 18, 19, 20, 21, or 22) of the genes set forth in Table 1 that is at or above a reference expression level of the one or more genes, the method including administering to the individual an anti-cancer therapy comprising an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody)).

In another aspect, provided herein is a method for assessing a response of an individual having a cancer to treatment with an anti-cancer therapy including an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody), the method including: (a) determining the expression level of one or more (e.g., 1, 2, 3, 4, 5, 6, 7, 8, 9, 10, 11, 12, 13, 14, 15, 16, 17, 18, 19, 20, 21, or 22) of the genes listed in Table 1 in a sample from the individual at a time point during or after administration of an anti-cancer therapy comprising an immunotherapy and a suppressive stromal antagonist to the individual; and (b) maintaining, adjusting, or stopping the treatment based on a comparison of the expression level of the one or more genes in the sample with a reference expression level of the one or more genes, wherein a change in the expression level of the one or more genes in the sample from the individual compared to the reference expression level of the one or more genes is indicative of a response to treatment with the anti-cancer therapy.

In another aspect, provided herein is a method for monitoring the response of an individual having a cancer to treatment with an anti-cancer therapy including an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody), the method including: (a) determining the expression level of one or more (e.g., 1, 2, 3, 4, 5, 6, 7, 8, 9, 10, 11, 12, 13, 14, 15, 16, 17, 18, 19, 20, 21, or 22) of the genes listed in Table 1 in a sample from the individual at a time point during or after administration of an anti-cancer therapy comprising an immunotherapy and a suppressive stromal antagonist to the individual; and (b) comparing the expression level of the one or more genes in the sample from the individual with a reference expression level of the one or more genes, thereby monitoring the response of the individual undergoing treatment with the anti-cancer therapy.

In some embodiments of any of the preceding methods involving the 22-gene signature, the change is an increase in the expression level of the one or more genes and the treatment is adjusted or stopped. In other embodiments of any of the preceding methods, the change is a decrease in the expression level of the one or more genes and the treatment is maintained.

In some embodiments of any of the preceding methods involving the 22-gene signature, an increase in the expression level of the five or more genes is indicative of a lack of response of the individual to the treatment. In other embodiments of any of the preceding methods, a decrease in the expression level of the five or more genes is indicative of a response of the individual to the treatment.

In some embodiments of any of the preceding methods involving the 22-gene signature, a reference expression level is the expression level of the one or more (e.g., 1, 2, 3, 4, 5, 6, 7, 8, 9, 10, 11, 12, 13, 14, 15, 16, 17, 18, 19, 20, 21, or 22) genes (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in a reference population, for example, a population of individuals having a cancer (e.g., a bladder cancer (e.g., UC, e.g., mUC), a kidney cancer, a lung cancer, a liver cancer, an ovarian cancer, a pancreatic cancer, a colorectal cancer, or a breast cancer). In particular embodiments, the cancer is a bladder cancer (e.g., UC, e.g., mUC). In certain embodiments, a reference expression level is the median expression level of the one or more genes in a reference population, for example, a population of individuals having a cancer. In other embodiments, the reference expression level may be the top 40%, the top 30%, the top 20%, the top 10%, the top 5%, or the top 1% of the expression level in the reference population. In some embodiments, the reference expression level is determined by principle component analysis of Z-score-transformed expression levels. In certain embodiments, the reference expression level is a pre-assigned expression level for the one or more genes. In some embodiments, the reference expression level is the expression level of the one or more genes in a biological sample obtained from the patient at a previous time point, wherein the previous time point is following administration of the anti-cancer therapy. In some embodiments of any of the preceding methods, a reference expression level is the expression level of the one or more genes (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in a biological sample from the patient obtained prior to (e.g., minutes, hours, days, weeks (e.g., 1, 2, 3, 4, 5, 6, or 7 weeks), months, or years prior to) administration of the anti-cancer therapy. In other embodiments, the reference expression level is the expression level of the one or more genes in a biological sample obtained from the patient at a subsequent time point (e.g., minutes, hours, days, weeks, months, or years after administration of an anti-cancer therapy).

In some embodiments of any of the preceding methods involving the 22-gene signature, an expression level above a reference expression level, or an elevated or increased expression or number, refers to an overall increase of about any of 10%, 20%, 30%, 40%, 50%, 60%, 70%, 80%, 90%, 95%, 96%, 97%, 98%, 99% or greater, in the level or number of a biomarker (e.g., protein, nucleic acid (e.g., gene or mRNA), or cell), detected by methods such as those described herein and/or known in the art, as compared to a reference expression level, reference sample, reference cell, reference tissue, control sample, control cell, or control tissue. In certain embodiments, the elevated expression or number refers to the increase in expression level/amount of a biomarker (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in the sample wherein the increase is at least about any of 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× the expression level/amount of the respective biomarker in a reference expression level, reference sample, reference cell, reference tissue, control sample, control cell, or control tissue. In some embodiments, elevated expression or number refers to an overall increase in expression level/amount of a biomarker (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 22-gene signature, an expression level below a reference expression level, or reduced (decreased) expression or number, refers to an overall reduction of about any of 10%, 20%, 30%, 40%, 50%, 60%, 70%, 80%, 90%, 95%, 96%, 97%, 98%, 99% or greater, in the level of biomarker (e.g., protein, nucleic acid (e.g., gene or mRNA), or cell), detected by standard art known methods such as those described herein, as compared to a reference expression level, reference sample, reference cell, reference tissue, control sample, control cell, or control tissue. In certain embodiments, reduced expression or number refers to the decrease in expression level/amount of a biomarker (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference expression level, reference sample, reference cell, reference tissue, control sample, control cell, or control tissue. In some embodiments, reduced (decreased) expression or number refers to an overall decrease in expression level/amount of a biomarker (e.g., TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 22-gene signature, a tumor from the individual has an immune excluded phenotype characterized by the localization of CD8+ T-cells in the peri-tumoral stromal compartment. In some embodiments, the CD8+ T-cells localize at or near collagen fibers.

B. Exemplary 6-Gene Signature

In some embodiments, the methods and uses herein involve determining the expression level of one or more (e.g., 1, 2, 3, 4, 5, or 6) genes selected from a 6-gene signature which includes ACTA2, ADAM19, COMP, CTGF, TGFB1, and TGFBR2.

For example, in one embodiment, provided herein is a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from treatment with an anti-cancer therapy comprising an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method including (a) determining the expression level of one or more (e.g., 1, 2, 3, 4, 5, or 6) of the following genes in a sample from the individual: ACTA2, ADAM19, COMP, CTGF, TGFB1, or TGFBR2, wherein the expression level of one or more of ACTA2, ADAM19, COMP, CTGF, TGFB1, or TGFBR2 in the sample is determined to be at or above a reference expression level of the one or more genes; and (b) administering an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody) to the individual based on the expression level of the one or more genes determined in step (a)).

The method may include determining the expression level of one or more (e.g., 1, 2, 3, 4, 5, or 6) of ACTA2, ADAM19, COMP, CTGF, TGFB1, or TGFBR2. In some embodiments, the method includes determining the expression level of at least two, at least three, at least four, at least five, or all six of ACTA2, ADAM19, COMP, CTGF, TGFB1, and TGFBR2. In some embodiments, the method includes determining the expression level of two of ACTA2, ADAM19, COMP, CTGF, TGFB1, and TGFBR2, for example, any of the exemplary combinations shown in Table 2. In some embodiments, the method includes determining the expression level of three of ACTA2, ADAM19, COMP, CTGF, TGFB1, and TGFBR2, for example, any of the exemplary combinations shown in Table 3. In some embodiments, the method includes determining the expression level of four of ACTA2, ADAM19, COMP, CTGF, TGFB1, and TGFBR2, for example, any of the exemplary combinations shown in Table 4. In some embodiments, the method includes determining the expression level of five of ACTA2, ADAM19, COMP, CTGF, TGFB1, and TGFBR2, for example, any of the exemplary combinations shown in Table 5. In some embodiments, the method involves determining the expression level of ACTA2, ADAM19, COMP, CTGF, TGFB1, and TGFBR2.

In any of the preceding methods involving the 6-gene signature, the method may include determining the expression level of TGFB1 and/or TGFBR2. In any of the preceding methods, the method may include determining the expression level of TGFB1 and TGFBR2.

In some embodiments of any of the preceding methods involving the 6-gene signature, the one or more genes includes at least ADAM19 or COMP. In some embodiments, the one or more genes includes ADAM19. In other embodiments, the one or more genes includes COMP. In still further embodiments, the one or more genes includes ADAM19 and COMP.

In another embodiment, provided herein is a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from treatment with an anti-cancer therapy comprising an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method including administering to the individual an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), wherein prior to treatment the expression level of one or more (e.g., 1, 2, 3, 4, 5, or 6) of ACTA2, ADAM19, COMP, CTGF, TGFB1, or TGFBR2 in the sample has been determined to be at or above a reference expression level of the one or more genes.

In another aspect, the invention provides a method of treating cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) in an individual having been identified as having an expression level in a sample from the individual of one or more (e.g., 1, 2, 3, 4, 5, or 6) of ACTA2, ADAM19, COMP, CTGF, TGFB1, or TGFBR2 that is at or above a reference expression level of the one or more genes, the method including administering to the individual an anti-cancer therapy comprising an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody)).

In any of the preceding methods involving the 6-gene signature, the expression level of one or more (e.g., 1, 2, 3, 4, 5, or 6) of ACTA2, ADAM19, COMP, CTGF, TGFB1, or TGFBR2 has been determined to be at or above a reference level of the one or more genes. In some embodiments, the expression level of at least two, at least three, at least four, at least five, or all six of ACTA2, ADAM19, COMP, CTGF, TGFB1, and TGFBR2 has been determined to be at or above a reference level of the one or more genes. In some embodiments, the expression level of two of ACTA2, ADAM19, COMP, CTGF, TGFB1, and TGFBR2, for example, any of the exemplary combinations shown in Table 2, has been determined to be at or above a reference level of the one or more genes. In some embodiments, the expression level of three of ACTA2, ADAM19, COMP, CTGF, TGFB1, and TGFBR2, for example, any of the exemplary combinations shown in Table 3, has been determined to be at or above a reference level of the one or more genes. In some embodiments, the expression level of four of ACTA2, ADAM19, COMP, CTGF, TGFB1, and TGFBR2, for example, any of the exemplary combinations shown in Table 4, has been determined to be at or above a reference level of the one or more genes. In some embodiments, the expression level of five of ACTA2, ADAM19, COMP, CTGF, TGFB1, and TGFBR2, for example, any of the exemplary combinations shown in Table 5, has been determined to be at or above a reference level of the one or more genes. In some embodiments, the expression level of ACTA2, ADAM19, COMP, CTGF, TGFB1, and TGFBR2 has been determined to be at or above a reference level of ACTA2, ADAM19, COMP, CTGF, TGFB1, and TGFBR2.

In any of the preceding methods involving the 6-gene signature, the expression level of TGFB1 and/or TGFBR2 has been determined to be at or above a reference expression level of TGFB1 and/or TGFBR2. For example, in some embodiments, the expression level of TGFB1 is at or above a reference expression level of TGFB1. In some embodiments, the expression level of TGFBR1 is at or above a reference expression level of TGFBR1. In any of the preceding methods, the expression level of TGFB1 and TGFBR2 has been determined to be at or above a reference expression level of TGFB1 and TGFBR2.

In some embodiments of any of the preceding methods involving the 6-gene signature, the expression level of ADAM19 or COMP has been determined to be at or above a reference level of ADAM19 or COMP. In some embodiments, the expression level of ADAM19 has been determined to be at or above a reference level of ADAM19. In some embodiments, the expression level of COMP has been determined to be at or above a reference level of COMP. In still further embodiments, the one or more genes includes ADAM19 and COMP. In some embodiments, the expression level of ADAM19 and COMP has been determined to be at or above a reference level of ADAM19 and COMP.

In another aspect, provided herein is a method for assessing a response of an individual having a cancer to treatment with an anti-cancer therapy including an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method including: (a) determining the expression level of one or more (e.g., 1, 2, 3, 4, 5, or 6) of the following genes in a sample from the individual at a time point during or after administration of an anti-cancer therapy comprising an immunotherapy and a suppressive stromal antagonist to the individual: ACTA2, ADAM19, COMP, CTGF, TGFB1, or TGFBR2; and (b) maintaining, adjusting, or stopping the treatment based on a comparison of the expression level of the one or more genes in the sample with a reference expression level of the one or more genes, wherein a change in the expression level of the one or more genes in the sample from the individual compared to the reference expression level of the one or more genes is indicative of a response to treatment with the anti-cancer therapy.

In another aspect, provided herein is a method for monitoring the response of an individual having a cancer to treatment with an anti-cancer therapy including an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method including: (a) determining the expression level of one or more (e.g., 1, 2, 3, 4, 5, or 6) of the following genes in a sample from the individual at a time point during or after administration of an anti-cancer therapy comprising an immunotherapy and a suppressive stromal antagonist to the individual: ACTA2, ADAM19, COMP, CTGF, TGFB1, or TGFBR2; and (b) comparing the expression level of the one or more genes in the sample from the individual with a reference expression level of the one or more genes, thereby monitoring the response of the individual undergoing treatment with the anti-cancer therapy.

In any of the preceding methods involving the 6-gene signature, the method may include determining the expression level of one or more (e.g., 1, 2, 3, 4, 5, or 6) of ACTA2, ADAM19, COMP, CTGF, TGFB1, or TGFBR2. In some embodiments, the method includes determining the expression level of at least two, at least three, at least four, at least five, or all six of ACTA2, ADAM19, COMP, CTGF, TGFB1, or TGFBR2. In some embodiments, the method includes determining the expression level of two of ACTA2, ADAM19, COMP, CTGF, TGFB1, and TGFBR2, for example, any of the exemplary combinations shown in Table 2. In some embodiments, the method includes determining the expression level of three of ACTA2, ADAM19, COMP, CTGF, TGFB1, and TGFBR2, for example, any of the exemplary combinations shown in Table 3. In some embodiments, the method includes determining the expression level of four of ACTA2, ADAM19, COMP, CTGF, TGFB1, and TGFBR2, for example, any of the exemplary combinations shown in Table 4. In some embodiments, the method includes determining the expression level of five of ACTA2, ADAM19, COMP, CTGF, TGFB1, and TGFBR2, for example, any of the exemplary combinations shown in Table 5. In some embodiments, the method involves determining the expression level of ACTA2, ADAM19, COMP, CTGF, TGFB1, and TGFBR2.

In any of the preceding methods involving the 6-gene signature, the method may include determining the expression level of TGFB1 and/or TGFBR2. In any of the preceding methods, the method may include determining the expression level of TGFB1 and TGFBR2.

In some embodiments of any of the preceding methods involving the 6-gene signature, the one or more genes includes at least ADAM19 or COMP. In some embodiments, the one or more genes includes ADAM19. In other embodiments, the one or more genes includes COMP. In still further embodiments, the one or more genes includes ADAM19 and COMP.

In some embodiments of any of the preceding methods involving the 6-gene signature, the change is an increase in the expression level of the one or more genes and the treatment is adjusted or stopped. In other embodiments of any of the preceding methods, the change is a decrease in the expression level of the one or more genes and the treatment is maintained.

In some embodiments of any of the preceding methods involving the 6-gene signature, an increase in the expression level of the five or more genes is indicative of a lack of response of the individual to the treatment. In other embodiments of any of the preceding methods, a decrease in the expression level of the five or more genes is indicative of a response of the individual to the treatment.

In some embodiments of any of the preceding methods involving the 6-gene signature, a reference expression level is the expression level of the one or more (e.g., 1, 2, 3, 4, 5, or 6) genes (e.g., ACTA2, ADAM19, COMP, CTGF, TGFB1, and/or TGFBR2) in a reference population, for example, a population of individuals having a cancer (e.g., a bladder cancer (e.g., UC, e.g., mUC), a kidney cancer, a lung cancer, a liver cancer, an ovarian cancer, a pancreatic cancer, a colorectal cancer, or a breast cancer). In particular embodiments, the cancer is a bladder cancer (e.g., UC, e.g., mUC). In certain embodiments, a reference expression level is the median expression level of the one or more genes in a reference population, for example, a population of individuals having a cancer. In other embodiments, the reference expression level may be the top 40%, the top 30%, the top 20%, the top 10%, the top 5%, or the top 1% of the expression level in the reference population. In some embodiments, the reference expression level is determined by principle component analysis of Z-score-transformed expression levels. In certain embodiments, the reference expression level is a pre-assigned expression level for the one or more genes. In some embodiments, the reference expression level is the expression level of the one or more genes in a biological sample obtained from the patient at a previous time point, wherein the previous time point is following administration of the anti-cancer therapy. In some embodiments of any of the preceding methods, a reference expression level is the expression level of the one or more genes (e.g., ACTA2, ADAM19, COMP, CTGF, TGFB1, and/or TGFBR2) in a biological sample from the patient obtained prior to (e.g., minutes, hours, days, weeks (e.g., 1, 2, 3, 4, 5, 6, or 7 weeks), months, or years prior to) administration of the anti-cancer therapy. In other embodiments, the reference expression level is the expression level of the one or more genes in a biological sample obtained from the patient at a subsequent time point (e.g., minutes, hours, days, weeks, months, or years after administration of an anti-cancer therapy).

In some embodiments of any of the preceding methods involving the 6-gene signature, an expression level above a reference expression level, or an elevated or increased expression or number, refers to an overall increase of about any of 10%, 20%, 30%, 40%, 50%, 60%, 70%, 80%, 90%, 95%, 96%, 97%, 98%, 99% or greater, in the level or number of a biomarker (e.g., protein, nucleic acid (e.g., gene or mRNA), or cell), detected by methods such as those described herein and/or known in the art, as compared to a reference expression level, reference sample, reference cell, reference tissue, control sample, control cell, or control tissue. In certain embodiments, the elevated expression or number refers to the increase in expression level/amount of a biomarker (e.g., one or more of ACTA2, ADAM19, COMP, CTGF, TGFB1, and/or TGFBR2) in the sample wherein the increase is at least about any of 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× the expression level/amount of the respective biomarker in a reference expression level, reference sample, reference cell, reference tissue, control sample, control cell, or control tissue. In some embodiments, elevated expression or number refers to an overall increase in expression level/amount of a biomarker (e.g., ACTA2, ADAM19, COMP, CTGF, TGFB1, and/or TGFBR2) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 6-gene signature, an expression level below a reference expression level, or a reduced (decreased) expression or number, refers to an overall reduction of about any of 10%, 20%, 30%, 40%, 50%, 60%, 70%, 80%, 90%, 95%, 96%, 97%, 98%, 99% or greater, in the level of biomarker (e.g., protein, nucleic acid (e.g., gene or mRNA), or cell), detected by standard art known methods such as those described herein, as compared to a reference expression level, reference sample, reference cell, reference tissue, control sample, control cell, or control tissue. In certain embodiments, reduced expression or number refers to the decrease in expression level/amount of a biomarker (e.g., one or more of ACTA2, ADAM19, COMP, CTGF, TGFB1, and/or TGFBR2) in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference expression level, reference sample, reference cell, reference tissue, control sample, control cell, or control tissue. In some embodiments, reduced (decreased) expression or number refers to an overall decrease in expression level/amount of a biomarker (e.g., ACTA2, ADAM19, COMP, CTGF, TGFB1, and/or TGFBR2) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 6-gene signature, a tumor from the individual has an immune excluded phenotype characterized by the localization of CD8+ T-cells in the peri-tumoral stromal compartment. In some embodiments, the CD8+ T-cells localize at or near collagen fibers.

C. Exemplary 19-Gene Signature (Pan-F-TBRS)

In some embodiments, the methods and uses herein involve determining the expression level of one or more (e.g., 1, 2, 3, 4, 5, 6, 7, 8, 9, 10, 11, 12, 13, 14, 15, 16, 17, 18, or 19) genes selected from a 19-gene signature which includes ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1, which is also referred to herein as Pan-F-TBRS.

For example, in one embodiment, provided herein is a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including (a) determining the expression level of one or more (e.g., 1, 2, 3, 4, 5, 6, 7, 8, 9, 10, 11, 12, 13, 14, 15, 16, 17, 18, or 19) of the following genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1, wherein the expression level of one or more of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1 in the sample is determined to be at or above a reference expression level of the one or more genes; and (b) administering an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody) to the individual based on the expression level of the one or more genes determined in step (a)).

The method may include determining the expression level of one or more (e.g., 1, 2, 3, 4, 5, 6, 7, 8, 9, 10, 11, 12, 13, 14, 15, 16, 17, 18, or 19) of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, the method includes determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, the method involves determining the expression level of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1.

In some embodiments of any of the preceding methods involving the 19-gene signature, the method includes determining the expression level of one or more (e.g., 1, 2, 3, 4, 5, 6, 7, 8, 9, 10, 11, 12, 13, 14, or 15) genes selected from ADAM19, ACTG2, CNN1, CTPS1, FAM101B, FSTL3, HSPB1, IGFBP3, PXDC1, SEMA7A, SH3PXD2A, TAGLN, TGFBI, TNS1, and TPM1.

In another embodiment, provided herein is a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including administering to the individual an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), wherein prior to treatment the expression level of one or more (e.g., 1, 2, 3, 4, 5, 6, 7, 8, 9, 10, 11, 12, 13, 14, 15, 16, 17, 18, or 19) of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1 in the sample has been determined to be at or above a reference expression level of the one or more genes.

In another aspect, the invention provides a method of treating cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) in an individual having been identified as having an expression level in a sample from the individual of one or more (e.g., 1, 2, 3, 4, 5, 6, 7, 8, 9, 10, 11, 12, 13, 14, 15, 16, 17, 18, or 19) of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1 that is at or above a reference expression level of the one or more genes, the method including administering to the individual an anti-cancer therapy comprising an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody)).

In some embodiments of any of the preceding methods involving the 19-gene signature, the expression level of one or more (e.g., 1, 2, 3, 4, 5, 6, 7, 8, 9, 10, 11, 12, 13, 14, 15, 16, 17, 18, or 19) of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 has been determined to be at or above a reference expression level of the one or more genes. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 has been determined to be at or above a reference expression level of the one or more genes. In some embodiments, the expression level of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 has been determined to be at or above a reference expression level ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1.

In some embodiments of any of the preceding methods involving the 19-gene signature, the the expression level of one or more (e.g., 1, 2, 3, 4, 5, 6, 7, 8, 9, 10, 11, 12, 13, 14, or 15) of ADAM19, ACTG2, CNN1, CTPS1, FAM101B, FSTL3, HSPB1, IGFBP3, PXDC1, SEMA7A, SH3PXD2A, TAGLN, TGFBI, TNS1, and TPM1 has been determined to be at or above a reference level of the one or more genes.

In another aspect, provided herein is a method for assessing a response of an individual having a cancer to treatment with an anti-cancer therapy including an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method including: (a) determining the expression level of one or more (e.g., 1, 2, 3, 4, 5, 6, 7, 8, 9, 10, 11, 12, 13, 14, 15, 16, 17, 18, or 19) of the following genes in a sample from the individual at a time point during or after administration of an anti-cancer therapy comprising an immunotherapy and a suppressive stromal antagonist to the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1; and (b) maintaining, adjusting, or stopping the treatment based on a comparison of the expression level of the one or more genes in the sample with a reference expression level of the one or more genes, wherein a change in the expression level of the one or more genes in the sample from the individual compared to the reference expression level of the one or more genes is indicative of a response to treatment with the anti-cancer therapy.

In another aspect, provided herein is a method for monitoring the response of an individual having a cancer to treatment with an anti-cancer therapy including an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method including: (a) determining the expression level of one or more (e.g., 1, 2, 3, 4, 5, 6, 7, 8, 9, 10, 11, 12, 13, 14, 15, 16, 17, 18, or 19) of the following genes in a sample from the individual at a time point during or after administration of an anti-cancer therapy comprising an immunotherapy and a suppressive stromal antagonist to the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, or TPM1; and (b) comparing the expression level of the one or more genes in the sample from the individual with a reference expression level of the one or more genes, thereby monitoring the response of the individual undergoing treatment with the anti-cancer therapy.

In any of the preceding methods involving the 19-gene signature, the method may include determining the expression level of one or more (e.g., 1, 2, 3, 4, 5, 6, 7, 8, 9, 10, 11, 12, 13, 14, 15, 16, 17, 18, or 19) of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, the method includes determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, the method involves determining the expression level of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1.

In some embodiments of any of the preceding methods involving the 19-gene signature, the method includes determining the expression level of one or more (e.g., 1, 2, 3, 4, 5, 6, 7, 8, 9, 10, 11, 12, 13, 14, or 15) genes selected from ADAM19, ACTG2, CNN1, CTPS1, FAM101B, FSTL3, HSPB1, IGFBP3, PXDC1, SEMA7A, SH3PXD2A, TAGLN, TGFBI, TNS1, and TPM1.

In some embodiments of any of the preceding methods involving the 19-gene signature, the change is an increase in the expression level of the one or more genes and the treatment is adjusted or stopped. In other embodiments of any of the preceding methods, the change is a decrease in the expression level of the one or more genes and the treatment is maintained.

In some embodiments of any of the preceding methods involving the 19-gene signature, an increase in the expression level of the five or more genes is indicative of a lack of response of the individual to the treatment. In other embodiments of any of the preceding methods, a decrease in the expression level of the five or more genes is indicative of a response of the individual to the treatment.

In some embodiments of any of the preceding methods involving the 19-gene signature, a reference level is the expression level of the one or more (e.g., 1, 2, 3, 4, 5, 6, 7, 8, 9, 10, 11, 12, 13, 14, 15, 16, 17, 18, or 19) genes (e.g., ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in a reference population, for example, a population of individuals having a cancer (e.g., a bladder cancer (e.g., UC, e.g., mUC), a kidney cancer, a lung cancer, a liver cancer, an ovarian cancer, a pancreatic cancer, a colorectal cancer, or a breast cancer). In particular embodiments, the cancer is a bladder cancer (e.g., UC, e.g., mUC). In certain embodiments, a reference level is the median expression level of the one or more genes in a reference population, for example, a population of individuals having a cancer. In other embodiments, the reference level may be the top 40%, the top 30%, the top 20%, the top 10%, the top 5%, or the top 1% of the expression level in the reference population. In some embodiments, the reference expression level is determined by principle component analysis of Z-score-transformed expression levels. In certain embodiments, the reference level is a pre-assigned expression level for the one or more genes. In some embodiments, the reference level is the expression level of the one or more genes in a biological sample obtained from the patient at a previous time point, wherein the previous time point is following administration of the anti-cancer therapy. In some embodiments of any of the preceding methods, a reference level is the expression level of the one or more genes (e.g., ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in a biological sample from the patient obtained prior to (e.g., minutes, hours, days, weeks (e.g., 1, 2, 3, 4, 5, 6, or 7 weeks), months, or years prior to)

administration of the anti-cancer therapy. In other embodiments, the reference level is the expression level of the one or more genes in a biological sample obtained from the patient at a subsequent time point (e.g., minutes, hours, days, weeks, months, or years after administration of an anti-cancer therapy).

In some embodiments of any of the preceding methods involving the 19-gene signature, an expression level above a reference expression level, or an elevated or increased expression or number, refers to an overall increase of about any of 10%, 20%, 30%, 40%, 50%, 60%, 70%, 80%, 90%, 95%, 96%, 97%, 98%, 99% or greater, in the level or number of a biomarker (e.g., protein, nucleic acid (e.g., gene or mRNA), or cell), detected by methods such as those described herein and/or known in the art, as compared to a reference expression level, reference sample, reference cell, reference tissue, control sample, control cell, or control tissue. In certain embodiments, the elevated expression or number refers to the increase in expression level/amount of a biomarker (e.g., one or more of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in the sample wherein the increase is at least about any of 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× the expression level/amount of the respective biomarker in a reference expression level, reference sample, reference cell, reference tissue, control sample, control cell, or control tissue. In some embodiments, elevated expression or number refers to an overall increase in expression level/amount of a biomarker (e.g., ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 19-gene signature, an expression level below a reference expression level, or a reduced (decreased) expression or number, refers to an overall reduction of about any of 10%, 20%, 30%, 40%, 50%, 60%, 70%, 80%, 90%, 95%, 96%, 97%, 98%, 99% or greater, in the level of biomarker (e.g., protein, nucleic acid (e.g., gene or mRNA), or cell), detected by standard art known methods such as those described herein, as compared to a reference expression level, reference sample, reference cell, reference tissue, control sample, control cell, or control tissue. In certain embodiments, reduced expression or number refers to the decrease in expression level/amount of a biomarker (e.g., one or more of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference expression level, reference sample, reference cell, reference tissue, control sample, control cell, or control tissue. In some embodiments, reduced (decreased) expression or number refers to an overall decrease in expression level/amount of a biomarker (e.g., ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and/or TPM1) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference expression level, reference sample, reference cell, reference tissue, control sample, control cell, control tissue, or internal control (e.g., housekeeping gene).

In some embodiments of any of the preceding methods involving the 19-gene signature, a tumor from the individual has an immune excluded phenotype characterized by the localization of CD8+ T-cells in the peri-tumoral stromal compartment. In some embodiments, the CD8+ T-cells localize at or near collagen fibers.

D. Exemplary Additional Biomarkers (e.g., Teff Genes and CAF Genes)

Any of the preceding methods (e.g., as described in Section III, Subsections A-C above, relating to the 22-, 6-, and 19-gene (Pan-F-TBRS) signatures, respectively) can further include determining the expression level in the sample of one or more (e.g., 1, 2, 3, 4, 5, 6, 7, 8 or 9) additional genes selected from the group consisting of PD-L1, CD8A, CXCL10, CXCL9, GZMA, GZMB, IFNG, PRF1, and TBX21. In some embodiments, the one or more additional gene is PD-L1. In other embodiments, the one or more (e.g., 1, 2, 3, 4, 5, 6, 7, or 8) additional genes is selected from the group consisting of CD8A, CXCL10, CXCL9, GZMA, GZMB, IFNG, PRF1, and TBX21. In some embodiments, the method further includes determining the expression level of at least two, at least three, at least four, at least five, at least six, at least seven, or all eight of CD8A, CXCL10, CXCL9, GZMA, GZMB, IFNG, PRF1, and TBX21. In some embodiments, the one or more additional genes are CD8A, CXCL10, CXCL9, GZMA, GZMB, IFNG, PRF1, and TBX21.

For example, provided herein is a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including (a) determining the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21, and one or more (e.g., 1, 2, 3, 4, 5, 6, 7, 8, 9, 10, 11, 12, 13, 14, 15, 16, 17, 18, 19, 20, 21, or 22) of the following 22-gene signature genes in the sample: TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1; and (b) administering an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) to the individual based on the expression level of the one or more Teff genes and the one or more Pan-F-TBRS genes determined in step (a)). In some embodiments, the expression level of the one or more Pan-F-TBRS genes is at or above a reference expression level, and the expression level of the one or more Teff genes is at or above or below a reference expression level, and the method comprises administering an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody) to the individual. In other embodiments, the expression level of the one or more Pan-F-TBRS genes is below a reference expression level, and the expression level of the one or more Teff genes is at or above a reference expression level, and the method comprises administering an anti-cancer therapy that includes an immunotherapy to the individual. In some embodiments, the immunotherapy is a monotherapy.

In yet another embodiment, provided herein is a method for treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including administering to the individual an anti-cancer therapy that includes an immunotherapy (e.g., a PD-L1 axis binding antagonist, e.g., an anti-PD-L1 antibody (e.g., atezolizumab)), wherein prior to treatment the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21 has been determined to be at or above a reference expression level of the one or more Teff genes, and the expression level of one or more (e.g., 1, 2, 3, 4, 5, 6, 7, 8, 9, 10, 11, 12, 13, 14, 15, 16, 17, 18, 19, 20, 21, or 22) of the following 22-gene signature genes in the sample: TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 has been determined to be below a reference expression level of the one or more 22-gene signature genes. In some embodiments, the immunotherapy is a monotherapy. In some embodiments, the method further includes administering the anti-cancer therapy to the patient.

In another embodiment, provided herein is a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including (a) determining the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21, and one or more (e.g., 1, 2, 3, 4, 5, or 6) of the following 6-gene signature genes in the sample: of ACTA2, ADAM19, COMP, CTGF, TGFB1, and TGFBR2; and (b) administering an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) to the individual based on the expression level of the one or more Teff genes and the one or more 6-gene signature genes determined in step (a)). In some embodiments, the expression level of the one or more 6-gene signature genes is at or above a reference expression level, and the expression level of the one or more Teff genes is at or above or below a reference expression level, and the method comprises administering an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody) to the individual. In other embodiments, the expression level of the one or more 6-gene signature genes is below a reference expression level, and the expression level of the one or more Teff genes is at or above a reference expression level, and the method comprises administering an anti-cancer therapy that includes an immunotherapy to the individual. In some embodiments, the immunotherapy is a monotherapy.

For example, provided herein is a method for treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including administering to the individual an anti-cancer therapy that includes an immunotherapy (e.g., a PD-L1 axis binding antagonist, e.g., an anti-PD-L1 antibody (e.g., atezolizumab)), wherein prior to treatment the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21 has been determined to be at or above a reference expression level of the one or more Teff genes, and the expression level of one or more (e.g., 1, 2, 3, 4, 5, or 6) of the following 6-gene signature genes in the sample: of ACTA2, ADAM19, COMP, CTGF, TGFB1, and TGFBR2 has been determined to be below a reference expression level of the one or more 6-gene signature genes. In some embodiments, the immunotherapy is a monotherapy.

In another embodiment, provided herein is a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including (a) determining the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21, and one or more (e.g., 1, 2, 3, 4, 5, 6, 7, 8, 9, 10, 11, 12, 13, 14, 15, 16, 17, 18, or 19) of the following Pan-F-TBRS genes in the sample: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1; and (b) administering an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) to the individual based on the expression level of the one or more Teff genes and the one or more Pan-F-TBRS genes determined in step (a)). In some embodiments, the expression level of the one or more Pan-F-TBRS genes is at or above a reference expression level, and the expression level of the one or more Teff genes is at or above or below a reference expression level, and the method comprises administering an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody) to the individual. In other embodiments, the expression level of the one or more Pan-F-TBRS genes is below a reference expression level, and the expression level of the one or more Teff genes is at or above a reference expression level, and the method comprises administering an anti-cancer therapy that includes an immunotherapy to the individual. In some embodiments, the immunotherapy is a monotherapy.

In yet another embodiment, provided herein is a method for treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including administering to the individual an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody), wherein prior to treatment the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21 has been determined to be at or above a reference expression level of the one or more Teff genes, and the expression level of one or more (e.g., 1, 2, 3, 4, 5, 6, 7, 8, 9, 10, 11, 12, 13, 14, 15, 16, 17, 18, or 19) of the following Pan-F-TBRS genes in the sample: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 has been determined to be below a reference expression level of the one or more Pan-F-TBRS genes. In some embodiments, the immunotherapy is a monotherapy. In some embodiments, the method further includes administering the anti-cancer therapy to the patient.

In another aspect, provided herein is a method for assessing a response of an individual having a cancer to treatment with an anti-cancer therapy including an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method including: (a) determining the expression level of one or more Teff genes (e.g., 1, 2, or 3 Teff genes selected from IFNG, GZMB, and ZAP70) and/or one or more CAF genes (e.g., 1, 2, or 3 CAF genes selected from LOXL2, TNC, and POSTN) in a sample from the individual at a time point during or after administration of an anti-cancer therapy comprising an immunotherapy and a suppressive stromal antagonist to the individual; and (b) maintaining, adjusting, or stopping the treatment based on a comparison of the expression level of the one or more Teff genes and/or the one or more CAF genes in the sample with a reference expression level of the one or more Teff genes and/or the one or more CAF genes, wherein a change in the expression level of the one or more Teff genes and/or the one or more CAF genes in the sample from the individual compared to the reference expression level of the one or more Teff genes and/or the one or more CAF genes is indicative of a response to treatment with the anti-cancer therapy. In some embodiments, the change is an increase in the expression level of one or more Teff genes (e.g., IFNG, GZMB, and/or ZAP70). In some embodiments, the change is a derease in the expression level of one or more CAF genes (e.g., LOXL2, TNC, and POSTN).

In another aspect, provided herein is a method for monitoring the response of an individual having a cancer to treatment with an anti-cancer therapy including an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the method including: (a) determining the expression level of one or more Teff genes (e.g., 1, 2, or 3 Teff genes selected from IFNG, GZMB, and ZAP70) and/or one or more CAF genes (e.g., 1, 2, or 3 CAF genes selected from LOXL2, TNC, and POSTN) in a sample from the individual at a time point during or after administration of an anti-cancer therapy comprising an immunotherapy and a suppressive stromal antagonist to the individual; and (b) comparing the expression level of the one or more Teff genes and/or the one or more CAF genes in the sample from the individual with a reference expression level of the one or more Teff genes and/or the one or more CAF genes, thereby monitoring the response of the individual undergoing treatment with the anti-cancer therapy.

E. Tumor Mutational Burden (TMB)

Any of the preceding embodiments (e.g., as described in Section III, Subsections A-C above, relating to the 22-, 6-, and 19-gene (Pan-F-TBRS) signatures, respectively, or in Section III, Subsection D) may include determining a TMB in a tumor sample from the individual. TMB may be determined using any suitable approach, for example, as described in Example 1 or in International Patent Application No.: PCT/US2017/055669, which is incorporated herein by reference in its entirety. In some embodiments, the individual may have a TMB in a tumor sample that is at or above a reference TMB. In other embodiments, the individual may have a TMB that is below a reference TMB.

The invention provides a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including: (a) determining (i) the expression level of one or more (e.g., 1, 2, 3, 4, 5, 6, 7, 8, 9, 10, 11, 12, 13, 14, 15, 16, 17, 18, 19, 20, 21, or 22) of the following 22-gene signature genes in a sample from the individual: TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1; and (ii) a TMB score from a tumor sample from the individual; and (b) administering an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) to the individual based on the expression level of the one or more 22-gene signature genes and TMB score determined in step (a)). In some embodiments, the expression level of the one or more 22-gene signature genes is at or above a reference expression level, and the TMB score from the tumor sample is at or above or below a reference TMB score, and the method comprises administering an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody) to the individual. In other embodiments, the expression level of the one or more 22-gene signature genes is below a reference expression level, and the TMB score from the tumor sample is at or above a reference TMB score, and the method comprises administering an anti-cancer therapy that includes an immunotherapy to the individual. In some embodiments, the immunotherapy is a monotherapy.

The invention further provides a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including: administering to the individual an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody), wherein prior to treatment the expression level of one or more (e.g., 1, 2, 3, 4, 5, 6, 7, 8, 9, 10, 11, 12, 13, 14, 15, 16, 17, 18, 19, 20, 21, or 22) of the following 22-gene signature genes in a sample from the individual: TGFB1, TGFBR2, ACTA2, ACTG2, ADAM12, ADAM19, COMP, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 has been determined to be below a reference expression level of the one or more 22-gene signature genes, and a TMB score in a tumor sample from the patient has been determined to be at or above a reference TMB score. In some embodiments, the immunotherapy is a monotherapy.

The invention provides a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including: (a) determining (i) the expression level of one or more (e.g., 1, 2, 3, 4, 5, or 6) of the following 6-gene signature genes in a sample from the individual: ACTA2, ADAM19, COMP, CTGF, TGFB1, and TGFBR2; and (ii) a TMB score from a tumor sample from the individual; and (b) administering an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) to the individual based on the expression level of the one or more 6-gene signature genes and TMB score determined in step (a)). In some embodiments, the expression level of the one or more 6-gene signature genes is at or above a reference expression level, and the TMB score from the tumor sample is at or above or below a reference TMB score, and the method comprises administering an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody) to the individual. In other embodiments, the expression level of the one or more 6-gene signature genes is below a reference expression level, and the TMB score from the tumor sample is at or above a reference TMB score, and the method comprises administering an anti-cancer therapy that includes an immunotherapy to the individual. In some embodiments, the immunotherapy is a monotherapy.

The invention further provides a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including: administering to the individual an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody), wherein prior to treatment the expression level of one or more (e.g., 1, 2, 3, 4, 5, or 6) of the following 6-gene signature genes in a sample from the individual: ACTA2, ADAM19, COMP, CTGF, TGFB1, and TGFBR2 has been determined to be below a reference expression level of the one or more 6-gene signature genes, and a TMB score in a tumor sample from the patient has been determined to be at or above a reference TMB score. In some embodiments, the immunotherapy is a monotherapy.

The invention provides a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including: (a) determining (i) the expression level of one or more (e.g., 1, 2, 3, 4, 5, 6, 7, 8, 9, 10, 11, 12, 13, 14, 15, 16, 17, 18, or 19) of the following Pan-F-TBRS genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1; and (ii) a TMB score from a tumor sample from the individual; and (b) administering an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) to the individual based on the expression level of the one or more Pan-F-TBRS genes and TMB score determined in step (a)). In some embodiments, the expression level of the one or more Pan-F-TBRS genes is at or above a reference expression level, and the TMB score from the tumor sample is at or above or below a reference TMB score, and the method comprises administering an anti-cancer therapy that includes an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody) to the individual. In other embodiments, the expression level of the one or more Pan-F-TBRS genes is below a reference expression level, and the TMB score from the tumor sample is at or above a reference TMB score, and the method comprises administering an anti-cancer therapy that includes an immunotherapy to the individual. In some embodiments, the immunotherapy is a monotherapy.

The invention further provides a method of treating an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer), the method including: administering to the individual an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody), wherein prior to treatment the expression level of one or more (e.g., 1, 2, 3, 4, 5, 6, 7, 8, 9, 10, 11, 12, 13, 14, 15, 16, 17, 18, or 19) of the following Pan-F-TBRS genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1 has been determined to be below a reference expression level of the one or more Teff genes, and a TMB score in a tumor sample from the patient has been determined to be at or above a reference TMB score. In some embodiments, the immunotherapy is a monotherapy. Any of the preceding methods involving TMB can further include determining the expression level of one or more (e.g., 1, 2, 3, 4, 5, 6, 7, or 8) of the following Teff genes in a sample from the individual: CD8A, CXCL10, CXCL9, GZMA, GZMB, IFNG, PRF1, or TBX21.

F. Exemplary Approaches for Determination of Biomarker Expression Levels

In some embodiments of any of the preceding embodiments (e.g., as described in Section III, Subsections A-C above, relating to the 22-, 6-, and 19-gene (Pan-F-TBRS) signatures, respectively, or in Section III, Subsections D and E), the sample is obtained from the individual prior to (e.g., minutes, hours, days, weeks (e.g., 1, 2, 3, 4, 5, 6, or 7 weeks), months, or years prior to) administration of the anti-cancer therapy. In some embodiments of any of the preceding methods, the sample from the individual is obtained about 2 to about 10 weeks (e.g., 2, 3, 4, 5, 6, 7, 8, 9, or 10 weeks) following administration of the anti-cancer therapy. In some embodiments, the sample from the individual is obtained about 4 to about 6 weeks following administration of the anti-cancer therapy.

In some embodiments of any of the preceding methods, the expression level or number of a biomarker is detected in a tissue sample, a primary or cultured cells or cell line, a cell supernatant, a cell lysate, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, or any combination thereof. In some embodiments, the sample is a tissue sample (e.g., a tumor tissue sample), a cell sample, a whole blood sample, a plasma sample, a serum sample, or a combination thereof. In some embodiments, the tumor tissue sample wherein the tumor tissue sample includes tumor cells, tumor-infiltrating immune cells, stromal cells, or a combination thereof. In some embodiments, the tumor tissue sample is a FFPE sample, an archival sample, a fresh sample, or a frozen sample.

For example, in some embodiments of any of the preceding methods, the expression level of a biomarker is detected in tumor-infiltrating immune cells, tumor cells, PBMCs, or combinations thereof using known techniques (e.g., flow cytometry or IHC). Tumor-infiltrating immune cells include, but are not limited to, intratumoral immune cells, peritumoral immune cells or any combinations thereof, and other tumor stroma cells (e.g., fibroblasts). Such tumor infiltrating immune cells may be T lymphocytes (such as CD8+T lymphocytes (e.g., CD8+ Teff cells) and/or CD4+T lymphocytes (e.g., CD4+ Teff cells), B lymphocytes, or other bone marrow-lineage cells including granulocytes (neutrophils, eosinophils, basophils), monocytes, macrophages, dendritic cells (e.g., interdigitating dendritic cells), histiocytes, and natural killer (NK) cells. In some embodiments, the staining for a biomarker is detected as membrane staining, cytoplasmic staining, or combinations thereof. In other embodiments, the absence of a biomarker is detected as absent or no staining in the sample, relative to a reference sample.

In particular embodiments of any of the preceding methods, the expression level of a biomarker is assessed in a sample that contains or is suspected to contain cancer cells. The sample may be, for example, a tissue biopsy or a metastatic lesion obtained from a patient suffering from, suspected to suffer from, or diagnosed with cancer (e.g., a bladder cancer (e.g., UC, e.g., mUC)). In some embodiments, the sample is a sample of bladder tissue, a biopsy of an bladder tumor, a known or suspected metastatic bladder cancer lesion or section, or a blood sample, e.g., a peripheral blood sample, known or suspected to comprise circulating cancer cells, e.g., bladder cancer cells. The sample may comprise both cancer cells, i.e., tumor cells, and non-cancerous cells (e.g., lymphocytes, such as T cells or NK cells), and, in certain embodiments, comprises both cancerous and non-cancerous cells. Methods of obtaining biological samples including tissue resections, biopsies, and body fluids, e.g., blood samples comprising cancer/tumor cells, are well known in the art.

In some embodiments of any of the preceding methods, the patient has carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. In some embodiments, the cancer is bladder cancer (e.g., UC, e.g., mUC), kidney cancer (e.g., renal cell carcinoma (RCC), e.g., advanced RCC or metastatic RCC (mRCC)), squamous cell cancer (e.g., epithelial squamous cell cancer), lung cancer (including small-cell lung cancer (SCLC), non-small cell lung cancer (NSCLC), adenocarcinoma of the lung, and squamous carcinoma of the lung), cancer of the peritoneum, hepatocellular cancer, gastric or stomach cancer including gastrointestinal cancer, pancreatic cancer (e.g., PDAC), glioblastoma, cervical cancer, ovarian cancer, liver cancer (e.g., HCC), hepatoma, breast cancer (including metastatic breast cancer), colon cancer, rectal cancer, colorectal cancer, endometrial or uterine carcinoma, salivary gland carcinoma, prostate cancer, vulval cancer, thyroid cancer, hepatic carcinoma, anal carcinoma, penile carcinoma, Merkel cell cancer, mycoses fungoids, testicular cancer, esophageal cancer, tumors of the biliary tract, head and neck cancer, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), abnormal vascular proliferation associated with phakomatoses, edema (such as that associated with brain tumors), or Meigs' syndrome. In some embodiments, the cancer is a bladder cancer (e.g., UC, e.g., mUC), a kidney cancer (e.g., RCC), a lung cancer (e.g., NSCLC), a liver cancer (e.g., HCC), an ovarian cancer, or a breast cancer (e.g., TNBC). In preferred embodiments, the patient has a bladder cancer (e.g., UC, e.g., mUC). The patient may optionally have an advanced, refractory, recurrent, chemotherapy-resistant, and/or platinum-resistant form of the cancer.

In certain embodiments, the presence and/or expression levels/amount of a biomarker in a first sample is increased or elevated as compared to presence/absence and/or expression levels/amount in a second sample. In certain embodiments, the presence/absence and/or expression levels/amount of a biomarker in a first sample is decreased or reduced as compared to presence and/or expression levels/amount in a second sample. In certain embodiments, the second sample is a reference sample, reference cell, reference tissue, control sample, control cell, or control tissue.

In certain embodiments, a reference sample, reference cell, reference tissue, control sample, control cell, or control tissue is a single sample or combined multiple samples from the same patient or individual that are obtained at one or more different time points than when the test sample is obtained. For example, a reference sample, reference cell, reference tissue, control sample, control cell, or control tissue is obtained at an earlier time point from the same patient or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combined multiple samples from one or more healthy individuals who are not the patient. In certain embodiments, a reference sample, reference cell, reference tissue, control sample, control cell, or control tissue is a combined multiple samples from one or more individuals with a disease or disorder (e.g., cancer) who are not the patient or individual. In certain embodiments, a reference sample, reference cell, reference tissue, control sample, control cell, or control tissue is pooled RNA samples from normal tissues or pooled plasma or serum samples from one or more individuals who are not the patient. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the patient.

G. Exemplary Therapeutic Approaches

In embodiments of any of the preceding methods and uses (e.g., as described in Section III, Subsections A-F), for the prevention or treatment of cancer, the dose of an anti-cancer therapy (e.g., an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody)) will depend on the type of cancer to be treated, as defined above, the severity and course of the cancer, whether the anti-cancer therapy is administered for preventive or therapeutic purposes, previous therapy, the patient's clinical history and response to the drug, and the discretion of the attending physician.

In some embodiments, the anti-cancer therapy (e.g., an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody)) may be suitably administered to the patient at one time or over a series of treatments. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g., every week or every three weeks (e.g., such that the patient receives, for example, from about two to about twenty, or e.g., about six doses of the anti-cancer therapy). An initial higher loading dose, followed by one or more lower doses may be administered. However, other dosage regimens may be useful. The progress of this therapy is easily monitored by conventional techniques and assays.

For example, as a general proposition, the therapeutically effective amount of an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) administered to human will be in the range of about 0.01 to about 50 mg/kg of patient body weight, whether by one or more administrations. In some embodiments, the therapeutic agent (e.g., antibody) used is about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg administered daily, weekly, every two weeks, every three weeks, or monthly, for example. In some embodiments, the antibody is administered at 15 mg/kg. However, other dosage regimens may be useful. In one embodiment, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) is administered to a human at a dose of about 50 mg, about 100 mg, about 200 mg, about 300 mg, about 400 mg, about 420 mg, about 500 mg, about 525 mg, about 600 mg, about 700 mg, about 800 mg, about 840 mg, about 900 mg, about 1000 mg, about 1050 mg, about 1100 mg, about 1200 mg, about 1300 mg, about 1400 mg, about 1500 mg, about 1600 mg, about 1700 mg, or about 1800 mg, for example, on day 1 of 21-day cycles (every three weeks, q3w). For example, the fixed dose may be approximately 420 mg, approximately 525 mg, approximately 840 mg, or approximately 1050 mg. In some embodiments, atezolizumab is administered at 1200 mg intravenously every three weeks (q3w). Where a fixed dose is administered, preferably it is in the range from about 5 mg to about 2000 mg. The dose of an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered as a single dose or as multiple doses (e.g., 2, 3, 4, 5, 6, 7, 8, 9, or 10 or more doses). Where a series of doses are administered, these may, for example, be administered approximately every week, approximately every 2 weeks, approximately every 3 weeks, or approximately every 4 weeks. The dose of the antagonist administered in a combination treatment may be reduced as compared to a single treatment. The progress of this therapy is easily monitored by conventional techniques.

Immunotherapies (e.g., a PD-L1 axis binding antagonist, e.g., an anti-PD-L1 antibody (e.g., atezolizumab)) described herein (and any additional therapeutic agent) may be formulated, dosed, and administered in a fashion consistent with good medical practice. Likewise, suppressive stromal antagonists (e.g., a TGF-β antagonist, e.g., an anti-TGF-β antibody) may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The immunotherapy (e.g., a PD-L1 axis binding antagonist, e.g., an anti-PD-L1 antibody (e.g., atezolizumab)) and/or the suppressive stromal antagonist (e.g., a TGF-β antagonist, e.g., an anti-TGF-β antibody) need not be, but is optionally formulated with and/or administered concurrently with one or more agents currently used to prevent or treat the disorder in question. The effective amount of such other agents depends on the amount of the immunotherapy (e.g., a PD-L1 axis binding antagonist, e.g., an anti-PD-L1 antibody (e.g., atezolizumab)) and/or the suppressive stromal antagonist (e.g., a TGF-β antagonist, e.g., an anti-TGF-β antibody) present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

In some embodiments, an immunotherapy (e.g., a PD-L1 axis binding antagonist, e.g., an anti-PD-L1 antibody (e.g., atezolizumab)) is administered concurrently with a suppressive stromal antagonist (e.g., a TGF-β antagonist, e.g., an anti-TGF-β antibody). In some embodiments, an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody) are administered as part of the same formulation. In other embodiments, an immunotherapy (e.g., a PD-L1 axis binding antagonist, e.g., an anti-PD-L1 antibody (e.g., atezolizumab)) is administered separately from a suppressive stromal antagonist (e.g., a TGF-β antagonist, e.g., an anti-TGF-β antibody).

In some embodiments, any of the preceding methods may further include administering an additional therapeutic agent. In some embodiments, the additional therapeutic agent is selected from the group consisting of an immunotherapy agent, a cytotoxic agent, a growth inhibitory agent, a radiation therapy agent, an anti-angiogenic agent, and combinations thereof.

In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) is administered concurrently with an agonist directed against an activating co-stimulatory molecule. In some embodiments, an activating co-stimulatory molecule may include CD40, CD226, CD28, OX40, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an antagonist directed against an inhibitory co-stimulatory molecule. In some embodiments, an inhibitory co-stimulatory molecule may include CTLA-4 (also known as CD152), TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, TIM-3, BTLA, VISTA, LAG-3, B7-H3, B7-H4, IDO, TIGIT, MICA/B, or arginase.

In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an antagonist directed against CTLA-4 (also known as CD152), e.g., a blocking antibody. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with ipilimumab (also known as MDX-010, MDX-101, or YERVOY®). In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with tremelimumab (also known as ticilimumab or CP-675,206). In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an antagonist directed against B7-H3 (also known as CD276), e.g., a blocking antibody. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with MGA271.

In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an agonist directed against CD137 (also known as TNFRSF9, 4-1 BB, or ILA), e.g., an activating antibody. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with urelumab (also known as BMS-663513). In some embodiments an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an agonist directed against CD40, e.g., an activating antibody. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with CP-870893. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an agonist directed against OX40 (also known as CD134), e.g., an activating antibody. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an anti-OX40 antibody (e.g., AgonOX). In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an agonist directed against CD27, e.g., an activating antibody. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with CDX-1127. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an antagonist directed against TIGIT, for example, an anti-TIGIT antibody. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an antagonist directed against indoleamine-2,3-dioxygenase (IDO). In some embodiments, the IDO antagonist is 1-methyl-D-tryptophan (also known as 1-D-MT).

In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with a cancer vaccine. In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci. 104:14-21, 2013). In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an adjuvant. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with a treatment comprising a TLR agonist, e.g., Poly-ICLC (also known as HILTONOL®), LPS, MPL, or CpG ODN. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with tumor necrosis factor (TNF) alpha. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with IL-1. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with HMGB1. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an IL-10 antagonist. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an IL-4 antagonist. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an IL-13 antagonist. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an HVEM antagonist. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an ICOS agonist, e.g., by administration of ICOS-L, or an agonistic antibody directed against ICOS. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with a treatment targeting CX3CL1. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with a treatment targeting CXCL9. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with a treatment targeting CXCL10. In some embodiments an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with a treatment targeting CCL5. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with an LFA-1 or ICAM1 agonist. In some embodiments, an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody) may be administered in conjunction with a Selectin agonist.

A chemotherapeutic agent, if administered, is usually administered at dosages known therefore, or optionally lowered due to combined action of the drugs or negative side effects attributable to administration of the chemotherapeutic agent. Preparation and dosing schedules for such chemotherapeutic agents may be used according to manufacturers' instructions or as determined empirically by the skilled practitioner. Where the chemotherapeutic agent is paclitaxel, preferably, it is administered at a dose between about 130 mg/m$^2$ to 200 mg/m$^2$ (e.g., approximately 175 mg/m$^2$), for instance, over 3 hours, once every 3 weeks. Where the chemotherapeutic agent is carboplatin, preferably it is administered by calculating the dose of carboplatin using the Calvert formula which is based on a patient's preexisting renal function or renal function and desired platelet nadir. Renal excretion is the major route of elimination for carboplatin. The use of this dosing formula, as compared to empirical dose calculation based on body surface area, allows compensation for patient variations in pretreatment renal function that might otherwise result in either underdosing (in patients with above average renal function) or overdosing (in patients with impaired renal function). The target AUC of 4-6 mg/mL/min using single agent carboplatin appears to provide the most appropriate dose range in previously treated patients.

In addition to the above therapeutic regimes, the patient may be subjected to surgical removal of tumors and/or cancer cells.

Such combination therapies noted above encompass combined administration (where two or more therapeutic agents are included in the same or separate formulations), and separate administration, in which case, administration of an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody), can occur prior to, simultaneously, and/or following, administration of the additional therapeutic agent or agents. In one embodiment, administration of an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody), and administration of an additional therapeutic agent occur within about one month, or within about one, two or three weeks, or within about one, two, three, four, five, or six days, of each other.

In embodiments where either the immunotherapy or the suppressive stromal antagonist is an antibody (e.g., an anti-PD-L1 antibody or an anti-TGF-β antibody), the administered antibody may be a naked antibody. The immunotherapy (e.g., a PD-L1 axis binding antagonist, e.g., an anti-PD-L1 antibody (e.g., atezolizumab)) and/or the suppressive stromal antagonist (e.g., a TGF-β antagonist, e.g., an anti-TGF-β antibody) administered may be conjugated with a cytotoxic agent. Preferably, the conjugated and/or antigen to which it is bound is/are internalized by the cell, resulting in increased therapeutic efficacy of the conjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases, and DNA endonucleases.

The compositions utilized in the methods described herein can be administered by any suitable method, including, for example, intravenously, intramuscularly, subcutaneously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, orally, topically, transdermally, intravitreally (e.g., by intravitreal injection), parenterally, by eye drop, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In some embodiments, the immunotherapy (e.g., a PD-L1 axis binding antagonist, e.g., an anti-PD-L1 antibody (e.g., atezolizumab)) and/or the suppressive stromal antagonist (e.g., a TGF-β antagonist, e.g., an anti-TGF-β antibody) is administered intravenously, intramuscularly, subcutaneously, topically, orally, transdermally, intraperitoneally, intraorbitally, by implantation, by inhalation, intrathecally, intraventricularly, or intranasally. In some embodiments, the multi-targeted tyrosine kinase inhibitor is administered orally. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

IV. Compositions and Pharmaceutical Formulations

In one aspect, the invention is based, in part, on the discovery that biomarkers of the invention can be used to identify individuals having a cancer (including, but not limited to, a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from anti-cancer therapies that include immunotherapies (including, but not limited to, a PD-L1 axis binding antagonist, e.g., an anti-PD-L1 antibody (e.g., atezolizumab)) and/or a suppressive stromal antagonists (including, but not limited to, a TGF-β antagonist, e.g., an anti-TGF-β antibody). In some embodiments, the individual is less likely to respond to the immunotherapy alone. In another aspect, the invention is based, in part, on the discovery that biomarkers of the invention can be used to monitor and/or assess treatment response for individuals having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who are treated with anti-cancer therapies that include immunotherapies (e.g., a PD-L1 axis binding antagonist, e.g., an anti-PD-L1 antibody (e.g., atezolizumab)) and/or a suppressive stromal antagonists (e.g., a TGF-β antagonist, e.g., an anti-TGF-β antibody). These agents, and combinations thereof, are useful for the treatment of cancer, e.g., as part of any of the methods and uses described herein, for example, in Sections II and III above. Any suitable immunotherapy and/or suppressive stromal antagonist can be used in the methods and uses described herein. Non-limiting examples suitable for use in the methods and uses of the invention are described further below.

A. Exemplary Immunotherapies

Any suitable immunotherapy may be used in the context of the invention. Immunotherapies are described in the art (see, e.g., Chen et al. *Immunity* 39:1-10, 2013). The immunotherapy may be an activating immunotherapy or a suppressing immunotherapy. In some embodiments, the activating immunotherapy includes a CD28, OX40, GITR, CD137, CD27, ICOS, HVEM, NKG2D, MICA, 2B4, IL-2, IL-12, IFNγ, IFNα, TNFα, IL-1, CDN, HMBG1, or TLR agonist. In particular embodiments, the agonist (e.g., a CD28, OX40, GITR, CD137, CD27, ICOS, HVEM, NKG2D, MICA, 2B4, IL-2, IL-12, IFNγ, IFNα, TNFα, IL-1, CDN, HMBG1, or TLR agonist) increases, enhances, or stimulates an immune response or function in a patient having cancer. In some embodiments, the agonist modulates the expression and/or activity of a ligand (e.g., a T cell receptor ligand), and/or increases or stimulates the interaction of the ligand with its immune receptor, and/or increases or stimulates the intracellular signaling mediated by ligand binding to the immune receptor. In other embodiments, the suppressing immunotherapy includes a PD-L1 axis, CTLA-4, TIM-3, BTLA, VISTA, LAG-3, B7H4, CD96, TIGIT, CD226, prostaglandin, VEGF, endothelin B, IDO, arginase, MICA/MICB, TIM-3, IL-10, IL-4, or IL-13 antagonist. In particular embodiments, the antagonist (e.g., a PD-L1 axis, CTLA-4, TIM-3, BTLA, VISTA, LAG-3, B7H4, CD96, TIGIT, CD226, prostaglandin, VEGF, endothelin B, IDO, arginase, MICA/MICB, TIM-3, IL-10, IL-4, or IL-13 antagonist) is an agent that inhibits and/or blocks the interaction of a ligand (e.g., a T cell receptor ligand) with its immune receptor or is an antagonist of ligand and/or receptor expression and/or activity, or is an agent that blocks the intracellular signaling mediated by a ligand (e.g., a T cell receptor ligand) with its immune receptor. In some embodiments, the immunotherapy is an immune checkpoint inhibitor. Immunotherapy antibodies may have any of the features, singly or in combination, described in Sections i-vii of Subsection D below.

B. Exemplary PD-L1 Axis Binding Antagonists

PD-L1 axis binding antagonists include PD-1 binding antagonists, PD-L1 binding antagonists, and PD-L2 binding antagonists. PD-1 (programmed death 1) is also referred to in the art as "programmed cell death 1," "PDCD1," "CD279," and "SLEB2." An exemplary human PD-1 is shown in UniProtKB/Swiss-Prot Accession No. Q15116. PD-L1 (programmed death ligand 1) is also referred to in the art as "programmed cell death 1 ligand 1," "PDCD1 LG1," "CD274," "B7-H," and "PDL1." An exemplary human PD-L1 is shown in UniProtKB/Swiss-Prot Accession No. Q9NZQ7.1. PD-L2 (programmed death ligand 2) is also referred to in the art as "programmed cell death 1 ligand 2," "PDCD1LG2," "CD273," "B7-DC," "Btdc," and "PDL2." An exemplary human PD-L2 is shown in UniProtKB/Swiss-Prot Accession No. Q9BQ51. In some embodiments, PD-1, PD-L1, and PD-L2 are human PD-1, PD-L1, and PD-L2. The PD-L1 axis binding antagonist may, in some instances, be a PD-1 binding antagonist, a PD-L1 binding antagonist, or a PD-L2 binding antagonist. It is expressly contemplated that such PD-L1 axis binding antagonist antibodies (e.g., anti-PD-L1 antibodies, anti-PD-1 antibodies, and anti-PD-L2 antibodies), or other antibodies described herein (e.g., anti-PD-L1 antibodies for detection of PD-L1 expression levels) for use in any of the embodiments enumerated herein may have any of the features, singly or in combination, described in Sections i-vii of Subsection D below.

(i) PD-L1 Binding Antagonists

In some instances, the PD-L1 binding antagonist inhibits the binding of PD-L1 to one or more of its ligand binding partners. In other instances, the PD-L1 binding antagonist inhibits the binding of PD-L1 to PD-1. In yet other instances, the PD-L1 binding antagonist inhibits the binding of PD-L1 to B7-1. In some instances, the PD-L1 binding antagonist inhibits the binding of PD-L1 to both PD-1 and B7-1. The PD-L1 binding antagonist may be, without limitation, an antibody, an antigen-binding fragment thereof, an immunoadhesin, a fusion protein, an oligopeptide, or a small molecule. In some embodiments, the PD-L1 binding antagonist is a small molecule that inhibits PD-L1. In some embodiments, the PD-L1 binding antagonist is a small molecule that inhibits PD-L1 and VISTA. In some embodiments, the PD-L1 binding antagonist is CA-170 (also known as AUPM-170). In some embodiments, the PD-L1 binding antagonist is a small molecule that inhibits PDL1 and TIM3. In some embodiments, the small molecule is a compound described in WO2015/033301 and WO2015/033299.

In some embodiments, the PD-L1 binding antagonist is an anti-PD-L1 antibody. A variety of anti-PD-L1 antibodies are contemplated and described herein. In any of the embodiments herein, the isolated anti-PD-L1 antibody can bind to a human PD-L1, for example a human PD-L1 as shown in UniProtKB/Swiss-Prot Accession No. Q9NZQ7.1, or a variant thereof. In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')2 fragments. In some embodiments, the anti-PD-L1 antibody is a chimeric or humanized antibody. In some embodiments, the anti-PD-L1 antibody is a human antibody. Examples of anti-PD-L1 antibodies useful in the methods of this invention and methods of making them are described in International Patent Application Publication No. WO 2010/077634 and U.S. Pat. No. 8,217,149, each of which is incorporated herein by reference in its entirety.

In some embodiments, the anti-PD-L1 antibody is atezolizumab (CAS Registry Number: 1422185-06-5). Atezolizumab (Genentech), also known as MPDL3280A, is an anti-PD-L1 antibody.

Atezolizumab comprises:

(a) an HVR-H1, HVR-H2, and HVR-H3 sequence of GFTFSDSWIH (SEQ ID NO: 63), AWISPYGGSTYY-ADSVKG (SEQ ID NO: 64) and RHWPGGFDY (SEQ ID NO: 65), respectively, and (b) an HVR-L1, HVR-L2, and HVR-L3 sequence of RASQDVSTAVA (SEQ ID NO: 66), SASFLYS (SEQ ID NO:67) and QQYLYHPAT (SEQ ID NO: 68), respectively.

Atezolizumab comprises a heavy chain and a light chain sequence, wherein:

(a) the heavy chain variable region sequence comprises the amino acid sequence:

```
                                        (SEQ ID NO: 69)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYVVGQGTLVTVSS,
```

and (b) the light chain variable region sequence comprises the amino acid sequence:

```
                                        (SEQ ID NO: 70)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In some instances, the anti-PD-L1 antibody comprises (a) a VH domain comprising an amino acid sequence comprising having at least 95% sequence identity (e.g., at least 95%, 96%, 97%, 98%, or 99% sequence identity) to, or the sequence of (SEQ ID NO: 69); (b) a VL domain comprising an amino acid sequence comprising having at least 95% sequence identity (e.g., at least 95%, 96%, 97%, 98%, or 99% sequence identity) to, or the sequence of (SEQ ID NO: 70); or (c) a VH domain as in (a) and a VL domain as in (b).

Atezolizumab comprises a heavy chain and a light chain sequence, wherein:

(a) the heavy chain comprises the amino acid sequence:

```
                                        (SEQ ID NO: 71)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG,
```

and (b) the light chain comprises the amino acid sequence:

(SEQ ID NO: 72)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some embodiments, the anti-PD-L1 antibody is avelumab (CAS Registry Number: 1537032-82-8). Avelumab, also known as MSB0010718C, is a human monoclonal IgG1 anti-PD-L1 antibody (Merck KGaA, Pfizer). Avelumab comprises a heavy chain and a light chain sequence, wherein:

(a) the heavy chain comprises the amino acid sequence:

(SEQ ID NO: 73)
EVQLLESGGGLVQPGGSLRLSCAASGFTFSSYIMMWVRQAPGKGLEWVSS

IYPSGGITFYADTVKGRFTISRDNSKNTLYLQMNSLRAEDTAVYYCARIK

LGTVTTVDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG, and (b) the light chain comprises the amino acid sequence:

(SEQ ID NO: 74)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVLGQPKANPTVTLFPPSSEELQANKATLVCLISDFYPGAVTV

AWKADGSPVKAGVETTKPSKQSNNKYAASSYLSLTPEQWKSHRSYSCQVT

HEGSTVEKTVAPTECS.

In some embodiments, the anti-PD-L1 antibody comprises the six HVR sequences from SEQ ID NO: 73 and SEQ ID NO: 74 (e.g., the three heavy chain HVRs from SEQ ID NO: 73 and the three light chain HVRs from SEQ ID NO: 74). In some embodiments, the anti-PD-L1 antibody comprises the heavy chain variable domain from SEQ ID NO: 73 and the light chain variable domain from SEQ ID NO: 74.

In some embodiments, the anti-PD-L1 antibody is durvalumab (CAS Registry Number: 1428935-60-7). Durvalumab, also known as MED14736, is an Fc-optimized human monoclonal IgG1 kappa anti-PD-L1 antibody (MedImmune, AstraZeneca) described in WO2011/066389 and US2013/034559. Durvalumab comprises a heavy chain and a light chain sequence, wherein:

(a) the heavy chain comprises the amino acid sequence:

(SEQ ID NO: 75)
EVQLVESGGGLVQPGGSLRLSCAASGFTFSRYWMSWVRQAPGKGLEWVAN

IKQDGSEKYYVDSVKGRFT!SRDNAKNSLYLQMNSLRAEDTAVYYCAREG

GWFGELAFDYVVGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPEFEGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPASIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

G, and (b) the light chain comprises the amino acid sequence:

(SEQ ID NO: 76)
EIVLTQSPGTLSLSPGERATLSCRASQRVSSSYLAWYQQKPGQAPRLLIY

DASSRATGIPDRFSGSGSGTDFTLTISRLEPEDFAVYYCQQYGSLPWTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC.

In some embodiments, the anti-PD-L1 antibody comprises the six HVR sequences from SEQ ID NO: 75 and SEQ ID NO: 76 (e.g., the three heavy chain HVRs from SEQ ID NO: 75 and the three light chain HVRs from SEQ ID NO: 76). In some embodiments, the anti-PD-L1 antibody comprises the heavy chain variable domain from SEQ ID NO: 75 and the light chain variable domain from SEQ ID NO: 76.

In some embodiments, the anti-PD-L1 antibody is MDX-1105 (Bristol Myers Squibb). MDX-1105, also known as BMS-936559, is an anti-PD-L1 antibody described in WO2007/005874.

In some embodiments, the anti-PD-L1 antibody is LY3300054 (Eli Lilly).

In some embodiments, the anti-PD-L1 antibody is STI-A1014 (Sorrento). STI-A1014 is a human anti-PD-L1 antibody.

In some embodiments, the anti-PD-L1 antibody is KN035 (Suzhou Alphamab). KN035 is single-domain antibody (dAB) generated from a camel phage display library.

In some embodiments, the anti-PD-L1 antibody comprises a cleavable moiety or linker that, when cleaved (e.g., by a protease in the tumor microenvironment), activates an antibody antigen binding domain to allow it to bind its antigen, e.g., by removing a non-binding steric moiety. In some embodiments, the anti-PD-L1 antibody is CX-072 (CytomX Therapeutics).

In some embodiments, the anti-PD-L1 antibody comprises the six HVR sequences (e.g., the three heavy chain HVRs and the three light chain HVRs) and/or the heavy chain variable domain and light chain variable domain from an anti-PD-L1 antibody described in US20160108123 (Assigned to Novartis), WO2016/000619 (Applicant: Beigene), WO2012/145493 (Applicant: Amplimmune), U.S. Pat. No. 9,205,148 (Assigned to MedImmune), WO2013/181634 (Applicant: Sorrento), and WO2016/061142 (Applicant: Novartis).

In some instances, the anti-PD-L1 antibody is selected from the group consisting of atezolizumab, YW243.55.S70, MDX-1105, MED14736 (durvalumab), and MSB0010718C (avelumab). Antibody YW243.55.S70 is an anti-PD-L1 described in PCT Pub. No. WO 2010/077634. Further examples of anti-PD-L1 antibodies useful for the methods of this invention, and methods for making thereof are described in PCT Pub. Nos. WO 2010/077634, WO 2007/005874, and WO 2011/066389, and also in U.S. Pat. No. 8,217,149, and U.S. Pub. No. 2013/034559, which are incorporated herein by reference.

In a still further specific aspect, the anti-PD-L1 antibody has reduced or minimal effector function. In a still further specific aspect the minimal effector function results from an "effector-less Fc mutation" or aglycosylation mutation. In still a further embodiment, the effector-less Fc mutation is an N297A or D265A/N297A substitution in the constant region. In some embodiments, the isolated anti-PD-L1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites from an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site with another amino acid residue (e.g., glycine, alanine, or a conservative substitution).

(ii) PD-1 Binding Antagonists

In some instances, the PD-L1 axis binding antagonist is a PD-1 binding antagonist. For example, in some instances, the PD-1 binding antagonist inhibits the binding of PD-1 to one or more of its ligand binding partners. In some instances, the PD-1 binding antagonist inhibits the binding of PD-1 to PD-L1. In other instances, the PD-1 binding antagonist inhibits the binding of PD-1 to PD-L2. In yet other instances, the PD-1 binding antagonist inhibits the binding of PD-1 to both PD-L1 and PD-L2. The PD-1 binding antagonist may be, without limitation, an antibody, an antigen-binding fragment thereof, an immunoadhesin, a fusion protein, an oligopeptide, or a small molecule. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). For example, in some instances, the PD-1 binding antagonist is an Fc-fusion protein. In some embodiments, the PD-1 binding antagonist is AMP-224. AMP-224, also known as B7-DCIg, is a PD-L2-Fc fusion soluble receptor described in WO 2010/027827 and WO 2011/066342. In some embodiments, the PD-1 binding antagonist is a peptide or small molecule compound. In some embodiments, the PD-1 binding antagonist is AUNP-12 (PierreFabre/Aurigene). See, e.g., WO2012/168944, WO2015/036927, WO2015/044900, WO2015/033303, WO2013/144704, WO2013/132317, and WO2011/161699. In some embodiments, the PD-1 binding antagonist is a small molecule that inhibits PD-1.

In some embodiments, the PD-1 binding antagonist is an anti-PD-1 antibody. A variety of anti-PD-1 antibodies can be utilized in the methods and uses disclosed herein. In any of the embodiments herein, the PD-1 antibody can bind to a human PD-1 or a variant thereof. In some embodiments the anti-PD-1 antibody is a monoclonal antibody. In some embodiments, the anti-PD-1 antibody is an antibody fragment selected from the group consisting of Fab, Fab', Fab'-SH, Fv, scFv, and (Fab')2 fragments. In some embodiments, the anti-PD-1 antibody is a chimeric or humanized antibody. In other embodiments, the anti-PD-1 antibody is a human antibody.

In some embodiments, the anti-PD-1 antibody is nivolumab (CAS Registry Number: 946414-94-4). Nivolumab (Bristol-Myers Squibb/Ono), also known as MDX-1106-04, MDX-1106, ONO-4538, BMS-936558, and OPDIVO®, is an anti-PD-1 antibody described in WO2006/121168. Nivolumab comprises a heavy chain and a light chain sequence, wherein:

(a) the heavy chain comprises the amino acid sequence:

```
                                          (SEQ ID NO: 77)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK,
```

and (b) the light chain comprises the amino acid sequence:

```
                                          (SEQ ID NO: 78)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

In some embodiments, the anti-PD-1 antibody comprises the six HVR sequences from SEQ ID NO: 77 and SEQ ID NO: 78 (e.g., the three heavy chain HVRs from SEQ ID NO: 77 and the three light chain HVRs from SEQ ID NO: 78). In some embodiments, the anti-PD-1 antibody comprises the heavy chain variable domain from SEQ ID NO: 77 and the light chain variable domain from SEQ ID NO: 78.

In some embodiments, the anti-PD-1 antibody is pembrolizumab (CAS Registry Number: 1374853-91-4). Pembrolizumab (Merck), also known as MK-3475, Merck 3475, lambrolizumab, SCH-900475, and KEYTRUDA®, is an anti-PD-1 antibody described in WO2009/114335. Pembrolizumab comprises a heavy chain and a light chain sequence, wherein:

(a) the heavy chain comprises the amino acid sequence:

```
                                        (SEQ ID NO: 79)
QVQLVQSGVEVKKPGASVKVSCKASGYTFTNYYMYWVRQAPGQGLEWMGG

INPSNGGTNFNEKFKNRVTLTTDSSTTTAYMELKSLQFDDTAVYYCARRD

YRFDMGFDYWGQGTTVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK,
```

and (b) the light chain comprises the amino acid sequence:

```
                                        (SEQ ID NO: 80)
EIVLTQSPATLSLSPGERATLSCRASKGVSTSGYSYLHWYQQKPGQAPRL

LIYLASYLESGVPARFSGSGSGTDFTLTISSLEPEDFAVYYCQHSRDLPL

TFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

In some embodiments, the anti-PD-1 antibody comprises the six HVR sequences from SEQ ID NO: 79 and SEQ ID NO: 80 (e.g., the three heavy chain HVRs from SEQ ID NO: 79 and the three light chain HVRs from SEQ ID NO: 80). In some embodiments, the anti-PD-1 antibody comprises the heavy chain variable domain from SEQ ID NO: 79 and the light chain variable domain from SEQ ID NO: 80.

In some embodiments, the anti-PD-1 antibody is MEDI-0680 (AMP-514; AstraZeneca). MEDI-0680 is a humanized IgG4 anti-PD-1 antibody.

In some embodiments, the anti-PD-1 antibody is PDR001 (CAS Registry No. 1859072-53-9; Novartis). PDR001 is a humanized IgG4 anti-PD-1 antibody that blocks the binding of PD-L1 and PD-L2 to PD-1.

In some embodiments, the anti-PD-1 antibody is REGN2810 (Regeneron). REGN2810 is a human anti-PD-1 antibody.

In some embodiments, the anti-PD-1 antibody is BGB-108 (BeiGene). In some embodiments, the anti-PD-1 antibody is BGB-A317 (BeiGene).

In some embodiments, the anti-PD-1 antibody is JS-001 (Shanghai Junshi). JS-001 is a humanized anti-PD-1 antibody.

In some embodiments, the anti-PD-1 antibody is STI-A1110 (Sorrento). STI-A1110 is a human anti-PD-1 antibody.

In some embodiments, the anti-PD-1 antibody is INCSHR-1210 (Incyte). INCSHR-1210 is a human IgG4 anti-PD-1 antibody.

In some embodiments, the anti-PD-1 antibody is PF-06801591 (Pfizer).

In some embodiments, the anti-PD-1 antibody is TSR-042 (also known as ANB011; Tesaro/AnaptysBio).

In some embodiments, the anti-PD-1 antibody is AM0001 (ARMO Biosciences).

In some embodiments, the anti-PD-1 antibody is ENUM 244C8 (Enumeral Biomedical Holdings). ENUM 244C8 is an anti-PD-1 antibody that inhibits PD-1 function without blocking binding of PD-L1 to PD-1.

In some embodiments, the anti-PD-1 antibody is ENUM 388D4 (Enumeral Biomedical Holdings). ENUM 388D4 is an anti-PD-1 antibody that competitively inhibits binding of PD-L1 to PD-1.

In some embodiments, the anti-PD-1 antibody comprises the six HVR sequences (e.g., the three heavy chain HVRs and the three light chain HVRs) and/or the heavy chain variable domain and light chain variable domain from an anti-PD-1 antibody described in WO2015/112800 (Applicant: Regeneron), WO2015/112805 (Applicant: Regeneron), WO2015/112900 (Applicant: Novartis), US20150210769 (Assigned to Novartis), WO2016/089873 (Applicant: Celgene), WO2015/035606 (Applicant: Beigene), WO2015/085847 (Applicants: Shanghai Hengrui Pharmaceutical/Jiangsu Hengrui Medicine), WO2014/206107 (Applicants: Shanghai Junshi Biosciences/Junmeng Biosciences), WO2012/145493 (Applicant: Amplimmune), U.S. Pat. No. 9,205,148 (Assigned to MedImmune), WO2015/119930 (Applicants: Pfizer/Merck), WO2015/119923 (Applicants: Pfizer/Merck), WO2016/032927 (Applicants: Pfizer/Merck), WO2014/179664 (Applicant: AnaptysBio), WO2016/106160 (Applicant: Enumeral), and WO2014/194302 (Applicant: Sorrento).

In a still further embodiment, provided is an isolated anti-PD-1 antibody comprising a heavy chain variable region comprising the heavy chain variable region amino acid sequence from SEQ ID NO: 61 and/or a light chain variable region comprising the light chain variable region amino acid sequence from SEQ ID NO: 62.

In a still further embodiment, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

```
                                        (SEQ ID NO: 61)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK,
```

and (b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 62)
EIVLTQSPATLSLSPGERATLSCRASQSVSSYLAWYQQKPGQAPRLLIYD
ASNRATGIPARFSGSGSGTDFTLTISSLEPEDFAVYYCQQSSNWPRTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC.

In a still further specific aspect, the anti-PD-1 antibody has reduced or minimal effector function. In a still further specific aspect the minimal effector function results from an "effector-less Fc mutation" or aglycosylation mutation. In still a further embodiment, the effector-less Fc mutation is an N297A or D265A/N297A substitution in the constant region. In some embodiments, the isolated anti-PD-1 antibody is aglycosylated. Removal of glycosylation sites from an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site with another amino acid residue (e.g., glycine, alanine, or a conservative substitution).

(iii) PD-L2 Binding Antagonists

In some embodiments, the PD-L2 binding antagonist is a molecule that inhibits the binding of PD-L2 to its ligand binding partners. In a specific aspect, the PD-L2 binding ligand partner is PD-1. The PD-L2 binding antagonist may be, without limitation, an antibody, an antigen-binding fragment thereof, an immunoadhesin, a fusion protein, an oligopeptide, or a small molecule.

In some embodiments, the PD-L2 binding antagonist is an anti-PD-L2 antibody. In any of the embodiments herein, the anti-PD-L2 antibody can bind to a human PD-L2 or a variant thereof. In some embodiments the anti-PD-L2 antibody is a monoclonal antibody. In some embodiments, the anti-PD-L2 antibody is an antibody fragment selected from the group consisting of Fab, Fab', Fab'-SH, Fv, scFv, and (Fab')2 fragments. In some embodiments, the anti-PD-L2 antibody is a chimeric or humanized antibody. In other embodiments, the anti-PD-L2 antibody is a human antibody. In a still further specific aspect, the anti-PD-L2 antibody has reduced or minimal effector function. In a still further specific aspect the minimal effector function results from an "effector-less Fc mutation" or aglycosylation mutation. In still a further embodiment, the effector-less Fc mutation is an N297A or D265A/N297A substitution in the constant region. In some embodiments, the isolated anti-PD-L2 antibody is aglycosylated.

C. Exemplary Suppressive Stromal Antagonists

Any suitable suppressive stromal antagonist can be used in the context of the invention. Targets for stromal gene antagonists are known in the art; for example, see Turley et al., *Nature Reviews Immunology* 15:669-682, 2015 and Rosenbloom et al., *Biochimica et Biophysica Acta* 1832: 1088-1103, 2013. In some embodiments, the suppressive stromal antagonist targets TGF-β (e.g., TGF-β1 and TGF-β2). In some embodiments, the suppressive stromal antagonist targets a surface glycoprotein, including, without limitation, endoglin (CD105), 3G5 antigen, FAP, CSPG4 (NG2), and/or podoplanin (GP38). In some embodiments, the suppressive stromal antagonist targets an adhesion molecule, including, without limitation, PECAM (CD31), VCAM (CD106), ICAM1 (CD54), THY1 (CD90) and/or P31 integrin (CD29). In some embodiments, the suppressive stromal antagonist targets a growth factor receptor, including, without limitation, VEGFR1 (FLT1), VEGFR2 (KDR), VEGFR3 (FLT4), PDGFRα (CD140a), and/or PDGFRβ (CD14013). In some embodiments, the suppressive stromal antagonist targets an intracellular structural protein, including, without limitation, vimentin, αSMA (ACTA2) and/or desmin. Other targets for suppressive stromal antagonist include, but are not limited to, 5NT (CD73 or NT5E) RGS3, endosialin (CD248), and FSP1 (S100A4). In some embodiments, the suppressive stromal antagonist targets a cancer-associated fibroblast associated polypeptide. Examples of cancer-associated fibroblast associated polypeptides include, but are not limited to, endoglin (CD105), FAP, podopalin, VCAM1, THY1, β1 integrin, PDGFRα, PDGFRβ, vimentin, αSMA, desmin, endosialin, and/or FSP1.

In some embodiments, the suppressive stromal antagonist targets TGF-β expression and activation. Examples include pirfenidone, αvβ6 antibodies, ATI and ATII receptor blockers, ACE inhibitors, CAT-192 (anti-TGF-β1 monoclonal AB), and caveolin scaffolding domain (CSD). In some embodiments, the suppressive stromal antagonist targets TGF-β signaling pathways including canonical signaling pathways TBR1 (exemplary inhibitor is SM305) and SMAD3 (exemplary inhibitor is SIS3). In some embodiments, the suppressive stromal antagonist targets TGF-β signaling pathways including noncanonical signaling pathways including c-Abl (exemplary inhibitor is imatinib mesylate), PDGFR (exemplary inhibitor is dasatinib), c-kit (exemplary inhibitor is nilotinib), and PKC-6 (exemplary inhibitors include small specific polypeptides and rottlerin derivatives). In some embodiments, the suppressive stromal antagonist targets CTGF (exemplary inhibitors include monoclonal CTGF antibodies). In some embodiments, the suppressive stromal antagonist targets inhibition of fibrocyte homing, including CXCL12 (exemplary inhibitor includes CXCL12 antibodies), CXCR4 (exemplary inhibitors include AMD3100), and CCR2 (exemplary inhibitors include PF-04136309). In some embodiments, the suppressive stromal antagonist targets Src (exemplary inhibitors includes dasatinib and SU6656). In some embodiments, the suppressive stromal antagonist targets VEGFR (exemplary inhibitors include nintedanib and BIBF1120). In some embodiments, the suppressive stromal antagonist targets FGFR (exemplary inhibitor includes sorafenib). In some embodiments, the suppressive stromal antagonist targets IL-13 (exemplary inhibitor includes humanized monoclonal antibodies to IL-13). In some embodiments, the suppressive stromal antagonist targets IL-6 receptor (exemplary inhibitor includes tocilizumab). In some embodiments, the suppressive stromal antagonist targets TLR (exemplary inhibitors include TLR inhibitors E5564, TAK-242). In some embodiments, the suppressive stromal antagonist targets Nox4 (ROS) (exemplary inhibitor includes GKT136901). In some embodiments, the suppressive stromal antagonist targets ET-1 (exemplary inhibitors include Bosentan and other ET receptor blockers). In some embodiments, the suppressive stromal antagonist is a TGF-β, PDPN, LAIR-1, SMAD, ALK, connective tissue growth factor (CTGF/CCN2), endothelial-1 (ET-1), AP-1, IL-13, PDGF, LOXL2, endoglin (CD105), FAP, podoplanin (GP38), VCAM1 (CD106), THY1, β1 integrin (CD29), PDGFRα (CD140a), PDGFRβ (CD1403), vimentin, αSMA (ACTA2), desmin, endosialin (CD248), or FSP1 (S100A4) antagonist.

In some embodiments, the suppressive stromal antagonist is pirfenidone, galunisertib, dasetininb, nintedanib, nilotinib, rottlerin and derivatives, or sorafenib.

In some embodiments, the suppressive stromal antagonist is a TGF-β antagonist. In some embodiments, the TGF-β antagonist inhibits the binding of TGF-β to its ligand binding partners. In some embodiments, the TGF-β antagonist inhibits the binding of TGF-β to a cellular receptor of TGF-β. In some embodiments, the TGF-β antagonist inhibits activation of TGF-β. In some embodiments, the TGF-β antagonist targets TGF-β1. In some embodiments, the TGF-β antagonist targets TGF-β2. In some embodiments, the TGF-β antagonist targets TGF-β3. In some embodiments, the TGF-β antagonist targets TGF-β receptor 1. In some embodiments, the TGF-β antagonist targets one or more of TGF-β1, TGF-β2, or TGF-β3. In some embodiments, the TGF-β antagonist targets TGF-β receptor 2. In some embodiments, the TGF-β antagonist targets TGF-β receptor 3. In some embodiments, the TGF-β antagonist targets one or more of TGF-β receptor 1, TGF-β receptor 2, or TGF-β receptor 3.

In some embodiments, the TGF-β antagonist is an anti-TGF-β antibody. In some embodiments, the anti-TGF-β antibody is capable of inhibiting binding between anti-TGF-β and one or more of its ligands. In some embodiments, the anti-TGF-β antibody is capable of inhibiting activation of TGF-β. In some embodiments, the anti-TGF-β antibody is a monoclonal antibody. In some embodiments, the anti-TGF-β antibody is an antibody fragment selected from the group consisting of Fab, Fab'-SH, Fv, scFv, and (Fab')2 fragments. In some embodiments, the anti-TGF-β antibody is a humanized antibody. In some embodiments, the anti-TGF-β antibody is a human antibody. In some embodiments, the anti-TGF-β antibody inhibits TGF-β1, TGF-β2, and/or TGF-β. In some embodiments, the anti-TGF-β antibody inhibits TGF-β1, TGF-β2, and TGF-β. In some embodiments, the anti-TGF-β antibody is a pan-specific anti-TGF-β antibody. In some embodiments, the anti-TGF-β antibody may be any anti-TGF-β antibody disclosed in, for example, U.S. Pat. No. 5,571,714 or in International Patent Application Nos. WO 92/00330, WO 92/08480, WO 95/26203, WO 97/13844, WO 00/066631, WO 05/097832, WO 06/086469, WO 05/010049, WO 06/116002, WO 07/076391, WO 12/167143, WO 13/134365, WO 14/164709, or WO 16/201282, each of which is incorporated herein by reference in its entirety. In particular embodiments, the anti-TGF-β antibody is fresolimumab, metelimumab, lerdelimumab, 1D11, 2G7, or a derivative thereof. It is expressly contemplated that such suppressive stromal antagonist antibodies (e.g., anti-TGF-β antibodies) for use in any of the embodiments enumerated herein may have any of the features, singly or in combination, described in Sections i-vii of Subsection D below.

In some embodiments, treatment with the suppressive stromal antagonist allows increased immune cell infiltration in a tissue. Without being bound by theory, the suppressive stromal antagonist modulates the stromal in the target tissue to facilitate infiltration of immune cells to the target tissue. For example, treatment of a fibrotic tumor expressing a biomarker described herein with a suppressive stromal antagonist modulates the stroma in and around the tumor to allow infiltration of immune cells (e.g., modulated by the immunotherapy) to the tumor. In some embodiments, the increased immune cell infiltration is an increased infiltration of one or more of T-cells, B cells, macrophages, or dendritic cells. In some embodiments, the T-cells are CD8+ T-cells and/or Teff cells. In some embodiments, the individual is resistant to immunotherapy prior to treatment with the suppressive stromal antagonist. In some embodiments, the individual has already been administered monotherapy immunotherapy.

D. Antibodies i. Antibody Affinity

In certain embodiments, an antibody provided herein (e.g., an anti-PD-L1 antibody, an anti-PD-1 antibody, or an anti-TGF-β antibody) has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881, 1999). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, for example, Chen et al., (*J. Mol. Biol.* 293:865-881, 1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

ii. Antibody Fragments

In certain embodiments, an antibody (e.g., an anti-PD-L1 antibody, an anti-PD-1 antibody, or an anti-TGF-β antibody) provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. (*Nat. Med.* 9:129-134, 2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994). See also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097, WO 1993/01161, Hudson et al. *Nat. Med.* 9:129-134, 2003, and Hollinger et al. *Proc. Natl. Acad. Sci. USA* 90: 6444-6448, 1993. Triabodies and tetrabodies are also described in Hudson et al. (*Nat. Med.* 9:129-134, 2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), according to known methods.

iii. Chimeric and Humanized Antibodies

In certain embodiments, an antibody (e.g., an anti-PD-L1 antibody, an anti-PD-1 antibody, or an anti-TGF-β antibody) provided herein is a chimeric antibody. Certain chimeric antibodies are described, e.g., in U.S. Pat. No. 4,816,567; and Morrison et al. (*Proc. Natl. Acad. Sci. USA,* 81:6851-6855, 1984). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, (Front. Biosci. 13:1619-1633, 2008), and are further described, e.g., in Riechmann et al. (*Nature* 332:323-329, 1988); Queen et al. (*Proc. Natl. Acad. Sci. USA* 86:10029-10033, 1989); U.S. Pat. Nos. 5,821,337, 7,527,791, 6,982,321, and 7,087,409; Kashmiri et al. (*Methods* 36:25-34, 2005) (describing specificity determining region (SDR) grafting); Padlan, (*Mol. Immunol.* 28:489-498, 1991) (describing "resurfacing"); Dall'Acqua et al. (*Methods* 36:43-60, 2005) (describing "FR shuffling"); Osbourn et al. (*Methods* 36:61-68, 2005), and Klimka et al. (*Br. J. Cancer,* 83:252-260, 2000) (describing the "guided selection" approach to FR shuffling).

Human framework regions that may be used for humanization include but are not limited to: framework regions selected using the "best-fit" method (see, e.g., Sims et al. *J. Immunol.* 151:2296, 1993); framework regions derived from the consensus sequence of human antibodies of a particular subgroup of light or heavy chain variable regions (see, e.g., Carter et al. *Proc. Natl. Acad. Sci. USA,* 89:4285, 1992; and Presta et al. *J. Immunol.,* 151:2623, 1993); human mature (somatically mutated) framework regions or human germline framework regions (see, e.g., Almagro and Fransson, *Front. Biosci.* 13:1619-1633, 2008); and framework regions derived from screening FR libraries (see, e.g., Baca et al., *J. Biol. Chem.* 272:10678-10684, 1997; and Rosok et al. *J. Biol. Chem.* 271:22611-22618, 1996).

iv. Human Antibodies

In certain embodiments, an antibody (e.g., an anti-PD-L1 antibody, an anti-PD-1 antibody, or an anti-TGF-β antibody) provided herein is a human antibody. Human antibodies can be produced using various techniques known in the art. Human antibodies are described generally in van Dijk and van de Winkel, (*Curr. Opin. Pharmacol.* 5: 368-74, 2001) and Lonberg (*Curr. Opin. Immunol.* 20:450-459, 2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, (Nat. Biotech. 23:1117-1125, 2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. See, e.g., Kozbor, (*J. Immunol.* 133: 3001, 1984); Brodeur et al. (*Monoclonal Antibody*

*Production Techniques and Applications*, pp. 51-63, Marcel Dekker, Inc., New York, 1987); and Boerner et al. (*J. Immunol.,* 147: 86, 1991). Human antibodies generated via human B-cell hybridoma technology are also described in Li et al., *Proc. Natl. Acad. Sci. USA,* 103:3557-3562, 2006. Additional methods include those described, for example, in U.S. Pat. No. 7,189,826 (describing production of monoclonal human IgM antibodies from hybridoma cell lines) and Ni, (*Xiandai Mianyixue,* 26(4):265-268, 2006) (describing human-human hybridomas). Human hybridoma technology (Trioma technology) is also described in Vollmers and Brandlein, (*Histology and Histopathology,* 20(3):927-937, 2005) and Vollmers and Brandlein, (*Methods and Findings in Experimental and Clinical Pharmacology,* 27(3):185-91, 2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

v. Library-Derived Antibodies

Antibodies (e.g., anti-PD-L1 antibodies, anti-PD-1 antibodies, or anti-TGF-β antibodies) may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. (*Methods in Molecular Biology* 178:1-37, O'Brien et al., ed., Human Press, Totowa, N.J., 2001) and further described, e.g., in McCafferty et al. (*Nature* 348:552-554, 1990); Clackson et al. (*Nature* 352: 624-628, 1991); Marks et al. (*J. Mol. Biol.* 222: 581-597, 1992); Marks and Bradbury, (*Methods in Molecular Biology* 248: 161-175, Lo, ed., Human Press, Totowa, N.J., 2003); Sidhu et al. (*J. Mol. Biol.* 338(2): 299-310, 2004); Lee et al. (*J. Mol. Biol.* 340(5): 1073-1093, 2004); Fellouse, (*Proc. Natl. Acad. Sci. USA* 101 (34): 12467-12472, 2004); and Lee et al. (*J. Immunol. Methods* 284(1-2): 119-132, 2004).

In certain phage display methods, repertoires of VH and VL genes are separately cloned by polymerase chain reaction (PCR) and recombined randomly in phage libraries, which can then be screened for antigen-binding phage as described in Winter et al. (*Ann. Rev. Immunol.,* 12: 433-455, 1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and self antigens without any immunization as described by Griffiths et al. (*EMBO J,* 12: 725-734, 1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, (*J. Mol. Biol.,* 227: 381-388, 1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

vi. Multispecific Antibodies

In any one of the above aspects, an antibody (e.g., an anti-PD-L1 antibody, an anti-PD-1 antibody, or an anti-TGF-β antibody) provided herein may be a multispecific antibody, for example, a bispecific antibody. Multispecific antibodies are monoclonal antibodies that have binding specificities for at least two different sites. In certain embodiments, an antibody provided herein is a multispecific antibody, e.g., a bispecific antibody. In certain embodiments, one of the binding specificities is for PD-L1 and the other is for any other antigen. In certain embodiments, one of the binding specificities is for TGF-β and the other is for any other antigen. In certain embodiments, bispecific antibodies may bind to two different epitopes of PD-L1. In certain embodiments, bispecific antibodies may bind to two different epitopes of TGF-β. Bispecific antibodies may also be used to localize cytotoxic agents to cells which express PD-L1 or TGF-β. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537, 1983), WO 93/08829 and Traunecker et al. *EMBO J.* 10: 3655, 1991) and "knob-in-hole" engineering (see, e.g., U.S. Pat. No. 5,731,168). Multi-specific antibodies may also be made by engineering electrostatic steering effects for making antibody Fc-heterodimeric molecules (see, e.g., WO 2009/089004A1); cross-linking two or more antibodies or fragments (see, e.g., U.S. Pat. No. 4,676,980, and Brennan et al. *Science* 229: 81, 1985); using leucine zippers to produce bi-specific antibodies (see, e.g., Kostelny et al. *J. Immunol.* 148(5): 1547-1553, 1992); using "diabody" technology for making bispecific antibody fragments (see, e.g., Hollinger et al. *Proc. Natl. Acad. Sci. USA* 90:6444-6448, 1993); and using single-chain Fv (sFv) dimers (see, e.g., Gruber et al. *J. Immunol.* 152:5368, 1994); and preparing trispecific antibodies as described, e.g., in Tutt et al. *J. Immunol.* 147: 60, 1991).

Engineered antibodies with three or more functional antigen binding sites, including "Octopus antibodies," are also included herein (see, e.g., US 2006/0025576A1).

The antibody or fragment herein includes a "Dual Acting FAb" or "DAF" comprising an antigen binding site that binds to PD-L1 and another, different antigen. The antibody or fragment herein also includes a DAF comprising an antigen binding site that binds to VEGF and another, different antigen.

vii. Antibody Variants

In certain embodiments, amino acid sequence variants of the antibodies (e.g., anti-PD-L1 antibodies, anti-PD-1 antibodies, and anti-TGF-β antibodies) are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 6 under the heading of "preferred substitutions." More substantial changes are provided in Table 6 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 6

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gin;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity and/or reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196, 2008), and/or residues that contact antigen, with the resulting variant VH or VL being tested for binding affinity. Affinity maturation by constructing and reselecting from secondary libraries has been described, e.g., in Hoogenboom et al. (*Methods in Molecular Biology* 178: 1-37, O'Brien et al., ed., Human Press, Totowa, N.J., 2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen-contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (*Science,* 244:1081-1085, 1989). In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b. Glycosylation Variants

In certain embodiments, antibodies of the invention can be altered to increase or decrease the extent to which the antibody is glycosylated. Addition or deletion of glycosylation sites to an antibody of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, for example, U.S. Patent Publication Nos. US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. (*J. Mol. Biol.* 336:1239-1249, 2004); and Yamane-Ohnuki et al. (*Biotech. Bioeng.* 87: 614, 2004). Examples of cell lines capable of producing defucosylated antibodies include Lec13 CHO cells deficient in protein fucosylation (Ripka et al. *Arch. Biochem. Biophys.* 249:533-545, 1986); U.S. Pat. Appl. No. US 2003/0157108 A1; and WO 2004/056312 A1, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614, 2004; Kanda, Y. et al. *Biotechnol. Bioeng.* 94(4):680-688, 2006; and WO 2003/085107).

Antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c. Fc Region Variants

In certain embodiments, one or more amino acid modifications may be introduced into the Fc region of an antibody of the invention, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, (*Annu. Rev. Immunol.* 9:457-492, 1991). Non-limiting examples of in vitro assays to assess ADCC activity of a molecule of interest is described in U.S. Pat. No. 5,500,362 (see, e.g., Hellstrom, I. et al. *Proc. Natl. Acad. Sci. USA* 83:7059-7063, 1986) and Hellstrom, I et al. *Proc. Natl. Acad. Sci. USA* 82:1499-1502, 1985; U.S. Pat. No. 5,821,337; Bruggemann et al. *J. Exp. Med.* 166:1351-1361, 1987). Alternatively, non-radioactive assays methods may be employed (see, for example, ACTI™ non-radioactive cytotoxicity assay for flow cytometry (CellTechnology, Inc. Mountain View, Calif.; and CYTOTOX 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. (*Proc. Natl. Acad. Sci. USA* 95:652-656, 1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al. *J. Immunol. Methods* 202:163, 1996; Cragg et al. *Blood.* 101:1045-1052, 2003; and Cragg et al. Blood. 103:2738-2743, 2004). FcRn binding and in vivo clearance/half-life determinations can also be performed using methods known in the art (see, e.g., Petkova et al. *Int'l. Immunol.* 18(12):1759-1769, 2006).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

Certain antibody variants with improved or diminished binding to FcRs are described (see, e.g., U.S. Pat. No. 6,737,056; WO 2004/056312, and Shields et al., *J. Biol. Chem.* 9(2): 6591-6604, 2001).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. (*J. Immunol.* 164: 4178-4184, 2000).

Antibodies with increased half-lives and improved binding to the neonatal Fc receptor (FcRn), which is responsible for the transfer of maternal IgGs to the fetus (Guyer et al., *J. Immunol.* 117:587, 1976; and Kim et al. *J. Immunol.* 24:249, 1994), are described in U.S. Pub. No. 2005/0014934A1. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan and Winter, (*Nature* 322:738-40, 1988); U.S. Pat. Nos. 5,648,260; 5,624,821; and WO 94/29351, concerning other examples of Fc region variants.

d. Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e. Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al. *Proc. Natl. Acad. Sci. USA* 102: 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

f. Immunoconjugates

The invention also provides immunoconjugates comprising an antibody herein (e.g., an anti-PD-L1 antibody, an anti-PD-1 antibody, or an anti-TGF-β antibody) conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020 and 5,416,064 and European Patent EP 0 425 235 B1); an auristatin such as monomethylauristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al. *Cancer Res.* 53:3336-3342, 1993; and Lode et al. *Cancer Res.* 58:2925-2928, 1998); an anthracycline such as daunomycin or doxorubicin (see Kratz et al. *Current Med. Chem.* 13:477-523, 2006; Jeffrey et al. *Bioorganic & Med. Chem. Letters* 16:358-362, 2006; Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532, 2002; King et al., *J. Med. Chem.* 45:4336-4343, 2002; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron. Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p- diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. (Science 238:1098, 1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al. *Cancer Res.* 52:127-131, 1992; and U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

D. Pharmaceutical Formulations

Therapeutic formulations of the therapeutic agents, e.g., immunotherapies (e.g., PD-L1 axis binding antagonists such as anti-PD-L1 antibodies (e.g., atezolizumab)) and/or the suppressive stromal antagonists (e.g., TGF-β antagonists such as an anti-TGF-β antibody) used in accordance with the present invention are prepared for storage by mixing the therapeutic agent having the desired degree of purity with optional pharmaceutically acceptable carriers, excipients, or stabilizers in the form of lyophilized formulations or aqueous solutions. For general information concerning formulations, see, e.g., Gilman et al. (eds.) *The Pharmacological Bases of Therapeutics,* 8th Ed., Pergamon Press, 1990; A. Gennaro (ed.), *Remington's Pharmaceutical Sciences,* 18th Edition, Mack Publishing Co., Pennsylvania, 1990; Avis et al. (eds.) *Pharmaceutical Dosage Forms: Parenteral Medications* Dekker, New York, 1993; Lieberman et al. (eds.) *Pharmaceutical Dosage Forms: Tablets* Dekker, New York, 1990; Lieberman et al. (eds.), *Pharmaceutical Dosage Forms: Disperse Systems* Dekker, New York, 1990; and Walters (ed.) *Dermatological and Transdermal Formulations* (Drugs and the Pharmaceutical Sciences), Vol 119, Marcel Dekker, 2002.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, preferably those with complementary activities that do not adversely affect each other. The type and effective amounts of such medicaments depend, for example, on the amount and type of therapeutic agent present in the formulation, and clinical parameters of the patients.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in *Remington's Pharmaceutical Sciences* 16th edition, Osol, A. Ed., 1980.

Sustained-release preparations may be prepared. Suitable examples of sustained-release preparations include semipermeable matrices of solid hydrophobic polymers containing the therapeutic agent, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, nondegradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

V. Articles of Manufacture and Kits

In another aspect of the invention, a kit or an article of manufacture containing materials useful for the treatment, prevention, diagnosis, and/or monitoring of individuals is provided.

In some instances, such kits or articles of manufacture can be used to identify an individual having a cancer (including, but not limited to, a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from an anti-cancer therapy that includes an immunotherapy (including, but not limited to, a PD-L1 axis binding antagonist, e.g., an anti-PD-L1 antibody (e.g., atezolizumab)) and/or a suppressive stromal antagonist (including, but not limited to, a TGF-β antagonist, e.g., an anti-TGF-β antibody). Such articles of manufacture or kits may include (a) reagents for determining the expression level of one or more genes set forth in Table 1, or any combination thereof (e.g., any combination set forth in any one of Tables 2-5) in a sample from the individual and (b) instructions for using the reagents to identify an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) who may benefit from treatment with a an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody). In additional aspects, the articles of manufacture or kits may include (a) reagents for determining the expression level of one or more genes set forth in Table 1, or any combination thereof (e.g., any combination set forth in any one of Tables 2-5) in a sample from the individual and (b) instructions for using the reagents to monitor and/or assess the response of an individual having a cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer) to treatment with a an anti-cancer therapy that includes an immunotherapy (e.g., a PD-L1 axis binding antagonist, e.g., an anti-PD-L1 antibody (e.g., atezolizumab)) and/or a suppressive stromal antagonist (e.g., a TGF-β antagonist, e.g., an anti-TGF-β antibody).

Any of the kits or articles of manufacture described may include a carrier means being compartmentalized to receive in close confinement one or more container means such as vials, tubes, and the like, each of the container means comprising one of the separate elements to be used in the method. Where the article of manufacture or kit utilizes nucleic acid hybridization to detect the target nucleic acid, the kit may also have containers containing nucleotide(s) for amplification of the target nucleic acid sequence and/or a container comprising a reporter-means, such as an enzymatic, florescent, or radioisotope label.

In some instances, the article of manufacture or kit includes the container described above and one or more other containers including materials desirable from a commercial and user standpoint, including buffers, diluents, filters, needles, syringes, and package inserts with instructions for use. A label may be present on the container to indicate that the composition is used for a specific application, and may also indicate directions for either in vivo or in vitro use, such as those described above. For example, the article of manufacture or kit may further include a container including a pharmaceutically-acceptable buffer, such as bacteriostatic water for injection (BWFI), phosphate-buffered saline, Ringer's solution, and dextrose solution.

The kits or articles of manufacture described herein may have a number of embodiments. In one instance, the kits or articles of manufacture includes a container, a label on said container, and a composition contained within said container, wherein the composition includes one or more polynucleotides that hybridize to a complement of a gene listed herein (e.g., a gene set forth in Table 1, or any combination of genes set forth in Tables 2-5) under stringent conditions, and the label on said container indicates that the composition can be used to evaluate the presence of a gene listed herein (e.g., a gene set forth in Table 1, or any combination of genes set forth in Tables 2-5) in a sample, and wherein the kit includes instructions for using the polynucleotide(s) for evaluating the presence of the gene RNA or DNA in a particular sample type.

For oligonucleotide-based articles of manufacture or kits, the article of manufacture or kit can include, for example: (1) an oligonucleotide, e.g., a detectably labeled oligonucleotide, which hybridizes to a nucleic acid sequence encoding a protein or (2) a pair of primers useful for amplifying a nucleic acid molecule. The article of manufacture or kit can also include, e.g., a buffering agent, a preservative, or a protein stabilizing agent. The article of manufacture or kit can further include components necessary for detecting the detectable label (e.g., an enzyme or a substrate). The article of manufacture or kit can also contain a control sample or a series of control samples that can be assayed and compared to the test sample. Each component of the article of manufacture or kit can be enclosed within an individual container and all of the various containers can be within a single package, along with instructions for interpreting the results of the assays performed using the kit.

Provided herein is a kit for identifying an individual having a cancer who may benefit from treatment with an anti-cancer therapy including an immunotherapy (e.g., a PD-L1 axis binding antagonist, e.g., an anti-PD-L1 antibody (e.g., atezolizumab)) and a suppressive stromal antagonist (e.g., a TGF-β antagonist, e.g., an anti-TGF-β antibody), the kit including: (a) reagents for determining the expression level of one or more (e.g., 1, 2, 3, 4, 5, 6, 7, 8, 9, 10, 11, 12, 13, 14, 15, 16, 17, 18, 19, 20, 21, or 22) of the genes set forth in Table 1 in a sample from the individual; and, optionally, (b) instructions for using the reagents to identify an individual having a cancer who may benefit from a treatment with an anti-cancer therapy comprising an immunotherapy and a suppressive stromal antagonist.

In another example, provided herein is a kit for monitoring and/or assessing the response of an individual having a cancer to treatment with an anti-PD-L1 antibody (e.g., atezolizumab)) and a suppressive stromal antagonist (e.g., a TGF-β antagonist, e.g., an anti-TGF-β antibody), the kit including: (a) reagents for determining the expression level of one or more (e.g., 1, 2, 3, 4, 5, 6, 7, 8, 9, 10, 11, 12, 13, 14, 15, 16, 17, 18, 19, 20, 21, or 22) of the genes set forth in Table 1 in a sample from the individual; and, optionally, (b) instructions for using the reagents to monitor and/or assess the response of an individual having a cancer to treatment with an anti-cancer therapy comprising an immunotherapy and a suppressive stromal antagonist.

For example, provided herein is a kit for identifying an individual having a cancer who may benefit from treatment with an anti-PD-L1 antibody (e.g., atezolizumab)) and a suppressive stromal antagonist (e.g., a TGF-β antagonist, e.g., an anti-TGF-β antibody), the kit including: (a) reagents for determining the expression level of one or more (e.g., 1, 2, 3, 4, 5, or 6) of the following genes in a sample from the individual: ACTA2, ADAM19, COMP, CTGF, TGFB1, or TGFBR2; and, optionally, (b) instructions for using the reagents to identify an individual having a cancer who may benefit from a treatment with an anti-cancer therapy comprising an immunotherapy and a suppressive stromal antagonist.

In yet another example, provided herein is a kit for monitoring and/or assessing the response of an individual having a cancer to treatment with an anti-PD-L1 antibody (e.g., atezolizumab)) and a suppressive stromal antagonist (e.g., a TGF-β antagonist, e.g., an anti-TGF-β antibody), the kit including: (a) reagents for determining the expression level of one or more (e.g., 1, 2, 3, 4, 5, or 6) of the following genes in a sample from the individual: ACTA2, ADAM19, COMP, CTGF, TGFB1, or TGFBR2; and, optionally, (b) instructions for using the reagents to monitor and/or assess the response of an individual having a cancer to treatment with an anti-cancer therapy comprising an immunotherapy and a suppressive stromal antagonist.

In any of the preceding embodiments, the kit may include reagents for determining the expression level of one or more (e.g., 1, 2, 3, 4, 5, or 6) of ACTA2, ADAM19, COMP, CTGF, TGFB1, or TGFBR2. In some embodiments, the kit includes reagents for determining the expression level of at least two, at least three, at least four, at least five, or all six of ACTA2, ADAM19, COMP, CTGF, TGFB1, and TGFBR2. In some embodiments, the kit includes reagents for includes determining the expression level of two of ACTA2, ADAM19, COMP, CTGF, TGFB1, and TGFBR2, for example, any of the exemplary combinations shown in Table 2. In some embodiments, the kit includes reagents for includes determining the expression level of three of ACTA2, ADAM19, COMP, CTGF, TGFB1, and TGFBR2, for example, any of the exemplary combinations shown in Table 3. In some embodiments, the kit includes reagents for includes determining the expression level of four of ACTA2, ADAM19, COMP, CTGF, TGFB1, and TGFBR2, for example, any of the exemplary combinations shown in Table 4. In some embodiments, the kit includes reagents for includes determining the expression level of five of ACTA2, ADAM19, COMP, CTGF, TGFB1, and TGFBR2, for example, any of the exemplary combinations shown in Table 5. In some embodiments, the kit includes reagents for involves determining the expression level of ACTA2, ADAM19, COMP, CTGF, TGFB1, and TGFBR2.

In any of the preceding methods, the kit may include reagents determining the expression level of TGFB1 and/or TGFBR2. In any of the preceding methods, the kit may include reagents for determining the expression level of TGFB1 and TGFBR2.

In some embodiments of any of the preceding kits, the one or more genes includes at least ADAM19 or COMP. In some embodiments, the one or more genes includes ADAM19. In other embodiments, the one or more genes includes COMP. In still further embodiments, the one or more genes includes ADAM19 and COMP.

For example, provided herein is a kit for identifying an individual having a cancer who may benefit from treatment with an anti-PD-L1 antibody (e.g., atezolizumab)) and a suppressive stromal antagonist (e.g., a TGF-β antagonist, e.g., an anti-TGF-β antibody), the kit including: (a) reagents for determining the expression level of one or more (e.g., 1, 2, 3, 4, 5, 6, 7, 8, 9, 10, 11, 12, 13, 14, 15, 16, 17, 18, or 19) of the following genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1; and, optionally, (b) instructions for using the reagents to identify an individual having a cancer who may benefit from a treatment with an anti-cancer therapy comprising an immunotherapy and a suppressive stromal antagonist.

In yet another example, provided herein is a kit for monitoring and/or assessing the response of an individual having a cancer to treatment with an anti-PD-L1 antibody (e.g., atezolizumab)) and a suppressive stromal antagonist (e.g., a TGF-β antagonist, e.g., an anti-TGF-β antibody), the kit including: (a) reagents for determining the expression level of one or more (e.g., 1, 2, 3, 4, 5, 6, 7, 8, 9, 10, 11, 12, 13, 14, 15, 16, 17, 18, or 19) of the following genes in a sample from the individual: ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1; and, optionally, (b) instructions for using the reagents to monitor and/or assess the response of an individual having a cancer to treatment with an anti-cancer therapy comprising an immunotherapy and a suppressive stromal antagonist.

In any of the preceding methods, the kit may include reagents for determining the expression level of one or more (e.g., 1, 2, 3, 4, 5, 6, 7, 8, 9, 10, 11, 12, 13, 14, 15, 16, 17, 18, or 19) of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, the kit includes reagents for determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or all nineteen of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1. In some embodiments, the kit includes reagents for determining the expression level of ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, and TPM1.

In some embodiments of any of the preceding kits, the one or more genes includes at least one or more (e.g., 1, 2, 3, 4, 5, 6, 7, 8, 9, 10, 11, 12, 13, 14, or 15) of ADAM19, ACTG2, CNN1, CTPS1, FAM101B, FSTL3, HSPB1, IGFBP3, PXDC1, SEMA7A, SH3PXD2A, TAGLN, TGFBI, TNS1, or TPM1.

VI. EXAMPLES

The following is an example of the methods of the invention. It is understood that various other embodiments may be practiced, given the general description provided above. The following examples are offered by way of illustration and not by way of limitation.

Materials and Methods

A. Study Design, Patient Cohort, PD-L1 Testing, Response Assessment

Samples for this analysis were collected from IMvigor210, which was a single-arm phase II study investigating atezolizumab (1200 mg every 3 weeks (q3w)) in metastatic urothelial carcinoma (mUC) patients (Clinical Trial Identifier: NCT02108652). The primary endpoint of the trial was to achieve a partial response (PR) rate of over 10% (Response Evaluation Criteria In Solid Tumors (RECIST) v1.1). Patients who had failed previous platinum-based chemotherapy or previously untreated patients who were not eligible for platinum-based chemotherapy were eligible. The primary endpoint was met for both previously treated and untreated populations. It was a requirement for all patients to have tumor tissue taken in the 2 years prior to study entry. The tissues were initially used for PD-L1 analysis (SP142 antibody using the Ventana platform). PD-L1 positivity was defined as more that 5% of cells staining in the immune component of the tumor tissue. Additional tissue was used for exploratory analysis. All patients had measurable disease at baseline facilitating response assessment. RECIST v1.1 was used to assess response to therapy. Cross-sectional imaging was performed every 6 weeks. All patients gave appropriate ethical approval for this analysis.

B. PD-L1 Immunohistochemistry (IHC)

PD-L1 IHC has been previously described in Powles et al. *Nature* 515:558-562, 2014. Briefly, the pre-screening biopsies were collected from archived paraffin-embedded tissue. Patients were required to have tissue sent to the central laboratory before study entry. Samples were processed at the time of screening. FFPE tumor tissue was stained prospectively for PD-L1 by immunohistochemistry using a proprietary diagnostic anti-human PD-L1 monoclonal antibody (SP142). Samples were scored for PD-L1 expression on tumor-infiltrating immune cells, which included macrophages, dendritic cells, and lymphocytes. Specimens were scored as immunohistochemistry IC 0, 1, 2, or 3 if <1%, ≥1% but <5%, ≥5% but <10%, or ≥10% of tumor-infiltrating immune cells were PD-L1-positive, respectively. PD-L1 scores in patients with multiple specimens from different time points or samples were based on the highest score. This assay was validated for investigational use in clinical trials at the IC1 and IC2 cutoff. An exploratory analysis of PD-L1 expression on tumor cells (TC) was conducted. Specimens were scored as immunohistochemistry TC0, TC1, TC2, or TC3 if <1%, ≥1% but <5%, ≥5% but <50%, or ≥50% of tumor cells were PD-L1-positive, respectively.

C. Nucleic Acid Sample Preparation

The pathologic diagnosis of each case was confirmed by review of H&E-stained slides and all samples that advanced to nucleic acid extraction contained a minimum of 20% tumor cells. H&E images were marked for macrodissection by a pathologist. RNA (High Pure FFPET RNA Isolation Kit, Roche) and DNA (QIAAMP® DNA FFPE Tissue Kit, Qiagen) were then extracted from the macro-dissected sections.

FIG. 5 shows the number of efficacy-evaluable patients that had a known PD-L1 IC status and at least one of the other molecular data points analyzed here: whole-exome sequencing, FMOne-based mutational profiling, RNA sequencing, and cancer-immune phenotyping. Table 7 provides demographic details of the biomarker-evaluable patient (BEP) population. Patients for which RNA sequencing data were generated were chosen as a representative BEP, and distribution of key clinical covariates are listed as compared to the intent-to-treat (ITT) population; efficacy evaluable patients only were assessed. Both the number of patients as well as percentages (in parentheses) are given. BCG: Bacille Calmette Guerin, ECOG: Eastern Cooperative Oncology Group.

TABLE 7

Demographics of ITT and BEP population

| Covariate | | ITT (%) | BEP (%) |
|---|---|---|---|
| Male sex | | 337 (79%) | 233 (78%) |
| White race | | 390 (91%) | 270 (91%) |
| Intravesical BCG administered | | 106 (25%) | 67 (22%) |
| PD-L1 | IC0 | 142 (33%) | 84 (28%) |
| | IC1 | 155 (36%) | 112 (38%) |
| | IC2+ | 132 (31%) | 102 (34%) |
| ECOG | 0 | 162 (38%) | 121 (41%) |
| | 1 | 243 (57%) | 165 (55%) |
| | 2 | 24 (6%) | 12 (4%) |
| Tobacco use | current | 42 (10%) | 32 (11%) |
| | previous | 245 (57%) | 168 (56%) |
| | never | 142 (33%) | 98 (33%) |
| Metastatic sites at baseline | liver | 121 (28%) | 81 (27%) |
| | LN Only | 74 (17%) | 51 (17%) |
| | visceral | 200 (47%) | 139 (47%) |
| | NA | 34 (8%) | 27 (9%) |

D. Mutational Profiling (Whole-Exome Sequencing (WES) and FOUNDATIONONE® (FMOne) Panel)

WES data were generated for 250 patients, sequencing DNA extracted from both tumor as well as peripheral blood mononuclear cells using the Agilent SURESELECT® v5 (51 MB) kit on a HISEQ® 2500 (ILLUMINA®) sequencer. FASTQ format reads were aligned to the human reference genome (NCBI Build 38) using GSNAP (Wu et al. *Bioinformatics* 26:873-881, 2010; Wu et al. *Methods Mol. Biol.* 1418:283-334, 2016) version '2013-10-10' (parameters: '-M 2 -n 10 -B 2 -i 1 --pairmax-dna=1000 --terminal-threshold=1000--gmap-mode=none --clip-overlap'). Duplicate reads in the resulting BAM file were marked using PicardTools, and indels realigned using the GATK IndelRealigner tool.

Somatic variants were called using a union of Lofreq v2.1.2 (Wilm et al. *Nucleic Acids Res.* 40:11189-11201, 2012) and Strelka (Saunders et al. *Bioinformatics* 28:1811-1817, 2012) calls. Indel qualities were assigned to the alignments using "lofreq indelqual -dindel," and somatic mutations were called using "lofreq somatic" with the "--call-indels" option. Strelka-based somatic mutations were called using the Strelka-provided configuration file "strelka_config_bwa_default.ini," with the only modification being the setting "isSkipDepthFilters=1" instead of "isSkipDepthFilters=0." Somatic mutations were annotated for effects on transcripts using Ensembl Variant Effect Predictor (McLaren et al. *Genome Biol.* 17:122, 2016) on Refseq-based gene models.

In order to identify expressed mutations, RNAseq alignments were tallied for somatic mutations identified in the exome data using the tallyVariants function from the R package VariantTools (Lawrence et al. *VariantTools: Tools for Working with Genetic Variants* Version 1.12.0). Neoantigen potential of each mutation was predicted after identifying HLA genotypes of the subjects and assigning the optimal HLA-neoepitope pair across all HLA alleles and 8-11 mer peptides containing the mutation, based on minimum IC50 value predicted by NetMHCcons (Karosiene et al. *Immunogenetics* 64:177-186, 2012). HLA genotyping was done on whole exome data from peripheral blood mononuclear cells (PBMCs), using Polysolver (Shukla et al. *Nat. Biotech.* 33:1152-1158, 2015).

In addition, DNA was extracted from FFPE 10 micron sections from 293 patients and submitted to a Clinical Laboratory Improvement Amendments (CLIA)-certified, New York State-accredited, and College of American Pathologists (CAP)-accredited laboratory (Foundation Medicine, Cambridge, Mass.) for targeted next-generation sequencing (NGS)-based genomic profiling. Adaptor-ligated DNA underwent hybrid capture for all coding exons of 395 cancer-related genes plus select introns from 31 genes frequently rearranged in cancer (FMOne panel).

Captured libraries were sequenced to a median exon coverage depth of >500× (DNA) or 3M unique reads (RNA) using Agilent SURESELECT® v5 kit at 51 Mb on the ILLUMINA® HISEQ® 2500, and resultant sequences were analyzed for base substitutions, small insertions and deletions (indels), copy number alterations (focal amplifications and homozygous deletions), and gene fusions/rearrangements, as previously described (Frampton et al. *Nat. Biotechnol.* 31:1023-1031, 2013). Frequent germline variants from the 1000 Genomes Project (dbSNP142) were removed. To maximize mutation-detection accuracy (sensitivity and specificity) in impure clinical specimens, the test was previously optimized and validated to detect base substitutions at a ≥5% mutant allele frequency (MAF), indels with a ≥10% MAF with ≥99% accuracy, and fusions occurring within baited introns/exons with >99% sensitivity (Frampton et al. supra). Known confirmed somatic alterations deposited in the Catalog of Somatic Mutations in Cancer (COSMIC v62) are called at allele frequencies ≥1% (Forbes et al. *Nucleic Acids Res.* 39:D945-D950, 2011).

From the FMOne panel, tumor mutational burden was calculated from the number of short variants in coding regions (substitutions and indels, including synonymous alterations) that were detected. Known and predicted germline alterations as well as known somatic and likely somatic variants are not counted. The mutation burden per Mb is the number of mutations counted divided by the Mb of genomic target territory of the FMOne panel. Unless otherwise indicated, FMOne-based mutation burden was used for all analyses around mutation burden.

E. Association Between Mutations and Response to Atezolizumab or Mutation Burden For each gene, a patient was called mutant if a known or likely mutation was reported for that gene. For pathway-based analyses, a patient was called mutant in a pathway if any gene within the pathway was reported to have a known or likely mutation. Otherwise, a patient was considered to be non-mutant. A Fisher's Exact Test was used to determine whether the number of mutant patients differed between responders (complete and partial responders) and non-responders (stable and progressive disease). An association between mutation status and mutation burden was tested using a Wilcoxon Rank Sum Test. Single gene p-values were corrected for the number of tests performed using Benjamini and Hochberg adjustment. For pathway-based analyses, nominal p-values are reported.

F. Gene Expression Profiling

Whole transcriptome profiles were generated for 368 patients using TRUSEQ® RNA Access technology (ILLUMINA®). RNAseq reads were first aligned to ribosomal RNA sequences to remove ribosomal reads. The remaining reads were aligned to the human reference genome (NCBI Build 38) using GSNAP (Wu et al. *Bioinformatics* 26:873-881, 2010; Wu et al. *Methods Mol. Biol.* 1418:283-334, 2016) version '2013-10-10', allowing maximum of two mismatches per 75 base sequence (parameters: '-M 2-n 10-B 2 -i 1 -N 1 -w 200000 -E 1 --pairmax-rna=200000 --clip-overlap). To quantify gene expression levels, the number of reads mapped to the exons of each RefSeq gene was calculated in a strand-specific manner using the functionality provided by the R/Bioconductor package GenomicAlignments (Lawrence et al. *PLoS Comput. Biol.* 0:e1003118, 2013).

G. Differential Gene Expression and Association with Mutation Burden or PD-L1 IHC After quality control using the R/Bioconductor package arrayQualityMetrics (Kauffmann et al. *Genomics* 95:138-142, 2010), count data was normalized using trimmed mean of M-values (TMM) and transformed with voom to log 2-counts per million with associated precision weights (Law et al. *Genome Biol.* 15:R29, 2014).

Figure 1B:
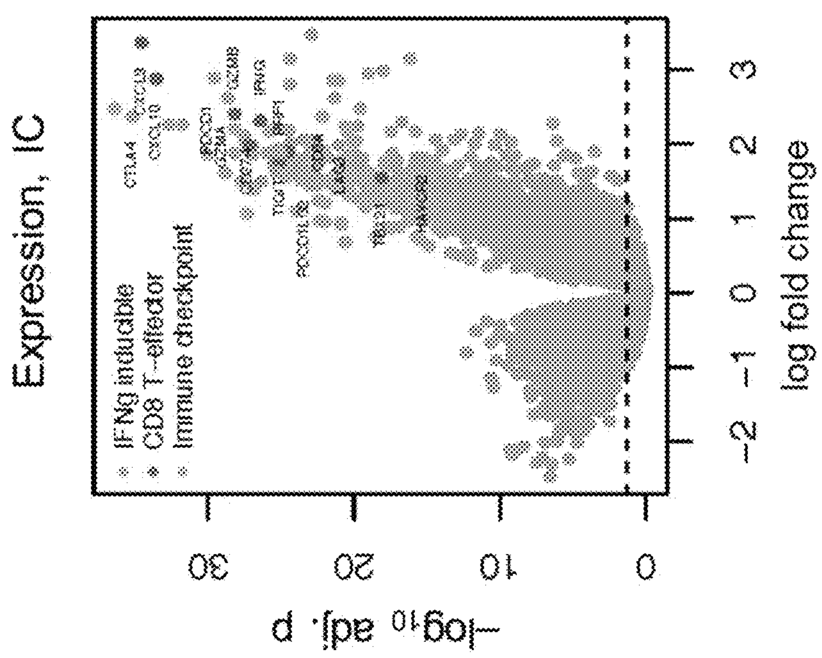
FIG. 1B is a graph showing genes associated with PD-L1 immunohistochemistry (IHC) positivity on IC. Normalized log 2-transformed gene expression was compared with PD-L1 IC protein expression, and adjusted p values ($-\log_{10}$ transformed, y-axis) and effect size of the association (x-axis) are plotted. Interferon gamma-stimulated ("IFNg inducible") genes and previously-reported CD8 T-effector and immune checkpoint molecule gene sets were among the most dramatically up-regulated.

To identify genes associated with PD-L1 protein staining on immune cells (IC), a linear regression model was fitted, using each gene's normalized, log 2-transformed expression as the response variable and log 2-transformed percent of immune cells identified as PD-L1 positive (ICp) as independent variables. Reported effect sizes represent the coefficients from the model fit, scaled by twice the standard deviation of the log 2-transformed ICp multiplied by the slope of the regression. FIG. 1C plots effect size and adjusted p-value for the PD-L1 IC positivity term only.

To identify biologies associated with response to atezolizumab, we grouped patients into responders (complete and partial responders) and non-responders (stable and progressive disease). Differentially expressed genes between these two groups were determined using the R/Bioconductor package limma (Ritchie et al. *Nucleic Acids Res.* 43:e47, 2015), which implements an empirical Bayesian approach to estimate gene expression changes using moderated t-tests.

To identify genes associated with tumor mutational burden, a linear regression model was fitted, using each gene's normalized, log 2-transformed expression as the response variable and mutation burden, batch, as well as cohort as independent variables (as these latter two we found to be correlated with TMB). Using R's anova( ) function, F-test p-values were calculated. Reported effect sizes represent the coefficients from the model fit, scaled by twice the standard deviation of TMB.

H. Gene Set Enrichment Analysis Using Kyoto Encyclopedia of Genes and Genomes (KEGG)

Following association testing (gene expression with response or mutation burden), Fios Genomics analyzed the top 1,000 genes (ranked by p-value) for enrichment of KEGG pathway membership using a hypergeometric test (Falcon et al. *Bioinformatics* 23:257-258, 2007), assessing up- and down-regulated genes separately. Enrichment p-values were corrected for the number of pathways tested using the Benjamini and Hochberg procedure. Complete results from the enrichment analyses are reported in Table 8 (response) and Table 9 (mutation burden). Table 8 lists KEGG gene sets significantly (FDR<0.1) enriched in genes differentially expressed by response (CR/PR vs. SD/PD). "Direction" indicates whether the category was enriched in genes up- ("Up") or down-regulated ("Down") in responders. "Identified genes" lists all genes within a given category that were found to be associated with response. "S" indicates the number of these genes, "N" gives the total number of genes in a category, while "p (adj.)" holds the adjusted enrichment p-values (hypergeometric test). Table 9 lists KEGG gene sets significantly (FDR<0.05) enriched in genes correlated with TMB. "Direction" indicates whether the category was enriched in genes positively ("Up") or negatively ("Down") correlated with TMB. "Identified genes" lists all genes within a given category that were found to be correlated with TMB. "S," "N," and "p (adj.)" are as in Table 8.

TABLE 8

Pathways associated with response

| Direction | Name | Identified Genes | S | N | p (adj.) |
|---|---|---|---|---|---|
| Up | DNA replication | DNA2, FEN1, LIG1, MCM2, MCM4, MCM6, MCM7, PCNA, POLA2, POLE, POLE2, PRIM1, PRIM2, RFC2, RFC3, RFC4, RFC5, RNASEH2A, RPA1, RPA3 | 20 | 36 | 0.0000 |
| Up | Cell cycle | BUB1, BUB1B, CCNA2, CCNB2, CCNE1, CCNE2, CDC20, CDC25A, CDC25C, CDC6, CDK1, CDK2, CDKN2A, DBF4, E2F1, E2F2, ESPL1, MAD2L1, MAD2L2, MCM2, MCM4, MCM6, MCM7, ORC1, ORC6, PCNA, PLK1, SKP2, SMC3, TFDP1, TTK, YWHAB | 32 | 124 | 0.0000 |

TABLE 8-continued

| Pathways associated with response | | | | | |
|---|---|---|---|---|---|
| Direction | Name | Identified Genes | S | N | p (adj.) |
| Up | Fanconi anemia pathway | BLM, BRCA1, BRCA2, BRIP1, EME1, ERCC4, FANCA, FANCB, FANCD2, FANCI, PALB2, RAD51, RAD51C, RMI1, RMI2, RPA1, RPA3, TOP3A, UBE2T | 19 | 53 | 0.0000 |
| Up | Systemic lupus erythematosus | H2AFV, H2AFZ, HIST1H2AB, HIST1H2AG, HIST1H2AH, HIST1H2AI, HIST1H2AM, HIST1H2BC, HIST1H2BD, HIST1H2BF, HIST1H2BJ, HIST1H2BK, HIST1H2BL, HIST1H2BN, HIST1H2BO, HIST1H3B, HIST1H3D, HIST1H3H, HIST1H4A, HIST1H4B, HIST2H2AB, HIST2H2AC, HIST2H2BE, HIST2H2BF, HIST2H3D, HIST3H2A, IFNG | 27 | 134 | 0.0000 |
| Up | Alcoholism | CREB3L4, H2AFV, H2AFZ, HIST1H2AB, HIST1H2AG, HIST1H2AH, HIST1H2AI, HIST1H2AM, HIST1H2BC, HIST1H2BD, HIST1H2BF, HIST1H2BJ, HIST1H2BK, HIST1H2BL, HIST1H2BN, HIST1H2BO, HIST1H3B, HIST1H3D, HIST1H3H, HIST1H4A, HIST1H4B, HIST2H2AB, HIST2H2AC, HIST2H2BE, HIST2H2BF, HIST2H3D, HIST3H2A | 27 | 179 | 0.0000 |
| Up | Homologous recombination | BLM, BRCA2, EME1, RAD51, RAD51C, RAD54L, RPA1, RPA3, TOP3A, XRCC2, XRCC3 | 11 | 28 | 0.0000 |
| Up | Mismatch repair | EXO1, LIG1, PCNA, RFC2, RFC3, RFC4, RFC5, RPA1, RPA3 | 9 | 23 | 0.0000 |
| Up | Nucleotide excision repair | CETN2, ERCC4, LIG1, PCNA, POLE, POLE2, RFC2, RFC3, RFC4, RFC5, RPA1, RPA3 | 12 | 47 | 0.0000 |
| Up | Oocyte meiosis | AURKA, BUB1, CCNB2, CCNE1, CCNE2, CDC20, CDC25C, CDK1, CDK2, ESPL1, FBXO5, MAD2L1, MAD2L2, PLK1, SGOL1, SMC3, YWHAB | 17 | 113 | 0.0000 |
| Up | Viral carcinogenesis | CCNA2, CCNE1, CCNE2, CDC20, CDK1, CDK2, CDKN2A, CREB3L4, GTF2E1, HIST1H2BC, HIST1H2BD, HIST1H2BF, HIST1H2BJ, HIST1H2BK, HIST1H2BL, HIST1H2BN, HIST1H2BO, HIST1H4A, HIST1H4B, HIST2H2BE, HIST2H2BF, SKP2, YWHAB | 23 | 206 | 0.0000 |
| Up | Base excision repair | FEN1, LIG1, NEIL3, PARP1, PARP2, PCNA, POLE, POLE2, UNG | 9 | 33 | 0.0000 |
| Up | p53 signaling pathway | CCNB2, CCNE1, CCNE2, CDK1, CDK2, CDKN2A, GTSE1, PPM1D, RFWD2, RRM2 | 10 | 68 | 0.0008 |
| Up | Spliceosome | HNRNPM, LSM3, LSM4, LSM5, MAGOHB, PRPF19, SF3B2, SF3B3, SF3B4, SNRNP40, SNRPA1, SNRPC, USP39, WBP11 | 14 | 132 | 0.0013 |
| Up | Proteasome | IFNG, PSMA4, PSMB2, PSMB4, PSMC4, PSMD4, PSMD7 | 7 | 44 | 0.0045 |
| Up | Progesterone-mediated oocyte maturation | BUB1, CCNA2, CCNB2, CDC25A, CDC25C, CDK1, CDK2, MAD2L1, MAD2L2, PLK1 | 10 | 88 | 0.0054 |
| Up | MicroRNAs in cancer | BRCA1, CCNE1, CCNE2, CDC25A, CDC25C, CDCA5, CDKN2A, DNMT1, E2F1, E2F2, EZH2, KIF23, STMN1, TRIM71 | 14 | 186 | 0.0298 |
| Up | Pyrimidine metabolism | CTPS1, DTYMK, POLA2, POLE, POLE2, PRIM1, PRIM2, RRM2, TYMS | 9 | 104 | 0.0515 |
| Up | RNA degradation | CNOT10, EXOSC2, EXOSC8, LSM3, LSM4, LSM5, PARN | 7 | 76 | 0.0771 |
| Down | Cytokine-cytokine receptor interaction | ACVR1, CCL24, FLT4, IFNGR1, IL4R, IL6ST, KIT, LIF, PDGFA, PDGFRB, TGFB1, TGFBR2, TNFRSF10B, TNFRSF14, TNFRSF1A | 15 | 264 | 0.0835 |

TABLE 9

| Pathways associated with TMB | | | | | |
|---|---|---|---|---|---|
| Direction | Name | Identified Genes | S | N | p (adj.) |
| Up | DNA replication | FEN1, LIG1, MCM2, MCM4, MCM7, POLD1, POLE, POLE3, RFC2, RNASEH2A, RPA1 | 11 | 36 | 0.0000 |
| Up | Cell cycle | ANAPC2, CCNB1, CDC20, CDC25A, CDC45, CDC6, CDKN2B, E2F1, E2F2, ESPL1, MCM2, MCM4, MCM7, PKMYT1, TFDP1, TTK | 16 | 124 | 0.0001 |

TABLE 9-continued

| Pathways associated with TMB | | | | | |
|---|---|---|---|---|---|
| Direction | Name | Identified Genes | S | N | p (adj.) |
| Up | Nucleotide excision repair | LIG1, POLD1, POLE, POLE3, RAD23A, RAD23B, RFC2, RPA1 | 8 | 47 | 0.0039 |
| Up | Huntington's disease | ATP5D, ATP5G1, ATP5O, BAX, COX5B, COX6B1, COX7B2, NDUFA13, NDUFA8, NDUFB7, NDUFS7, PLCB3, POLR2I, POLR2L, SLC25A5 | 15 | 193 | 0.0311 |
| Up | Fanconi anemia pathway | ATRIP, EME1, FANCC, FANCG, RAD51, RMI1, RPA1 | 7 | 53 | 0.0326 |
| Up | Homologous recombination | EME1, POLD1, RAD51, RAD54L, RPA1 | 5 | 28 | 0.0361 |
| Up | Citrate cycle (TCA cycle) | ACLY, MDH1, MDH2, PCK2, SUCLG1 | 5 | 30 | 0.0418 |
| Up | Non-alcoholic fatty liver disease (NAFLD) | BAX, COX5B, COX6B1, COX7B2, GSK3A, NDUFA13, NDUFA8, NDUFB7, NDUFS7, RXRA, SREBF1, TRAF2 | 12 | 151 | 0.0418 |
| Up | Oxidative phosphorylation | ATP5D, ATP5G1, ATP5O, ATP6V1F, COX5B, COX6B1, COX7B2, NDUFA13, NDUFA8, NDUFB7, NDUFS7 | 11 | 133 | 0.0418 |
| Up | Base excision repair | FEN1, LIG1, POLD1, POLE, POLE3 | 5 | 33 | 0.0462 |
| Down | Complement and coagulation cascades | CFH, F8, PROC, SERPINA5, SERPIND1, TFPI | 6 | 69 | 0.0267 |
| Down | PI3K-Akt signaling pathway | DDIT4, EGF, FGF7, GNG11, ITGAV, ITGB3, JAK1, KIT, LAMA4, LPAR1, LPAR6, NGFR, PTEN, RBL2 | 14 | 345 | 0.0267 |
| Down | Pathways in cancer | AGTR1, EDNRA, EGF, FGF7, GNG11, HIF1A, ITGAV, JAK1, KIT, LAMA4, LPAR1, LPAR6, PTEN, TGFBR2, TRAF5 | 15 | 397 | 0.0267 |

I. Gene Sets Used for Signatures

Because KEGG pathways often include large numbers of genes with only loosely related functions, we constructed refined gene sets (Table 10) for the four core biologies called out in the text. Specifically:

(i) for DNA damage repair genes, we used a gene set as described by Lange et al. Nat. Rev. Cancer 11:96-110, 2011;

(ii) for cell cycle regulator genes, we used genes within the p53/Rb pathway that TCGA reported to be frequently reported in bladder cancer (The Cancer Genome Atlas Research *Nature* 507:315-322, 2014);

(iii) for CD8 T-effector genes, we used our previously-published signature (Rosenberg et al. *Lancet* 387:1909-1920, 2016; Balar et al. *Lancet* 389:67-76, 2017); and (iv) for TGF-β, we considered three different signatures. First, for monitoring input of the pathway, we evaluated ligands (TGFB1, TGFB2, and TGFB3) and receptors (TGFBR1, TGFBR2, and TGFBR3) for association with outcome in IMvigor210. TGFB1 and TGFBR2 were significantly associated with outcome (adj. $p=8.956\times10^{-3}$ and adj. $p=1.070\times10^{-2}$, respectively), and the two were used as our TGF-β two-gene signature. Second, for monitoring output of the pathway, we generated a pan-fibroblast TGF-β response signature (Pan-F-TBRS), as described below. Further, in FIG. 2A, we also show a larger set of genes reported to be involved in extracellular matrix organization (Sjödahl et al. *Clin. Cancer. Res.* 18:3377-3386, 2012).

J. Signature Score Computation

For gene expression analysis, the expression of each gene in a signature was first z-score transformed. Then, a principal component analysis was performed, and principal component 1 was extracted to serve as gene signature score. This approach has the advantage of focusing the score for the set on the largest block of well-correlated (or anti-correlated) genes in the set, while down-weighting contributions from genes that do not track with other set members.

K. Associations Between Gene Signature Scores or Tumor Mutation Burden and Traits of Interest Below are the statistical methods that were used for the various tests throughout the Examples:

(i) for associations with response, only efficacy evaluable patients were considered; these were grouped into responders (CR/PR) and non-responders (SD/PD), unless otherwise stated;

(ii) for associations of binary traits, e.g., response, with normally distributed continuous traits, such gene expression scores, two sample t-tests were performed; if multiple pairwise tests were performed within one gene signature—trait combination, p-values were Bonferroni corrected;

(iii) for associations of binary traits, e.g. response or mutation status, with TMB that showed a skewed distribution, Wilcoxon signed-rank tests were performed. TMB was $\log_2$ transformed; one outlier patient with 0 TMB was excluded from analysis;

(iv) for assessment of associations between two categorical traits, e.g., response and IC level, Fisher's exact tests were performed;

(v) for associations with immune phenotype, immune phenotype was treated as an ordered factor (desert<excluded<infiltrated) and likelihood ratio test p-values were calculated using ANOVA. An exception from this was testing the association with TMB, where a Kruskal Wallis H test was used; and (vi) likelihood ratio tests were also used to test for associations between a continuous trait, such as gene expression signature score and a categorical trait with more than 2 groups, such IC level. In addition, the same test was used to assess interaction between two traits, comparing a model where the two traits were included as two independent variables to a model including an interaction term between these two variables.

In visualizations of TMB on $log_2$ scale, patients with no mutations were dropped (depending on the exact biomarker evaluable population, this was one or two patients only). In all graphs, the number of patients within each group is given at the top.

L. Explained Variance in Response

Generalized linear models were fit using binary response (CR/PR vs. SD/PD) as the dependent variable and scores from single/combinations of different signatures or TMB as independent variables. Logistic regression pseudo-$R^2$ was extracted as a measure of "explained variance" in patient response, i.e., the percent of variation in patient response that can be attributed to the contributions of the biological inputs (see Dobson et al. *An Introduction to Generalized Linear Models*. Chapman and Hall/CRC Press, 2008).

M. Molecular Subtyping

TCGA subtypes were assigned according to methodology described in Rosenberg et al. supra.

For assigning Lund subtypes, a data set of centroids of gene expression for 1038 genes was provided by Sjödahl et al. (Sjödahl et al. *Clin. Cancer Res.* 18:3377-3386, 2012; Sjödahl et al. *Am. J. Pathol.* 183:681-691, 2013). A reduced set of 884 centroids that overlapped with the genes detected in the reported RNAseq data was used to assign a molecular subtype (MS1a, MS1b, MS2a1, MS2a2, MS2b1, MS2b2.1 and MS2b2.2). Since these centroids were based on gene expression profiles from microarrays, which cannot be simply carried over to another platform like RNA sequencing, we chose to perform the molecular subtype assignment by calculating the Spearman correlation distance between the median-centered (log 2) expression levels of these 884 genes and the centroids. In using a rank-based approach, we aimed to minimize platform-specific effects (however, it is noteworthy that using Pearson instead of Spearman yielded very similar results). Each sample was assigned the molecular subtype with the shortest distance. Subsequently, clusters MS1a and MS1 b were combined to urothelial A, MS2a1, and MS2a2 to genomically unstable subtypes, respectively; clusters MS2b1, MS2b2.1, and MS2b2.2 are equivalent to the infiltrated, urothelial B, and basal/SCC-like subtypes, respectively.

Note that "urothelial-like" has recently been suggested as a replacement for the original "urobasal" (Lerner et al. *Bladder Cancer* 2:37-47, 2016). We use the updated nomenclature here. Similarly, "basal/SCC-like" is now preferred over the original "SCC-like."

N. Gene Sets Used for Subtype Heatmap

Figure 2A:
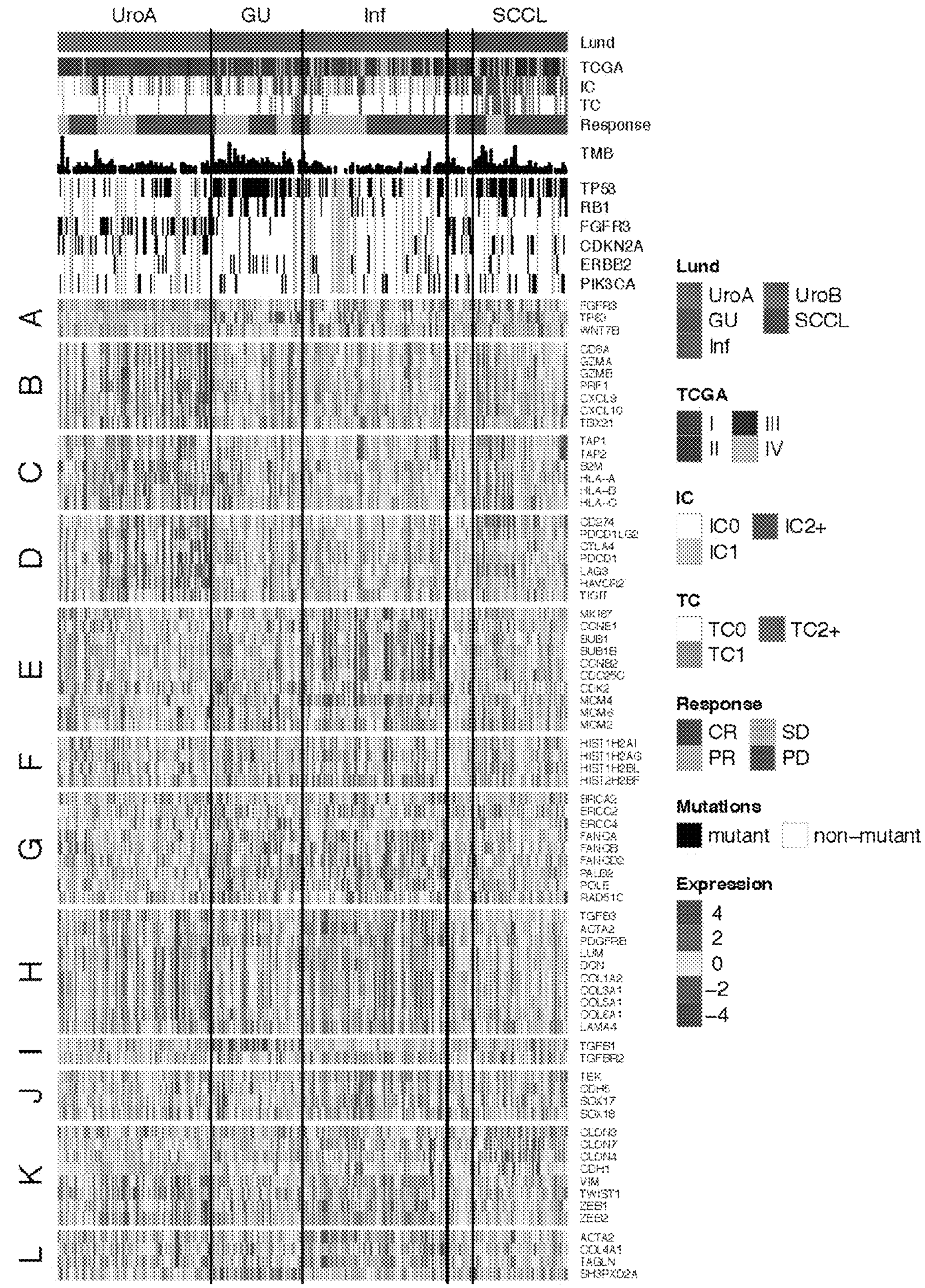
FIG. 2A is a heatmap representing all patients evaluated, sorted by molecular subtype and then response. For comparison, immune cell (IC) and tumor cell (TC) PD-L1 status are given. In addition, TMB and mutation status (gray: patients without mutation data) for key genes of interest are shown. The rows of the heat map show expression (Z-scores) of genes of interest, grouped into the following pathways: A: FGFR3 gene signature, B: Teff signature, C: antigen processing machinery, D: immune checkpoint signature, E: MKI67 and cell cycle genes, F: DNA replication-dependent histones, G: DNA damage repair genes, H: extracellular matrix (ECM) organization gene set, I: TGF-β 2-gene signature, J: angiogenesis signature, K: epithelial-mesenchymal transition (EMT) markers, and L: cancer-associated fibroblast genes.
Figure 2B:
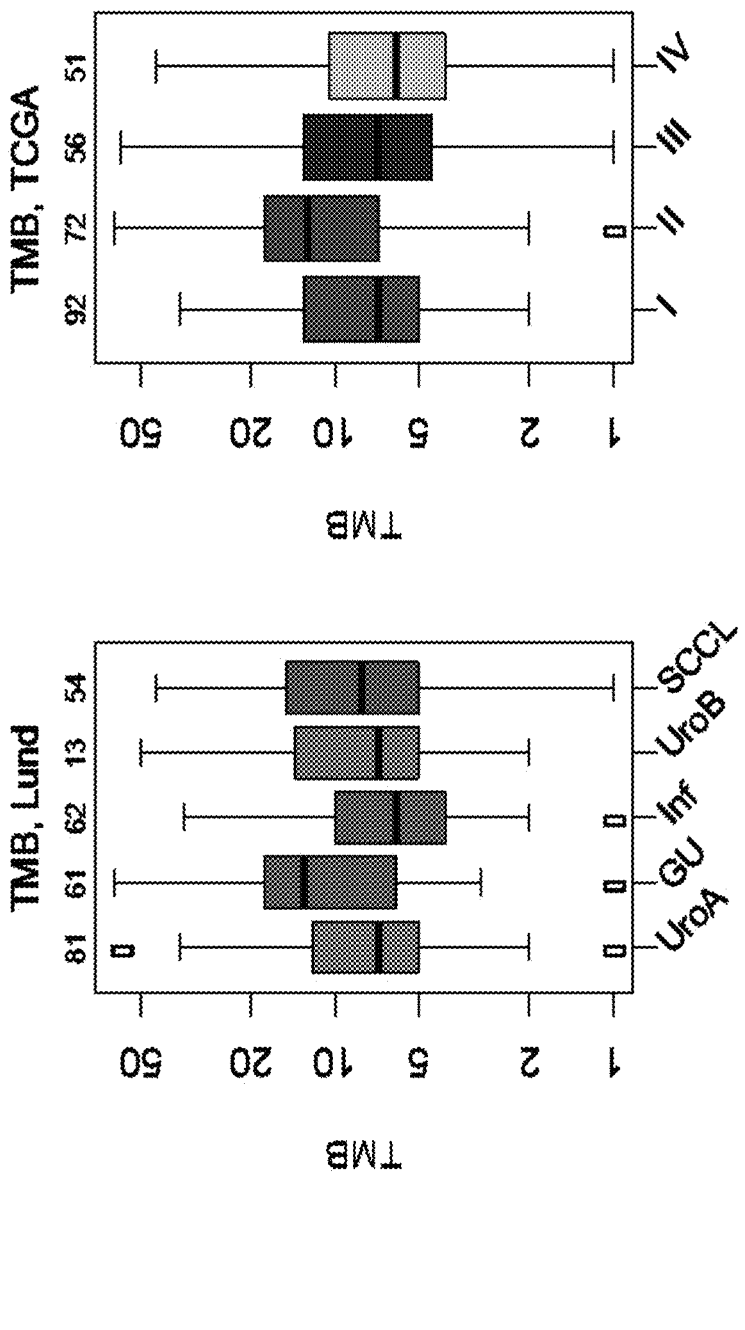
Figure 2C:
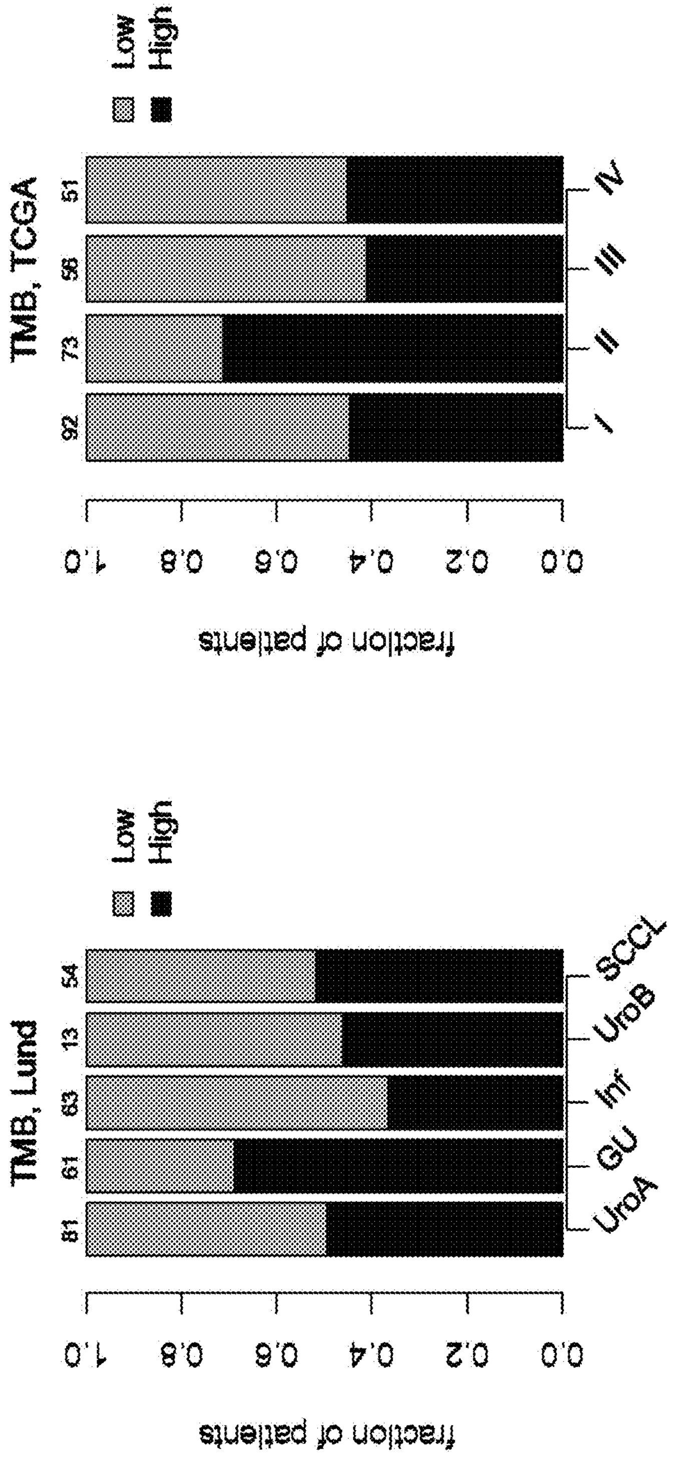
FIG. 2C is a graph showing patients split into TMB low (grey) and TMB high (black) subgroups, based on median TMB, and the fraction of patients in these two subgroups is shown for each of the Lund (left panel) and TCGA (right panel) molecular subtypes, respectively.
Figure 2E:
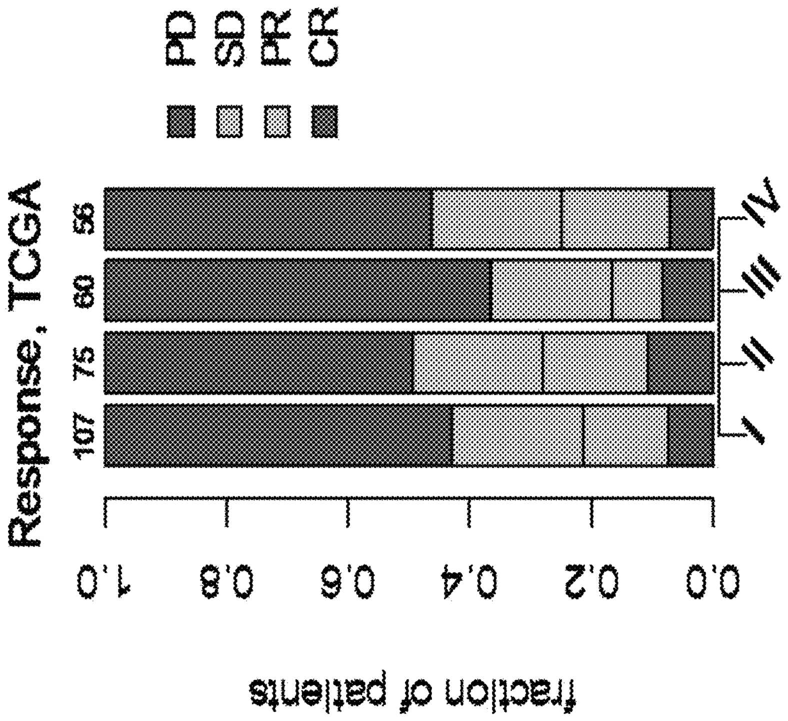
FIG. 2E is a graph showing the fraction of patients in each of the indicated response categories, divided by TCGA subtype. Although the luminal II subgroup achieved the highest response rate, consistent with previously reported results for the platinum-resistant cohort alone, the difference between luminal II versus other subtypes was not significant (Fisher exact test; p=0.12).
Figure 2D:
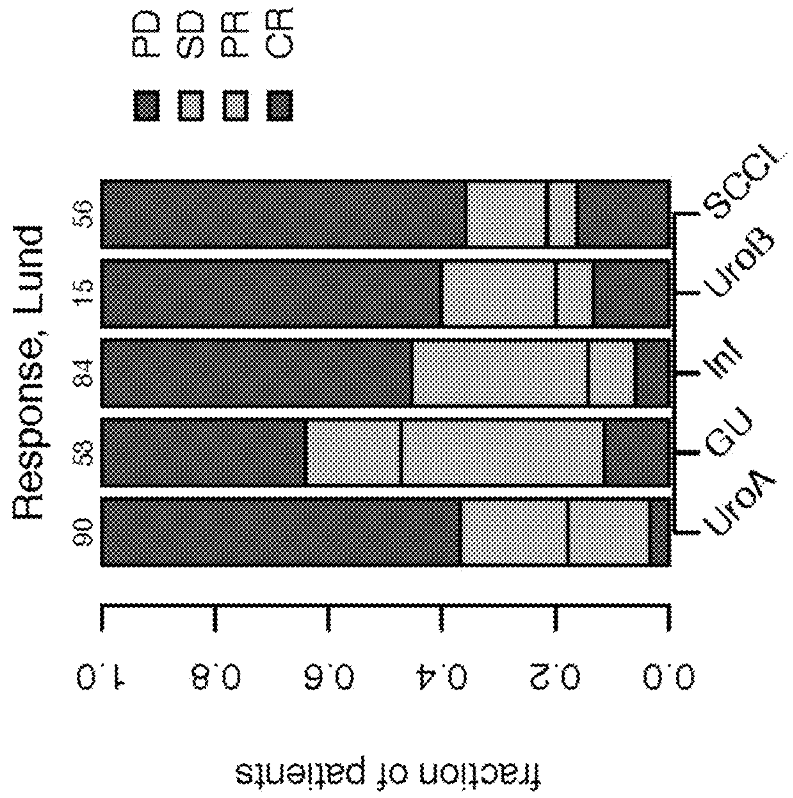
FIG. 2D is a graph showing the fraction of patients in each of the indicated response categories, divided by Lund molecular subtype. The GU subtype had a significantly higher response rate compared with all other subtypes (Fisher exact test; $p=1.6\times10^{-5}$).
Figure 2F:
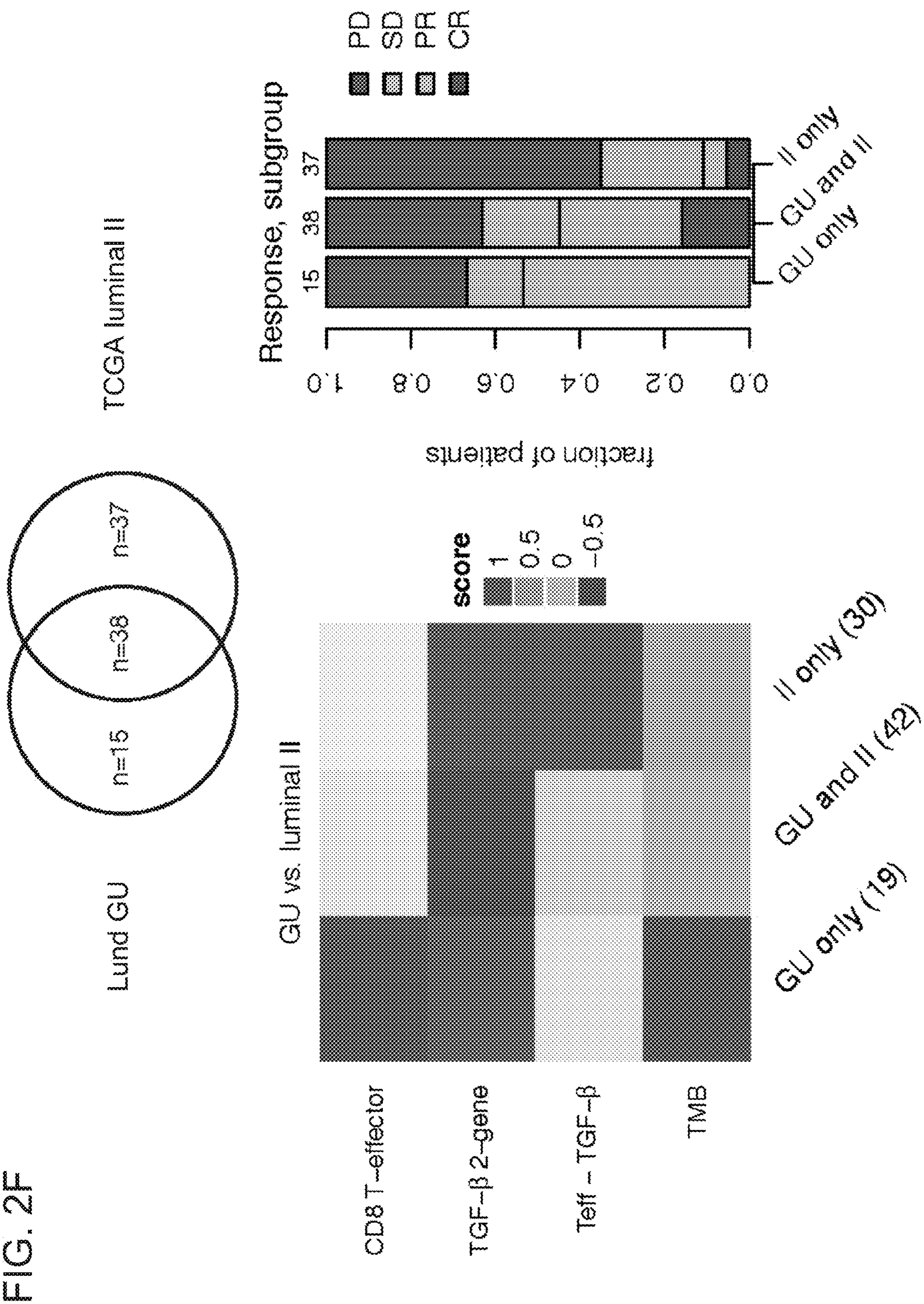
FIG. 2F is a graph showing that TGF-β is a likely driver of differential response in Lund GU and TCGA luminal II subtypes. The Venn diagram represents the three subgroups dissected further: (i) Lund subtyped as GU but not TCGA luminal II (GU only), (ii) both GU Lund luminal II (GU and II), or (iii) luminal II, but not GU (II only). The heat map shows the assessment of CD8 Teff and TGF-β 2-gene signatures as well as TMB in these subgroups (columns). Biologies of interest (rows) were scaled before medians were calculated across groups. Red means high, blue means low. Response differed significantly between the three subgroups (p=0.00062), as shown in the bar graph: while "GU only" and "GU and II" have a high fraction of partial and/or complete responders, "II only" shows limited response. Teff—TGF-β indicates CD8 Teff signature score minus TGF-β 2-gene signature score.
Figure 2G:
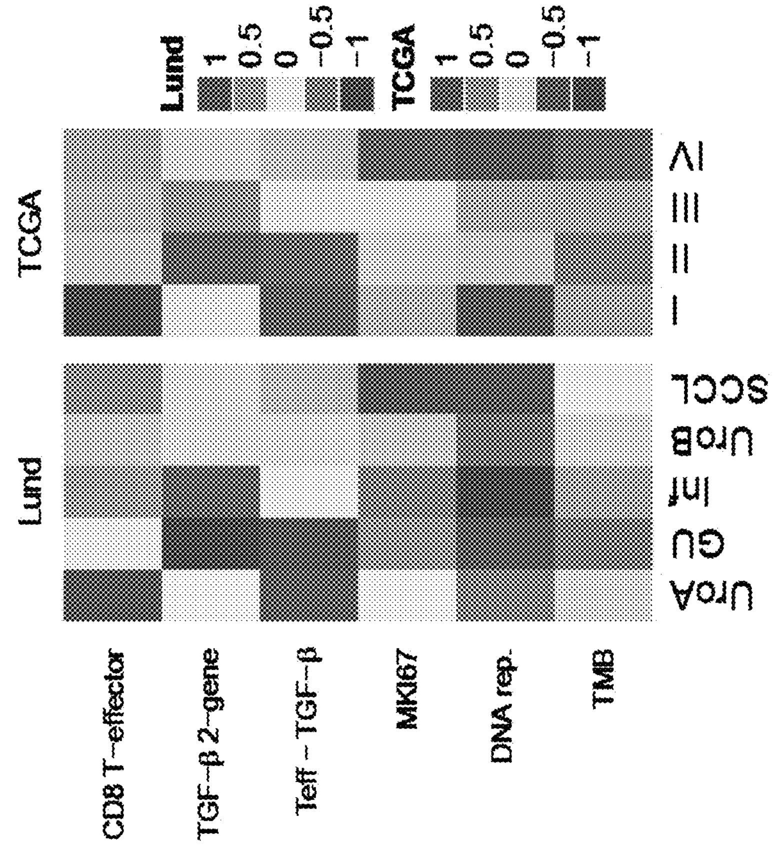
FIG. 2G is a heatmap showing assessment of MKI67 expression and signatures of interest as well as TMB relative to molecular subtypes. Biologies of interest were scaled before medians were calculated across the Lund (left) and TCGA (right) molecular subtypes (columns). Red means high, blue means low. DNA rep.: DNA replication.
Figure 2H:
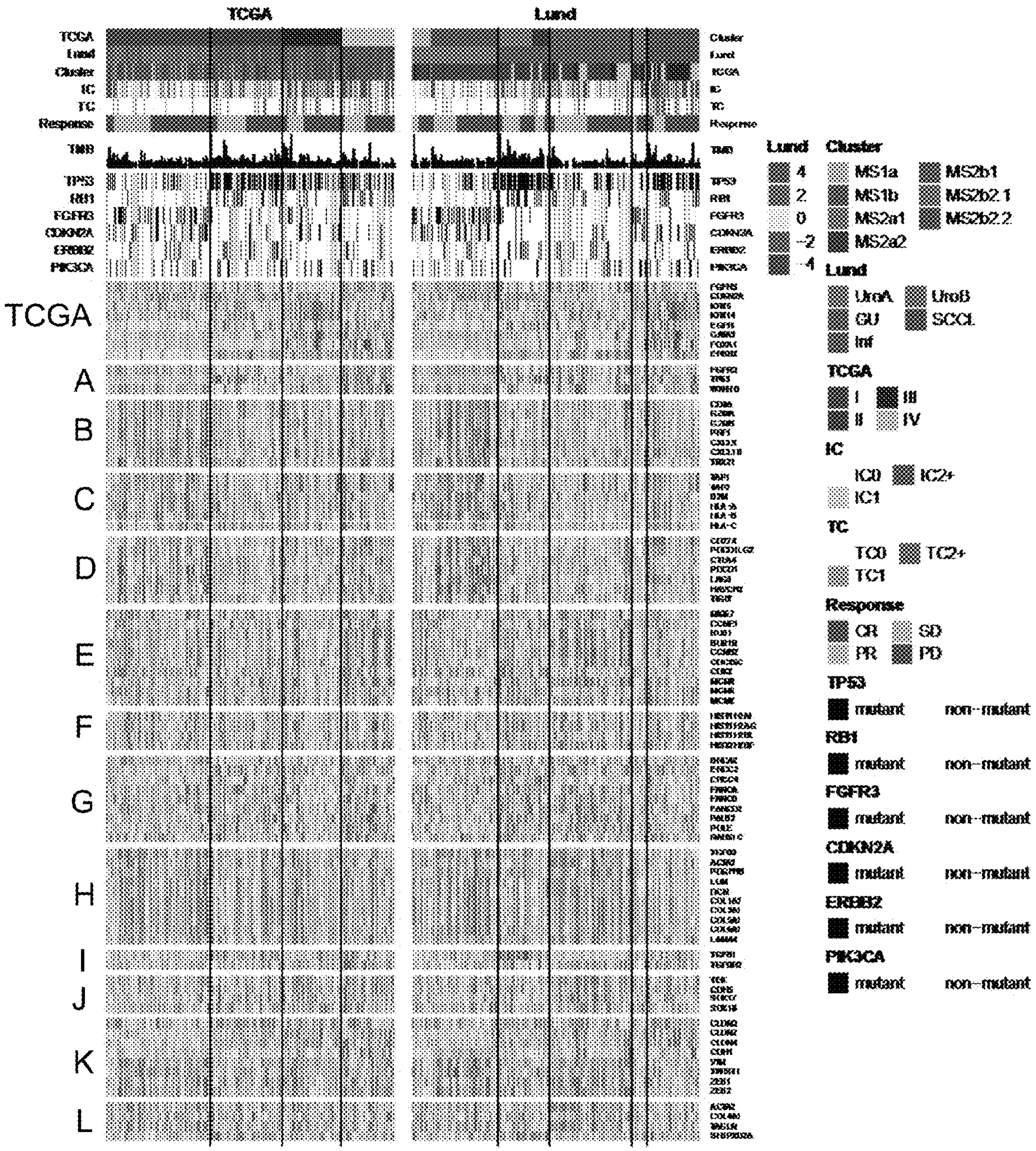
FIG. 2H is a heatmap showing a comparison between Lund and TCGA subtyping schemes. The heatmap represents all patients evaluated, except for patients without defined response, arranged in columns and sorted first by molecular subtype, then by response to atezolizumab. For the left hand panel, patients were sorted based on a TCGA-based subtyping scheme; for the right hand panel, patients were sorted by a Lund-based subtyping scheme (like FIG. 2A). IC and TC PD-L1 status are given. In addition, TMB and mutation status (either mutated, black, or not-mutated, white; grey indicates patients without mutation data) for a few genes of interest are shown. The rows of the heatmap show expression (z-scores) of genes of interest, grouped into the following biologies/pathways: TCGA: TCGA subtyping genes, A: FGFR3 gene signature, B: Teff signature, C.

Lund subtype labels were assigned as described above. To better understand the relationship between these subtypes and various axes of biology considered in this manuscript, FIGS. 2A and 2H show gene expression values for additional genes (i.e., genes that were not necessarily used for subtype assignment) from 13 biologies. Displayed genes are representative members of larger gene sets constructed as follows:

A: FGFR3 gene signature reported by Sjödahl et al. 2012, supra (representatives were selected);

B: CD8 T-effector signature (Rosenberg et al. supra);

C: antigen processing machinery reported by Şenbabaoğlu et al. *Genome Biol.* 17:231, 2016;

D: immune checkpoint signature;

E: MKI67 and select cell cycle genes (KEGG) that contributed to gene set enrichment for association with response (Table 8);

F: DNA replication-dependent histones (representatives of histones discovered in Table 8);

G: select members of the DNA damage repair gene set, introduced above;

H: extracellular matrix organization (ECM) set reported by Sjödahl et al. 2012 (representatives were selected);

I: TGF-β two-gene signature;

J: angiogenesis signature reported by Sjödahl et al. 2012 (representatives were selected);

K: epithelial-mesenchymal transition (EMT) markers reported by Damrauer et al. *Proc. Natl. Acad. Sci. USA* 111:3110-3115, 2014;

L: Pan-F-TBRS, determined as described below; and

TCGA: genes expressed TCGA subtype-specifically, as reported by The Cancer Genome Atlas Research *Nature*, supra (FIG. 2H).

O. CD8/Trichrome Dual Staining

The combined CD8/trichrome dual staining was performed on 4 μm FFPE sections. The IHC procedure was performed first using the anti-human CD8 rabbit monoclonal antibody SP16 (Spring Bioscience; Cat. No. M3160) at 1:100 dilution for one hour at room temperature following antigen retrieval using Cell Conditioning 1 reagent (CC1, Ventana Medical Systems; Cat. No. 950-124). Specifically bound primary antibody was visualized using the OMNI-MAP™ DAB kit (Ventana, Cat. No. 760-149). After completion of the IHC procedure and rinsing with distilled water, slides were fixed in Bouin's fixative at 60° C. for 1 h and then taken through a routine trichrome stain consisting of Weigert's hematoxylin, Biebrich scarlet-acid fuchsin, phosphomolybdic-phosphotungstic acid, and anilin blue as described previously (*Laboratory Methods in Histotechnology*, Armed Forces Institute of Pathology, 1992, p. 132). At the conclusion of the staining procedure, slides were dehydrated in increasing ethanol concentration, immersed in xylene, and then coverslipped using a synthetic mounting medium.

P. In Vivo Studies

The EMT6 murine mammary carcinoma cell line was obtained from American Type Culture Collection (Manassas, Va.). Cells were cultured in Roswell Park Memorial Institute (RPMI) 1640 medium plus 2 mM L-glutamine with 10% fetal bovine serum (HYCLONE®). Cells in log-phase growth were centrifuged, washed once with Hank's balanced salt solution (HBSS), counted, and resuspended in 50% HBSS and 50% MATRIGEL™ (BD Biosciences) at a concentration of $1\times10^6$ cells/mL for injection into mice. Female Balb/c mice were obtained from Charles River Laboratories (Hollister, Calif.). The mice were housed in standard rodent micro-isolator cages and were acclimated to study conditions for at least 3 days before tumor cell implantation. Animals were 8-10 weeks old. Only animals that appeared to be healthy and free of obvious abnormalities were used for the study. Mice were inoculated in the left mammary fat pad #5 with $1\times10^5$ EMT6 cells in 100 μl of HBSS MATRIGEL™ (1:1). When tumor reached a volume of 130-230 $mm^3$ (approximately 8 days after inoculation), animals were distributed into treatment groups based on tumor volume and treated with isotype control antibodies, anti-PD-L1 (10 mg/kg first dose followed by 5 mg/kg thereafter), anti-TGF beta (10 mg/kg), or a combination of anti-PD-L1 with anti-TGF beta. Seven days after treatment initiation, mice were euthanized and tumors collected for either IHC or flow cytometry analysis. For efficacy studies, antibodies were administered three times a week for 3 weeks (intravenously for the first dose and intraperitoneally thereafter). Tumors were measured two times per week by caliper, and tumor volumes were calculated using the modified ellipsoid formula, ½×(length×width$^2$). When tumor volumes fell below 32 mm$^3$ (lowest limit of detection) they were considered complete regressions (CR) (100% tumor growth inhibition). Mice were euthanized if tumor volumes exceeded 2000 mm$^3$. No mice met criteria for euthanasia because of body weight loss nor exhibited adverse clinical signs during the study. All animal studies herein were approved by the Genentech Institutional Animal Care and Use Committee. The group sizes used for this study were estimated to be the smallest necessary to generate meaningful data.

Q. Whole Tumor RNA and Protein Quantification from Mice

TGF-β isoform abundance in untreated EMT6 tumors was analyzed both at the RNA and protein levels, by RNAseq and ELISA, respectively. For RNAseq analysis, tumors of an average size of 300 mm$^3$ were collected. For ELISA quantification of TGF-β protein, tumors were collected 14 days after inoculation into the mammary fat pad, flash frozen, and subsequently lysed with radioimmunoprecipitation assay (RIPA) buffer on a TissueLyser disruption system (Qiagen). Total protein was quantified by bicinchoninic acid (BCA) assay, and total protein input was normalized across samples. The TGF-β in the samples was acid-activated and measured following the ELISA kit instructions (Mouse TGF-β1 and TGF-β2, R&D Systems; Mouse TGF-133, LSBio). VEGF was quantified using Mouse VEGF QUANTIKINE® ELISA Kit (R&D Systems) in plasma collected seven days after treatment onset.

R. Preparation of Single Cell Suspension and Antibody Staining for Flow Cytometry Tumors were collected seven days after treatment initiation. Tumors were weighed and enzymatically digested using a cocktail of dispase (Life Technologies), collagenase P, and DNaseI (Roche) for 45 min at 37° C., to obtain a single cell suspension. Cells were counted using a VI-CELL® XR (Beckman Coulter).

For phospho-SMAD (pSMAD) staining, cells were fixed and permeabilized using BD PHOSFLOW™ Lyse/Fix Buffer and BD PHOSFLOW™ Perm Buffer III (BD Biosciences) following the manufacturer's instructions. The cells were stained with a phycoerythrin (PE)-conjugated antibody against the phosphorylated form of SMAD2 and SMAD3 for 1 h on ice at a concentration of 0.08 μg/ml (clone 072-670, BD Biosciences, San Jose, Calif.). For T-cell staining, cells were first incubated with mouse BD Fc block (clone 2.4G2, 5 μg/ml, BD Biosciences) and a viability stain (LIVE/DEAD® Aqua Fixable Dead Cell Stain, Invitrogen) for 30 min on ice. The cells were then stained with the following antibodies: CD45 (BV605, clone 30-F11, 0.67 μg/ml, BD Biosciences), TCRb (PE, clone H57-597, 2 μg/ml, Biolegend), CD8 (APC-Cy7, clone 53-6.7, 1 μg/ml, Biolegend) for 30 min on ice. Cells were fixed and permeabilized (EBIOSCIENCE™ Foxp3/Transcription Factor Staining Buffer Set, Thermo Fisher Scientific Inc.) to stain for Granzyme B (FITC, clone NGZB, 5 μg/ml, EBIOSCIENCE™, Thermo Fisher Scientific Inc.).

Flow cytometry data were collected with a BD LSR-FORTESSA™ cell analyzer or FACSYMPHONY™ (BD Biosciences) and analyzed using FLOWJO® Software (Version 10.2, FlowJo, LLC).

S. Immunohistochemistry on Mouse Tissue

Tumors were collected seven days after treatment initiation. Tumors were fixed in 10% neutral buffered formalin (NBF) and paraffin embedded. IHC was performed on 4 μm thick paraffin-embedded tissue sections mounted on SUPERFROST™ Plus glass slides. Staining was performed on the LAB VISION™ Autostainer (ThermoFisher Scientific). Sections were de-paraffinized and rehydrated to deionized water. Antigen retrieval was performed with 1×DAKO Target Retrieval Solution (Agilent Technologies) for 20 min at 99° C. and cooled to 74° C. Subsequently, endogenous peroxidase was quenched by incubating in sections in 3% $H_2O_2$ for 4 min at room temperature. CD3 (ThermoFisher Scientific, clone SP7, cat. no. RM-9107-S, 1:200 dilution) was detected using an anti-rabbit (7.5 μg/mL) secondary antibody with the ABC Peroxidase Elite Detection Kit (Vector Laboratories, cat. no. PK-6100). Sections were counterstained with Mayer's hematoxylin, dehydrated, mounted with permanent mounting medium, and coverslipped.

T. Generation of Pan-Fibroblast TGF-β Response Signature (Pan-F-TBRS)

Primary fibroblast cells from bladder (PHBR, primary normal bladder fibroblast cells, PCS-420-013™ ATCC), colon (CCD-18Co, CRL-1459™, ATCC), breast (HMF, #7630, ScienCell Research Laboratories), lung (IMR90, CCL-186™, ATCC), pancreas (HPaSteC, #3836, ScienCell Research Laboratories), and ovary (HOF, #7336, ScienCell Research Laboratories) were serum-starved overnight before treatment with (1) control, (2) TGF-β1 (10 ng/mL, #), or (3) TGF-β1 (10 ng/mL)+the TGF-β inhibitor galunisertib (10 μM) in duplicates for 24 h. TGF-β-induced genes were identified by RNAseq transcriptome analysis comparing the above three conditions. The F-TBRS was determined using the following criteria: (1) expression level at least 2-fold higher in TGF-β1-treated group compared with controls (false discovery rate (FDR) 0.1); (2) expression level at least 2-fold lower in the TGF-β1+inhibitor group compared to TGF-β1 treatment alone (FDR 0.1); (3) meet criteria (1) and (2) in all 6 fibroblast cell types. The genes that passed these three criteria (n=79) were ranked according to the strength of inhibition (control versus TGF-β1+TGF-β inhibitor); and filtered by at least 5 counts per million mean reduction to define a pan-tissue 19-gene F-TBRS.

U. Generation of Pan-Tissue 6-Gene F-TBRS (6-Gene Signature)

We developed a pan-tissue 6-gene F-TBRS based on the 19-gene Pan-F-TBRS data described above but further prioritizing TGF-β pathway components (TGFB1 and TGFBR2) and targets (CTGF, ADAM19, ACTA2, and COMP). To validate the predictive value of the 6-gene signature, we calculated hazard ratios for prognostic effects (using univariate continuous Cox proportional hazards regression models) and predictive effects, and calculated hazard ratios for predictive effects (using the log-rank test with median cutoff) in atezolizumab clinical trials. Our analysis demonstrated that high expression of the 6-gene signature is associated with lack of response to atezolimumab (atezo) monotherapy in UC, non-small cell lung cancer (NSCLC), triple-negative breast cancer (TNBC), and pancreatic ductal adenocarcinoma (PDAC) trials. See, e.g., FIGS. 6B and 6C, which show data from IMvigor210 and the POPLAR study (NCT01903993), respectively. In addition, in the TCGA colorectal cancer (CRC) data set, high expression of the 6-gene signature was also significantly associated with poor overall survival and enriched in CMS4 molecular subtype, which correlates with a poor survival subgroup of CRC patients (Guinney et al. *Nat. Med.* 21(11): 1350-1356, 2015). See FIGS. 6A, 7A, and 7B.

V. Macrophage and T-Cell TGF-β Response Signatures (M- and T-Cell-TBRS)

The macrophage- and T-cell-specific TBRS were adopted from Calon et al. *Nat. Genet.* 47:320-329, 2015; 1178 and 69 genes, respectively. Signature scores were computed by (1) deriving the first principal component (PC1) of signature genes on the EMT6 RNAseq data, (2) obtaining the signature genes having at least 0.8 Spearman-rank correlation with PC1, and (3) taking the average of Z-scores for genes from step (2). The filtering in step (2) resulted in 101 and 10 genes for M-TBRS and T-cell-TBRS, respectively.

W. Statistical Analysis of T-Cell Infiltration

Bright field images were acquired by Hamamatsu NanoZoomer automated slide-scanning platforms at a final magnification of 200×. The images were analyzed with the 2016b version of the MATLAB® software package (MathWorks). Regions of interest (ROIs) were defined by a pathologist. Cells marked with CD3+ that lay within the ROI border were identified by intensity thresholding and simple morphological filtering. Immune cell infiltration was evaluated for each slide (i.e., each mouse) by calculating the mean nearest distance to the ROI border over all CD3+ marked cells within the ROI on that slide. Mean distances were then normalized per slide by dividing by the maximum distance from the ROI border to the ROI center. Normalized mean distances were then pooled across the three studies (666, 1430, 1436) and analyzed by linear regression with treatment group as a fixed categorical variable and ROI area and total number of CD3+ cells within the ROI as covariates. Covariate-adjusted means and 95% confidence intervals were reported for each treatment group. Pairwise comparisons among treatment groups were made using Tukey's honest significant difference (HSD) test. All analyses were performed using R, and distance calculations were made using the R package 'spatstat' (Baddeley et al. *Spatial Point Patterns: Methodology and Applications with R.* Chapman and Hall/CRC Press, 2015).

Example 1: Pre-Existing Tumor Immunity is Associated with Complete Responses in Inflamed Tumors Most human solid tumors appear to exhibit one of three distinct immune phenotypes: the "immune inflamed" phenotype, characterized by robust CD8+ T-cell infiltration and PD-L1 expression; the "immune excluded" phenotype, in which T-cells accumulate in the extracellular matrix-rich stroma, and the "immune desert" phenotype, with a distinct paucity of infiltrating lymphocytes within the tumor or surrounding stroma. Inflamed tumors are thought to be more responsive to checkpoint blockade compared with immune excluded or immune desert phenotypes, which are predicted to be weakly or non-responsive. However, this association has not been systematically tested in the context of large clinical trials or within a single tumor type. To understand response to atezolizumab therapy in mUC, we combined integrated molecular and histological analyses with a reverse translation approach to test our findings functionally.

For investigation of the clinical activity of PD-L1 blockade with atezolizumab, 429 patients with advanced mUC were enrolled in a phase 2, single arm clinical trial (IMvigor210; NCT02108652). Objective response rate was assessed per RECIST v1.1 and served as a trial endpoint. Patients who achieved a complete response (CR) or partial response were categorized as responders and compared with non-responders, who displayed stable disease (SD) or progressive disease (PD). Assessment of the association of PD-L1 expression on tumor-infiltrating immune cells (IC) on baseline tumors with response (objective response rate) was a co-primary endpoint. PD-L1 IC status was defined by the percentage of PD-L1-positive immune cells in the tumor microenvironment (TME): IC0 (<1%), IC1 (≥1% but <5%) and IC2+(≥5%).

Figure 1A:
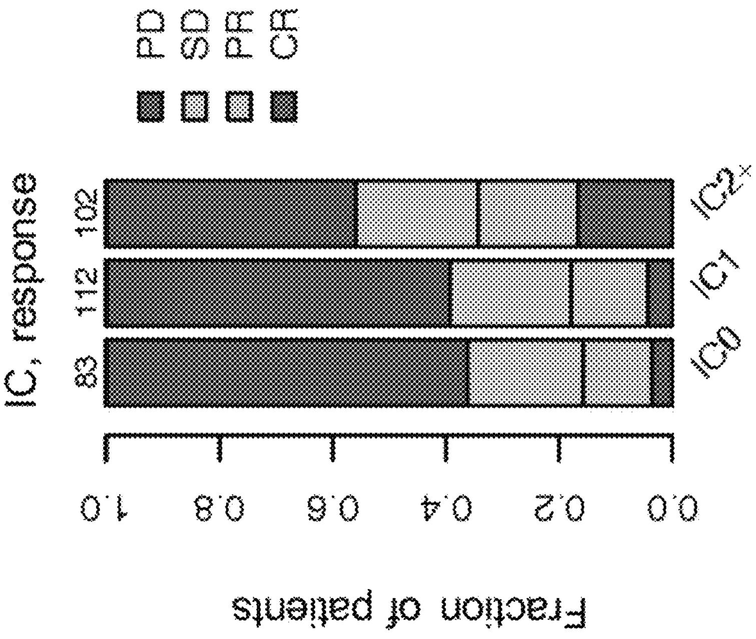
FIG. 1A is a graph showing that programmed death-ligand 1 (PD-L1) protein expression on tumor-infiltrating immune cells (IC) is associated with response to atezolizumab (Fisher exact test; p=0.0038). IC2+ tumors had a significantly higher complete response (CR) rate (p=0.0006), but the proportion of the partial responders (PR) was similar across all IC levels (p=0.53).
Figure 1D:
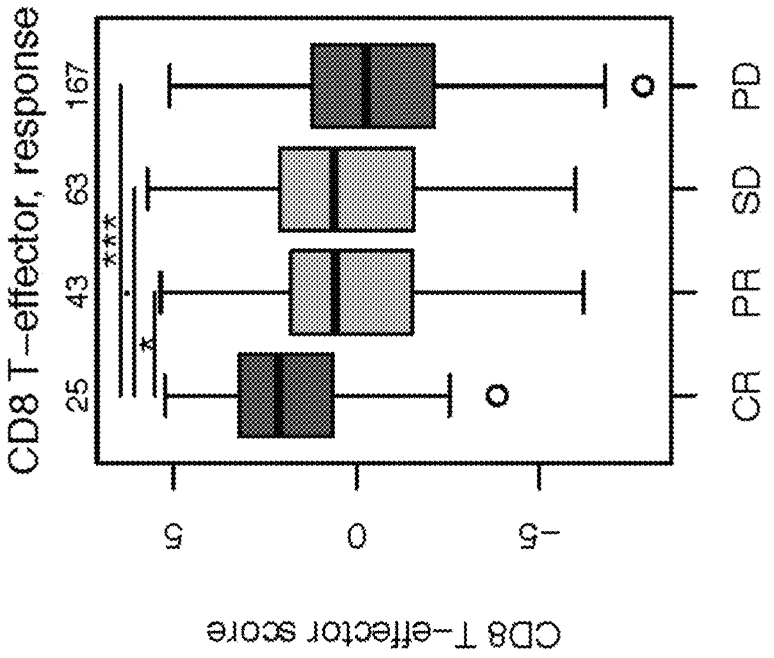
FIGS. 1C and 1D are a series of graphs showing an association between CD8 T-effector signature score and PD-L1 IC or response. CD8+T-effector signature score (y-axis) is plotted against PD-L1 IC score (FIG. 1C) and response category (FIG. 1D). There was a significant positive relationship between the signature score and both PD-L1 IC staining ($p=4.2\times10^{-35}$) and response to atezolizumab (p=0.0087). The association between CD8 T-effector signature and response was driven by the CR group, which had a significantly higher CD8 T-effector signature (t test; p=0.002); differences among the other three response groups were not significant (analysis of variance (ANOVA) p=0.08).
Figure 1C:
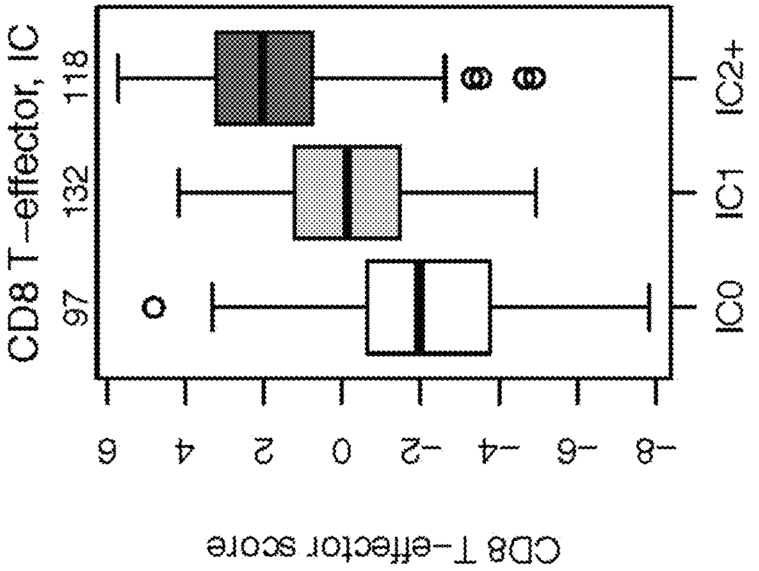
Figure 1E:
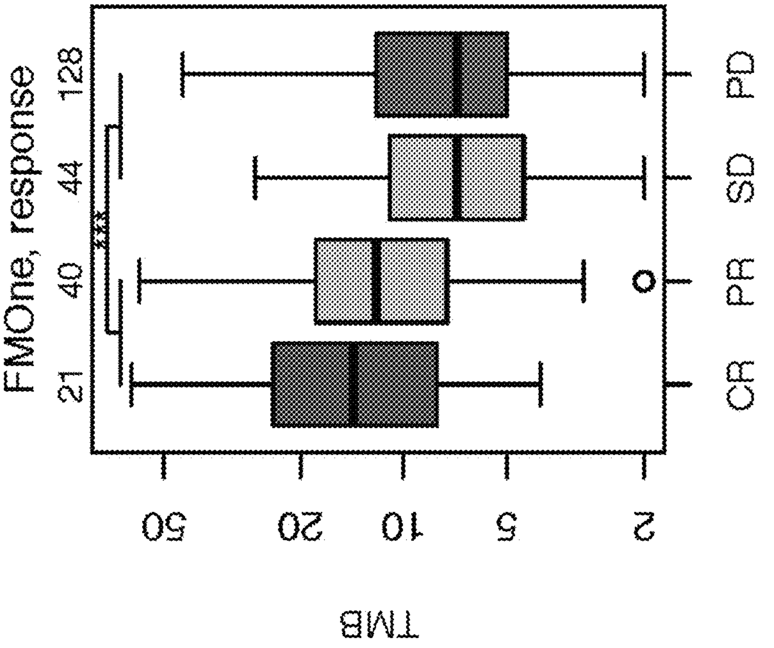
FIGS. 1E and 1F are a series of graphs showing the relationship between response status and tumor mutation burden (TMB) or tumor neoantigen burden (TNB). Shown are mutations per megabase (y-axis) as determined by Foundation Medicine's FOUNDATIONONE® (also referred to herein as "FMOne") panel (FIG. 1E) or whole-exome filtering for those mutations that are predicted to be expressed neoantigens (FIG. 1F). Both metrics are positively associated with response to atezolizumab (Wilcoxon p for FMOne-based mutations$=1.4\times10^{-7}$, for predicted neoantigens$=5.3\times10^{-9}$).
Figure 1F:
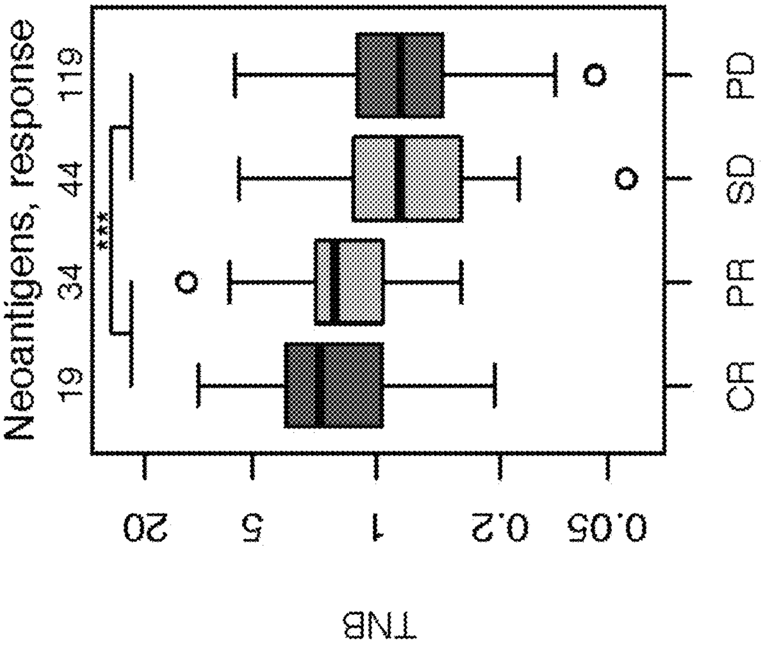
Figure 1G:
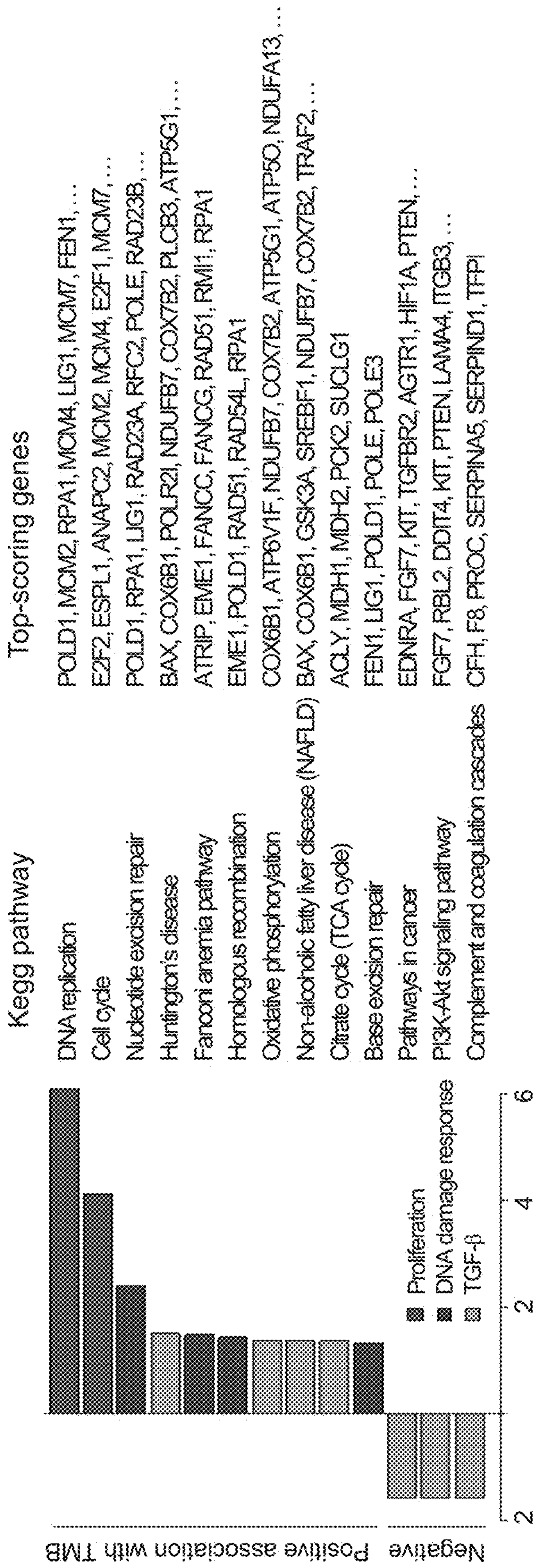
FIG. 1G is a graph showing KEGG pathways enriched in genes whose expression is correlated with TMB. Shown are adjusted $-\log_{10}$ p-values for enrichment of KEGG gene sets significantly (FDR<0.05) enriched in genes that are correlated with TMB. Sets inferred to reflect key underlying biological processes are colored as follows: proliferation (turquoise), DNA damage response (DDR) (magenta), TGF-β signaling (orange). Only the top seven genes per set (ranked by single-gene p-value) are shown.
Figure 1H:
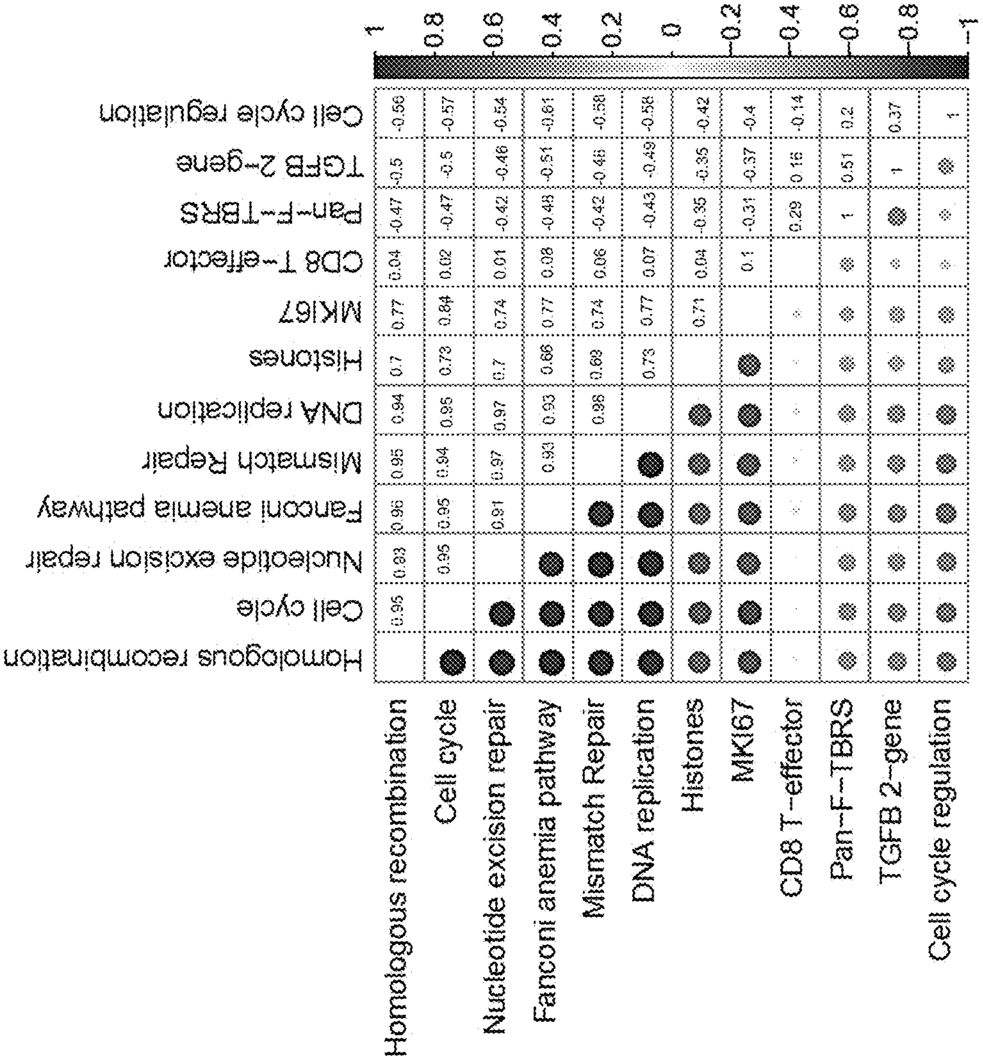
FIG. 1H is a graph showing the relationship between different gene expression signatures as well as the single-gene expression values for MKI67, a marker for proliferation. In the left corner, correlation between signature scores/gene expression is visualized; in the right corner, Pearson correlation coefficients are given. Gene set membership is given in Table 10. See Example 1 for information regarding computation of signature scores. Pan-F-TBRS: pan-fibroblast TGF-β response signature.
Figure 1I:
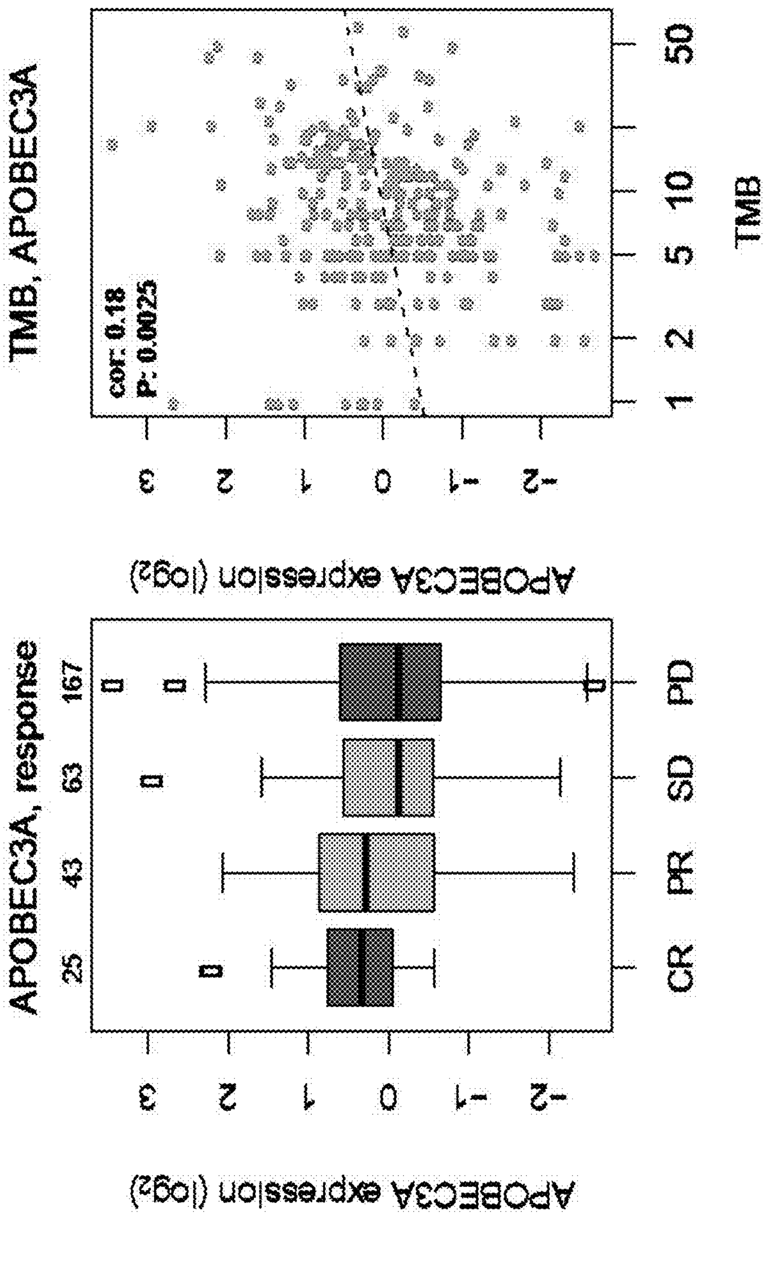
FIGS. 1I and 1J are a series of graphs showing apolipoprotein B mRNA editing enzyme, catalytic polypeptide-like (APOBEC) 3A (FIG. 1I) and APOBEC3B (FIG. 1J) gene expression and its association with response and TMB. Normalized log 2-transformed counts for gene expression are shown on the y-axes; response categories and TMB are shown on the x-axes. Both APOBEC3A (p=0.015) and APOBEC3B (p=0.0025) exhibited higher mean expression in responders. For TMB, Pearson correlation coefficients and p-values are given. Trend lines for the relationship between gene expression and TMB are plotted. For FIG. 1J, the two extreme expression outliers were excluded when calculating correlation between gene expression and TMB.
Figure 1J:
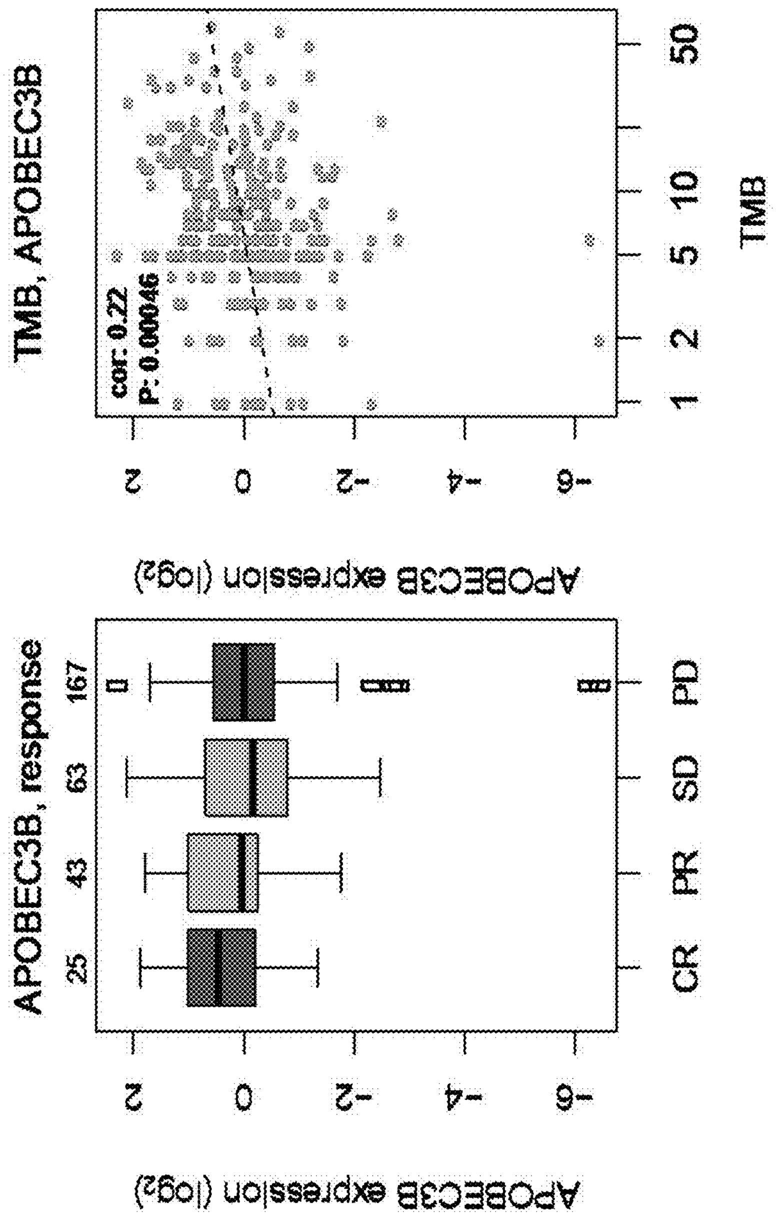
Figure 1L:
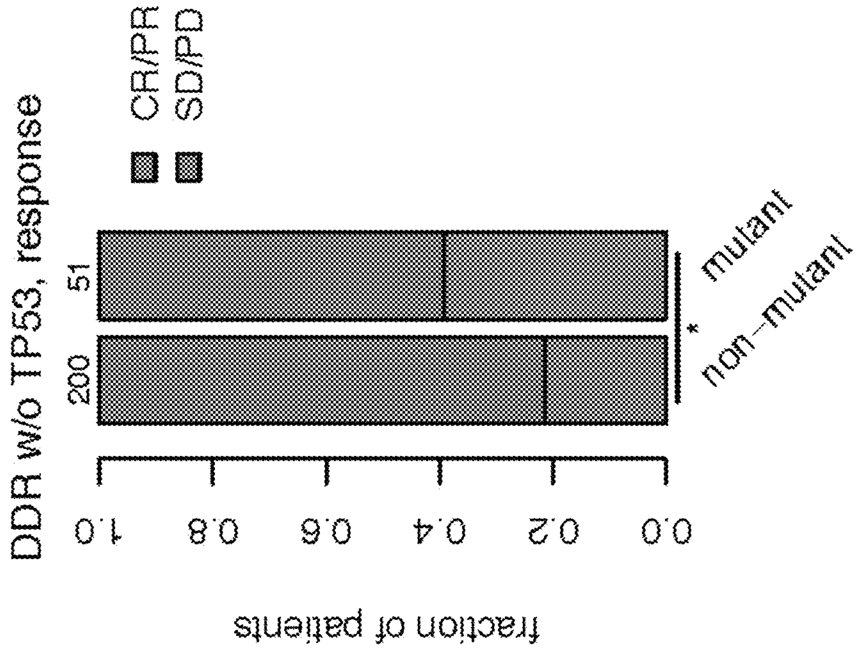
FIG. 1L is a graph showing set-wise mutation status for DDR genes versus response. Patients were labelled DDR mutant if they harbored a mutation in one or more DDR genes, excluding TP53. The fraction of responders (CR/PR) and non-responders (stable disease (SD)/progressive disease (PD)) is plotted for these two patient subgroups. There was a significant association between DDR mutation status and response (p=0.0117).
Figure 1K:
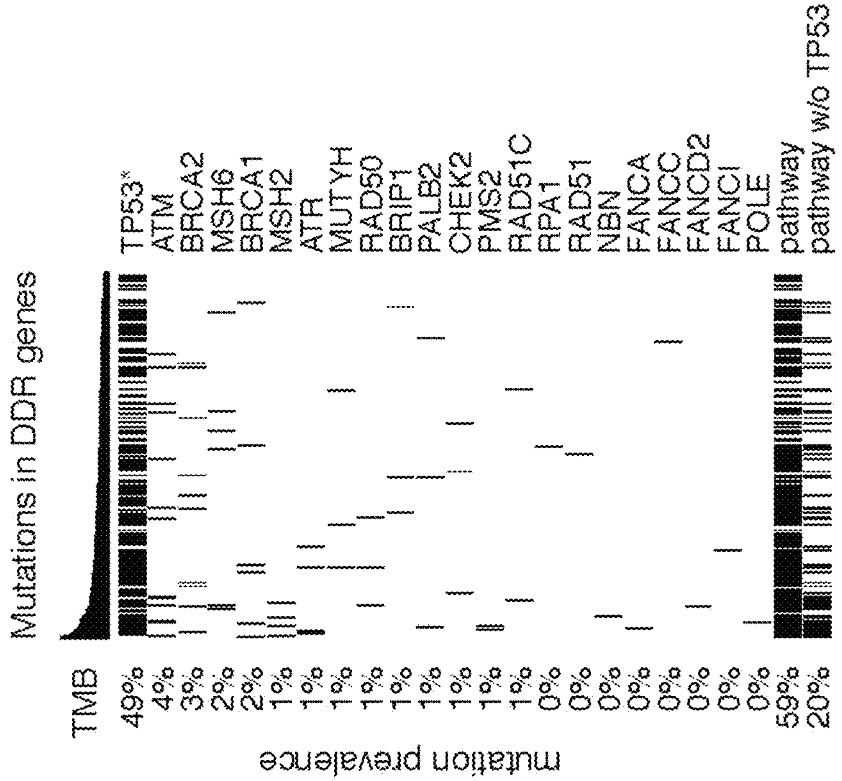
FIG. 1K is a graph showing that mutations in DDR genes are associated with TMB. Genes are in rows and patients are in columns, with a mutation marked with a black rectangle. The upper bar graph depicts TMB, with patients sorted from high to low TMB. The lower rows represent the mutation status of the entire pathway, with or without inclusion of TP53. The percentage of patients carrying a mutation in a gene or pathway is given to the left.

As found previously in a smaller cohort of patients, PD-L1 expression on IC was significantly associated with response, and tumors with high PD-L1 expression (IC2+) displayed the highest CR rate (FIG. 1A). Improved OS benefit from atezolizumab was observed in patients with high PD-L1 IC scores (IC2/3) relative to patients with lower PD-L1 IC scores (IC0/1) (FIG. 8A). Whole transcriptome RNA sequencing was performed in pre-treatment tissues from 298 IMvigor210 participants to evaluate features associated with response to atezolizumab and identify genes that had expression levels associated with PD-L1 expression on IC (FIG. 1B). Interferon-γ (IFN-γ)-inducible genes were among the most highly correlated. Gene sets associated with CD8+T-effector (Teff) cells and immune checkpoint molecules (Table 10), many of which are IFN-γ-stimulated genes, showed the most differential expression (FIGS. 1B and 1C). The CD8+ Teff gene set was also significantly associated with response, particularly with CR (FIG. 1D). The CD8+ Teff score quartiles were associated with overall survival (FIG. 1U). This suggests that PD-L1 expression on IC marks tumor tissues that have pre-existing CD8+ T-cell immunity and adaptive immune suppression but are still poised to respond to anti-PD-L1 therapy.

TABLE 10

Gene sets used for signature analyses

| Gene Signature | Platform | Genes | Source |
|---|---|---|---|
| CD8 T-effector (Teff) | Gene expression profiling | CD8A, CXCL10, CXCL9, GZMA, GZMB, IFNG, PRF1, TBX21 | PMID: 26952546 |
| DNA damage repair | Gene expression profiling | ALKBH2, ALKBH3, APEX1, APEX2, APLF, ATM, ATR, ATRIP, BLM, BRCA1, BRCA2, BRIP1, CCNH, CDK7, CETN2, CHAF1A, CHEK1, CHEK2, CLK2, DCLRE1C, DDB1, DDB2, DUT, ENDOV, ERCC1, ERCC2, ERCC3, ERCC4, ERCC5, ERCC6, ERCC8, FAN1, FANCA, FANCB, FANCC, FANCD2, FANCE, FANCF, FANCG, FANCL, FANCM, GTF2H1, GTF2H2, GTF2H3, GTF2H4, GTF2H5, H2AFX, HLTF, HUS1, LIG1, LIG3, LIG4, MBD4, MDC1, MGMT, MLH1, MLH3, MMS19, MNAT1, MPG, MSH2, MSH3, MSH4, MSH5, MSH6, MUTYH, NEIL1, NEIL2, NEIL3, NHEJ1, NTHL1, | Lange et al. supra |

TABLE 10-continued

Gene sets used for signature analyses

| Gene Signature | Platform | Genes | Source |
|---|---|---|---|
| | | NUDT1, OGG1, PALB2, PARP1, PARP2, PARP3, PCNA, PER1, PMS1, PMS2, PNKP, POLB, POLD1, POLE, POLG, POLH, POLL, POLM, POLQ, PRKDC, RAD1, RAD17, RAD18, RAD23A, RAD23B, RAD51C, RAD9A, RECQL4, RECQL5, RIF1, RNF168, RNF4, RNF8, RPA1, RPA2, RPA3, RPA4, RRM2B, SETMAR, SHPRH, SMUG1, TDP1, TDP2, TOPBP1, TP53, TREX1, UBE2A, UBE2B, UBE2N, UBE2V2, UNG, UVSSA, WRN, XAB2, XPA, XPC, XRCC1, XRCC4, XRCC5, XRCC6 | |
| TGF-β 2-gene | Gene expression profiling | TGFB1, TGFBR2 | Single-gene association with response in this study. |
| Pan-F-TBRS | Gene expression profiling | ACTA2, ACTG2, ADAM12, ADAM19, CNN1, COL4A1, CTGF, CTPS1, FAM101B, FSTL3, HSPB1, IGFBP3, PXDC1, SEMA7A, SH3PXD2A, TAGLN, TGFBI, TNS1, TPM1 | Experimentally determined pan-fibroblast TGF-β response signature. |
| Antigen processing machinery | Gene expression profiling | B2M, HLA-A, HLA-B, HLA-C, TAP1, TAP2 | PMID: 27855702 |
| Immune checkpoint | Gene expression profiling | CD274, CTLA4, HAVCR2, LAG3, PDCD1, PDCD1LG2, TIGIT | |
| EMT | Gene expression profiling | CLDN3, CLDN7, CLDN4, CDH1, VIM, TWIST1, ZEB1, ZEB2 | PMID: 24520177 |
| ECM | Gene expression profiling | ACTA2, COL1A2, COL3A1, COL5A1, COL6A1, DCN, LAMA4, LUM, PDGFRB, TGFBR3 | PMID: 22553347 |
| FGFR3-related genes | Gene expression profiling | FGFR3, TP63, WNT7B | PMID: 22553347 |
| KEGG discovered histones | Gene expression profiling | HIST1H2AG, HIST1H2AI, HIST1H2BL, HIST2H2BF | This study. |
| Angiogenesis | Gene expression profiling | CDH5, SOX17, SOX18, TEK | PMID: 22553347 |
| Fanconi anemia | Gene expression profiling | APITD1, ATR, ATRIP, BLM, BRCA1, BRCA2, BRIP1, C17orf70, C19orf40, EME1, EME2, ERCC1, ERCC4, FAN1, FANCA, FANCB, FANCC, FANCD2, FANCE, FANCF, FANCG, FANCI, FANCL, FANCM, HES1, MLH1, MUS81, PALB2, PMS2, POLH, POLI, POLK, POLN, RAD51, RAD51C, REV1, REV3L, RMI1, RMI2, RPA1, RPA2, RPA3, RPA4, SLX4, STRA13, TELO2, TOP3A, TOP3B, UBE2T, USP1, WDR48 | KEGG hsa03460 |
| Cell cycle | Gene expression profiling | ABL1, ANAPC1, ANAPC10, ANAPC11, ANAPC13, ANAPC2, ANAPC4, ANAPC5, ANAPC7, ATM, ATR, BUB1, BUB1B, BUB3, CCNA1, CCNA2, CCNB1, CCNB2, CCNB3, CCND1, CCND2, CCND3, CCNE1, CCNE2, CCNH, CDC14A, CDC14B, CDC16, CDC20, CDC23, CDC25A, CDC25B, CDC25C, CDC26, CDC27, CDC45, CDC6, CDC7, CDK1, CDK2, CDK4, CDK6, CDK7, CDKN1A, CDKN1B, CDKN1C, CDKN2A, CDKN2B, CDKN2C, CDKN2D, CHEK1, CHEK2, CREBBP, CUL1, DBF4, E2F1, E2F2, E2F3, E2F4, E2F5, EP300, ESPL1, FZR1, GADD45A, GADD45B, GADD45G, GSK3B, HDAC1, HDAC2, MAD1L1, MAD2L1, MAD2L2, MCM2, MCM3, MCM4, MCM5, MCM6, MCM7, MDM2, MYC, ORC1, ORC2, ORC3, ORC4, ORC5, ORC6, PCNA, PKMYT1, PLK1, PRKDC, PTTG1, PTTG2, RAD21, RB1, RBL1, RBL2, RBX1, SFN, SKP1, SKP2, SMAD2, SMAD3, SMAD4, SMC1A, SMC1B, SMC3, STAG1, STAG2, TFDP1, TFDP2, TGFB1, TGFB2, TGFB3, TP53, TTK, WEE1, YWHAB, YWHAE, YWHAG, YWHAH, YWHAQ, YWHAZ, ZBTB17 | KEGG hsa4110 |

TABLE 10-continued

Gene sets used for signature analyses

| Gene Signature | Platform | Genes | Source |
|---|---|---|---|
| DNA replication | Gene expression profiling | DNA2, FEN1, LIG1, MCM2, MCM3, MCM4, MCM5, MCM6, MCM7, PCNA, POLA1, POLA2, POLD1, POLD2, POLD3, POLD4, POLE, POLE2, POLE3, POLE4, PRIM1, PRIM2, RFC1, RFC2, RFC3, RFC4, RFC5, RNASEH1, RNASEH2A, RNASEH2B, RNASEH2C, RPA1, RPA2, RPA3, RPA4, SSBP1 | KEGG hsa3030 |
| Nucleotide excision repair | Gene expression profiling | CCNH, CDK7, CETN2, CUL4A, CUL4B, DDB1, DDB2, ERCC1, ERCC2, ERCC3, ERCC4, ERCC5, ERCC6, ERCC8, GTF2H1, GTF2H2, GTF2H3, GTF2H4, GTF2H5, LIG1, MNAT1, PCNA, POLD1, POLD2, POLD3, POLD4, POLE, POLE2, POLE3, POLE4, RAD23A, RAD23B, RBX1, RFC1, RFC2, RFC3, RFC4, RFC5, RPA1, RPA2, RPA3, RPA4, XPA, XPC | KEGG hsa3420 |
| Homologous recombination | Gene expression profiling | BLM, BRCA2, EME1, MRE11A, MUS81, NBN, POLD1, POLD2, POLD3, POLD4, RAD50, RAD51, RAD51B, RAD51C, RAD51D, RAD52, RAD54B, RAD54L, RPA1, RPA2, RPA3, RPA4, SHFM1, SSBP1, TOP3A, TOP3B, XRCC2, XRCC3 | KEGG hsa3440 |
| Mismatch repair | Gene expression profiling | EXO1, LIG1, MLH1, MLH3, MSH2, MSH3, MSH6, PCNA, PMS2, POLD1, POLD2, POLD3, POLD4, RFC1, RFC2, RFC3, RFC4, RFC5, RPA1, RPA2, RPA3, RPA4, SSBP1 | KEGG hsa3430 |
| Cell cycle regulators | Gene expression and mutational profiling | ATM, CCND1, CCNE1, CDKN1A, CDKN2A, E2F3, FBXW7, MDM2, RB1, TP53 | PMID: 24476821 |
| DNA damage repair | Mutational profiling | ATM, ATR, BLM, BRCA1, BRCA2, BRIP1, CHEK1, CHEK2, ERCC4, FANCA, FANCC, FANCD2, FANCE, FANCF, FANCG, FANCL, FANCM, MLH1, MSH2, MSH6, MUTYH, NUDT1, PALB2, PARP1, PARP2, PARP3, PMS2, POLD1, POLE, PRKDC, RAD51C, RPA1, TP53 | Lange et al. supra |

Example 2: Tumor Mutational Burden (TMB), Driven by Proliferation, APOBEC Expression, or DNA Damage Repair Deficiencies, is Associated with Response to Atezolizumab Bladder cancer, along with melanoma and non-small cell lung cancer, is characterized by one of the highest somatic TMBs among human cancers. Response to atezolizumab was significantly associated with TMB in mUC, and this association was also significant in the complete IMvigor210 data set (FIG. 1E). The relevance of TMB is likely via increased potential for immunogenic neoantigens, and consistent with this, predicted tumor neoantigen burden (TNB) was also significantly associated with response (FIG. 1F). TMB and TNB were also associated with OS (FIGS. 1V and 1W). For example, improved OS benefit from atezolizumab was observed in patients with high TMB relative to patients with low TMB, using median TMB as a cutoff (FIG. 8B). Improved OS from atezolizumab was also observed in patients with both high TMB and high PD-L1 IC scores (FIG. 8C).

We next assessed the transcriptional and mutational correlates of TMB in mUC. We first performed differential gene expression analysis, followed by gene set enrichment analysis. The pathways most significantly associated with TMB were those involved in cell cycle, DNA replication and DNA damage, detection and repair (FIG. 1G, Table 9). Signatures for these pathways were correlated with MKI67 and, thus, with proliferation (FIG. 1H). Secondly, we observed that expression levels for apolipoprotein B mRNA editing enzyme, catalytic polypeptide-like 3A (APOBEC3A) and APOBEC3B, two cytidine deaminases up-regulated in bladder and other cancers, were weakly but significantly correlated with TMB and response (FIGS. 1I and 1J). Thirdly, we examined loss-of-function mutations in members of the DNA damage response (DDR) or, given the relevance of proliferation rate, cell cycle regulator gene sets for correlation with TMB. Tumors with one or more mutations in the DDR gene set showed significantly higher response rates and TMB, both with and without ("w/o") inclusion of TP53 (FIGS. 1K and 1L, Table 11). Table 11 shows DNA repair (DDR) and cell cycle regulation gene sets were tested for association with response (CR/PR vs. SD/PD) and TMB ("category"), with or without inclusion of TP53. The number of patients with at least one mutation in the genes belonging to a gene set ("n mutant"), the effect size ("estimate") as well as nominal p-values are reported. MKI67 expression and DNA replication score were also associated with response to atezolizumab (FIG. 1Z).

TABLE 11

Mutation status of DNA repair and cell cycle regulation pathways and association with response and TMB

| Pathway | n mutant | category | estimate | p |
|---|---|---|---|---|
| Cell cycle regulation | 177 | response | 0.47948 | 0.038621 |
| Cell cycle regulation w/o TP53 | 125 | response | 0.735606 | 0.31104 |
| DDR | 145 | response | 0.50265 | 0.0274968 |
| DDR w/o TP53 | 51 | response | 0.426164 | 1.17E−02 |

TABLE 11-continued

| Mutation status of DNA repair and cell cycle regulation pathways and association with response and TMB | | | | |
|---|---|---|---|---|
| Pathway | n mutant | category | estimate | p |
| Cell cycle regulation | 214 | TMB | −3.6 | 2.04E−06 |
| Cell cycle regulation w/o TP53 | 150 | TMB | −0.91003 | 4.76E−02 |
| DDR pathway | 173 | TMB | −3.59998 | 8.64E−07 |
| DDR pathway w/o TP53 | 60 | TMB | −5.39995 | 1.84E−06 |

Figure 1M:
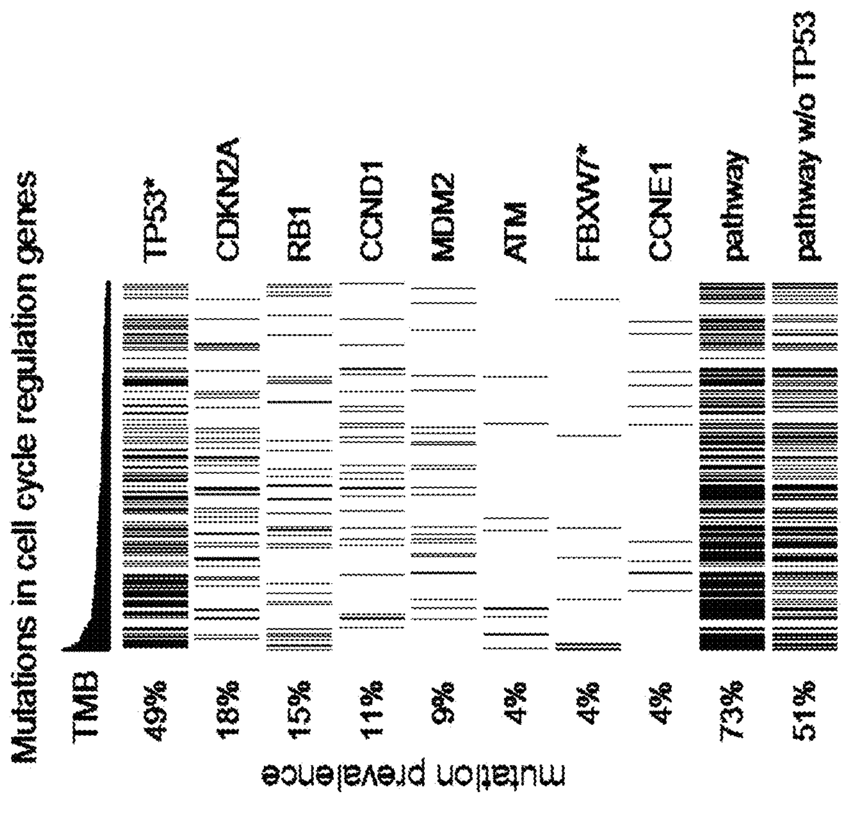
FIG. 1M is a graph showing that mutations in cell cycle regulator genes are associated with TMB. Genes are plotted in rows and patients in columns, marking patients with a mutation with a black rectangle. The upper bar plot depicts TMB in each patient, with patients sorted from TMB high to TMB low. The final rows represent the mutation status of the pathway as a whole, with or without TP53. Percentages to the left of the plot indicate prevalence. Genes with significant single gene associations with TMB are marked by an asterisk.
Figure 1N:
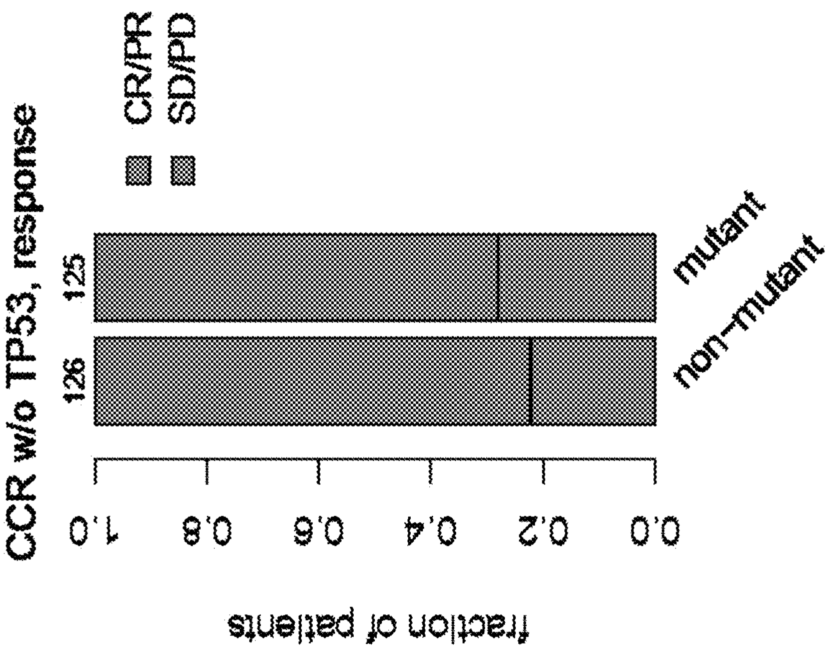
FIG. 1N is a graph showing mutation status in cell cycle regulation (CCR) pathway by response. For each patient, it was determined whether they harbor any mutation in a gene belonging to the CCR pathway, except for TP53. If patients harbored mutation(s) in CCR pathway gene(s), they were called mutant for the pathway. Otherwise, they were considered non-mutant. The fraction of responders (CR/PR) and non-responders (SD/PD) is plotted for these two patient subgroups. Excluding TP53, there was no association between mutation status for the CCR pathway and response (p=0.31104; Table 6).

Tumors with one or more mutations in the cell cycle regulator set also exhibited significantly higher TMB and response rates, although association with response here was driven by TP53 (FIGS. 1M and 1N, Tables 11 and 12). Together, these results demonstrate that multiple factors, including proliferation, APOBEC activity and defects in DDR or cell cycle regulation, contribute to TMB in bladder cancer, leading to increased responses to PD-L1 blockade. In Table 12, symbols and the number of mutant patients are given for each tested gene. Association with mutation status was tested for both response (CR/PR vs. SD/PD) and TMB ("category"). Effect size ("estimate") as well as nominal ("p") and adjusted p-values ("p (adj.)") are reported. The last two columns indicate whether a given gene is member of the DDR and/or the Cell cycle regulator ("CCReg") gene set.

TABLE 12

| Mutation status of single genes and association with response and TMB | | | | | | | |
|---|---|---|---|---|---|---|---|
| Gene | n mutant | category | estimate | p | p (adj.) | In DDR | In CCReg |
| ACVR1B | 3 | TMB | −0.900043 | 6.93E−01 | 0.900459333 | FALSE | FALSE |
| ACVR1B | 3 | response | Inf | 5.75E−01 | 1 | FALSE | FALSE |
| AKT1 | 3 | TMB | −1.79995 | 0.685694 | 0.900459333 | FALSE | FALSE |
| AKT1 | 3 | response | 0.667846 | 1 | 1 | FALSE | FALSE |
| AKT2 | 2 | TMB | −7.20994 | 0.166424 | 0.453154506 | FALSE | FALSE |
| AKT2 | 2 | response | 0.333324 | 0.439745 | 1 | FALSE | FALSE |
| AKT3 | 2 | TMB | −0.899936 | 0.886628 | 0.938081009 | FALSE | FALSE |
| AKT3 | 2 | response | Inf | 1 | 1 | FALSE | FALSE |
| APC | 9 | TMB | −2.70005 | 0.23619 | 0.550298351 | FALSE | FALSE |
| APC | 9 | response | 0.660537 | 0.69521 | 1 | FALSE | FALSE |
| ARAF | 1 | TMB | −18.0201 | 0.137297 | 0.437029887 | FALSE | FALSE |
| ARAF | 1 | response | 0 | 0.250996 | 0.872612588 | FALSE | FALSE |
| ARFRP1 | 1 | TMB | 0.899972 | 0.854389 | 0.92832651 | FALSE | FALSE |
| ARFRP1 | 1 | response | Inf | 1 | 1 | FALSE | FALSE |
| ARID1A | 70 | TMB | −4.50999 | 6.45E−07 | 0.000145851 | FALSE | FALSE |
| ARID1A | 62 | response | 0.559204 | 0.0904854 | 0.872612588 | FALSE | FALSE |
| ARID2 | 7 | TMB | −14.41 | 0.00512586 | 0.150903898 | FALSE | FALSE |
| ARID2 | 5 | response | 0.496176 | 0.601863 | 1 | FALSE | FALSE |
| ASXL1 | 5 | TMB | −18.0199 | 0.0137686 | 0.207446907 | FALSE | FALSE |
| ASXL1 | 5 | response | 0.216728 | 0.10244 | 0.872612588 | FALSE | FALSE |
| ATM | 13 | TMB | −4.50002 | 0.0350601 | 0.3433731 | TRUE | TRUE |
| ATM | 11 | response | 0.261315 | 0.0317334 | 0.872612588 | TRUE | TRUE |
| ATR | 4 | TMB | −13.51 | 0.00734488 | 0.150903898 | TRUE | FALSE |
| ATR | 3 | response | 0.164576 | 0.156242 | 0.872612588 | TRUE | FALSE |
| ATRX | 2 | TMB | −15.3101 | 0.0395031 | 0.3433731 | FALSE | FALSE |
| ATRX | 2 | response | 0.333324 | 0.439745 | 1 | FALSE | FALSE |
| AURKA | 1 | TMB | 0.899972 | 0.854389 | 0.92832651 | FALSE | FALSE |
| AURKA | 1 | response | Inf | 1 | 1 | FALSE | FALSE |
| AXIN1 | 2 | TMB | −8.11002 | 0.155164 | 0.445262375 | FALSE | FALSE |
| AXIN1 | 2 | response | 0.333324 | 0.439745 | 1 | FALSE | FALSE |
| AXL | 1 | TMB | −27.03 | 0.113957 | 0.408798127 | FALSE | FALSE |
| AXL | 1 | response | 0 | 0.250996 | 0.872612588 | FALSE | FALSE |
| BACH1 | 1 | TMB | −27.03 | 0.113957 | 0.408798127 | FALSE | FALSE |
| BACH1 | 0 | response | 0 | 1 | 1 | FALSE | FALSE |
| BAP1 | 5 | TMB | −0.900021 | 0.705022 | 0.905312341 | FALSE | FALSE |
| BAP1 | 5 | response | 1.34632 | 1 | 1 | FALSE | FALSE |
| BARD1 | 1 | TMB | −1.80005 | 0.731325 | 0.922679337 | FALSE | FALSE |
| BARD1 | 1 | response | Inf | 1 | 1 | FALSE | FALSE |
| BCL2L1 | 4 | TMB | 1.80993 | 0.34711 | 0.68131722 | FALSE | FALSE |
| BCL2L1 | 1 | response | Inf | 1 | 1 | FALSE | FALSE |
| BCL2L2 | 2 | TMB | −1.80991 | 0.548746 | 0.843650313 | FALSE | FALSE |
| BCL2L2 | 2 | response | 0.333324 | 0.439745 | 1 | FALSE | FALSE |
| BCOR | 1 | TMB | −25.22 | 0.119477 | 0.416119176 | FALSE | FALSE |
| BCOR | 1 | response | 0 | 0.250996 | 0.872612588 | FALSE | FALSE |
| BCORL1 | 3 | TMB | −13.51 | 0.065011 | 0.408798127 | FALSE | FALSE |
| BCORL1 | 3 | response | 0.667846 | 1 | 1 | FALSE | FALSE |
| BRAF | 6 | TMB | −2.11E−06 | 0.918449 | 0.956541355 | FALSE | FALSE |
| BRAF | 5 | response | 0.216728 | 0.10244 | 0.872612588 | FALSE | FALSE |
| BRCA1 | 6 | TMB | −7.21004 | 0.111409 | 0.408798127 | FALSE | FALSE |
| BRCA1 | 4 | response | 0.329736 | 0.262556 | 0.872612588 | FALSE | FALSE |
| BRCA2 | 10 | TMB | −2.71 | 0.162778 | 0.452443732 | TRUE | FALSE |
| BRCA2 | 9 | response | 0.660537 | 0.69521 | 1 | TRUE | FALSE |
| BRD4 | 1 | TMB | −27.93 | 0.107343 | 0.408798127 | FALSE | FALSE |
| BRD4 | 0 | response | 0 | 1 | 1 | FALSE | FALSE |
| BRIP1 | 3 | TMB | 0.900061 | 0.736787 | 0.922679337 | TRUE | FALSE |
| BRIP1 | 2 | response | 0.333324 | 0.439745 | 1 | TRUE | FALSE |
| CASP8 | 2 | TMB | −21.6199 | 0.0254157 | 0.294538267 | FALSE | FALSE |

TABLE 12-continued

Mutation status of single genes and association with response and TMB

| Gene | n mutant | category | estimate | p | p (adj.) | In DDR | In CCReg |
|---|---|---|---|---|---|---|---|
| CASP8 | 1 | response | 0 | 0.250996 | 0.872612588 | FALSE | FALSE |
| CCND1 | 32 | TMB | 2.35E−05 | 0.824791 | 0.92832651 | FALSE | TRUE |
| CCND1 | 26 | response | 1.13041 | 1 | 1 | FALSE | TRUE |
| CCND2 | 1 | TMB | 4.50997 | 0.222643 | 0.529786821 | FALSE | FALSE |
| CCND2 | 0 | response | 0 | 1 | 1 | FALSE | FALSE |
| CCND3 | 5 | TMB | 0.900012 | 0.73896 | 0.922679337 | FALSE | FALSE |
| CCND3 | 5 | response | 1.34632 | 1 | 1 | FALSE | FALSE |
| CCNE1 | 12 | TMB | 0.909984 | 0.417896 | 0.75467319 | FALSE | TRUE |
| CCNE1 | 8 | response | 0.322416 | 0.111683 | 0.872612588 | FALSE | TRUE |
| CD274 | 4 | TMB | −0.234732 | 0.888785 | 0.938081009 | FALSE | FALSE |
| CD274 | 2 | response | 0.333324 | 0.439745 | 1 | FALSE | FALSE |
| CDC73 | 1 | TMB | −2.35E−05 | 0.962226 | 0.968688231 | FALSE | FALSE |
| CDC73 | 1 | response | Inf | 1 | 1 | FALSE | FALSE |
| CDH1 | 6 | TMB | −29.7301 | 0.00360566 | 0.135813193 | FALSE | FALSE |
| CDH1 | 3 | response | 0.667846 | 1 | 1 | FALSE | FALSE |
| CDH2 | 1 | TMB | −27.03 | 0.113957 | 0.408798127 | FALSE | FALSE |
| CDH2 | 0 | response | 0 | 1 | 1 | FALSE | FALSE |
| CDK4 | 2 | TMB | −3.59996 | 0.413533 | 0.753697242 | FALSE | FALSE |
| CDK4 | 2 | response | Inf | 1 | 1 | FALSE | FALSE |
| CDK6 | 5 | TMB | −0.900046 | 0.808321 | 0.92832651 | FALSE | FALSE |
| CDK6 | 4 | response | Inf | 0.574746 | 1 | FALSE | FALSE |
| CDK8 | 2 | TMB | −3.77E−06 | 1 | 1 | FALSE | FALSE |
| CDK8 | 1 | response | 0 | 0.250996 | 0.872612588 | FALSE | FALSE |
| CDKN1B | 6 | TMB | −3.60991 | 0.338032 | 0.68131722 | FALSE | FALSE |
| CDKN1B | 5 | response | 1.34632 | 1 | 1 | FALSE | FALSE |
| CDKN2A | 54 | TMB | −0.899978 | 0.343403 | 0.68131722 | FALSE | TRUE |
| CDKN2A | 44 | response | 1.9556 | 0.130946 | 0.872612588 | FALSE | TRUE |
| CDKN2B | 41 | TMB | −6.38E−05 | 0.795052 | 0.92832651 | FALSE | FALSE |
| CDKN2B | 34 | response | 2.11029 | 0.200236 | 0.872612588 | FALSE | FALSE |
| CEBPA | 2 | TMB | −13.51 | 0.0482635 | 0.39863575 | FALSE | FALSE |
| CEBPA | 1 | response | Inf | 1 | 1 | FALSE | FALSE |
| CHD2 | 2 | TMB | −13.51 | 0.0626281 | 0.408798127 | FALSE | FALSE |
| CHD2 | 1 | response | Inf | 1 | 1 | FALSE | FALSE |
| CHD4 | 1 | TMB | −7.21006 | 0.300198 | 0.646140457 | FALSE | FALSE |
| CHD4 | 1 | response | 0 | 0.250996 | 0.872612588 | FALSE | FALSE |
| CHEK2 | 3 | TMB | −1.79997 | 0.510214 | 0.81554169 | TRUE | FALSE |
| CHEK2 | 3 | response | Inf | 0.574746 | 1 | TRUE | FALSE |
| CREBBP | 30 | TMB | −7.21 | 2.35E−05 | 0.002656438 | FALSE | FALSE |
| CREBBP | 27 | response | 0.441408 | 0.0598306 | 0.872612588 | FALSE | FALSE |
| CRKL | 2 | TMB | 3.60996 | 0.157615 | 0.445262375 | FALSE | FALSE |
| CRKL | 2 | response | Inf | 1 | 1 | FALSE | FALSE |
| CTCF | 2 | TMB | −20.7201 | 0.0265376 | 0.294538267 | FALSE | FALSE |
| CTCF | 2 | response | 0.333324 | 0.439745 | 1 | FALSE | FALSE |
| CTNNB1 | 8 | TMB | −1.79998 | 0.612614 | 0.872346467 | FALSE | FALSE |
| CTNNB1 | 7 | response | 0.436474 | 0.37208 | 1 | FALSE | FALSE |
| CUL3 | 2 | TMB | 1.79994 | 0.74361 | 0.923383846 | FALSE | FALSE |
| CUL3 | 2 | response | Inf | 1 | 1 | FALSE | FALSE |
| CYLD | 1 | TMB | −27.03 | 0.113957 | 0.408798127 | FALSE | FALSE |
| CYLD | 1 | response | 0 | 0.250996 | 0.872612588 | FALSE | FALSE |
| DAXX | 1 | TMB | −27.93 | 0.107343 | 0.408798127 | FALSE | FALSE |
| DAXX | 1 | response | 0 | 0.250996 | 0.872612588 | FALSE | FALSE |
| DICER1 | 3 | TMB | −5.40006 | 0.21188 | 0.529786821 | FALSE | FALSE |
| DICER1 | 3 | response | 0.667846 | 1 | 1 | FALSE | FALSE |
| DNMT3A | 8 | TMB | −1.79996 | 0.630572 | 0.872346467 | FALSE | FALSE |
| DNMT3A | 6 | response | 0.664231 | 0.642647 | 1 | FALSE | FALSE |
| EGFR | 11 | TMB | 0.900018 | 0.619994 | 0.872346467 | FALSE | FALSE |
| EGFR | 10 | response | 3.10714 | 0.458956 | 1 | FALSE | FALSE |
| EMSY | 1 | TMB | 1.79997 | 0.644251 | 0.872346467 | FALSE | FALSE |
| EMSY | 1 | response | Inf | 1 | 1 | FALSE | FALSE |
| EP300 | 16 | TMB | −2.70004 | 0.154497 | 0.445262375 | FALSE | FALSE |
| EP300 | 11 | response | 0.889329 | 1 | 1 | FALSE | FALSE |
| EPHA3 | 1 | TMB | 2.69992 | 0.462896 | 0.798583939 | FALSE | FALSE |
| EPHA3 | 1 | response | 0 | 0.250996 | 0.872612588 | FALSE | FALSE |
| EPHA6 | 2 | TMB | −1.80005 | 0.785188 | 0.92832651 | FALSE | FALSE |
| EPHA6 | 1 | response | 0 | 0.250996 | 0.872612588 | FALSE | FALSE |
| EPHA7 | 1 | TMB | −23.42 | 0.125204 | 0.416119176 | FALSE | FALSE |
| EPHA7 | 0 | response | 0 | 1 | 1 | FALSE | FALSE |
| EPHB1 | 2 | TMB | 0.90002 | 0.64461 | 0.872346467 | FALSE | FALSE |
| EPHB1 | 2 | response | Inf | 1 | 1 | FALSE | FALSE |
| ERBB2 | 31 | TMB | −2.7 | 0.0624137 | 0.408798127 | FALSE | FALSE |
| ERBB2 | 28 | response | 0.819104 | 0.647802 | 1 | FALSE | FALSE |
| ERBB3 | 18 | TMB | −1.80996 | 0.222186 | 0.529786821 | FALSE | FALSE |
| ERBB3 | 16 | response | 0.403958 | 0.130846 | 0.872612588 | FALSE | FALSE |
| ERBB4 | 3 | TMB | −8.10995 | 0.0665214 | 0.408798127 | FALSE | FALSE |
| ERBB4 | 2 | response | 0.333324 | 0.439745 | 1 | FALSE | FALSE |

TABLE 12-continued

Mutation status of single genes and association with response and TMB

| Gene | n mutant | category | estimate | p | p (adj.) | In DDR | In CCReg |
|---|---|---|---|---|---|---|---|
| ERRFI1 | 1 | TMB | −40.54 | 0.0915622 | 0.408798127 | FALSE | FALSE |
| ERRFI1 | 1 | response | 0 | 0.250996 | 0.872612588 | FALSE | FALSE |
| EZH2 | 1 | TMB | −13.51 | 0.1571 | 0.445262375 | FALSE | FALSE |
| EZH2 | 1 | response | Inf | 1 | 1 | FALSE | FALSE |
| FAM123B | 1 | TMB | −18.0201 | 0.137297 | 0.437029887 | FALSE | FALSE |
| FAM123B | 1 | response | 0 | 0.250996 | 0.872612588 | FALSE | FALSE |
| FANCA | 1 | TMB | −29.73 | 0.0998104 | 0.408798127 | TRUE | FALSE |
| FANCA | 1 | response | 0 | 0.250996 | 0.872612588 | TRUE | FALSE |
| FANCC | 1 | TMB | 3.60996 | 0.319946 | 0.668246752 | TRUE | FALSE |
| FANCC | 1 | response | Inf | 1 | 1 | TRUE | FALSE |
| FANCD2 | 1 | TMB | −13.51 | 0.1571 | 0.445262375 | TRUE | FALSE |
| FANCD2 | 1 | response | Inf | 1 | 1 | TRUE | FALSE |
| FANCI | 1 | TMB | −6.30005 | 0.355732 | 0.68131722 | FALSE | FALSE |
| FANCI | 1 | response | Inf | 1 | 1 | FALSE | FALSE |
| FAS | 2 | TMB | −10.81 | 0.0720309 | 0.408798127 | FALSE | FALSE |
| FAS | 1 | response | Inf | 1 | 1 | FALSE | FALSE |
| FAT1 | 11 | TMB | −0.900028 | 0.602166 | 0.872346467 | FALSE | FALSE |
| FAT1 | 9 | response | 0.404735 | 0.234402 | 0.872612588 | FALSE | FALSE |
| FBXW7 | 13 | TMB | −12.61 | 0.000827519 | 0.046754824 | FALSE | TRUE |
| FBXW7 | 12 | response | 0.220239 | 0.0125031 | 0.86158545 | FALSE | TRUE |
| FGF10 | 17 | TMB | −6.77E−05 | 0.872111 | 0.938081009 | FALSE | FALSE |
| FGF10 | 12 | response | 0.450284 | 0.182862 | 0.872612588 | FALSE | FALSE |
| FGF14 | 3 | TMB | −3.59994 | 0.501442 | 0.81554169 | FALSE | FALSE |
| FGF14 | 3 | response | 0.164576 | 0.156242 | 0.872612588 | FALSE | FALSE |
| FGF19 | 20 | TMB | 0.89991 | 0.670271 | 0.894242118 | FALSE | FALSE |
| FGF19 | 16 | response | 1.48364 | 0.767315 | 1 | FALSE | FALSE |
| FGF23 | 1 | TMB | 4.50997 | 0.222643 | 0.529786821 | FALSE | FALSE |
| FGF23 | 0 | response | 0 | 1 | 1 | FALSE | FALSE |
| FGF3 | 22 | TMB | 0.900045 | 0.471973 | 0.802974602 | FALSE | FALSE |
| FGF3 | 18 | response | 1.18599 | 1 | 1 | FALSE | FALSE |
| FGF4 | 13 | TMB | 1.80002 | 0.256311 | 0.585114 | FALSE | FALSE |
| FGF4 | 10 | response | 3.10714 | 0.458956 | 1 | FALSE | FALSE |
| FGF6 | 2 | TMB | 4.51001 | 0.0638199 | 0.408798127 | FALSE | FALSE |
| FGF6 | 0 | response | 0 | 1 | 1 | FALSE | FALSE |
| FGFR1 | 7 | TMB | −2.69998 | 0.311112 | 0.663314264 | FALSE | FALSE |
| FGFR1 | 7 | response | 0.126038 | 0.0119594 | 0.86158545 | FALSE | FALSE |
| FGFR2 | 3 | TMB | −0.899953 | 0.797003 | 0.92832651 | FALSE | FALSE |
| FGFR2 | 3 | response | 0.667846 | 1 | 1 | FALSE | FALSE |
| FGFR3 | 56 | TMB | −5.97E−05 | 0.84819 | 0.92832651 | FALSE | FALSE |
| FGFR3 | 50 | response | 0.829608 | 0.588823 | 1 | FALSE | FALSE |
| FLCN | 3 | TMB | −1.80006 | 0.458804 | 0.798583939 | FALSE | FALSE |
| FLCN | 3 | response | 0.667846 | 1 | 1 | FALSE | FALSE |
| FLT3 | 1 | TMB | 1.79997 | 0.644251 | 0.872346467 | FALSE | FALSE |
| FLT3 | 0 | response | 0 | 1 | 1 | FALSE | FALSE |
| FOXP1 | 7 | TMB | 1.79994 | 0.395267 | 0.732215918 | FALSE | FALSE |
| FOXP1 | 7 | response | 2.03921 | 0.683488 | 1 | FALSE | FALSE |
| FRS2 | 23 | TMB | −0.899976 | 0.639385 | 0.872346467 | FALSE | FALSE |
| FRS2 | 19 | response | 0.42895 | 0.0970036 | 0.872612588 | FALSE | FALSE |
| FUBP1 | 2 | TMB | 3.6 | 0.504942 | 0.81554169 | FALSE | FALSE |
| FUBP1 | 2 | response | Inf | 1 | 1 | FALSE | FALSE |
| GATA1 | 1 | TMB | 1.79997 | 0.644251 | 0.872346467 | FALSE | FALSE |
| GATA1 | 1 | response | Inf | 1 | 1 | FALSE | FALSE |
| GATA2 | 1 | TMB | −3.60E+00 | 0.561803 | 0.852130725 | FALSE | FALSE |
| GATA2 | 1 | response | Inf | 1 | 1 | FALSE | FALSE |
| GATA3 | 3 | TMB | 1.80E+00 | 0.597378 | 0.872346467 | FALSE | FALSE |
| GATA3 | 3 | response | 0.667846 | 1 | 1 | FALSE | FALSE |
| GATA4 | 1 | TMB | 2.69992 | 0.462896 | 0.798583939 | FALSE | FALSE |
| GATA4 | 1 | response | 0.00E+00 | 0.250996 | 0.872612588 | FALSE | FALSE |
| GATA6 | 3 | TMB | 1.80001 | 0.51242 | 0.81554169 | FALSE | FALSE |
| GATA6 | 2 | response | 0.333324 | 0.439745 | 1 | FALSE | FALSE |
| GNA13 | 3 | TMB | −3.59998 | 0.525757 | 0.825146403 | FALSE | FALSE |
| GNA13 | 2 | response | Inf | 1 | 1 | FALSE | FALSE |
| GNAS | 6 | TMB | 1.80005 | 0.322296 | 0.668246752 | FALSE | FALSE |
| GNAS | 6 | response | 0.32612 | 0.168613 | 0.872612588 | FALSE | FALSE |
| GPR124 | 1 | TMB | 0.899972 | 0.854389 | 0.92832651 | FALSE | FALSE |
| GPR124 | 0 | response | 0.00E+00 | 1 | 1 | FALSE | FALSE |
| GRIN2A | 1 | TMB | 0.899972 | 0.854389 | 0.92832651 | FALSE | FALSE |
| GRIN2A | 1 | response | Inf | 1 | 1 | FALSE | FALSE |
| HGF | 1 | TMB | −42.34 | 0.089309 | 0.408798127 | FALSE | FALSE |
| HGF | 0 | response | 0 | 1 | 1 | FALSE | FALSE |
| HNF1A | 2 | TMB | −18.02 | 0.0335033 | 0.3433731 | FALSE | FALSE |
| HNF1A | 2 | response | 0.333324 | 0.439745 | 1 | FALSE | FALSE |
| HRAS | 12 | TMB | 0.899988 | 0.62817 | 0.872346467 | FALSE | FALSE |
| HRAS | 11 | response | 1.53E+00 | 0.735541 | 1 | FALSE | FALSE |
| IGF1 | 2 | TMB | −5.39992 | 0.284939 | 0.631335431 | FALSE | FALSE |

TABLE 12-continued

| Gene | n mutant | category | estimate | p | p (adj.) | In DDR | In CCReg |
|---|---|---|---|---|---|---|---|
| Mutation status of single genes and association with response and TMB | | | | | | | |
| IGF1 | 2 | response | Inf | 1 | 1 | FALSE | FALSE |
| IGF2R | 1 | TMB | −27.03 | 0.113957 | 0.408798127 | FALSE | FALSE |
| IGF2R | 1 | response | 0 | 0.250996 | 0.872612588 | FALSE | FALSE |
| IKBKE | 1 | TMB | 2.70E+00 | 0.462896 | 0.798583939 | FALSE | FALSE |
| IKBKE | 0 | response | 0 | 1 | 1 | FALSE | FALSE |
| INPP4B | 1 | TMB | −5.05E+01 | 0.0871006 | 0.408798127 | FALSE | FALSE |
| INPP4B | 1 | response | 0.00E+00 | 0.250996 | 0.872612588 | FALSE | FALSE |
| IRS2 | 5 | TMB | −2.70008 | 0.367558 | 0.698051328 | FALSE | FALSE |
| IRS2 | 5 | response | 4.96E−01 | 0.601863 | 1 | FALSE | FALSE |
| JAK1 | 2 | TMB | −2.43E+01 | 0.0232944 | 0.292474133 | FALSE | FALSE |
| JAK1 | 2 | response | 0.00E+00 | 0.062247 | 0.872612588 | FALSE | FALSE |
| JAK2 | 3 | TMB | 1.81E+00 | 0.519066 | 0.82034207 | FALSE | FALSE |
| JAK2 | 2 | response | 3.33E−01 | 0.439745 | 1 | FALSE | FALSE |
| JUN | 1 | TMB | −6.30E+00 | 0.355732 | 0.68131722 | FALSE | FALSE |
| JUN | 1 | response | Inf | 1 | 1 | FALSE | FALSE |
| KDM5A | 1 | TMB | 7.21E+00 | 0.0998104 | 0.408798127 | FALSE | FALSE |
| KDM5A | 1 | response | Inf | 1 | 1 | FALSE | FALSE |
| KDM5C | 4 | TMB | −6.30E+00 | 0.260724 | 0.586228337 | FALSE | FALSE |
| KDM5C | 4 | response | 3.30E−01 | 0.262556 | 0.872612588 | FALSE | FALSE |
| KDM6A | 55 | TMB | −1.8 | 0.121569 | 0.416119176 | FALSE | FALSE |
| KDM6A | 47 | response | 0.515273 | 0.0624163 | 0.872612588 | FALSE | FALSE |
| KDR | 2 | TMB | 0.899949 | 0.896573 | 0.938081009 | FALSE | FALSE |
| KDR | 1 | response | 0 | 0.250996 | 0.872612588 | FALSE | FALSE |
| KEAP1 | 1 | TMB | −27.03 | 0.113957 | 0.408798127 | FALSE | FALSE |
| KEAP1 | 1 | response | 0 | 0.250996 | 0.872612588 | FALSE | FALSE |
| KEL | 2 | TMB | −11.7101 | 0.088666 | 0.408798127 | FALSE | FALSE |
| KEL | 1 | response | 0 | 0.250996 | 0.872612588 | FALSE | FALSE |
| KIT | 3 | TMB | 3.51E−06 | 0.939854 | 0.961117665 | FALSE | FALSE |
| KIT | 2 | response | 0.333324 | 0.439745 | 1 | FALSE | FALSE |
| KRAS | 6 | TMB | 0.900048 | 0.571685 | 0.861338733 | FALSE | FALSE |
| KRAS | 5 | response | 1.34632 | 1 | 1 | FALSE | FALSE |
| LRP1B | 10 | TMB | −9.01002 | 0.00902982 | 0.17006161 | FALSE | FALSE |
| LRP1B | 9 | response | 0.155516 | 0.00896804 | 0.86158545 | FALSE | FALSE |
| LRP6 | 1 | TMB | −27.03 | 0.113957 | 0.408798127 | FALSE | FALSE |
| LRP6 | 1 | response | 0 | 0.250996 | 0.872612588 | FALSE | FALSE |
| LYN | 4 | TMB | −5.79284 | 0.261987 | 0.586228337 | FALSE | FALSE |
| LYN | 4 | response | Inf | 0.574746 | 1 | FALSE | FALSE |
| LZTR1 | 1 | TMB | −18.0201 | 0.137297 | 0.437029887 | FALSE | FALSE |
| LZTR1 | 1 | response | 0 | 0.250996 | 0.872612588 | FALSE | FALSE |
| MAGI2 | 2 | TMB | −0.899977 | 0.811092 | 0.92832651 | FALSE | FALSE |
| MAGI2 | 2 | response | Inf | 1 | 1 | FALSE | FALSE |
| MAP2K4 | 1 | TMB | −12.61 | 0.171459 | 0.45461214 | FALSE | FALSE |
| MAP2K4 | 1 | response | Inf | 1 | 1 | FALSE | FALSE |
| MAP3K1 | 2 | TMB | −9.91004 | 0.0878833 | 0.408798127 | FALSE | FALSE |
| MAP3K1 | 2 | response | 0.333324 | 0.439745 | 1 | FALSE | FALSE |
| MAP3K13 | 1 | TMB | −12.61 | 0.171459 | 0.45461214 | FALSE | FALSE |
| MAP3K13 | 1 | response | Inf | 1 | 1 | FALSE | FALSE |
| MCL1 | 8 | TMB | −4.49997 | 0.106906 | 0.408798127 | FALSE | FALSE |
| MCL1 | 7 | response | 0.833937 | 1 | 1 | FALSE | FALSE |
| MDM2 | 25 | TMB | −0.89997 | 0.54233 | 0.843650313 | FALSE | TRUE |
| MDM2 | 20 | response | 0.470372 | 0.114587 | 0.872612588 | FALSE | TRUE |
| MDM4 | 1 | TMB | −6.30005 | 0.355732 | 0.68131722 | FALSE | FALSE |
| MDM4 | 1 | response | Inf | 1 | 1 | FALSE | FALSE |
| MEN1 | 3 | TMB | −1.80996 | 0.546091 | 0.843650313 | FALSE | FALSE |
| MEN1 | 2 | response | 0 | 0.062247 | 0.872612588 | FALSE | FALSE |
| MET | 2 | TMB | −1.80003 | 0.830658 | 0.92832651 | FALSE | FALSE |
| MET | 0 | response | 0 | 1 | 1 | FALSE | FALSE |
| MITF | 1 | TMB | 4.50997 | 0.222643 | 0.529786821 | FALSE | FALSE |
| MITF | 1 | response | Inf | 1 | 1 | FALSE | FALSE |
| MLL2 | 63 | TMB | −0.899944 | 0.501383 | 0.81554169 | FALSE | FALSE |
| MLL2 | 53 | response | 1.18463 | 0.723338 | 1 | FALSE | FALSE |
| MLL3 | 4 | TMB | −21.6299 | 0.00550322 | 0.150903898 | FALSE | FALSE |
| MLL3 | 3 | response | 0 | 0.0152493 | 0.86158545 | FALSE | FALSE |
| MPL | 1 | TMB | −5.40005 | 0.420747 | 0.75467319 | FALSE | FALSE |
| MPL | 1 | response | 0 | 0.250996 | 0.872612588 | FALSE | FALSE |
| MSH2 | 4 | TMB | −25.2199 | 0.00171259 | 0.077409068 | TRUE | FALSE |
| MSH2 | 3 | response | 0.667846 | 1 | 1 | TRUE | FALSE |
| MSH6 | 6 | TMB | −0.899991 | 0.720075 | 0.914252528 | TRUE | FALSE |
| MSH6 | 5 | response | 1.34632 | 1 | 1 | TRUE | FALSE |
| MST1R | 1 | TMB | 0.899972 | 0.854389 | 0.92832651 | FALSE | FALSE |
| MST1R | 1 | response | Inf | 1 | 1 | FALSE | FALSE |
| MTOR | 3 | TMB | −4.51002 | 0.183279 | 0.475640114 | FALSE | FALSE |
| MTOR | 2 | response | 0.333324 | 0.439745 | 1 | FALSE | FALSE |
| MUTYH | 3 | TMB | −2.69997 | 0.460887 | 0.798583939 | TRUE | FALSE |
| MUTYH | 3 | response | 0.667846 | 1 | 1 | TRUE | FALSE |

TABLE 12-continued

| Mutation status of single genes and association with response and TMB | | | | | | | |
|---|---|---|---|---|---|---|---|
| Gene | n mutant | category | estimate | p | p (adj.) | In DDR | In CCReg |
| MYC | 13 | TMB | −1.07E−05 | 0.894618 | 0.938081009 | FALSE | FALSE |
| MYC | 10 | response | 1.354 | 1 | 1 | FALSE | FALSE |
| MYCL1 | 9 | TMB | −1.8 | 0.472547 | 0.802974602 | FALSE | FALSE |
| MYCL1 | 9 | response | 0.660537 | 0.69521 | 1 | FALSE | FALSE |
| MYCN | 5 | TMB | −9.90994 | 0.0702785 | 0.408798127 | FALSE | FALSE |
| MYCN | 5 | response | 0.216728 | 0.10244 | 0.872612588 | FALSE | FALSE |
| MYST3 | 7 | TMB | −3.59996 | 0.185205 | 0.475640114 | FALSE | FALSE |
| MYST3 | 6 | response | 0.664231 | 0.642647 | 1 | FALSE | FALSE |
| NBN | 1 | TMB | −23.42 | 0.125204 | 0.416119176 | FALSE | FALSE |
| NBN | 1 | response | 0 | 0.250996 | 0.872612588 | FALSE | FALSE |
| NCOR1 | 10 | TMB | −7.20992 | 0.0119391 | 0.192731186 | FALSE | FALSE |
| NCOR1 | 9 | response | 1.17881 | 1 | 1 | FALSE | FALSE |
| NF1 | 6 | TMB | −5.39999 | 0.0883754 | 0.408798127 | FALSE | FALSE |
| NF1 | 5 | response | 0.496176 | 0.601863 | 1 | FALSE | FALSE |
| NF2 | 6 | TMB | −0.900005 | 0.71461 | 0.912439887 | FALSE | FALSE |
| NF2 | 4 | response | 0.329736 | 0.262556 | 0.872612588 | FALSE | FALSE |
| NFE2L2 | 2 | TMB | 1.80004 | 0.394637 | 0.732215918 | FALSE | FALSE |
| NFE2L2 | 2 | response | 0.333324 | 0.439745 | 1 | FALSE | FALSE |
| NFKBIA | 2 | TMB | 0.90002 | 0.64461 | 0.872346467 | FALSE | FALSE |
| NFKBIA | 2 | response | Inf | 1 | 1 | FALSE | FALSE |
| NKX2−1 | 6 | TMB | 0.899935 | 0.615534 | 0.872346467 | FALSE | FALSE |
| NKX2−1 | 6 | response | Inf | 0.341617 | 1 | FALSE | FALSE |
| NOTCH1 | 4 | TMB | −1.79998 | 0.690117 | 0.900459333 | FALSE | FALSE |
| NOTCH1 | 4 | response | 1.00538 | 1 | 1 | FALSE | FALSE |
| NOTCH2 | 4 | TMB | 3.16E−06 | 0.884086 | 0.938081009 | FALSE | FALSE |
| NOTCH2 | 3 | response | 0.667846 | 1 | 1 | FALSE | FALSE |
| NOTCH3 | 2 | TMB | 1.79999 | 0.510315 | 0.81554169 | FALSE | FALSE |
| NOTCH3 | 2 | response | Inf | 1 | 1 | FALSE | FALSE |
| NOTCH4 | 5 | TMB | −3.17E−05 | 0.934137 | 0.960632518 | FALSE | FALSE |
| NOTCH4 | 3 | response | 0.667846 | 1 | 1 | FALSE | FALSE |
| NRAS | 2 | TMB | −13.52 | 0.059729 | 0.408798127 | FALSE | FALSE |
| NRAS | 2 | response | 0 | 0.062247 | 0.872612588 | FALSE | FALSE |
| NTRK1 | 1 | TMB | −6.30005 | 0.355732 | 0.68131722 | FALSE | FALSE |
| NTRK1 | 1 | response | 0 | 0.250996 | 0.872612588 | FALSE | FALSE |
| NTRK3 | 1 | TMB | 6.30992 | 0.125204 | 0.416119176 | FALSE | FALSE |
| NTRK3 | 1 | response | Inf | 1 | 1 | FALSE | FALSE |
| NUP93 | 4 | TMB | −1.79997 | 0.67266 | 0.894242118 | FALSE | FALSE |
| NUP93 | 3 | response | 0.667846 | 1 | 1 | FALSE | FALSE |
| PALB2 | 3 | TMB | −1.80003 | 0.621392 | 0.872346467 | TRUE | FALSE |
| PALB2 | 3 | response | 0.667846 | 1 | 1 | TRUE | FALSE |
| PARK2 | 1 | TMB | −13.51 | 0.1571 | 0.445262375 | FALSE | FALSE |
| PARK2 | 1 | response | Inf | 1 | 1 | FALSE | FALSE |
| PARP4 | 1 | TMB | 5.40997 | 0.164161 | 0.452443732 | FALSE | FALSE |
| PARP4 | 1 | response | Inf | 1 | 1 | FALSE | FALSE |
| PAX5 | 3 | TMB | −2.78E−05 | 0.92622 | 0.960209725 | FALSE | FALSE |
| PAX5 | 2 | response | Inf | 1 | 1 | FALSE | FALSE |
| PBRM1 | 5 | TMB | −9.01005 | 0.222102 | 0.529786821 | FALSE | FALSE |
| PBRM1 | 4 | response | 0.108148 | 0.0499291 | 0.872612588 | FALSE | FALSE |
| PDCD1LG2 | 4 | TMB | 0.910011 | 0.701112 | 0.905312341 | FALSE | FALSE |
| PDCD1LG2 | 3 | response | 0.667846 | 1 | 1 | FALSE | FALSE |
| PDGFRA | 2 | TMB | 0.899949 | 0.896573 | 0.938081009 | FALSE | FALSE |
| PDGFRA | 1 | response | 0 | 0.250996 | 0.872612588 | FALSE | FALSE |
| PIK3C2B | 1 | TMB | −6.30005 | 0.355732 | 0.68131722 | FALSE | FALSE |
| PIK3C2B | 1 | response | Inf | 1 | 1 | FALSE | FALSE |
| PIK3CA | 45 | TMB | −0.900037 | 0.297028 | 0.646140457 | FALSE | FALSE |
| PIK3CA | 38 | response | 0.793515 | 0.547066 | 1 | FALSE | FALSE |
| PIK3CB | 1 | TMB | 0.899972 | 0.854389 | 0.92832651 | FALSE | FALSE |
| PIK3CB | 1 | response | Inf | 1 | 1 | FALSE | FALSE |
| PIK3CG | 1 | TMB | −42.34 | 0.089309 | 0.408798127 | FALSE | FALSE |
| PIK3CG | 0 | response | 0 | 1 | 1 | FALSE | FALSE |
| PIK3R1 | 4 | TMB | −7.92E−05 | 0.964402 | 0.968688231 | FALSE | FALSE |
| PIK3R1 | 4 | response | 0.329736 | 0.262556 | 0.872612588 | FALSE | FALSE |
| PIK3R2 | 1 | TMB | −4.50006 | 0.484823 | 0.81554169 | FALSE | FALSE |
| PIK3R2 | 0 | response | 0 | 1 | 1 | FALSE | FALSE |
| PMS2 | 2 | TMB | −28.83 | 0.0208602 | 0.292474133 | TRUE | FALSE |
| PMS2 | 1 | response | 0 | 0.250996 | 0.872612588 | TRUE | FALSE |
| POLE | 1 | TMB | −27.03 | 0.113957 | 0.408798127 | TRUE | FALSE |
| POLE | 1 | response | 0 | 0.250996 | 0.872612588 | TRUE | FALSE |
| PRKCI | 4 | TMB | 4.80E−05 | 0.872354 | 0.938081009 | FALSE | FALSE |
| PRKCI | 3 | response | 0.667846 | 1 | 1 | FALSE | FALSE |
| PRSS8 | 1 | TMB | −9.91006 | 0.229453 | 0.540170604 | FALSE | FALSE |
| PRSS8 | 1 | response | 0 | 0.250996 | 0.872612588 | FALSE | FALSE |
| PTCH2 | 1 | TMB | −29.73 | 0.0998104 | 0.408798127 | FALSE | FALSE |
| PTCH2 | 1 | response | 0 | 0.250996 | 0.872612588 | FALSE | FALSE |
| PTEN | 11 | TMB | −1.81007 | 0.404451 | 0.74313761 | FALSE | FALSE |

TABLE 12-continued

Mutation status of single genes and association with response and TMB

| Gene | n mutant | category | estimate | p | p (adj.) | In DDR | In CCReg |
|---|---|---|---|---|---|---|---|
| PTEN | 8 | response | 0.322416 | 0.111683 | 0.872612588 | FALSE | FALSE |
| PTPN11 | 1 | TMB | −3.60006 | 0.561803 | 0.852130725 | FALSE | FALSE |
| PTPN11 | 1 | response | Inf | 1 | 1 | FALSE | FALSE |
| PTPRD | 3 | TMB | 0.899972 | 0.791712 | 0.92832651 | FALSE | FALSE |
| PTPRD | 2 | response | Inf | 1 | 1 | FALSE | FALSE |
| RAD50 | 3 | TMB | −7.21005 | 0.0779225 | 0.408798127 | FALSE | FALSE |
| RAD50 | 3 | response | Inf | 0.574746 | 1 | FALSE | FALSE |
| RAD51 | 1 | TMB | −2.35E−05 | 0.962226 | 0.968688231 | FALSE | FALSE |
| RAD51 | 1 | response | Inf | 1 | 1 | FALSE | FALSE |
| RAD51C | 2 | TMB | −1.81006 | 0.656689 | 0.88340306 | TRUE | FALSE |
| RAD51C | 1 | response | 0 | 0.250996 | 0.872612588 | TRUE | FALSE |
| RAF1 | 16 | TMB | 0.900031 | 0.388914 | 0.732215918 | FALSE | FALSE |
| RAF1 | 14 | response | 0.584639 | 0.349916 | 1 | FALSE | FALSE |
| RB1 | 44 | TMB | −1.80008 | 0.108637 | 0.408798127 | FALSE | TRUE |
| RB1 | 38 | response | 0.683208 | 0.316049 | 1 | FALSE | TRUE |
| RBM10 | 12 | TMB | −4.50005 | 0.038652 | 0.3433731 | FALSE | FALSE |
| RBM10 | 10 | response | 0.774318 | 0.715047 | 1 | FALSE | FALSE |
| REL | 2 | TMB | −17.12 | 0.0379235 | 0.3433731 | FALSE | FALSE |
| REL | 2 | response | 0 | 0.062247 | 0.872612588 | FALSE | FALSE |
| RICTOR | 22 | TMB | 2.81E−05 | 0.830895 | 0.92832651 | FALSE | FALSE |
| RICTOR | 16 | response | 0.535247 | 0.242047 | 0.872612588 | FALSE | FALSE |
| RNF43 | 2 | TMB | −27.93 | 0.0220481 | 0.292474133 | FALSE | FALSE |
| RNF43 | 2 | response | 0 | 0.062247 | 0.872612588 | FALSE | FALSE |
| ROS1 | 2 | TMB | −1.80997 | 0.687275 | 0.900459333 | FALSE | FALSE |
| ROS1 | 2 | response | Inf | 1 | 1 | FALSE | FALSE |
| RPA1 | 1 | TMB | 0.899972 | 0.854389 | 0.92832651 | TRUE | FALSE |
| RPA1 | 1 | response | Inf | 1 | 1 | TRUE | FALSE |
| RPTOR | 1 | TMB | −13.51 | 0.1571 | 0.445262375 | FALSE | FALSE |
| RPTOR | 1 | response | Inf | 1 | 1 | FALSE | FALSE |
| RUNX1 | 2 | TMB | −7.20997 | 0.139933 | 0.439234139 | FALSE | FALSE |
| RUNX1 | 2 | response | 0.333324 | 0.439745 | 1 | FALSE | FALSE |
| SDHA | 1 | TMB | −7.21006 | 0.300198 | 0.646140457 | FALSE | FALSE |
| SDHA | 1 | response | Inf | 1 | 1 | FALSE | FALSE |
| SETD2 | 6 | TMB | −6.30994 | 0.0273686 | 0.294538267 | FALSE | FALSE |
| SETD2 | 6 | response | 1.69097 | 1 | 1 | FALSE | FALSE |
| SF3B1 | 7 | TMB | 1.87E−05 | 0.935129 | 0.960632518 | FALSE | FALSE |
| SF3B1 | 3 | response | 0.164576 | 0.156242 | 0.872612588 | FALSE | FALSE |
| SLIT2 | 4 | TMB | 1.80005 | 0.610903 | 0.872346467 | FALSE | FALSE |
| SLIT2 | 3 | response | Inf | 0.574746 | 1 | FALSE | FALSE |
| SMAD2 | 1 | TMB | −36.03 | 0.0950275 | 0.408798127 | FALSE | FALSE |
| SMAD2 | 1 | response | Inf | 1 | 1 | FALSE | FALSE |
| SMAD3 | 1 | TMB | −2.35E−05 | 0.962226 | 0.968688231 | FALSE | FALSE |
| SMAD3 | 1 | response | Inf | 1 | 1 | FALSE | FALSE |
| SMAD4 | 3 | TMB | 4.50999 | 0.0493885 | 0.39863575 | FALSE | FALSE |
| SMAD4 | 2 | response | Inf | 1 | 1 | FALSE | FALSE |
| SMARCA4 | 9 | TMB | −3.61005 | 0.172994 | 0.45461214 | FALSE | FALSE |
| SMARCA4 | 8 | response | 0.547957 | 0.418026 | 1 | FALSE | FALSE |
| SOX10 | 1 | TMB | −2.70008 | 0.640011 | 0.872346467 | FALSE | FALSE |
| SOX10 | 1 | response | Inf | 1 | 1 | FALSE | FALSE |
| SOX2 | 1 | TMB | 3.60996 | 0.319946 | 0.668246752 | FALSE | FALSE |
| SOX2 | 1 | response | Inf | 1 | 1 | FALSE | FALSE |
| SOX9 | 3 | TMB | −1.80001 | 0.49275 | 0.81554169 | FALSE | FALSE |
| SOX9 | 3 | response | Inf | 0.574746 | 1 | FALSE | FALSE |
| SPEN | 4 | TMB | −7.20994 | 0.0704492 | 0.408798127 | FALSE | FALSE |
| SPEN | 2 | response | 0.333324 | 0.439745 | 1 | FALSE | FALSE |
| SPTA1 | 5 | TMB | −0.900026 | 0.806257 | 0.92832651 | FALSE | FALSE |
| SPTA1 | 5 | response | Inf | 0.335003 | 1 | FALSE | FALSE |
| SRC | 1 | TMB | 0.899972 | 0.854389 | 0.92832651 | FALSE | FALSE |
| SRC | 1 | response | Inf | 1 | 1 | FALSE | FALSE |
| STAG2 | 21 | TMB | −2.69996 | 0.222698 | 0.529786821 | FALSE | FALSE |
| STAG2 | 17 | response | 0.591772 | 0.383584 | 1 | FALSE | FALSE |
| STAT4 | 2 | TMB | −0.899977 | 0.811092 | 0.92832651 | FALSE | FALSE |
| STAT4 | 2 | response | 0.333324 | 0.439745 | 1 | FALSE | FALSE |
| STK11 | 2 | TMB | 0.899989 | 0.772323 | 0.92832651 | FALSE | FALSE |
| STK11 | 1 | response | Inf | 1 | 1 | FALSE | FALSE |
| TBX3 | 3 | TMB | −7.21003 | 0.0706912 | 0.408798127 | FALSE | FALSE |
| TBX3 | 2 | response | 0 | 0.062247 | 0.872612588 | FALSE | FALSE |
| TERT | 186 | TMB | −1.80005 | 0.00617139 | 0.150903898 | FALSE | FALSE |
| TERT | 159 | response | 0.991699 | 1 | 1 | FALSE | FALSE |
| TET2 | 5 | TMB | −11.71 | 0.0113234 | 0.192731186 | FALSE | FALSE |
| TET2 | 3 | response | 0.667846 | 1 | 1 | FALSE | FALSE |
| TNFRSF14 | 1 | TMB | 0.899972 | 0.854389 | 0.92832651 | FALSE | FALSE |
| TNFRSF14 | 1 | response | Inf | 1 | 1 | FALSE | FALSE |
| TNKS | 2 | TMB | 1.79999 | 0.629643 | 0.872346467 | FALSE | FALSE |
| TNKS | 2 | response | Inf | 1 | 1 | FALSE | FALSE |

TABLE 12-continued

Mutation status of single genes and association with response and TMB

| Gene | n mutant | category | estimate | p | p (adj.) | In DDR | In CCReg |
|---|---|---|---|---|---|---|---|
| TOP1 | 1 | TMB | 0.899972 | 0.854389 | 0.92832651 | FALSE | FALSE |
| TOP1 | 1 | response | Inf | 1 | 1 | FALSE | FALSE |
| TOP2A | 3 | TMB | −22.52 | 0.00709567 | 0.150903898 | FALSE | FALSE |
| TOP2A | 3 | response | 0.667846 | 1 | 1 | FALSE | FALSE |
| TP53 | 145 | TMB | −2.70001 | 0.000173155 | 0.013044343 | TRUE | TRUE |
| TP53 | 120 | response | 0.720106 | 0.307979 | 1 | TRUE | TRUE |
| TRRAP | 1 | TMB | −13.51 | 0.1571 | 0.445262375 | FALSE | FALSE |
| TRRAP | 1 | response | Inf | 1 | 1 | FALSE | FALSE |
| TSC1 | 19 | TMB | 3.68E−06 | 0.82796 | 0.92832651 | FALSE | FALSE |
| TSC1 | 19 | response | 1.27769 | 0.789154 | 1 | FALSE | FALSE |
| TSC2 | 1 | TMB | 0.899972 | 0.854389 | 0.92832651 | FALSE | FALSE |
| TSC2 | 1 | response | Inf | 1 | 1 | FALSE | FALSE |
| VEGFA | 2 | TMB | 1.81002 | 0.504942 | 0.81554169 | FALSE | FALSE |
| VEGFA | 2 | response | Inf | 1 | 1 | FALSE | FALSE |
| WT1 | 2 | TMB | −6.30991 | 0.254046 | 0.585114 | FALSE | FALSE |
| WT1 | 1 | response | 0 | 0.250996 | 0.872612588 | FALSE | FALSE |
| ZNF217 | 2 | TMB | 0.89999 | 0.791643 | 0.92832651 | FALSE | FALSE |
| ZNF217 | 2 | response | Inf | 1 | 1 | FALSE | FALSE |
| ZNF703 | 17 | TMB | −0.900011 | 0.354452 | 0.68131722 | FALSE | FALSE |
| ZNF703 | 16 | response | 0.535247 | 0.242047 | 0.872612588 | FALSE | FALSE |

Example 3: The TGF-β Axis is Associated with Primary Immune Escape

Figure 1O:
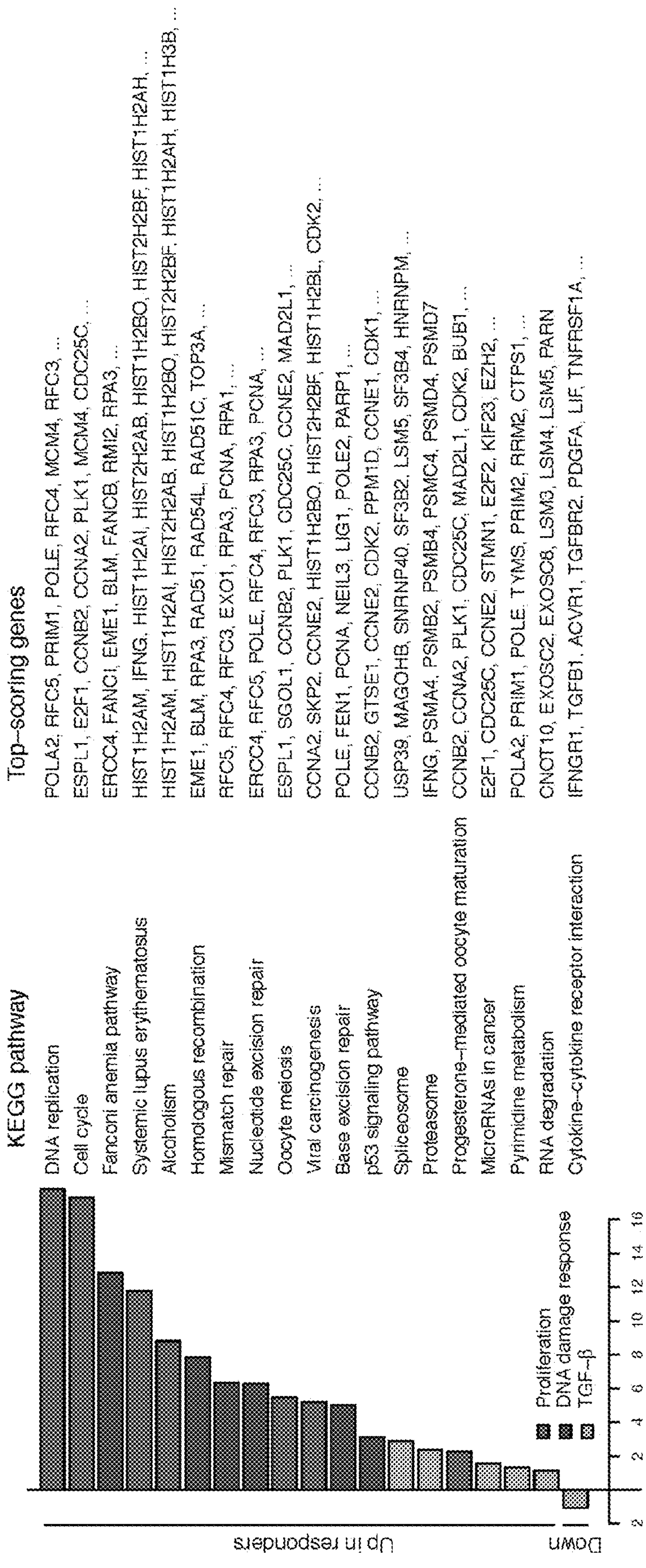
FIG. 1O shows KEGG pathways that are significantly associated with response to atezolizumab. Shown are adjusted $-\log_{10}$ p-values for KEGG pathways significantly (adj. p<0.1) enriched in genes associated with response. Sets inferred to reflect key underlying biological processes are colored: proliferation (turquoise), DDR (magenta), TGF-β signaling (orange). Only the top seven genes per set (ranked by single-gene p-value) are shown. Complete lists of differentially expressed genes are given in Table 3.

Next, we sought to identify any additional features beyond CD8+ T-cell immunity and TMB that were associated with response. Consistent with a positive relationship between proliferation and TMB, gene sets associated with DNA replication, cell cycle, and histones were significantly enriched in responders (FIG. 1O, Table 8). Gene set enrichment analysis also identified the cytokine-cytokine receptor gene set as the sole feature associated with non-response (FIG. 1O, Table 8). Importantly, the most significantly associated genes within this pathway were IFNGR1 and genes involved in the TGF-β signaling pathway, including TGFB1, ACVR1, and TGFBR2. While IFN-γ is known to have favorable effects on anti-tumor immunity, this cytokine is also emerging as a key player in primary resistance to checkpoint therapy and acquired immune escape. In our large cohort of patients with mUC, we observed significantly enhanced expression of IFN-γ in responders, whereas IFNGR1 expression was enriched in non-responders. This is in line with recent studies suggesting that IFN-γ signaling promotes expression of multiple T-cell inhibitory ligands and induces epigenetic mechanisms that suppress T-cells.

Figure 1P:
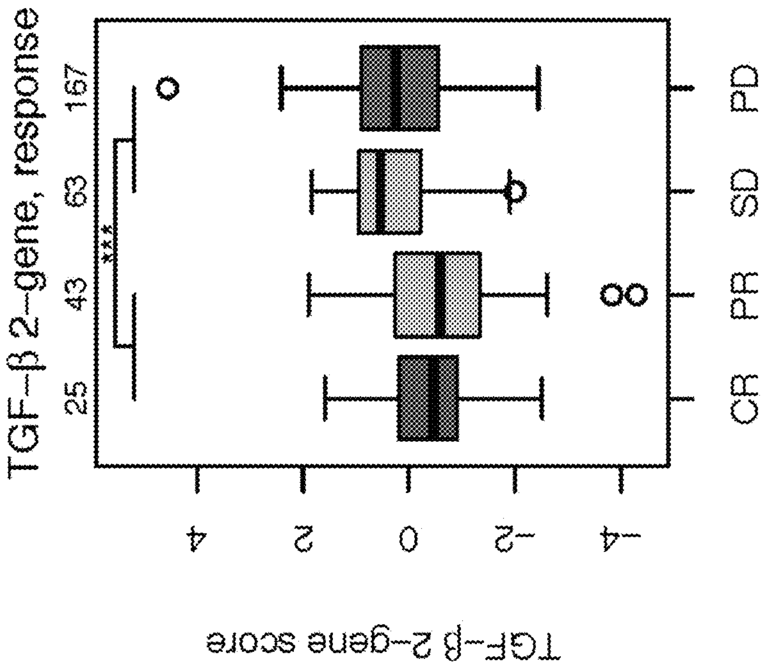
FIG. 1P is a graph showing that the TGF-β 2-gene signature (y-axis) comprised of TGFB1 and TGFBR2 was significantly associated with lack of response to atezolizumab ($p=9.6\times10^{-6}$).
Figure 1Q:
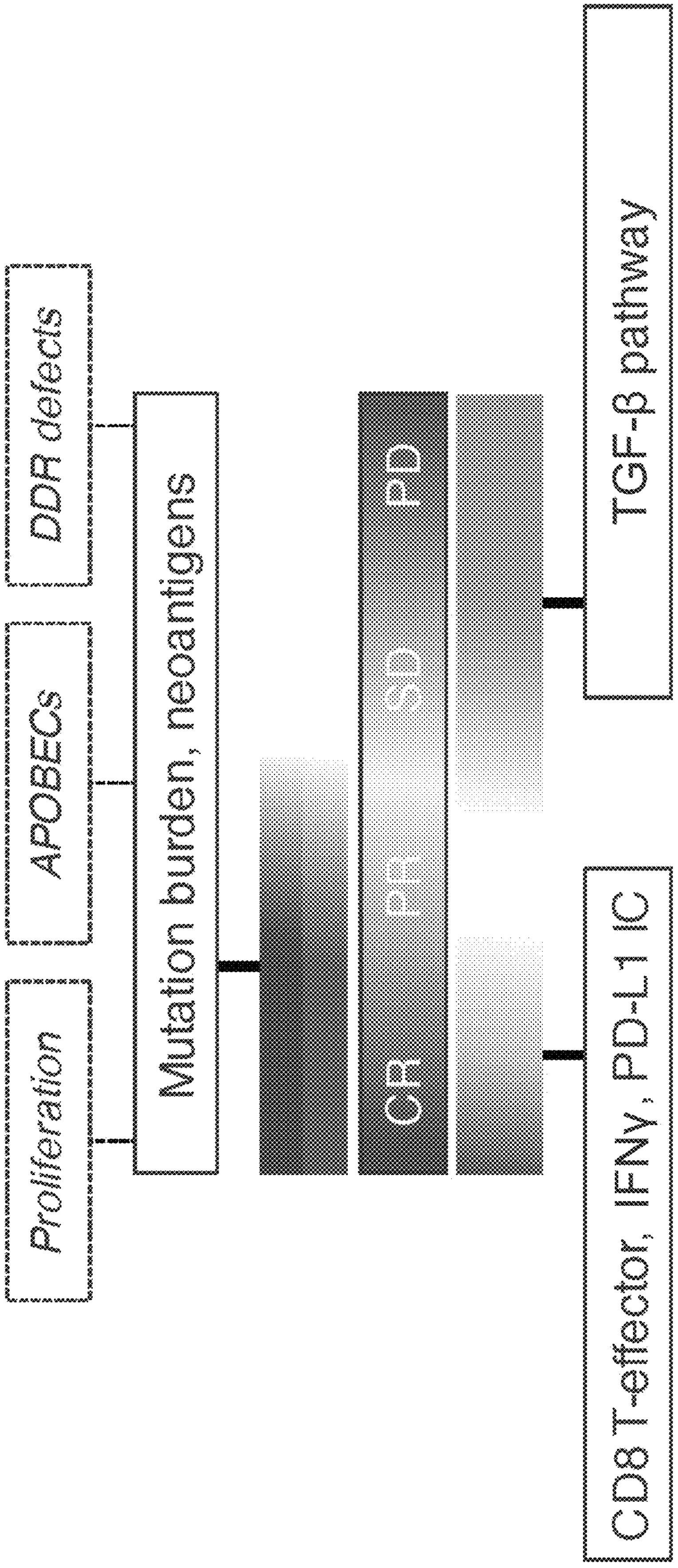
FIG. 1Q is a schematic representation of the relationship between three core axes, assays that interrogate those axes, and patient response.
Figure 1S:
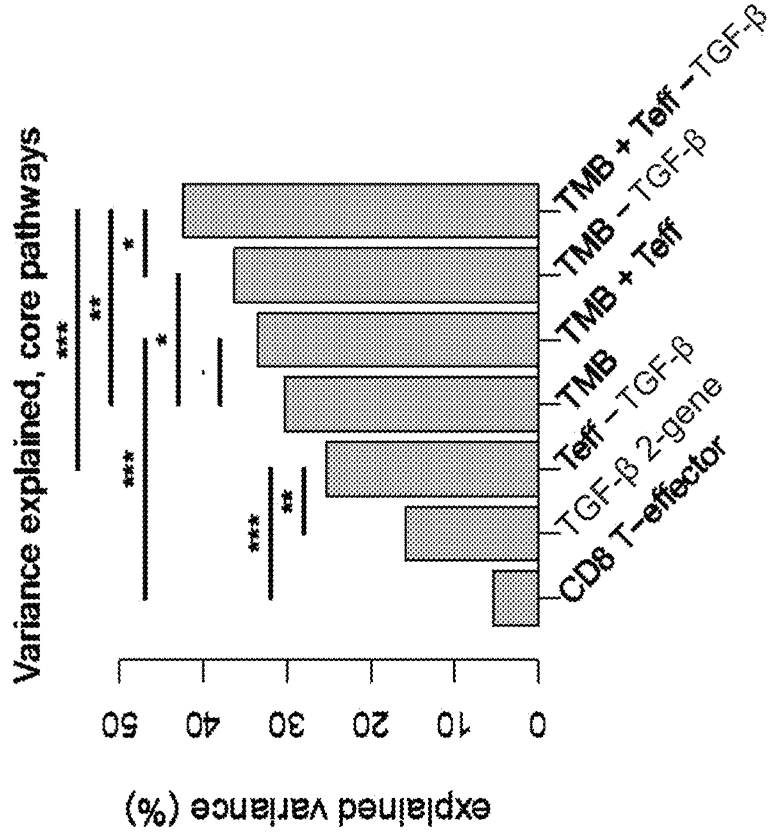
FIG. 1S is a graph showing explained variation in patient response. Generalized linear models were fit using binary response (CR/PR versus SD/PD) as the dependent variable and scores from single input or input combinations (x-axis) as independent variables. Percent explained variance of response is plotted on the y-axis. Comparisons between different models were made via likelihood ratio test; a significant p-value means that the additional variable contributed independent information to the model. The triple model including TMB as well as Teff and TGF-β 2-gene signatures explains 42% of the variance observed in response and significantly improves on all singleton and two-biology models. This shows that all three biologies have non-redundant explanatory value.
Figure 1R:
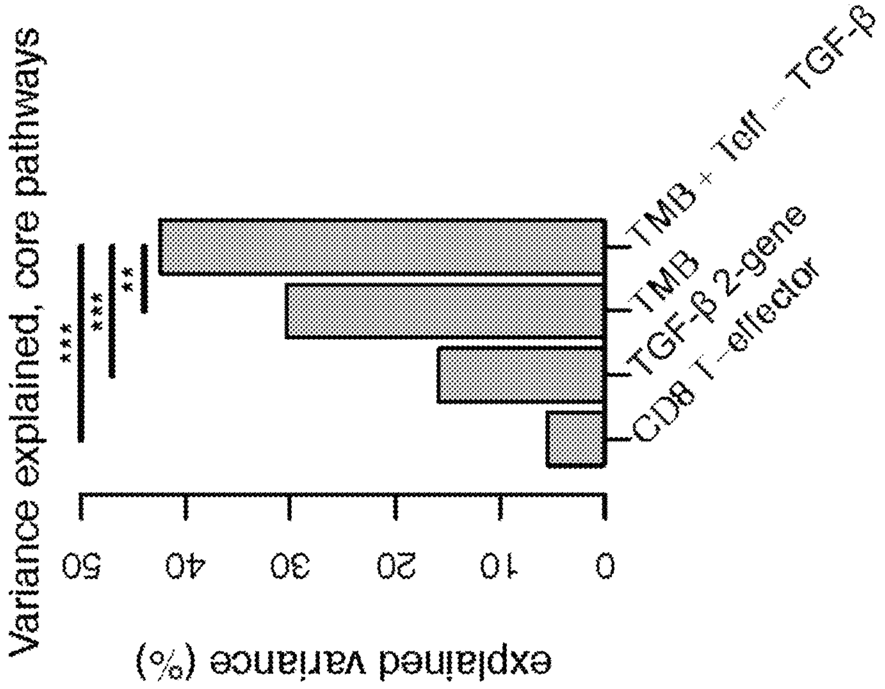
FIG. 1R is a graph showing explained variance in patient response. Generalized linear models were fit using binary response (CR/PR versus SD/PD) as the dependent variable and scores from single input or input combinations (x-axis) as independent variables. Percent explained variance of response is plotted on the y-axis. Comparisons between different models were made via likelihood ratio test. A model that includes both DNA (TMB) and RNA markers (CD8+T-effector (Teff) and TGF-β 2-gene sets) explained 42% of the variance observed in response, and it significantly improved on all singleton models.
Figure 1T:
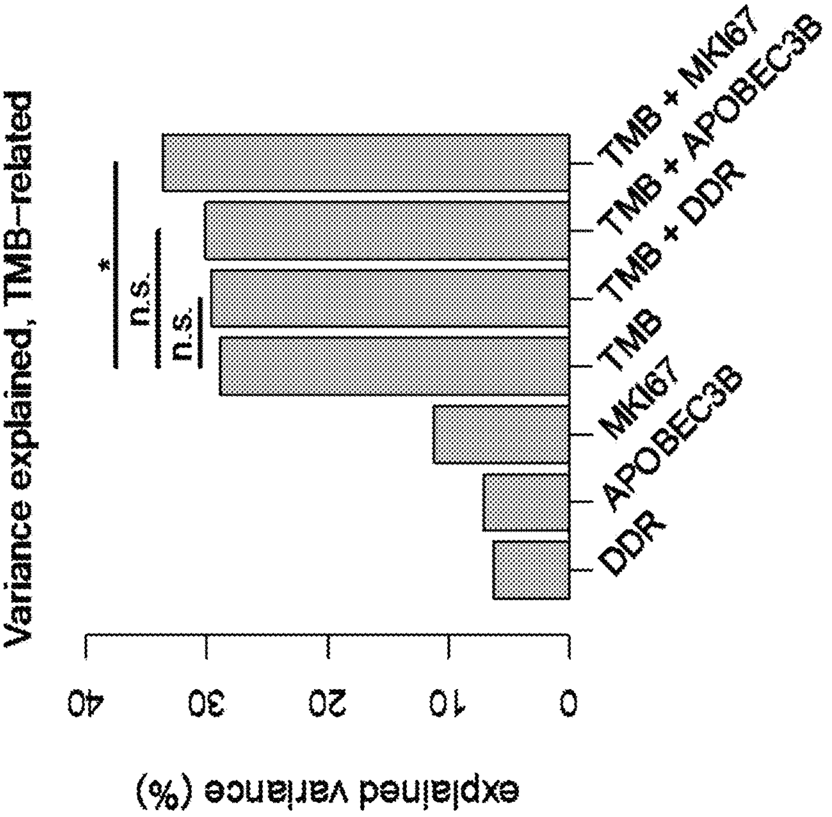
FIG. 1T is a graph showing explained variation in patient response. Generalized linear models were fit using binary response (CR/PR vs. SD/PD) as the dependent variable and scores from single input or input combinations (x-axis) as independent variables. Percent explained variance of response is plotted on the y-axis. Comparisons between different models were made via likelihood ratio test. The association between TMB with response was significantly stronger than that of its proxy measurements (APOBEC3B expression, MKI67 expression or mutation in members of the DDR set). APOBEC3B and DDR gene set mutation provided no additional explanatory information that was independent of direct measurement of TMB. Combining TMB with MKI67 expression did marginally improve on TMB alone, possibly through MKI67's negative association with TFG-β (see FIG. 1H).
Figure 1U:
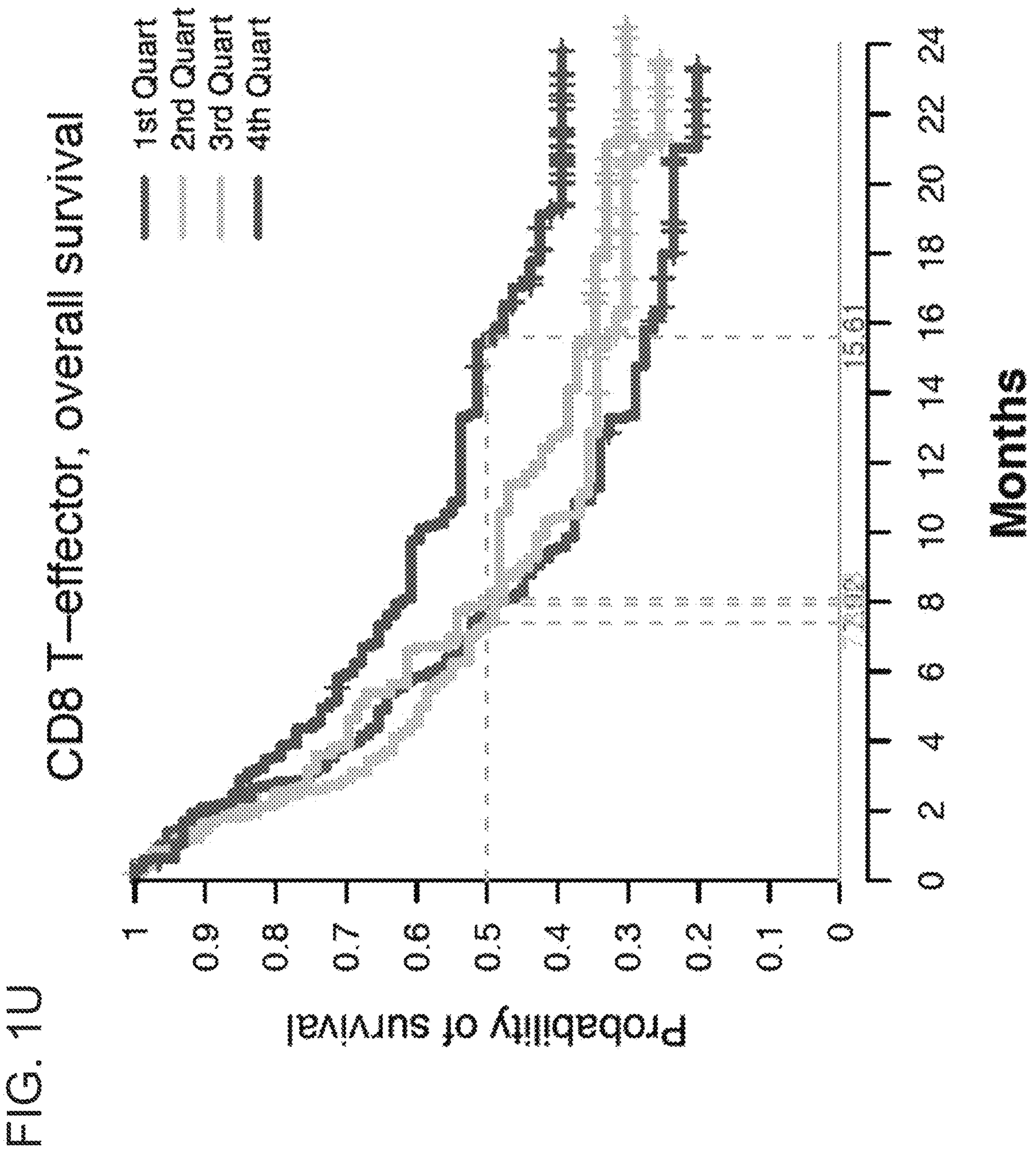
FIG. 1U is a graph showing that Teff signature score quartiles ("quart") were associated with overall survival (OS) (p=0.0092).
Figure 1V:
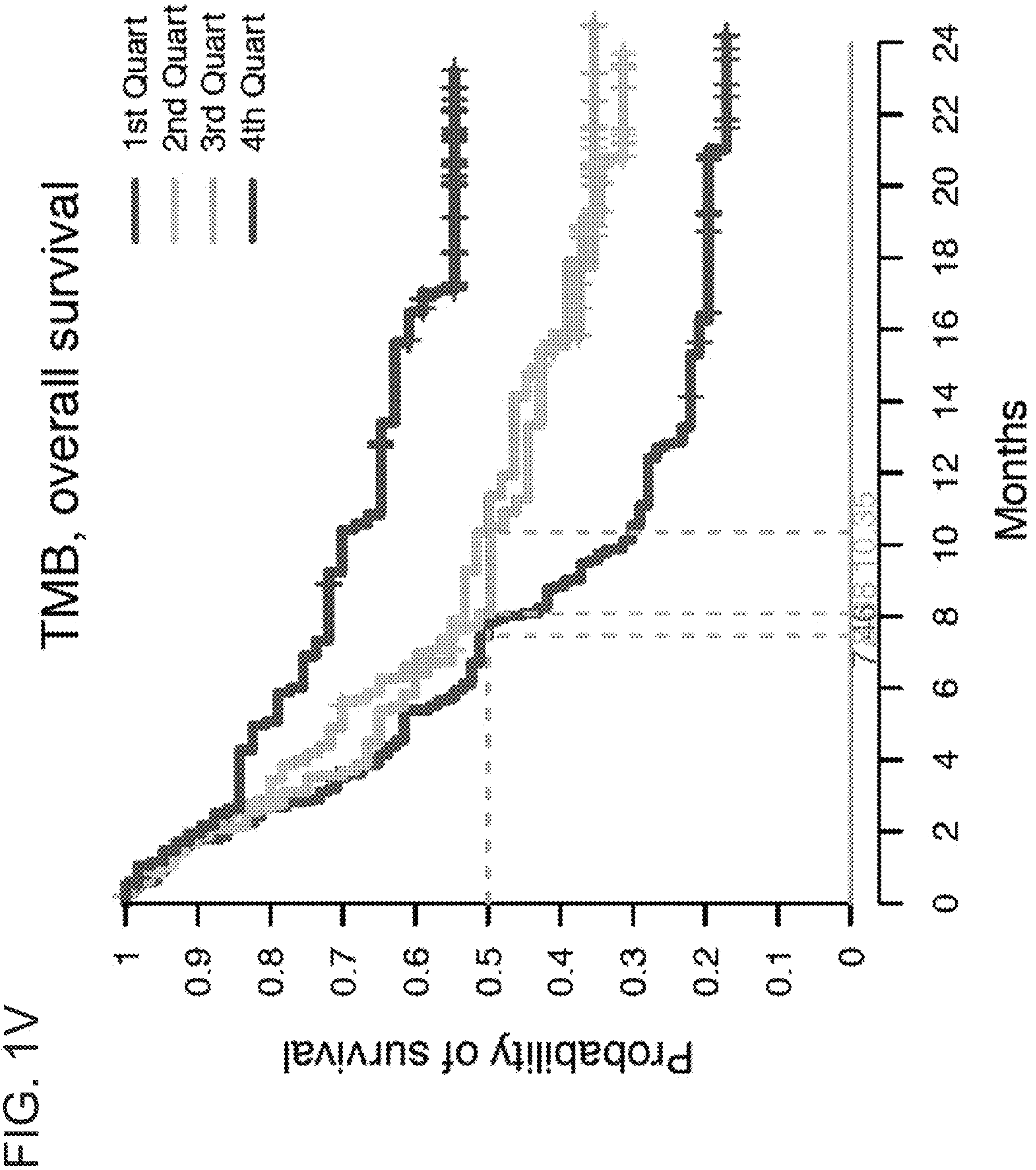
FIG. 1V is a graph showing that TMB was associated with overall survival (OS) (likelihood ratio test $p=2\times10^{-5}$).
Figure 1W:
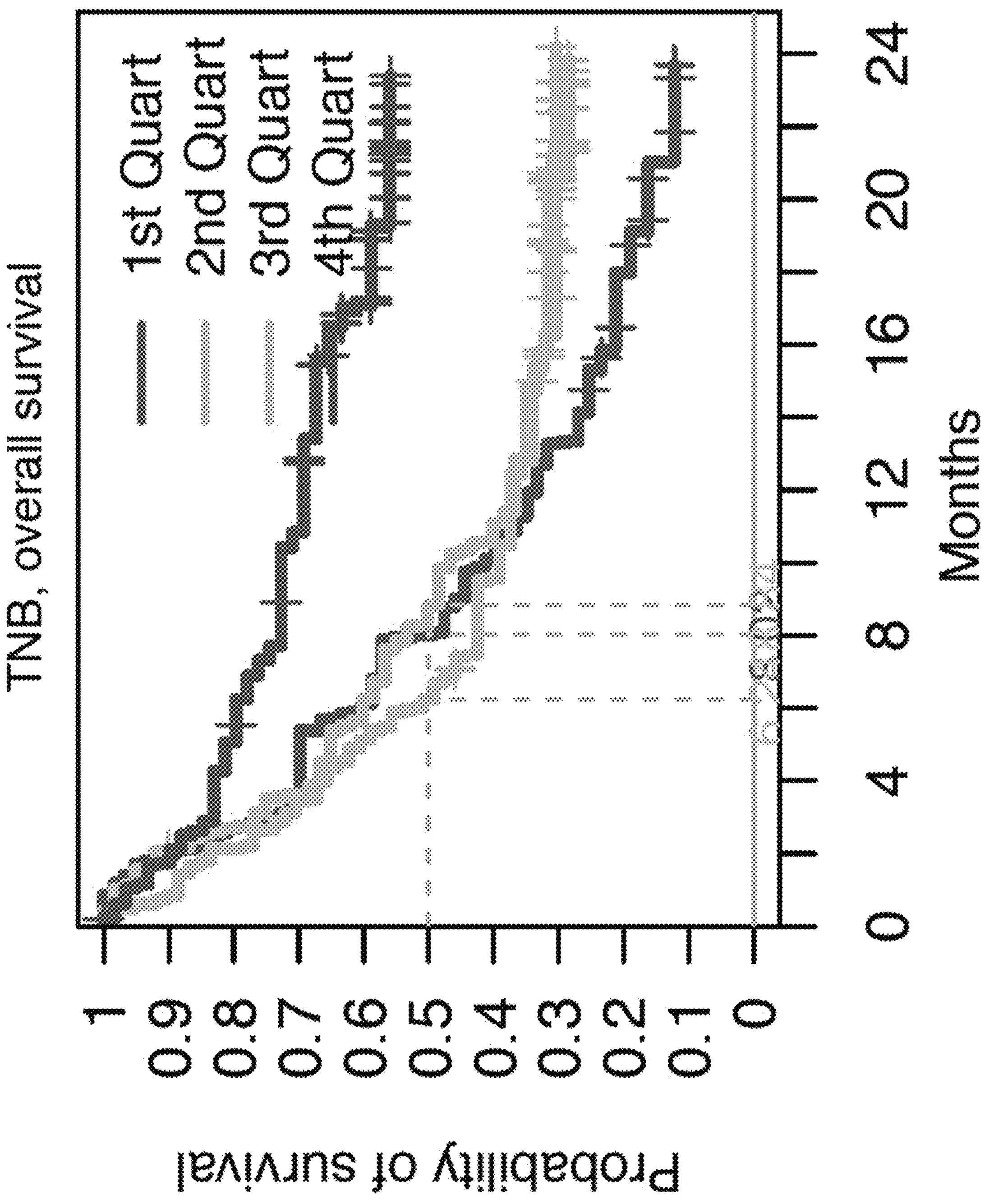
FIG. 1W is a graph showing that TNB was associated with OS (likelihood ratio test p=0.00015).
Figure 1X:
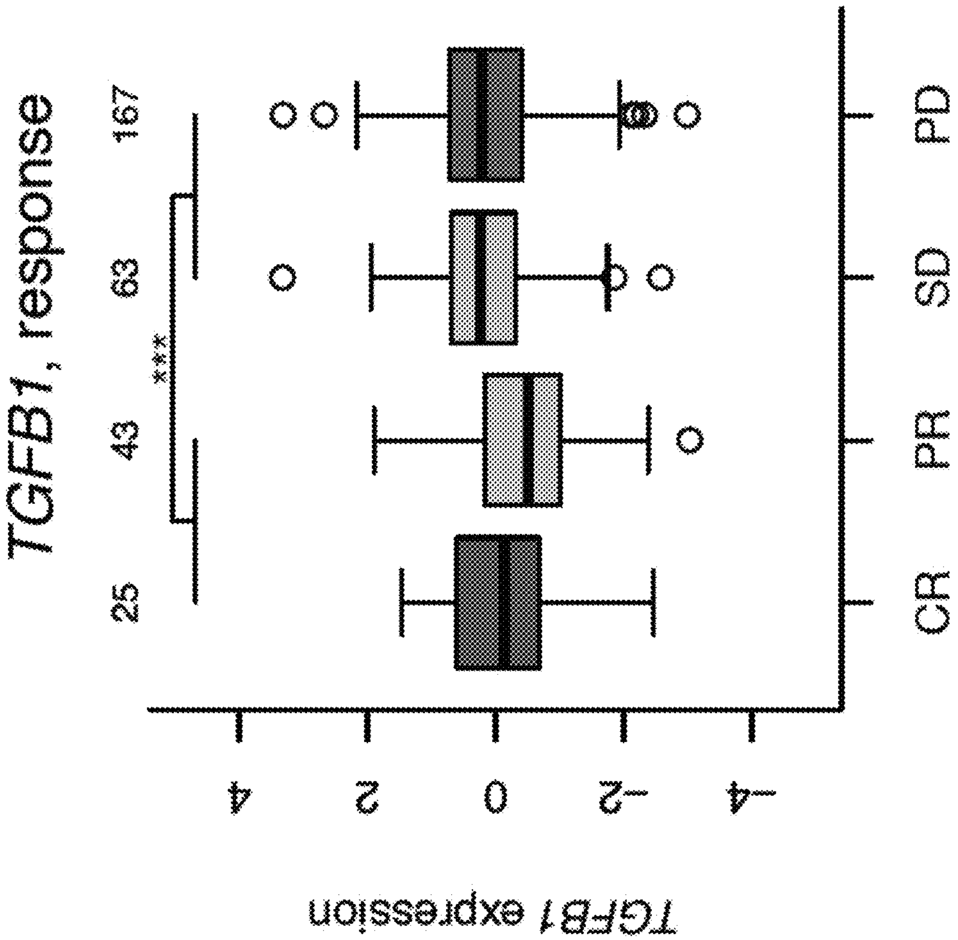
FIG. 1X is a graph showing that TGFB1 expression was associated with poor objective response (p=0.0001).
Figure 1Y:
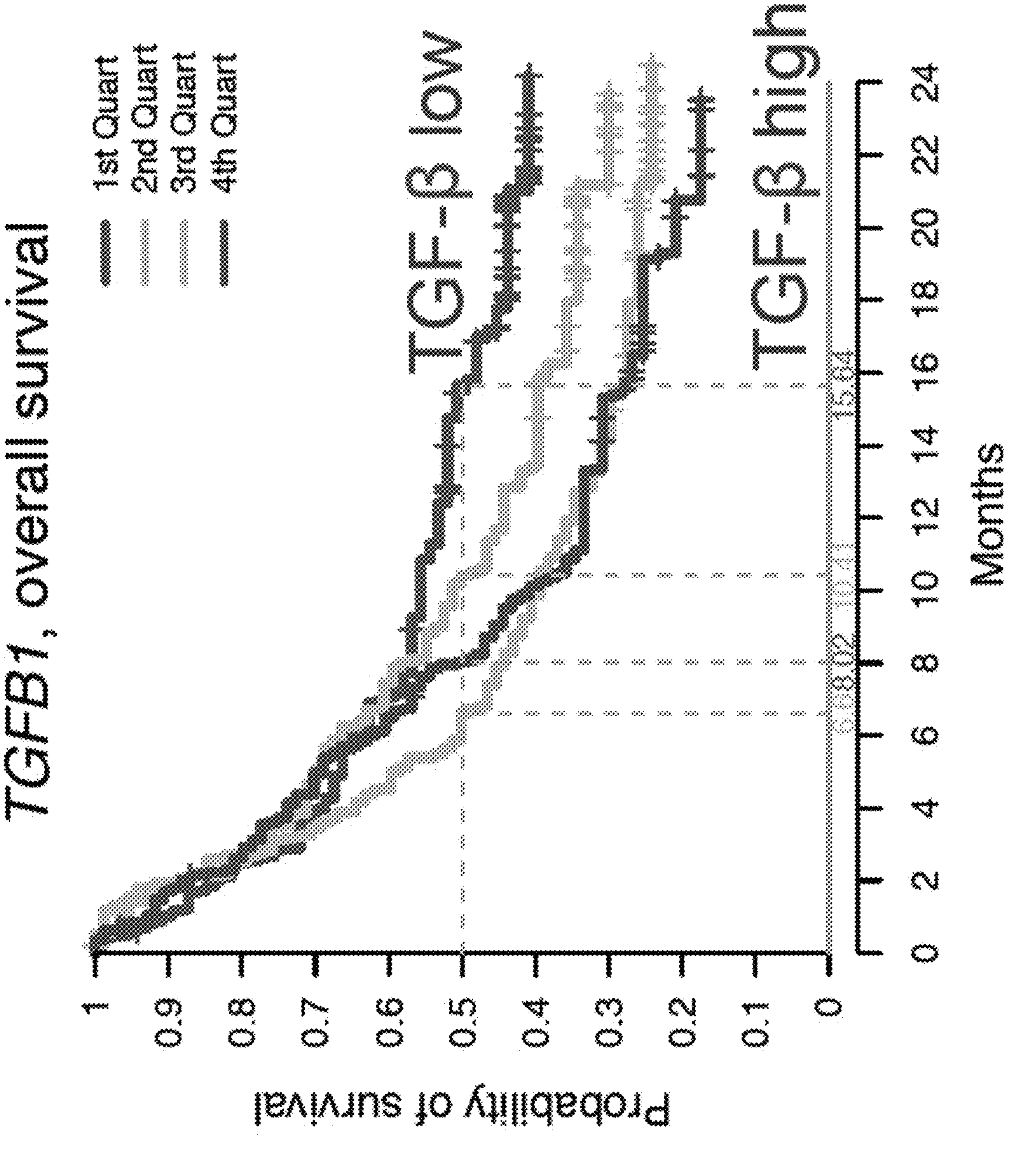
FIG. 1Y is a graph showing that TGFB1 expression quartiles were associated with reduced OS.
Figure 1Z:
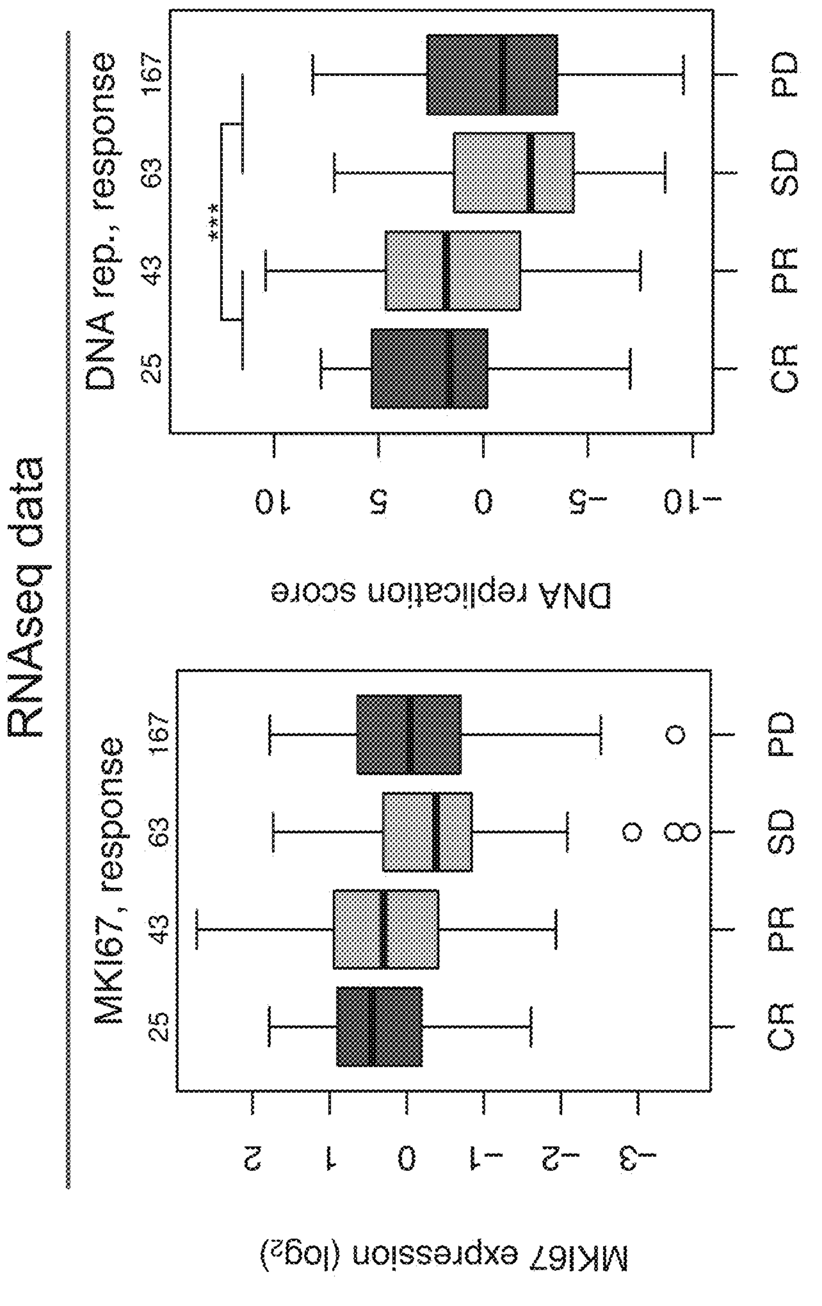
FIG. 1Z is a series of graphs showing that MKI67 expression (left panel) and DNA replication score (right panel) are associated with response to atezolizumab.

TGF-β is a pleiotropic cytokine associated with poor prognosis in multiple tumor types. TGF-β signaling is generally thought to play a pro-tumorigenic role in advanced cancers by promoting immunosuppression, angiogenesis, metastasis, epithelial to mesenchymal transition (EMT), fibroblast activation, and desmoplasia. In IMvigor210, a signature based on the two top-scoring TGF-β pathway genes comprised of TGFB1 and TGFBR2 showed increased mean expression in non-responders (FIG. 1P). TGFB1 expression was associated with poor objective response, and, when split by quartiles, was also associated with reduced OS (FIGS. 1X and 1Y). Given that elevated TGF-β expression could indicate increased T regulatory cell function, EMT, and/or stromal-associated immunosuppression, it is likely to play a significant role in restricting response to atezolizumab.

Example 4: Three Core Pathways Drive Response and Resistance to Anti-PD-L1 Therapy Collectively, these data suggest that response to checkpoint inhibition in bladder cancer is dictated by the combination of three core biological axes: pre-existing T-cell immunity and TMB are positively associated with response to atezolizumab, whereas TGF-β pathway activity is associated with disease progression and lack of response (FIG. 1Q).

To better understand how these three pathways relate to one another, and to reveal their relative importance in predicting outcome, a statistical analysis of competing models was performed. Logistic regression pseudo-$R^2$ was used as a measure of "explained variance" in overall patient response (i.e., the percent of variation in patient response that can be attributed to the biological inputs) (see, e.g., Dobson et al. supra). When single inputs were considered, the CD8+ Teff signature explained 5% of variability in patient response, while the two-gene TGF-β signature explained 16% and TMB explained 30% (FIG. 1R). We next asked whether these three biological inputs are interchangeable or if they independently contribute to predicting response. A model combining all three axes increased explained variance in patient response to 42% and improved over each single-axis model (FIG. 1R). The model combining all three axes also significantly improved on all two-axis models (FIG. 1S), indicating that the information provided by each axis is at least partially independent of the other two.

Example 5: Molecular Taxonomy Reveals Relationships Among Drivers of Response and Resistance To highlight the power of the present framework of three pathways described above (i.e., pre-existing T-cell immunity, TMB, and TGF-β pathway activity) and illustrate the relevance of TGF-β signaling, we explored the relationship between established tumor molecular subtyping and the three pathways. Multiple taxonomic classification methods based on gene expression were recently described (Lerner et al. supra). We previously applied The Cancer Genome Atlas (TCGA) taxonomy (Calon et al. *Nat. Genet.* 47:320-329, 2015) to IMvigor210 samples but also explored the Lund taxonomy (Sjödahl et al. *Clin. Cancer Res.* 18:3377-3386, 2012; Sjödahl et al. *Am. J. Pathol.* 183:681-691, 2013), which further classifies mUC to include a genomically unstable (GU) subtype (FIG. 2A). Given the demonstrated importance of TMB, we hypothesized that the GU subtype would significantly enrich for responders. Indeed, GU enriched for high-TMB tumors (FIGS. 2A-2C) and had a much higher response rate (47.2%) than the other Lund subtypes (17.6%) (FIG. 2D). The boost in response rate in the GU subtype exceeded differences observed among TCGA subtypes (FIG. 2E), but, unexpectedly, this could not be attributed to mutation burden, as the TCGA luminal II subtype similarly enriched for high-TMB tumors (FIGS. 2B and 2C). Instead, we identified the source of the difference by separately evaluating patients classified as TCGA luminal II only, Lund GU only, or both (FIG. 2F). While luminal II tumors had higher CD8+ Teff gene expression regardless of their Lund label, only those luminal II tumors that were also classified as GU had a low TGF-β signature. Thus, an unfavorable TGF-β signature, leading to an unfavorable CD8 Teff to TGF-β ratio, trumped high TMB in this patient group, resulting in poor response.

An association between expression subtypes defined by The Cancer Genome Atlas (TCGA) and clinical response to atezolizumab monotherapy in individual cohorts of IMvigor210 has been identified. We have found that TMB is strongly related to response and, further, at least partially captured by patterns of gene expression. With this in mind, we explored an alternative molecular classification for UC, the Lund taxonomy (Sjödahl et al. *Clin. Cancer Res.* 18:3377-3386, 2012; Sjödahl et al. *Am. J. Pathol.* 183:681-691, 2013), which includes a genomically-unstable (GU) subtype (FIG. 2A).

The Lund GU subtype had a dramatically higher response rate than the other Lund subtypes (FIG. 2D), and strongly enriched for high-TMB tumors (FIGS. 2B and 2C). The Lund GU subtype also had the highest mutation rates for TP53 (34%) and RB1 (43%), consistent with an association between proliferation and mutation (FIG. 2A).

The basal/SCC-like (SCCL) and Urothelial-like B (UroB) subtypes were associated with high expression of CD8+T-effector genes and their correlates, including high PD-L1 expression on IC (FIG. 2A). While these tumors showed similar CR rates to GU tumors, the overall response rate was lower (FIG. 2D). This could in part be due to the low TMB and the relative enrichment of the TGF-β signature (FIGS. 2A and 2G).

Urothelial-like A (UroA) tumors shared many molecular features with the luminal I subtype by the TCGA classification, e.g., high FGFR3, TP63, and WNT7B expression (FIG. 2H). The minimal response rate observed in the UroA subtype is likely a reflection of low TMB and limited pre-existing immunity.

The Lund Infiltrated subtype was named as such due to the presence of both T-cells and myofibroblasts. In line with this classification, infiltrated tumors had elevated expression of CD8+T-effector genes, but also the highest relative expression of genes associated with pro-tumorigenic and immunosuppressive pathways, including TGF-β, stromal activation and angiogenesis, extracellular matrix, and EMT, leading to an unfavorable ratio of CD8+T-effector to TGF-β signature (FIGS. 2A and 2G). The Infiltrated subtype also had the lowest median TMB (FIGS. 2B and 2C), and this, in combination with the unfavorable CD8+T-effector to TGF-β ratio, is consistent with the infiltrated subtype showing the poorest response rate (FIG. 2D).

Example 6: TGF-β Pathway Activation Restricts Responses to Anti-PD-L1 in Immune Excluded Tumors Given the association of TGF-β signaling with stromal components and the negative impact that stromal cells can have on CD8+ T-cells, we next examined the relationship between tumor-immune phenotype and response to atezolizumab. We used immunohistochemistry to evaluate CD8+ T-cell infiltration and classified tumors into immune desert, immune excluded, or immune inflamed phenotypes based on the presence and location of CD8+ T-cells in the TME (FIG. 3A). A significant proportion of bladder tumors (approximately 48%) exhibited the immune excluded phenotype, whereas immune desert and immune inflamed tumors constituted approximately 26% each. The immune excluded phenotype was characterized by the localization of CD8+ T-cells primarily in the peri-tumoral stromal compartment, juxtaposed to collagen fibers (revealed by trichrome staining; FIG. 3B).

The proximity of CD8 T-cells to desmoplastic stroma in immune excluded tumors (FIGS. 3A and 3B) and the association of TGF-β ligand and receptor gene expression with lack of response (FIG. 1O) both implicate the TGF-β pathway. To better understand this pathway's role, we considered two different gene signatures. The first is a two-gene signature (TGFB1 and TGFBR2, described above) that represents input to the pathway. The two-gene input signature showed no difference in expression level across immune phenotypes, but it was elevated in non-responders in immune excluded tumors only (FIG. 3C). The second signature was developed to measure TGF-β pathway output specifically in fibroblasts from different tissues. The "pan-fibroblast TGF-β response signature" (Pan-F-TBRS) includes 19 genes that are strongly and specifically induced by TGFB1 across a panel of human primary fibroblast cell lines derived from six tissues. As with the two-gene signature, lack of response in immune excluded tumors was significantly associated with higher Pan-F-TBRS scores (FIG. 3D). Unlike the two-gene signature, the Pan-F-TBRS score was elevated in both immune inflamed and immune excluded tumors. Consistent with the 2-gene TGF-β signature, however, the Pan-F-TBRS stratified non-responders and responders only in immune excluded tumors, with a significant enrichment in patients who progressed on therapy. These results suggest that the observed association between TGF-β pathway genes and non-response can be at least in part attributed to this pathway's impact on fibroblasts in the tissue microenvironment (TME).

Example 7: TGF-β Inhibition Improves T-Cell Infiltration and Therapeutic Responses to Anti-PD-L1

Perhaps the most unexpected implication of the biomarker analysis is the association of the TGF-β pathway with a lack of response to atezolizumab in IMvigor210 (FIGS. 1O, 1P, 3C, and 3D). TGF-β signaling can have many complex effects on both tumors and the immune system, such as directly impeding tumor growth at early stage, promoting tumor EMT and metastasis, favoring the development of T regulatory cells, and promoting stromal investment of tumors. Observing elevated Pan-F-TBRS levels in the immune excluded phenotype suggested that the effects of TGF-β signaling on activated stroma may lead to the restriction of both T-cell influx and efficacy. Indeed, activated CD8− T-cells were not absent from immune excluded tumors (as opposed to immune desert tumors; FIG. 3A), and they did not exhibit low TMB (FIG. 3E), suggesting that the physical exclusion of T-cells from the tumor parenchyma by the stromal barrier was an important feature limiting response to therapy in this group.

We therefore established a mouse model to investigate a barrier role for a TGF-β-activated stroma. For this purpose, we utilized the EMT6 mouse mammary carcinoma model because it recapitulates the immune excluded phenotype in which T-cells are localized to the periphery of the tumor in association with the collagen fibers (FIG. 4A) and all TGF-β isoforms and PD-L1 are expressed in the TME (FIGS. 4B and 4C). EMT6 tumor cells were orthotopically implanted into BALB/c mice. Once tumors reached approximately 160 $mm^3$, treatment with anti-PD-L1 and/or 1D11, a pan-specific TGF-β-blocking antibody, was initiated. 1D11 treatment reduced TGF-β signaling, as demonstrated by reduced levels of phosphorylated SMAD2/3 in the tumor (FIG. 4L) and VEGF-A in the plasma (FIG. 4M). Dual blockade of PD-L1 and TGF-β in mice with established tumors led to complete tumor regression in the majority of mice, whereas anti-PD-L1 alone led to fewer complete regressions (FIGS. 4D-4F). Blockade of TGF-β alone had no effect on tumor growth in vivo (FIGS. 4D-4F). Dual antibody blockade also led to an increase in the abundance of tumor infiltrating T-cells (FIGS. 4G-4I and 4O). Granzyme B levels also increased on a per CD8+ T-cell basis in the combination therapy arm (FIGS. 4J and 4N). Notably, combined PD-L1 and TGF-β blockade altered the distribution of T-cells from a largely peri-tumoral localization to a more intratumoral pattern (FIGS. 4G, 4K, and 4O). Thus, dual blockade of TGF-β and PD-L1 promoted T-cell localization to tumor islets and improved therapeutic responses, To better understand the mechanisms underlying response to this dual blockade, we performed RNA sequencing on tumors from each of the four treatment conditions. The CD8+ Teff signature used to analyze human tumors was elevated in mouse tumors treated with a combination of anti-PD-L1 and anti-TGF-β (FIGS. 4P and 4T). Despite anti-PD-L1 monotherapy increasing expression of the Teff gene signature, the effect was not significant (FIG. 4P). These results suggested that TGF-β inhibition potentiated the effect of anti-PD-L1 in a significant way to enhance anti-tumor immunity. We then evaluated TGF-β expression signature in different stromal cell populations within the tumor. The Pan-F-TBRS was significantly reduced in the combination treatment (FIG. 4Q). In contrast, no reduction was observed in the TBRS associated with T-cells or macrophages (FIG. 4R). Consistent with these results, phospho-flow analysis in EMT6 tumors demonstrated that TGF-β signaling, as reflected by pSMAD2/3, was significantly reduced in CD45− but not in CD45+ cells following combination therapy (FIG. 4L). The competing effects of the Teff signature and Pan-F-TBRS in the TME can be integrated with the Teff to Pan-F-TBRS ratio. This ratio score showed an increase in the combination treatment compared with control and single antibody treatments (FIG. 4S). Expression of CD8+ Teff genes was elevated in mouse tumors treated with a combination of anti-PD-L1 and anti-TGF-β, while expression of cancer-associated fibroblast (CAF) remodeling genes was decreased (FIGS. 4T and 4U). For example, expression of IFNG, GZMB, and Zeta-chain associated protein kinase 70 (ZAP70) was elevated in mouse tumors treated with a combination of anti-PD-L1 and anti-TGF-β, and expression of lysyl oxidase homolog 2 (LOXL2), tenascin C (TNC), and periostin (POSTN) was decreased in mouse tumors treated with a combination of anti-PD-L1 and anti-TGF-β (FIG. 4U). Without wishing to be bound by theory, dual therapeutic blockade of TGF-β and PD-L1 may switch an immune excluded tumor to an inflamed tumor by reprogramming CAFs and modifying the stromal architecture.

In sum, blockade of TGF-β can synergize with anti-PD-L1 antibodies to increase CD8+ Teff cell counts in the tumor bed and drive robust anti-tumor immunity. Although elevated TGF-β signaling may have additional consequences, these results are consistent with the idea that the TGF-β-activated stroma in the immune excluded group acts to dampen Teff function and physically restrict T-cell entry into the tumor itself.

Pan-Cancer Signatures

We performed a comprehensive evaluation of the molecular, cellular, and tumor genetic factors associated with response and primary immune escape to checkpoint blockade in patients enrolled in a phase 2, single arm study testing the efficacy of atezolizumab in mUC. Given the large size of the cohort used for this analysis, we reached several important, functional conclusions regarding tumor characteristics that govern the likelihood of response. Indeed, three biological axes were found to play distinct and independent roles: (1) pre-existing immunity, as represented by PD-L1 expression on IC and gene expression or histological correlates of CD8+ Teff activity; (2) TMB, measured directly but also reflected in molecular signatures of proliferation and DNA damage response or in loss-of-function mutations impacting these processes; and (3) TGF-β pathway signalling. While each contributes significantly to the multifactorial basis of response, TGF-β signalling and TMB together provide the greatest explanatory power for bladder cancer.

Based on the enrichment of the TGF-β signature in non-responding immune excluded mUC tumors, as well as a possible role in offsetting high TMB and/or pre-existing immunity in Lund subtypes enriched for non-response, we hypothesized that TGF-β signalling may counteract anti-tumor immunity. To test this hypothesis and better understand the functional role of TGF-β in restraining response to immune checkpoint blockade, we used a mouse model that emulates several aspects of immune excluded tumors in patients. In this model, simultaneous inhibition of TGF-β and PD-L1 signalling converted tumors from an excluded phenotype to an inflamed phenotype, resulting in enhanced tumor infiltration by CD8+ Teff cells and a marked increase in tumor regression.

The multifactorial basis of response to immunotherapy described herein is expected to be applicable to other tumor types beyond bladder cancer, and pan-cancer response rates to immune checkpoint blockade may be improved further by taking all three axes into account. Likewise, the determinants of response and resistance to anti-PD-L1 therapy are expected to extend to other immune checkpoint inhibitors.

In total, these data support use of the biomarkers and signatures described herein (e.g., the pan-F-TBRS), for example, as predictive and pharmacodynamic biomarkers for predicting and monitoring response of cancer patients (e.g., bladder cancer patients) to anti-cancer therapy that includes an immunotherapy (e.g., a PD-L1 axis binding antagonist such as an anti-PD-L1 antibody (e.g., atezolizumab)) and a suppressive stromal antagonist (e.g., a TGF-β antagonist such as an anti-TGF-β antibody).

VII. Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of identifying and treating an individual having a cancer who may benefit from treatment with an anti-cancer therapy comprising a PD-L1 binding antagonist and a TGF-β antagonist, the method comprising:

(i) determining the expression level of the following genes in a sample from the individual prior to treatment with the PD-L1 binding antagonist and the TGF-β antagonist:

ACTA2, ADAM19, COMP, CTGF, TGFB1, and TGFBR2, wherein the expression level of ACTA2, ADAM19, COMP, CTGF, TGFB1, and TGFBR2 in the sample is at or above a reference expression level of ACTA2, ADAM19, COMP, CTGF, TGFB1, and TGFBR2;

thereby identifying the individual as one who may benefit from treatment with an anti-cancer therapy comprising a PD-L1 binding antagonist and a TGF-β antagonist, wherein the cancer is urothelial carcinoma (UC), non-small cell lung cancer (NSCLC), triple-negative breast cancer (TNBC), or pancreatic ductal adenocarcinoma (PDAC), and wherein the PD-L1 binding antagonist is an anti-PD-L1 antibody comprising the following hypervariable regions (HVRs):

(a) an HVR-H1 sequence of GFTFSDSWIH (SEQ ID NO: 63);

(b) an HVR-H2 sequence of AWISPYGGSTYY-ADSVKG (SEQ ID NO: 64);

(c) an HVR-H3 sequence of RHWPGGFDY (SEQ ID NO: 65);

(d) an HVR-L1 sequence of RASQDVSTAVA (SEQ ID NO: 66);

(e) an HVR-L2 sequence of SASFLYS (SEQ ID NO: 67); and (f) an HVR-L3 sequence of QQYLYHPAT (SEQ ID NO: 68); and (ii) administering an effective amount of an anti-cancer therapy comprising a PD-L1 binding antagonist and a TGF-β antagonist to the individual identified in step (i) as being one who may benefit from treatment with an anti-cancer therapy comprising a PD-L1 binding antagonist and a TGF-β antagonist.

2. A method of treating an individual having a cancer, the method comprising administering to the individual an anti-cancer therapy comprising a PD-L1 binding antagonist and a TGF-β antagonist, wherein prior to treatment the expression level of ACTA2, ADAM19, COMP, CTGF, TGFB1, and TGFBR2 in the sample has been determined to be at or above a reference expression level of ACTA2, ADAM19, COMP, CTGF, TGFB1, and TGFBR2, wherein the cancer is UC, NSCLC, TNBC, or PDAC, and wherein the PD-L1 binding antagonist is an anti-PD-L1 antibody comprising the following HVRs:

(a) an HVR-H1 sequence of GFTFSDSWIH (SEQ ID NO: 63);

(b) an HVR-H2 sequence of AWISPYGGSTYY-ADSVKG (SEQ ID NO: 64);

(c) an HVR-H3 sequence of RHWPGGFDY (SEQ ID NO: 65);

(d) an HVR-L1 sequence of RASQDVSTAVA (SEQ ID NO: 66);

(e) an HVR-L2 sequence of SASFLYS (SEQ ID NO: 67); and (f) an HVR-L3 sequence of QQYLYHPAT (SEQ ID NO: 68).

3. The method of claim 2, further comprising determining:

(i) the expression level in the sample of one or more additional genes selected from PD-L1, CD8A, CXCL10, CXCL9, GZMA, GZMB, IFNG, PRF1, and TBX21; and/or (ii) a tumor mutational burden (TMB) score in a tumor sample from the individual.

4. The method of claim 2, wherein:

(i) a tumor from the individual has an immune excluded phenotype characterized by the localization of CD8+ T-cells in the peri-tumoral stromal compartment;

(ii) the reference expression level is determined from a population of individuals having a cancer;

(iii) the expression level is a nucleic acid expression level;

(iv) the expression level is a protein expression level; and/or (v) the sample is a tissue sample, a cell sample, a whole blood sample, a plasma sample, a serum sample, or a combination thereof.

5. The method of claim 2, wherein the TGF-β antagonist is a polypeptide, a small molecule, or a nucleic acid.

6. The method of claim 5, wherein:

(i) the polypeptide is an anti-TGF-β antibody, a soluble TGF-β receptor, or a peptide;

(ii) the small molecule is galunisertib (LY2157299), LY2382770, LY3022859, SB-431542, SD208, SM16, tranilast, pirfenidone, TEW-7197, PF-03446962, or pyrrole-imidazole polyamide; or (iii) the nucleic acid is trabedersen (AP12009) or belagen-pumatucel-L.

7. The method of claim 6, wherein:
(i) the anti-TGF-β antibody is fresolimumab, metelimumab, lerdelimumab, 1D11, 2G7, or derivatives thereof; or
(ii) the peptide is disitertide (P144).

8. The method of claim 2, wherein the anti-PD-L1 antibody is atezolizumab.

9. The method of claim 2, wherein the anti-PD-L1 antibody comprises:
(a) a VH domain comprising the amino acid sequence of SEQ ID NO: 69; and
(b) a VL domain comprising the amino acid sequence of SEQ ID NO: 70.

10. The method of claim 2, further comprising administering an additional therapeutic agent to the individual.

11. The method of claim 10, wherein the additional therapeutic agent is an immunotherapy agent, a cytotoxic agent, a growth inhibitory agent, a radiation therapy agent, an anti-angiogenic agent, or a combination thereof.

12. The method of claim 1, wherein the anti-PD-L1 antibody is atezolizumab.

13. The method of claim 1, wherein the cancer is a UC.

14. The method of claim 13, wherein the UC is a metastatic UC.

15. The method of claim 2, wherein the cancer is a UC.

16. The method of claim 15, wherein the UC is a metastatic UC.

17. The method of claim 1, wherein the reference expression level is determined from a population of individuals having the cancer.

18. The method of claim 17, wherein the reference expression level is a median expression level or is determined by principal component analysis of Z-score-transformed expression levels.

19. The method of claim 2, wherein the reference expression level is determined from a population of individuals having the cancer.

20. The method of claim 19, wherein the reference expression level is a median expression level or is determined by principal component analysis of Z-score-transformed expression levels.

21. A method of treating an individual having a metastatic UC, the method comprising administering to the individual an anti-cancer therapy comprising atezolizumab and an anti-TGF-β antibody, wherein prior to treatment the expression level of ACTA2, ADAM19, COMP, CTGF, TGFB1, and TGFBR2 in the sample has been determined to be at or above a reference expression level of ACTA2, ADAM19, COMP, CTGF, TGFB1, and TGFBR2.

* * * * *

SEQUENCE LISTING

<160> NUMBER OF SEQ ID NOS: 82

<210> SEQ ID NO 1
<211> LENGTH: 2741
<212> TYPE: RNA
<213> ORGANISM: Homo sapiens

<400> SEQUENCE: 1
accucccucc gcggagcagc cagacagcga gggccccggc cgggggcagg ggggacgccc 60
cguccggggc acccccccgg cucugagccg cccgcggggc cggccucggc ccggagcgga 120
ggaaggaguc gccgaggagc agccugaggc cccagagucu gagacgagcc gccgccgccc 180
ccgccacugc ggggaggagg gggaggagga gcgggaggag ggacgagcug gucgggagaa 240
gaggaaaaaa acuuuugaga cuuuuccguu gccgcuggga gccggaggcg cggggaccuc 300
uuggcgcgac gcugccccgc gaggaggcag gacuugggga ccccagaccg ccucccuuug 360
ccgccgggga cgcuugcucc cucccugccc ccuacacggc gucccucagg cgcccccauu 420
ccggaccagc ccucgggagu cgccgacccg gccucccgca aagacuuuuc cccagaccuc 480
gggcgcaccc ccugcacgcc gccuucaucc ccggccuguc uccugagccc ccgcgcaucc 540
uagacccuuu cuccuccagg agacggaucu cucuccgacc ugccacagau ccccuauuca 600
agaccaccca ccuucuggua ccagaucgcg cccaucuagg uuauuuccgu gggauacuga 660
gacacccccg guccaagccu ccccuccacc acugcgcccu ucucccugag gaccucagcu 720
uucccucgag gcccuccuac cuuuugccgg gagaccccca gccccugcag ggcggggcc 780 uccccaccac accagcccug uucgcgcucu cggcagugcc ggggggcgcc gccuccccca 840
ugccgcccuc cgggcugcgg cugcugccgc ugcugcuacc gcugcugugg cuacuggugc 900
ugacgccugg ccggccggcc gcgggacuau ccaccugcaa gacuaucgac auggagcugg 960
ugaagcggaa gcgcaucgag gccauccgcg gccagauccu guccaagcug cggcucgcca 1020 gcccccccgag ccagggggag gugccgcccg gcccgcugcc cgaggccgug cucgcccugu 1080
acaacagcac ccgcgaccgg guggccgggg agagugcaga accggagccc gagccugagg 1140
ccgacuacua cgccaaggag gucacccgcg ugcuaauggu ggaaacccac aacgaaaucu 1200
augacaaguu caagcagagu acacacagca uauauauguu cuucaacaca ucagagcucc 1260
gagaagcggu accugaaccc guguugcucu cccgggcaga gcugcgucug cugaggcuca 1320
aguuaaaagu ggagcagcac guggagcugu accagaaaua cagcaacaau uccuggcgau 1380
accucagcaa ccggcugcug gcacccagcg acucgccaga gugguuaucu uuugauguca 1440
ccggaguugu gcggcagugg uugagccgug gaggggaaau ugagggcuuu cgccuuagcg 1500
cccacugcuc cugugacagc agggauaaca cacugcaagu ggacaucaac ggguucacua 1560
ccggccgccg aggugaccug gccaccauuc auggcaugaa ccggccuuuc cugcuucuca 1620
uggccacccc gcuggagagg gcccagcauc ugcaaagcuc ccggcaccgc cgagcccugg 1680
acaccaacua uugcuucagc uccacggaga agaacugcug cgugcggcag cuguacauug 1740
acuuccgcaa ggaccucggc uggaagugga uccacgagcc caagggcuac caugccaacu 1800
ucugccucgg gcccugcccc uacauuugga gccuggacac gcaguacagc aagguccugg 1860
cccuguacaa ccagcauaac ccgggcgccu cggcggcgcc gugcugcgug ccgcaggcgc 1920
uggagccgcu gcccaucgug uacuacgugg gccgcaagcc caagguggag cagcugucca 1980
acaugaucgu gcgcuccugc aagugcagcu gaggucccgc cccgccccgc cccgccccgg 2040
caggcccggc cccaccccgc cccgcccccg cugccuugcc caugggggcu guauuuaagg 2100
acacccgugc cccaagccca ccuggggccc cauuaaagau ggagagagga cugcggaucu 2160
cugugucauu gggcgccugc cuggggucuc caucccugac guucccccac ucccacuccc 2220
ucucucuccc ucucugccuc cuccugccug ucugcacuau ucccuuugccc ggcaucaagg 2280 cacaggggac caguggggaa cacuacugua guuagaucua uuuauugagc accuugggca 2340
cuguugaagu gccuuacauu aaugaacuca uucagucacc auagcaacac ucugagaugc 2400
agggacucug auaacaccca uuuuaaaggu gaggaaacaa gcccagagag guuaagggag 2460
gaguuccugc ccaccaggaa ccugcuuuag ugggggauag ugaagaagac aauaaaagau 2520
aguaguucag gccaggcggg guggcucacg ccuguaaucc uagcacuuuu gggaggcaga 2580
gaugggagga uuacuugaau ccaggcauuu gagaccagcc ugguaacau agugagaccc 2640 uaucucuaca aaacacuuuu aaaaaaugua caccugugu cccagcuacu cuggaggcua 2700
aggugggagg aucacuugau ccugggaggu caaggcugca g 2741

<210> SEQ ID NO 2
<211> LENGTH: 390
<212> TYPE: PRT
<213> ORGANISM: Homo sapiens

<400> SEQUENCE: 2

Met Pro Pro Ser Gly Leu Arg Leu Leu Leu Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

```
Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390
```

<210> SEQ ID NO 3
<211> LENGTH: 4704
<212> TYPE: RNA
<213> ORGANISM: Homo sapiens

<400> SEQUENCE: 3

```
ggagagggag aaggcucucg ggcggagaga gguccugccc agcuguuggc gaggaguuuc     60

cuguuucccc cgcagcgcug aguugaaguu gagugaguca cucgcgcgca cggagcgacg    120

acacccccgc gcgugcaccc gcucgggaca ggagccggac uccugugcag cuuccccucgg   180

ccgccggggg ccucccccgcg ccucgccggc cuccaggccc ccuccuggcu ggcgagcggg   240

cgccacaucu ggcccgcaca ucugcgcugc cggcccggcg cggggucgg agagggcgcg     300

gcgcggaggc gcagccaggg guccgggaag gcgccguccg cugcgcuggg ggcucggucu    360

augacgagca gcggggucug ccaugggucg ggggcugcuc aggggccugu ggccgcugca    420

caucguccug uggacgcgua ucgccagcac gaucccaccg cacguucaga agucggaugu    480

ggaaauggag gcccagaaag augaaaucau cugccccagc uguaauagga cugcccaucc    540

acugagacau auuaauaacg acaugauagu cacugacaac aacggugcag ucaaguuucc    600

acaacugugu aaauuuugug augugagauu uuccaccugu gacaaccaga aauccugcau    660

gagcaacugc agcaucaccu ccaucugu ga gaagccacag gaagucugug uggcuguaug   720

gagaaagaau gacgagaaca uaacacuaga gacaguuugc caugacccca agcuccccua    780

ccaugacuuu auucuggaag augcugcuuc uccaaagugc auuaugaagg aaaaaaaaaa    840

gccugguggag acuuucuuca uguguuccug uagcucugau gagugcaaug acaacaucau   900

cuucucagaa gaauauaaca ccagcaaucc ugacuuguug cuagucauau uucaagugac    960

aggcaucagc cuccugccac cacugggagu ugccauaucu gucaucauca ucuucuacug   1020

cuaccgcguu aaccggcagc agaagcugag uucaaccugg gaaaccggca agacgcggaa   1080

gcucauggag uucagcgagc acugugccau cauccuggaa gaugaccgcu cugacaucag   1140

cuccacgugu gccaacaaca ucaaccacaa cacagagcug cugcccauug agcuggacac   1200

ccuggugggg aaaggucgcu uugcugaggu cuauaaggcc aagcugaagc agaacacuuc   1260

agagcaguuu gagacagugg cagucaagau cuuucccuau gaggaguaug ccucuuggaa   1320
```

-continued gacagagaag gacaucuucu cagacaucaa ucugaagcau gagaacauac uccaguuccu 1380
gacggcugag gagcggaaga cggaguuggg gaaacaauac uggcugauca ccgccuucca 1440
cgccaagggc aaccuacagg aguaccugac gcggcauguc aucagcuggg aggaccugcg 1500
caagcugggc agcucccucg cccgggggau ugcucaccuc cacagugauc acacuccaug 1560
ugggaggccc aagaugccca ucgugcacag ggaccucaag agcuccaaua uccucgugaa 1620
gaacgaccua accugcugcc ugugugacuu ugggcuuucc cugcgucugg acccuacucu 1680
gucuguggau gaccuggcua acagugggca gguggggaacu gcaagauaca uggcuccaga 1740
aguccuagaa uccaggauga auuuggagaa uguugagucc uucaagcaga ccgaugucua 1800
cuccauggcu cuggugcucu gggaaaugac aucucgcugu aaugcagugg gagaaguaaa 1860
agauuaugag ccuccauuug guuccaaggu gcgggagcac cccugugucg aaagcaugaa 1920
ggacaacgug uugagagauc gagggcgacc agaaauuccc agcuucuggc ucaaccacca 1980
gggcauccag auggugugug agacguugac ugagugcugg gaccacgacc cagaggcccg 2040
ucucacagcc cagugugugg cagaacgcuu cagugagcug gagcaucugg acaggcucuc 2100
ggggaggagc ugcucggagg agaagauucc ugaagacggc ucccuaaaca cuaccaaaua 2160
gcucuucugg ggcaggcugg gccaugucca aagaggcugc cccucucacc aaagaacaga 2220
ggcagcagga agcugccccu gaacugaugc uuccuggaaa accaaggggg ucacuccccu 2280
cccuguaagc uguggggaua agcagaaaca acagcagcag ggagugggug acauagagca 2340
uucuaugccu uugacauugu cauaggauaa gcuguguuag cacuuccuca ggaaaugaga 2400
uugauuuuua caauagccaa uaacauuugc acuuuauuaa ugccuguaua uaaauaugaa 2460
uagcuauguu uuauauauau auauauauau cuauauaugu cuauagcucu auauauauag 2520
ccauaccuug aaaagagaca aggaaaaaca ucaaauauuc ccaggaaauu gguuuuauug 2580
gagaacucca gaaccaagca gagaaggaag ggacccauga cagcauuagc auuugacaau 2640
cacacaugca gugguucucu gacuguaaaa cagugaacuu ugcaugagga aagaggcucc 2700
augucucaca gccagcuaug accacauugc acuugcuuuu gcaaaauaau cauucccugc 2760
cuagcacuuc ucuucuggcc auggaacuaa guacaguggc acuguuugag gaccaguguu 2820
cccggggguuc cugugugccc uuauuucucc uggacuuuuc auuuaagcuc caagccccaa 2880
aucugggggg cuaguuuaga aacucucccu caaccuaguu uagaaacucu accccaucuu 2940
uaauaccuug aauguuuuga accccacuuu uuaccuucau ggguugcaga aaaaucagaa 3000
cagaugucccc cauccaugcg auugccccac caucuacuaa ugaaaaauug uucuuuuuuu 3060
caucuuuccc cugcacuuau guuacuauuc ucugcuccca gccuucaucc uuuucuaaaa 3120
aggagcaaau ucucacucua ggcuuuaucg uguuuacuuu uucauuacac uugacuugau 3180
uuucuaguuu ucuauacaaa caccaauggg uuccaucuuu cugggcuccu gauugcucaa 3240
gcacaguuug gccugaugaa gaggauuuca acuacacaau acuaucauug ucaggacuau 3300
gaccucaggc acucuaaaca uauguuuugu uuggucagca cagcguuuca aaaagugaag 3360
ccacuuuaua aauauuugga gauuuugcag gaaaaucugg auccccaggu aaggauagca 3420
gaugguuuuc aguuaucucc aguccacguu cacaaaaugu gaaggugugg agacacuuac 3480
aaagcugccu cacuucucac uguaaacauu agcucuuucc acugccuacc uggaccccag 3540
ucuaggaauu aaaucugcac cuaaccaagg ucccuuguaa gaaaugucca uucaagcagu 3600
cauucucugg guauauaaua ugauuuugac uaccuuaucu gguguuaaga uuugaaguug 3660
gccuuuuauu ggacuaaagg ggaacuccuu uaagggucuc aguuagccca aguuucuuuu 3720

```
gcuuauaugu uaauaguuuu acccucugca uuggagagag gagugcuuua cuccaagaag   3780

cuuuccucau gguuaccguu cucuccauca ugccagccuu cucaaccuuu gcagaaauua   3840

cuagagagga uuugaaugug ggacacaaag gucccauuug caguuagaaa auuugugucc   3900

acaaggacaa gaacaaagua ugagcuuuaa aacuccauag gaaacuuguu aaucaacaaa   3960

gaaguguuaa ugcugcaagu aaucucuuuu uuaaaacuuu uugaagcuac uuauuuucag   4020

ccaaauagga auauuagaga gggacuggua gugagaauau cagcucuguu uggauggugg   4080

aaggucucau uuuauugaga uuuuuaagau acaugcaaag guuuggaaau agaaccucua   4140

ggcacccucc ucaguguggg ugggcugaga guuaaagaca guguggcugc aguagcauag   4200

aggcgccuag aaauuccacu ugcaccguag ggcaugcuga uaccauccca auagcuguug   4260

cccauugacc ucuaguggug aguuucuaga auacuggucc auucaugaga uauucaagau   4320

ucaagaguau ucucacuucu ggguuaucag cauaaacugg aauguagugu cagaggauac   4380

uguggcuugu uuuguuuaug uuuuuuuuuc uuauucaaga aaaaagacca aggaauaaca   4440

uucuguaguu ccuaaaaaua cugacuuuuu ucacuacuau acauaaaggg aaaguuuuau   4500

ucuuuuaugg aacacuucag cuguacucau guauuaaaau aggaauguga augcuauaua   4560

cucuuuuuau aucaaaaguc ucaagcacuu auuuuuauuc uaugcauugu uugucuuuua   4620

cauaaauaaa auguuuauua gauugaauaa agcaaaauac ucaggugagc auccugccuc   4680

cuguucccau uccuaguagc uaaa                                          4704
```

```
<210> SEQ ID NO 4
<211> LENGTH: 566
<212> TYPE: PRT
<213> ORGANISM: Homo sapiens

<400> SEQUENCE: 4

Gly Arg Gly Leu Leu Arg Gly Leu Trp Pro Leu His Ile Val Leu Trp
1               5                   10                  15

Thr Arg Ile Ala Ser Thr Ile Pro Pro His Val Gln Lys Ser Val Asn
            20                  25                  30

Asn Asp Met Ile Val Thr Asp Asn Asn Gly Ala Val Lys Phe Pro Gln
        35                  40                  45

Leu Cys Lys Phe Cys Asp Val Arg Phe Ser Thr Cys Asp Asn Gln Lys
    50                  55                  60

Ser Cys Met Ser Asn Cys Ser Ile Thr Ser Ile Cys Glu Lys Pro Gln
65                  70                  75                  80

Glu Val Cys Val Ala Val Trp Arg Lys Asn Asp Glu Asn Ile Thr Leu
                85                  90                  95

Glu Thr Val Cys His Asp Pro Lys Leu Pro Tyr His Asp Phe Ile Leu
            100                 105                 110

Glu Asp Ala Ala Ser Pro Lys Cys Ile Met Lys Glu Lys Lys Lys Pro
        115                 120                 125

Gly Glu Thr Phe Phe Met Cys Ser Cys Ser Ser Asp Glu Cys Asn Asp
    130                 135                 140

Asn Ile Ile Phe Ser Glu Glu Tyr Asn Thr Ser Asn Pro Asp Leu Leu
145                 150                 155                 160

Leu Val Ile Phe Gln Val Thr Gly Ile Ser Leu Leu Pro Pro Leu Gly
                165                 170                 175

Val Ala Ile Ser Val Ile Ile Ile Phe Tyr Cys Tyr Arg Val Asn Arg
            180                 185                 190
```

-continued

```
Gln Gln Lys Leu Ser Ser Thr Trp Glu Thr Gly Lys Thr Arg Lys Leu
        195                 200                 205

Met Glu Phe Ser Glu His Cys Ala Ile Ile Leu Glu Asp Asp Arg Ser
    210                 215                 220

Asp Ile Ser Ser Thr Cys Ala Asn Asn Ile Asn His Asn Thr Glu Leu
225                 230                 235                 240

Leu Pro Ile Glu Leu Asp Thr Leu Val Gly Lys Gly Arg Phe Ala Glu
                245                 250                 255

Val Tyr Lys Ala Lys Leu Lys Gln Asn Thr Ser Glu Gln Phe Glu Thr
            260                 265                 270

Val Ala Val Lys Ile Phe Pro Tyr Glu Glu Tyr Ala Ser Trp Lys Thr
        275                 280                 285

Glu Lys Asp Ile Phe Ser Asp Ile Asn Leu Lys His Glu Asn Ile Leu
    290                 295                 300

Gln Phe Leu Thr Ala Glu Glu Arg Lys Thr Glu Leu Gly Lys Gln Tyr
305                 310                 315                 320

Trp Leu Ile Thr Ala Phe His Ala Lys Gly Asn Leu Gln Glu Tyr Leu
                325                 330                 335

Thr Arg His Val Ile Ser Trp Glu Asp Leu Arg Lys Leu Gly Ser Ser
            340                 345                 350

Leu Ala Arg Gly Ile Ala His Leu His Ser Asp His Thr Pro Cys Gly
        355                 360                 365

Arg Pro Lys Met Pro Ile Val His Arg Asp Leu Lys Ser Ser Asn Ile
    370                 375                 380

Leu Val Lys Asn Asp Leu Thr Cys Cys Leu Cys Asp Phe Gly Leu Ser
385                 390                 395                 400

Leu Arg Leu Asp Pro Thr Leu Ser Val Asp Asp Leu Ala Asn Ser Gly
                405                 410                 415

Gln Val Gly Thr Ala Arg Tyr Met Ala Pro Glu Val Leu Glu Ser Arg
            420                 425                 430

Met Asn Leu Glu Asn Val Glu Ser Phe Lys Gln Thr Asp Val Tyr Ser
        435                 440                 445

Met Ala Leu Val Leu Trp Glu Met Thr Ser Arg Cys Asn Ala Val Gly
    450                 455                 460

Glu Val Lys Asp Tyr Glu Pro Pro Phe Gly Ser Lys Val Arg Glu His
465                 470                 475                 480

Pro Cys Val Glu Ser Met Lys Asp Asn Val Leu Arg Asp Arg Gly Arg
                485                 490                 495

Pro Glu Ile Pro Ser Phe Trp Leu Asn His Gln Gly Ile Gln Met Val
            500                 505                 510

Cys Glu Thr Leu Thr Glu Cys Trp Asp His Asp Pro Glu Ala Arg Leu
        515                 520                 525

Thr Ala Gln Cys Val Ala Glu Arg Phe Ser Glu Leu Glu His Leu Asp
    530                 535                 540

Arg Leu Ser Gly Arg Ser Cys Ser Glu Glu Lys Ile Pro Glu Asp Gly
545                 550                 555                 560

Ser Leu Asn Thr Thr Lys
                565
```

<210> SEQ ID NO 5
<211> LENGTH: 1805
<212> TYPE: RNA
<213> ORGANISM: Homo sapiens

<400> SEQUENCE: 5

```
gcaggcucuc uccccgcccc cgcggggcgg cgcgcacuca cccacccgcg ccggagcgga     60

ccuuuggcuu ggcuugucag ggcuugucca ggaguuccgc uccucucucc aaccggggguc    120

ccccuccagc gacccuaaag cuucccagac uuccgcuuca auuccugucc gcaccccacg    180

cccaccucaa cguggagcgc aguggucucc gaggagcgcc ggagcugccc cgccugccca    240

gcggggucag cacuucgcau caaggcccaa gaaaagcaag uccuccagcg uucugagcac    300

ccgggccuga gggaagcucc uaacagcccc cgggagccag ucuccaacgc cucccgcagc    360

agcccgccgc ucccaggugc ccgcgugcgc cgcugccgcc gcaaucccgc acgcgucccg    420

cgcccgcccc acuuugccua uccccgggac uaagacggga auccugugaa gcagcuccag    480

cuauguguga agaagaggac agcacugccu ugguguguga caauggcucu gggcucugua    540

aggccggcuu ugcuggggac gaugcuccca gggcuguuuu cccauccauu gugggacguc    600

ccagacauca gggggugaug gugggaaugg gacaaaaaga cagcuacgug ggugacgaag    660

cacagagcaa aagaggaauc cugacccuga aguacccgau agaacauggc aucaucacca    720

acugggacga cauggaaaag aucuggcacc acucuuucua caaugagcuu cguguugccc    780

cugaagagca ucccacccug cucacggagg caccccugaa ccccaaggcc aaccgggaga    840

aaaugacuca aauuauguuu gagacuuuca augucccagc cauguaugug gcuauccagg    900

cggugcuguc ucucuaugcc ucuggacgca caacuggcau cgugcuggac ucuggagaug    960

gugucaccca caaugucccc aucuaugagg gcuaugccuu gccccaugcc aucaugcguc   1020

uggaucuggc uggccgagau cucacugacu accucaugaa gauccugacu gagcguggcu   1080

auuccuucgu uacuacugcu gagcgugaga uuguccggga caucaaggag aaacuguguu   1140

auguagcucu ggacuuugaa aaugagaugg ccacugccgc auccucaucc ucccuugaga   1200

agaguuacga guugccugau gggcaaguga ucaccaucgg aaaugaacgu uuccgcugcc   1260

cagagacccu guuccagcca uccuucaucg ggauggaguc ugcuggcauc caugaaacca   1320

ccuacaacag caucaugaag ugugauauug acaucaggaa ggaccucuau gcuaacaaug   1380

uccuaucagg gggcaccacu auguacccug gcauugccga ccgaaugcag aaggagauca   1440

cggcccuagc acccagcacc augaagauca agaucauugc cccuccggag cgcaaauacu   1500

cugucuggau cgguggcucc auccuggccu cucuguccac cuuccagcag auguggauca   1560

gcaaacagga auacgaugaa gccgggccuu ccauugucca ccgcaaaugc uucuaaaaca   1620

cuuuccugcu ccucucuguc ucuagcacac aacugugaau guccugugga auuaugccuu   1680

caguucuuuu ccaaaucauu ccuagccaaa gcucugacuc guuaccuaug uguuuuuuaa   1740

uaaaucugaa auaggcuacu gguaaaaaaa aaaaaaaaaa aaaaaaaaaa aaaaaaaaaa   1800

aaaaa                                                                1805
```

<210> SEQ ID NO 6
<211> LENGTH: 377
<212> TYPE: PRT
<213> ORGANISM: Homo sapiens

<400> SEQUENCE: 6

```
Met Cys Glu Glu Glu Asp Ser Thr Ala Leu Val Cys Asp Asn Gly Ser
1               5                   10                  15

Gly Leu Cys Lys Ala Gly Phe Ala Gly Asp Asp Ala Pro Arg Ala Val
            20                  25                  30

Phe Pro Ser Ile Val Gly Arg Pro Arg His Gln Gly Val Met Val Gly
        35                  40                  45
```

```
Met Gly Gln Lys Asp Ser Tyr Val Gly Asp Glu Ala Gln Ser Lys Arg
    50                  55                  60

Gly Ile Leu Thr Leu Lys Tyr Pro Ile Glu His Gly Ile Ile Thr Asn
65                  70                  75                  80

Trp Asp Asp Met Glu Lys Ile Trp His His Ser Phe Tyr Asn Glu Leu
                85                  90                  95

Arg Val Ala Pro Glu Glu His Pro Thr Leu Leu Thr Glu Ala Pro Leu
            100                 105                 110

Asn Pro Lys Ala Asn Arg Glu Lys Met Thr Gln Ile Met Phe Glu Thr
        115                 120                 125

Phe Asn Val Pro Ala Met Tyr Val Ala Ile Gln Ala Val Leu Ser Leu
    130                 135                 140

Tyr Ala Ser Gly Arg Thr Thr Gly Ile Val Leu Asp Ser Gly Asp Gly
145                 150                 155                 160

Val Thr His Asn Val Pro Ile Tyr Glu Gly Tyr Ala Leu Pro His Ala
                165                 170                 175

Ile Met Arg Leu Asp Leu Ala Gly Arg Asp Leu Thr Asp Tyr Leu Met
            180                 185                 190

Lys Ile Leu Thr Glu Arg Gly Tyr Ser Phe Val Thr Thr Ala Glu Arg
        195                 200                 205

Glu Ile Val Arg Asp Ile Lys Glu Lys Leu Cys Tyr Val Ala Leu Asp
    210                 215                 220

Phe Glu Asn Glu Met Ala Thr Ala Ala Ser Ser Ser Ser Leu Glu Lys
225                 230                 235                 240

Ser Tyr Glu Leu Pro Asp Gly Gln Val Ile Thr Ile Gly Asn Glu Arg
                245                 250                 255

Phe Arg Cys Pro Glu Thr Leu Phe Gln Pro Ser Phe Ile Gly Met Glu
            260                 265                 270

Ser Ala Gly Ile His Glu Thr Thr Tyr Asn Ser Ile Met Lys Cys Asp
        275                 280                 285

Ile Asp Ile Arg Lys Asp Leu Tyr Ala Asn Asn Val Leu Ser Gly Gly
    290                 295                 300

Thr Thr Met Tyr Pro Gly Ile Ala Asp Arg Met Gln Lys Glu Ile Thr
305                 310                 315                 320

Ala Leu Ala Pro Ser Thr Met Lys Ile Lys Ile Ile Ala Pro Pro Glu
                325                 330                 335

Arg Lys Tyr Ser Val Trp Ile Gly Gly Ser Ile Leu Ala Ser Leu Ser
            340                 345                 350

Thr Phe Gln Gln Met Trp Ile Ser Lys Gln Glu Tyr Asp Glu Ala Gly
        355                 360                 365

Pro Ser Ile Val His Arg Lys Cys Phe
    370                 375
```

<210> SEQ ID NO 7
<211> LENGTH: 1345
<212> TYPE: RNA
<213> ORGANISM: Homo sapiens

<400> SEQUENCE: 7

```
gccucugggg uuuuauauug cucugguauu caugccaaag acacaccagc ccucagucac      60

ugggagaaga accucucaua cccucggugc uccagucccc agcucacuca gccacacaca     120

ccauguguga agaggagacc accgcgcucg ugugugacaa uggcucuggc cugugcaagg     180

caggcuucgc aggagaugau gcccccc ggg cugucuuccc cuccauugug ggccgcccuc     240
```

```
gccaccaggg ugugauggug ggaaugggcc agaaagacag cuaugugggg gaugaggcuc    300

agagcaagcg agggauccua acucucaaau accccauuga acacggcauc aucaccaacu    360

gggaugacau ggagaagauc uggcaccacu ccuucuacaa ugagcugcgu guagcaccug    420

aagagcaccc cacccugcuc acagaggcuc cccuaaaucc caaggccaac agggaaaaga    480

ugacccagau cauguuugaa accuucaaug ucccugccau guacgucgcc auucaagcug    540

ugcucucccu cuaugccucu ggccgcacga caggcaucgu ccuggauuca ggugauggcg    600

ucacccacaa uguccccauc uaugaaggcu augcccugcc ccaugccauc augcgccugg    660

acuuggcugg ccgugaccuc acggacuacc ucaugaagau ccucacagag agaggcuauu    720

ccuuugugac cacagcugag agagaaauug ugcgagacau caaggagaag cugugcuaug    780

uggcccugga uuuugagaau gagauggcca cagcagcuuc cucuuccucc cuggagaaga    840

gcuaugagcu gccagauggg cagguuauca ccauuggcaa ugagcgcuuc cgcugcccug    900

agacccucuu ccagccuucc uuuauuggca uggaguccgc uggaauucau gagacaaccu    960

acaauuccau caugaagugu gacauugaca uccguaagga cuuauaugcc aacaaugucc   1020

ucucuggggg caccaccaug uacccuggca uugcugacag gaugcagaag gagaucacag   1080

cccuggcccc cagcaccaug aagaucaaga uuauugcucc cccagagcgg aaguacucag   1140

ucuggaucgg gggcucuauc cuggccucuc ucuccaccuu ccagcagaug uggaucagca   1200

agccugagua ugaugaggca gggcccucca uuguccacag gaagugcuuc uaaagucaga   1260

acagguucuc caaggauccc cucgagacua cucuguuacc agucaugaaa cauuaaaacc   1320

uacaagccuu aaaaaaaaaa aaaaa                                           1345
```

<210> SEQ ID NO 8
<211> LENGTH: 376
<212> TYPE: PRT
<213> ORGANISM: Homo sapiens

<400> SEQUENCE: 8

```
Met Cys Glu Glu Glu Thr Thr Ala Leu Val Cys Asp Asn Gly Ser Gly
1               5                   10                  15

Leu Cys Lys Ala Gly Phe Ala Gly Asp Asp Ala Pro Arg Ala Val Phe
            20                  25                  30

Pro Ser Ile Val Gly Arg Pro Arg His Gln Gly Val Met Val Gly Met
        35                  40                  45

Gly Gln Lys Asp Ser Tyr Val Gly Asp Glu Ala Gln Ser Lys Arg Gly
    50                  55                  60

Ile Leu Thr Leu Lys Tyr Pro Ile Glu His Gly Ile Ile Thr Asn Trp
65                  70                  75                  80

Asp Asp Met Glu Lys Ile Trp His His Ser Phe Tyr Asn Glu Leu Arg
                85                  90                  95

Val Ala Pro Glu Glu His Pro Thr Leu Leu Thr Glu Ala Pro Leu Asn
            100                 105                 110

Pro Lys Ala Asn Arg Glu Lys Met Thr Gln Ile Met Phe Glu Thr Phe
        115                 120                 125

Asn Val Pro Ala Met Tyr Val Ala Ile Gln Ala Val Leu Ser Leu Tyr
    130                 135                 140

Ala Ser Gly Arg Thr Thr Gly Ile Val Leu Asp Ser Gly Asp Gly Val
145                 150                 155                 160

Thr His Asn Val Pro Ile Tyr Glu Gly Tyr Ala Leu Pro His Ala Ile
                165                 170                 175
```

-continued

```
Met Arg Leu Asp Leu Ala Gly Arg Asp Leu Thr Asp Tyr Leu Met Lys
            180                 185                 190

Ile Leu Thr Glu Arg Gly Tyr Ser Phe Val Thr Thr Ala Glu Arg Glu
        195                 200                 205

Ile Val Arg Asp Ile Lys Glu Lys Leu Cys Tyr Val Ala Leu Asp Phe
    210                 215                 220

Glu Asn Glu Met Ala Thr Ala Ala Ser Ser Ser Ser Leu Glu Lys Ser
225                 230                 235                 240

Tyr Glu Leu Pro Asp Gly Gln Val Ile Thr Ile Gly Asn Glu Arg Phe
                245                 250                 255

Arg Cys Pro Glu Thr Leu Phe Gln Pro Ser Phe Ile Gly Met Glu Ser
            260                 265                 270

Ala Gly Ile His Glu Thr Thr Tyr Asn Ser Ile Met Lys Cys Asp Ile
        275                 280                 285

Asp Ile Arg Lys Asp Leu Tyr Ala Asn Asn Val Leu Ser Gly Gly Thr
    290                 295                 300

Thr Met Tyr Pro Gly Ile Ala Asp Arg Met Gln Lys Glu Ile Thr Ala
305                 310                 315                 320

Leu Ala Pro Ser Thr Met Lys Ile Lys Ile Ile Ala Pro Pro Glu Arg
                325                 330                 335

Lys Tyr Ser Val Trp Ile Gly Gly Ser Ile Leu Ala Ser Leu Ser Thr
            340                 345                 350

Phe Gln Gln Met Trp Ile Ser Lys Pro Glu Tyr Asp Glu Ala Gly Pro
        355                 360                 365

Ser Ile Val His Arg Lys Cys Phe
    370                 375
```

<210> SEQ ID NO 9
<211> LENGTH: 8050
<212> TYPE: RNA
<213> ORGANISM: Homo sapiens

<400> SEQUENCE: 9

```
acgccgccaa cuggcggggg ugcgggggag acaauaauuu guuccgcggu aauaagaacg     60

gugacugcug gccguggauc cauuucacag gccugccuuc ucucacuaac gcucuuccua    120

guccccgggc caacucggac aguuugcuca uuuauugcaa cggucaaggc uggcuugugc    180

cagaacggcg cgcgcgcgcg cacgcacgca cacacacggg gggaaacuuu uuuaaaaaug    240

aaaggcuaga agagcucagc ggcggcgcgg gcgcugcgcg agggcuccgg agcugacucg    300

ccgaggcagg aaaucccucc ggucgcgacg cccggccccg gcucggcgcc cgcgugggau    360

ggugcagcgc ucgccgccgg gcccgagagc ugcugcacug aaggccggcg acgauggcag    420

cgcgcccgcu gcccgugucc cccgcccgcg cccuccugcu cgcccuggcc ggugcucugc    480

ucgcgcccug cgaggcccga ggggugagcu uauggaacca aggaagagcu gaugaaguug    540

ucagugccuc uguugggagu ggggaccucu ggaucccagu gaagagcuuc gacuccaaga    600

aucauccaga agugcugaau auucgacuac aacgggaaag caaagaacug aucauaaauc    660

uggaaagaaa ugaaggucuc auugccagca guuucacgga aacccacuau cugcaagacg    720

guacugaugu cucccucgcu cgaaauuaca cgguaauucu gggucacugu uacuaccaug    780

gacauguacg ggauauucu gauucagcag ucagucucag cacguguucu ggucucaggg    840

gacuuauugu guuugaaaau gaaagcuaug ucuuagaacc aaugaaaagu gcaaccaaca    900

gauacaaacu cuucccagcg aagaagcuga aaagcguccg ggaucaugu ggaucacauc    960
```

acaacacacc aaaccucgcu gcaaagaaug uguuuccacc acccucucag acaugggcaa 1020
gaaggcauaa aagagagacc cucaaggcaa cuaaguaugu ggagcuggug aucguggcag 1080
acaaccgaga guuucagagg caaggaaaag aucuggaaaa aguuaagcag cgauuaauag 1140
agauugcuaa ucacguugac aaguuuuaca gaccacugaa cauucggauc guguugguag 1200
gcguggaagu guggaaugac auggacaaau gcucuguaag ucaggaccca uucaccagcc 1260
uccaugaauu ucuggacugg aggaagauga agcuucuacc ucgcaaaucc caugacaaug 1320
cgcagcuugu caguggggguu uauuuccaag ggaccaccau cggcauggcc ccaaucauga 1380
gcaugugcac ggcagaccag ucuggggaa uugucaugga ccauucagac aauccccuug 1440
gugcagccgu gacccuggca caugagcugg gccacaauuu cgggaugaau caugacacac 1500
uggacagggg cuguagcugu caaauggcgg uugagaaagg aggcugcauc augaacgcuu 1560
ccaccgggua cccauuuccc augguguuca gcaguugcag caggaaggac uuggagacca 1620
gccuggagaa aggaaugggg gugugccugu uuaaccugcc ggaagucagg gagucuuucg 1680
ggggccagaa gugugggaac agauuugugg aagaaggaga ggagugugac uguggggagc 1740
cagaggaaug uaugaaucgc ugcugcaaug ccaccaccug uacccugaag ccggacgcug 1800
ugugcgcaca ugggcugugc ugugaagacu gccagcugaa gccugcagga acagcgugca 1860
gggacuccag caacuccugu gaccucccag aguucugcac aggggccagc ccucacugcc 1920
cagccaacgu guaccugcac gaugggcacu caugucagga uguggacggc uacugcuaca 1980
auggcaucug ccagacucac gagcagcagu gugucacgcu cuggggacca ggugcuaaac 2040
cugccccugg gaucugcuuu gagagaguca auucugcagg ugauccuuau ggcaacugug 2100
gcaaagucuc gaagaguucc uuugccaaau gcgagaugag agaugcuaaa uguggaaaaa 2160
uccaguguca aggaggugcc agccggccag ucauugguac caaugccguu uccauagaaa 2220
caaacauccc ccugcagcaa ggaggccgga uucugugccg gggacccac guguacuugg 2280 gcgaugacau gccggaccca gggcuugugc uugcaggcac aaagugugca gauggaaaaa 2340
ucugccugaa ucgucaaugu caaaauauua gugucuuugg gguucacgag ugugcaaugc 2400
agugccacgg cagaggggug ugcaacaaca ggaagaacug ccacugcgag gcccacuggg 2460
caccucccuu cugugacaag uuuggcuuug gaggaagcac agacagcggc cccauccggc 2520
aagcagauaa ccaagguuua accauaggaa uucuggugac cauccugugu cuucuugcug 2580
ccggauuugu gguuuaucuc aaaaggaaga ccuugauacg acugcuguuu acaaauaaga 2640
agaccaccau ugaaaaacua aggugugugc gcccuucccg gccaccccgu ggcuuccaac 2700
ccugucaggc ucaccucggc caccuuggaa aaggccugau gaggaagccg ccagauuccu 2760
acccaccgaa ggacaauccc aggagauugc ugcaguguca gaauguugac aucagcagac 2820
cccucaacgg ccugaauguc ccucagcccc agucaacuca gcgagugcuu ccucccccucc 2880 accgggcucc acgugcaccu agcgucccug ccagaccccu gccagccaag ccugcacuua 2940
ggcaggccca ggggaccugu aagccaaacc ccccucagaa gccucugccu gcagauccuc 3000
uggccagaac aacucggcuc acucaugccu uggccaggac cccaggacaa ugggagacug 3060
ggcuccgccu ggcacccccuc agaccugcuc cacaauaucc acaccaagug cccagaucca 3120
cccacaccgc cuauauuaag ugagaagccg acaccuuuuu ucaacaguga agacagaagu 3180
uugcacuauc uuucagcucc aguuggaguu uuuuguacca acuuuuagga uuuuuuuuaa 3240
uguuuaaaac aucauuacua uaagaacuuu gagcuacugc cgucagugcu gugcugugcu 3300

-continued

```
auggugcucu gucuacuugc ucagguacuu guaaauuauu aauuuaugca gaauguugau   3360
uacagugcag ugcgcuguag uaggcauuuu uaccaucacu gaguuuucca uggcaggaag   3420
gcuuguugug cuuuuaguau uuuagugaac uugaaauauc cugcuugaug ggauucugga   3480
caggaugugu uugcuuucug aucaaggccu uauuggaaag caguccccca acuaccccca   3540
gcugugcuua ugguaccaga ugcagcucaa gagaucccaa guagaaucuc aguugauuuu   3600
cuggauuccc caucucaggc cagagccaag ggcuucagg uccaggcugu guuuggcuuu   3660
cagggaggcc cugugccccu ugacaacugg caggcaggcu cccagggaca ccugggagaa   3720
aucuggcuuc uggccaggaa gcuuugguga gaaccugggu ugcagacagg aaucuuaagg   3780
uguagccaca ccaggauaga gacuggaaca cuagacaagc cagaacuuga cccugagcug   3840
accagccgug agcauguuug gaaggggucu guagugucac ucaaggcggu gcuugauaga   3900
aaugccaagc acuucuuuuu cucgcugucc uuucuagagc acugccacca guagguuauu   3960
uagcuuggga aagguggugu uucuguaaga aaccuacugc ccaggcacug caaaccgcca   4020
ccucccuaua cugcuuggag cugagcaaau caccacaaac uguaauacaa ugauccugua   4080
uucagacaga ugaggcuuuc caugggacca caacuauuuu cagaugugaa ccauuaacca   4140
gaucuaguca aucaagucug uuuacugcaa gguucaacuu auuaacaauu aggcagacuc   4200
uuuaugcuug caaaaacuac aaccaaugga augugauguu caugguauaa guucaugucu   4260
gcuaucauua uucguagaua uuggacaaag aaccuucucu augggcauc cucuuuuucc    4320
aacuuggcug caggaaucuu uaaaagaugc uuuuaacaga gucugaaccu auuucuuaaa   4380
cacuugcaac cuaccuguug agcaucacag aaugugauaa ggaaaucaac uugcuuauca   4440
acuuccuaaa uauuaugaga ugcuggcuug ggcagcaucc ccuugaacuc uucacucuuc   4500
aaaugccuga cuagggagcc auguuucaca aggucuuuaa agugacuaau ggcaugagaa   4560
auacaaaaau acucagauaa gguaaaaugc caugaugccu cugucuucug gacugguuuu   4620
cacauuagaa gacaauugac aacaguuaca uaauucacuc ugaguguuuu augagaaagc   4680
cuucuuuugg gggucaacag uuuuccuaug cuuugaaaca gaaaaauaug uaccaagaau   4740
cuugguuugc cuuccagaaa acaaaacugc auuucacuuu cccggguguuc cccacuguau  4800
cuaggcaaca uaguauucau gacuauggau aaacuaaaca cgugacacaa acacacacaa   4860
aagggaaccc agcucuaaua cauuccaacu cguauagcau gcaucuguuu auucuauagu   4920
uauuaaguuc uuuaaaaugu aaagccaugc uggaaaauaa uacugcugag auacauacag   4980
aauuacugua acugauuaca cuugguaauu guacuaaagc caaacauaua uauacuauua   5040
aaaagguuua cagaauuuua uggugcauua cgugggcauu gucuuuuuag augcccaaau   5100
ccuuagaucu ggcauguuag cccuuccucc aauuauaaga ggauaugaac ugaguuuuuc   5160
uuuuguuguu uguucuuagc uguaauuccu augcuucuau uucagagagc caggagaguu   5220
ugauauuaaa ggagguuaaa acugugaucu uaugccaugu caucaauggc cacuuagggg   5280
ccauggcuga ugacacauuc uuaucucuac aguacuaaug uguuauuaua gagccaugca   5340
uuuuauuucu gaauaagaac auauuuaaac uaauauuccc uuacaauaug gacaguauua   5400
auccuuccaa gaugcaguau uuaucaagug aagcauauuu agcagcaaau uccauuuuaa   5460
cauaacuuag gaaccaauaa ccagggugUU uuguggUUgg gggaggcacg ggguggagua   5520
uucuuuuuua uauccucaaa acaaaaaaaa ucaauacuua uauuucaaug gcaaucuagu   5580
auuuuuuuaa aagacuguau aggcaugaau aauagaggug guuugaguuu uguagggcca   5640
ucaccuggaa agucaaugug acuagacaca aaguagccca gaggcuacuu uucuuccuac   5700
```

agcuuauuau aguuguaggu ucuaugaccu cacuucaugg guuccaggca auuccgcuga 5760
aagguuuguc uccugaaauu uuuuaaguuu guuuuccuga cacauguaau cagaugugua 5820
gcaaccgagg gaaacgaagc cuaacauucu ccauugugga aauacacaca ggagguuaca 5880
uuucacagcg uggauuuuuc cagcuuacac augugggaug acaucacaga aaccacaaaa 5940
gcagcaaauu aaacuguagg agagucaaua cuccugacga gucucggggg gggggcauuu 6000
uuaugccuuc uuaacuuuau gagaauucuc aggcugaacu auaggccauu guucccaggc 6060
aaaucaauac aucaaugcau ccucaaaaaa aaaaaaaaaa aaaaaaaacc ggcuaaaacu 6120
gugucaaaau guucuuaagg agccuauggu cuccacggug cuaaaaagag ccuggugcug 6180
ggccgacugg cagggcugag cauccuccug cccccucgcc acugauguuu acuaagcacu 6240
cugagccaau gagaccccca gcagcagaaa gggcacaagg uggcgccagg gcagcagggc 6300
cagaucuuuc ucaugcaccu cgaccucuug cagacuuucu ucgugagaug uacuacucau 6360
uucaaaacug cuuugcaggg cuccccuaug uauucggggg gcccacggca cacucaggcu 6420
ggagauccuu ccucacugcg cucaagaugg ccucagccag acaccaguua cccagcugaa 6480
agucacaauc ccucccagaa gucucccaac acuagugcug accagaggug gggcucucag 6540
gcuaggaguu ucacacacaa ugacaggcug cugggggaca uugcaggacc ccuuuuccuc 6600
uccucuccau gcuagaagcc agcccuaggc agcugcaguu acucccugug acucagcagc 6660
aggcugauuc aacacagcug cccacacaaa gccaguggcu aauacaucug uuuaccuuuc 6720
ccuaucaccc agacacaagc cccuuuccca ggucaaacca caggccgaug caucuccagu 6780
uugacaguca aaucacuacu uccauugcua cuuuagauca gccaaagugg ugacugcugc 6840
agugugugggc uaucccuaca aggcccaccc aagggaugcc caaagcccaa ccuucuccag 6900
ggcugcagcc cagagcaacc ccaccagccu aaguccagca gaggaccucc cacccaaugu 6960
cuuguucuaa uuagaagggg aaguuagcca cagaaaauca acuuaucuau aauuacaaaa 7020
uucucuugac ucaccuuaaa guuccuauug acaucuacug cuuuuaaacc uauuugaaaa 7080
cucugauacu aaaacaaaug acacucuaag aaaguuuggg agccccaugc ugagaaccau 7140
uucugugcag ugaggauguu uccagaagcu acuuaccuac augugaaugu gccauuuucu 7200
uuccuuuugu agagaaaauc cccuuuacuu uuuggaacag uaauggcagc uucuaguaca 7260
gccauuacag uuucauauga gaaaaauuaa gaauaacuau aaaauuguua aaauauccaa 7320
uaauggauaa ugauggccag aagauuuaac auacaaagua auucucaaug uaaagcuauu 7380
cagcucuucc agguugaaug cccuguaacc cacccugacc uuccacauca ucuucaaaaa 7440
gcaguuucuc uguuccccau gauucuccua uaagguaacu cuuuaguccu ccauuuagca 7500
cauuuuaaau ccuccaaaga auaaguauca ugugauuauu uuagcuuuac aaaaaaaaag 7560
uugaauggcg uuuuauuuuc auggccuaua agcagguacc uuaguagggc agauauagga 7620
aaaacaaauu agagcaaaac aaauccucua caaauccaag gcaggaaaag ugguggcaga 7680
gugacucauu cuccugaccc ucccaucagg ucaaaucagg aggcugcagu gaaugccugu 7740
ucuuugaaug uguagcaguu guuccuguaa cucuuuaaaa cuuggcuaua ggcuguuuag 7800
cacaguacag auuaaagaua caguuacgua aacagcaaag uaauuuuaua gugcuucauc 7860
cauuuaucau gcuuugguuu gcuaauuuuu ucacauaccu uuuucuauca cagucuguug 7920
cuuuuguaca cauuucucau auuggggguuc gacagguaaa cacaaacugc uauuucagua 7980
gaaaaaguua uuguuaugaa uauuaaaccc aauaaaaugu auaaagguaa auaucaaaaa 8040
aaaaaaaaaa 8050

<210> SEQ ID NO 10
<211> LENGTH: 909
<212> TYPE: PRT
<213> ORGANISM: Homo sapiens

<400> SEQUENCE: 10

Met Ala Ala Arg Pro Leu Pro Val Ser Pro Ala Arg Ala Leu Leu Leu
1 5 10 15

Ala Leu Ala Gly Ala Leu Leu Ala Pro Cys Glu Ala Arg Gly Val Ser
20 25 30

Leu Trp Asn Gln Gly Arg Ala Asp Glu Val Val Ser Ala Ser Val Gly
35 40 45

Ser Gly Asp Leu Trp Ile Pro Val Lys Ser Phe Asp Ser Lys Asn His
50 55 60

Pro Glu Val Leu Asn Ile Arg Leu Gln Arg Glu Ser Lys Glu Leu Ile
65 70 75 80

Ile Asn Leu Glu Arg Asn Glu Gly Leu Ile Ala Ser Ser Phe Thr Glu
85 90 95

Thr His Tyr Leu Gln Asp Gly Thr Asp Val Ser Leu Ala Arg Asn Tyr
100 105 110

Thr Val Ile Leu Gly His Cys Tyr Tyr His Gly His Val Arg Gly Tyr
115 120 125

Ser Asp Ser Ala Val Ser Leu Ser Thr Cys Ser Gly Leu Arg Gly Leu
130 135 140

Ile Val Phe Glu Asn Glu Ser Tyr Val Leu Glu Pro Met Lys Ser Ala
145 150 155 160

Thr Asn Arg Tyr Lys Leu Phe Pro Ala Lys Lys Leu Lys Ser Val Arg
165 170 175

Gly Ser Cys Gly Ser His His Asn Thr Pro Asn Leu Ala Ala Lys Asn
180 185 190

Val Phe Pro Pro Pro Ser Gln Thr Trp Ala Arg Arg His Lys Arg Glu
195 200 205

Thr Leu Lys Ala Thr Lys Tyr Val Glu Leu Val Ile Val Ala Asp Asn
210 215 220

Arg Glu Phe Gln Arg Gln Gly Lys Asp Leu Glu Lys Val Lys Gln Arg
225 230 235 240

Leu Ile Glu Ile Ala Asn His Val Asp Lys Phe Tyr Arg Pro Leu Asn
245 250 255

Ile Arg Ile Val Leu Val Gly Val Glu Val Trp Asn Asp Met Asp Lys
260 265 270

Cys Ser Val Ser Gln Asp Pro Phe Thr Ser Leu His Glu Phe Leu Asp
275 280 285

Trp Arg Lys Met Lys Leu Leu Pro Arg Lys Ser His Asp Asn Ala Gln
290 295 300

Leu Val Ser Gly Val Tyr Phe Gln Gly Thr Thr Ile Gly Met Ala Pro
305 310 315 320

Ile Met Ser Met Cys Thr Ala Asp Gln Ser Gly Gly Ile Val Met Asp
325 330 335

His Ser Asp Asn Pro Leu Gly Ala Ala Val Thr Leu Ala His Glu Leu
340 345 350

Gly His Asn Phe Gly Met Asn His Asp Thr Leu Asp Arg Gly Cys Ser
355 360 365

```
Cys Gln Met Ala Val Glu Lys Gly Gly Cys Ile Met Asn Ala Ser Thr
    370                 375                 380

Gly Tyr Pro Phe Pro Met Val Phe Ser Ser Cys Ser Arg Lys Asp Leu
385                 390                 395                 400

Glu Thr Ser Leu Glu Lys Gly Met Gly Val Cys Leu Phe Asn Leu Pro
                405                 410                 415

Glu Val Arg Glu Ser Phe Gly Gly Gln Lys Cys Gly Asn Arg Phe Val
            420                 425                 430

Glu Glu Gly Glu Glu Cys Asp Cys Gly Glu Pro Glu Glu Cys Met Asn
        435                 440                 445

Arg Cys Cys Asn Ala Thr Thr Cys Thr Leu Lys Pro Asp Ala Val Cys
    450                 455                 460

Ala His Gly Leu Cys Cys Glu Asp Cys Gln Leu Lys Pro Ala Gly Thr
465                 470                 475                 480

Ala Cys Arg Asp Ser Ser Asn Ser Cys Asp Leu Pro Glu Phe Cys Thr
                485                 490                 495

Gly Ala Ser Pro His Cys Pro Ala Asn Val Tyr Leu His Asp Gly His
            500                 505                 510

Ser Cys Gln Asp Val Asp Gly Tyr Cys Tyr Asn Gly Ile Cys Gln Thr
        515                 520                 525

His Glu Gln Gln Cys Val Thr Leu Trp Gly Pro Gly Ala Lys Pro Ala
    530                 535                 540

Pro Gly Ile Cys Phe Glu Arg Val Asn Ser Ala Gly Asp Pro Tyr Gly
545                 550                 555                 560

Asn Cys Gly Lys Val Ser Lys Ser Ser Phe Ala Lys Cys Glu Met Arg
                565                 570                 575

Asp Ala Lys Cys Gly Lys Ile Gln Cys Gln Gly Gly Ala Ser Arg Pro
            580                 585                 590

Val Ile Gly Thr Asn Ala Val Ser Ile Glu Thr Asn Ile Pro Leu Gln
        595                 600                 605

Gln Gly Gly Arg Ile Leu Cys Arg Gly Thr His Val Tyr Leu Gly Asp
    610                 615                 620

Asp Met Pro Asp Pro Gly Leu Val Leu Ala Gly Thr Lys Cys Ala Asp
625                 630                 635                 640

Gly Lys Ile Cys Leu Asn Arg Gln Cys Gln Asn Ile Ser Val Phe Gly
                645                 650                 655

Val His Glu Cys Ala Met Gln Cys His Gly Arg Gly Val Cys Asn Asn
            660                 665                 670

Arg Lys Asn Cys His Cys Glu Ala His Trp Ala Pro Pro Phe Cys Asp
        675                 680                 685

Lys Phe Gly Phe Gly Gly Ser Thr Asp Ser Gly Pro Ile Arg Gln Ala
    690                 695                 700

Asp Asn Gln Gly Leu Thr Ile Gly Ile Leu Val Thr Ile Leu Cys Leu
705                 710                 715                 720

Leu Ala Ala Gly Phe Val Val Tyr Leu Lys Arg Lys Thr Leu Ile Arg
                725                 730                 735

Leu Leu Phe Thr Asn Lys Lys Thr Thr Ile Glu Lys Leu Arg Cys Val
            740                 745                 750

Arg Pro Ser Arg Pro Pro Arg Gly Phe Gln Pro Cys Gln Ala His Leu
        755                 760                 765

Gly His Leu Gly Lys Gly Leu Met Arg Lys Pro Pro Asp Ser Tyr Pro
    770                 775                 780

Pro Lys Asp Asn Pro Arg Arg Leu Leu Gln Cys Gln Asn Val Asp Ile
```

785 790 795 800

Ser Arg Pro Leu Asn Gly Leu Asn Val Pro Gln Pro Gln Ser Thr Gln
805 810 815

Arg Val Leu Pro Pro Leu His Arg Ala Pro Arg Ala Pro Ser Val Pro
820 825 830

Ala Arg Pro Leu Pro Ala Lys Pro Ala Leu Arg Gln Ala Gln Gly Thr
835 840 845

Cys Lys Pro Asn Pro Pro Gln Lys Pro Leu Pro Ala Asp Pro Leu Ala
850 855 860

Arg Thr Thr Arg Leu Thr His Ala Leu Ala Arg Thr Pro Gly Gln Trp
865 870 875 880

Glu Thr Gly Leu Arg Leu Ala Pro Leu Arg Pro Ala Pro Gln Tyr Pro
885 890 895

His Gln Val Pro Arg Ser Thr His Thr Ala Tyr Ile Lys
900 905

<210> SEQ ID NO 11
<211> LENGTH: 6554
<212> TYPE: RNA
<213> ORGANISM: Homo sapiens

<400> SEQUENCE: 11
gagggcuggg agccgggugg ggaggcgcgg ggcgagccgg ggggguuccag acgcgccucc 60 accgccgggc agugggcagg uauggcugag ggcgugugag cgccgagcgc uaagggccgc 120
cgccaccaug ccaggggggcg caggcgccgc ccggcucugc uugcuggcgu uugcccugca 180
gccccuccgg ccgcgggcgg cgcgggagcc uggauggaca agaggaagug aggaaggcag 240
ccccaagcug cagcaugaac uuaucauacc ucaguggaag acuucagaaa gccccgugag 300
agaaaagcau ccacucaaag cugagcucag gguaauggcu gaggggcgag aacugauccu 360
ggaccuggag aagaaugagc aacuuuuugc uccuuccuac acagaaaccc auuauacuuc 420
aagugguaac ccucaaacca ccacacggaa auuggaggau cacugcuuuu accacggcac 480
ggugagggag acagaacugu ccagcgucac gcucagcacu ugccgaggaa uuagaggacu 540
gauuacggug agcagcaacc ucagcuacgu caucgagccc cucccugaca gcaagggcca 600
acaccuuauu uacagaucug aacaucucaa gccgcccccg ggaaacugug gguucgagca 660
cuccaagccc accaccaggg acugggcucu ucaguuuaca caacagacca agaagcgacc 720
ucgcaggaug aaaagggaag auuuaaacuc caugaaguau guggagcuuu accucguggc 780
ugauuauuua gaguuucaga agaaucgacg agaccaggac gccaccaaac acaagcucau 840
agagaucgcc aacuauguug auaaguuuua ccgauccuug aacauccgga uugcucucgu 900
gggcuuggaa guguggaccc acgggaacau gugugaaguu ucagagaauc cauauucuac 960
ccucuggucc uuucucaguu ggaggcgcaa gcugcuugcc cagaaguacc augacaacgc 1020
ccaauuaauc acgggcaugu ccuuccacgg caccaccauc ggccuggccc cccucauggc 1080
caugugcucu guguaccagu cuggaggagu caacauggac cacuccgaga augccauugg 1140
cguggcugcc accauggccc acgagauggg ccacaacuuu ggcaugaccc augauucugc 1200
agauugcugc ucggccagug cggcugaugg ugggugcauc auggcagcug ccacugggca 1260
ccccuuuccc aaaguguuca auggaugcaa caggagggag cuggacaggu aucugcaguc 1320
agguggugga augugucucu ccaacaugcc agacaccagg auguuguaug gaggccggag 1380
gugugggaac ggguaucugg aagaugggga agagugugac uguggagaag aagaggaaug 1440

-continued

```
uaacaacccc ugcugcaaug ccucuaauug uacccugagg ccgggggcgg agugugcuca   1500
cggcuccugc ugccaccagu guaagcuguu ggcuccuggg acccugugcc gcgagcaggc   1560
caggcagugu gaccucccgg aguucuguac gggcaagucu ccccacugcc cuaccaacuu   1620
cuaccagaug gaugguaccc ccugugaggg cggccaggcc uacugcuaca acggcaugug   1680
ccucaccuac caggagcagu gccagcagcu guggggaccc ggagcccgac cugccccuga   1740
ccucugcuuc gagaaggu ga auguggcagg agacaccuuu ggaaacugug gaaaggacau   1800
gaauggugaa cacaggaagu gcaacaugag agaugcgaag ugugggaaga uccaguguca   1860
gagcucugag gcccggcccc uggaguccaa cgcggugccc auugacacca cuaucaucau   1920
gaaugggagg cagauccagu gccggggcac ccacgucuac cgagguccug aggaggaggg   1980
ugacaugcug gacccagggc uggugaugac uggaaccaag uguggcuaca accauauuug   2040
cuuugagggg cagugcagga acaccuccuu cuuugaaacu gaaggcugug ggaagaagug   2100
caauggccau ggggucugua acaacaacca gaacugccac ugccugccgg gcugggcccc   2160
gcccuucugc aacacaccgg gccacggggg caguaucgac agugggccua ugccccccuga  2220
gaguguggu ccugugguag cuggaguguu gguggccauc uuggugcugg cgguccucau   2280
gcugauguac uacugcugca gacagaacaa caaacuaggc caacucaagc ccucagcucu   2340
cccuuccaag cugaggcaac aguucaguug ucccuucagg guuucucaga acagcgggac   2400
uggucaugcc aacccaacuu ucaagcugca gacgccccag ggcaagcgaa aggugaucaa   2460
cacuccggaa auccugcgga agcccuccca gccuccuccc cggccccccuc cagauuaucu  2520
gcgugguggg uccccaccug caccacugcc agcucaccug agcagggcug cuaggaacuc   2580
cccagggccc gggucucaaa uagagaggac ggagucgucc aggaggccuc cuccaagccg   2640
gccaauuccc cccgcaccaa auugcaucgu uucccaggac uucuccaggc cucggccgcc   2700
ccagaaggca cucccggcaa acccagugcc aggccgcagg agccuccccca ggccaggagg  2760
ugcaucccca cugcggcccc cuggugcugg cccucagcag ucccggccuc uggcagcacu   2820
ugccccaaag uuuccagaau acagaucaca gagggcugga gggaugauua gcucgaaaau   2880
cuagaccugu ccaaggggcu ucucccuuuc cuugagcucu cuggacacug cagaggaccc   2940
auggccaugg aacccugaag aagcaugucu ggccgccucu gagcuccucc cacccuccuc   3000
caggaaccuc cacaucucca aaaaucuccc uguugacuca gugccuccuc ggcuuccuug   3060
gaagcccaga gggacuauga ucugauggcc ucuagguguu guuuugugca auauacagcc   3120
ccagguaggg aggggagagu augaggaggg ugacuggcag cuucuccucc agacuccuag   3180
ccccgaggug cugauggaga ugcucaaggc cagcaagccc cucaggccag cacuucgcuu   3240
gcagaagcca uccauucacu ccuggggugc agggcacgca agagagcuuc ccauugcuuc   3300
ugcucuccuc agaggucccg ggcuggaugg aggcugguac uuacccaccc cuuuuagcuu   3360
uuagggauua aggaagggguc aagccagcca cugcuguggc ccugcccagg gcuugguuga  3420
gggaacggcu ucuggcugua uggcugcaug ugacaagcca cguccccucc caccucuccc   3480
caaaccccug caucccugua uucacacggg ucacucugac ucagacaggu acuauucgua   3540
ggcaguguag acagcaggag gagcaccggg cuugggcuuc cucugagccg ugaugccaaa   3600
gguugcgacu ccugacucug gauaauuuuu aguugcucuu uguuuucucu gccgcacuuu   3660
ccuggugccc cacgcuuuuc ucucuuccuu ccccucucau ucucccucua augugguggug  3720
cuuuggugag caaacccuca gcaguccuga ccuucgggug accaggugcu ugugaccuac   3780
aagucagagu ccucucucac agucggccac uggauuuccc ucacuggcuc ucaggagugu   3840
```

gaccagagua gacuuggggc auggccauug gggucauaug uuuauuuuuc auuguguuuu 3900
gugaccucag cagggugggg gucuuccucc uuacucuaag cuaaaucuag gugagguuuc 3960
cccuuaggga gcccagcuau uuacaaagua cacacgaggg agcaggcugg ucauugacuu 4020
cgggcuggac cguugcccuc ugagcagaga acagacccau uucugggagc ugcccgagau 4080
cacuggagaa ggcagccagc agcagcugca cuggaacagu cagagcaggg agccucuucc 4140
ucaacccagc uuuuugucau ucacuuccuu uuguucucuc ucuggucacu gcccuuaccu 4200
gacccucaca gaaagagagc ucugagcagg ugaggggguc ugcgguggcu ccugucuucc 4260
cugcagcagg gaaggagggc cguguggugc uuugcuagau aggacgguuu uugcaaagca 4320
ccuggagaug uuugcuggga gauagacucc cacuccacaa aggugcuggg uggcucuccg 4380
gacaggagcu ggccugacuc ucacuccucu gaggcuuucc uggggccucc ucccauccug 4440
ccaugagcaa uuguuugcuc uugaaaaccu cacugcaagg cugaggcuga gcuucugauu 4500
caccacccca gggccuccuu auaguucucu gcacacaaua ggugcuucuu ggauguucuu 4560
ggguuuggaa auaaguggaa aauacgggau guaccccugg gggaaaagcc uggguugggu 4620
uuagaaagau cucaggaaaa ugaguuucuc uucccucagg guggcuguga uacagguucc 4680
ccauguccuu gccguggguc auccuugcug ugggucaucc uugcugugga gauccauucc 4740
ccaccuuucc uguggcccaa ccuuuuauuu aaaugugcua cccucugccu caaggcuugg 4800
uuccuggaaa guaaagguga aaacaucccc uuucaccccu cugcaaaaca aacaagcaac 4860
auccucaaaa cccaacccca ugccucacag agcuuccugu ggcuucucca gccuuucucc 4920
cucacaucag gagguagaua gcucugaaau gacagcgcca cagccauagu gacugcauga 4980
gccaucugaa ccugcagucc acccucccug gaaccacacc agaaagagac cuggguuguc 5040
guuuucuugc uuuuuguuuu guuuuguuuu auuauuuuca uaucaccucc aucccauaaa 5100
guuguacugu gaacuggaag augguggaau guuuuggaau uugauagacu uucggcaacc 5160
aguucuacua augcuucacu ccuggcucug uucagggagg cugcccagga ggaagacugg 5220
ccauuaugca uccccuuuuc uuuccagugc ccaguaugcu guuuugaggu gucaaauaca 5280
aauaaaucug ggcuuaggga aggagagacc uuauuccaaa gcacgauugc agaaggggaa 5340
agggaauauu gcaaaaggga gaggaagggg ccuuauggga auagugaaaa ggcucagacc 5400
gaccgauggc aagaucugca agcgucucaa agcccaggca gaaaaggacu uuucuuuuau 5460
uggaagaagu aaacauggcu agaaagaacc acguucaggg aaugacguug ugcccagccu 5520
uuuuuuuuuu uuuuuuuuuu uuugucuccag gggaggggcu guuugcuggc ucaggcugag 5580
gauggcccaa aguccagggu cuggugggga ggagggaagc uuaacucaag uuuggguuag 5640
ugaguuagca agcucuuugu gcagaugggg auguagguaa aucuuuuuaa aagugaaauu 5700
aaccuccugc caauuuuaca acccaagaau uuuuuuuuaa gggccuugga gccaucucua 5760
aaacaaaccu caagggauuu agugcccugu cucccugucu cuagaagccu uagccugggc 5820
accuggcuca aucuuguaac ugccugcuag ccauagauuc cuuucagccu ugcugacuuc 5880
ucccuauaaa aguaaagccu uuuucugccc cagcucugag acacuugcag aucuuaaggu 5940
cugagacuug cugauuuucu gguuggagug uuuuuuugua uugccauagu cccuuccccc 6000
ugaagcaaua gccccucccc accuccugca auacgccuuu ccaaucuuua uuggaagucu 6060
cucccugccu acuuccuaau uuauucuuau uugacagagg guauggaaga cuugcaauuu 6120
gaaaacuggg gaccaguucc aaagucagua auuguguuaa ccacguguau aacagcucug 6180
cuggacaccc aagaaagcca ugggaacgcc aacuggaaag guccccuucc ccaggggagc 6240
cugcgaagga gagguucugu agaauccaag cccacauuuc caaagucacc cccaacgcgu 6300
ccucucacac cguccacugu gcguuuguau gugucuggga uccagggcaa ugugaauuuu 6360
cuuuuuauuu gggagauugu ucacggaaaa cagaucuucu ucucucuugu ccaccuauua 6420
auuguuuaca auauuuguac aucuaugcaa aauacuugaa ugggccaugg ugccuuuuuu 6480
ccuuguuagu auuuaauuaa aaaugaauug uuugucauuu gcaauguuaa aaaaaaaaaa 6540
aaaaaaaaaa aaaa 6554

<210> SEQ ID NO 12
<211> LENGTH: 955
<212> TYPE: PRT
<213> ORGANISM: Homo sapiens

<400> SEQUENCE: 12

Met Pro Gly Gly Ala Gly Ala Ala Arg Leu Cys Leu Leu Ala Phe Ala
1 5 10 15

Leu Gln Pro Leu Arg Pro Arg Ala Ala Arg Glu Pro Gly Trp Thr Arg
20 25 30

Gly Ser Glu Glu Gly Ser Pro Lys Leu Gln His Glu Leu Ile Ile Pro
35 40 45

Gln Trp Lys Thr Ser Glu Ser Pro Val Arg Glu Lys His Pro Leu Lys
50 55 60

Ala Glu Leu Arg Val Met Ala Glu Gly Arg Glu Leu Ile Leu Asp Leu
65 70 75 80

Glu Lys Asn Glu Gln Leu Phe Ala Pro Ser Tyr Thr Glu Thr His Tyr
85 90 95

Thr Ser Ser Gly Asn Pro Gln Thr Thr Thr Arg Lys Leu Glu Asp His
100 105 110

Cys Phe Tyr His Gly Thr Val Arg Glu Thr Glu Leu Ser Ser Val Thr
115 120 125

Leu Ser Thr Cys Arg Gly Ile Arg Gly Leu Ile Thr Val Ser Ser Asn
130 135 140

Leu Ser Tyr Val Ile Glu Pro Leu Pro Asp Ser Lys Gly Gln His Leu
145 150 155 160

Ile Tyr Arg Ser Glu His Leu Lys Pro Pro Pro Gly Asn Cys Gly Phe
165 170 175

Glu His Ser Lys Pro Thr Thr Arg Asp Trp Ala Leu Gln Phe Thr Gln
180 185 190

Gln Thr Lys Lys Arg Pro Arg Arg Met Lys Arg Glu Asp Leu Asn Ser
195 200 205

Met Lys Tyr Val Glu Leu Tyr Leu Val Ala Asp Tyr Leu Glu Phe Gln
210 215 220

Lys Asn Arg Arg Asp Gln Asp Ala Thr Lys His Lys Leu Ile Glu Ile
225 230 235 240

Ala Asn Tyr Val Asp Lys Phe Tyr Arg Ser Leu Asn Ile Arg Ile Ala
245 250 255

Leu Val Gly Leu Glu Val Trp Thr His Gly Asn Met Cys Glu Val Ser
260 265 270

Glu Asn Pro Tyr Ser Thr Leu Trp Ser Phe Leu Ser Trp Arg Arg Lys
275 280 285

Leu Leu Ala Gln Lys Tyr His Asp Asn Ala Gln Leu Ile Thr Gly Met
290 295 300

-continued

```
Ser Phe His Gly Thr Thr Ile Gly Leu Ala Pro Leu Met Ala Met Cys
305                 310                 315                 320

Ser Val Tyr Gln Ser Gly Gly Val Asn Met Asp His Ser Glu Asn Ala
                325                 330                 335

Ile Gly Val Ala Ala Thr Met Ala His Glu Met Gly His Asn Phe Gly
            340                 345                 350

Met Thr His Asp Ser Ala Asp Cys Cys Ser Ala Ser Ala Ala Asp Gly
        355                 360                 365

Gly Cys Ile Met Ala Ala Ala Thr Gly His Pro Phe Pro Lys Val Phe
    370                 375                 380

Asn Gly Cys Asn Arg Arg Glu Leu Asp Arg Tyr Leu Gln Ser Gly Gly
385                 390                 395                 400

Gly Met Cys Leu Ser Asn Met Pro Asp Thr Arg Met Leu Tyr Gly Gly
                405                 410                 415

Arg Arg Cys Gly Asn Gly Tyr Leu Glu Asp Gly Glu Glu Cys Asp Cys
            420                 425                 430

Gly Glu Glu Glu Glu Cys Asn Asn Pro Cys Cys Asn Ala Ser Asn Cys
        435                 440                 445

Thr Leu Arg Pro Gly Ala Glu Cys Ala His Gly Ser Cys Cys His Gln
    450                 455                 460

Cys Lys Leu Leu Ala Pro Gly Thr Leu Cys Arg Glu Gln Ala Arg Gln
465                 470                 475                 480

Cys Asp Leu Pro Glu Phe Cys Thr Gly Lys Ser Pro His Cys Pro Thr
                485                 490                 495

Asn Phe Tyr Gln Met Asp Gly Thr Pro Cys Glu Gly Gly Gln Ala Tyr
            500                 505                 510

Cys Tyr Asn Gly Met Cys Leu Thr Tyr Gln Glu Gln Cys Gln Gln Leu
        515                 520                 525

Trp Gly Pro Gly Ala Arg Pro Ala Pro Asp Leu Cys Phe Glu Lys Val
    530                 535                 540

Asn Val Ala Gly Asp Thr Phe Gly Asn Cys Gly Lys Asp Met Asn Gly
545                 550                 555                 560

Glu His Arg Lys Cys Asn Met Arg Asp Ala Lys Cys Gly Lys Ile Gln
                565                 570                 575

Cys Gln Ser Ser Glu Ala Arg Pro Leu Glu Ser Asn Ala Val Pro Ile
            580                 585                 590

Asp Thr Thr Ile Ile Met Asn Gly Arg Gln Ile Gln Cys Arg Gly Thr
        595                 600                 605

His Val Tyr Arg Gly Pro Glu Glu Glu Gly Asp Met Leu Asp Pro Gly
    610                 615                 620

Leu Val Met Thr Gly Thr Lys Cys Gly Tyr Asn His Ile Cys Phe Glu
625                 630                 635                 640

Gly Gln Cys Arg Asn Thr Ser Phe Phe Glu Thr Glu Gly Cys Gly Lys
                645                 650                 655

Lys Cys Asn Gly His Gly Val Cys Asn Asn Asn Gln Asn Cys His Cys
            660                 665                 670

Leu Pro Gly Trp Ala Pro Pro Phe Cys Asn Thr Pro Gly His Gly Gly
        675                 680                 685

Ser Ile Asp Ser Gly Pro Met Pro Pro Glu Ser Val Gly Pro Val Val
    690                 695                 700

Ala Gly Val Leu Val Ala Ile Leu Val Leu Ala Val Leu Met Leu Met
705                 710                 715                 720

Tyr Tyr Cys Cys Arg Gln Asn Asn Lys Leu Gly Gln Leu Lys Pro Ser
```

-continued

```
                725                 730                 735

Ala Leu Pro Ser Lys Leu Arg Gln Gln Phe Ser Cys Pro Phe Arg Val
            740                 745                 750

Ser Gln Asn Ser Gly Thr Gly His Ala Asn Pro Thr Phe Lys Leu Gln
        755                 760                 765

Thr Pro Gln Gly Lys Arg Lys Val Ile Asn Thr Pro Glu Ile Leu Arg
    770                 775                 780

Lys Pro Ser Gln Pro Pro Pro Arg Pro Pro Pro Asp Tyr Leu Arg Gly
785                 790                 795                 800

Gly Ser Pro Pro Ala Pro Leu Pro Ala His Leu Ser Arg Ala Ala Arg
            805                 810                 815

Asn Ser Pro Gly Pro Gly Ser Gln Ile Glu Arg Thr Glu Ser Ser Arg
            820                 825                 830

Arg Pro Pro Pro Ser Arg Pro Ile Pro Pro Ala Pro Asn Cys Ile Val
        835                 840                 845

Ser Gln Asp Phe Ser Arg Pro Arg Pro Pro Gln Lys Ala Leu Pro Ala
    850                 855                 860

Asn Pro Val Pro Gly Arg Arg Ser Leu Pro Arg Pro Gly Gly Ala Ser
865                 870                 875                 880

Pro Leu Arg Pro Pro Gly Ala Gly Pro Gln Gln Ser Arg Pro Leu Ala
            885                 890                 895

Ala Leu Ala Pro Lys Val Ser Pro Arg Glu Ala Leu Lys Val Lys Ala
            900                 905                 910

Gly Thr Arg Gly Leu Gln Gly Gly Arg Cys Arg Val Glu Lys Thr Lys
        915                 920                 925

Gln Phe Met Leu Leu Val Val Trp Thr Glu Leu Pro Glu Gln Lys Pro
    930                 935                 940

Arg Ala Lys His Ser Cys Phe Leu Val Pro Ala
945                 950                 955


<210> SEQ ID NO 13
<211> LENGTH: 1646
<212> TYPE: RNA
<213> ORGANISM: Homo sapiens

<400> SEQUENCE: 13

gggaggggaa ggcagcugag guuguggggg gaggugcccc gccccuuggc aggccccuac      60

agccaaugga acggcccugg aagagacccg ggucgccucc ggagcuucaa aaacauguga     120

ggagggaaga gugugcagac ggaacuucag ccgcugccuc uguucucagc gucagugccg     180

ccacugcccc cgccagagcc caccggccag cauguccucu gcucacuuca accgaggccc     240

ugccuacggg cugucagccg agguuaagaa caagcuggcc cagaaguaug accaccagcg     300

ggagcaggag cugagagagu ggaucgaggg ggugacaggc cgucgcaucg gcaacaacuu     360

cauggacggc cucaaagaug gcaucauucu uugcgaauuc aucaauaagc ugcagccagg     420

cuccgugaag aagaucaaug agucaaccca aaauuggcac cagcuggaga acaucggcaa     480

cuucaucaag gccaucacca aguauggggu gaagccccac gacauuuuug aggccaacga     540

ccuguuugag aacaccaacc auacacaggu gcaguccacc cuccuggcuu uggccagcau     600

ggcgaagacg aaaggaaaca aggugaacgu gggagugaag uacgcagaga agcaggagcg     660

gaaauucgag ccggggaagc uaagagaagg gcggaacauc auugggcugc agaugggcac     720

caacaaguuu gccagccagc agggcaugac ggccuauggc acccggcgcc accucuacga     780

ccccaagcug ggcacagacc agccucugga ccaggcgacc aucagccugc agaugggcac     840
```

caacaaagga gccagccagg cuggcaugac ugcgccaggg accaagcggc agaucuucga 900
gccggggcug ggcauggagc acugcgacac gcucaauguc agccugcaga ugggcagcaa 960
caagggcgcc ucgcagcggg gcaugacggu guaugggcug ccacgccagg ucuacgaccc 1020
caaguacugu cugacucccg aguacccaga gcugggugag cccgcccaca accaccacgc 1080
acacaacuac uacaauuccg ccuagggcca caaggccuuc ccuguuuucc ccccaaggga 1140
ggcugcugcu gcucuuggcu ggacccagcc aggcccagcc gacccccucu cccugcaugg 1200
cauccuccag ccccuguaga acucaaccuc uacaggguua gaguuuggag agagcagacu 1260 ggcgggggc ccauuggggg gaaggggacc cuccgcucug uagugcuaca ggguccaaca 1320
uagagccggg uguccccaac agcgcccaaa ggacgcacug agcaacgcua uuccagcugu 1380
ccccccacuc ccucacaagu ggguaccccc aggaccagaa gcucccccag caaagccccc 1440
agagcccagg cucggccugc ccccacccca uucccgcagu gggagcaaac ugcaugccca 1500
gagacccagc ggacacacgc gguuugguuu gcagcgacug gcauacuaug uggaugugac 1560
aguggcguuu guaaugagag cacuuucuuu uuuuucuauu ucacuggagc acaauaaaug 1620
gcuguaaaau cucaaaaaaa aaaaaa 1646

<210> SEQ ID NO 14
<211> LENGTH: 297
<212> TYPE: PRT
<213> ORGANISM: Homo sapiens

<400> SEQUENCE: 14

Met Ser Ser Ala His Phe Asn Arg Gly Pro Ala Tyr Gly Leu Ser Ala
1               5                   10                  15

Glu Val Lys Asn Lys Leu Ala Gln Lys Tyr Asp His Gln Arg Glu Gln
            20                  25                  30

Glu Leu Arg Glu Trp Ile Glu Gly Val Thr Gly Arg Arg Ile Gly Asn
        35                  40                  45

Asn Phe Met Asp Gly Leu Lys Asp Gly Ile Ile Leu Cys Glu Phe Ile
    50                  55                  60

Asn Lys Leu Gln Pro Gly Ser Val Lys Lys Ile Asn Glu Ser Thr Gln
65                  70                  75                  80

Asn Trp His Gln Leu Glu Asn Ile Gly Asn Phe Ile Lys Ala Ile Thr
                85                  90                  95

Lys Tyr Gly Val Lys Pro His Asp Ile Phe Glu Ala Asn Asp Leu Phe
            100                 105                 110

Glu Asn Thr Asn His Thr Gln Val Gln Ser Thr Leu Leu Ala Leu Ala
        115                 120                 125

Ser Met Ala Lys Thr Lys Gly Asn Lys Val Asn Val Gly Val Lys Tyr
    130                 135                 140

Ala Glu Lys Gln Glu Arg Lys Phe Glu Pro Gly Lys Leu Arg Glu Gly
145                 150                 155                 160

Arg Asn Ile Ile Gly Leu Gln Met Gly Thr Asn Lys Phe Ala Ser Gln
                165                 170                 175

Gln Gly Met Thr Ala Tyr Gly Thr Arg Arg His Leu Tyr Asp Pro Lys
            180                 185                 190

Leu Gly Thr Asp Gln Pro Leu Asp Gln Ala Thr Ile Ser Leu Gln Met
        195                 200                 205

Gly Thr Asn Lys Gly Ala Ser Gln Ala Gly Met Thr Ala Pro Gly Thr
    210                 215                 220

-continued

```
Lys Arg Gln Ile Phe Glu Pro Gly Leu Gly Met Glu His Cys Asp Thr
225                 230                 235                 240

Leu Asn Val Ser Leu Gln Met Gly Ser Asn Lys Gly Ala Ser Gln Arg
                245                 250                 255

Gly Met Thr Val Tyr Gly Leu Pro Arg Gln Val Tyr Asp Pro Lys Tyr
            260                 265                 270

Cys Leu Thr Pro Glu Tyr Pro Glu Leu Gly Glu Pro Ala His Asn His
        275                 280                 285

His Ala His Asn Tyr Tyr Asn Ser Ala
    290                 295


<210> SEQ ID NO 15
<211> LENGTH: 6545
<212> TYPE: RNA
<213> ORGANISM: Homo sapiens

<400> SEQUENCE: 15

aggucuccgc uuggagccgc cgcacccggg acggugcgua gcgcuggaag uccggccuuc     60

cgagagcuag cuguccgccg cggcccccgc acgccgggca gccgucccuc gccgccucgg    120

gcgcgccacc auggggcccc ggcucagcgu cuggcugcug cugcugcccg ccgcccuucu    180

gcuccacgag gagcacagcc gggccgcugc gaagggugge ugugcuggcu cuggcugugg    240

caaaugugac ugccauggag ugaagggaca aaagggugaa agaggccucc cgggguuaca    300

aggugucauu ggguuuccug gaaugcaagg accugagggg ccacagggac caccaggaca    360

aaagggugau acuggagaac caggacuacc uggaacaaaa gggacaagag gaccuccggg    420

agcaucuggc uacccuggaa acccaggacu ucccggaauu ccuggccaag acggcccgcc    480

aggcccccca gguauuccag gaugcaaugg cacaaagggg gagagagggc cgcucgggcc    540

uccuggcuug ccugguuucg cuggaaaucc cggaccacca ggcuuaccag ggaugaaggg    600

ugauccaggu gagauacuug gccaugugcc cgggaugcug uugaaaggug aaagaggauu    660

ucccggaauc ccagggacuc caggcccacc aggacugcca gggcuucaag guccuguugg    720

gccuccagga uuuaccggac caccaggucc cccaggcccu cccggcccuc caggugaaaa    780

gggacaaaug ggcuuaaguu uucaaggacc aaaaggugac aagggugacc aagggggucag    840

ugggccucca ggaguaccag gacaagcuca aguucaagaa aaaggagacu ucgccaccaa    900

gggagaaaag ggccaaaaag gugaaccugg auuucagggg augccagggg ucggagagaa    960

aggugaaccc ggaaaaccag gacccagagg caaacccgga aaagauggug acaaagggga   1020

aaaagggagu cccgguuuuc cuggugaacc cggguaccca ggacucauag gccgccaggg   1080

cccgcaggga gaaaagggug aagcaggucc uccuggccca ccuggaauug uuauaggcac   1140

aggaccuuug ggagaaaaag gagagagggg cuacccugga acuccggggc caagaggaga   1200

gccaggccca aaagguuucc caggacuacc aggccaaccc ggaccuccag gccucccugu   1260

accugggcag gcuggugccc cuggcuuccc uggugaaaga ggagaaaaag gugaccgagg   1320

auuuccuggu acaucucugc caggaccaag uggaagagau gggcucccgg guccuccugg   1380

uuccccuggg cccccugggc agccuggcua cacaaaugga auuguggaau gucagcccgg   1440

accuccaggu gaccaggguc cuccuggaau uccagggcag ccaggauuua uaggcgaaau   1500

uggagagaaa ggucaaaaag gagagaguug ccucaucugu gauauagacg gauaucgggg   1560

gccucccggg ccacagggac ccccgggaga aauagguuuc ccagggcagc caggggccaa   1620

gggcgacaga gguuugccug gcagagaugg uguugcagga gugccaggcc cucaagguac   1680
```

-continued

```
accagggcug auaggccagc caggagccaa gggggagccu ggugaguuuu auuucgacuu   1740
gcggcucaaa ggugacaaag gagacccagg cuuuccagga cagcccggca ugccagggag   1800
agcggguucu ccuggaagag auggccaucc gggucuuccu ggccccaagg gcucgccggg   1860
uucuguagga uugaaaggag agcguggccc cccuggagga guuggauucc caggcagucg   1920
uggugacacc ggcccccug ggccuccagg auauggucu gcuggucca uuggugacaa   1980
aggacaagca ggcuuuccug gaggcccugg aucccaggc cugccagguc caaaggguga   2040
accaggaaaa auuguuccuu uaccaggccc cccuggagca gaaggacugc cggggucccc   2100
aggcuuccca gguccccaag gagaccgagg cuuucccgga accccaggaa ggccaggccu   2160
gccaggagag aagggcgcug ugggccagcc aggcauugga uuuccagggc cccccggccc   2220
caaaggugu gacggcuuac cuggagacau ggggccaccg gggacuccag gucgcccggg   2280
auuuaauggc uuaccuggga acccaggugu gcagggccag aagggagagc cuggaguugg   2340
ucuaccggga cucaaagguu ugccaggucu ucccggcauu ccuggcacac ccggggagaa   2400
ggggagcauu ggguaccag gcguuccugg agaacaugga gcgaucggac ccccugggcu   2460
ucaggggauc agaggugaac cgggaccucc uggauugcca ggcuccgugg ggucuccagg   2520
aguuccagga auaggccccc cuggagcuag ggguccccu ggaggacagg gaccaccggg   2580
guugucaggc ccuccuggaa uaaaaggaga gaaggguuuc cccggauucc cuggacugga   2640
caugccgggc ccuaaaggag auaaagggc ucaaggacuc ccuggcauaa cgggacaguc   2700
ggggcucccu ggccuuccug gacagcaggg ggcuccuggg auuccugggu uuccagguuc   2760
caagggagaa augggcguca uggggacccc cgggcagccg ggcucaccag gaccaguggg   2820
ugcuccugga uuaccgggug aaaaagggga ccauggcuuu ccgggcuccu caggacccag   2880
gggagacccu ggcuugaaag gugauaaggg ggaugucggu cucccuggca agccuggcuc   2940
cauggauaag guggacaugg gcagcaugaa gggccagaaa ggagaccaag gagagaaagg   3000
acaaauugga ccaauuggug agaagggauc ccgaggagac ccugggaccc caggagugcc   3060
uggaaaggac gggcaggcag gacagccugg gcagccagga ccuaaaggug auccagguau   3120
aaguggaacc ccaggugcuc caggacuucc gggaccaaaa ggaucuguug guggaauggg   3180
cuugccagga acaccuggag agaaaggugu gccuggcauc ccuggcccac aagguucacc   3240
uggcuuaccu ggagacaaag gugcaaaagg agagaaaggg caggcaggcc caccuggcau   3300
aggcauccca gggcugcgag gugaaaaggg agaucaaggg auagcggguu ucccaggaag   3360
cccuggagag aagggagaaa aaggaagcau ugggauccca ggaaugccag gguccccagg   3420
ccuuaaaggg ucucccggga guguuggcua uccaggaagu ccugggcuac cuggagaaaa   3480
aggugacaaa ggccucccag gauuggaugg caucccuggu gucaaaggag aagcaggucu   3540
uccugggacu ccuggcccca caggcccagc uggccagaaa ggggagccag gcagugaugg   3600
aaucccgggg ucagcaggag agaaggguga accaggucua ccaggaagag gauucccagg   3660
guuuccaggg gccaaaggag acaaagguuc aaagggugag gugggguucc caggauuagc   3720
cgggagccca ggaauuccug gauccaaagg agagcaagga uucauggguc cuccggggcc   3780
ccagggacag ccgggguuac cgggaucccc aggccaugcc acggaggggc ccaaaggaga   3840
ccgcggaccu cagggccagc cuggccugcc aggacuuccg ggacccaugg ggccuccagg   3900
gcuuccuggg auugauggag uuaaagguga caaaggaaau ccaggcuggc caggagcacc   3960
cggugucca gggcccaagg gagacccugg auuccagggc augccuggua uugguggcuc   4020
uccaggaauc acaggcucua aggguaua ggggccucca ggaguuccag gauuucaagg   4080
```

uccaaaaggu cuuccuggcc uccagggaau uaaaggugau caaggcgauc aaggcguccc 4140
gggagcuaaa ggucucccgg guccuccugg ccccccaggu ccuuacgaca ucaucaaagg 4200
ggagcccggg cucccugguc cugagggccc cccagggcug aaagggcuuc agggacugcc 4260
aggcccgaaa ggccagcaag guguuacagg auuggugggu auaccuggac cuccagguau 4320
uccuggguuu gacggugccc cuggccagaa aggagagaug ggaccugccg ggccuacugg 4380
uccaagagga uuuccagguc caccaggccc cgauggguug ccaggaucca uggggccccc 4440
aggcacccca ucuguugauc acggcuuccu ugugaccagg cauagucaaa caauagauga 4500
cccacagugu ccuucuggga ccaaaauucu uuaccacggg uacucuuugc ucuacgugca 4560
aggcaaugaa cgggcccaug gccaggacuu gggcacggcc ggcagcugcc ugcgcaaguu 4620
cagcacaaug cccuuccugu ucugcaauau uaacaacgug ugcaacuuug caucacgaaa 4680
ugacuacucg uacuggcugu ccaccccuga gcccaugccc augucaaugg cacccaucac 4740
gggggaaaac auaagaccau uuauuaguag gugugcugug ugugaggcgc cugccauggu 4800
gauggccgug cacagccaga ccauucagau cccaccgugc cccagcgggu gguccucgcu 4860
guggaucggc uacucuuuug ugaugcacac cagcgcuggu gcagaaggcu cuggccaagc 4920
ccuggcgucc cccggcuccu gccuggagga guuuagaagu gcgccauuca ucgaguguca 4980
cggccguggg accugcaauu acuacgcaaa cgcuuacagc uuuuggcucg ccaccauaga 5040
gaggagcgag auguucaaga agccuacgcc guccaccuug aaggcagggg agcugcgcac 5100
gcacgucagc cgcugccaag ucuguaugag aagaacauaa ugaagccuga cucagcuaau 5160
gucacaacau ggugcuacuu cuucuucuuu uuguuaacag caacgaaccc uagaaauaua 5220
uccuguguac cucacugucc aauaugaaaa ccguaaagug ccuuauagga auuugcguaa 5280
cuaacacacc cugcuucauu gaccucuacu ugcugaagga gaaaaagaca gcgauaagcu 5340
uucaauagug gcauaccaaa uggcacuuuu gaugaaauaa aauaucaaua uuuucugcaa 5400
uccaaugcac ugauguguga agugagaacu ccaucagaaa accaaagggu gcuaggaggu 5460
gugggugccu uccauacugu uugcccauuu ucauucuugu auuauaauua auuuucuacc 5520
cccagagaua aauguuuguu uauaucacug ucuagcuguu ucaaaauuua ggucccuugg 5580
ucuguacaaa uaauagcaau guaaaaaugg uuuuuugaac cuccaaaugg aauuacagac 5640
ucaguagcca uaucuuccaa ccccccagua uaaauuucug ucuuucugcu augugugua 5700
cuuugcagcu gcuuuugcag aaaucacaau uuuccugugg aauaaagaug guccaaaaau 5760
agucaaaaau uaaauauaua uauauauuag uaauuuauau agaugucagc aauuaggcag 5820
aucaagguuu aguuuaacuu ccacuguuaa aauaaagcuu acauaguuuu cuuccuuuga 5880
aagacugugc uguccuuuaa cauagguuuu uaaagacuag gauauugaau gugaaacauc 5940
cguuuucauu guucacuucu aaaccaaaaa uuauguguug ccaaaaccaa acccagguuc 6000
augaauaugg ugucuauuau agugaaacau guacuuugag cuuauuguuu uuauucugua 6060
uuaaauauuu ucaggguuuu aaacacuaau cacaaacuga augacuugac uucaaaagca 6120
acaaccuuaa aggccgucau uucauuagua uuccucauuc ugcauccugg cuugaaaaac 6180
agcucuguug aaucacagua ucaguauuuu cacacguaag cacauucggg ccauuuccgu 6240
gguuucucau gagcuguguu cacagaccuc agcagggcau cgcauggacc gcaggagggc 6300
agauucggac cacuaggccu gaaaugacau uucacuaaaa gucuccaaaa cauuucuaag 6360
acuacuaagg ccuuuuaugu aauuucuuua aauguguauu ucuuaagaau ucaaauuugu 6420

-continued aauaaaacua uuuguauaaa aauuaagcuu uuauuaauuu guugcuagua uugccacaga 6480
cgcauuaaaa gaaacuuacu gcacaagcug cuaauaaauu uguaagcuuu gcauaccuua 6540
gauua 6545

<210> SEQ ID NO 16
<211> LENGTH: 1669
<212> TYPE: PRT
<213> ORGANISM: Homo sapiens

<400> SEQUENCE: 16

Met Gly Pro Arg Leu Ser Val Trp Leu Leu Leu Leu Pro Ala Ala Leu
1 5 10 15

Leu Leu His Glu Glu His Ser Arg Ala Ala Ala Lys Gly Gly Cys Ala
20 25 30

Gly Ser Gly Cys Gly Lys Cys Asp Cys His Gly Val Lys Gly Gln Lys
35 40 45

Gly Glu Arg Gly Leu Pro Gly Leu Gln Gly Val Ile Gly Phe Pro Gly
50 55 60

Met Gln Gly Pro Glu Gly Pro Gln Gly Pro Pro Gly Gln Lys Gly Asp
65 70 75 80

Thr Gly Glu Pro Gly Leu Pro Gly Thr Lys Gly Thr Arg Gly Pro Pro
85 90 95

Gly Ala Ser Gly Tyr Pro Gly Asn Pro Gly Leu Pro Gly Ile Pro Gly
100 105 110

Gln Asp Gly Pro Pro Gly Pro Pro Gly Ile Pro Gly Cys Asn Gly Thr
115 120 125

Lys Gly Glu Arg Gly Pro Leu Gly Pro Pro Gly Leu Pro Gly Phe Ala
130 135 140

Gly Asn Pro Gly Pro Pro Gly Leu Pro Gly Met Lys Gly Asp Pro Gly
145 150 155 160

Glu Ile Leu Gly His Val Pro Gly Met Leu Leu Lys Gly Glu Arg Gly
165 170 175

Phe Pro Gly Ile Pro Gly Thr Pro Gly Pro Pro Gly Leu Pro Gly Leu
180 185 190

Gln Gly Pro Val Gly Pro Pro Gly Phe Thr Gly Pro Pro Gly Pro Pro
195 200 205

Gly Pro Pro Gly Pro Pro Gly Glu Lys Gly Gln Met Gly Leu Ser Phe
210 215 220

Gln Gly Pro Lys Gly Asp Lys Gly Asp Gln Gly Val Ser Gly Pro Pro
225 230 235 240

Gly Val Pro Gly Gln Ala Gln Val Gln Glu Lys Gly Asp Phe Ala Thr
245 250 255

Lys Gly Glu Lys Gly Gln Lys Gly Glu Pro Gly Phe Gln Gly Met Pro
260 265 270

Gly Val Gly Glu Lys Gly Glu Pro Gly Lys Pro Gly Pro Arg Gly Lys
275 280 285

Pro Gly Lys Asp Gly Asp Lys Gly Glu Lys Gly Ser Pro Gly Phe Pro
290 295 300

Gly Glu Pro Gly Tyr Pro Gly Leu Ile Gly Arg Gln Gly Pro Gln Gly
305 310 315 320

Glu Lys Gly Glu Ala Gly Pro Pro Gly Pro Pro Gly Ile Val Ile Gly
325 330 335

Thr Gly Pro Leu Gly Glu Lys Gly Glu Arg Gly Tyr Pro Gly Thr Pro
340 345 350

```
Gly Pro Arg Gly Glu Pro Gly Pro Lys Gly Phe Pro Gly Leu Pro Gly
        355                 360                 365

Gln Pro Gly Pro Pro Gly Leu Pro Val Pro Gly Gln Ala Gly Ala Pro
    370                 375                 380

Gly Phe Pro Gly Glu Arg Gly Glu Lys Gly Asp Arg Gly Phe Pro Gly
385                 390                 395                 400

Thr Ser Leu Pro Gly Pro Ser Gly Arg Asp Gly Leu Pro Gly Pro Pro
                405                 410                 415

Gly Ser Pro Gly Pro Pro Gly Gln Pro Gly Tyr Thr Asn Gly Ile Val
            420                 425                 430

Glu Cys Gln Pro Gly Pro Pro Gly Asp Gln Gly Pro Pro Gly Ile Pro
        435                 440                 445

Gly Gln Pro Gly Phe Ile Gly Glu Ile Gly Glu Lys Gly Gln Lys Gly
    450                 455                 460

Glu Ser Cys Leu Ile Cys Asp Ile Asp Gly Tyr Arg Gly Pro Pro Gly
465                 470                 475                 480

Pro Gln Gly Pro Pro Gly Glu Ile Gly Phe Pro Gly Gln Pro Gly Ala
                485                 490                 495

Lys Gly Asp Arg Gly Leu Pro Gly Arg Asp Gly Val Ala Gly Val Pro
            500                 505                 510

Gly Pro Gln Gly Thr Pro Gly Leu Ile Gly Gln Pro Gly Ala Lys Gly
        515                 520                 525

Glu Pro Gly Glu Phe Tyr Phe Asp Leu Arg Leu Lys Gly Asp Lys Gly
    530                 535                 540

Asp Pro Gly Phe Pro Gly Gln Pro Gly Met Thr Gly Arg Ala Gly Ser
545                 550                 555                 560

Pro Gly Arg Asp Gly His Pro Gly Leu Pro Gly Pro Lys Gly Ser Pro
                565                 570                 575

Gly Ser Val Gly Leu Lys Gly Glu Arg Gly Pro Pro Gly Gly Val Gly
            580                 585                 590

Phe Pro Gly Ser Arg Gly Asp Thr Gly Pro Pro Gly Pro Pro Gly Tyr
        595                 600                 605

Gly Pro Ala Gly Pro Ile Gly Asp Lys Gly Gln Ala Gly Phe Pro Gly
    610                 615                 620

Gly Pro Gly Ser Pro Gly Leu Pro Gly Pro Lys Gly Glu Pro Gly Lys
625                 630                 635                 640

Ile Val Pro Leu Pro Gly Pro Pro Gly Ala Glu Gly Leu Pro Gly Ser
                645                 650                 655

Pro Gly Phe Pro Gly Pro Gln Gly Asp Arg Gly Phe Pro Gly Thr Pro
            660                 665                 670

Gly Arg Pro Gly Leu Pro Gly Glu Lys Gly Ala Val Gly Gln Pro Gly
        675                 680                 685

Ile Gly Phe Pro Gly Pro Pro Gly Pro Lys Gly Val Asp Gly Leu Pro
    690                 695                 700

Gly Asp Met Gly Pro Pro Gly Thr Pro Gly Arg Pro Gly Phe Asn Gly
705                 710                 715                 720

Leu Pro Gly Asn Pro Gly Val Gln Gly Gln Lys Gly Glu Pro Gly Val
                725                 730                 735

Gly Leu Pro Gly Leu Lys Gly Leu Pro Gly Leu Pro Gly Ile Pro Gly
            740                 745                 750

Thr Pro Gly Glu Lys Gly Ser Ile Gly Val Pro Gly Val Pro Gly Glu
        755                 760                 765
```

```
His Gly Ala Ile Gly Pro Pro Gly Leu Gln Gly Ile Arg Gly Glu Pro
    770                 775                 780

Gly Pro Pro Gly Leu Pro Gly Ser Val Gly Ser Pro Gly Val Pro Gly
785                 790                 795                 800

Ile Gly Pro Pro Gly Ala Arg Gly Pro Pro Gly Gly Gln Gly Pro Pro
                805                 810                 815

Gly Leu Ser Gly Pro Pro Gly Ile Lys Gly Glu Lys Gly Phe Pro Gly
            820                 825                 830

Phe Pro Gly Leu Asp Met Pro Gly Pro Lys Gly Asp Lys Gly Ala Gln
        835                 840                 845

Gly Leu Pro Gly Ile Thr Gly Gln Ser Gly Leu Pro Gly Leu Pro Gly
    850                 855                 860

Gln Gln Gly Ala Pro Gly Ile Pro Gly Phe Pro Gly Ser Lys Gly Glu
865                 870                 875                 880

Met Gly Val Met Gly Thr Pro Gly Gln Pro Gly Ser Pro Gly Pro Val
                885                 890                 895

Gly Ala Pro Gly Leu Pro Gly Glu Lys Gly Asp His Gly Phe Pro Gly
            900                 905                 910

Ser Ser Gly Pro Arg Gly Asp Pro Gly Leu Lys Gly Asp Lys Gly Asp
        915                 920                 925

Val Gly Leu Pro Gly Lys Pro Gly Ser Met Asp Lys Val Asp Met Gly
    930                 935                 940

Ser Met Lys Gly Gln Lys Gly Asp Gln Gly Glu Lys Gly Gln Ile Gly
945                 950                 955                 960

Pro Ile Gly Glu Lys Gly Ser Arg Gly Asp Pro Gly Thr Pro Gly Val
                965                 970                 975

Pro Gly Lys Asp Gly Gln Ala Gly Gln Pro Gly Gln Pro Gly Pro Lys
            980                 985                 990

Gly Asp Pro Gly Ile Ser Gly Thr  Pro Gly Ala Pro Gly  Leu Pro Gly
        995                 1000                1005

Pro Lys  Gly Ser Val Gly Gly  Met Gly Leu Pro Gly  Thr Pro Gly
    1010                1015                1020

Glu Lys  Gly Val Pro Gly Ile  Pro Gly Pro Gln Gly  Ser Pro Gly
    1025                1030                1035

Leu Pro  Gly Asp Lys Gly Ala  Lys Gly Glu Lys Gly  Gln Ala Gly
    1040                1045                1050

Pro Pro  Gly Ile Gly Ile Pro  Gly Leu Arg Gly Glu  Lys Gly Asp
    1055                1060                1065

Gln Gly  Ile Ala Gly Phe Pro  Gly Ser Pro Gly Glu  Lys Gly Glu
    1070                1075                1080

Lys Gly  Ser Ile Gly Ile Pro  Gly Met Pro Gly Ser  Pro Gly Leu
    1085                1090                1095

Lys Gly  Ser Pro Gly Ser Val  Gly Tyr Pro Gly Ser  Pro Gly Leu
    1100                1105                1110

Pro Gly  Glu Lys Gly Asp Lys  Gly Leu Pro Gly Leu  Asp Gly Ile
    1115                1120                1125

Pro Gly  Val Lys Gly Glu Ala  Gly Leu Pro Gly Thr  Pro Gly Pro
    1130                1135                1140

Thr Gly  Pro Ala Gly Gln Lys  Gly Glu Pro Gly Ser  Asp Gly Ile
    1145                1150                1155

Pro Gly  Ser Ala Gly Glu Lys  Gly Glu Pro Gly Leu  Pro Gly Arg
    1160                1165                1170

Gly Phe  Pro Gly Phe Pro Gly  Ala Lys Gly Asp Lys  Gly Ser Lys
```

```
    1175                1180                1185

Gly Glu  Val Gly Phe Pro Gly  Leu Ala Gly Ser Pro  Gly Ile Pro
    1190                1195                1200

Gly Ser  Lys Gly Glu Gln Gly  Phe Met Gly Pro Pro  Gly Pro Gln
    1205                1210                1215

Gly Gln  Pro Gly Leu Pro Gly  Ser Pro Gly His Ala  Thr Glu Gly
    1220                1225                1230

Pro Lys  Gly Asp Arg Gly Pro  Gln Gly Gln Pro Gly  Leu Pro Gly
    1235                1240                1245

Leu Pro  Gly Pro Met Gly Pro  Pro Gly Leu Pro Gly  Ile Asp Gly
    1250                1255                1260

Val Lys  Gly Asp Lys Gly Asn  Pro Gly Trp Pro Gly  Ala Pro Gly
    1265                1270                1275

Val Pro  Gly Pro Lys Gly Asp  Pro Gly Phe Gln Gly  Met Pro Gly
    1280                1285                1290

Ile Gly  Gly Ser Pro Gly Ile  Thr Gly Ser Lys Gly  Asp Met Gly
    1295                1300                1305

Pro Pro  Gly Val Pro Gly Phe  Gln Gly Pro Lys Gly  Leu Pro Gly
    1310                1315                1320

Leu Gln  Gly Ile Lys Gly Asp  Gln Gly Asp Gln Gly  Val Pro Gly
    1325                1330                1335

Ala Lys  Gly Leu Pro Gly Pro  Pro Gly Pro Pro Gly  Pro Tyr Asp
    1340                1345                1350

Ile Ile  Lys Gly Glu Pro Gly  Leu Pro Gly Pro Glu  Gly Pro Pro
    1355                1360                1365

Gly Leu  Lys Gly Leu Gln Gly  Leu Pro Gly Pro Lys  Gly Gln Gln
    1370                1375                1380

Gly Val  Thr Gly Leu Val Gly  Ile Pro Gly Pro Pro  Gly Ile Pro
    1385                1390                1395

Gly Phe  Asp Gly Ala Pro Gly  Gln Lys Gly Glu Met  Gly Pro Ala
    1400                1405                1410

Gly Pro  Thr Gly Pro Arg Gly  Phe Pro Gly Pro Pro  Gly Pro Asp
    1415                1420                1425

Gly Leu  Pro Gly Ser Met Gly  Pro Pro Gly Thr Pro  Ser Val Asp
    1430                1435                1440

His Gly  Phe Leu Val Thr Arg  His Ser Gln Thr Ile  Asp Asp Pro
    1445                1450                1455

Gln Cys  Pro Ser Gly Thr Lys  Ile Leu Tyr His Gly  Tyr Ser Leu
    1460                1465                1470

Leu Tyr  Val Gln Gly Asn Glu  Arg Ala His Gly Gln  Asp Leu Gly
    1475                1480                1485

Thr Ala  Gly Ser Cys Leu Arg  Lys Phe Ser Thr Met  Pro Phe Leu
    1490                1495                1500

Phe Cys  Asn Ile Asn Asn Val  Cys Asn Phe Ala Ser  Arg Asn Asp
    1505                1510                1515

Tyr Ser  Tyr Trp Leu Ser Thr  Pro Glu Pro Met Pro  Met Ser Met
    1520                1525                1530

Ala Pro  Ile Thr Gly Glu Asn  Ile Arg Pro Phe Ile  Ser Arg Cys
    1535                1540                1545

Ala Val  Cys Glu Ala Pro Ala  Met Val Met Ala Val  His Ser Gln
    1550                1555                1560

Thr Ile  Gln Ile Pro Pro Cys  Pro Ser Gly Trp Ser  Ser Leu Trp
    1565                1570                1575
```

```
Ile Gly  Tyr Ser Phe Val Met  His Thr Ser Ala Gly  Ala Glu Gly
    1580                 1585                 1590

Ser Gly  Gln Ala Leu Ala Ser  Pro Gly Ser Cys Leu  Glu Glu Phe
    1595                 1600                 1605

Arg Ser  Ala Pro Phe Ile Glu  Cys His Gly Arg Gly  Thr Cys Asn
    1610                 1615                 1620

Tyr Tyr  Ala Asn Ala Tyr Ser  Phe Trp Leu Ala Thr  Ile Glu Arg
    1625                 1630                 1635

Ser Glu  Met Phe Lys Lys Pro  Thr Pro Ser Thr Leu  Lys Ala Gly
    1640                 1645                 1650

Glu Leu  Arg Thr His Val Ser  Arg Cys Gln Val Cys  Met Arg Arg
    1655                 1660                 1665

Thr


<210> SEQ ID NO 17
<211> LENGTH: 2358
<212> TYPE: RNA
<213> ORGANISM: Homo sapiens

<400> SEQUENCE: 17

aaacucacac aacaacucuu ccccgcugag aggagacagc cagugcgacu ccacccucca      60

gcucgacggc agccgccccg gccgacagcc ccgagacgac agcccggcgc gucccggucc     120

ccaccuccga ccaccgccag cgcuccaggc cccgccgcuc cccgcucgcc gccaccgcgc     180

ccuccgcucc gcccgcagug ccaaccauga ccgccgccag uaugggcccc guccgcgucg     240

ccuucguggu ccuccucgcc cucugcagcc ggccggccgu cggccagaac ugcagcgggc     300

cgugccggug cccggacgag ccggcgccgc gcugcccggc gggcgugagc cucgugcugg     360

acggcugcgg cugcugccgc gucugcgcca agcagcuggg cgagcugugc accgagcgcg     420

accccugcga cccgcacaag ggccucuucu gugacuucgg cuccccggcc aaccgcaaga     480

ucggcgugug caccgccaaa gauggugcuc ccugcaucuu cggugguacg guguaccgca     540

gcggagaguc cuuccagagc agcugcaagu accagugcac gugccuggac ggggcggugg     600

gcugcaugcc ccugugcagc auggacguuc gucugcccag cccugacugc cccuucccga     660

ggagggucaa gcugcccggg aaaugcugcg aggagugggu gugugacgag cccaaggacc     720

aaaccguggu ugggccugcc cucgcggcuu accgacugga agacacguuu ggcccagacc     780

caacuaugau uagagccaac ugccuggucc agaccacaga guggagcgcc uguuccaaga     840

ccugugggau gggcaucucc acccggguua ccaaugacaa cgccuccugc aggcuagaga     900

agcagagccg ccugugcaug gucaggccuu gcgaagcuga ccuggaagag aacauuaaga     960

agggcaaaaa gugcauccgu acucccaaaa ucuccaagcc uaucaaguuu gagcuuucug    1020

gcugcaccag caugaagaca uaccgagcua aauucugugg aguauguacc gacggccgau    1080

gcugcacccc ccacagaacc accacccugc cgguggaguu caagugcccu gacggcgagg    1140

ucaugaagaa gaacaugaug uucaucaaga ccugugccug ccauuacaac ugucccggag    1200

acaaugacau cuuugaaucg cuguacuaca ggaagaugua cggagacaug gcaugaagcc    1260

agagagugag agacauuaac ucauuagacu ggaacuugaa cugauucaca ucucauuuuu    1320

ccguaaaaau gauuucagua gcacaaguua uuuaaaucug uuuuucuaac uggggggaaaa    1380

gauucccacc caauucaaaa cauugugcca ugucaaacaa auagucuauc aaccccagac    1440

acugguuuga agaauguuaa gacuugacag uggaacuaca uuaguacaca gcaccagaau    1500
```

-continued

```
guauauuaag guguggcuuu aggagcagug ggaggguacc agcagaaagg uuaguaucau   1560

cagauagcau cuuauacgag uaauaugccu gcuauuugaa guguaauuga gaaggaaaau   1620

uuuagcgugc ucacugaccu gccuguagcc ccagugacag cuaggaugug cauucuccag   1680

ccaucaagag acugagucaa guuguuccuu aagucagaac agcagacuca gcucugacau   1740

ucugauucga augacacugu ucaggaaucg gaauccuguc gauuagacug gacagcuugu   1800

ggcaagugaa uuugccugua acaagccaga uuuuuuaaaa uuuauauugu aaauauugug   1860

ugugugugug ugugguguaua uauauauaua uguacaguua ucuaaguuaa uuuaaaguug   1920

uuugugccuu uuuauuuuug uuuuuaaugc uuugauauuu caauguuagc cucaauuucu   1980

gaacaccaua gguagaaugu aaagcuuguc ugaucguuca aagcaugaaa uggauacuua   2040

uauggaaauu cugcucagau agaaugacag uccgucaaaa cagauuguuu gcaaagggga   2100

ggcaucagug uccuuggcag gcugauuucu agguaggaaa ugugguagcc ucacuuuuaa   2160

ugaacaaaug gccuuuauua aaaacugagu gacucuauau agcugaucag uuuuuucacc   2220

uggaagcauu uguuucuacu uugauaugac uguuuuucgg acaguuuauu uguugagagu   2280

gugaccaaaa guuacauguu ugcaccuuuc uaguugaaaa uaaaguguau auuuuuucua   2340

uaaaaaaaaa aaaaaaaa                                                 2358
```

```
<210> SEQ ID NO 18
<211> LENGTH: 349
<212> TYPE: PRT
<213> ORGANISM: Homo sapiens

<400> SEQUENCE: 18

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys His Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220
```

```
Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345


<210> SEQ ID NO 19
<211> LENGTH: 3248
<212> TYPE: RNA
<213> ORGANISM: Homo sapiens

<400> SEQUENCE: 19

acuuccgucu uggaggccag gguggcgcug ccgccguccc ucgcccggag gcagagaugc      60

gcuggcgcau caccgccagg agcccacagu gaaagaccau cggauggaag gcgacgccca     120

gaacuccagg agaccgcugu gggaggacgc gaggccaggu gacgaauagg ccaggcguga     180

guucccaaac agccuccucc ccuucaagag aguaagcuug ggccacaggc ugggacggaa     240

gcagaggggc agacacgcca ccacccgccc ggccucgaac cuacggcggc acaguucagc     300

ggaggcggcc cagcgguccu gucccgcgcc ugcgcacucc aggccccgcc ccgccccgcg     360

cccuccaggc ccggcccgcc cuccaaccuc ugcgugcgca cagccuagag cccgccuccg     420

ugaaagacug ccgggcgcau gcggucgggg uuguucacug gcuguccggg gcuccgcgcg     480

cgucgccggc ccagcucugu cgcugacggg aggaucugaa gccggccgca ggucaaagag     540

uaaaaugaag uacauucugg uuacuggugg uguuauauca ggaauuggaa aaggaaucau     600

ugccagcagu gugggcacaa uacucaaguc augugguuua cauguaacuu caaucaaaau     660

ugaccccuac auuaacauug augcaggaac auucucuccu uaugagcaug gugagguuuu     720

ugugcuggau gaugguggg aaguagaccu ugaccugggu aacuaugagc gguuccuuga     780

cauccgccuc accaaggaca auaaucugac cacuggaaag auauaccagu augucauuaa     840

caaggaacgg aaaggagauu acuuggggaa aacuguccaa guugucccuc auaucacaga     900

ugcaauccag gagugggguga ugagacaggc guuaauaccu guagaugaag auggccugga     960

accucaagug uguguuauug agcuuggugg aaccguggg gacauagaaa gcaugcccuu    1020

uauugaggcc uuccgucagu uccaauucaa ggucaaaaga gagaacuuuu guaacaucca    1080

cgucagucua guuccccagc caaguucaac aggggaacag aagacuaaac cuacccagaa    1140

uaguguucgg gaacuuagag gacuugggcu uuccccagau cugguuguau gcaggugcuc    1200

aaauccacuu gacacaucag ugaaggagaa aauaucaaug uucugccaug uugagccuga    1260

acaagugauc uguguccacg augucucauc caucuaccga guccccuugu uguuagagga    1320

gcaaggggguu guagauuauu uucuucgaag acuugaccuu ccuauugaga ggcagccaag    1380
```

```
aaaaaugcug augaaaugga aagagauggc ugacagauau gaucgcuugc uggagaccug   1440
cucuauugcc cuugugggca aauacacgaa guucucagac uccuaugccu cugucauuaa   1500
ggcucuggag cauucugcac uggccaucaa ccacaaauug gaaaucaagu acauagauuc   1560
ugcggacuug gagcccauca ccucgcaaga agagcccgug cgcuaccacg aagcuuggca   1620
gaagcucugu agugcucaug gagugcuggu uccaggagga uuuggugguuc gaggaacaga  1680
aggaaaaauc caagcaauug ccugggcucg gaaucagaaa aagccuuuuu ugggcgugug   1740
cuuagggaug caguuggcag ugguugaauu cucaagaaac gugcugggau ggcaagaugc   1800
caauucuaca gaguuugacc cuacgaccag ucaucccgug gucguagaca ugccagaaca   1860
caacccaggg cagaugggcg gaaccaugag gcugggcaag aggagaaccc uguuccagac   1920
caagaacuca gucaugagga aacucuaugg agacgcagac uacuuggaag agaggcaccg   1980
ccaccgauuu gaggugaauc cagucuggaa aaaguguuug gaagaacaag gcuugaaguu   2040
uguuggccaa gauguugaag gagagagaau ggaaauugug gaguuagaag aucaucccuu   2100
uuuuguuggg guucaguacc acccugaguu ccuguccagg ccuaucaagc ccucccccacc  2160
auacuuuggc cuccuccugg ccucuguggg gcggcucuca cauuaccucc agaaaggcug   2220
caggcucuca cccagggaca ccuauaguga caggagugga agcagcuccc cugacucuga   2280
aaucaccgaa cugaaguuuc caucaauaaa ucaugacuga ucuuguagcg gaugauucuu   2340
caagagaccc uucaaacuug gguagaguuu acagcucuga cuuuacacuc ggcuuuggag   2400
acuuucuuua aauuauguuu uuauuaagau uauuuuauua ugcggaaagg uauuugggaa   2460
acuugucacu ugcaaguccc aucacgugua cuggcuccuc uguggugucu gccuguugcg   2520
ugacacucuc cuugcaguuc uugaguugcg gcagaacauc gcgaugggaa ccgauggugg   2580
guggggcugc agagugcccc aucggucacc uuguuucuca acuaccucgc aucauugcag   2640
augcuagcgc guugccuguc gcuuucccuu ggauaccuag accguuauaa agugugccac   2700
auggacuuac cgagcaugga gagaggauuu uagcuaggau uugaacacuu ggugcuggga   2760
accucagggu auugcuugcc acuaagccau gaaaccagag acaaaaucuc uauacugccc   2820
ugaguugggg ggaauucuca gugccaacug uggcuggucc ucauucaaag ggacggucag   2880
uuuggugguca acaugaaaca ccaagauguc ugucucugaa gcgugauuuu aaaaucccca  2940
ugccuguggc ugcgcuuccu auuucuaggg cugggaaaca cuccuugcau caaggggguca  3000
cuuacagaac aaagaaucuu uuggggggaaa cuuccucuaa aacccucuca uauauagaca 3060
gcuuugacug gaggguccau uuuucuucca ggaugguguu acugcaguug aaagggcaau   3120
augaaguuac uuucuuaaug ugaccuagca auaggcauag cuacguggca cuauauucug   3180
gccagacucg auguguacuc uaacuuaaga aauaaaucag uaaggcagaa caagagaaaa   3240
aaaaaaaa                                                           3248
```

<210> SEQ ID NO 20
<211> LENGTH: 591
<212> TYPE: PRT
<213> ORGANISM: Homo sapiens

<400> SEQUENCE: 20

```
Met Lys Tyr Ile Leu Val Thr Gly Gly Val Ile Ser Gly Ile Gly Lys
1               5                   10                  15

Gly Ile Ile Ala Ser Ser Val Gly Thr Ile Leu Lys Ser Cys Gly Leu
            20                  25                  30

His Val Thr Ser Ile Lys Ile Asp Pro Tyr Ile Asn Ile Asp Ala Gly
```

```
        35                  40                  45

Thr Phe Ser Pro Tyr Glu His Gly Glu Val Phe Val Leu Asp Asp Gly
    50                  55                  60

Gly Glu Val Asp Leu Asp Leu Gly Asn Tyr Glu Arg Phe Leu Asp Ile
65                  70                  75                  80

Arg Leu Thr Lys Asp Asn Asn Leu Thr Thr Gly Lys Ile Tyr Gln Tyr
                85                  90                  95

Val Ile Asn Lys Glu Arg Lys Gly Asp Tyr Leu Gly Lys Thr Val Gln
            100                 105                 110

Val Val Pro His Ile Thr Asp Ala Ile Gln Glu Trp Val Met Arg Gln
        115                 120                 125

Ala Leu Ile Pro Val Asp Glu Asp Gly Leu Glu Pro Gln Val Cys Val
    130                 135                 140

Ile Glu Leu Gly Gly Thr Val Gly Asp Ile Glu Ser Met Pro Phe Ile
145                 150                 155                 160

Glu Ala Phe Arg Gln Phe Gln Phe Lys Val Lys Arg Glu Asn Phe Cys
                165                 170                 175

Asn Ile His Val Ser Leu Val Pro Gln Pro Ser Ser Thr Gly Glu Gln
            180                 185                 190

Lys Thr Lys Pro Thr Gln Asn Ser Val Arg Glu Leu Arg Gly Leu Gly
        195                 200                 205

Leu Ser Pro Asp Leu Val Val Cys Arg Cys Ser Asn Pro Leu Asp Thr
    210                 215                 220

Ser Val Lys Glu Lys Ile Ser Met Phe Cys His Val Glu Pro Glu Gln
225                 230                 235                 240

Val Ile Cys Val His Asp Val Ser Ser Ile Tyr Arg Val Pro Leu Leu
                245                 250                 255

Leu Glu Glu Gln Gly Val Val Asp Tyr Phe Leu Arg Arg Leu Asp Leu
            260                 265                 270

Pro Ile Glu Arg Gln Pro Arg Lys Met Leu Met Lys Trp Lys Glu Met
        275                 280                 285

Ala Asp Arg Tyr Asp Arg Leu Leu Glu Thr Cys Ser Ile Ala Leu Val
    290                 295                 300

Gly Lys Tyr Thr Lys Phe Ser Asp Ser Tyr Ala Ser Val Ile Lys Ala
305                 310                 315                 320

Leu Glu His Ser Ala Leu Ala Ile Asn His Lys Leu Glu Ile Lys Tyr
                325                 330                 335

Ile Asp Ser Ala Asp Leu Glu Pro Ile Thr Ser Gln Glu Glu Pro Val
            340                 345                 350

Arg Tyr His Glu Ala Trp Gln Lys Leu Cys Ser Ala His Gly Val Leu
        355                 360                 365

Val Pro Gly Gly Phe Gly Val Arg Gly Thr Glu Gly Lys Ile Gln Ala
    370                 375                 380

Ile Ala Trp Ala Arg Asn Gln Lys Lys Pro Phe Leu Gly Val Cys Leu
385                 390                 395                 400

Gly Met Gln Leu Ala Val Val Glu Phe Ser Arg Asn Val Leu Gly Trp
                405                 410                 415

Gln Asp Ala Asn Ser Thr Glu Phe Asp Pro Thr Thr Ser His Pro Val
            420                 425                 430

Val Val Asp Met Pro Glu His Asn Pro Gly Gln Met Gly Gly Thr Met
        435                 440                 445

Arg Leu Gly Lys Arg Arg Thr Leu Phe Gln Thr Lys Asn Ser Val Met
    450                 455                 460
```

Arg Lys Leu Tyr Gly Asp Ala Asp Tyr Leu Glu Glu Arg His Arg His
465 470 475 480

Arg Phe Glu Val Asn Pro Val Trp Lys Lys Cys Leu Glu Glu Gln Gly
485 490 495

Leu Lys Phe Val Gly Gln Asp Val Glu Gly Glu Arg Met Glu Ile Val
500 505 510

Glu Leu Glu Asp His Pro Phe Phe Val Gly Val Gln Tyr His Pro Glu
515 520 525

Phe Leu Ser Arg Pro Ile Lys Pro Ser Pro Pro Tyr Phe Gly Leu Leu
530 535 540

Leu Ala Ser Val Gly Arg Leu Ser His Tyr Leu Gln Lys Gly Cys Arg
545 550 555 560

Leu Ser Pro Arg Asp Thr Tyr Ser Asp Arg Ser Gly Ser Ser Ser Pro
565 570 575

Asp Ser Glu Ile Thr Glu Leu Lys Phe Pro Ser Ile Asn His Asp
580 585 590

<210> SEQ ID NO 21
<211> LENGTH: 3895
<212> TYPE: RNA
<213> ORGANISM: Homo sapiens

<400> SEQUENCE: 21
gucugcgccc cucgcugucc cgcgaccccg gcgcgggugc cucgggcccc ccucgcgcgc 60
cgccauggug ggccggcuga gccuacagga ugugcccgag cucguggacg cgaagaagaa 120
gggcgacggc guccuggaca gcccggacuc ggggcugccc cccagcccca gccccagcca 180
cugggggcuc gcggcgggcg gaggcggcgg agagcgcgcg gcggcaccgg ggacgcugga 240
gcccgacgcg gcggcggcga cccccgcggc uccgagucca gcgucucucc cccuggcucc 300
cggcugugcg cugaggcuuu guccccuguc cuuuggcgaa ggaguggagu uugaccccuu 360
accaccaaag gaaguaaggu acaccuccuu ggucaaguac gacuccgaga ggcacuucau 420
cgacgacgug cagcugcccc ugggccuggc gguggccucc ugcagccaga cggucaccug 480
uguccccaau ggcacguggc gcaacuacaa ggccgaggug cgcuucgagc cacgccacag 540
gcccacccgc uuccucagua ccaccaucgu guaccccaag uaccccaagg ccgucuacac 600
caccacccug gauuacaacu gccgcaagac gcugaggagg uuucugucca gcguggagcu 660
cgaagccgcg gagcucccgg gcagcgacga ccucucugau gaaugcugac ccagcaggcu 720
gggcuggggu cggaccggcu cucccgcugu ccugccccccg acugcccugg ccaagcuggg 780
cgaccuuacc cuucacguca uuccagcccc agaggagucu aaccuagaga uaccuccaag 840
cgcggccggg ggaagagaaa aaaaagaaaa aaucacugca ucucauaauu auugagaucu 900
uuguguugua auuuucaagc uguuuuuaga gggaauauau guccugguuu gcugcugugu 960
uguuucccca aagucucaau cagaugaggc aacaaaaaga ccaccagaau ugcaggaaag 1020
cagcagcagu cugggauagg gagggggggag gagagcucuc ccuccguggu caguuuguca 1080
gaagaaaagc auggaaaaag ugagauuuaa gaaaucucag ccacgggugu cuucacugca 1140
caaaaguggu gcuaauucag uaaacaguga caccugugug gguucaaucu guggagaguu 1200
gaguuccauu ccuuuguuuu uaaauuucca ccuccauuug uguuuccuau uaaccuaaac 1260
ucuuguaauu cucuaaaucu uuuuucauga uauaaaaaaa aaagaaaauc ccaaaccaca 1320
auuuaagaug ccuuuuuuuu uuaaaaaaaa agguucuccg uguugccacc ugcuccggga 1380

-continued aggccaggcc gaugggcggc cagguuuggg agcagcggcu ucggcuccga uugcuuccug 1440
acggucaguu ccaagcacag gcucugagaa acgccucgaa cccuugguau cuggugaccg 1500
ucuccgcagg cuuccgugag ucuccgauag guguuuuggg cuuuuggaau acuuucagaa 1560
uacuuuccca uuuuuucaua aggcaaaacg gaguggacgg ccuuuuuuug agagaaacag 1620
cauucuaaga gugugcuugg aaaacacacu uuuugggagu ccacgugggg aguggacacu 1680
caggacagga agcgguggcc cuaagaccug cggccacccg gaggaggcag acgcaggcga 1740
ugaccugguu caucaugaga ggagcuagag uugacucagu cuuaggaucu cgauggcguc 1800
agaauugcag aggguuucug ccagugccuu aggucuaauu cagaaagcaa ggaaggcugg 1860 gcacggugge uggcgccugu agucucagcu acuuggaaac ugaggcagga ggaucucuug 1920
agcccaagaa uucgagaccg gucuggcaac auagugagcc uccaucucua aaaaaaagug 1980
gcaaagcuga ggaaaucugu gcccccaucc cccgacacca gacaagcuaa ggugcauuca 2040
gaguagggaa cgaugucaaa accuggccgc cgugguggcg cgcauuccuc ucacaccacc 2100
guacggaggc aggugacagu caacugaaau guccccaagg accgugugaa uucggcuggc 2160
guggcccagc agcgggugg accagggugc gguggcuuca gaccugccuc ccgccacccc 2220
guccuccccu aaccccuucu ugggaccucc ugccaauccc ugugguguuu gaguaaagaa 2280
aguggcugau gguuuuacuu uuuucuucca auauuggaaa gaacaaacua gauauucccc 2340
uugaacacau ccaaauuauu uccagugccu gaggguuacc gagcacugua agcucagcuc 2400
ggcuguagcu ccggguuucu gccgauggcc uccaucugcg ccgaaagcug aacugagccc 2460
cgcggugccc cggagccaca gcagcaggug cagcgacaau cgccgucgug cgcagucgcu 2520
ggaguccugg agagccacgc uguccucugc agacaacagc aucaguccgc ugugccccaa 2580
ugcaucgacg cccuguggac ggggccugca guccacccgu ggucugagcu ugccgggcug 2640
aagcucggcu gggacccagg gaggggccac ccugggaccc acagucuccu cagucacgug 2700
cagagcaaaa aaugcuuccu guguuuggaa gagcaaguga cgcagcauuu auugauaaaa 2760
auggauuuuu cugucugauu ucaugcugug gucguuuaag uggucaaugu cuuuuuuuuu 2820
uuuuuuuuug acauggaguc ucgcucuguu gcccaggcug aguggaaugg cgccaacuca 2880
gcucacugca accuucaccu cccaggcuca agcgacucuc cugccucagc cuccugagca 2940
gcugggauua caggugccca ccaccacgcc cagcuaauuu uuguauuuuu aguagagacg 3000
ggguuucacc auguuggcca ggcuggucuc gaacaccuga ccuugugauc cacccgccuc 3060
ggccucccaa uaauuuguaa guuauguuag cgggauccuc aaggccuugc uuugccccgu 3120
ggagacgcuu gcucggauga gcucaggaaa caguaccggc ugcguggcag gucugggugu 3180
ugugugcgag gacguggccu uugaacaccg cuguguucuc agagguccuu aggagauauu 3240
uuuuuuuguc uuagggggac uguguuaagu ucagacaaau caugcugggu guguagagag 3300
ugugaaauac gucagugaag uaaguagcag ugagcgauug ugaaugugua auguaaaugg 3360
aaaaccgggu uuuaccgugu uaaguuauuc acuagggagc cagucguagu ucuuuguaau 3420
ccucuuucuu ccaaaccugc uuugcugaaa guugcagaaa aggaagugug uggagagaaa 3480
cagaacccuu cagggugggu cagaggacgc cauccacagu ggauucgugu ucguuugcag 3540
guggaagcag ugauuuuuag gacccacuga uuaaaaacaa acauucccaa gugucucuga 3600
gagaugcugu uuauuuguua auuaaaaagc uuuuuucucu gucuuuuaaa uuauggcuuu 3660
cauguaauaa ggauauuuuu agugaaaaau uguuuuccuu ucaaauuaca gaccuuuuaa 3720
aaaaacuuaa uuugagcgag uaccuuuuca uuugacacuu uuccuguuuc uaaccuuagg 3780

```
aaaccagaau agcguuuggc agacacgacg uuuucaguuu accuuugaca ccugccccac   3840

uccauuuugc uuugugaugu cuucauuuaa caauaaauua ucugaaaaaa caaaa        3895


<210> SEQ ID NO 22
<211> LENGTH: 214
<212> TYPE: PRT
<213> ORGANISM: Homo sapiens

<400> SEQUENCE: 22

Met Val Gly Arg Leu Ser Leu Gln Asp Val Pro Glu Leu Val Asp Ala
1               5                   10                  15

Lys Lys Lys Gly Asp Gly Val Leu Asp Ser Pro Asp Ser Gly Leu Pro
            20                  25                  30

Pro Ser Pro Ser Pro Ser His Trp Gly Leu Ala Ala Gly Gly Gly Gly
        35                  40                  45

Gly Glu Arg Ala Ala Ala Pro Gly Thr Leu Glu Pro Asp Ala Ala Ala
    50                  55                  60

Ala Thr Pro Ala Ala Pro Ser Pro Ala Ser Leu Pro Leu Ala Pro Gly
65                  70                  75                  80

Cys Ala Leu Arg Leu Cys Pro Leu Ser Phe Gly Glu Gly Val Glu Phe
                85                  90                  95

Asp Pro Leu Pro Pro Lys Glu Val Arg Tyr Thr Ser Leu Val Lys Tyr
            100                 105                 110

Asp Ser Glu Arg His Phe Ile Asp Asp Val Gln Leu Pro Leu Gly Leu
        115                 120                 125

Ala Val Ala Ser Cys Ser Gln Thr Val Thr Cys Val Pro Asn Gly Thr
    130                 135                 140

Trp Arg Asn Tyr Lys Ala Glu Val Arg Phe Glu Pro Arg His Arg Pro
145                 150                 155                 160

Thr Arg Phe Leu Ser Thr Thr Ile Val Tyr Pro Lys Tyr Pro Lys Ala
                165                 170                 175

Val Tyr Thr Thr Thr Leu Asp Tyr Asn Cys Arg Lys Thr Leu Arg Arg
            180                 185                 190

Phe Leu Ser Ser Val Glu Leu Glu Ala Ala Glu Leu Pro Gly Ser Asp
        195                 200                 205

Asp Leu Ser Asp Glu Cys
    210


<210> SEQ ID NO 23
<211> LENGTH: 2525
<212> TYPE: RNA
<213> ORGANISM: Homo sapiens

<400> SEQUENCE: 23

gggaagucgg ugccgcugcc gucucugcgu ucgccaugcg ucccggggcg ccagggccac     60

ucuggccucu gcccuggggg gcccuggcuu gggccguggg cuucgugagc uccaugggcu    120

cggggaaccc cgcgcccggu gguguuugcu ggcuccagca gggccaggag gccaccugca    180

gccuggugcu ccagacugau gucacccggg ccgagugcug ugccuccggc aacauugaca    240

ccgccugguc caaccucacc cacccgggga acaagaucaa ccuccucggc uucuugggcc    300

uuguccacug ccuucccugc aaagauucgu gcgacggcgu ggagugcggc ccgggcaagg    360

cgugccgcau gcugggggc cgcccgcgcu gcgagugcgc gcccgacugc ucggggcucc    420

cggcgcggcu gcaggucugc ggcucagacg gcgccaccua ccgcgacgag ugcgagcugc    480
```

gcgccgcgcg cugccgcggc cacccggacc ugagcgucau guaccggggc cgcugccgca 540
aguccuguga gcacguggug ugcccgcggc cacagucgug cgucguggac cagacgggca 600
gcgcccacug cguggugugu cgagcggcgc ccugcccugu gcccuccagc cccggccagg 660
agcuuugcgg caacaacaac gucaccuaca ucuccucgug ccacaugcgc caggccaccu 720
gcuuccuggg ccgcuccauc ggcgugcgcc acgcgggcag cugcgcaggc accccugagg 780
agccgccagg uggugagucu gcagaagagg aagagaacuu cgugugagcc ugcaggacag 840
gccugggccu ggugcccgag gcccccccauc auccccuguu auuuauugcc acagcagagu 900
cuaauuuaua ugccacggac acuccuuaga gcccggauuc ggaccacuug gggaucccag 960
aaccucccug acgauauccu ggaaggacug aggaagggag gccugggggc cggcuggugg 1020
gugggauaga ccugcguucc ggacacugag cgccugauuu agggcccuuc ucuaggaugc 1080
cccagccccu acccuaagac cuauugccgg ggaggauucc acacuuccgc uccuuugggg 1140
auaaaccuau uaauuauugc uacuaucaag agggcugggc auucucugcu gguaauuccu 1200
gaagaggcau gacugcuuuu cucagcccca agccucuagu cuggguguguu acggaggguc 1260 uagccugggu guguacggag ggucuagccu gggugaguac ggagggucua gccugggguga 1320 guacggaggg ucuagccugg gugaguacgg agggucuagc cuggguguguu auggaggauc 1380 uagccugggu gaguauggag ggucuagccu gggugaguau ggagggucua gccugggugu 1440
guauggaggg ucuagccugg gugaguaugg agggucuagc cuggguguguu auggaggguc 1500 uagccugggu gaguauggag ggucuagccu gggugguguac ggagggucua gucugagugc 1560 gugugggggac cucagaacac ugugaccuua gcccagcaag ccaggcccuu caugaaggcc 1620
aagaaggcug ccaccauucc cugccagccc aagaacucca gcuuccccac ugccucugug 1680
ugccccuuug cguccuguga aggccauuga gaaaugccca gugugccccc ugggaaaggg 1740
cacggccugu gcuccugaca cgggcugugc uuggccacag aaccacccag cgucuccccu 1800
gcugcugucc acgucaguuc augaggcaac gucgcguggu cucagacgug gagcagccag 1860
cggcagcuca gagcagggca cuguguccgg cggagccaag uccacucugg gggagcucug 1920
gcggggacca cgggccacug cucacccacu ggccccgagg ggggguguaga cgccaagacu 1980 cacgcaugug ugacauccgg aguccuggag ccggguguccc caguggcacc acuaggugcc 2040
ugcugccucc acaguggggu ucacacccag ggcuccuugg ucccccacaa ccugccccgg 2100
ccaggccugc agacccagac uccagccaga ccugccucac ccaccaaugc agccggggcu 2160
ggcgacacca gccaggugcu ggucuugggc caguucuccc acgacggcuc acccuccccu 2220
ccaucugcgu ugaugcucag aaucgccuac cugugccugc guguaaacca cagccucaga 2280
ccagcuaugg ggagaggaca acacggagga uauccagcuu ccccggucug ggguggaggaa 2340 ugugggggagc uugggcaucc uccuccagcc uccuccagcc cccaggcagu gccuuaccug 2400
uggugcccag aaaagugccc cuagguuggu gggucuacag gagccucagc caggcagccc 2460
accccacccu ggggcccugc cucaccaagg aaauaaagac ucaagccauu uaaaaaaaaa 2520
aaaaa 2525

<210> SEQ ID NO 24
<211> LENGTH: 263
<212> TYPE: PRT
<213> ORGANISM: Homo sapiens

<400> SEQUENCE: 24

Met Arg Pro Gly Ala Pro Gly Pro Leu Trp Pro Leu Pro Trp Gly Ala

-continued

```
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
        195                 200                 205

Glu Leu Cys Gly Asn Asn Asn Val Thr Tyr Ile Ser Ser Cys His Met
    210                 215                 220

Arg Gln Ala Thr Cys Phe Leu Gly Arg Ser Ile Gly Val Arg His Ala
225                 230                 235                 240

Gly Ser Cys Ala Gly Thr Pro Glu Glu Pro Pro Gly Gly Glu Ser Ala
                245                 250                 255

Glu Glu Glu Glu Asn Phe Val
            260


<210> SEQ ID NO 25
<211> LENGTH: 914
<212> TYPE: RNA
<213> ORGANISM: Homo sapiens

<400> SEQUENCE: 25

gcauggggag gggcggcccu caaacggguc auugccauua auagagaccu caaacaccgc      60

cugcuaaaaa uacccgacug gaggagcaua aaagcgcagc cgagcccagc gccccgcacu     120

uuucugagca gacguccaga gcagagucag ccagcaugac cgagcgccgc guccccuucu     180

cgcuccugcg gggccccagc ugggaccccu uccgcgacug guacccgcau agccgccucu     240

ucgaccaggc cuucgggcug ccccggcugc cggaggagug gucgcagugg uuaggcggca     300

gcagcuggcc aggcuacgug cgcccccugc cccccgccgc caucgagagc cccgcagugg     360

ccgcgcccgc cuacagccgc gcgcucagcc ggcaacucag cagcggggu c ucggagaucc     420

ggcacacugc ggaccgcugg cgcguguccc uggaugucaa ccacuucgcc ccggacgagc     480

ugacggucaa gaccaaggau ggcguggugg agaucaccgg caagcacgag gagcggcagg     540

acgagcaugg cuacaucucc cggugcuuca cgcggaaaua cacgcugccc cccggugugg     600

accccaccca aguuuccucc ucccuguccc cugagggcac acugaccgug gaggccccca     660
```

```
ugcccaagcu agccacgcag uccaacgaga ucaccauccc agucaccuuc gagucgcggg    720

cccagcuugg gggcccagaa gcugcaaaau ccgaugagac ugccgccaag uaaagccuua    780

gcccggaugc ccaccccugc ugccgccacu ggcugugccu cccccgccac cugugugucc    840

uuuugauaca uuuaucuucu guuuuucuca aauaaaguuc aaagcaacca ccugucaaaa    900

aaaaaaaaaa aaaa                                                      914
```

<210> SEQ ID NO 26
<211> LENGTH: 205
<212> TYPE: PRT
<213> ORGANISM: Homo sapiens

<400> SEQUENCE: 26

```
Met Thr Glu Arg Arg Val Pro Phe Ser Leu Leu Arg Gly Pro Ser Trp
1               5                   10                  15

Asp Pro Phe Arg Asp Trp Tyr Pro His Ser Arg Leu Phe Asp Gln Ala
            20                  25                  30

Phe Gly Leu Pro Arg Leu Pro Glu Glu Trp Ser Gln Trp Leu Gly Gly
        35                  40                  45

Ser Ser Trp Pro Gly Tyr Val Arg Pro Leu Pro Pro Ala Ala Ile Glu
    50                  55                  60

Ser Pro Ala Val Ala Ala Pro Ala Tyr Ser Arg Ala Leu Ser Arg Gln
65                  70                  75                  80

Leu Ser Ser Gly Val Ser Glu Ile Arg His Thr Ala Asp Arg Trp Arg
                85                  90                  95

Val Ser Leu Asp Val Asn His Phe Ala Pro Asp Glu Leu Thr Val Lys
            100                 105                 110

Thr Lys Asp Gly Val Val Glu Ile Thr Gly Lys His Glu Glu Arg Gln
        115                 120                 125

Asp Glu His Gly Tyr Ile Ser Arg Cys Phe Thr Arg Lys Tyr Thr Leu
    130                 135                 140

Pro Pro Gly Val Asp Pro Thr Gln Val Ser Ser Ser Leu Ser Pro Glu
145                 150                 155                 160

Gly Thr Leu Thr Val Glu Ala Pro Met Pro Lys Leu Ala Thr Gln Ser
                165                 170                 175

Asn Glu Ile Thr Ile Pro Val Thr Phe Glu Ser Arg Ala Gln Leu Gly
            180                 185                 190

Gly Pro Glu Ala Ala Lys Ser Asp Glu Thr Ala Ala Lys
        195                 200                 205
```

<210> SEQ ID NO 27
<211> LENGTH: 2638
<212> TYPE: RNA
<213> ORGANISM: Homo sapiens

<400> SEQUENCE: 27

```
agaugcgagc acugcggcug ggcgcugagg aucagccgcu uccugccugg auuccacagc     60

uucgcgccgu guacugucgc cccaucccug cgcgcccagc cugccaagca gcgugccccg    120

guugcaggcg ucaugcagcg ggcgcgaccc acgcucuggg ccgcugcgcu gacucugcug    180

gugcugcucc gcgggccgcc gguggcgcgg gcuggcgcga gcucggcggg cuugggucccc   240

guggugcgcu gcgagccgug cgacgcgcgu gcacuggccc agugcgcgcc uccgcccgcc    300

gugugcgcgg agcuggugcg cgagccgggc ugcggcugcu gccugacgug cgcacugagc    360

gagggccagc cgugcggcau cuacaccgag cgcuguggcu ccggccuucg cugccagccg    420
```

```
ucgcccgacg aggcgcgacc gcugcaggcg cugcuggacg gccgcgggcu cugcgucaac    480
gcuagugccg ucagccgccu gcgcgccuac cugcugccag cgccgccagc uccaggugag    540
ccgcccgcgc caggaaaugc uagugagucg gaggaagacc gcagcgccgg caguguggag    600
agcccguccg ucuccagcac gcaccgggug ucugauccca aguuccaccc ccuccauuca    660
aagauaauca ucaucaagaa agggcaugcu aaagacagcc agcgcuacaa aguugacuac    720
gagucucaga gcacagauac ccagaacuuc uccuccgagu ccaagcggga gacagaauau    780
ggucccugcc guagagaaau ggaagacaca cugaaucacc ugaaguuccu caaugugcug    840
agucccaggg guguacacau ucccaacugu gacaagaagg gauuuuauaa gaaaaagcag    900
ugucgcccuu ccaaaggcag gaagcggggc uucugcuggu guguggauaa guaugggcag    960
ccucucccag gcuacaccac caaggggaag gaggacgugc acugcuacag caugcagagc   1020
aaguagacgc cugccgcaag guuaaugugg agcucaaaua ugccuuauuu ugcacaaaag   1080
acugccaagg acaugaccag cagcuggcua cagccucgau uuauauuucu guuuguggug   1140
aacugauuuu uuuuaaacca aaguuuagaa agagguuuuu gaaaugccua ugguuucuuu   1200
gaaugguaaa cuugagcauc uuuucacuuu ccaguaguca gcaaagagca guuugaauuu   1260
ucuugucgcu uccuaucaaa auauucagag acucgagcac agcacccaga cuucaugcgc   1320
ccguggaaug cucaccacau guuggucgaa gcggccgacc acugacuuug ugacuuaggc   1380
ggcuguguug ccuauguaga gaacacgcuu cacccccacu ccccguacag ugcgcacagg   1440
cuuuaucgag aauaggaaaa ccuuuaaacc ccggucaucc ggacauccca acgcaugcuc   1500
cuggagcuca cagccuucug uggugucauu ucugaaacaa gggcguggau cccucaacca   1560
agaagaaugu uuaugucuuc aagugaccug uacugcuugg ggacuauugg agaaaauaag   1620
guggaguccu acuuguuuaa aaaauaugua ucuaagaaug uucuagggca cucugggaac   1680
cuauaaaggc agguauuucg ggcccuccuc uucaggaauc uuccugaaga cauggcccag   1740
ucgaaggccc aggauggcuu uugcugcggc cccguggggu aggagggaca gagagacagg   1800
gagagucagc cuccacauuc agaggcauca caaguaaugg cacaauucuu cggaugacug   1860
cagaaaauag uguuuuguag uucaacaacu caagacgaag cuuauuucug aggauaagcu   1920
cuuuaaaggc aaagcuuuau uuucaucucu caucuuuugu ccuccuuagc acaauguaaa   1980
aaagaauagu aauaucagaa caggaaggag gaauggcuug cuggggagcc cauccaggac   2040
acugggagca cauagagauu cacccauguu uguugaacuu agagucauuc ucaugcuuuu   2100
cuuuauaauu cacacauaua ugcagagaag auauguucuu guuaacauug uauacaacau   2160
agccccaaau auaguaagau cuauacuaga uaauccuaga ugaaauguua gagaugcuau   2220
augauacaac uguggccaug acugaggaaa ggagcucacg cccagagacu gggcugcucu   2280
cccggaggcc aaacccaaga aggucuggca aagucaggcu cagggagacu cugcccugcu   2340
gcagaccucg guguggacac acgcugcaua gagcucuccu ugaaaacaga ggggucucaa   2400
gacauucugc cuaccuauua gcuuuucuuu auuuuuuuaa cuuuuugggg ggaaaaguau   2460
uuuugagaag uuugucuugc aauguauuua uaaauaguaa auaaaguuuu uaccauuaaa   2520
aaaauaucuu ucccuuuguu auugaccauc ucugggcuuu guaucacuaa uuauuuuauu   2580
uuauuauaua auaauuauuu uauuauaaua aaauccugaa aggggaaaau aaaaaaaa     2638
```

<210> SEQ ID NO 28
<211> LENGTH: 291
<212> TYPE: PRT

<213> ORGANISM: Homo sapiens

<400> SEQUENCE: 28

```
Met Gln Arg Ala Arg Pro Thr Leu Trp Ala Ala Ala Leu Thr Leu Leu
1               5                   10                  15

Val Leu Leu Arg Gly Pro Pro Val Ala Arg Ala Gly Ala Ser Ser Ala
            20                  25                  30

Gly Leu Gly Pro Val Val Arg Cys Glu Pro Cys Asp Ala Arg Ala Leu
        35                  40                  45

Ala Gln Cys Ala Pro Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
        115                 120                 125

Pro Ala Pro Pro Ala Pro Gly Asn Ala Ser Glu Ser Glu Glu Asp Arg
    130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Ile Lys
                165                 170                 175

Lys Gly His Ala Lys Asp Ser Gln Arg Tyr Lys Val Asp Tyr Glu Ser
            180                 185                 190

Gln Ser Thr Asp Thr Gln Asn Phe Ser Ser Glu Ser Lys Arg Glu Thr
        195                 200                 205

Glu Tyr Gly Pro Cys Arg Arg Glu Met Glu Asp Thr Leu Asn His Leu
    210                 215                 220

Lys Phe Leu Asn Val Leu Ser Pro Arg Gly Val His Ile Pro Asn Cys
225                 230                 235                 240

Asp Lys Lys Gly Phe Tyr Lys Lys Lys Gln Cys Arg Pro Ser Lys Gly
                245                 250                 255

Arg Lys Arg Gly Phe Cys Trp Cys Val Asp Lys Tyr Gly Gln Pro Leu
            260                 265                 270

Pro Gly Tyr Thr Thr Lys Gly Lys Glu Asp Val His Cys Tyr Ser Met
        275                 280                 285

Gln Ser Lys
    290
```

<210> SEQ ID NO 29
<211> LENGTH: 2211
<212> TYPE: RNA
<213> ORGANISM: Homo sapiens

<400> SEQUENCE: 29

```
agucaccgac cugcggcucc ggggccgcga gggaggaggc gcggggggcg cgaggcgggg      60

gcgagcgcuu gggacucggc ccggcucccg gcuccggggg uucucguggc cgcggcagcg     120

cggucucugc ggaggcggcg ggggcgcggc cagccggacc ucuuccuuuc cagagcggcc     180

cgcggcgccc guuccgcggg aggcgggcgg gaggcggacg cggccuaacc ucgacgucga     240

cuaccgcgcc gcccgcgaug ggaagcgccu uauaaagccg cgcccggccg gcccgagcca     300
```

```
cucgccgccg cgccgccccg cugccccgaa cgcgggccau acgcagccuc cuuggaguga    360
cgggccgacc ccggacgacc ccggccacgg acagacccgg gacgaccccg gccggggcgc    420
gccuccugcg ggcgggcggg cggcggggcu ggggagcccu uggcgggggc augcgugcga    480
cauggccucg gcgguguuug agggcacguc gcucgugaac auguucgugc gcggcugcug    540
ggugaacggc auccgcaggc ucaucgucag ccggcgcggc gacgaagagg aguucuucga    600
gauccgcacg gaguggucgg accgcagcgu gcucuaccug caccgcagcc uggcggaccu    660
gggccgccug uggcagcgcc ugcgcgacgc cuuucccgag gaccgguccg aacuggcgca    720
ggggccgcug cggcaaggac ugguugccau aaaggaagcc cacgacauag agaccaggcu    780
uaaugaggug gagaagcugc ugaagacgau cauaagcaug cccuguaaau auucuagauc    840
ggaaguugug cucaccuucu ucgaaagauc uccucuggau cagguguuaa aaaaugauaa    900
ugugcauaaa auucaaccca gcuuucaaag uccagucaaa auaucagaaa ucaugagguc    960
caauggauuu uguuuagcaa auaccgaaac aauaguuauu gaccacagua uaccaaaugg   1020
aagagaccag cagcugggcg uggacccaac agagcauuua uuugagaaug gcagugaguu   1080
ucccucagag cuggaggacg gggacgaccc agcagccuac gucaccaacc ugucauauua   1140
ccaccugguc cccuucgaga cagacauuug ggacugaacc ucucuaucag gccuccccg    1200
ccucagcugu ucacugccag cucugaugcu guccacugug cuggcccca ugucacagc     1260
ugcugcccca gcucuggaac ucccagacgu cccaggcccc acugacgcca ggaggccugg   1320
guguccugca aguggagcag caggggcucc uagugggcca ggcugaccgc agagucucca   1380
gcaagcugag gucacagccg gaggccacag ggccuguguu cugagggucu ucacucccug   1440
cuuggugccc acagggcugc gcacugccag ggcagggaca guuccugugg ggcucgcucu   1500
cacugcuacu gcuuccuggg aggugcaucc cucuuggguga aguggccuag ugcccccag    1560
ccacccugac uccccaccau ucccucccac ggcaaacgca caaaacgucu ugagggagau   1620
uuugacaagu cacccauucc aggugccaca ggcaggggau guuuaguaau ccaggauuuc   1680
ucugagaacu gggauaugug gccuuuuuuu uuuucuuuuu aucuuuuauc uggaaacugg   1740
guuuggguca accccaggag uauuugcaga aggcccagca caguggggg uauuggcugc    1800
agggcaggga aggcauugcc gacuagauaa ccgugugagc uuggacugag cguuggugu    1860
ucuucccaaa ggaaaggaau uucuucccgg ccugccaggu cucugggccu ucagcgcggg   1920
uccuggugcu gcggccacac cacccugggg ugcucauuga cagagcugcc auaaugaacu   1980
ugaaaggacg ggaaucacga gggaagcugg ggcuccccug cccacaggag aggaucccccg  2040
uucuucaagc uucucugcuc agugucuacu aacgaccgac auuugcuaau guaaauaaua   2100
guaaauuauu gagaauucua auucuuuuac acagucuguu uuuaaucuau uuuaauuaaa   2160
uaaaaucuau gacucuacuu ugaucugucc aggaaaaaaa aaaaaaaaaa a            2211
```

<210> SEQ ID NO 30
<211> LENGTH: 231
<212> TYPE: PRT
<213> ORGANISM: Homo sapiens

<400> SEQUENCE: 30

```
Met Ala Ser Ala Val Phe Glu Gly Thr Ser Leu Val Asn Met Phe Val
1               5                   10                  15

Arg Gly Cys Trp Val Asn Gly Ile Arg Arg Leu Ile Val Ser Arg Arg
            20                  25                  30

Gly Asp Glu Glu Glu Phe Phe Glu Ile Arg Thr Glu Trp Ser Asp Arg
```

-continued

```
        35                  40                  45

Ser Val Leu Tyr Leu His Arg Ser Leu Ala Asp Leu Gly Arg Leu Trp
    50                  55                  60

Gln Arg Leu Arg Asp Ala Phe Pro Glu Asp Arg Ser Glu Leu Ala Gln
65                  70                  75                  80

Gly Pro Leu Arg Gln Gly Leu Val Ala Ile Lys Glu Ala His Asp Ile
                85                  90                  95

Glu Thr Arg Leu Asn Glu Val Glu Lys Leu Leu Lys Thr Ile Ile Ser
            100                 105                 110

Met Pro Cys Lys Tyr Ser Arg Ser Glu Val Val Leu Thr Phe Phe Glu
        115                 120                 125

Arg Ser Pro Leu Asp Gln Val Leu Lys Asn Asp Asn Val His Lys Ile
    130                 135                 140

Gln Pro Ser Phe Gln Ser Pro Val Lys Ile Ser Glu Ile Met Arg Ser
145                 150                 155                 160

Asn Gly Phe Cys Leu Ala Asn Thr Glu Thr Ile Val Ile Asp His Ser
                165                 170                 175

Ile Pro Asn Gly Arg Asp Gln Gln Leu Gly Val Asp Pro Thr Glu His
            180                 185                 190

Leu Phe Glu Asn Gly Ser Glu Phe Pro Ser Glu Leu Glu Asp Gly Asp
        195                 200                 205

Asp Pro Ala Ala Tyr Val Thr Asn Leu Ser Tyr Tyr His Leu Val Pro
    210                 215                 220

Phe Glu Thr Asp Ile Trp Asp
225                 230


<210> SEQ ID NO 31
<211> LENGTH: 3389
<212> TYPE: RNA
<213> ORGANISM: Homo sapiens

<400> SEQUENCE: 31

cagucucggc ugauugccgc ugucgcuccc ggggccacgg gaugacgccu ccuccgcccg      60

gacgugccgc ccccagcgca ccgcgcgccc gcgucccugg cccgccggcu cgguuggggc     120

uuccgcugcg gcugcggcug cugcugcugc ucugggcggc cgccgccucc gcccagggcc     180

accuaaggag cggaccccgc aucuucgccg ucuggaaagg ccauguaggg caggaccggg     240

uggacuuugg ccagacugag ccgcacacgg ugcuuuucca cgagccaggc agcuccucug     300

ugugggu ggg aggacguggc aaggucuacc ucuuugacuu ccccgagggc aagaacgcau     360

cugugcgcac ggugaauauc ggcuccacaa aggggucug ucuggauaag cgggacugcg     420

agaacuacau cacucuccug gagaggcgga gugaggggcu gcuggccugu ggcaccaacg     480

cccggcaccc cagcugcugg aaccugguga auggcacugu ggugccacuu ggcgagauga     540

gaggcuacgc cccuucagc ccggacgaga acucccuggu ucuguuugaa ggggacgagg     600

uguauuccac cauccggaag caggaauaca augggaagau cccucgguuc cgccgcaucc     660

ggggcgagag ugagcuguac accagugaua cugucaugca gaacccacag uucaucaaag     720

ccaccaucgu gcaccaagac caggcuuacg augacaagau cuacuacuuc uuccgagagg     780

acaauccuga caagaauccu gaggcuccuc ucaauguguc ccguguggcc caguugugca     840

ggggggacca gggugggggaa aguucacugu cagucuccaa guggaacacu uuucugaaag     900

ccaugcuggu augcagugau gcugccacca acaagaacuu caacaggcug caagacgucu     960

uccugcuccc ugaccccagc ggccagugga gggacaccag ggucuauggu guuuucucca    1020
```

-continued

```
accccuggaa cuacucagcc gucugugugu auucccucgg ugacauugac aaggucuucc   1080
guaccuccuc acucaagggc uaccacucaa gccuucccaa cccgcggccu ggcaagugcc   1140
ucccagacca gcagccgaua cccacagaga ccuuccaggu ggcugaccgu cacccagagg   1200
uggcgcagag gguggagccc augggccuc ugaagacgcc auuguuccac ucuaaauacc   1260
acuaccagaa aguggccguc caccgcaugc aagccagcca cggggagacc uuucaugugc   1320
uuuaccuaac uacagacagg ggcacuaucc acaagguggu ggaaccgggg gagcaggagc   1380
acagcuucgc cuucaacauc auggagaucc agcccuuccg ccgcgcggcu gccauccaga   1440
ccaugucgcu ggaugcugag cggaggaagc uguaugugag cucccagugg gaggugagcc   1500
aggugccccu ggaccugugu gaggucuaug gcgggggcug ccacgguugc cucaugcccc   1560
gagaccccua cugcggcugg gaccaaggcc gcugcaucuc caucuacagc uccgaacggu   1620
cagugcugca auccauuaau ccagccgagc cacacaagga gugucccaac cccaaaccag   1680
acaaggcccc acugcagaag guuucccugg ccccaaacuc ucgcuacuac cugagcugcc   1740
ccauggaauc ccgccacgcc accuacucau ggcgccacaa ggagaacgug gagcagagcu   1800
gcgaaccugg ucaccagagc cccaacugca uccuguucau cgagaaccuc acggcgcagc   1860
aguacggcca cuacuucugc gaggcccagg agggcuccua cuuccgcgag gcucagcacu   1920
ggcagcugcu gcccgaggac ggcaucaugg ccgagcaccu gcugggucau gccugugccc   1980
uggccgccuc ccucuggcug ggggugcugc ccacacucac ucuuggcuug cugguccacu   2040
agggccuccc gaggcugggc augccucagg cuucugcagc ccagggcacu agaacgucuc   2100
acacucagag ccggcuggcc cgggagcucc uugccugcca cuucuuccag ggacagaau    2160
aacccagugg aggaugccag gccuggagac guccagccgc aggcggcugc ugggccccag   2220
guggcgcacg gauggugagg ggcugagaau gagggcaccg acugugaagc uggggcaucg   2280
augacccaag acuuuaucuu cuggaaaaua uuuuucagac ucccucaaacu ugacuaaaug  2340
cagcgaugcu cccagcccaa gagcccaugg gucggggagu ggguuuggau aggagagcug   2400
ggacuccauc ucgacccugg ggcugaggcc ugaguccuuc uggacucuug guacccacau   2460
ugccuccuuc cccucccucu cucauggcug ggugggcuggu guuccugaag acccagggcu  2520
acccucuguc cagcccuguc cucugcagcu cccucucugg uccugggucc cacaggacag   2580
ccgccuugca uguuuauuga aggauguuug cuuuccggac ggaaggacgg aaaaagcucu   2640
auuuuuaugu uaggcuuauu ucauguauag cuacuuccga cugcaucugu augaaaauac   2700
caaaacuaca ugcggggggg uggguggaa agggaggggc ugggaaggga uggguugggg    2760
agcgggggug aucccagucu gaggcucccg gggaugagau aagagucugg agacgggcau   2820
ggguucuugg agaguggcau gagcuggcuc ugcccuggga gcccggucug agggggacgu   2880
uguuggagcc ccuaguguug gggguggua ugggaggggg uggggugagg gaaacgggag    2940
aaugaaggag aaaacugagc ccuaguuuca ccguguucau uuggaaggac gagccggguc   3000
cucaggggga gguuccagga cucugcccuu ggcguugagg guuggggggc ggggggccuc   3060
cucccuuccu cucagccccc uuccccaggg gcugugcuuc caugcuccua gccucccacc   3120
uucgcucagg acauguuaua acuuaggcua aacugugaaa auuccggugg ggauggccug   3180
ggccgagcuc uccaggcagg cggcccugcc cccagcccug uccauccauu ucagggggga   3240
gcugggcccu ucuccggcug ugucuggcca cccagggcag uggcuggggc caguggccuu   3300
ccagcuuugg ccccugcacc ucuucucaau gcacuuuaau aauguaacau auuacuaaua   3360
```

aacaagcuau uuauuuaccu gcaaaaaaa 3389

<210> SEQ ID NO 32
<211> LENGTH: 666
<212> TYPE: PRT
<213> ORGANISM: Homo sapiens

<400> SEQUENCE: 32

```
Met Thr Pro Pro Pro Pro Gly Arg Ala Ala Pro Ser Ala Pro Arg Ala
1               5                   10                  15

Arg Val Pro Gly Pro Pro Ala Arg Leu Gly Leu Pro Leu Arg Leu Arg
            20                  25                  30

Leu Leu Leu Leu Leu Trp Ala Ala Ala Ala Ser Ala Gln Gly His Leu
        35                  40                  45

Arg Ser Gly Pro Arg Ile Phe Ala Val Trp Lys Gly His Val Gly Gln
    50                  55                  60

Asp Arg Val Asp Phe Gly Gln Thr Glu Pro His Thr Val Leu Phe His
65                  70                  75                  80

Glu Pro Gly Ser Ser Ser Val Trp Val Gly Gly Arg Gly Lys Val Tyr
                85                  90                  95

Leu Phe Asp Phe Pro Glu Gly Lys Asn Ala Ser Val Arg Thr Val Asn
            100                 105                 110

Ile Gly Ser Thr Lys Gly Ser Cys Leu Asp Lys Arg Asp Cys Glu Asn
        115                 120                 125

Tyr Ile Thr Leu Leu Glu Arg Arg Ser Glu Gly Leu Leu Ala Cys Gly
    130                 135                 140

Thr Asn Ala Arg His Pro Ser Cys Trp Asn Leu Val Asn Gly Thr Val
145                 150                 155                 160

Val Pro Leu Gly Glu Met Arg Gly Tyr Ala Pro Phe Ser Pro Asp Glu
                165                 170                 175

Asn Ser Leu Val Leu Phe Glu Gly Asp Glu Val Tyr Ser Thr Ile Arg
            180                 185                 190

Lys Gln Glu Tyr Asn Gly Lys Ile Pro Arg Phe Arg Arg Ile Arg Gly
        195                 200                 205

Glu Ser Glu Leu Tyr Thr Ser Asp Thr Val Met Gln Asn Pro Gln Phe
    210                 215                 220

Ile Lys Ala Thr Ile Val His Gln Asp Gln Ala Tyr Asp Asp Lys Ile
225                 230                 235                 240

Tyr Tyr Phe Phe Arg Glu Asp Asn Pro Asp Lys Asn Pro Glu Ala Pro
                245                 250                 255

Leu Asn Val Ser Arg Val Ala Gln Leu Cys Arg Gly Asp Gln Gly Gly
            260                 265                 270

Glu Ser Ser Leu Ser Val Ser Lys Trp Asn Thr Phe Leu Lys Ala Met
        275                 280                 285

Leu Val Cys Ser Asp Ala Ala Thr Asn Lys Asn Phe Asn Arg Leu Gln
    290                 295                 300

Asp Val Phe Leu Leu Pro Asp Pro Ser Gly Gln Trp Arg Asp Thr Arg
305                 310                 315                 320

Val Tyr Gly Val Phe Ser Asn Pro Trp Asn Tyr Ser Ala Val Cys Val
                325                 330                 335

Tyr Ser Leu Gly Asp Ile Asp Lys Val Phe Arg Thr Ser Ser Leu Lys
            340                 345                 350

Gly Tyr His Ser Ser Leu Pro Asn Pro Arg Pro Gly Lys Cys Leu Pro
        355                 360                 365
```

-continued

```
Asp Gln Gln Pro Ile Pro Thr Glu Thr Phe Gln Val Ala Asp Arg His
    370                 375                 380

Pro Glu Val Ala Gln Arg Val Glu Pro Met Gly Pro Leu Lys Thr Pro
385                 390                 395                 400

Leu Phe His Ser Lys Tyr His Tyr Gln Lys Val Ala Val His Arg Met
                405                 410                 415

Gln Ala Ser His Gly Glu Thr Phe His Val Leu Tyr Leu Thr Thr Asp
            420                 425                 430

Arg Gly Thr Ile His Lys Val Val Glu Pro Gly Glu Gln Glu His Ser
        435                 440                 445

Phe Ala Phe Asn Ile Met Glu Ile Gln Pro Phe Arg Arg Ala Ala Ala
    450                 455                 460

Ile Gln Thr Met Ser Leu Asp Ala Glu Arg Arg Lys Leu Tyr Val Ser
465                 470                 475                 480

Ser Gln Trp Glu Val Ser Gln Val Pro Leu Asp Leu Cys Glu Val Tyr
                485                 490                 495

Gly Gly Gly Cys His Gly Cys Leu Met Ser Arg Asp Pro Tyr Cys Gly
            500                 505                 510

Trp Asp Gln Gly Arg Cys Ile Ser Ile Tyr Ser Ser Glu Arg Ser Val
        515                 520                 525

Leu Gln Ser Ile Asn Pro Ala Glu Pro His Lys Glu Cys Pro Asn Pro
    530                 535                 540

Lys Pro Asp Lys Ala Pro Leu Gln Lys Val Ser Leu Ala Pro Asn Ser
545                 550                 555                 560

Arg Tyr Tyr Leu Ser Cys Pro Met Glu Ser Arg His Ala Thr Tyr Ser
                565                 570                 575

Trp Arg His Lys Glu Asn Val Glu Gln Ser Cys Glu Pro Gly His Gln
            580                 585                 590

Ser Pro Asn Cys Ile Leu Phe Ile Glu Asn Leu Thr Ala Gln Gln Tyr
        595                 600                 605

Gly His Tyr Phe Cys Glu Ala Gln Glu Gly Ser Tyr Phe Arg Glu Ala
    610                 615                 620

Gln His Trp Gln Leu Leu Pro Glu Asp Gly Ile Met Ala Glu His Leu
625                 630                 635                 640

Leu Gly His Ala Cys Ala Leu Ala Ala Ser Leu Trp Leu Gly Val Leu
                645                 650                 655

Pro Thr Leu Thr Leu Gly Leu Leu Val His
            660                 665
```

<210> SEQ ID NO 33
<211> LENGTH: 11264
<212> TYPE: RNA
<213> ORGANISM: Homo sapiens

<400> SEQUENCE: 33

```
ccgggagucc gggcagcguu cggcgcgccg ggccggggug gcgggcggcc ccgggacccc      60

ggcagcugga gaaggagccg gagcccggcc gggaugagaa ggugacgccg ccgggggcgc     120

cacucgcuuu gugggggaag augcucgccu acugcgugca ggaugccacc gugguggacg     180

uggagaagcg gaggaacccc uccaagcacu acguauacau aaucaaugug accuggucug     240

acuccaccuc ccagacuauc uaccggaggu acagcaaguu cuuugaccug cagaugcagc     300

uuuuggauaa guuucccauu gaagguggcc agaaggaccc caagcaaagg aucaucccccu     360

uccucccagg caagauccuc uuccgcagaa gccacauccg ggacguagcu gugaagagac     420
```

-continued ugaagcccau cgaugaauac ugccgggcac uuguccggcu gcccccccac aucucacagu 480
gugacgaagu cuuccgguuc uucgaggcuc gacccgagga ugucaacccu ccaaaagagg 540
acuauggcag uuccaagagg aaaucagugu ggcuguccag cugggcugag ucgcccaaga 600
aggacgugac aggugccgac gccaccgccg agcccaugau ccuggaacag uacguggugg 660
uguccaacua uaagaagcag gagaacucgg agcugagccu ccaggccggg gagguggugg 720
augucaucga gaagaacgag agcggcuggu gguucgugag cacuucugag gagcagggcu 780
gggucccugc caccuaccug gaggcccaga augguacucg ggaugacucc gacaucaaca 840
ccucuaagac uggagaagag gagaaguaug ucaccgugca gccuuacacc agccaaagca 900
aggacgagau uggcuuugag aagggcguca caguggaggu gauccggaag aaucuggaag 960
gcugguggua uaucagauac cugggcaaag agggcugggc gccagcaucc uaccugaaga 1020
aggccaagga ugaccugcca acccggaaga agaaccuggc cggcccagug gagaucauug 1080
ggaacaucau ggagaucagc aaccugcuga acaagaaggc gucuggggac aaggaaacuc 1140
caccagccga aggcgagggc caugaggccc ccauugccaa gaaggagauc agccugccca 1200
uccucugcaa ugccuccaau ggcagugccg ugggcguucc ugacaggacu gucuccaggc 1260
uggcccaggg cucuccagcu guggccagga uugccccuca gcgggcccag aucagcuccc 1320
cgaaccuacg gacaagaccu ccaccacgca gagaauccag ccugggguuc caacugccaa 1380
agccaccaga gcccccuucu guugaggugg aguacuacac cauugccgaa uuccagucgu 1440
gcauuuccga uggcaucagc uuucggggug gacagaaggc agaggucauu gauaagaacu 1500
cagguggcug gugguacgug cagaucggug agaaggaggg cugggccccc gcaucauaca 1560
ucgauaagcg caagaagccc aaccugagcc gccgcacaag cacgcugacc cggcccaagg 1620
ugcccccgcc agcacccccc agcaagccca aggaggccga ggagggcccu acgggggcca 1680
gugagagcca ggacuccccg cggaagcuca aguaugagga gccugaguau gacaucccug 1740
cauucggcuu ugacucagag ccugagcuga gcgaggagcc cguggaggac agagccucag 1800
gggagaggcg gccugcccag ccccaccggc ccucgccggc cucuucucug cagcgggccc 1860
gcuucaaggu gggugagucu ucagaggaug uggcccugga agaggagacc aucuaugaga 1920
augagggcuu ccggccauau gcagaggaca cccugucagc cagaggcucc uccggggaca 1980
gcgacucccc aggcagcucc ucgcuguccc ugaccaggaa aaacuccccc aaaucaggcu 2040
cccccaaguc aucaucacuc cuaaagcuca aggcagagaa gaaugcccag gcagaaaugg 2100
ggaagaacca cuccucagcc uccuuuuccu cauccaucac caucaacacc acuugcugcu 2160
ccuccucuuc cuccuccucc ucuuccuugu ccaaaaccag uggcgaccug aagccccgcu 2220
cugcuucgga cgcaggcauc cgcggcacuc ccaaggucag ggcaaagaag gaugcugaug 2280
cgaacgcugg gcugaccucc uguccccggg ccaagccauc gguccggccc aagccauucc 2340
uaaaccgagc agagucgcag agccaagaga agauggacau cagcacuuua cggcgccagc 2400
ugagacccac aggccagcuc cguggagggc ucaagggcuc caagagugag gauucggagc 2460
ugcccccgca gacggccucc gaggcuccca gugagggguc uaggagaagc ucauccgacc 2520
ucaucacccu cccagccacc acucccccau gucccaccaa gaaggaaugg gaagggccag 2580
ccaccucgua caugacaugc agcgccuacc agaaggucca ggacucggag aucagcuucc 2640
ccgcgggcgu ggaggugcag gugcuggaga agcaggagag cggguggugg uaugugaggu 2700
uuggggagcu ggagggcugg gccccuuccc acuauuuggu gcuggaugag aacgagcaac 2760
cugaccccuc uggcaaagag cuggacacag ugcccgccaa gggcaggcag aacgaaggca 2820

-continued

```
aaucagacag ccuggagaag aucgagaggc gcguccaagc acugaacacc gucaaccaga   2880
gcaagaaggc cacgcccccc auccccucca aaccucccgg gggcuucggc aagaccucag   2940
gcacuccagc ggugaagaug aggaacggag ugcggcaggu ggcggucagg ccccagucgg   3000
uguuuguguc cccgccaccc aaggacaaca accuguccug cgcccugcgg aggaaugagu   3060
cacucacggc cacugauggc cuccgaggcg uccgacggaa cuccuccuuu agcacugcuc   3120
gcuccgcugc cgccgaggcc aagggccgcc uggccgaacg ggcugccagc cagggguucag   3180
acucaccccu acugcccgcc cagcgcaaca gcauacccgu gucccugug cgccccaagc   3240
ccaucgagaa gucucaguuc auccacaaua accucaaaga uguguacguc ucuaucgcag   3300
acuacgaggg ggaugaggag acagcaggcu uccaggaggg ggugguccaug gagguucugg   3360
agaggaaccc uaauggcugg ugguacugcc agauccugga uggugugaag cccuucaaag   3420
gcuggggugcc uuccaacuac cuugagaaaa agaacuagca gagggccugg gcucuuccag   3480
ccucagugug ccucucuggc cgcccacugg augagcggug agacgaacaa aagggaaagg   3540
aaaaaauggg ggugggggu ggggggugga caacauucaa cacugcagaa ugggugaccu   3600
caaagaugcc cccuguccaa gccaucccac agcuggaagg uaggggaugg gggugcccac   3660
acugagugag gaagggaaug gaccagggag ucccaggccu gggacccaga gccaagaaag   3720
cugagauauc cugugcacca uagggacuuc accaauggau uacaugccau cugggacagg   3780
ccauguggga gaccccaguu gugccuuugc uacagaucug gaaaagacaa ggucaugggg   3840
gccuccagug uccugccccu gcuuggccca guuuugauug cuggcaucuu gccaccccag   3900
guaucccugg uauuguccua agcuguauuu gugaauugug cugguuuccu gggcauugcc   3960
acgccuacca caggugggua cauuagaagc caccacuggc uuucaggcuu gggggugucu   4020
ucugagcuca agccugcuuc ugggccaggc cauugucacu guuaguugaa gaaaaagcag   4080
uucccaggug ccagcaaaga ccaucuuuca uaacugucac ugucuuggcc uugagaagag   4140
agcccgcucu ccguggggca ccccauggag gacacaguac cagaguuuac agagagggug   4200
ggcgaagcca ccggucucuu ccuaaucugc acagacuauu uuggguauuu cugggcgggc   4260
aguuccuuug cauguuucgg gagagguuug uugauuuggg gcuuauaugu caggccuuug   4320
guuugcgucu uauuuuaggg guuguuuggg ggccugggug gucggccuca caugggaagg   4380
ggaugggguag uggaugggggu uucuguugua ucuugugggc gggugauuuu gcuuuuguuu   4440
uuguuucaca uucuuccccc uccacaagcc aaagucguuu cauuugguuu ccacugugug   4500
gacugugcug gagcuuggcg ccugccagaa aaauuugggg cuaggcaagc cccagguugc   4560
agacauggug aagcagagaa acuguucuuc ugguuccugc acaaccucag aggggcaaaa   4620
acccucccca ggaaggagga ggguguucag gagccagacu uuuggagaga aggcagcucc   4680
cagccugcug ggugaccgcc auucugcgug uguuccccag cugggcaggg cuggaagccu   4740
uacguaugaa gcauggagaa gcagccauug uccccacuau gggcagaggg gggacccggc   4800
uggccccuug ggucagacug gagccaacac cgccagccac ccccucuggc cugcuggcaa   4860
ugccacaggu gcccaagaag auggaggauc ccugugccag gagccaaccu ggucuucccg   4920
agggucagug ccccagugaa gacagaagcg agagaauaaa guucccugua gguccucugu   4980
caccuuuggg uuguguuuuu caauuguuga cauuucagag gggacccucc agaagcccag   5040
ccggcuuccc ccaaggacuc ccccuucgcu gggaguggau uuccacacgu gccuuugauu   5100
ucggacagau ugggccucac agccaccgau ucagcugcca ggguccccugg acuggggguu   5160
```

-continued ggugguuucu auagaggagg aaaggcccuc ccucacccug cuccccaccc aggcagggca 5220
gcaugggacc cagugucuca gugccuucaa aacccacccc caccccuacc cuaccccacc 5280
acaccccauc ccagaggccu ugccugggca acccuaagcc ccugucccuc gccauacacu 5340
gaugccuggc agcuagagca aauggcucgu guucuuuguc gaaggccugu ggugagauug 5400
uuuuguuucc uuuuguuuug ugaguuuguu uaaaauugaa auuaguuauu uucuucugcu 5460
ggacaguauu aaauagagca ggauguugag uuaaucugcu agauugcagu acuaauggua 5520
gugguuuagu gucuucaugu uaauauuauu uguacuuauu ugaacaauaa ugauaaagaa 5580
gugguucauu auuuuuuaau uaaugcacuu uaaauaaggu agaauggaaa aaacccagag 5640
agcaaagugc auuacuuaaa gaugcaguau auacuuuucu cauuuuuaaa cagcacauau 5700
uuauuaagag aaaaaaagua auuuaugacu auuuaaaaua aaauuuaaaa guagagugac 5760
ugucagguaa agaaccuuca auguagcuau cuuccagggg gagggcccug cagccucgcu 5820
ccucagaugu cugcacugag ccaguucagu cacuagugcg ccagccaggc caggagggag 5880
ugcagagcau gucugccaag cacagagcau cucaguugga cuggaccaca gugcuccccga 5940 gagccugccu uuccugcccu uccccaccac cugcacugcc ccccacauuc ucccagcccc 6000
ccccaaggac ccccucuccu ugacccccag ugcuguaagu aauagaguca uuaaaaugca 6060
ggacugaaag agaccucaga ggucucuauc ccaucccuuc cuguuacugc ggcccaagga 6120
caggaaacaa cuuuuccaaa aucccacagc uaguuaauga cagaucuccc cacuacauua 6180
aucccgugcu ccuccucacu gccauuauag uuuauugugu ggucauguuu acauugugac 6240
auccagcccc aaggauggcu gggaguugcu caggcaucca ggaaaagugg ggaaugcugc 6300
caucugguga cagcauguag auuugggcag ugaacaggga uugccaugcc ccagucuucg 6360
caccucgccc ccucaccccc uaacucacag cacaaacccu gcaaacccaa agagaauauu 6420
aauacuugaa gcaagaaggg ugcaugccag uccuucuccg acauggccag gggguaccag 6480
gccuugugcg ccuggccucc uagcccuagc cagggcgaga gggccuuucc cuugagcuac 6540
ugagcugcuu ugugaugcug aaggauacug ccggcagcag gcagaggagg gaggggccu 6600 agggcucuga cccaucugga ggaaaaccag aucggacuaa aaaaggaaaa agaaaaacaa 6660
aaucuccgca guguccaaac cuaguuuccc augaguugcg acugaaaaug ugaaacgaca 6720
cuguauugcu guauacugca acuuuaacca uaaugagccc uucugagguc auuauugagg 6780
uucauauaau gcccgaagau gcagcauuug gugcuuuguu uuccuuuccg uuucaagacc 6840
uuuuucuuuu auugcaaggg gaaaaaaaug ucaucucccc ccaccucauc ccucuuugug 6900
acagcagacc uggcuguguu gccccucucc uccucacuau ucucaccagg ccaugggacu 6960
uugggggcag ugagagagag cuggaaaggg gcaacccuga gcagcaggug ugccccaugc 7020 ccugugggguu uccccuaugu ccaaugacug uagacgggcu gucuugccag gccucagccc 7080
cgucuacccu aagccuggcc ccaaagguuu cucuuucuuc cuccuugauu uuccaucuug 7140
acgaaggcau uauauagaau cauuuuaauc acuuucagau guuagagcag cguauuuuac 7200
aggcauuuau auccauugcu uuccucagca aggcauguua cuacuuuuau caucuaagga 7260
aaaaagacaa gggaauucca gucaggcauu auuuuccuau uacuaguguu ugcagaauag 7320
guguaggacu auuuaaguuu agaccuuggu uugguaguuc uuguuuuuaa uaaggggaaa 7380
aagauaaaau aaccccuauu uuuccuguua uuguauuuaa cuaauauauu auuucuuuaa 7440
gguuacucac uuccccuacc ccuccaaaua ccuugcauuc ucaaucaaaa auggaaacaa 7500
ucugagagac aggaaaagug caauauuacc aagauggaug ccagggcuca uuggggacaa 7560

```
uggagggaau accaguggcg cucagagagc aagaggcagg gagcggggug cugaaggaau   7620
ccuagcugug gaacaggugg gugggguugg uggaguuugau cuuguggcgu ucuccucucc   7680
cccuucuuug ggaagaugau aggggucccu gccagaucca cccagaagaa agggauucag   7740
gcauggggcc cuugaccucu aggccccagu cccuggagca gaggcaggcc cucgggagcu   7800
guuccuuguu uugauuucug uuguggugca gccagcugcu cagagagacc uggccuaaaa   7860
augacuccca gcagcccucu cucaccccag uguccugaua uuugggcugu gauccuucug   7920
guguauguuu gaaucuuucu aaaacugggu gcccucaguu caguuucuag gcaggaagcc   7980
uagaagucac cagaucuuuu ugggggaugu gagaaccuug agccgcgcac acccuggugua  8040
gacaccaauu cccacaagcc ugcagcaggg ccuggggcug agccugggcu gcccauucau   8100
cucagcgacu ucagccugag aagugagccc ugccugggcu ccacacccag agaguccaua   8160
caaauucugc uccgggaaga gucggggggu cuauucaagu uucucugcag acaaaacuuc   8220
ccacaacagg uaccaaucug gccuccuucc ucagcaccgg uagagaaagc aacagaaugg   8280
gaaguuuccu cuggguugga gccucagagc ucugccccuc aaggugacag ggacgucccu   8340
guggcuuguu cccuccaccu ccaguacugu augcuugcua cuucaacccc cuauuuggug   8400
aauuucugca cagacacaga ucucugugcc uggaauggga cugugcccug ugcgggucuc   8460
ucccuuggcg uauauccauc uagauauuua gucuuugaga aucucaaagc agagcucucu   8520
gggaagagaa cuguccacau ugcuaaauaa uuaagauucc cucacuuuuu ugagggccau   8580
guguugugag agagagagag agagagagag ugugugugug ugugugugug ugugugugu    8640
uguguaugca aguguuggua acuucccacu ugaacuaaau aacauggggu uagagaaaaa   8700
aaaauaccag gcaagcuguc uccauugaac aaguccuugg caaugggcag gucccaaggg   8760
acucacagcu ucuggcagca agugugucau ucacacacau cauucuggcu ggagagugca   8820
augugucauu uuuuuucuu uuuguaauua uuuuauuaag uauuuaguug gaaauuucac    8880
acuggcauua acaggucuag cauaaguggc cuaggcaguc aucccaggcu ccaaaaugaa   8940
gaugugcaaa agagaugcca cugggaauag aaacacugag uugguucagu uaggucaucc   9000
ccugcagacg ugucaucgag caggcugacu cccaccccuc agccaugcca uggguaugag   9060
aagccccuua uaaugaaagc ugccagcccu uucguccuug uuucagaggg ugggucaggu   9120
gguuggggug agaacuugcu cacggugcac ccaacaagac cugcaggugc auauaaguuu   9180
agucccaacu gcagggccag accaaacacu uccugggaag ugugugggagg gcugugcuag  9240
accuuccuga guuucuggcu aaaucaucag cccuguuugg ugcagucuca ugucucugug   9300
guucccaagc ugcaugauca gagccaguga gaagacagga ucagugaccc acagcuuugg   9360
ggaaaaacag ccccacuguu aacuucccuc cugcaaaccu ggguccccag gccauaaggu   9420
gggcacacug gugcuuacag acugggugga gagcccuacc uuccaagguc uugaucccag   9480
ccugccuaua agguugggau uagcaugcaa ucccccuucc ccaauccugu cuuuuuaaaa   9540
ucucaaguuu gcacuuaacc uugacaacag cacccucucc uacuccaguc cuagaacuca   9600
guggccuuag agaauggggu ccccugcacu gaagguuccc gccuugcucc caguuccauc   9660
cuggccaaua ggcugcgccu caagagguga aagagaaaaa agggagggag ggaggaagaa   9720
uuauuuagaa caaaaggaug gcucgagcac guuagaggca agugagaggc acguuggugua  9780
gaagagcaug ugcauguuug ggguagcugg ggccuacugu cccuucauua gggaaggagg   9840
cuuccagaag cggaugucuu cuagaaagaa aaauugugug aaggcugaaa aggggcuugg   9900
```

-continued

```
aguuuugucu uuguugauua gaaagaagga agaagucagc ucugaguguu ucaggaagaa   9960

gagagcaggu agaaagggaa uuuagugauu uaacacccaa ggguccagcc auagcagguu  10020

ggaaaauccu ccaaauuugg ccacagaaac uggcuaggaa aaaacugcca cucauugggc  10080

cacacgcugg guccccauca guucucaaug aauggucauu gauuuacuua gcagagagaa  10140

gucaccagcc acaaaccaau cuuugaguuu gcaggcccug auuccagaau auaugcaucc  10200

agcucccggg uucucagcug guuuugccca cuucccuuug acuguccaau ccaaagccag  10260

ucucucaagu uguauggcuc aaagagcagu gaccacaaug ggucauacag uagggaccca  10320

ccuccacaaa uuagaaccag aguucagacu ccauugggca caucugggag gaaggcaacc  10380

uccuuugucg ucuuguuggu accagucauu cucaaguauc ucugacaccu gugguggguuc  10440

aguuugcuga gccugccacc ugguaugaau uagacugggu gugaugaaca uucauccaug  10500

gauauacccu accauuuugc guugccuuau aaccaaggca cacuccccau aagaguuuac  10560

ugcagagaaa gaacagcaaa acagccaccc uccuugaauu uacaacucau uaucugcaac  10620

agguuuucuu uaaauccaag acacaggaug ggaaaugggu uuccccacca gguacucaga  10680

ggucugcagg aagugacucc cgggcaaggc agacuucagu aaucccugaa gcgugagcau  10740

guggacugca uggcugggug gggacuggug gaugucucug gagcuccaga accuuggaga  10800

auuccucaug gaauuccccu cccagcucuu agugggcucu guggggucag gaggagcccu  10860

ucccuccaggu uuuccuucuu ucccuccucag cagagaaacu ggagaaagga cauuaaacuc  10920

agugcagucg auuugagugc ugaaauauuu ccagaaucaa ugguggugcu aaacuaucuc  10980

cauguuucua gcauuuuuaa uaguggaguu gguuuguuuu uaaucucauc acaaaaaugc  11040

agugcccuug gggaagggac cagccccuug gccugccacu uuccaggugu ccuuuaucac  11100

uuugacggga cucuuugguc ugcagaaaau gcucugucuu ggcaugcuuc uagacuguaa  11160

gauuuggguu uuguuuugua uuuuauguuu acaugcaucu uauauuuccc ugaaaacuaa  11220

auaaaguuuu gggccuuuuu aaccgaaaaa aaaaaaaaaa aaaa                   11264
```

<210> SEQ ID NO 34
<211> LENGTH: 1133
<212> TYPE: PRT
<213> ORGANISM: Homo sapiens

<400> SEQUENCE: 34

```
Met Leu Ala Tyr Cys Val Gln Asp Ala Thr Val Val Asp Val Glu Lys
1               5                   10                  15

Arg Arg Asn Pro Ser Lys His Tyr Val Tyr Ile Ile Asn Val Thr Trp
            20                  25                  30

Ser Asp Ser Thr Ser Gln Thr Ile Tyr Arg Arg Tyr Ser Lys Phe Phe
        35                  40                  45

Asp Leu Gln Met Gln Leu Leu Asp Lys Phe Pro Ile Glu Gly Gly Gln
    50                  55                  60

Lys Asp Pro Lys Gln Arg Ile Ile Pro Phe Leu Pro Gly Lys Ile Leu
65                  70                  75                  80

Phe Arg Arg Ser His Ile Arg Asp Val Ala Val Lys Arg Leu Lys Pro
                85                  90                  95

Ile Asp Glu Tyr Cys Arg Ala Leu Val Arg Leu Pro Pro His Ile Ser
            100                 105                 110

Gln Cys Asp Glu Val Phe Arg Phe Phe Glu Ala Arg Pro Glu Asp Val
        115                 120                 125

Asn Pro Pro Lys Glu Asp Tyr Gly Ser Ser Lys Arg Lys Ser Val Trp
```

```
    130                 135                 140

Leu Ser Ser Trp Ala Glu Ser Pro Lys Lys Asp Val Thr Gly Ala Asp
145                 150                 155                 160

Ala Thr Ala Glu Pro Met Ile Leu Glu Gln Tyr Val Val Val Ser Asn
                165                 170                 175

Tyr Lys Lys Gln Glu Asn Ser Glu Leu Ser Leu Gln Ala Gly Glu Val
            180                 185                 190

Val Asp Val Ile Glu Lys Asn Glu Ser Gly Trp Trp Phe Val Ser Thr
        195                 200                 205

Ser Glu Glu Gln Gly Trp Val Pro Ala Thr Tyr Leu Glu Ala Gln Asn
    210                 215                 220

Gly Thr Arg Asp Asp Ser Asp Ile Asn Thr Ser Lys Thr Gly Glu Val
225                 230                 235                 240

Ser Lys Arg Arg Lys Ala His Leu Arg Arg Leu Asp Arg Arg Trp Thr
                245                 250                 255

Leu Gly Gly Met Val Asn Arg Gln His Ser Arg Glu Glu Lys Tyr Val
            260                 265                 270

Thr Val Gln Pro Tyr Thr Ser Gln Ser Lys Asp Glu Ile Gly Phe Glu
        275                 280                 285

Lys Gly Val Thr Val Glu Val Ile Arg Lys Asn Leu Glu Gly Trp Trp
    290                 295                 300

Tyr Ile Arg Tyr Leu Gly Lys Glu Gly Trp Ala Pro Ala Ser Tyr Leu
305                 310                 315                 320

Lys Lys Ala Lys Asp Asp Leu Pro Thr Arg Lys Lys Asn Leu Ala Gly
                325                 330                 335

Pro Val Glu Ile Ile Gly Asn Ile Met Glu Ile Ser Asn Leu Leu Asn
            340                 345                 350

Lys Lys Ala Ser Gly Asp Lys Glu Thr Pro Pro Ala Glu Gly Glu Gly
        355                 360                 365

His Glu Ala Pro Ile Ala Lys Lys Glu Ile Ser Leu Pro Ile Leu Cys
    370                 375                 380

Asn Ala Ser Asn Gly Ser Ala Val Gly Val Pro Asp Arg Thr Val Ser
385                 390                 395                 400

Arg Leu Ala Gln Gly Ser Pro Ala Val Ala Arg Ile Ala Pro Gln Arg
                405                 410                 415

Ala Gln Ile Ser Ser Pro Asn Leu Arg Thr Arg Pro Pro Pro Arg Arg
            420                 425                 430

Glu Ser Ser Leu Gly Phe Gln Leu Pro Lys Pro Pro Glu Pro Pro Ser
        435                 440                 445

Val Glu Val Glu Tyr Tyr Thr Ile Ala Glu Phe Gln Ser Cys Ile Ser
    450                 455                 460

Asp Gly Ile Ser Phe Arg Gly Gly Gln Lys Ala Glu Val Ile Asp Lys
465                 470                 475                 480

Asn Ser Gly Gly Trp Trp Tyr Val Gln Ile Gly Glu Lys Glu Gly Trp
                485                 490                 495

Ala Pro Ala Ser Tyr Ile Asp Lys Arg Lys Lys Pro Asn Leu Ser Arg
            500                 505                 510

Arg Thr Ser Thr Leu Thr Arg Pro Lys Val Pro Pro Pro Ala Pro Pro
        515                 520                 525

Ser Lys Pro Lys Glu Ala Glu Glu Gly Pro Thr Gly Ala Ser Glu Ser
    530                 535                 540

Gln Asp Ser Pro Arg Lys Leu Lys Tyr Glu Glu Pro Glu Tyr Asp Ile
545                 550                 555                 560
```

```
Pro Ala Phe Gly Phe Asp Ser Glu Pro Glu Leu Ser Glu Glu Pro Val
                565                 570                 575

Glu Asp Arg Ala Ser Gly Glu Arg Arg Pro Ala Gln Pro His Arg Pro
            580                 585                 590

Ser Pro Ala Ser Ser Leu Gln Arg Ala Arg Phe Lys Val Gly Glu Ser
        595                 600                 605

Ser Glu Asp Val Ala Leu Glu Glu Glu Thr Ile Tyr Glu Asn Glu Gly
    610                 615                 620

Phe Arg Pro Tyr Ala Glu Asp Thr Leu Ser Ala Arg Gly Ser Ser Gly
625                 630                 635                 640

Asp Ser Asp Ser Pro Gly Ser Ser Ser Leu Ser Leu Thr Arg Lys Asn
                645                 650                 655

Ser Pro Lys Ser Gly Ser Pro Lys Ser Ser Ser Leu Leu Lys Leu Lys
            660                 665                 670

Ala Glu Lys Asn Ala Gln Ala Glu Met Gly Lys Asn His Ser Ser Ala
        675                 680                 685

Ser Phe Ser Ser Ser Ile Thr Ile Asn Thr Thr Cys Cys Ser Ser Ser
    690                 695                 700

Ser Ser Ser Ser Ser Ser Leu Ser Lys Thr Ser Gly Asp Leu Lys Pro
705                 710                 715                 720

Arg Ser Ala Ser Asp Ala Gly Ile Arg Gly Thr Pro Lys Val Arg Ala
                725                 730                 735

Lys Lys Asp Ala Asp Ala Asn Ala Gly Leu Thr Ser Cys Pro Arg Ala
            740                 745                 750

Lys Pro Ser Val Arg Pro Lys Pro Phe Leu Asn Arg Ala Glu Ser Gln
        755                 760                 765

Ser Gln Glu Lys Met Asp Ile Ser Thr Leu Arg Arg Gln Leu Arg Pro
    770                 775                 780

Thr Gly Gln Leu Arg Gly Gly Leu Lys Gly Ser Lys Ser Glu Asp Ser
785                 790                 795                 800

Glu Leu Pro Pro Gln Thr Ala Ser Glu Ala Pro Ser Glu Gly Ser Arg
                805                 810                 815

Arg Ser Ser Ser Asp Leu Ile Thr Leu Pro Ala Thr Thr Pro Pro Cys
            820                 825                 830

Pro Thr Lys Lys Glu Trp Glu Gly Pro Ala Thr Ser Tyr Met Thr Cys
        835                 840                 845

Ser Ala Tyr Gln Lys Val Gln Asp Ser Glu Ile Ser Phe Pro Ala Gly
    850                 855                 860

Val Glu Val Gln Val Leu Glu Lys Gln Glu Ser Gly Trp Trp Tyr Val
865                 870                 875                 880

Arg Phe Gly Glu Leu Glu Gly Trp Ala Pro Ser His Tyr Leu Val Leu
                885                 890                 895

Asp Glu Asn Glu Gln Pro Asp Pro Ser Gly Lys Glu Leu Asp Thr Val
            900                 905                 910

Pro Ala Lys Gly Arg Gln Asn Glu Gly Lys Ser Asp Ser Leu Glu Lys
        915                 920                 925

Ile Glu Arg Arg Val Gln Ala Leu Asn Thr Val Asn Gln Ser Lys Lys
    930                 935                 940

Ala Thr Pro Pro Ile Pro Ser Lys Pro Pro Gly Gly Phe Gly Lys Thr
945                 950                 955                 960

Ser Gly Thr Pro Ala Val Lys Met Arg Asn Gly Val Arg Gln Val Ala
                965                 970                 975
```

```
Val Arg Pro Gln Ser Val Phe Val Ser Pro Pro Pro Lys Asp Asn Asn
            980                 985                 990

Leu Ser Cys Ala Leu Arg Arg Asn  Glu Ser Leu Thr Ala  Thr Asp Gly
        995                 1000                 1005

Leu Arg  Gly Val Arg Arg Asn  Ser Ser Phe Ser Thr  Ala Arg Ser
    1010                 1015                 1020

Ala Ala  Ala Glu Ala Lys Gly  Arg Leu Ala Glu Arg  Ala Ala Ser
    1025                 1030                 1035

Gln Gly  Ser Asp Ser Pro Leu  Leu Pro Ala Gln Arg  Asn Ser Ile
    1040                 1045                 1050

Pro Val  Ser Pro Val Arg Pro  Lys Pro Ile Glu Lys  Ser Gln Phe
    1055                 1060                 1065

Ile His  Asn Asn Leu Lys Asp  Val Tyr Val Ser Ile  Ala Asp Tyr
    1070                 1075                 1080

Glu Gly  Asp Glu Glu Thr Ala  Gly Phe Gln Glu Gly  Val Ser Met
    1085                 1090                 1095

Glu Val  Leu Glu Arg Asn Pro  Asn Gly Trp Trp Tyr  Cys Gln Ile
    1100                 1105                 1110

Leu Asp  Gly Val Lys Pro Phe  Lys Gly Trp Val Pro  Ser Asn Tyr
    1115                 1120                 1125

Leu Glu  Lys Lys Asn
    1130
```

<210> SEQ ID NO 35
<211> LENGTH: 1574
<212> TYPE: RNA
<213> ORGANISM: Homo sapiens

<400> SEQUENCE: 35

```
ucaccacggc ggcagcccuu uaaaccccuc acccagccag cgccccaucc ugucuguccg     60

aacccagaca caagucuuca cuccuuccug cgagcccuga ggaagccuug ugagugcauu    120

ggcuggggcu uggagggaag uugggcugga gcuggacagg agcagugggu gcauuucagg    180

caggcucucc ugagguccca ggcgccagcu ccagcucccu ggcuagggaa acccacccuc    240

ucagucagca ugggggccca agcuccaggc agggugggcu ggaucacuag cguccuggau    300

cucucucaga cugggcagcc ccgggcucau ugaaaugccc cggaugacuu ggcuagugca    360

gaggaauuga uggaaaccac cggggugaga gggaggcucc ccaucucagc cagccacauc    420

cacaaggugu guguaagggu gcaggcgccg gccgguuagg ccaaggcucu acugucuguu    480

gccccuccag gagaacuucc aaggagcuuu ccccagacau ggccaacaag gguccuuccu    540

auggcaugag ccgcgaagug caguccaaaa ucgagaagaa guaugacgag gagcuggagg    600

agcggcuggu ggaguggauc auagugcagu guggcccuga ugugggccgc ccagaccgug    660

ggcgcuuggg cuuccagguc uggcugaaga auggcgugau ucugagcaag cuggugaaca    720

gccuguaccc ugauggcucc aagccgguga aggugcccga gaacccaccc uccauggucu    780

ucaagcagau ggagcaggug gcucaguucc ugaaggcggc ugaggacuau ggggucauca    840

agacugacau guuccagacu guugaccucu uugaaggcaa agacauggca gcagugcaga    900

ggacccugau ggcuuugggc agcuuggcag ugaccaagaa ugaugggcac uaccguggag    960

aucccaacug guuuaugaag aaagcgcagg agcauaagag ggaauucaca gagagccagc   1020

ugcaggaggg aaagcauguc auuggccuuc agaugggcag caacagaggg gccucccagg   1080

ccggcaugac aggcuacgga cgaccucggc agaucaucag uuagagcgga gagggcuagc   1140
```

```
ccugagcccg gcccuccccc agcuccuugg cugcagccau cccgcuuagc cugccucacc   1200

cacacccgug ugguaccuuc agcccuggcc aagcuuugag gcucugucac ugagcaaugg   1260

uaacugcacc ugggcagcuc cucccugugc ccccagccuc agcccaacuu cuuacccgaa   1320

agcaucacug ccuuggcccc ucccucccgg cugcccccau caccucuacu gucuccuccc   1380

ugggcuaagc aggggagaag cgggcugggg guagccugga ugugggccaa guccacuguc   1440

cuccuuggcg gcaaaagccc auugaagaag aaccagccca gccugccccc uaucuugucc   1500

uggaauauuu uuggggguugg aacucaaaaa aaaaaaaaaa aaaucaaucu uuucucaaaa   1560

aaaaaaaaaa aaaa                                                      1574
```

<210> SEQ ID NO 36
<211> LENGTH: 201
<212> TYPE: PRT
<213> ORGANISM: Homo sapiens

<400> SEQUENCE: 36

```
Met Ala Asn Lys Gly Pro Ser Tyr Gly Met Ser Arg Glu Val Gln Ser
1               5                   10                  15

Lys Ile Glu Lys Lys Tyr Asp Glu Glu Leu Glu Glu Arg Leu Val Glu
            20                  25                  30

Trp Ile Ile Val Gln Cys Gly Pro Asp Val Gly Arg Pro Asp Arg Gly
        35                  40                  45

Arg Leu Gly Phe Gln Val Trp Leu Lys Asn Gly Val Ile Leu Ser Lys
    50                  55                  60

Leu Val Asn Ser Leu Tyr Pro Asp Gly Ser Lys Pro Val Lys Val Pro
65                  70                  75                  80

Glu Asn Pro Pro Ser Met Val Phe Lys Gln Met Glu Gln Val Ala Gln
                85                  90                  95

Phe Leu Lys Ala Ala Glu Asp Tyr Gly Val Ile Lys Thr Asp Met Phe
            100                 105                 110

Gln Thr Val Asp Leu Phe Glu Gly Lys Asp Met Ala Ala Val Gln Arg
        115                 120                 125

Thr Leu Met Ala Leu Gly Ser Leu Ala Val Thr Lys Asn Asp Gly His
    130                 135                 140

Tyr Arg Gly Asp Pro Asn Trp Phe Met Lys Lys Ala Gln Glu His Lys
145                 150                 155                 160

Arg Glu Phe Thr Glu Ser Gln Leu Gln Glu Gly Lys His Val Ile Gly
                165                 170                 175

Leu Gln Met Gly Ser Asn Arg Gly Ala Ser Gln Ala Gly Met Thr Gly
            180                 185                 190

Tyr Gly Arg Pro Arg Gln Ile Ile Ser
        195                 200
```

<210> SEQ ID NO 37
<211> LENGTH: 2805
<212> TYPE: RNA
<213> ORGANISM: Homo sapiens

<400> SEQUENCE: 37

```
cuccuugcac gggccggccc agcuuccccg ccccuggcgu ccgcucccuc ccgcucgcag     60

cuuacuuaac cuggcccggg cggcggaggc gcucucacuu cccuggagcc gcccgcuugc    120

ccgucggucg cuagcucgcu cggugcgcgu cgucccgcuc cauggcgcuc uucgugcggc    180

ugcuggcucu cgcccuggcu cuggcccugg gccccgccgc gacccuggcg ggucccgcca    240
```

-continued

```
agucgcccua ccagcuggug cugcagcaca gcaggcuccg gggccgccag cacggcccca    300
acgugugugc ugugcagaag guuauuggca cuaauaggaa guacuucacc aacugcaagc    360
agugguacca aaggaaaauc uguggcaaau caacagucau cagcuacgag ugcuguccug    420
gauaugaaaa gguccuggg gagaagggcu guccagcagc ccuaccacuc ucaaaccuuu    480
acgagacccu gggagucguu ggauccacca ccacucagcu guacacggac cgcacggaga    540
agcugaggcc ugagauggag gggcccggca gcuucaccau cuucgccccu agcaacgagg    600
ccugggccuc cuugccagcu gaagugcugg acucccuggu cagcaauguc aacauugagc    660
ugcucaaugc ccuccgcuac cauaugguggg gcaggcgagu ccugacugau gagcugaaac    720
acggcaugac ccucaccucu auguaccaga auuccaacau ccagauccac cacuauccua    780
augggauugu aacugugaac ugugcccggc ugcugaaagc cgaccaccau gcaaccaacg    840
ggguggugca ccucaucgau aaggucaucu ccaccaucac caacaacauc cagcagauca    900
uugagaucga ggacaccuuu gagacccuuc gggcugcugu ggcugcauca gggcucaaca    960
cgaugcuuga agguaacggc caguacacgc uuuuggcccc gaccaaugag gccuucgaga   1020
agaucccuag ugagacuuug aaccguaucc ugggcgaccc agaagcccug agagaccugc   1080
ugaacaacca caucuugaag ucagcuaugu gugcugaagc caucguugcg gggcugucug   1140
uagagacccu ggagggcacg acacuggagg ugggcugcag cggggacaug cucacuauca   1200
acgggaaggc gaucaucucc aauaaagaca uccuagccac caacggggug auccacuaca   1260
uugaugagcu acucauccca gacucagcca agacacuauu ugaauuggcu gcagagucug   1320
auguguccac agccauugac cuuuucagac aagccggccu cggcaaucau cucucuggaa   1380
gugagcgguu gacccuccug gcuccccuga auucuguauu caaagaugga accccuccaa   1440
uugaugccca uacaaggaau uugcuucgga accacauaau uaaagaccag cuggccucua   1500
aguaucugua ccauggacag acccuggaaa cucugggcgg caaaaaacug agaguuuuug   1560
uuuaucguaa uagccucugc auugagaaca gcugcaucgc ggcccacgac aagaggggga   1620
gguacgggac ccuguucacg auggaccggg ugcugacccc cccaaugggg acugucaugg   1680
auguccugaa gggagacaau cgcuuuagca ugcugguagc ugccauccag ucugcaggac   1740
ugacggagac ccucaaccgg gaaggagucu acacagucuu ugcucccaca aaugaagccu   1800
uccgagcccu gccaccaaga gaacggagca gacucuuggg agaugccaag gaacuugcca   1860
acauccugaa auaccacauu ggugaugaaa uccugguuag cggaggcauc ggggcccugg   1920
ugcggcuaaa gucucuccaa ggugacaagc uggaagucag cuugaaaaac aaugugguga   1980
gugucaacaa ggagccuguu gccgagccug acaucauggc cacaaauggc gugguccaug   2040
ucaucaccaa uguucugcag ccuccagcca acagaccuca ggaaagaggg gaugaacuug   2100
cagacucugc gcuugagauc uucaaacaag caucagcguu uuccagggcu ucccagaggu   2160
cugugcgacu agccccuguc uaucaaaagu uauuagagag gaugaagcau uagcuugaag   2220
cacuacagga ggaaugcacc acggcagcuc uccgccaauu ucucucagau uuccacagag   2280
acuguuugaa uguuuucaaa accaaguauc acacuuuaau guacaugggc cgcaccauaa   2340
ugagauguga gccuugugca ugugggggag gagggagaga gauguacuuu uuaaaucaug   2400
uucccccuaa acauggcugu uaacccacug caugcagaaa cuuggauguc acugccugac   2460
auucacuucc agagaggacc uaucccaaau guggaauuga cugccuaugc caagucccug   2520
gaaaaggagc uucaguauug uggggcucau aaaacaugaa ucaagcaauc cagccucaug   2580
ggaaguccug gcacaguuuu uguaaagccc uugcacagcu ggagaaaugg caucauuaua   2640
```

```
agcuaugagu ugaaauguuc ugucaaaugu gucucacauc uacacguggc uuggaggcuu   2700

uuauggggcc cuguccaggu agaaaagaaa ugguauguag agcuuagauu ucccuauugu   2760

gacagagcca uggugugguuu guaauaauaa aaccaaagaa acaua                  2805


<210> SEQ ID NO 38
<211> LENGTH: 683
<212> TYPE: PRT
<213> ORGANISM: Homo sapiens

<400> SEQUENCE: 38

Met Ala Leu Phe Val Arg Leu Leu Ala Leu Ala Leu Ala Leu Ala Leu
1               5                   10                  15

Gly Pro Ala Ala Thr Leu Ala Gly Pro Ala Lys Ser Pro Tyr Gln Leu
            20                  25                  30

Val Leu Gln His Ser Arg Leu Arg Gly Arg Gln His Gly Pro Asn Val
        35                  40                  45

Cys Ala Val Gln Lys Val Ile Gly Thr Asn Arg Lys Tyr Phe Thr Asn
    50                  55                  60

Cys Lys Gln Trp Tyr Gln Arg Lys Ile Cys Gly Lys Ser Thr Val Ile
65                  70                  75                  80

Ser Tyr Glu Cys Cys Pro Gly Tyr Glu Lys Val Pro Gly Glu Lys Gly
                85                  90                  95

Cys Pro Ala Ala Leu Pro Leu Ser Asn Leu Tyr Glu Thr Leu Gly Val
            100                 105                 110

Val Gly Ser Thr Thr Thr Gln Leu Tyr Thr Asp Arg Thr Glu Lys Leu
        115                 120                 125

Arg Pro Glu Met Glu Gly Pro Gly Ser Phe Thr Ile Phe Ala Pro Ser
    130                 135                 140

Asn Glu Ala Trp Ala Ser Leu Pro Ala Glu Val Leu Asp Ser Leu Val
145                 150                 155                 160

Ser Asn Val Asn Ile Glu Leu Leu Asn Ala Leu Arg Tyr His Met Val
                165                 170                 175

Gly Arg Arg Val Leu Thr Asp Glu Leu Lys His Gly Met Thr Leu Thr
            180                 185                 190

Ser Met Tyr Gln Asn Ser Asn Ile Gln Ile His His Tyr Pro Asn Gly
        195                 200                 205

Ile Val Thr Val Asn Cys Ala Arg Leu Leu Lys Ala Asp His His Ala
    210                 215                 220

Thr Asn Gly Val Val His Leu Ile Asp Lys Val Ile Ser Thr Ile Thr
225                 230                 235                 240

Asn Asn Ile Gln Gln Ile Ile Glu Ile Glu Asp Thr Phe Glu Thr Leu
                245                 250                 255

Arg Ala Ala Val Ala Ala Ser Gly Leu Asn Thr Met Leu Glu Gly Asn
            260                 265                 270

Gly Gln Tyr Thr Leu Leu Ala Pro Thr Asn Glu Ala Phe Glu Lys Ile
        275                 280                 285

Pro Ser Glu Thr Leu Asn Arg Ile Leu Gly Asp Pro Glu Ala Leu Arg
    290                 295                 300

Asp Leu Leu Asn Asn His Ile Leu Lys Ser Ala Met Cys Ala Glu Ala
305                 310                 315                 320

Ile Val Ala Gly Leu Ser Val Glu Thr Leu Glu Gly Thr Thr Leu Glu
                325                 330                 335

Val Gly Cys Ser Gly Asp Met Leu Thr Ile Asn Gly Lys Ala Ile Ile
```

```
            340                 345                 350

Ser Asn Lys Asp Ile Leu Ala Thr Asn Gly Val Ile His Tyr Ile Asp
        355                 360                 365

Glu Leu Leu Ile Pro Asp Ser Ala Lys Thr Leu Phe Glu Leu Ala Ala
    370                 375                 380

Glu Ser Asp Val Ser Thr Ala Ile Asp Leu Phe Arg Gln Ala Gly Leu
385                 390                 395                 400

Gly Asn His Leu Ser Gly Ser Glu Arg Leu Thr Leu Leu Ala Pro Leu
                405                 410                 415

Asn Ser Val Phe Lys Asp Gly Thr Pro Pro Ile Asp Ala His Thr Arg
            420                 425                 430

Asn Leu Leu Arg Asn His Ile Ile Lys Asp Gln Leu Ala Ser Lys Tyr
        435                 440                 445

Leu Tyr His Gly Gln Thr Leu Glu Thr Leu Gly Gly Lys Lys Leu Arg
    450                 455                 460

Val Phe Val Tyr Arg Asn Ser Leu Cys Ile Glu Asn Ser Cys Ile Ala
465                 470                 475                 480

Ala His Asp Lys Arg Gly Arg Tyr Gly Thr Leu Phe Thr Met Asp Arg
                485                 490                 495

Val Leu Thr Pro Pro Met Gly Thr Val Met Asp Val Leu Lys Gly Asp
            500                 505                 510

Asn Arg Phe Ser Met Leu Val Ala Ala Ile Gln Ser Ala Gly Leu Thr
        515                 520                 525

Glu Thr Leu Asn Arg Glu Gly Val Tyr Thr Val Phe Ala Pro Thr Asn
    530                 535                 540

Glu Ala Phe Arg Ala Leu Pro Pro Arg Glu Arg Ser Arg Leu Leu Gly
545                 550                 555                 560

Asp Ala Lys Glu Leu Ala Asn Ile Leu Lys Tyr His Ile Gly Asp Glu
                565                 570                 575

Ile Leu Val Ser Gly Gly Ile Gly Ala Leu Val Arg Leu Lys Ser Leu
            580                 585                 590

Gln Gly Asp Lys Leu Glu Val Ser Leu Lys Asn Asn Val Val Ser Val
        595                 600                 605

Asn Lys Glu Pro Val Ala Glu Pro Asp Ile Met Ala Thr Asn Gly Val
    610                 615                 620

Val His Val Ile Thr Asn Val Leu Gln Pro Pro Ala Asn Arg Pro Gln
625                 630                 635                 640

Glu Arg Gly Asp Glu Leu Ala Asp Ser Ala Leu Glu Ile Phe Lys Gln
                645                 650                 655

Ala Ser Ala Phe Ser Arg Ala Ser Gln Arg Ser Val Arg Leu Ala Pro
            660                 665                 670

Val Tyr Gln Lys Leu Leu Glu Arg Met Lys His
        675                 680
```

<210> SEQ ID NO 39
<211> LENGTH: 10294
<212> TYPE: RNA
<213> ORGANISM: Homo sapiens

<400> SEQUENCE: 39

```
cucaguugcu cccagcagug gcccugggac cagcucugcu ccuugcaccc cgcuccccugc      60

cuggacacag gcucacucgc ugccuucuuc ugggggaaac cagcuucuug ccagccacag     120

cugcugccuc cgccacuggc caccgccccu guccugggag ucccuuggcc cagacaccca     180
```

-continued ccugacuuag uggcuccucu gcaggaaagg uggcugcccc cugcguuccu ccauccaacc 240
augagcuggu gcccaucacc acugagaaug caccaaagaa uguaguggac aagggagaag 300
gagccucccg ggguggaaac acacggaaaa gccucgagga caacggcucc accaggguca 360
ccccgagugu ccagccccac cuccagccca ucagaaacau gagugugagc cggaccaugg 420
aggacagcug ugagcuggac cugguguacg ucacagagag gaucaucgcu gucuccuucc 480
ccagcacagc caaugaggag aacuuccgga gcaaccuccg ugagguggcg cagaugcuca 540
aguccaaaca uggaggcaac uaccugcugu ucaaccucuc ugagcggaga ccugacauca 600
cgaagcucca ugccaaggua cuggaauuug gcuggcccga ccuccacacc ccagcccugg 660
agaagaucug cagcaucugu aaggccaugg acacauggcu caaugcagac ccucacaaug 720
ucguuguucu acacaacaag ggaaaccgag gcaggauagg aguugucauc gcggcuuaca 780
ugcacuacag caacauuucu gccagugcgg accaggcucu ggaccgguuu gcaaugaagc 840
gguucuauga ggauaagauu gugcccauug gccagccauc ccaaagaagg uacgugcauu 900
acuucagugg ccugcucucc ggcuccauca aaaugaacaa caagcccuug uuucugcacc 960
acgugaucau gcacggcauc cccaacuuug agucuaaagg aggaugucgg ccauuucucc 1020
gcaucuacca ggccaugcaa ccuguguaca caucuggcau cuacaacauc ccaggagaca 1080
gccagacuag cgucugcauc accaucgagc caggacugcu cuugaaggga gacaucuugc 1140
ugaagugcua ccacaagaag uuccgaagcc cagcccgaga cgucaucuuc cgugugcagu 1200
uccacaccug ugccauccau gaccuggggg uugucuuugg gaaggaggac cuugaugaug 1260
cuuucaaaga ugaucgauuu ccagaguaug gcaaagugga guuuguauuu ucuuaugggc 1320
cagagaaaau ucaaggcaug gagcaccugg agaacgggcc gagcgugucu guggacuaua 1380
acaccuccga cccccucauc cgcugggacu ccuacgacaa cuucaguggg caucgagaug 1440
acggcaugga ggagguggug ggacacacgc aggggccacu agaugggagc cuguaugcua 1500
aggugaagaa gaaagacucc cugcacggca gcaccggggc uguuaaugcc acacguccua 1560
cacugucggc cacccccaac cacguggaac acacgcuuuc ugugagcagc gacucgggca 1620
acuccacagc cuccaccaag accgacaaga ccgacgagcc uguccccggg gccuccagug 1680
ccacugcugc cuugaguccc caggagaagc gggagcugga ccgccugcug aguggcuuug 1740
gcuuagagcg agagaagcaa ggcgccaugu accacaccca gcaccucagg ucccgcccag 1800
cagggggcuc ggcugugccc uccucuggac gccacguugu cccagcccag guucauguca 1860 auggugggc guuagcaucu gagcgggaga cagacauccu ggacgaugaa uugccaaacc 1920
aggaugguca cagugcgggc agcaugggca cacucucuuc ucuggacggg gucaccaaca 1980
ccagugaggg gggcuaccca gaggcccugu ccccacugac caacggucug gacaaguccu 2040
accccaugga gccuaugguc aauggaggag gcuaccccua cgagucugcc agccgggcgg 2100
ggccugccca ugcuggccac acggccccca ugcggcccuc cuacucugca caggaggguu 2160
uagcuggcua ccagagggag gggccccacc cagccuggcc acagccagug accaccuccc 2220
acuaugccca ugaccccagc gguauguucc gcucucaauc cuuuucggaa gcugaacccc 2280
agcugccccc agcuccgguc cgagggggaa gcagccggga ggcugugcaa aggggacuga 2340
auucguggca gcagcagcag cagcagcagc agcagccucg cccaccucca cgccagcagg 2400
aaagagccca cuuggagagu cuuguagcca gcaggcccag cccucagcca uuggcagaga 2460
cccccauccc cagucucccu gaguucccgc gagcagccuc ccagcaggag auugaacagu 2520
ccaucgaaac acucaauaug cugaugcugg accuggagcc agccuccgcu gcugccccac 2580

-continued uacacaaguc ccagaguguc cccggggccu ggccaggggc uucuccacuc uccucccagc 2640
cccucucugg auccucccgu caguccoauc cacugaccca guccagaucu ggcuauaucc 2700
ccagugggca uucguuggga accccugagc cagccccacg ggccucucug gagucugucc 2760
cuccuggcag gucuuacuca ccuuaugacu aucagccaug uuuggcuggg ccuaaccagg 2820
auuuccauuc aaagagccca gccucuuccu ccuugccugc cuuccuuccg accacccaca 2880
gcccuccagg gccucagcaa cccccagccu cucucccugg ccucacugcu cagccucugc 2940
ucucaccaaa ggaagcgacu ucagaccccu cccggacucc agaggaggag ccauugaauu 3000
uagaagggcu gguggcccac aggguagcag ggguacaggc ucgggagaag cagccugcag 3060
agcccccagc cccucugcgg aggcgggcgg ccagugaugg acaguaugag aaccagucuc 3120
cagaagccac auccccucgu agcccugggg uucgcucccc uguccagugu gucuccccgg 3180
agcuggcucu uaccaucgcu cucaauccug gagggcggcc caaagagccc cauuugcaca 3240
gcuacaagga ggccuucgag gagauggagg gaaccucccc gagcagccca ccacccagug 3300
gggugcgguc ccccccgggu cuggccaaga caccccuguc ugcucugggc cugaaaccuc 3360
acaacccagc ggacauccug uugcacccca caggaguuac cagaagacgg auccagccag 3420
aggaagauga ggggaaggug guggucaggc ugucagaaga gccccggagc uauguggagu 3480
cuguggcacg gacagcggug gcuggacccc gagcucagga cucugagccc aagagcuuua 3540
gugcuccagc cacccaggcc uauggccaug agauaccccu gaggaacggg acccugggug 3600
gcuccuuugu cucccccagc cccucuccca ccagcagccc cauccucagu gcugacagca 3660
cuucaguggg gaguuucccg ucgggagaga gcagugacca ggguccccgg acgcccaccc 3720
agccucuguu ggagucuggc uuccgcucag gcagccuggg acagcccagc ccgucugccc 3780
agagaaacua ccagagcucu ucuccucucc cgacuguggg caguagcuac agcagccccg 3840
acuacucacu ucagcauuuc agcuccucuc cggaaagcca ggcucgagcu caguucagug 3900
uggcuggcgu ccacacggug ccugggagcc cucaggcgcg ccacagaaca gugggcacca 3960
acacuccccc uaguccuggc uucggcuggc gggccaucaa ucccagcaug gcugccccca 4020
gcagucccag uuugagccau caccagauga uggguccacc aggcacuggc uuccauggua 4080
gcacugucuc cagcccccag agcagugcag cgaccacccc ggggagcccc agccuguguc 4140
ggcacccagc aggggucuac cagguuucug gccuccacaa caaaguggcc accaccccgg 4200 ggaguccoag ccugggccgg cacccugggg cucaccaagg caaccuggcc uccggucuuc 4260
auagcaaugc aauagccagc ccuggaagcc ccagccuggg ccgucaccuc ggagggucug 4320
gaucuguggu ucccggcagc ccugcuugg accggcaugu ggccuauggu ggcuauucua 4380
ccccggagga ucggagaccc acacuguccc ggcagagcag ugccucuggc uaccaggcuc 4440
cuuccacgcc cuccuucccu gucuccccug ccuacuaccc uggccugagc agcccugcca 4500 ccucccccguc accagacucc gcagccuucc ggcaagggag cccaacacca gccuugccag 4560
agaagcgaag gaugucagug ggagaccggg caggcagccu ccccaacuau gccaccauca 4620
augggaaggu gucuucgccu gucgccagcg gcauguccag ucccaguggg ggcagcaccg 4680
ucuccuucuc ccacacucug cccgacuucu ccaaguacuc caugccagac aacagcccgg 4740
agacgcgggc uaaagugaag uuuguccagg acacuucuaa guauugguac aagccugaga 4800
ucuccaggga gcaggccauc gcgcuccuca aggaccagga gccgggggcc uucaucaucc 4860
gcgacaguca cuccuuccga ggcgcguacg ggcuggccau gaaggugucu ucgccaccuc 4920

-continued

```
caaccaucau gcagcagaau aaaaaaggag acaugaccca ugagcugguc aggcauuuuc   4980
ugauagagac uggccccaga ggagucaagc ucaagggcug ccccaaugag ccaaacuucg   5040
gaucgcuguc ugcccugguc uaccagcacu ccaucauccc auuggcccug ccuugcaagc   5100
uggucauucc aaaccgagac cccacagaug aaucgaaaga uagcuccggc ccugccaacu   5160
caacugcaga ccugcugaaa caaggggcag ccugcaaugu gcucuucguc aacucugugg   5220
acauggaguc acucacuggg ccacaggcca ucucuaaagc cacaucugag acguuggcug   5280
cagaccccac gccagcugcc accaucguuc acuucaaagu cucugcccag ggaaucacuc   5340
ugacugacaa ccagagaaag cucuuuuuca gacgccacua cccucucaac acugucaccu   5400
ucugugaccu ggauccacag gaaagaaagu ggaugaaaac agagggugu gccccugcua    5460
agcucuucgg cuucguggcc cggaagcagg gcagcaccac ggacaacgcc ugccaccucu   5520
uugcugagcu ugaccccaac cagccggccu cugccaucgu caacuucguc uccaagguca   5580
ugcugaaugc cggccaaaag agaugaaccc ugccccuugc ccagggccag ugccaugggg   5640
aaggggcuug uggggagggg acccaugaau ccugaccacu cuugaaccca gaaggaggac   5700
uuugggccaa uuucggagga gagaagaaag ugcaacgugg ggagagggaa gugaauugca   5760
gaggggaggg ggaaaagaga gagagagaga gagagagaga gagagagaaa gauggaggag   5820
aagaacuugg auuccccugg guagauggaa acugcaaaaa cccaaagccu ccaaaacuaa   5880
ccagguccac cuaacacccc cucccucccc uaagaagaug gauguccuca aaagagaagg   5940
aacaaaccuc cuugggaauc cacauuuuuu gggggaaugg aaaagcucug ucucccuaac   6000
ucaacugcuu ugcaagggga aaucaagcug ggagaaucuu uuucuggcca ccugugggu    6060
agguugucaa accaaacaga gccaccgugg gacaucaagu ggaagaacuu guuugcuuga   6120
aaguaucuca gacccaaggc accucagguc ucuuugcugu gccuccacua uauugucgug   6180
ugggugugug ucugcaccca cauccucaca cauugaucua gaucugccuu uauccacucg   6240
aauuauaaac agcucggcuu guccuugucc cauguguuug uagacacaca ugcauacugu   6300
ccaaagauua ggguuggugg uggcagugca gcaggggagg gacaaacaac caagcuaugg   6360
gugacagagg cucucuccug gugccugcac cugcacucua gugacccugg gugccgccag   6420
acccuucucu ucuacaaaga ccccagcagg agugggaggg ucugcaaugg caucgcccug   6480
uccugccuug gccagaagcc uggagcuuug guuugaggag guagagauau guguauccau   6540
aggaagagau cugucagaac aggcagcugu ugagcucggg gugucuuccc caaggcaugu   6600
ggcucagcag caagaaaggc aaguugcucc ugcuggggcc cuggacucug ccuuagcucc   6660
caccucucag ccuuguuauu ggguuucaug ccccuggacc agccuuaucu cagaccugcu   6720
uaccugcaug augccuuuuu gggggcuggg gauugagucu ugcugcucug cccagcccug   6780
uucuauucug caggguccu guguuggaau ucucccuggg gaaccuacuu ucugcucagu    6840
gaggcuccgg ccagaaaccu ggaguccuua ucucuccccuc uguaaguguu uuagggucug  6900
gcuuuugcag gcacccucug accucagcag agcuccuggg ccugcugccu gcacaccaca   6960
ucgccuaccu acaaugccaa agccucacug ucacccuuuc ugccuugguu ucccuagcug   7020
agccacgcug cccaugcagc agagggcaga aggcuugcac uugggccaaa gggccuaagg   7080
uccacuggac aguugggaaa acaccugacc accauuuaag gacucuaagc cagaauggaa   7140
aauucaccag gacuccauuc uuaagccuau gcgaguccccc uagagagagg cauuguacug  7200
auauauaaau auuauauaau auauacauga gacauacuga cagaaucugu aagcuaauaa   7260
aauguaagaa aagguuaaaa aaagaauagg uaaauugaca agaaguauuu auuguuuuuc   7320
```

cauauugcuu uauugccuuc cuuggggaua aaccaauucc uauccuuuuu uauaugugua 7380
aguaaagccu gaaguguagg gggccuuugu ucuugaagca gccagggucu ccuugcccug 7440
gccuuggccu ucccuagacu gugugggggcu cagcauuggg aggggguugca caugucccag 7500
ccuuuggccc ccuuacuuuu cagcaagcca ggggcccagc agucagcucc caggaugugu 7560
ggggagcugu cccugacucu gcaggccuga gcgagugugu gagcaugcgg ggacaugggu 7620
guguauggca cacauaggug cgugugugugc uuuuguauuu uuucuccucc aaggagcugu 7680
gucagugugg acguucuguu ucagggaguu ggaaaggagg gugucugcag aagguggaga 7740
gcaggggcag aggccccacu ggccaccccc ugcuucccag agugaaaccu ugugccuggu 7800
gaccaaaguc ccuccaaagu gcucuuccuu cuggguuauu caagccaaau aucuggguuu 7860
cccccucucc ucauucccua gcaaacccca auuaucuucc aagauaggag auauuuccca 7920
uccccuuccu uuguaaauau cucaucuccc acuggagagc ccaggagccu auuccuggca 7980
uggauguucu guccacacuu gaggcugggc gguguaucag acccuucaag cagccuggcu 8040
ggggcccagg acugagucug ggucagcuu ucacggucgc uuuucccuuc cucaccaccc 8100
accacagccc accuugcaug cauggccagc cccuccacuc cagccugagc caugugugcc 8160
ccugcgggag gacccauuca ugccagaaag cugguaacuc ccucccagca ucccugcgga 8220
aggagucagu uucugagagu gugacuuuuc aaggcgaaug auggggaagg guuccccagu 8280
ccccacagug gccccaccuc ugggcccugc accagagccc uucuguguca cggcgggcug 8340
ugcacccaug cacacaccua cgcacacaca acacuccgca cugcaguaua uucuugccaa 8400
agauuuccuu uaaaagcaag cacuuuuacu aauuauuauu uuguaaaugu uuaucuucuu 8460
cugucuucuc ccucccugaa ucuauuuuac uguuguuuau uguugaaucu gugugucagc 8520
caggagagcg cugucuggcc uugaacaugg gcugggaugg gaaagggucu gggagaagau 8580
gggcaacaaa gagccaggga gucauggaca ucgcagcgac gcagacccca gcagguucag 8640
ucccgugcug ccaccagcug uccagcuggg ugucuggagg gaagagggca gaggaggguc 8700
augucccuuc agcuggggga ggggcccagu gagcuccacg uggcuuuuuc ccaaagggag 8760
caagagggaa ggauugggcg agaaaacaau ggagagggga ccugcgaagg aaaacaggga 8820
ggaagugagc gguuugauca gccugcuauc acgguguucu ggcucucuua uuuagccagg 8880
cgcuuaaggg acagauacau cacauccuaa guuugggaaa ggccuuugac ccaugucauc 8940
ugagcgucuc cuccaguagc ucugaaagcu guggacacca auggccagga uuccuucucc 9000
ccugguuuuu gaggaucccu gggucuucug agacuggcca ggagagggau ggugggggcca 9060
gugguugugu gaaagcagga ggggcagccc uccuggacaa gugugauccc ccuauaaacg 9120
gcucucagga gguuagugag uaggagauuc ugccuuguuc ugaugagccu gugcaggggc 9180
uccaggggag caugcugucc agggggcaca gaagggguggu gagugugauc aaaucuaguc 9240
ucacucccac uuuuuagucu cacuccuacu uuuguccacc accccugccu ccuggaucuu 9300
cucccacuuu uuuuuucagc uuuaggaccu ggggagaucc ugugagucaa ggcagacacc 9360
caauccugcc cccacacucg ggguccucca agagguuggg gggcagaguc ccagagcagc 9420
ccuuuacccc agguccaggc ccuggaaucc ugagacucgc guuuccuugg ccagugguaa 9480
cacaggacgu gugugcgcau gugcaagugu ggauguaugu gugugcgugu guuuugcuca 9540
uuucuuuagg gaacuuggga gucgggguug gaggugcugg gcaauggaac uucaaauuca 9600
augucgccca gcagugaggg gagucgggag gugaggccug uaggccaacc aauuggugga 9660
gucucagcga uagcccaggu gagaagugguu ucacccagag gggcagggug ggggccucgg 9720
gcagaucugu cccucuuggc accucugucc ucaaaugucc aaaauguugg aggaccucug 9780
uucauauccc acgccugggc ucuugccagc aguggaguua cuguagaggg augucccaag 9840
cuuguuuucc aaucaguguu aagcuguuug aaacucuccu gugucugugu uuuguuugug 9900
cgugugugug agagcacauc agugugugca ggcuguguuu ccccauuucu cuccucccuu 9960
cagacccauc auugagaaca aauguaagaa aucccuuccc accacccucc cugccuccca 10020
ggcccucugc gggggaaaca agaucaccca gcauccuucc ccaccccagc uguguauuua 10080
uauagaugga aauauacuuu auauuuugua ucaucgugcc uauagccgcu gccaccgugu 10140
auaaauccug guguaugcuc cuuauccugg acaugaaugu auuguacacu gacgcguccc 10200
cacuccugua cagcugcuuu guuucuuugc aaugcauugu auggcuuuau aaaugauaaa 10260
guuaaagaaa acucugaaaa aaaaaaaaaa aaaa 10294

<210> SEQ ID NO 40
<211> LENGTH: 1735
<212> TYPE: PRT
<213> ORGANISM: Homo sapiens

<400> SEQUENCE: 40

Met Ser Val Ser Arg Thr Met Glu Asp Ser Cys Glu Leu Asp Leu Val
1 5 10 15

Tyr Val Thr Glu Arg Ile Ile Ala Val Ser Phe Pro Ser Thr Ala Asn
20 25 30

Glu Glu Asn Phe Arg Ser Asn Leu Arg Glu Val Ala Gln Met Leu Lys
35 40 45

Ser Lys His Gly Gly Asn Tyr Leu Leu Phe Asn Leu Ser Glu Arg Arg
50 55 60

Pro Asp Ile Thr Lys Leu His Ala Lys Val Leu Glu Phe Gly Trp Pro
65 70 75 80

Asp Leu His Thr Pro Ala Leu Glu Lys Ile Cys Ser Ile Cys Lys Ala
85 90 95

Met Asp Thr Trp Leu Asn Ala Asp Pro His Asn Val Val Val Leu His
100 105 110

Asn Lys Gly Asn Arg Gly Arg Ile Gly Val Val Ile Ala Ala Tyr Met
115 120 125

His Tyr Ser Asn Ile Ser Ala Ser Ala Asp Gln Ala Leu Asp Arg Phe
130 135 140

Ala Met Lys Arg Phe Tyr Glu Asp Lys Ile Val Pro Ile Gly Gln Pro
145 150 155 160

Ser Gln Arg Arg Tyr Val His Tyr Phe Ser Gly Leu Leu Ser Gly Ser
165 170 175

Ile Lys Met Asn Asn Lys Pro Leu Phe Leu His His Val Ile Met His
180 185 190

Gly Ile Pro Asn Phe Glu Ser Lys Gly Gly Cys Arg Pro Phe Leu Arg
195 200 205

Ile Tyr Gln Ala Met Gln Pro Val Tyr Thr Ser Gly Ile Tyr Asn Ile
210 215 220

Pro Gly Asp Ser Gln Thr Ser Val Cys Ile Thr Ile Glu Pro Gly Leu
225 230 235 240

Leu Leu Lys Gly Asp Ile Leu Leu Lys Cys Tyr His Lys Lys Phe Arg
245 250 255

Ser Pro Ala Arg Asp Val Ile Phe Arg Val Gln Phe His Thr Cys Ala

-continued

```
            260                 265                 270

Ile His Asp Leu Gly Val Val Phe Gly Lys Glu Asp Leu Asp Asp Ala
        275                 280                 285

Phe Lys Asp Asp Arg Phe Pro Glu Tyr Gly Lys Val Glu Phe Val Phe
    290                 295                 300

Ser Tyr Gly Pro Glu Lys Ile Gln Gly Met Glu His Leu Glu Asn Gly
305                 310                 315                 320

Pro Ser Val Ser Val Asp Tyr Asn Thr Ser Asp Pro Leu Ile Arg Trp
                325                 330                 335

Asp Ser Tyr Asp Asn Phe Ser Gly His Arg Asp Asp Gly Met Glu Glu
            340                 345                 350

Val Val Gly His Thr Gln Gly Pro Leu Asp Gly Ser Leu Tyr Ala Lys
        355                 360                 365

Val Lys Lys Lys Asp Ser Leu His Gly Ser Thr Gly Ala Val Asn Ala
    370                 375                 380

Thr Arg Pro Thr Leu Ser Ala Thr Pro Asn His Val Glu His Thr Leu
385                 390                 395                 400

Ser Val Ser Ser Asp Ser Gly Asn Ser Thr Ala Ser Thr Lys Thr Asp
                405                 410                 415

Lys Thr Asp Glu Pro Val Pro Gly Ala Ser Ser Ala Thr Ala Ala Leu
            420                 425                 430

Ser Pro Gln Glu Lys Arg Glu Leu Asp Arg Leu Leu Ser Gly Phe Gly
        435                 440                 445

Leu Glu Arg Glu Lys Gln Gly Ala Met Tyr His Thr Gln His Leu Arg
    450                 455                 460

Ser Arg Pro Ala Gly Gly Ser Ala Val Pro Ser Ser Gly Arg His Val
465                 470                 475                 480

Val Pro Ala Gln Val His Val Asn Gly Gly Ala Leu Ala Ser Glu Arg
                485                 490                 495

Glu Thr Asp Ile Leu Asp Asp Glu Leu Pro Asn Gln Asp Gly His Ser
            500                 505                 510

Ala Gly Ser Met Gly Thr Leu Ser Ser Leu Asp Gly Val Thr Asn Thr
        515                 520                 525

Ser Glu Gly Gly Tyr Pro Glu Ala Leu Ser Pro Leu Thr Asn Gly Leu
    530                 535                 540

Asp Lys Ser Tyr Pro Met Glu Pro Met Val Asn Gly Gly Gly Tyr Pro
545                 550                 555                 560

Tyr Glu Ser Ala Ser Arg Ala Gly Pro Ala His Ala Gly His Thr Ala
                565                 570                 575

Pro Met Arg Pro Ser Tyr Ser Ala Gln Glu Gly Leu Ala Gly Tyr Gln
            580                 585                 590

Arg Glu Gly Pro His Pro Ala Trp Pro Gln Pro Val Thr Thr Ser His
        595                 600                 605

Tyr Ala His Asp Pro Ser Gly Met Phe Arg Ser Gln Ser Phe Ser Glu
    610                 615                 620

Ala Glu Pro Gln Leu Pro Pro Ala Pro Val Arg Gly Gly Ser Ser Arg
625                 630                 635                 640

Glu Ala Val Gln Arg Gly Leu Asn Ser Trp Gln Gln Gln Gln Gln Gln
                645                 650                 655

Gln Gln Gln Pro Arg Pro Pro Pro Arg Gln Gln Glu Arg Ala His Leu
            660                 665                 670

Glu Ser Leu Val Ala Ser Arg Pro Ser Pro Gln Pro Leu Ala Glu Thr
        675                 680                 685
```

-continued

```
Pro Ile Pro Ser Leu Pro Glu Phe Pro Arg Ala Ala Ser Gln Gln Glu
    690                 695                 700

Ile Glu Gln Ser Ile Glu Thr Leu Asn Met Leu Met Leu Asp Leu Glu
705                 710                 715                 720

Pro Ala Ser Ala Ala Ala Pro Leu His Lys Ser Gln Ser Val Pro Gly
                725                 730                 735

Ala Trp Pro Gly Ala Ser Pro Leu Ser Ser Gln Pro Leu Ser Gly Ser
            740                 745                 750

Ser Arg Gln Ser His Pro Leu Thr Gln Ser Arg Ser Gly Tyr Ile Pro
        755                 760                 765

Ser Gly His Ser Leu Gly Thr Pro Glu Pro Ala Pro Arg Ala Ser Leu
    770                 775                 780

Glu Ser Val Pro Pro Gly Arg Ser Tyr Ser Pro Tyr Asp Tyr Gln Pro
785                 790                 795                 800

Cys Leu Ala Gly Pro Asn Gln Asp Phe His Ser Lys Ser Pro Ala Ser
                805                 810                 815

Ser Ser Leu Pro Ala Phe Leu Pro Thr Thr His Ser Pro Pro Gly Pro
            820                 825                 830

Gln Gln Pro Pro Ala Ser Leu Pro Gly Leu Thr Ala Gln Pro Leu Leu
        835                 840                 845

Ser Pro Lys Glu Ala Thr Ser Asp Pro Ser Arg Thr Pro Glu Glu Glu
    850                 855                 860

Pro Leu Asn Leu Glu Gly Leu Val Ala His Arg Val Ala Gly Val Gln
865                 870                 875                 880

Ala Arg Glu Lys Gln Pro Ala Glu Pro Pro Ala Pro Leu Arg Arg Arg
                885                 890                 895

Ala Ala Ser Asp Gly Gln Tyr Glu Asn Gln Ser Pro Glu Ala Thr Ser
            900                 905                 910

Pro Arg Ser Pro Gly Val Arg Ser Pro Val Gln Cys Val Ser Pro Glu
        915                 920                 925

Leu Ala Leu Thr Ile Ala Leu Asn Pro Gly Gly Arg Pro Lys Glu Pro
    930                 935                 940

His Leu His Ser Tyr Lys Glu Ala Phe Glu Glu Met Glu Gly Thr Ser
945                 950                 955                 960

Pro Ser Ser Pro Pro Pro Ser Gly Val Arg Ser Pro Pro Gly Leu Ala
                965                 970                 975

Lys Thr Pro Leu Ser Ala Leu Gly Leu Lys Pro His Asn Pro Ala Asp
            980                 985                 990

Ile Leu Leu His Pro Thr Gly Val  Thr Arg Arg Arg Ile  Gln Pro Glu
        995                 1000                1005

Glu Asp  Glu Gly Lys Val Val  Val Arg Leu Ser Glu  Glu Pro Arg
    1010                1015                1020

Ser Tyr  Val Glu Ser Val Ala  Arg Thr Ala Val Ala  Gly Pro Arg
    1025                1030                1035

Ala Gln  Asp Ser Glu Pro Lys  Ser Phe Ser Ala Pro  Ala Thr Gln
    1040                1045                1050

Ala Tyr  Gly His Glu Ile Pro  Leu Arg Asn Gly Thr  Leu Gly Gly
    1055                1060                1065

Ser Phe  Val Ser Pro Ser Pro  Leu Ser Thr Ser Ser  Pro Ile Leu
    1070                1075                1080

Ser Ala  Asp Ser Thr Ser Val  Gly Ser Phe Pro Ser  Gly Glu Ser
    1085                1090                1095
```

-continued

```
Ser Asp  Gln Gly Pro Arg Thr  Pro Thr Gln Pro Leu  Leu Glu Ser
    1100                 1105                 1110

Gly Phe  Arg Ser Gly Ser Leu  Gly Gln Pro Ser Pro  Ser Ala Gln
    1115                 1120                 1125

Arg Asn  Tyr Gln Ser Ser Ser  Pro Leu Pro Thr Val  Gly Ser Ser
    1130                 1135                 1140

Tyr Ser  Ser Pro Asp Tyr Ser  Leu Gln His Phe Ser  Ser Ser Pro
    1145                 1150                 1155

Glu Ser  Gln Ala Arg Ala Gln  Phe Ser Val Ala Gly  Val His Thr
    1160                 1165                 1170

Val Pro  Gly Ser Pro Gln Ala  Arg His Arg Thr Val  Gly Thr Asn
    1175                 1180                 1185

Thr Pro  Pro Ser Pro Gly Phe  Gly Trp Arg Ala Ile  Asn Pro Ser
    1190                 1195                 1200

Met Ala  Ala Pro Ser Ser Pro  Ser Leu Ser His His  Gln Met Met
    1205                 1210                 1215

Gly Pro  Pro Gly Thr Gly Phe  His Gly Ser Thr Val  Ser Ser Pro
    1220                 1225                 1230

Gln Ser  Ser Ala Ala Thr Thr  Pro Gly Ser Pro Ser  Leu Cys Arg
    1235                 1240                 1245

His Pro  Ala Gly Val Tyr Gln  Val Ser Gly Leu His  Asn Lys Val
    1250                 1255                 1260

Ala Thr  Thr Pro Gly Ser Pro  Ser Leu Gly Arg His  Pro Gly Ala
    1265                 1270                 1275

His Gln  Gly Asn Leu Ala Ser  Gly Leu His Ser Asn  Ala Ile Ala
    1280                 1285                 1290

Ser Pro  Gly Ser Pro Ser Leu  Gly Arg His Leu Gly  Gly Ser Gly
    1295                 1300                 1305

Ser Val  Val Pro Gly Ser Pro  Cys Leu Asp Arg His  Val Ala Tyr
    1310                 1315                 1320

Gly Gly  Tyr Ser Thr Pro Glu  Asp Arg Arg Pro Thr  Leu Ser Arg
    1325                 1330                 1335

Gln Ser  Ser Ala Ser Gly Tyr  Gln Ala Pro Ser Thr  Pro Ser Phe
    1340                 1345                 1350

Pro Val  Ser Pro Ala Tyr Tyr  Pro Gly Leu Ser Ser  Pro Ala Thr
    1355                 1360                 1365

Ser Pro  Ser Pro Asp Ser Ala  Ala Phe Arg Gln Gly  Ser Pro Thr
    1370                 1375                 1380

Pro Ala  Leu Pro Glu Lys Arg  Arg Met Ser Val Gly  Asp Arg Ala
    1385                 1390                 1395

Gly Ser  Leu Pro Asn Tyr Ala  Thr Ile Asn Gly Lys  Val Ser Ser
    1400                 1405                 1410

Pro Val  Ala Ser Gly Met Ser  Ser Pro Ser Gly Gly  Ser Thr Val
    1415                 1420                 1425

Ser Phe  Ser His Thr Leu Pro  Asp Phe Ser Lys Tyr  Ser Met Pro
    1430                 1435                 1440

Asp Asn  Ser Pro Glu Thr Arg  Ala Lys Val Lys Phe  Val Gln Asp
    1445                 1450                 1455

Thr Ser  Lys Tyr Trp Tyr Lys  Pro Glu Ile Ser Arg  Glu Gln Ala
    1460                 1465                 1470

Ile Ala  Leu Leu Lys Asp Gln  Glu Pro Gly Ala Phe  Ile Ile Arg
    1475                 1480                 1485

Asp Ser  His Ser Phe Arg Gly  Ala Tyr Gly Leu Ala  Met Lys Val
```

```
    1490                1495                1500

Ser Ser  Pro Pro Pro Thr Ile  Met Gln Gln Asn Lys  Lys Gly Asp
    1505                1510                1515

Met Thr  His Glu Leu Val Arg  His Phe Leu Ile Glu  Thr Gly Pro
    1520                1525                1530

Arg Gly  Val Lys Leu Lys Gly  Cys Pro Asn Glu Pro  Asn Phe Gly
    1535                1540                1545

Ser Leu  Ser Ala Leu Val Tyr  Gln His Ser Ile Ile  Pro Leu Ala
    1550                1555                1560

Leu Pro  Cys Lys Leu Val Ile  Pro Asn Arg Asp Pro  Thr Asp Glu
    1565                1570                1575

Ser Lys  Asp Ser Ser Gly Pro  Ala Asn Ser Thr Ala  Asp Leu Leu
    1580                1585                1590

Lys Gln  Gly Ala Ala Cys Asn  Val Leu Phe Val Asn  Ser Val Asp
    1595                1600                1605

Met Glu  Ser Leu Thr Gly Pro  Gln Ala Ile Ser Lys  Ala Thr Ser
    1610                1615                1620

Glu Thr  Leu Ala Ala Asp Pro  Thr Pro Ala Ala Thr  Ile Val His
    1625                1630                1635

Phe Lys  Val Ser Ala Gln Gly  Ile Thr Leu Thr Asp  Asn Gln Arg
    1640                1645                1650

Lys Leu  Phe Phe Arg Arg His  Tyr Pro Leu Asn Thr  Val Thr Phe
    1655                1660                1665

Cys Asp  Leu Asp Pro Gln Glu  Arg Lys Trp Met Lys  Thr Glu Gly
    1670                1675                1680

Gly Ala  Pro Ala Lys Leu Phe  Gly Phe Val Ala Arg  Lys Gln Gly
    1685                1690                1695

Ser Thr  Thr Asp Asn Ala Cys  His Leu Phe Ala Glu  Leu Asp Pro
    1700                1705                1710

Asn Gln  Pro Ala Ser Ala Ile  Val Asn Phe Val Ser  Lys Val Met
    1715                1720                1725

Leu Asn  Ala Gly Gln Lys Arg
    1730                1735
```

<210> SEQ ID NO 41
<211> LENGTH: 1246
<212> TYPE: RNA
<213> ORGANISM: Homo sapiens

<400> SEQUENCE: 41

```
ggaagggggg caggagaaaa aagcuuuucc aaaaaaguau uggcugucuu gaggaaugcg      60

gucgccccu ugggaaagua cauaucuggg agaagcaggc ggcuccgcgc ucgcacuccc      120

gcuccuccgc ccgaccgcgc gcucgccccg ccgcuccugc ugcagcccca gggccccucg      180

ccgccgccac cauggacgcc aucaagaaga agaugcagau gcugaagcuc gacaaggaga      240

acgccuugga ucgagcugag caggcggagg ccgacaagaa ggcggcggaa gacaggagca      300

agcagcugga agaugagcug gugucacugc aaaagaaacu caagggcacc gaagaugaac      360

uggacaaaua cucugaggcu cucaaagaug cccaggagaa gcuggagcug gcagagaaaa      420

aggccaccga ugcugaagcc gacguagcuu cucugaacag acgcauccag cugguugagg      480

aagaguugga ucgugcccag gagcgucugg caacagcuuu gcagaagcug gaggaagcug      540

agaaggcagc agaugagagu gagagaggca ugaaagucau ugagagucga gcccaaaaag      600

augaagaaaa aauggaaauu caggagaucc aacugaaaga ggccaagcac auugcugaag      660
```

```
augccgaccg caaauaugaa gagguggccc guaagcuggu caucauugag agcgaccugg    720

aacgugcaga ggagcgggcu gagcucucag aaggcaaaug ugccgagcuu gaagaagaau    780

ugaaaacugu gacgaacaac uugaagucac uggaggcuca ggcugagaag uacucgcaga    840

aggaagacag auaugaggaa gagaucaagg uccuuuccga caagcugaag gaggcugaga    900

cucgggcuga guuugcggag aggucaguaa cuaaauugga gaaaagcauu gaugacuuag    960

aagacgagcu guacgcucag aaacugaagu acaaagccau cagcgaggag cuggaccacg   1020

cucucaacga uaugacuucc auauaaguuu cuuugcuuca cuucucccaa gacucccucg   1080

ucgagcugga ugucccaccu cucugagcuc ugcauuuguc uauucuccag cugacccugg   1140

uucucucucu uagcauccug ccuuagagcc aggcacacac ugugcuuucu auuguacaga   1200

agcucuucgu uucaguguca aauaaacacu guguaagcua aaaaaa                  1246
```

<210> SEQ ID NO 42
<211> LENGTH: 284
<212> TYPE: PRT
<213> ORGANISM: Homo sapiens

<400> SEQUENCE: 42

```
Met Asp Ala Ile Lys Lys Lys Met Gln Met Leu Lys Leu Asp Lys Glu
1               5                   10                  15

Asn Ala Leu Asp Arg Ala Glu Gln Ala Glu Ala Asp Lys Lys Ala Ala
            20                  25                  30

Glu Asp Arg Ser Lys Gln Leu Glu Asp Glu Leu Val Ser Leu Gln Lys
        35                  40                  45

Lys Leu Lys Gly Thr Glu Asp Glu Leu Asp Lys Tyr Ser Glu Ala Leu
    50                  55                  60

Lys Asp Ala Gln Glu Lys Leu Glu Leu Ala Glu Lys Lys Ala Thr Asp
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Ser Arg Ala Gln Lys Asp Glu Glu Lys Met Glu Ile Gln
    130                 135                 140

Glu Ile Gln Leu Lys Glu Ala Lys His Ile Ala Glu Asp Ala Asp Arg
145                 150                 155                 160

Lys Tyr Glu Glu Val Ala Arg Lys Leu Val Ile Ile Glu Ser Asp Leu
                165                 170                 175

Glu Arg Ala Glu Glu Arg Ala Glu Leu Ser Glu Gly Lys Cys Ala Glu
            180                 185                 190

Leu Glu Glu Glu Leu Lys Thr Val Thr Asn Asn Leu Lys Ser Leu Glu
        195                 200                 205

Ala Gln Ala Glu Lys Tyr Ser Gln Lys Glu Asp Arg Tyr Glu Glu Glu
    210                 215                 220

Ile Lys Val Leu Ser Asp Lys Leu Lys Glu Ala Glu Thr Arg Ala Glu
225                 230                 235                 240

Phe Ala Glu Arg Ser Val Thr Lys Leu Glu Lys Ser Ile Asp Asp Leu
                245                 250                 255

Glu Asp Glu Leu Tyr Ala Gln Lys Leu Lys Tyr Lys Ala Ile Ser Glu
            260                 265                 270
```

```
Glu Leu Asp His Ala Leu Asn Asp Met Thr Ser Ile
        275                 280


<210> SEQ ID NO 43
<211> LENGTH: 1975
<212> TYPE: RNA
<213> ORGANISM: Homo sapiens

<400> SEQUENCE: 43

acuuucccccc cucggcgccc caccggcucc cgcgcgccuc cccucgcgcc cgagcuucga      60

gccaagcagc guccuggggga gcgcgucaug gccuuaccag ugaccgccuu gcuccugccg     120

cuggccuugc ugcuccacgc cgccaggccg agccaguucc gggugucgcc gcuggaucgg     180

accuggaacc ugggcgagac aguggagcug aagugccagg ugcugcuguc caacccgacg     240

ucgggcugcu cguggcucuu ccagccgcgc ggcgccgccg ccagucccac cuuccuccua     300

uaccucuccc aaaacaagcc caaggcggcc gaggggcugg acacccagcg guucucgggc     360

aagagguugg gggacaccuu cguccucacc cugagcgacu uccgccgaga gaacgagggc     420

uacuauuucu gcucggcccu gagcaacucc aucauguacu ucagccacuu cgugccgguc     480

uuccugccag cgaagcccac cacgacgcca gcgccgcgac caccaacacc ggcgcccacc     540

aucgcgucgc agccccuguc ccugcgccca gaggcgugcc ggccagcggc gggggggcgca     600

gugcacacga gggggcugga cuucgccugu gauaucuaca ucugggcgcc ccuggccggg     660

acuuguggggg uccuucuccu gucacugguu aucacccuuu acugcaacca caggaaccga     720

agacguguuu gcaaaugucc ccggccugug gucaaaucgg gagacaagcc cagccuuucg     780

gcgagauacg ucuaacccug ugcaacagcc acuacauuac uucaaacuga gauccuuccu     840

uuugagggag caaguccuuc ccuuucauuu uuuccagucu uccucccugu guauucauuu     900

ucaugauuau uauuuuagug ggggcggggu gggaaagauu acuuuuucuu uauguguuug     960

acgggaaaca aaacuaggua aaaucuacag uacaccacaa gggucacaau acuguugugc    1020

gcacaucgcg guagggcgug gaaaggggca ggccagagcu acccgcagag uucucagaau    1080

caugcugaga gagcuggagg cacccaugcc aucucaaccu cuuccccgcc cguuuuacaa    1140

agggggaggc uaaagcccag agacagcuug aucaaaggca cacagcaagu cagggguugga   1200

gcaguagcug gagggaccuu gucucccagc ucagggcucu uuccuccaca ccauucaggu    1260

cuuucuuucc gaggccccug ucucagggug aggugcuuga gucuccaacg gcaagggaac    1320

aaguacuucu ugauaccugg gauacugugc ccagagccuc gaggagguaa ugaauuaaag    1380

aagagaacug ccuuuggcag aguucuauaa uguaaacaau aucagacuuu uuuuuuuuau    1440

aaucaagccu aaaauuguau agaccuaaaa uaaaaugaag uggugagcuu aacccuggaa    1500

aaugaauccc ucuaucucua aagaaaaucu cugugaaacc ccuacgugga ggcggaauug    1560

cucucccagc ccuugcauug cagaggggcc caugaaagag gacaggcuac ccccuuuacaa   1620

auagaauuug agcaucagug agguuaaacu aaggcccucu ugaaucucug aauuugagau    1680

acaaacaugu uccugggauc acugaugacu uuuuauacuu uguaaagaca auuguuggag    1740

agccccucac acagcccugg ccuccgcuca acuagcagau acagggauga ggcagaccug    1800

acucucuuaa ggaggcugag agcccaaacu gcugucccaa acaugcacuu ccuugcuuaa    1860

gguaugguac aagcaaugcc ugcccauugg agagaaaaaa cuuaaguaga uaaggaaaua    1920

agaaccacuc auaauucuuc accuuaggaa uaaucuccug uuaauauggu guaca         1975
```

<210> SEQ ID NO 44
<211> LENGTH: 235
<212> TYPE: PRT
<213> ORGANISM: Homo sapiens

<400> SEQUENCE: 44

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235
```

<210> SEQ ID NO 45
<211> LENGTH: 2545
<212> TYPE: RNA
<213> ORGANISM: Homo sapiens

<400> SEQUENCE: 45

```
auccaauaca ggagugacuu ggaacuccau ucuaucacua ugaagaaaag ugguguucuu      60

uuccucuugg gcaucaucuu gcugguucug auuggagugc aaggaacccc aguagugaga     120

aagggucgcu guuccugcau cagcaccaac caagggacua uccaccuaca auccuugaaa     180

gaccuuaaac aauuugcccc aagcccuucc ugcgagaaaa uugaaaucau ugcuacacug     240

aagaauggag uucaaacaug ucuaaaccca gauucagcag augugaagga acugauuaaa     300

aagugggaga aacaggucag ccaaaagaaa aagcaaaaga augggaaaaa acaucaaaaa     360

aagaaaguuc ugaaaguucg aaaaucucaa cguucucguc aaaagaagac uacauaagag     420

accacuucac caauaaguau ucuguguuaa aaauguucua uuuuaauuau accgcuauca     480

uuccaaagga ggauggcaua uaauacaaag gcuuauuaau uugacuagaa aauuuaaaac     540

auuacucuga aauuguaacu aaaguuagaa aguugauuuu aagaauccaa acguuaagaa     600
```

uuguuaaagg cuaugauugu cuuuguucuu cuaccaccca ccaguugaau uucaucaugc 660
uuaaggccau gauuuuagca auacccaugu cuacacagau guucacccaa ccacauccca 720
cucacaacag cugccuggaa gagcagcccu aggcuuccac guacugcagc cuccagagag 780
uaucugaggc acaugucagc aaguccuaag ccuguuagca ugcuggugag ccaagcaguu 840
ugaaauugag cuggaccuca ccaagcugcu guggccauca accucuguau uugaaucagc 900
cuacaggccu cacacacaau gugucugaga gauucaugcu gauuguuauu ggguaucacc 960
acuggagauc accagugugu ggcuuucaga gccuccuuuc uggcuuugga agccauguga 1020
uuccaucuug cccgcucagg cugaccacuu uauuucuuuu uguuccccuu ugcuucauuc 1080
aagucagcuc uucuccaucc uaccacaaug cagugccuuu cuucucucca gugcaccugu 1140
cauaugcucu gauuuaucug agucaacucc uuucucaucu uguccccaac accccacaga 1200
agugcuuucu ucucccaauu cauccucacu caguccagcu uaguucaagu ccugccucuu 1260
aaauaaaccu uuuuggacac acaaauuauc uuaaaacucc uguuucacuu gguucaguac 1320
cacaugggug aacacucaau gguuaacuaa uucuugggug uuuauccuau cucuccaacc 1380
agauugucag cuccuugagg gcaagagcca caguauauuu cccuguuucu uccacagugc 1440 cuaauaaauac uguggaacua gguuuuaaua auuuuuuaau ugauguuguu augggcagga 1500
uggcaaccag accauugucu cagagcaggu gcuggcucuu uccuggcuac uccauguugg 1560
cuagccucug guaaccucuu acuuauuauc uucaggacac ucacuacagg gaccagggau 1620
gaugcaacau ccuugucuuu uuaugacagg auguuugcuc agcuucucca acaauaagaa 1680
gcacguggua aaacacuugc ggauauucug gacuguuuuu aaaaaauaua caguuuaccg 1740
aaaaucauau aaucuuacaa ugaaaaggac uuuauagauc agccagugac caaccuuuuc 1800
ccaaccauac aaaaauuccu uuucccgaag gaaaagggcu uucucaauaa gccucagcuu 1860
ucuaagaucu aacaagauag ccaccgagau ccuuaucgaa acucauuuua ggcaaauaug 1920
aguuuuauug uccguuuacu uguuucagag uuuguauugu gauuaucaau uaccacacca 1980
ucucccauga agaaagggaa cggugaagua cuaagcgcua gaggaagcag ccaagucggu 2040
uaguggaagc augauuggug cccaguuagc cucugcagga uguggaaacc uccuuccagg 2100
ggagguucag ugaauugugu aggagagguu gucuguggcc agaauuuaaa ccuauacuca 2160
cuuucccaaa uugaaucacu gcucacacug cugaugauuu agagugcugu ccgguggaga 2220
ucccacccga acgucuuauc uaaucaugaa acucccuagu uccuucaugu aacuucccug 2280
aaaaaucuaa guguuucaua aauuugagag ucugugaccc acuuaccuug caucucacag 2340
guagacagua uauaacuaac aaccaaagac uacauauugu cacugacaca cacguuauaa 2400
ucauuuauca uauauauaca uacaugcaua cacucucaaa gcaaauaauu uuucacuuca 2460
aaacaguauu gacuuguaua ccuuguaauu ugaaauauuu ucuuuguuaa aauagaaugg 2520
uaucaauaaa uagaccauua aucag 2545

<210> SEQ ID NO 46
<211> LENGTH: 125
<212> TYPE: PRT
<213> ORGANISM: Homo sapiens

<400> SEQUENCE: 46

Met Lys Lys Ser Gly Val Leu Phe Leu Leu Gly Ile Ile Leu Leu Val
1 5 10 15

Leu Ile Gly Val Gln Gly Thr Pro Val Val Arg Lys Gly Arg Cys Ser

```
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
        115                 120                 125


<210> SEQ ID NO 47
<211> LENGTH: 1172
<212> TYPE: RNA
<213> ORGANISM: Homo sapiens

<400> SEQUENCE: 47

gagacauucc ucaauugcuu agacauauuc ugagccuaca gcagaggaac cuccagucuc      60

agcaccauga aucaaacugc gauucugauu ugcugccuua ucuuucugac ucuaaguggc     120

auucaaggag uaccucucuc uagaaccgua cgcuguaccu gcaucagcau uaguaaucaa     180

ccuguuaauc caaggucuuu agaaaaacuu gaaauuauuc cugcaagcca auuuugucca     240

cguguugaga ucauugcuac aaugaaaaag aagggugaga agagaugucu gaauccagaa     300

ucgaaggcca ucaagaauuu acugaaagca guuagcaagg aaaugucuaa aagaucuccu     360

uaaaaccaga ggggagcaaa aucgaugcag ugcuuccaag gauggaccac acagaggcug     420

ccucucccau cacuucccua cauggaguau augucaagcc auaauuguuc uuaguuugca     480

guuacacuaa aaggugacca augaugguca ccaaaucagc ugcuacuacu ccuguaggaa     540

gguuaauguu caucauccua agcuauucag uaauaacucu acccuggcac uauaauguaa     600

gcucuacuga ggugcuaugu ucuuagugga uguucugacc cugcuucaaa uauuucccuc     660

accuuuccca ucuuccaagg guacuaagga aucuuucugc uuugggguuu aucagaauuc     720

ucagaaucuc aaauaacuaa aagguaugca aucaaaucug cuuuuuaaag aaugcucuuu     780

acuucaugga cuuccacugc cauccuccca aggggcccaa auucuuucag uggcuaccua     840

cauacaauuc caaacacaua caggaaggua gaaauaucug aaaauguaug uguaaguauu     900

cuuauuuaau gaaagacugu acaaaguaua agucuuagau guauauauuu ccuauauugu     960

uuucagugua cauggaauaa cauguaauua aguacuaugu aucaaugagu aacaggaaaa    1020

uuuuaaaaau acagauagau auaugcucug cauguuacau aagauaaaug ugcugaaugg    1080

uuuucaaaua aaaaugaggu acucuccugg aaauauuaag aaagacuauc uaaauguuga    1140

aagaucaaaa gguuaauaaa guaauuauaa cu                                  1172


<210> SEQ ID NO 48
<211> LENGTH: 98
<212> TYPE: PRT
<213> ORGANISM: Homo sapiens

<400> SEQUENCE: 48

Met Asn Gln Thr Ala Ile Leu Ile Cys Cys Leu Ile Phe Leu Thr Leu
1               5                   10                  15
```

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 49
<211> LENGTH: 849
<212> TYPE: RNA
<213> ORGANISM: Homo sapiens

<400> SEQUENCE: 49
augaggaacu ccuauagauu ucuggcaucc ucucucucag uugucguuuc ucuccugcua 60
auuccugaag augucuguga aaaaauuauu ggaggaaaug aaguaacucc ucauucaaga 120
cccuacaugg uccuacuuag ucuugacaga aaaaccaucu gugcuggggc uuugauugca 180
aaagacuggg uguugacugc agcucacugu aacuugaaca aaaggaccca ggucauucuu 240
ggggcucacu caauaaccag ggaagagcca acaaaacaga uaaugcuugu uaagaaagag 300
uuucccuauc caugcuauga cccagccaca cgcgaaggug accuuaaacu uuuacagcug 360
acggaaaaag caaaaauuaa caaauaugug acuauccuuc aucuaccuaa aaagggggau 420
gaugugaaac caggaaccau gugccaaguu gcagggu ggg ggaggacuca caauagugca 480
ucuugguccg auacucugag agaagucaau aucaccauca uagacagaaa agucugcaau 540
gaucgaaauc acuauaauuu uaacccugug auuggaauga auaugguuug ugcuggaagc 600
cuccgaggug gaagagacuc gugcaaugga gauucuggaa gcccuuuguu gugcgagggu 660
guuuuccgag gggucacuuc cuuuggccuu gaaaauaaau gcggagaccc ucgugggccu 720
ggugucuaua uucuucucuc aaagaaacac cucaacugga uaauuaugac uaucaaggga 780
gcaguuuaaa uaaccguuuc cuuucauuua cuguggcuuc uuaaucuuuu cacaaauaaa 840
aucaauuug 849

<210> SEQ ID NO 50
<211> LENGTH: 262
<212> TYPE: PRT
<213> ORGANISM: Homo sapiens

<400> SEQUENCE: 50

Met Arg Asn Ser Tyr Arg Phe Leu Ala Ser Ser Leu Ser Val Val Val
1               5                   10                  15

Ser Leu Leu Leu Ile Pro Glu Asp Val Cys Glu Lys Ile Ile Gly Gly
            20                  25                  30

Asn Glu Val Thr Pro His Ser Arg Pro Tyr Met Val Leu Leu Ser Leu
        35                  40                  45

Asp Arg Lys Thr Ile Cys Ala Gly Ala Leu Ile Ala Lys Asp Trp Val
    50                  55                  60

Leu Thr Ala Ala His Cys Asn Leu Asn Lys Arg Ser Gln Val Ile Leu
65                  70                  75                  80

Gly Ala His Ser Ile Thr Arg Glu Glu Pro Thr Lys Gln Ile Met Leu

```
                85                  90                  95

Val Lys Lys Glu Phe Pro Tyr Pro Cys Tyr Asp Pro Ala Thr Arg Glu
            100                 105                 110

Gly Asp Leu Lys Leu Leu Gln Leu Met Glu Lys Ala Lys Ile Asn Lys
        115                 120                 125

Tyr Val Thr Ile Leu His Leu Pro Lys Lys Gly Asp Asp Val Lys Pro
    130                 135                 140

Gly Thr Met Cys Gln Val Ala Gly Trp Gly Arg Thr His Asn Ser Ala
145                 150                 155                 160

Ser Trp Ser Asp Thr Leu Arg Glu Val Asn Ile Thr Ile Ile Asp Arg
                165                 170                 175

Lys Val Cys Asn Asp Arg Asn His Tyr Asn Phe Asn Pro Val Ile Gly
            180                 185                 190

Met Asn Met Val Cys Ala Gly Ser Leu Arg Gly Gly Arg Asp Ser Cys
        195                 200                 205

Asn Gly Asp Ser Gly Ser Pro Leu Leu Cys Glu Gly Val Phe Arg Gly
    210                 215                 220

Val Thr Ser Phe Gly Leu Glu Asn Lys Cys Gly Asp Pro Arg Gly Pro
225                 230                 235                 240

Gly Val Tyr Ile Leu Leu Ser Lys Lys His Leu Asn Trp Ile Ile Met
                245                 250                 255

Thr Ile Lys Gly Ala Val
            260


<210> SEQ ID NO 51
<211> LENGTH: 934
<212> TYPE: RNA
<213> ORGANISM: Homo sapiens

<400> SEQUENCE: 51

ugagaagaug caaccaaucc ugcuucugcu ggccuuccuc cugcugccca gggcagaugc      60

aggggagauc aucgggggac augaggccaa gccccacucc cgccccuaca uggcuuaucu     120

uaugaucugg gaucagaagu cucugaagag gugcggaggc uuccugauac aagacgacuu     180

cgugcugaca gcugcucacu guuggggaag cuccauaaau gucaccuugg gggcccacaa     240

uaucaaagaa caggagccga cccagcaguu uaucccugug aaaagaccca ucccccaucc     300

agccuauaau ccuaagaacu ucuccaacga caucaugcua cugcagcugg agagaaaggc     360

caagcggacc agagcugugc agccccucag gcuaccuagc aacaaggccc aggugaagcc     420

agggcagaca ugcagugugg ccggcugggg gcagacggcc ccccugggaa aacacucaca     480

cacacuacaa gaggugaaga ugacagugca ggaagaucga aagugcgaau cugacuuacg     540

ccauuauuac gacaguacca uugaguugug cgugggggac ccagagauua aaaagacuuc     600

cuuuaagggg gacucuggag gcccucuugu guguaacaag guggcccagg gcauugucuc     660

cuauggacga aacaauggca ugccuccacg agccugcacc aaagucucaa gcuuuguaca     720

cuggauaaag aaaaccauga aacgcuacua acuacaggaa gcaaacuaag cccccgcugu     780

aaugaaacac cuucucugga gccaagucca gauuuacacu gggagaggug ccagcaacug     840

aauaaauacc ucucccagug uaaaucugga gccaagucca gauuuacacu gggagaggug     900

ccagcaacug aauaaauacc ucuuagcuga gugg                                 934


<210> SEQ ID NO 52
<211> LENGTH: 247
<212> TYPE: PRT
```

-continued

<213> ORGANISM: Homo sapiens

<400> SEQUENCE: 52

```
Met Gln Pro Ile Leu Leu Leu Leu Ala Phe Leu Leu Leu Pro Arg Ala
1               5                   10                  15

Asp Ala Gly Glu Ile Ile Gly Gly His Glu Ala Lys Pro His Ser Arg
            20                  25                  30

Pro Tyr Met Ala Tyr Leu Met Ile Trp Asp Gln Lys Ser Leu Lys Arg
        35                  40                  45

Cys Gly Gly Phe Leu Ile Arg Asp Asp Phe Val Leu Thr Ala Ala His
    50                  55                  60

Cys Trp Gly Ser Ser Ile Asn Val Thr Leu Gly Ala His Asn Ile Lys
65                  70                  75                  80

Glu Gln Glu Pro Thr Gln Gln Phe Ile Pro Val Lys Arg Pro Ile Pro
                85                  90                  95

His Pro Ala Tyr Asn Pro Lys Asn Phe Ser Asn Asp Ile Met Leu Leu
            100                 105                 110

Gln Leu Glu Arg Lys Ala Lys Arg Thr Arg Ala Val Gln Pro Leu Arg
        115                 120                 125

Leu Pro Ser Asn Lys Ala Gln Val Lys Pro Gly Gln Thr Cys Ser Val
    130                 135                 140

Ala Gly Trp Gly Gln Thr Ala Pro Leu Gly Lys His Ser His Thr Leu
145                 150                 155                 160

Gln Glu Val Lys Met Thr Val Gln Glu Asp Arg Lys Cys Glu Ser Asp
                165                 170                 175

Leu Arg His Tyr Tyr Asp Ser Thr Ile Glu Leu Cys Val Gly Asp Pro
            180                 185                 190

Glu Ile Lys Lys Thr Ser Phe Lys Gly Asp Ser Gly Gly Pro Leu Val
        195                 200                 205

Cys Asn Lys Val Ala Gln Gly Ile Val Ser Tyr Gly Arg Asn Asn Gly
    210                 215                 220

Met Pro Pro Arg Ala Cys Thr Lys Val Ser Ser Phe Val His Trp Ile
225                 230                 235                 240

Lys Lys Thr Met Lys Arg Tyr
                245
```

<210> SEQ ID NO 53
<211> LENGTH: 1668
<212> TYPE: RNA
<213> ORGANISM: Homo sapiens

<400> SEQUENCE: 53

```
auggcagccc gucugcuccu ccugggcauc cuucuccugc ugcugccccu gcccgucccu      60

gccccgugcc acacagccgc acgcucagag ugcaagcgca gccacaaguu cgugccuggu     120

gcauggcugg ccggggaggg uguggacgug accagccucc gccgcucggg cuccuuccca     180

guggacacac aaagguuccu gcggcccgac ggcaccugca cccucuguga aaaugcccua     240

caggagggca cccuccagcg ccugccucug gcgcucacca acuggcgggc ccagggcucu     300

ggcugccagc gccauguaac cagggccaaa gucagcucca cugaagcugu ggcccgggau     360

gcggcucgua gcauccgcaa cgacuggaag gucgggcugg acgugacucc uaagcccacc     420

agcaaugugc augugucugu ggccggcuca cacucacagg cagccaacuu ugcagcccag     480

aagacccacc aggaccagua cagcuucagc acugacacgg uggagugccg cuucuacagu     540

uuccauguggg uacacacucc cccgcugcac ccugacuuca agagggcccu cggggaccug     600
```

```
ccccaccacu ucaacgccuc cacccagccc gccuaccuca ggcuuaucuc caacuacggc    660

acccacuuca uccgggcugu ggagcugggu ggccgcauau cggcccucac ugcccugcgc    720

accugcgagc uggcccugga agggcucacg gacaacgagg uggaggacug ccugacuguc    780

gaggcccagg ucaacauagg cauccacggc agcaucucug ccgaagccaa ggccugugag    840

gagaagaaga agaagcacaa gaugacggcc uccuuccacc aaaccuaccg ggagcgccac    900

ucggaagugg uuggcggcca ucacaccucc auuaacgacc ugcuguucgg gauccaggcc    960

gggcccgagc aguacucagc cuggguaaac uccgugcccg gcagcccugg ccugguggac   1020

uacacccugg aaccccugca cgugcugcug gacagccagg acccgcggcg ggaggcacug   1080

aggagggccc ugagucagua ccugacggac agggcucgcu ggagggacug cagccggccg   1140

ugcccaccag ggcggcagaa gagcccccga gacccaugcc agugugugug ccauggcuca   1200

gcggucacca cccaggacug cugcccucgg cagaggggcc uggcccagcu ggaggugacc   1260

uucauccaag cauggagccu gugggggggac ugguucacug ccacggaugc cuaugugaag   1320

cucuucuuug guggccagga gcugaggacg agcaccgugu gggacaauaa caaccccauc   1380

uggucagugc ggcuggauuu uggggaugug cuccuggcca caggggggcc ccugagguug   1440

caggucuggg aucaggacuc uggcagggac gaugaccucc uuggcaccug ugaucaggcu   1500

cccaagucug guucccauga ggugagaugc aaccugaauc auggccaccu aaaauuccgc   1560

uaucaugcca ggugcuugcc ccaccuggga ggaggcaccu gccuggacua uguccccccaa   1620

augcuucugg gggagccucc aggaaaccgg aguggggccg ugugguga                1668
```

<210> SEQ ID NO 54
<211> LENGTH: 555
<212> TYPE: PRT
<213> ORGANISM: Homo sapiens

<400> SEQUENCE: 54

```
Met Ala Ala Arg Leu Leu Leu Leu Gly Ile Leu Leu Leu Leu Leu Pro
1               5                   10                  15

Leu Pro Val Pro Ala Pro Cys His Thr Ala Ala Arg Ser Glu Cys Lys
            20                  25                  30

Arg Ser His Lys Phe Val Pro Gly Ala Trp Leu Ala Gly Glu Gly Val
        35                  40                  45

Asp Val Thr Ser Leu Arg Arg Ser Gly Ser Phe Pro Val Asp Thr Gln
    50                  55                  60

Arg Phe Leu Arg Pro Asp Gly Thr Cys Thr Leu Cys Glu Asn Ala Leu
65                  70                  75                  80

Gln Glu Gly Thr Leu Gln Arg Leu Pro Leu Ala Leu Thr Asn Trp Arg
                85                  90                  95

Ala Gln Gly Ser Gly Cys Gln Arg His Val Thr Arg Ala Lys Val Ser
            100                 105                 110

Ser Thr Glu Ala Val Ala Arg Asp Ala Ala Arg Ser Ile Arg Asn Asp
        115                 120                 125

Trp Lys Val Gly Leu Asp Val Thr Pro Lys Pro Thr Ser Asn Val His
    130                 135                 140

Val Ser Val Ala Gly Ser His Ser Gln Ala Ala Asn Phe Ala Ala Gln
145                 150                 155                 160

Lys Thr His Gln Asp Gln Tyr Ser Phe Ser Thr Asp Thr Val Glu Cys
                165                 170                 175

Arg Phe Tyr Ser Phe His Val Val His Thr Pro Pro Leu His Pro Asp
```

-continued

```
            180                 185                 190

Phe Lys Arg Ala Leu Gly Asp Leu Pro His His Phe Asn Ala Ser Thr
        195                 200                 205

Gln Pro Ala Tyr Leu Arg Leu Ile Ser Asn Tyr Gly Thr His Phe Ile
    210                 215                 220

Arg Ala Val Glu Leu Gly Gly Arg Ile Ser Ala Leu Thr Ala Leu Arg
225                 230                 235                 240

Thr Cys Glu Leu Ala Leu Glu Gly Leu Thr Asp Asn Glu Val Glu Asp
                245                 250                 255

Cys Leu Thr Val Glu Ala Gln Val Asn Ile Gly Ile His Gly Ser Ile
            260                 265                 270

Ser Ala Glu Ala Lys Ala Cys Glu Glu Lys Lys Lys Lys His Lys Met
        275                 280                 285

Thr Ala Ser Phe His Gln Thr Tyr Arg Glu Arg His Ser Glu Val Val
    290                 295                 300

Gly Gly His His Thr Ser Ile Asn Asp Leu Leu Phe Gly Ile Gln Ala
305                 310                 315                 320

Gly Pro Glu Gln Tyr Ser Ala Trp Val Asn Ser Leu Pro Gly Ser Pro
                325                 330                 335

Gly Leu Val Asp Tyr Thr Leu Glu Pro Leu His Val Leu Leu Asp Ser
            340                 345                 350

Gln Asp Pro Arg Arg Glu Ala Leu Arg Arg Ala Leu Ser Gln Tyr Leu
        355                 360                 365

Thr Asp Arg Ala Arg Trp Arg Asp Cys Ser Arg Pro Cys Pro Pro Gly
    370                 375                 380

Arg Gln Lys Ser Pro Arg Asp Pro Cys Gln Cys Val Cys His Gly Ser
385                 390                 395                 400

Ala Val Thr Thr Gln Asp Cys Cys Pro Arg Gln Arg Gly Leu Ala Gln
                405                 410                 415

Leu Glu Val Thr Phe Ile Gln Ala Trp Gly Leu Trp Gly Asp Trp Phe
            420                 425                 430

Thr Ala Thr Asp Ala Tyr Val Lys Leu Phe Phe Gly Gly Gln Glu Leu
        435                 440                 445

Arg Thr Ser Thr Val Trp Asp Asn Asn Asn Pro Ile Trp Ser Val Arg
    450                 455                 460

Leu Asp Phe Gly Asp Val Leu Leu Ala Thr Gly Gly Pro Leu Arg Leu
465                 470                 475                 480

Gln Val Trp Asp Gln Asp Ser Gly Arg Asp Asp Asp Leu Leu Gly Thr
                485                 490                 495

Cys Asp Gln Ala Pro Lys Ser Gly Ser His Glu Val Arg Cys Asn Leu
            500                 505                 510

Asn His Gly His Leu Lys Phe Arg Tyr His Ala Arg Cys Leu Pro His
        515                 520                 525

Leu Gly Gly Gly Thr Cys Leu Asp Tyr Val Pro Gln Met Leu Leu Gly
    530                 535                 540

Glu Pro Pro Gly Asn Arg Ser Gly Ala Val Trp
545                 550                 555
```

<210> SEQ ID NO 55
<211> LENGTH: 1193
<212> TYPE: RNA
<213> ORGANISM: Homo sapiens

<400> SEQUENCE: 55

```
ugaagaucag cuauuagaag agaaagauca guuaagaccu uuggaccuga ucagcuugau      60
acaagaacua cugauuucaa cuucuuuggc uuaauucucu cggaaacgau gaaauauaca     120
aguuauaucu uggcuuuuca gcucugcauc guuuugggguu cucuuggcug uuacugccag    180
gacccauaug uaaaagaagc agaaaaccuu aagaaauauu uuaaugcagg ucauucagau     240
guagcggaua auggaacucu uuucuuaggc auuuugaaga auuggaaaga ggagagugac     300
agaaaaauaa ugcagagcca aauugucucc uuuuacuuca aacuuuuuaa aaacuuuaaa     360
gaugaccaga gcauccaaaa gagugugggag accaucaagg aagacaugaa ugucaaguuu    420
uucaauagca acaaaaagaa acgagaugac uucgaaaagc ugacuaauua uucgguaacu     480
gacuugaaug uccaacgcaa agcaauacau gaacucaucc aagugauggc ugaacugucg     540
ccagcagcua aaacagggaa gcgaaaaagg agucagaugc uguuucaagg ucgaagagca     600
ucccaguaau gguuguccug ccugcaauau uugaauuuua aaucuaaauc uauuuauuaa     660
uauuuaacau uauuuauaug gggaauauau uuuuagacuc aucaaucaaa uaaguauuua     720
uaauagcaac uuuuguguaa ugaaaaugaa uaucuauuaa uauauguauu auuuauaauu     780
ccuauauccu gugacugucu cacuuaaucc uuuguuuucu gacuaauuag gcaaggcuau     840
gugauuacaa ggcuuuaucu caggggccaa cuaggcagcc aaccuaagca agaucccaug     900
gguugugugu uuauuucacu ugaugauaca augaacacuu auaagugaag ugauacuauc     960
caguuacugc cgguuugaaa auaugccugc aaucugagcc agugcuuuaa uggcauguca    1020
gacagaacuu gaauguguca ggugacccug augaaaacau agcaucucag gagauuucau    1080
gccuggugcu uccaaauauu guugacaacu gugacuguac ccaaauggaa aguaacucau    1140
uuguuaaaau uaucaauauc uaauauauau gaauaaagug uaaguucaca acu           1193
```

<210> SEQ ID NO 56
<211> LENGTH: 166
<212> TYPE: PRT
<213> ORGANISM: Homo sapiens

<400> SEQUENCE: 56

```
Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
```

165

<210> SEQ ID NO 57
<211> LENGTH: 2589
<212> TYPE: RNA
<213> ORGANISM: Homo sapiens

<400> SEQUENCE: 57
cggcccgcug gagaggaagc ccgagagcug ccgcgcgccu gccggacgag ggcguagaag 60
ccaggcguca gagcccgggc uccggugggg ucccccaccc ggcccucggg ucccccgccc 120
ccugcucccu gcccauccca gcccacgcga cccucucgcg cgcggagggg cggguccucg 180
acggcuacgg gaaggugcca gcccgccccg gaugggcauc guggagccgg guugcggaga 240
caugcugacg ggcaccgagc cgaugccggg gagcgacgag ggccgggcgc cuggcgccga 300
cccgcagcac cgcuacuucu acccggagcc gggcgcgcag gacgcggacg agcgucgcgg 360
gggcggcagc cuggggucuc ccuacccggg gggcgccuug gugcccgccc cgccgagccg 420
cuuccuugga gccuacgccu acccgccgcg accccaggcg gccggcuucc ccggcgcggg 480
cgaguccuuc ccgccgcccg cggacgccga gggcuaccag ccgggcgagg gcuacgccgc 540
cccggacccg cgcgccgggc ucuacccggg gccgcgugag gacuacgcgc uacccgcggg 600
acuggaggug ucggggaaac ugagggucgc gcucaacaac caccuguugu gguccaaguu 660
uaaucagcac cagacagaga ugaucaucac caagcaggga cggcggaugu ucccauuccu 720
gucauuuacu guggccgggc uggagcccac cagccacuac aggauguuug uggacguggu 780
cuugguggac cagcaccacu ggcgguacca gagcggcaag ugggugcagu guggaaaggc 840
cgagggcagc augccaggaa accgccugua cguccacccg gacuccccca acacaggagc 900
gcacuggaug cgccaggaag uuucauuugg gaaacuaaag cucacaaaca acaagggggc 960
guccaacaau gugacccaga ugauugugcu ccagucccuc cauaaguacc agccccggcu 1020
gcauaucguu gaggugaacg acggagagcc agaggcagcc ugcaacgcuu ccaacacgca 1080
uaucuuuacu uuccaagaaa cccaguucau ugccgugacu gccuaccaga augccgagau 1140
uacucagcug aaaauugaua auaaccccuu ugccaaagga uuccgggaga acuuugaguc 1200
cauguacaca ucuguugaca ccagcauccc cuccccgccu ggacccaacu gucaauuccu 1260
ugggggagau cacuacucuc cucuccuacc caaccaguau ccuguuccca gccgcuucua 1320
ccccgaccuu ccuggccagg cgaaggaugu gguuccccag gcuuacuggc ugggggcccc 1380
ccgggaccac agcuaugagg cugaguuucg agcagucagc augaagccug cauucuugcc 1440
cucugccccu gggcccacca uguccuacua ccgaggccag gagguccugg caccuggagc 1500
uggcuggccu guggcacccc aguacccucc caagaugggc ccggccagcu gguuccgccc 1560
uaugcggacu cugcccaugg aacccggccc uggaggcuca gagggacggg gaccagagga 1620
ccagggucec cccuuggugu ggacugagau ugcccccauc cggccggaau ccagugauuc 1680
aggacugggc gaaggagacu cuaagaggag gcgcgugucc ccuauccuu ccagugguga 1740
cagcuccucc ccugcugggg ccccuucucc uuuugauaag gaagcugaag gacaguuuua 1800
uaacuauuuu cccaacugag cagaugacau gaugaaagga acagaaacag uguuauuagg 1860
uuggaggaca ccgacuaauu ugggaaacgg augaaggacu gagaaggccc ccgcuccuc 1920
uggcccuucu cuguuuagua guugguuggg gaaguggggc ucaagaagga uuuugggguu 1980
caccagaugc uuccuggccc acgaugaaac cugagagggg uguccccuug ccccauccuc 2040
ugcccuaacu acagucguuu accuggugcu gcgucuugcu uuugguuucc agcuggagaa 2100

```
aagaagacaa gaaagucuug ggcaugaagg agcuuuuugc aucuaguggg ugggaggggu   2160

caggugugg acaugggagc aggagacucc acuuucuucc uuuguacagu aacuuucaac   2220

cuuuucguug gcaugugugu uaaucccuga uccaaaaaga acaaauacac guauguuaua   2280

accaucagcc cgccaggguc agggaaagga cucaccugac uuuggacagc uggccugggc   2340

ucccccugcu caaacacagu ggggaucaga gaaaaggggc uggaaagggg ggaauggccc   2400

acaucucaag aagcaagaua uuguuugugg ugguugugug ugggugugug uuuuuucuuu   2460

uucuuucuuu uuauuuuuuu ugaauggggg aggcuauuua uuguacugag aguggugucu   2520

ggauauauuc cuuuugucuu caucacuuuc ugaaaauaaa cauaaaacug uuaaaaaaaa   2580

aaaaaaaaa                                                          2589
```

<210> SEQ ID NO 58
<211> LENGTH: 535
<212> TYPE: PRT
<213> ORGANISM: Homo sapiens

<400> SEQUENCE: 58

```
Met Gly Ile Val Glu Pro Gly Cys Gly Asp Met Leu Thr Gly Thr Glu
1               5                   10                  15

Pro Met Pro Gly Ser Asp Glu Gly Arg Ala Pro Gly Ala Asp Pro Gln
            20                  25                  30

His Arg Tyr Phe Tyr Pro Glu Pro Gly Ala Gln Asp Ala Asp Glu Arg
        35                  40                  45

Arg Gly Gly Gly Ser Leu Gly Ser Pro Tyr Pro Gly Gly Ala Leu Val
    50                  55                  60

Pro Ala Pro Pro Ser Arg Phe Leu Gly Ala Tyr Ala Tyr Pro Pro Arg
65                  70                  75                  80

Pro Gln Ala Ala Gly Phe Pro Gly Ala Gly Glu Ser Phe Pro Pro Pro
                85                  90                  95

Ala Asp Ala Glu Gly Tyr Gln Pro Gly Glu Gly Tyr Ala Ala Pro Asp
            100                 105                 110

Pro Arg Ala Gly Leu Tyr Pro Gly Pro Arg Glu Asp Tyr Ala Leu Pro
        115                 120                 125

Ala Gly Leu Glu Val Ser Gly Lys Leu Arg Val Ala Leu Asn Asn His
    130                 135                 140

Leu Leu Trp Ser Lys Phe Asn Gln His Gln Thr Glu Met Ile Ile Thr
145                 150                 155                 160

Lys Gln Gly Arg Arg Met Phe Pro Phe Leu Ser Phe Thr Val Ala Gly
                165                 170                 175

Leu Glu Pro Thr Ser His Tyr Arg Met Phe Val Asp Val Val Leu Val
            180                 185                 190

Asp Gln His His Trp Arg Tyr Gln Ser Gly Lys Trp Val Gln Cys Gly
        195                 200                 205

Lys Ala Glu Gly Ser Met Pro Gly Asn Arg Leu Tyr Val His Pro Asp
    210                 215                 220

Ser Pro Asn Thr Gly Ala His Trp Met Arg Gln Glu Val Ser Phe Gly
225                 230                 235                 240

Lys Leu Lys Leu Thr Asn Asn Lys Gly Ala Ser Asn Asn Val Thr Gln
                245                 250                 255

Met Ile Val Leu Gln Ser Leu His Lys Tyr Gln Pro Arg Leu His Ile
            260                 265                 270

Val Glu Val Asn Asp Gly Glu Pro Glu Ala Ala Cys Asn Ala Ser Asn
```

```
        275                 280                 285

Thr His Ile Phe Thr Phe Gln Glu Thr Gln Phe Ile Ala Val Thr Ala
    290                 295                 300

Tyr Gln Asn Ala Glu Ile Thr Gln Leu Lys Ile Asp Asn Asn Pro Phe
305                 310                 315                 320

Ala Lys Gly Phe Arg Glu Asn Phe Glu Ser Met Tyr Thr Ser Val Asp
                325                 330                 335

Thr Ser Ile Pro Ser Pro Pro Gly Pro Asn Cys Gln Phe Leu Gly Gly
            340                 345                 350

Asp His Tyr Ser Pro Leu Leu Pro Asn Gln Tyr Pro Val Pro Ser Arg
        355                 360                 365

Phe Tyr Pro Asp Leu Pro Gly Gln Ala Lys Asp Val Val Pro Gln Ala
    370                 375                 380

Tyr Trp Leu Gly Ala Pro Arg Asp His Ser Tyr Glu Ala Glu Phe Arg
385                 390                 395                 400

Ala Val Ser Met Lys Pro Ala Phe Leu Pro Ser Ala Pro Gly Pro Thr
                405                 410                 415

Met Ser Tyr Tyr Arg Gly Gln Glu Val Leu Ala Pro Gly Ala Gly Trp
            420                 425                 430

Pro Val Ala Pro Gln Tyr Pro Pro Lys Met Gly Pro Ala Ser Trp Phe
        435                 440                 445

Arg Pro Met Arg Thr Leu Pro Met Glu Pro Gly Pro Gly Gly Ser Glu
    450                 455                 460

Gly Arg Gly Pro Glu Asp Gln Gly Pro Pro Leu Val Trp Thr Glu Ile
465                 470                 475                 480

Ala Pro Ile Arg Pro Glu Ser Ser Asp Ser Gly Leu Gly Glu Gly Asp
                485                 490                 495

Ser Lys Arg Arg Arg Val Ser Pro Tyr Pro Ser Ser Gly Asp Ser Ser
            500                 505                 510

Ser Pro Ala Gly Ala Pro Ser Pro Phe Asp Lys Glu Ala Glu Gly Gln
        515                 520                 525

Phe Tyr Asn Tyr Phe Pro Asn
    530                 535
```

<210> SEQ ID NO 59
<211> LENGTH: 3691
<212> TYPE: RNA
<213> ORGANISM: Homo sapiens

<400> SEQUENCE: 59

```
ggcgcaacgc ugagcagcug gcgcgucccg cgcggcccca guucugcgca gcuucccgag      60

gcuccgcacc agccgcgcuu cuguccgccu gcagggcauu ccagaaagau gaggauauuu     120

gcugucuuua uauucaugac cuacuggcau uugcugaacg cauuuacugu cacgguuccc     180

aaggaccuau augugguaga guaugguagc aauaugacaa uugaaugcaa auucccagua     240

gaaaaacaau uagaccuggc ugcacuaauu gucuauuggg aaauggagga uaagaacauu     300

auucaauuug ugcauggaga ggaagaccug aagguucagc auaguagcua cagacagagg     360

gcccggcugu ugaaggacca gcucucccug ggaaaugcug cacuucagau cacagaugug     420

aaauugcagg augcaggggu guaccgcugc augaucagcu augguggugc cgacuacaag     480

cgaauuacug ugaaagucaa ugccccauac aacaaaauca accaaagaau uuugguugug     540

gauccaguca ccucugaaca ugaacugaca ugucaggcug agggcuaccc caaggccgaa     600

gucaucugga caagcaguga ccaucaaguc cugaguggua agaccaccac caccaauucc     660
```

-continued

```
aagagagagg agaagcuuuu caaugugacc agcacacuga gaaucaacac aacaacuaau    720
gagauuuucu acugcacuuu uaggagauua gauccugagg aaaaccauac agcugaauug    780
gucaucccag aacuaccucu ggcacauccu ccaaaugaaa ggacucacuu gguaauucug    840
ggagccaucu uauuaugccu ugguguagca cugacauuca ucuuccguuu aagaaaaggg    900
agaaugaugg augugaaaaa auguggcauc caagauacaa acucaaagaa gcaaagugau    960
acacauuugg aggagacgua auccagcauu ggaacuucug aucuucaagc agggauucuc   1020
aaccuguggu uuaggggguuc aucggggcug agcgugacaa gaggaaggaa ugggcccgug   1080
ggaugcaggc aaugugggac uuaaaaggcc caagcacuga aaauggaacc uggcgaaagc   1140
agaggaggag aaugaagaaa gauggaguca aacagggagc cuggagggag accuugauac   1200
uuucaaaugc cugaggggcu caucgacgcc ugugacaggg agaaaggaua cuucugaaca   1260
aggagccucc aagcaaauca uccauugcuc auccuaggaa gacggguuga gaaucccuaa   1320
uuugaggguc aguuccugca gaagugcccu uugccuccac ucaaugccuc aauuuguuuu   1380
cugcaugacu gagagucuca guguuggaac gggacaguau uuauguauga guuuuuccua   1440
uuuauuuuga gucugugagg ucuucuuguc augugagugu gguugugaau gauuucuuuu   1500
gaagauauau uguaguagau guuacaauuu ugucgccaaa cuaaacuugc ugcuuaauga   1560
uuugcucaca ucuaguaaaa cauggaguau uuguaaggug cuuggucucc ucuauaacua   1620
caaguauaca uuggaagcau aaagaucaaa ccguugguug cauaggaugu caccuuuauu   1680
uaacccauua auacucuggu ugaccuaauc uuauucucag accucaagug ucugugcagu   1740
aucuguucca uuuaaauauc agcuuuacaa uuauguggua gccuacacac auaaucucau   1800
uucaucgcug uaaccacccu guugugauaa ccacuauuau uuuacccauc guacagcuga   1860
ggaagcaaac agauuaagua acuugcccaa accaguaaau agcagaccuc agacugccac   1920
ccacuguccu uuuauaauac aauuuacagc uauauuuuac uuuaagcaau ucuuuuauuc   1980
aaaaaccauu uauuaagugc ccuugcaaua ucaaucgcug ugccaggcau ugaaucuaca   2040
gaugugagca agacaaagua ccuguccuca aggagcucau aguauaauga ggagauuaac   2100
aagaaaaugu auuauuacaa uuuaguccag ugucauagca uaaggaugau gcgaggggaa   2160
aacccgagca guguugccaa gaggaggaaa uaggccaaug uggucuggga cgguuggaua   2220
uacuuaaaca ucuuaauaau cagaguaauu uucauuuaca aagagagguc gguacuuaaa   2280
auaacccuga aaaauaacac uggaauuccu uuucuagcau uauauuuauu ccugauuugc   2340
cuuugccaua uaaucuaaug cuuguuuaua uagugucugg uauuguuuaa caguucuguc   2400
uuuucuauuu aaaugccacu aaauuuuaaa uucauaccuu uccaugauuc aaaauucaaa   2460
agaucccaug ggagaugguu ggaaaaucuc cacuucaucc uccaagccau ucaaguuucc   2520
uuuccagaag caacugcuac ugccuuucau ucauauguuc uucuaaagau agucuacauu   2580
uggaaaugua uguuaaaagc acguauuuuu aaaauuuuuu uccuaaauag uaacacauug   2640
uaugucugcu guguacuuug cuauuuuuau uuauuuuagu guuucuuaua uagcagaugg   2700
aaugaauuug aaguucccag ggcugaggau ccaugccuuc uuuguuucua aguuaucuuu   2760
cccauagcuu uucauuaucu uucauaugau ccaguauaug uuaaauaugu ccuacauaua   2820
cauuuagaca accaccauuu guuaaguauu ugcucuagga cagaguuugg auuuguuuau   2880
guuugcucaa aaggagaccc augggcucuc cagggugcac ugagucaauc uaguccuaaa   2940
aagcaaucuu auuauuaacu cuguaugaca gaaucauguc uggaacuuuu guuuucugcu   3000
```

```
uucugucaag uauaaacuuc acuuugaugc uguacuugca aaaucacauu uucuuucugg   3060

aaauuccggc aguguaccuu gacugcuagc uacccugugc cagaaaagcc ucauucguug   3120

ugcuugaacc cuugaaugcc accagcuguc aucacuacac agcccuccua agaggcuucc   3180

uggagguuuc gagauucaga ugcccuggga gaucccagag uuuccuuucc cucuuggcca   3240

uauucuggug ucaaugacaa ggaguaccuu ggcuuugcca caugucaagg cugaagaaac   3300

agugucucca acagagcucc uuguguuauc uguuuguaca ugugcauuug uacaguaauu   3360

ggugugacag uguucuuugu gugaauuaca ggcaagaauu guggcugagc aaggcacaua   3420

gucuacucag ucuauuccua aguccuaacu ccuccuugug guguuggauu uguaaggcac   3480

uuuaucccuu uugucucaug uuucaucgua aauggcauag gcagagauga uaccuaauuc   3540

ugcauuugau ugucacuuuu uguaccugca uuaauuuaau aaaauauucu uauuuauuuu   3600

guuacuuggu acaccagcau guccauuuuc uuguuuauuu uguguuuaau aaaauguuca   3660

guuuaacauc ccaguggaga aaguuaaaaa a                                  3691
```

<210> SEQ ID NO 60
<211> LENGTH: 290
<212> TYPE: PRT
<213> ORGANISM: Homo sapiens

<400> SEQUENCE: 60

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255
```

-continued

```
Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 61
<211> LENGTH: 440
<212> TYPE: PRT
<213> ORGANISM: Artificial Sequence
<220> FEATURE:
<223> OTHER INFORMATION: Synthetic Construct

<400> SEQUENCE: 61

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320
```

```
Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 62
<211> LENGTH: 214
<212> TYPE: PRT
<213> ORGANISM: Artificial Sequence
<220> FEATURE:
<223> OTHER INFORMATION: Synthetic Construct

<400> SEQUENCE: 62

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 63
```

<211> LENGTH: 10
<212> TYPE: PRT
<213> ORGANISM: Artificial Sequence
<220> FEATURE:
<223> OTHER INFORMATION: Synthetic Construct

<400> SEQUENCE: 63

Gly Phe Thr Phe Ser Asp Ser Trp Ile His
1 5 10

<210> SEQ ID NO 64
<211> LENGTH: 18
<212> TYPE: PRT
<213> ORGANISM: Artificial Sequence
<220> FEATURE:
<223> OTHER INFORMATION: Synthetic Construct

<400> SEQUENCE: 64

Ala Trp Ile Ser Pro Tyr Gly Gly Ser Thr Tyr Tyr Ala Asp Ser Val
1 5 10 15

Lys Gly

<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

<400> SEQUENCE: 65

Arg His Trp Pro Gly Gly Phe Asp Tyr
1 5

<210> SEQ ID NO 66
<211> LENGTH: 11
<212> TYPE: PRT
<213> ORGANISM: Artificial Sequence
<220> FEATURE:
<223> OTHER INFORMATION: Synthetic Construct

<400> SEQUENCE: 66

Arg Ala Ser Gln Asp Val Ser Thr Ala Val Ala
1 5 10

<210> SEQ ID NO 67
<211> LENGTH: 7
<212> TYPE: PRT
<213> ORGANISM: Artificial Sequence
<220> FEATURE:
<223> OTHER INFORMATION: Synthetic Construct

<400> SEQUENCE: 67

Ser Ala Ser Phe Leu Tyr Ser
1 5

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

Gln Gln Tyr Leu Tyr His Pro Ala Thr
1 5

<210> SEQ ID NO 69
<211> LENGTH: 118
<212> TYPE: PRT
<213> ORGANISM: Artificial Sequence
<220> FEATURE:
<223> OTHER INFORMATION: Synthetic Construct

<400> SEQUENCE: 69

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115
```

<210> SEQ ID NO 70
<211> LENGTH: 108
<212> TYPE: PRT
<213> ORGANISM: Artificial Sequence
<220> FEATURE:
<223> OTHER INFORMATION: Synthetic Construct

<400> SEQUENCE: 70

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105
```

<210> SEQ ID NO 71
<211> LENGTH: 447
<212> TYPE: PRT
<213> ORGANISM: Artificial Sequence
<220> FEATURE:
<223> OTHER INFORMATION: Synthetic Construct

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30
```

-continued

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 72
<211> LENGTH: 214
<212> TYPE: PRT
<213> ORGANISM: Artificial Sequence
<220> FEATURE:
<223> OTHER INFORMATION: Synthetic Construct

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 73
<211> LENGTH: 449
<212> TYPE: PRT
<213> ORGANISM: Artificial Sequence
<220> FEATURE:
<223> OTHER INFORMATION: Synthetic Construct

<400> SEQUENCE: 73

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Ile Lys Leu Gly Thr Val Thr Thr Val Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 74
<211> LENGTH: 216
<212> TYPE: PRT
<213> ORGANISM: Artificial Sequence
<220> FEATURE:
<223> OTHER INFORMATION: Synthetic Construct

<400> SEQUENCE: 74

-continued

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Ser Ser
85 90 95

Ser Thr Arg Val Phe Gly Thr Gly Thr Lys Val Thr Val Leu Gly Gln
100 105 110

Pro Lys Ala Asn Pro Thr Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Gly Ser Pro Val Lys
145 150 155 160

Ala Gly Val Glu Thr Thr Lys Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 75
<211> LENGTH: 450
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Glu Gly Gly Trp Phe Gly Glu Leu Ala Phe Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

-continued

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 76
<211> LENGTH: 215
<212> TYPE: PRT
<213> ORGANISM: Artificial Sequence
<220> FEATURE:
<223> OTHER INFORMATION: Synthetic Construct

<400> SEQUENCE: 76

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45
```

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 77
<211> LENGTH: 440
<212> TYPE: PRT
<213> ORGANISM: Artificial Sequence
<220> FEATURE:
<223> OTHER INFORMATION: Synthetic Construct

<400> SEQUENCE: 77

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

```
Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 78
<211> LENGTH: 214
<212> TYPE: PRT
<213> ORGANISM: Artificial Sequence
<220> FEATURE:
<223> OTHER INFORMATION: Synthetic Construct

<400> SEQUENCE: 78

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 79
<211> LENGTH: 447
<212> TYPE: PRT
<213> ORGANISM: Artificial Sequence
<220> FEATURE:
<223> OTHER INFORMATION: Synthetic Construct

<400> SEQUENCE: 79

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 80
<211> LENGTH: 218
<212> TYPE: PRT
<213> ORGANISM: Artificial Sequence
<220> FEATURE:
<223> OTHER INFORMATION: Synthetic Construct

<400> SEQUENCE: 80

Glu Ile Val Leu Thr Gln Ser Pro Ala Thr Leu Ser Leu Ser Pro Gly
1 5 10 15

Glu Arg Ala Thr Leu Ser Cys Arg Ala Ser Lys Gly Val Ser Thr Ser
20 25 30

Gly Tyr Ser Tyr Leu His Trp Tyr Gln Gln Lys Pro Gly Gln Ala Pro
35 40 45

Arg Leu Leu Ile Tyr Leu Ala Ser Tyr Leu Glu Ser Gly Val Pro Ala
50 55 60

Arg Phe Ser Gly Ser Gly Ser Gly Thr Asp Phe Thr Leu Thr Ile Ser
65 70 75 80

Ser Leu Glu Pro Glu Asp Phe Ala Val Tyr Tyr Cys Gln His Ser Arg
85 90 95

Asp Leu Pro Leu Thr Phe Gly Gly Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 81
<211> LENGTH: 2471
<212> TYPE: RNA
<213> ORGANISM: Homo sapiens

<400> SEQUENCE: 81

agaaagcgag cagccaccca gcucccgcc accgccaugg uccccgacac cgccugcguu     60

cuucugcuca cccuggcugc ccucggcgcg uccggacagg gccagagccc guugggcuca    120

gaccugggcc cgcagaugcu ucgggaacug caggaaacca acgcggcgcu gcaggacgug    180

cgggagcugc ugcggcagca ggucagggag aucacguucc ugaaaaacac ggugauggag    240

ugugacgcgu gcgggaugca gcagucagua cgcaccggcc uacccagcgu gcggcccug     300

cuccacugcg cgcccggcuu cugcuucccc ggcguggccu gcauccagac ggagagcggc    360

gcgcgcugcg gccccugccc cgcgggcuuc acgggcaacg gcucgcacug caccgacguc    420

aacgagugca acgcccaccc cugcuucccc cgaguccgcu guaucaacac cagcccgggg    480

uuccgcugcg aggcuugccc gccgggguac agcggcccca cccaccaggg cguggggcug    540

gcuuucgcca aggccaacaa gcagguuugc acggacauca acgaguguga gaccgggcaa    600

cauaacugcg uccccaacuc cgugugcauc aacacccggg gcuccuucca gugcggcccg    660

ugccagcccg gcuucguggg cgaccaggcg uccggcugcc agcggcgcgc acagcgcuuc    720

ugccccgacg gcucgcccag cgagugccac gagcaugcag acugcguccu agagcgcgau    780

ggcucgcggu cgugcgugug ugccguuggc ugggccggca acgggauccu cuguggucgc    840

gacacugacc uagacggcuu cccggacgag aagcugcgcu gcccggagcg ccagugccgu    900

aaggacaacu gcgugacugu gcccaacuca gggcaggagg auguggaccg cgauggcauc    960

ggagacgccu gcgauccgga ugccgacggg gacgggguccc ccaaugaaaa ggacaacugc  1020

ccgcuggugc ggaacccaga ccagcgcaac acggacgagg acaagugggg cgaugcgugc   1080

gacaacugcc gguccccagaa gaacgacgac caaaaggaca cagaccagga cggccggggc  1140

gaugcgugcg acgacgacau cgacggcgac cggauccgca accaggccga caacugcccu   1200

aggguaccca acucagacca gaaggacagu gauggcgaug guauagggga ugccugugac   1260

aacugucccc agaagagcaa cccggaucag gcggaugugg accacgacuu uguggggagau  1320

gcuugugaca gcgaucaaga ccaggaugga gacggacauc aggacucucg ggacaacugu   1380

cccacggugc cuaacagugc ccaggaggac ucagaccacg auggccaggg ugaugccugc   1440

gacgacgacg acgacaauga cggagucccu gacagucggg acaacugccg ccuggugccu   1500

aaccccggcc aggaggacgc ggacagggac ggcgugggcg acgugugcca ggacgacuuu   1560

gaugcagaca aggugguaga caagaucgac gugugucccgg agaacgcuga agucacgcuc  1620

accgacuuca gggccuucca gacagucgug cuggacccgg agggugacgc gcagauugac   1680

cccaacuggg uggugcucaa ccagggaagg gagaucgugc agacaaugaa cagcgaccca   1740

ggccuggcug uggguuacac ugccuucaau ggcguggacu ucgagggcac guuccaugug   1800

aacacggguca cggaugacga cuaugcgggc uucaucuuug gcuaccagga cagcuccagc  1860
```

-continued

```
uucuacgugg ucauguggaa gcagauggag caaacguauu ggcaggcgaa ccccuuccgu   1920

gcuguggccg agccuggcau ccaacucaag gcugugaagu cuuccacagg ccccggggaa   1980

cagcugcgga acgcucugug gcauacagga gacacagagu cccaggugcg gcugcugugg   2040

aaggacccgc gaaacguggg uuggaaggac aagaaguccu aucguugguu ccugcagcac   2100

cggccccaag ugggcuacau cagggugcga uucuaugagg gcccugagcu gguggccgac   2160

agcaacgugg ucuuggacac aaccaugcgg gguggccgcc ugggggucuu cugcuucucc   2220

caggagaaca ucaucugggc caaccugcgu uaccgcugca augacaccau cccagaggac   2280

uaugagaccc aucagcugcg gcaagccuag ggaccagggu gaggacccgc cggaugacag   2340

ccacccucac cgcggcugga ugggggcucu gcacccagcc ccaaggggug gccguccuga   2400

gggggaagug agaagggcuc agagaggaca aaauaaagug ugugugcagg gaaaaaaaaa   2460

aaaaaaaaaa a                                                         2471


<210> SEQ ID NO 82
<211> LENGTH: 757
<212> TYPE: PRT
<213> ORGANISM: Homo sapiens

<400> SEQUENCE: 82

Met Val Pro Asp Thr Ala Cys Val Leu Leu Leu Thr Leu Ala Ala Leu
1               5                   10                  15

Gly Ala Ser Gly Gln Gly Gln Ser Pro Leu Gly Ser Asp Leu Gly Pro
            20                  25                  30

Gln Met Leu Arg Glu Leu Gln Glu Thr Asn Ala Ala Leu Gln Asp Val
        35                  40                  45

Arg Glu Leu Leu Arg Gln Gln Val Arg Glu Ile Thr Phe Leu Lys Asn
    50                  55                  60

Thr Val Met Glu Cys Asp Ala Cys Gly Met Gln Gln Ser Val Arg Thr
65                  70                  75                  80

Gly Leu Pro Ser Val Arg Pro Leu Leu His Cys Ala Pro Gly Phe Cys
                85                  90                  95

Phe Pro Gly Val Ala Cys Ile Gln Thr Glu Ser Gly Ala Arg Cys Gly
            100                 105                 110

Pro Cys Pro Ala Gly Phe Thr Gly Asn Gly Ser His Cys Thr Asp Val
        115                 120                 125

Asn Glu Cys Asn Ala His Pro Cys Phe Pro Arg Val Arg Cys Ile Asn
    130                 135                 140

Thr Ser Pro Gly Phe Arg Cys Glu Ala Cys Pro Pro Gly Tyr Ser Gly
145                 150                 155                 160

Pro Thr His Gln Gly Val Gly Leu Ala Phe Ala Lys Ala Asn Lys Gln
                165                 170                 175

Val Cys Thr Asp Ile Asn Glu Cys Glu Thr Gly Gln His Asn Cys Val
            180                 185                 190

Pro Asn Ser Val Cys Ile Asn Thr Arg Gly Ser Phe Gln Cys Gly Pro
        195                 200                 205

Cys Gln Pro Gly Phe Val Gly Asp Gln Ala Ser Gly Cys Gln Arg Arg
    210                 215                 220

Ala Gln Arg Phe Cys Pro Asp Gly Ser Pro Ser Glu Cys His Glu His
225                 230                 235                 240

Ala Asp Cys Val Leu Glu Arg Asp Gly Ser Arg Ser Cys Val Cys Ala
                245                 250                 255

Val Gly Trp Ala Gly Asn Gly Ile Leu Cys Gly Arg Asp Thr Asp Leu
```

-continued

```
        260                 265                 270

Asp Gly Phe Pro Asp Glu Lys Leu Arg Cys Pro Glu Arg Gln Cys Arg
        275                 280                 285

Lys Asp Asn Cys Val Thr Val Pro Asn Ser Gly Gln Glu Asp Val Asp
    290                 295                 300

Arg Asp Gly Ile Gly Asp Ala Cys Asp Pro Asp Ala Asp Gly Asp Gly
305                 310                 315                 320

Val Pro Asn Glu Lys Asp Asn Cys Pro Leu Val Arg Asn Pro Asp Gln
                325                 330                 335

Arg Asn Thr Asp Glu Asp Lys Trp Gly Asp Ala Cys Asp Asn Cys Arg
            340                 345                 350

Ser Gln Lys Asn Asp Asp Gln Lys Asp Thr Asp Gln Asp Gly Arg Gly
        355                 360                 365

Asp Ala Cys Asp Asp Asp Ile Asp Gly Asp Arg Ile Arg Asn Gln Ala
    370                 375                 380

Asp Asn Cys Pro Arg Val Pro Asn Ser Asp Gln Lys Asp Ser Asp Gly
385                 390                 395                 400

Asp Gly Ile Gly Asp Ala Cys Asp Asn Cys Pro Gln Lys Ser Asn Pro
                405                 410                 415

Asp Gln Ala Asp Val Asp His Asp Phe Val Gly Asp Ala Cys Asp Ser
            420                 425                 430

Asp Gln Asp Gln Asp Gly Asp Gly His Gln Asp Ser Arg Asp Asn Cys
        435                 440                 445

Pro Thr Val Pro Asn Ser Ala Gln Glu Asp Ser Asp His Asp Gly Gln
    450                 455                 460

Gly Asp Ala Cys Asp Asp Asp Asp Asp Asn Asp Gly Val Pro Asp Ser
465                 470                 475                 480

Arg Asp Asn Cys Arg Leu Val Pro Asn Pro Gly Gln Glu Asp Ala Asp
                485                 490                 495

Arg Asp Gly Val Gly Asp Val Cys Gln Asp Asp Phe Asp Ala Asp Lys
            500                 505                 510

Val Val Asp Lys Ile Asp Val Cys Pro Glu Asn Ala Glu Val Thr Leu
        515                 520                 525

Thr Asp Phe Arg Ala Phe Gln Thr Val Val Leu Asp Pro Glu Gly Asp
    530                 535                 540

Ala Gln Ile Asp Pro Asn Trp Val Val Leu Asn Gln Gly Arg Glu Ile
545                 550                 555                 560

Val Gln Thr Met Asn Ser Asp Pro Gly Leu Ala Val Gly Tyr Thr Ala
                565                 570                 575

Phe Asn Gly Val Asp Phe Glu Gly Thr Phe His Val Asn Thr Val Thr
            580                 585                 590

Asp Asp Asp Tyr Ala Gly Phe Ile Phe Gly Tyr Gln Asp Ser Ser Ser
        595                 600                 605

Phe Tyr Val Val Met Trp Lys Gln Met Glu Gln Thr Tyr Trp Gln Ala
    610                 615                 620

Asn Pro Phe Arg Ala Val Ala Glu Pro Gly Ile Gln Leu Lys Ala Val
625                 630                 635                 640

Lys Ser Ser Thr Gly Pro Gly Glu Gln Leu Arg Asn Ala Leu Trp His
                645                 650                 655

Thr Gly Asp Thr Glu Ser Gln Val Arg Leu Leu Trp Lys Asp Pro Arg
            660                 665                 670

Asn Val Gly Trp Lys Asp Lys Lys Ser Tyr Arg Trp Phe Leu Gln His
        675                 680                 685
```

-continued

```
Arg Pro Gln Val Gly Tyr Ile Arg Val Arg Phe Tyr Glu Gly Pro Glu
    690                 695                 700

Leu Val Ala Asp Ser Asn Val Val Leu Asp Thr Thr Met Arg Gly Gly
705                 710                 715                 720

Arg Leu Gly Val Phe Cys Phe Ser Gln Glu Asn Ile Ile Trp Ala Asn
                725                 730                 735

Leu Arg Tyr Arg Cys Asn Asp Thr Ile Pro Glu Asp Tyr Glu Thr His
            740                 745                 750

Gln Leu Arg Gln Ala
        755
```